(12) United States Patent
Mjalli et al.

(10) Patent No.: US 11,649,230 B2
(45) Date of Patent: *May 16, 2023

(54) SUBSTITUTED FUSED IMIDAZOLE DERIVATIVES, PHARMACEUTICAL COMPOSITIONS, AND METHODS OF USE THEREOF

(71) Applicant: vTv Therapeutics LLC, High Point, NC (US)

(72) Inventors: Adnan M. M. Mjalli, Oak Ridge, NC (US); Dharma Rao Polisetti, High Point, NC (US); Jareer Nabeel Kassis, Colfax, NC (US); Matthew J. Kostura, Hillsborough, NC (US); Mustafa Guzel, Jamestown, NC (US); Otis Clinton Attucks, Winston-Salem, NC (US); Robert Carl Andrews, Jamestown, NC (US); Samuel Victory, Winston-Salem, NC (US); Suparna Gupta, Waverly, IA (US)

(73) Assignee: VTV THERAPEUTICS LLC, High Point, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 17/399,338

(22) Filed: Aug. 11, 2021

(65) Prior Publication Data

US 2022/0169641 A1    Jun. 2, 2022

Related U.S. Application Data

(60) Division of application No. 17/028,226, filed on Sep. 22, 2020, now Pat. No. 11,130,753, which is a division of application No. 16/739,493, filed on Jan. 10, 2020, now Pat. No. 10,889,580, which is a division of application No. 16/292,524, filed on Mar. 5, 2019, now Pat. No. 10,570,126, which is a division of application No. 16/007,532, filed on Jun. 13, 2018, now Pat. No. 10,287,284, which is a division of application No. 14/215,873, filed on Mar. 17, 2014, now Pat. No. 10,030,011, which is a continuation of application No. 13/028,406, filed on Feb. 16, 2011, now Pat. No. 8,759,535.

(60) Provisional application No. 61/305,724, filed on Feb. 18, 2010.

(51) Int. Cl.

| | | |
|---|---|---|
| *A61P 1/16* | (2006.01) | |
| *A61K 31/4168* | (2006.01) | |
| *A61K 31/4188* | (2006.01) | |
| *A61K 31/428* | (2006.01) | |
| *A61K 31/437* | (2006.01) | |
| *C07D 417/12* | (2006.01) | |
| *C07D 417/14* | (2006.01) | |
| *C07D 471/04* | (2006.01) | |
| *C07D 235/30* | (2006.01) | |
| *C07D 513/04* | (2006.01) | |

(52) U.S. Cl.
CPC ........ *C07D 417/12* (2013.01); *A61K 31/4168* (2013.01); *A61K 31/4188* (2013.01); *A61K 31/428* (2013.01); *A61K 31/437* (2013.01); *A61P 1/16* (2018.01); *C07D 235/30* (2013.01); *C07D 417/14* (2013.01); *C07D 471/04* (2013.01); *C07D 513/04* (2013.01)

(58) Field of Classification Search
None
See application file for complete search history.

(56) References Cited

U.S. PATENT DOCUMENTS

| | | |
|---|---|---|
| 5,140,103 A | 8/1992 | Eyre |
| 5,300,434 A | 4/1994 | Eyre |
| 5,320,970 A | 6/1994 | Eyre |
| 5,561,134 A | 10/1996 | Spada et al. |
| 6,358,978 B1 | 3/2002 | Ritzeler et al. |
| 6,509,376 B1 | 1/2003 | Joshi et al. |
| 6,562,854 B2 | 5/2003 | Church et al. |
| 7,030,139 B2 | 4/2006 | Cheng et al. |
| 7,030,150 B2 | 4/2006 | Lackey et al. |
| 7,238,813 B2 | 7/2007 | Cheung et al. |
| 7,320,999 B2 | 1/2008 | Joshi et al. |
| 7,355,052 B2 | 4/2008 | Poitout et al. |
| 7,407,968 B2 | 8/2008 | Page et al. |
| 7,413,578 B2 | 8/2008 | Javet et al. |
| 7,429,608 B2 | 9/2008 | Norman et al. |
| 7,501,524 B2 | 3/2009 | Poitout et al. |
| 7,501,525 B2 | 3/2009 | Poitout et al. |

(Continued)

FOREIGN PATENT DOCUMENTS

| | | |
|---|---|---|
| AU | 1224595 A | 8/1995 |
| DE | 102005003362 A1 | 7/2006 |

(Continued)

OTHER PUBLICATIONS

Alam et al. How many transcription factors does it take to turn on the heme oxynegase-1 gene? Arm J Respir Cell Mat. Biol. 36:166-174 (2007).

(Continued)

*Primary Examiner* — Joseph R Kosack
(74) *Attorney, Agent, or Firm* — Wilson Sonsini Goodrich & Rosati

(57) ABSTRACT

Substituted fused imidazole derivatives, methods of their preparation, pharmaceutical compositions comprising a substituted fused imidazole derivative, and methods of use in treating renal diseases are provided. The substituted fused imidazole derivatives may control the activity or the amount or both the activity and the amount of heme-oxygenase.

29 Claims, No Drawings

(56) References Cited

U.S. PATENT DOCUMENTS

| | | |
|---|---|---|
| 7,517,893 B2 | 4/2009 | Tidwell et al. |
| 7,531,553 B2 | 5/2009 | Di et al. |
| 7,619,001 B2 | 11/2009 | Joshi et al. |
| 7,803,840 B2 | 9/2010 | Joshi et al. |
| 7,816,539 B2 | 10/2010 | Poitout et al. |
| 7,820,821 B2 | 10/2010 | Mjalli et al. |
| 7,915,402 B2 | 3/2011 | Anderson et al. |
| 8,399,514 B2 | 3/2013 | Lukashev et al. |
| 8,455,544 B2 | 6/2013 | Sporn et al. |
| 8,524,773 B2 | 9/2013 | Joshi et al. |
| 8,633,243 B2 | 1/2014 | Walling et al. |
| 8,639,009 B2 | 1/2014 | Lang et al. |
| 8,759,535 B2 | 6/2014 | Mjalli et al. |
| 10,030,011 B2 | 7/2018 | Mjalli et al. |
| 10,085,967 B2 | 10/2018 | Essack et al. |
| 10,287,284 B2 | 5/2019 | Mjalli et al. |
| 10,570,126 B2 | 2/2020 | Mjalli et al. |
| 10,889,580 B2 | 1/2021 | Mjalli et al. |
| 11,130,753 B2 | 9/2021 | Mjalli et al. |
| 2004/0122235 A1 | 6/2004 | Polisetti et al. |
| 2007/0219235 A1 | 9/2007 | Mjalli et al. |
| 2010/0152170 A1 | 6/2010 | Mjalli et al. |
| 2013/0059904 A1 | 3/2013 | Van Rompaney et al. |
| 2013/0158077 A1 | 6/2013 | Kahrs |
| 2014/0171504 A1 | 6/2014 | Ganapathy |
| 2017/0056413 A1 | 3/2017 | Kassis et al. |
| 2017/0174716 A1 | 6/2017 | Motterlini et al. |
| 2021/0283111 A1 | 9/2021 | Attucks |
| 2021/0338644 A1 | 11/2021 | Attucks |

FOREIGN PATENT DOCUMENTS

| | | |
|---|---|---|
| EP | 0639573 A1 | 2/1995 |
| EP | 0668270 A2 | 8/1995 |
| EP | 1792613 A2 | 6/2007 |
| EP | 1726589 B1 | 10/2008 |
| JP | 2000038387 A | 2/2000 |
| JP | 2003344971 A | 12/2003 |
| JP | 2009149589 A | 7/2009 |
| WO | WO-9528160 A1 | 10/1995 |
| WO | WO-9845275 A1 | 10/1998 |
| WO | WO-9926932 A1 | 6/1999 |
| WO | WO-0005223 A2 | 2/2000 |
| WO | WO-0244156 A2 | 6/2002 |
| WO | WO-02085866 A1 | 10/2002 |
| WO | WO-02092575 A1 | 11/2002 |
| WO | WO-2004035548 A1 | 4/2004 |
| WO | WO-2004085425 A1 | 10/2004 |
| WO | WO-2005117890 A2 | 12/2005 |
| WO | WO-2006066879 A2 | 6/2006 |
| WO | WO-2006081244 A2 | 8/2006 |
| WO | WO-2007093600 A1 | 8/2007 |
| WO | WO-2007095124 A2 | 8/2007 |
| WO | WO-2007095601 A2 | 8/2007 |
| WO | WO-2008113255 A1 | 9/2008 |
| WO | WO-2008151437 A1 | 12/2008 |
| WO | WO-2008153701 A1 | 12/2008 |
| WO | WO-2009017701 A2 | 2/2009 |
| WO | WO-2009051796 A2 | 4/2009 |
| WO | WO-2009071650 A2 | 6/2009 |
| WO | WO-2009116074 A2 | 9/2009 |
| WO | WO-2009126635 A1 | 10/2009 |
| WO | WO-2009126691 A1 | 10/2009 |
| WO | WO-2009133127 A1 | 11/2009 |
| WO | WO-2009134850 A1 | 11/2009 |
| WO | WO-2010003197 A1 | 1/2010 |
| WO | WO-2010007316 A2 | 1/2010 |
| WO | WO-2010007317 A1 | 1/2010 |
| WO | WO-2010007318 A2 | 1/2010 |
| WO | WO-2010036613 A1 | 4/2010 |
| WO | WO-2010047982 A1 | 4/2010 |
| WO | WO-2010065674 A1 | 6/2010 |
| WO | WO-2010135014 A1 | 11/2010 |
| WO | WO-2011103018 A1 | 8/2011 |
| WO | WO-2012094580 A2 | 7/2012 |
| WO | WO-2013092269 A1 | 6/2013 |
| WO | WO-2016013004 A1 | 1/2016 |
| WO | WO-2016089648 A1 | 6/2016 |
| WO | WO-2020117886 A1 | 6/2020 |
| WO | WO-2020150306 A1 | 7/2020 |
| WO | WO-2020210339 A1 | 10/2020 |

OTHER PUBLICATIONS

Attucks et al. Induction of Heme Oxygenase I (HMOX1) by HPP-4382: A Novel Modulator of Bach1 Activity. PLoS One 9(7):0101044 (2014).

Barone et al. The Janus face of the heme oxygenase/biliverdin reductase system in Alzheimer disease: it's time for reconciliation. Neurobiol Dis 62:144-159 (2014).

Berge et al. Pharmaceutical Salts. Journal of Pharmaceutical Sciences 66(1):1-19 (Jan. 1977).

EP11745064.3 European Search Report dated Jan. 2, 2014.

FDA Approved Labeling Text dated Mar. 27, 2013 for TECFIDERA.

Gopal et al. Evidence of activation of the Nrf2 pathway in multiple sclerosis patients treated with delayed-release dimethyl fumarate in the Phase 3 DEFINE and CONFIRM studies. Mult Scler 23(14):1875-1883 (2017).

Gupta et al. Neurotherapeutic effects of novel HO-1 inhibitors in vitro and in a transgenic mouse model of Alzheimer's disease. J Neurochem 131:778-790 (2014).

Hamamura et al. Induction of heme oxygenase-1 by cobalt protoporphyrin enhances the antitumour effect of bortezomib in adult T-cell leukaemia cells. Br J Cancer 97:1099-1105 (2007).

Horig et al. From bench to clinic and back: Perspective on the 1st IQPC Translational Research conference. J Transl Med 2(1):44 (2004).

Kim et al. The novel Bach1 Inhibitor HPP971 uniquely activates Nrf2 and reduces disease severity in a mouse model of experimental autoimmune encephalomyelitis. Abstract submitted for presentation Sep. 11, 2014 at the Joint ACTRIMS-ECTRIMS Meeting in Boston, MA, Sep. 10-13, 2014.

Kim et al. The novel Bach1 Inhibitor HPP971 uniquely activates Nrf2 and reduces disease severity in a mouse model of experimental autoimmune encephalomyelitis. Poster presented Sep. 11, 2014 at the Joint ACTRIMS-ECTRIMS Meeting in Boston, MA, Sep. 10-13, 2014.

Kostura et al. Novel Bach1 Modulators Increase HMOX1 and Suppress Hypertension in the Goldblatt Model of Renovascular Hypertension, American Heart Association Scientific Sessions, Nov. 2013, Poster.

Li et al. Sulforaphane ameliorates the development of experimental autoimmune encephalomyelitis by antagonizing oxidative stress and Th17-related inflammation in mice. Exp. Neurol 250:239-249 (2013).

Linker et al. Fumaric acid esters exert neuroprotective effects in neuroinflammation via activation of the Nrf2 antioxidant pathway. Brain 134:678-692 (2011).

MacLeod et al. Characterization of cancer chemopreventive Nrf2-dependent gene battery in human keratinocytes: demonstration that the Keap1-Nrf2 pathway, and not the Bach1-Nrf2 pathway,controls cytoprotection against electrophiles as well as recox-cycling compounds. Carcinogenesis 30(9):1571 (2009).

Malhotra et al., Global mapping of binding sites for Nrf2 identifies novel targets in cell survival response through ChIP-Seq profiling and network analysis. Nucleic Acids Res 38:5718-5734 (2010).

Medicines in Development for Cancer. Pharmaceutical Research and Manufacturers of America, Washington, DC, pp. 1-103 (2009).

Medicines in Development for Neurological Disorders. Pharmaceutical Research and Manufacturers of America, pp. 1-43 (2008).

MX/a/2012/009628 Office Action dated Aug. 5, 2014.

Pareek et al. Triterpenoid modulation of IL-17 and Nrf-2 expression ameliorates neurainflammation and promotes remyelination in autoimmune encephalomyelitis. Sci Rep. 1:201 (2011).

PCT/US2011/024311 International Search Report and Written Opinion dated Apr. 11, 2011.

(56) References Cited

OTHER PUBLICATIONS

Satoh et al. Nrf2/ARE-mediated antioxidant actions of pro-electrophilic drugs. Free Rad Bio Med. 66:45-57 (2014).
Saw et al. Synergistic anti-inflammatory effects of low doses of curcumin in combination with polyunsaturated fatty acids: Docosahexaenoic acid or eicosapentaenoic acid. Biochem Pharmacol 79:421-430 (2010).
Schafer et al. Failure is an option: learning from unsuccessful proof-of-concept trials. Drug Discov Today 13(21-22):913-916 (2008).
Suzuki et al. Toward clinical application of the Keap1-Nrf2 pathway. Trends Pharmacol Sci 34:340-346 (2013).
Attucks et al. Non-electrophilic activation of the Nrf2 pathway ameliorated experimental Nonalcoholic Steatohepatitis Poster Presented at the EASL Non-Alcoholic Fatty Liver Disease (NAFLD) Summit. Sep. 2019.
Belcher et al. Control of Oxidative Stress and Inflammation in Sickle Cell Disease with the Nrf2 Activator Dimethyl Fumarate. Antioxid Redox Signal 26(14):748-762 (2014).
Boosalis et al. Novel Inducers of Fetal Globin Identified through High Throughput Screening (HTS) Are Active In Vivo in Anemic Baboons and Transgenic Mice. PLoS One 10(12):e0144660 (2015).
Cuadrado et al. Therapeutic targeting of Nrf2 and Keap1 partnership in chronic diseases. Nat Rev Drug Discov 18:295-317 (2019).
Estepp et al. A clinically meaningful fetal hemoglobin threshold for children with sickle cell anemia during hydroxyurea therapy. Am J Hematol. 92(12):1333-1339 (2017).

Fertrin et al. Sickle Cell Imaging Flow Cytometry Assay (SIFCA). Methods Mol Biol. 1389:279-292 (2016).
Florczyk-Soluch et al. Various roles of heme oxygenase-1 in response of bone marrow macrophages to RANKL and in the early stage of osteoclastogenesis. Sci Rep 8(1):10797 (2018).
Frenette et al. Sickle cell disease: old discoveries, new concepts, and future promise. J Clin Invest. 117:850-858 (2007).
Kanzaki et al. The Keap1/Nrf2 protein axis plays a role in osteoclast differentiation by regulating intracellular reactive oxygen species signaling. J Biol Chem 288(32):23009-20 (2013).
PCT/US2019/064372 International Search Report and Written Opinion dated Mar. 12, 2020.
PCT/US2020/013616 International Search Report and Written Opinion dated May 15, 2020.
Van Beers et al. Imaging flow cytometry for automated detection of hypoxia-induced erythrocyte shape change in sickle cell disease. Am J Hematol. 89(6):598-603 (2014).
Wada et al. Bach1 Inhibition Suppresses Osteoclastogenesis via Reduction of the Signaling via Reactive Oxygen Species by Reinforced Antioxidation. Front. Cell. Dev Biol. 8:740 (2020).
Yavropoulou et al. Osteoclastogenesis-current knowledge and future perspective. J. Musculoskelet Neuronal Interact 8:204-216 (2008).
Zein et al. Identification of fetal hemoglobin-inducing agents using the human leukemia KU812 cell line. Exp Biol Med (Maywood) 235:1385-94 (2010).
Hamda et al. A common molecular signature of patients with sickle cell disease revealed by microarray meta-analysis and a genome-wide association study. PLoS One 13(7):e0199461 (2018).
Wang et al. Paradoxical protection from atherosclerosis and thrombosis in a mouse model of sickle cell disease. Br J Haematol 162(1):120-129 (2013).

SUBSTITUTED FUSED IMIDAZOLE DERIVATIVES, PHARMACEUTICAL COMPOSITIONS, AND METHODS OF USE THEREOF

BACKGROUND OF THE INVENTION

Field of the Invention

The present invention provides substituted fused imidazole derivatives that may be useful for control of an inflammatory response. In addition, the invention provides compounds, pharmaceutical compositions, and methods of use thereof for controlling the activity or the amount, or both the activity and the amount, of heme-oxygenase in a mammalian subject.

Description of Related Art

Cellular damage due to oxidative stress caused by reactive oxygen species (ROS) has been demonstrated to be involved in the onset or progression of various chronic diseases, e.g., cardiovascular disease, including arteriosclerosis and hypertension; diabetes and diabetic related complications, such as glomerular nephropathy; cerebral nerve degenerative diseases, such as Alzheimer's disease, Parkinson's disease, ALS (amyotrophic lateral sclerosis) and multiple sclerosis; asthma, chronic obstructive pulmonary disease, skin diseases, eye diseases, and cancer. Enhancing the capability of protecting from oxidative stress may be useful in one or more of preventing these diseases, delaying their progress, or delaying their onset. Further, with the varied etiology associated with this diverse set of diseases, a general strategy to mitigate oxidative stress would be beneficial.

The basic biochemistry of a cell generates ROS, including superoxide anions, hydroxyl anions, nitric oxide, peroxynitrite, and hydrogen peroxide. All of these products serve critical cellular signaling needs, but also have deleterious effects if overproduced or left unchecked. Many disease conditions induce persistent levels of ROS that are associated with the establishment of chronic pathophysiologic changes seen within a variety of tissues. These complications, in and of themselves, may be the primary drivers of disease morbidity and mortality.

Under normal physiological conditions, production of ROS are counterbalanced by a well defined and conserved set of cellular pathways that respond to, limit, and repair the damage due to ROS. This adaptive set of genes, called the phase II system, encodes enzymes that degrade ROS directly (e.g., superoxide dismutase and catalase) as well as increase levels of a cell's endogenous antioxidant molecules, including glutathione and bilirubin. Examples of known phase II enzymes include glutathione S-transferase (GST), NAD(P)H:quinone oxidoreductase 1 (NQO1), glutamyl-cysteinyl ligase (GCL), heme oxygenase 1 (HMOX1), and thioredoxin reductase 1 (TXNRD1). A common sequence called antioxidant responsive element (ARE) is present in a promoter of each gene of these phase enzymes, and its expression is induced by the transcription factor Nrf2 (NF-E2 related factor 2).

Of the phase II enzyme system, HMOX1 has been found to be a key component. The role of HMOX1 is to metabolize heme into bilirubin, carbon monoxide, and free iron, as a first step of a two-step process to catabolize heme. The first, and rate-limiting reaction, is the production of biliverdin and carbon monoxide from heme by HMOX1. The second step is the production of bilirubin from biliverdin by biliverdin reductase. Both bilirubin and carbon monoxide have been shown to scavenge ROS and to have potent anti-oxidant and anti-inflammatory activity. Agents that induce production of HMOX1 have been shown to have beneficial activity in models of diabetes, cardiovascular disease, hypertension, and pulmonary function.

HMOX1 is found in the liver, kidneys, spleen, and skin, of humans and has also been localized to specific cell types, notably fibroblasts and macrophages. HMOX1 exists in at least three isoforms, one constitutive and the other two inducible. Heme, heavy metal ions (e.g., tin, gold, platinum, and mercury), transition metal ions (e.g., iron, cobalt, chromium, and nickel), and electrophiles (e.g., natural products such as sulforaphane and curcumin) can all induce production of HMOX1. Induction of HMOX1 and other phase II genes are controlled by a number of transcription factors that are responsive to heavy metals, heme, and electrophiles. The transcription factors Nrf2, Bach1, and Maf are particularly important in this process. In addition, there are cofactors and regulatory molecules that are important in regulating Phase II gene induction. These include Keap1, an adapter molecule targeting Nrf2 for ubiquitination, and two mitochondrial proteins, DJ-1 and frataxin (FXN) that serve to augment Nrf2 activation in the presence of electrophiles. HMOX1 is also induced as part of a generalized stress response to stimuli such as thermal shock, oxidative stress and cytokines such as interleukin-1 (IL-1), tumor necrosis factor and IL-6. The stress response is seen as beneficial in that it results in protection of vulnerable cell enzymes from inactivation.

BRIEF SUMMARY OF INVENTION

The invention provides substituted fused imidazole derivatives of Formula (I):

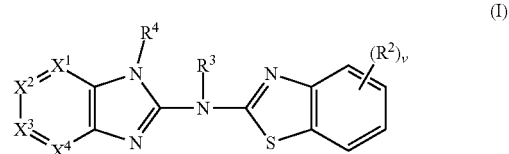

(I)

or pharmaceutically acceptable salts thereof, as described herein. In another aspect, the invention provides pharmaceutical compositions which may reduce oxidative stress and/or inflammation. In another aspect, the present invention provides methods for the preparation of compounds of Formula (I) and pharmaceutically acceptable salts thereof. In another aspect, the invention provides pharmaceutical compositions comprising a compound of Formula (I) or a pharmaceutically acceptable salt thereof. In another aspect, the present invention provides methods of treatment comprising: administering to a subject a compound of Formula (I) or a pharmaceutically acceptable salt thereof.

The compounds of Formula (I) and pharmaceutically acceptable salts thereof are useful as agents that induce the production of and/or increase the activity of HMOX1, and thus may be useful to treat various chronic diseases that are associated, at least in part, with oxidative stress including, but not limited to: cardiovascular disease including arteriosclerosis and hypertension; diabetes and diabetic related complications such as glomerular nephropathy; cerebral nerve degenerative diseases such as Alzheimers disease, Parkinson's disease, ALS (amyotrophic lateral sclerosis) and multiple sclerosis; asthma; chronic obstructive pulmonary disease; skin diseases; eye diseases including macular degeneration, cataracts, light retinopathy, and retinopathy of prematurity; and cancer.

BRIEF DESCRIPTION OF DRAWINGS

Not applicable

DETAILED DESCRIPTION

The following definitions are intended to clarify the terms defined. If a particular term used herein is not specifically defined, the term should not be considered to be indefinite. Rather, such undefined terms are to be construed in accordance with their plain and ordinary meaning to a person of ordinary skill in the field(s) of art to which the invention is directed.

As used herein the term "alkyl" refers to a straight or branched chain saturated hydrocarbon having one to ten carbon atoms, which may be optionally substituted, as herein further described, with multiple degrees of substitution being allowed. Examples of "alkyl" as used herein include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl.

The number carbon atoms in an alkyl group is represented by the phrase "$C_{x-y}$ alkyl," which refers to an alkyl group, as herein defined, containing from x to y, inclusive, carbon atoms. Thus, $C_{1-6}$ alkyl represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl.

As used herein, the term "alkylene" refers to a straight or branched chain divalent saturated hydrocarbon radical having from one to ten carbon atoms, which may be optionally substituted as herein further described, with multiple degrees of substitution being allowed.

Examples of "alkylene" as used herein include, but are not limited to, methylene, ethylene, n-propylene, 1-methylethylene, 2-methylethylene, dimethylmethylene, n-butylene, 1-methyl-n-propylene, and 2-methyl-n-propylene.

The number of carbon atoms in an alkylene group is represented by the phrase "$C_{x-y}$ alkylene," which refers to an alkylene group, as herein defined, containing from x to y, inclusive, carbon atoms. Similar terminology will apply for other terms and ranges as well. Thus, $C_{1-4}$ alkylene represents an alkylene chain having from 1 to 4 carbons atoms, and, for example, includes, but is not limited to, methylene, ethylene, n-propylene, 1-methylethylene, 2-methylethylene, dimethylmethylene, n-butylene, 1-methyl-n-propylene, and 2-methyl-n-propylene.

As used herein, the term "cycloalkyl" refers to a saturated, three- to ten-membered, cyclic hydrocarbon ring, which may be optionally substituted as herein further described, with multiple degrees of substitution being allowed. Such "cycloalkyl" groups are monocyclic, bicyclic, or tricyclic. Examples of "cycloalkyl" groups as used herein include, but are not limited to, cyclopropyl, cyclobutyl, cyclopentyl, cyclohexyl, cycloheptyl, norbornyl, and adamantyl.

The number of carbon atoms in a cycloalkyl group will be represented by the phrase "$C_{x-y}$ cycloalkyl," which refers to a cycloalkyl group, as herein defined, containing from x to y, inclusive, carbon atoms. Similar terminology will apply for other terms and ranges as well. Thus, $C_{3-10}$ cycloalkyl represents a cycloalkyl group having from 3 to 10 carbons as described above, and for example, includes, but is not limited to, cyclopropyl, cyclobutyl, cyclopentyl, cyclohexyl, cycloheptyl, norbornyl, and adamantyl.

As used herein, the term "heterocycle" or "heterocyclyl" refers to an optionally substituted mono- or polycyclic saturated ring system containing one or more heteroatoms. Such "hetercycle" or "heterocyclyl" groups may be optionally substituted as herein further described, with multiple degrees of substitution being allowed. The term "heterocycle" or "heterocyclyl," as used herein, does not include ring systems that contain one or more aromatic rings. Examples of heteroatoms include nitrogen, oxygen, or sulfur atoms, including N-oxides, sulfur oxides, and sulfur dioxides. Typically, the ring is three- to twelve-membered. Such rings may be optionally fused to one or more of another heterocyclic ring(s) or cycloalkyl ring(s). Examples of "heterocyclic" groups, as used herein include, but are not limited to, tetrahydrofuran, tetrahydropyran, 1,4-dioxane, 1,3-dioxane, piperidine, pyrrolidine, morpholine, tetrahydrothiopyran, and tetrahydrothiophene, where attachment can occur at any point on said rings, as long as attachment is chemically feasible. Thus, for example, "morpholine" refers to morpholin-2-yl, morpholin-3-yl, and morpholin-4-yl.

As used herein, when "heterocycle" or "heterocyclyl" is recited as a possible substituent, the "heterocycle" or "heterocyclyl" group can attach through either a carbon atom or any heteroatom, to the extent that attachment at that point is chemically feasible. For example, "heterocyclyl" would include pyrrolidin-1-yl, pyrrolidin-2-yl, and pyrrolidin-3-yl. When "heterocycle" or "heterocyclyl" groups contain a nitrogen atom in the ring, attachment through the nitrogen atom can alternatively be indicated by using an "-ino" suffix with the ring name. For example, pyrrolidino refers to pyrrolidin-1-yl.

As used herein the term "halogen" refers to fluorine, chlorine, bromine, or iodine.

As used herein, the term "oxo" refers to a >C=O substituent. When an oxo substituent occurs on an otherwise saturated group, such as with an oxo-substituted cycloalkyl group (e.g., 3-oxo-cyclobutyl), the substituted group is still intended to be a saturated group.

As used herein the term "haloalkyl" refers to an alkyl group, as defined herein, that is substituted with at least one halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include groups such as —$CF_3$, —$CH_2$—$CF_3$, and —$CF_2Cl$.

As used herein, the term "aryl" refers to a six- to ten-membered cyclic, aromatic hydrocarbon, which may be optionally substituted as herein further described, with multiple degrees of substitution being allowed. Examples of "aryl" groups as used herein include, but are not limited to, phenyl and naphthyl. As used herein, the term "aryl" also includes ring systems in which a phenyl or naphthyl group is optionally fused with one to three non-aromatic, saturated or unsaturated, carbocyclic rings. For example, "aryl" would include ring systems such as indene, with attachment possible to either the aromatic or the non-aromatic ring(s).

As used herein, the term "heteroaryl" refers to a five- to fourteen-membered optionally substituted mono- or polycyclic ring system, which contains at least one aromatic ring and also contains one or more heteroatoms. Such "heteroaryl" groups may be optionally substituted as herein further described, with multiple degrees of substitution being allowed. In a polycyclic "heteroaryl" group that contains at least one aromatic ring and at least one non-aromatic ring, the aromatic ring(s) need not contain a heteroatom. Thus, for example, "heteroaryl," as used herein, would include indolinyl. Further, the point of attachment may be to any ring within the ring system without regard to whether the ring containing the attachment point is aromatic or contains a heteroatom. Thus, for example, "heteroaryl," as used herein, would include indolin-1-yl, indolin-3-yl, and indolin-5-yl. Examples of heteroatoms include nitrogen, oxygen, or sulfur atoms, including N-oxides, sulfur oxides, and sulfur dioxides, where feasible. Examples of "heteraryl" groups, as used herein include, but are not limited to, furyl, thiophenyl, pyrrolyl, oxazolyl, thiazolyl, imidazolyl, isoxazolyl, isothiazolyl, 1,2,4-triazolyl, pyrazolyl, pyridinyl, pyridazinyl, pyrimidinyl, indolyl, isoindolyl, benzo[b]thiophenyl, benzimidazolyl, benzothiazolyl, pteridinyl, and phenazinyl, where attachment can occur at any point on said rings, as long as attachment is chemically feasible. Thus, for example, "thiazolyl" refers to thiazol-2-yl, thiazol-4-yl, and thiaz-5-yl.

As used herein, when "heteroaryl" is recited as a possible substituent, the "heteroaryl" group can attach through either a carbon atom or any heteroatom, to the extent that attachment at that point is chemically feasible.

As used herein, the term "heterocyclylene" refers to an optionally substituted bivalent heterocyclyl group (as defined above). The points of attachment may be to the same ring atom or to different ring atoms, as long as attachment is chemically feasible. The two points of attachment can each independently be to either a carbon atom or a heteroatom, as long as attachment is chemically feasible. Examples include, but are not limited to,

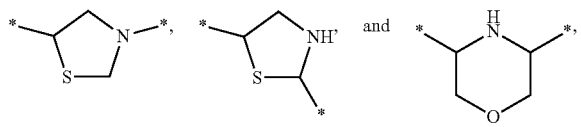

where the asterisks indicate points of attachment.

As used herein, the term "heteroarylene" refers to an optionally substituted bivalent heteroaryl group (as defined above). The points of attachment may be to the same ring atom or to different ring atoms, as long as attachment is chemically feasible. The two points of attachment can each independently be to either a carbon atom or a heteroatom, as long as attachment is chemically feasible. Examples include, but are not limited to,

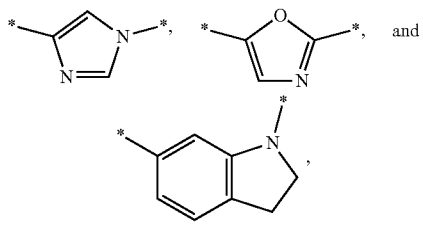

where the asterisks indicate points of attachment.

Various other chemical terms or abbreviations have their standard meaning to the skilled artisan. For example: "hydroxyl" refers to —OH; "methoxy" refers to —OCH$_3$; "cyano" refers to —CN; "amino" refers to —NH$_2$; "methylamino" refers to —NHCH$_3$; "sulfonyl" refers to —SO$_2$—; "carbonyl" refers to —C(O)—; "carboxy" or "carboxyl" refer to —CO$_2$H, and the like. Further, when a name recited multiple moieties, e.g., "methylaminocarbonyl-methyl", an earlier-recited moiety is further from the point of attachment than any later-recited moieties. Thus, a term such as "methylaminocarbonylmethyl" refers to —CH$_2$—C(O)—NH—CH$_3$.

As used herein, the term "substituted" refers to substitution of one or more hydrogens of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient. As used herein, the phrases "substituted with one or more . . . " or "substituted one or more times . . . " refer to a number of substituents that equals from one to the maximum number of substituents possible based on the number of available bonding sites, provided that the above conditions of stability and chemical feasibility are met.

As used herein, the various functional groups represented will be understood to have a point of attachment at the functional group having the hyphen or dash (-) or an asterisk (*). In other words, in the case of —CH$_2$CH$_2$CH$_3$, it will be understood that the point of attachment is the CH$_2$ group at the far left. If a group is recited without an asterisk or a dash, then the attachment point is indicated by the plain and ordinary meaning of the recited group.

When any variable occurs more than one time in any one constituent (e.g., R$^d$), or multiple constituents, its definition on each occurrence is independent of its definition on every other occurrence.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

As used herein, the term "optionally" means that the subsequently described event(s) may or may not occur.

As used herein, "administer" or "administering" means to introduce, such as to introduce to a subject a compound or composition. The term is not limited to any specific mode of delivery, and can include, for example, intravenous delivery, transdermal delivery, oral delivery, nasal delivery, and rectal delivery. Furthermore, depending on the mode of delivery, the administering can be carried out by various individuals, including, for example, a health-care professional (e.g., physician, nurse, etc.), a pharmacist, or the subject (i.e., self-administration).

As used herein, "treat" or "treating" or "treatment" can refer to one or more of delaying the progress of a disease or condition, controlling a disease or condition, delaying the onset of a disease or condition, ameliorating one or more symptoms characteristic of a disease or condition, or delaying the recurrence of a disease or condition or characteristic symptoms thereof, depending on the nature of a disease or condition and its characteristic symptoms.

As used herein, "subject" refers to any mammal such as, but not limited to, humans. In one embodiment, the subject is a human. In another embodiment, the subject is a human who exhibits one or more symptoms characteristic of a disease or condition. The term "subject" does not require one to have any particular status with respect to any hospital, clinic, or research facility (e.g., as an admitted patient, a study participant, or the like).

As used herein, the term "compound" includes free acids, free bases, and any salts thereof. Thus, phrases such as "compound of embodiment 1" or "compound of claim 1" refer to any free acids, free bases, and any salts thereof that are encompassed by embodiment 1 or claim 1, respectively.

As used herein, the term "pharmaceutical composition" is used to denote a composition that may be administered to a mammalian host, e.g., orally, topically, parenterally, by inhalation spray, or rectally, in unit dosage formulations containing conventional non-toxic carriers, diluents, adjuvants, vehicles, and the like. The term "parenteral" includes subcutaneous injections As used herein, "substituted fused imidazole derivatives" refers to compounds encompassed by Formula (I), described below.

Aspects of the present invention include substituted fused imidazole derivatives, pharmaceutical compositions comprising substituted fused imidazole derivatives, method of making substituted fused imidazole derivatives, methods of making pharmaceutical compositions comprising substituted fused imidazole derivatives, and methods of use thereof.

In a first aspect, the present invention provides substituted fused imidazole derivatives that induce production of HMOX1 and thus may be useful to treat various diseases associated at least in part with oxidative stress.

In a first embodiment (i.e., embodiment 1), the invention provides a compound of Formula (I) or a pharmaceutically acceptable salt thereof:

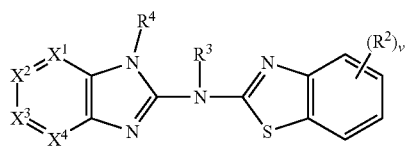

(I)

wherein
one of $X^1$, $X^2$, $X^3$, and $X^4$ is

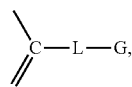

and the remaining members of $X^1$, $X^2$, $X^3$, and $X^4$ are independently N or

G is hydrogen, —$C_{1-8}$ alkyl, —$C_{3-10}$ cycloalkyl, —$C_{1-6}$ alkylene-$C_{3-10}$ cycloalkyl, heterocyclyl, —$C_{1-6}$ alkylene-$C_{3-10}$ heterocyclyl, phenyl, heteroaryl, or $NR^h R^k$, where the alkyl, alkylene, cycloalkyl, heterocyclyl, phenyl, and heteroaryl groups are optionally substituted one or more times with substituents independently selected from $R^c$;
or G is —$CH_2Y^3$, —$CH_2CH_2Y^3$, —$CH_2CH_2CH_2Y^3$, —$CH(CH_3)CH_2Y^3$, —$CH_2CH(Y^3)CH_3$, —$CH(Y^3)CH_3$, —$CH_2C(Y^3)(CH_3)_2$, —$C(Y^3)(CH_3)_2$, or

where $Y^3$ is cyclopropyl, —$CF_3$, —$OCF_3$, —$OCH_3$, —$OCH_2CH_3$, —F, —Cl, —OH, —$O(CH_2)_2$—OH, —$O(CH_2)_2$—F, —$SCH_3$, —$S(O)_2$—$CH_3$, —$SCH_2CH_3$, —$S(O)_2CH_2CH_3$, —NH—$CH_3$, —NH—$CH_2CH_3$, —$N(CH_3)_2$, tetrahydropyran-4-yl, tetrahydrofuran-2-yl, morpholin-2-yl, morpholin-4-yl, piperidin-1-yl, 4-hydroxy-piperidin-1-yl, 3-hydroxy-piperidin-1-yl, —NH—C(O)—$CH_3$, —NH—C(O)—$CH_2CH_3$, tetrahydrofuran-2-yl-methyloxy, or —C(O)—$Y^4$, where $Y^4$ is —OH, —$OCH_3$, —$OCH_2CH_3$, —$OC(CH_3)_3$, —$NH_2$, —NH—$CH_3$, —NH—$CH_2CH_3$, —$N(CH_3)_2$, —$N(CH_2CH_3)_2$, morpholin-4-yl, 4-methyl-piperazin-1-yl, pyrrolidin-1-yl, or piperazin-1-yl;

L is —$CH_2$—$C(O)N(R^6)$—, —$C(O)N(R^6)$—, —C(O)—O—, —$SO_2$—, —C(O)—, heteroarylene optionally substituted one or more times with substituents independently selected from $R^x$, or heterocyclylene optionally substituted one or more times with substituents independently selected from $R^x$; or the group -L-G is -cyano;

$R^1$ is hydrogen, $R^a$, phenyl, or heteroaryl, where the phenyl and heteroaryl groups are optionally substituted one or more times with substituents independently selected from $R^x$;

$R^2$ is $R^b$;

$R^3$ is hydrogen, —$C_{1-6}$ alkyl, or —$C_{1-6}$ alkylene-$C_{3-10}$ cycloalkyl, where the alkyl, alkylene, and cycloalkyl groups are optionally substituted one or more times with substituents independently selected from $R^z$;

$R^4$ is —$C_{1-6}$ alkyl or —$C_{1-6}$ alkylene-$C_{3-10}$ cycloalkyl, where the alkyl, alkylene, and cycloalkyl groups are optionally substituted one or more times with substituents independently selected from $R^y$;

$R^6$ is hydrogen, —$C_{1-6}$ alkyl, —$C_{1-6}$ alkylene-$C_{3-10}$ cycloalkyl, where the alkyl, alkylene, and cycloalkyl groups are optionally substituted one or more times with substituents independently selected from $R^x$;

$R^a$ is
 a) -halogen,
 b) —$C_{1-6}$ alkyl,
 c) —$C_{3-10}$ cycloalkyl,
 d) -heterocyclyl,
 e) -cyano,
 f) —$CF_3$,
 g) —$OCF_3$,
 h) —O—$R^d$,
 i) —$S(O)_w$—$R^d$,
 j) —$S(O)_2O$—$R^d$,
 k) —$NR^d R^e$,
 l) —C(O)—$R^d$,
 m) —C(O)—O—$R^d$,
 n) —OC(O)—$R^d$,
 o) —$C(O)NR^d R^e$,
 p) —C(O)-heterocyclyl,
 q) —$NR^d C(O)R^e$,
 r) —$OC(O)NR^d R^e$,
 s) —$NR^d C(O)OR^d$, or
 t) —$NR^d C(O)NR^d R^e$,
 where the alkyl, cycloalkyl, and heterocyclyl groups are optionally substituted one or more times with substituents independently selected from $R^y$;

$R^b$ is
 a) -halogen,
 b) —$C_{1-6}$ alkyl, c) —$C_{3-10}$ cycloalkyl,
d) -heterocyclyl,
e) -phenyl,
f) -heteroaryl,
g) -cyano,
h) —$CF_3$,
i) —$OCF_3$,
j) —O—$R^f$,
k) —$S(O)_w$—$R^f$,
l) —$S(O)_2O$—$R^f$,
m) —$NR^fR^g$,
n) —$C(O)$—$R^f$,
o) —$C(O)$—O—$R^f$,
p) —$OC(O)$—$R^f$,
q) —$C(O)NR^fR^g$,
r) —$C(O)$-heterocyclyl,
s) —$NR^f C(O)R^g$,
t) —$OC(O) NR^f R^g$,
u) —$NR^f C(O)OR^f$, or
v) —$NR^f C(O)NR^f R^g$,
  where the alkyl, cycloalkyl, heterocyclyl, phenyl, and heteroaryl groups are optionally substituted one or more times with substituents independently selected from $R^z$ $R^c$ is
a) -halogen,
b) —$C_{1-6}$ alkyl,
c) —$C_{3-10}$ cycloalkyl,
d) -heterocyclyl,
e) -cyano,
f) —$CF_3$,
g) —$OCF_3$,
h) —O—$R^h$,
i) —$S(O)_w$—$R^h$,
j) —$S(O)_2O$—$R^h$,
k) —$NR^hR^k$,
l) —$C(O)$—$R^h$,
m) —$C(O)$—O—$R^h$,
n) —$OC(O)$—$R^h$,
o) —$C(O)NR^h R^k$,
p) —$C(O)$-heterocyclyl,
q) —$NR^h C(O)R^k$,
r) —$OC(O)NR^h R^k$,
s) —$NR^h C(O)OR^k$,
t) —$NR^h C(O)NR^h R^k$,
u) —$NR^h S(O)_w R^k$,
v) -phenyl,
w) -heteroaryl, or
x) —O—($C_{1-4}$ alkylene)-O—($C_{1-4}$ alkylene)-N($R^h$)C(O)—$OR^k$,
  where the alkylene, alkyl, cycloalkyl, heterocyclyl, phenyl, and heteroaryl groups are optionally substituted one or more times with substituents independently selected from $R^x$;

$R^d$ and $R^e$ are independently hydrogen, $C_{1-6}$ alkyl, or $C_{3-10}$ cycloalkyl, where the alkyl and cycloalkyl groups are optionally substituted one or more times with substituents independently selected from $R^y$; or, if $R^d$ and $R^e$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, and azepano, where each ring is optionally substituted one or more times with substituents independently selected from $R^y$;

$R^f$ and $R^g$ are independently hydrogen, $C_{1-6}$ alkyl, $C_{3-10}$ cycloalkyl, phenyl, or heteroaryl, where the alkyl, cycloalkyl, phenyl, and heteroaryl groups are optionally substituted one or more times with substituents independently selected from $R^z$; or, if $R^f$ and $R^g$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, and azepano, where each ring is optionally substituted one or more times with substituents independently selected from $R^z$;

$R^h$ and $R^k$ are independently hydrogen, $C_{1-6}$ alkyl, $C_{3-10}$ cycloalkyl, heterocyclyl, phenyl, or heteroaryl, where the alkyl, cycloalkyl, heterocyclyl, phenyl, and heteroaryl groups are optionally substituted one or more times with substituents independently selected from $R^x$; or, if $R^h$ and $R^k$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, and azepano, where each ring is optionally substituted one or more times with substituents independently selected from $R^x$;

$R^y$ is
a) -halogen,
b) —$NH_2$,
c) -cyano,
d) -carboxy,
e) -hydroxy,
f) -thiol,
g) —$CF_3$,
h) —$OCF_3$,
i) —$C(O)$—$NH_2$,
j) —$S(O)_2$—$NH_2$,
k) oxo,
l) —$C_{1-6}$ alkyl, optionally substituted one or more times with substitutents selected independently from the group consisting of halogen, —OH, —O—$C_1$-alkyl, —$NH_2$, —NH—$C_{1-6}$ alkyl, and —N($C_{1-6}$ alkyl)$_2$,
m) -heterocyclyl optionally substituted one or more times with one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
n) —$C_{3-10}$ cycloalkyl optionally substituted one or more times with one or more times with substitutents selected independently from the group consisting of halogen, —OH, —O—$C_{1-6}$ alkyl, —$NH_2$, —NH—$C_{1-6}$ alkyl, and —N($C_{1-6}$ alkyl)$_2$,
o) —O—$C_{1-6}$ alkyl optionally substituted one or more times with one or more times with substitutents selected independently from the group consisting of halogen, —OH, —O—$C_{1-6}$ alkyl, —$NH_2$, —NH—$C_{1-6}$ alkyl, and —N($C_{1-6}$ alkyl)$_2$,
p) —O—$C_{3-10}$ cycloalkyl optionally substituted one or more times with one or more times with substitutents selected independently from the group consisting of halogen, —OH, —O—$C_{1-6}$ alkyl, —$NH_2$, —NH—$C_{1-6}$ alkyl, and —N($C_{1-6}$ alkyl)$_2$,
q) —NH—$C_{1-6}$ alkyl optionally substituted one or more times with one or more times with substitutents selected independently from the group consisting of halogen, —OH, —O—$C_{1-6}$ alkyl, —$NH_2$, —NH—$C_{1-6}$ alkyl, and —N($C_{1-6}$ alkyl)$_2$, r) —N($C_{1-6}$ alkyl)$_2$ optionally substituted one or more times with one or more times with substitutents selected independently from the group consisting of halogen, —OH, —O—$C_{1-6}$ alkyl, —NH$_2$, —NH—$C_{1-6}$ alkyl, and —N($C_{1-6}$ alkyl)$_2$,
s) —C(O)—$C_{1-6}$ alkyl, optionally substituted one or more times with one or more times with substitutents selected independently from the group consisting of halogen, —OH, —O—$C_{1-6}$ alkyl, —NH$_2$, —NH—$C_{1-6}$ alkyl, and —N($C_{1-6}$ alkyl)$_2$,
t) —C(O)—O—$C_{1-6}$ alkyl, optionally substituted one or more times one or more times with substitutents selected independently from the group consisting of halogen, —OH, —O—$C_{1-6}$ alkyl, —NH$_2$, —NH—$C_{1-6}$ alkyl, and —N($C_{1-6}$ alkyl)$_2$,
u) —S—$C_{1-6}$ alkyl, optionally substituted one or more times with one or more times with substitutents selected independently from the group consisting of halogen, —OH, —O—$C_{1-6}$ alkyl, —NH$_2$, —NH—$C_{1-6}$ alkyl, and —N($C_{1-6}$ alkyl)$_2$,
v) —S(O)$_2$—$C_{1-6}$ alkyl, optionally substituted one or more times one or more times with substitutents selected independently from the group consisting of halogen, —OH, —O—$C_{1-6}$ alkyl, —NH$_2$, —NH—$C_{1-6}$ alkyl, and —N($C_{1-6}$ alkyl)$_2$,
w) —C(O)—NH—$C_{1-}$ alkyl, optionally substituted one or more times one or more times with substitutents selected independently from the group consisting of halogen, —OH, —O—$C_{1-6}$ alkyl, —NH$_2$, —NH—$C_{1-6}$ alkyl, and —N($C_{1-6}$ alkyl)$_2$,
x) —C(O)—N($C_{1-6}$ alkyl)$_2$, optionally substituted one or more times one or more times with substitutents selected independently from the group consisting of halogen, —OH, —O—$C_{1-6}$ alkyl, —NH$_2$, —NH—$C_{1-6}$ alkyl, and —N($C_{1-6}$ alkyl)$_2$,
y) —S(O)$_2$—NH—$C_{1-6}$alkyl, optionally substituted one or more times one or more times with substitutents selected independently from the group consisting of halogen, —OH, —O—$C_{1-6}$ alkyl, —NH$_2$, —NH—$C_{1-6}$ alkyl, and —N($C_{1-6}$ alkyl)$_2$,
z) —S(O)$_2$—N($C_{1-6}$ alkyl)$_2$, optionally substituted one or more times one or more times with substitutents selected independently from the group consisting of halogen, —OH, —O—$C_{1-6}$ alkyl, —NH$_2$, —NH—$C_{1-6}$ alkyl, and —N($C_{1-6}$ alkyl)$_2$,
aa) —NH—C(O)—$C_{1-6}$ alkyl, optionally substituted one or more times one or more times with substitutents selected independently from the group consisting of halogen, —OH, —O—$C_{1-6}$ alkyl, —NH$_2$, —NH—$C_{1-6}$ alkyl, and —N($C_{1-6}$ alkyl)$_2$, or
bb) —NH—S(O)$_2$—$C_{1-6}$ alkyl, optionally substituted one or more times one or more times with substitutents selected independently from the group consisting of halogen, —OH, —O—$C_{1-6}$ alkyl, —NH$_2$, —NH—$C_{1-6}$ alkyl, and —N($C_{1-6}$ alkyl)$_2$;

$R^x$ is
a) —$R^y$
b) -phenyl, optionally substituted one or more times with one or more times with substitutents selected independently from the group consisting of halogen, —OH, —O—$C_{1-6}$ alkyl, —NH$_2$, —NH—$C_{1-6}$ alkyl, and —N($C_{1-6}$ alkyl)$_2$,
c) -heteroaryl, optionally substituted one or more times with one or more times with substitutents selected independently from the group consisting of halogen, —OH, —O—$C_{1-6}$ alkyl, —NH$_2$, —NH—$C_{1-6}$ alkyl, and —N($C_{1-6}$ alkyl)$_2$,
d) —O-phenyl,
e) —O-heteroaryl,
f) —C(O)-phenyl,
g) —C(O)-heteroaryl,
h) —C(O)—O-phenyl, or
i) —C(O)—O-heteroaryl;

$R^z$ is
a) —$R^y$
b) -phenyl,
c) -heteroaryl;
d) —O-phenyl,
e) —O-heteroaryl,
f) —C(O)-phenyl,
g) —C(O)-heteroaryl,
h) —C(O)—O-phenyl, or
i) —C(O)—O-heteroaryl;

v is an integer from 0 to 4, and
w is an integer from 0 to 2.

Embodiment 2: A compound according to embodiment 1 wherein
G is hydrogen, —$C_{1-8}$ alkyl, —$C_{3-10}$ cycloalkyl, —$C_{1-6}$ alkylene-$C_{3-10}$ cycloalkyl, heterocyclyl, phenyl, heteroaryl, or $NR^h R^k$, where the alkyl, alkylene, cycloalkyl, heterocyclyl, phenyl, and heteroaryl groups are optionally substituted one or more times with substituents independently selected from $R^c$; or G is —$CH_2Y^3$, —$CH_2CH_2Y^3$, —$CH_2CH_2CH_2Y^3$, —$CH(CH_3)CH_2Y^3$, —$CH_2CH(Y^3)CH_3$, —$CH(Y^3)CH_3$, —$CH_2C(Y^3)(CH_3)_2$, —$C(Y^3)(CH_3)_2$, or

where $Y^3$ is -cyclopropyl, —$CF_3$, —$OCF_3$, —$OCH_3$, —$OCH_2CH_3$, —F, —Cl, —OH, —O($CH_2$)$_2$—OH, —O($CH_2$)$_2$—F, —$SCH_3$, —$S(O)_2$—$CH_3$, —$SCH_2CH_3$, —$S(O)_2CH_2CH_3$, —NH—$CH_3$, —NH—$CH_2CH_3$, —N($CH_3$)$_2$, tetrahydropyran-4-yl, tetrahydrofuran-2-yl, morpholin-2-yl, morpholin-4-yl, piperidin-1-yl, 4-hydroxy-piperidin-1-yl, 3-hydroxy-piperidin-1-yl, —NH—C(O)—$CH_3$, —NH—C(O)—$CH_2CH_3$, tetrahydrofuran-2-yl-methyloxy, or —C(O)—$Y^4$, where $Y^4$ is —OH, —$OCH_3$, —$OCH_2CH_3$, —OC($CH_3$)$_3$, —NH$_2$, —NH—$CH_3$, —NH—$CH_2CH_3$, —N($CH_3$)$_2$, —N($CH_2CH_3$)$_2$, morpholin-4-yl, 4-methyl-piperazin-1-yl, pyrrolidin-1-yl, or piperazin-1-yl;

$R^c$ is
a) -halogen,
b) —$C_{1-6}$ alkyl,
c) —$C_{3-10}$ cycloalkyl,
d) -heterocyclyl,
e) -cyano,
f) —$CF_3$,
g) —$OCF_3$,
h) —O—$R^h$,
i) —S(O)$_w$—$R^h$,
j) —S(O)$_2$O—$R^h$,
k) —$NR^hR^k$,
l) —C(O)—$R^h$,
m) —C(O)—O—$R^h$,
n) —OC(O)—$R^h$,
o) —C(O)$NR^h R^k$,
p) —C(O)-heterocyclyl,
q) —$NR^h$ C(O)$R^k$,
r) —OC(O)$NR^h R^k$,
s) —$NR^h$ C(O)O$R^k$, t) —NR$^h$C(O)NR$^h$R$^k$,
u) -phenyl,
v) -heteroaryl, or
w) —O—(C$_{1-4}$ alkylene)-O—(C$_{1-4}$ alkylene)-N(R$^h$)C(O)—OR$^k$, where the alkylene, alkyl, cycloalkyl, heterocyclyl, phenyl, and heteroaryl groups are optionally substituted one or more times with substituents independently selected from R$^x$;

R$^h$ and R$^k$ are independently hydrogen, C$_{1-6}$ alkyl, C$_{3-10}$ cycloalkyl, phenyl, or heteroaryl, where the alkyl, cycloalkyl, phenyl, and heteroaryl groups are optionally substituted one or more times with substituents independently selected from R$^x$; or, if R$^h$ and R$^k$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, and azepano, where each ring is optionally substituted one or more times with substituents independently selected from R$^x$; and R$^y$ is
a) -halogen,
b) —NH$_2$,
c) -cyano,
d) -carboxy,
e) —C$_{1-6}$ alkyl, optionally substituted one or more times with halogen,
f) -heterocyclyl, optionally substituted one or more times with halogen,
g) —C$_{3-10}$ cycloalkyl, optionally substituted one or more times with halogen,
h) —O—C$_{1-6}$ alkyl, optionally substituted one or more times with halogen,
i) —O—C$_{3-10}$ cycloalkyl, optionally substituted one or more times with halogen,
j) -hydroxy,
k) -thiol,
l) —CF$_3$,
m) —OCF$_3$,
n) —C(O)—C$_{1-6}$ alkyl, optionally substituted one or more times with halogen,
o) —C(O)—O—C$_{1-6}$ alkyl, optionally substituted one or more times with halogen,
p) —S—C$_{1-6}$ alkyl, optionally substituted one or more times with halogen, or
q) —S(O)$_2$—C$_{1-6}$ alkyl, optionally substituted one or more times with halogen.

Embodiment 3: A compound according to embodiment 2, wherein
R$^3$ is hydrogen.

Embodiment 4: A compound according to embodiment 2, wherein
R$^3$ is methyl.

Embodiment 5: A compound according to embodiment 2, wherein
R$^3$ is ethyl.

Embodiment 6: A compound according to embodiment 2, wherein
R$^3$ is isopropyl.

Embodiment 7: A compound according to any one of embodiments 2 to 6, wherein
X$^3$ is

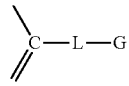

and X$^1$, X$^2$, and X$^4$ are

Embodiment 8: A compound according to any one of embodiments 2 to 6, wherein
X$^3$ is

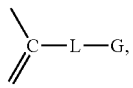

and X$^1$ and X$^4$ are

and X$^2$ is N.

Embodiment 9: A compound according to any one of embodiments 2 to 6, wherein
X$^3$ is

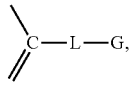

and X$^1$ and X$^2$ are

and X$^4$ is N.

Embodiment 10: A compound according to any one of embodiments 2 to 6, wherein
X is

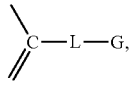

and X$^2$ and X$^4$ are

and X$^1$ is N.

Embodiment 11: A compound according to any one of embodiments 2 to 6, wherein
X² is

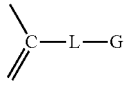

and X¹, X³, and X⁴ are

Embodiment 12: A compound according to any one of embodiments 2 to 6, wherein
X² is

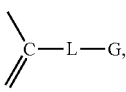

and X¹ and X⁴ are

and X³ is N.

Embodiment 13: A compound according to any one of embodiments 2 to 6, wherein
X² is

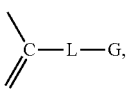

and X¹ and X³ are

and X⁴ is N.

Embodiment 14: A compound according to any one of embodiments 2 to 6, wherein
X² is

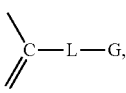

and X³ and X⁴ are

and X¹ is N.

Embodiment 15: A compound according to any one of embodiments 2 to 6, wherein
X² is

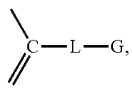

and two of X¹, X³, and X⁴ are N.

Embodiment 16: A compound according to any one of embodiments 2 to 6, wherein
X³ is

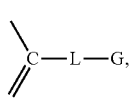

and two of X¹, X², and X⁴ are N.

Embodiment 17: A compound according to any one of embodiments 2 to 6, wherein
X² is

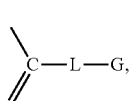

and X¹, X³, and X⁴ are N.

Embodiment 18: A compound according to any one of embodiments 2 to 6, wherein
X³ is

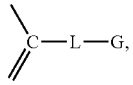

and X¹, X², and X⁴ are N.

Embodiment 19: A compound according to any one of embodiments 2 to 18, wherein
v is an integer from 0 to 2.

Embodiment 20: A compound according to any one of embodiments 2 to 18, wherein
v is 0 or 1.

Embodiment 21: A compound according to any one of embodiments 2 to 18, wherein
v is 1.

Embodiment 22: A compound according to any one of embodiments 2 to 18, wherein
v is 1, and R² is attached at either the 5-position or the 6-position of the benzothiazole ring.

Embodiment 23: A compound according to any one of embodiments 2 to 18, wherein
v is 1, and R² is attached at the 6-position of the benzothiazole ring.

Embodiment 24: A compound according to any one of embodiments 2 to 18, wherein
v is 2, and one $R^2$ is attached at the 6-position of the benzothiazole ring.

Embodiment 25: A compound according to any one of embodiments 2 to 18, wherein
v is 2, and $R^2$ is attached at the 5-position and the 6-position of the benzothiazole ring.

Embodiment 26: A compound according to any one of embodiments 2 to 25, wherein
$R^2$ is -halogen, —$C_{1-6}$ alkyl, —$CF_3$, —$OCF_3$, —O—$R^f$, or —S(O)$_w$—$R^f$, where the alkyl group is optionally substituted one or more times with substituents independently selected from $R^z$.

Embodiment 27: A compound according to any one of embodiments 2 to 25, wherein
$R^2$ is -halogen, -methyl, —$CF_3$, —$OCF_3$, —$SCF_3$, —O-heteroaryl, or —S(O)$_2$—$CH_3$.

Embodiment 28: A compound according to any one of embodiments 2 to 25, wherein
$R^2$ is selected from —Cl, —F, —$CF_3$, and —$OCF_3$.

Embodiment 29: A compound according to any one of embodiments 2 to 25, wherein
$R^2$ is —$OCF_3$.

Embodiment 30: A compound according to any one of embodiments 2 to 25, wherein
$R^2$ is —$CF_3$.

Embodiment 31: A compound according to any one of embodiments 2 to 25, wherein
$R^2$ is —F.

Embodiment 32: A compound according to any one of embodiments 2 to 25, wherein
$R^2$ is —$C_1$.

Embodiment 33: A compound according to any one of embodiments 2 to 32, wherein
$R^4$ is -methyl, -ethyl, -n-propyl, -isopropyl, -n-butyl, -sec-butyl, -isobutyl, -tert-butyl, —(CH$_2$)$_{1-2}$—OCH$_3$, —(CH$_2$)$_{1-2}$—F, —(CH$_2$)$_{1-2}$—Cl, —(CH$_2$)$_{1-2}$—OCF$_3$, —(CH$_2$)$_{1-2}$—NH$_2$, —(CH$_2$)$_{1-2}$—CN, —(CH$_2$)$_{1-2}$—OH, —(CH$_2$)$_{1-2}$—CF$_3$, —(CH$_2$)$_{1-2}$—CO$_2$H, —(CH$_2$)$_{1-2}$—SH, —(CH$_2$)$_{1-2}$—SCH$_3$, —(CH$_2$)$_{1-2}$—S(O)$_2$CH$_3$, —(CH$_2$)$_{1-2}$—OCH$_2$CH$_3$, —(CH$_2$)$_{1-2}$—SCH$_2$CH$_3$, —(CH$_2$)$_{1-2}$—S(O)$_2$CH$_2$CH$_3$, —(CH$_2$)$_{1-2}$—NH—CH$_3$, or —(CH$_2$)$_{1-2}$—N(CH$_3$)$_2$.

Embodiment 34: A compound according to any one of embodiments 2 to 33, wherein
$R^4$ is -methyl, -ethyl, -isopropyl, -isobutyl, —CH$_2$CH$_2$—OCH$_3$, —CH$_2$CH$_2$—F, or —CH$_2$CH$_2$—NH$_2$.

Embodiment 35: A compound according to any one of embodiments 2 to 34, wherein
$R^4$ is -methyl, -ethyl, -isopropyl, or -isobutyl.

Embodiment 36: A compound according to any one of embodiments 2 to 35, wherein
$R^4$ is -methyl.

Embodiment 37: A compound according to any one of embodiments 2 to 35, wherein
$R^4$ is -ethyl.

Embodiment 38: A compound according to any one of embodiments 2 to 33, wherein
$R^4$ is —(CH$_2$)$_2$—OCH$_3$, —(CH$_2$)$_2$—F, —(CH$_2$)$_2$—Cl, —(CH$_2$)$_2$—OCF$_3$, —(CH$_2$)$_2$—NH$_2$, —(CH$_2$)$_2$—CN, —(CH$_2$)$_2$—OH, —(CH$_2$)$_2$—CF$_3$, —(CH$_2$)$_2$—CO$_2$H, —(CH$_2$)$_2$—SH, —(CH$_2$)$_2$—SCH$_3$, or —(CH$_2$)$_2$—S(O)$_2$ CH$_3$.

Embodiment 39: A compound according to any one of embodiments 2 to 38, wherein
$R^1$ is independently selected from hydrogen, —OCH$_3$, —F, —Cl, —NH$_2$, -cyano, —OH, —CF$_3$, —OCF$_3$, —SH, —S—$C_{1-6}$ alkyl, —S(O)$_2$—$C_{1-6}$ alkyl, —CO$_2$H, —NH—$C_{1-6}$ alkyl, —N($C_{1-6}$ alkyl)$_2$, and —NH—$C_{1-6}$ alkyl.

Embodiment 40: A compound according to any one of embodiments 2 to 38, wherein
$R^1$ is independently selected from —OCH$_3$, —F, —CF$_3$, —OCF$_3$, —N(CH$_3$)$_2$, —N(CH$_2$CH$_3$)$_2$, and —N(CH$_3$)(CH$_2$CH$_3$).

Embodiment 41: A compound according to any one of embodiments 2 to 38, wherein
$R^1$ is independently selected from hydrogen, —OCH$_3$, and —F.

Embodiment 42: A compound according to any one of embodiments 2 to 38, wherein
$R^1$ is hydrogen.

Embodiment 43: A compound according to any one of embodiments 2 to 41, wherein
no more than one $R^1$ substituent is not hydrogen.

Embodiment 44: A compound according to any one of embodiments 2 to 43, wherein
G is hydrogen, —$C_{1-8}$ alkyl, —$C_{3-10}$ cycloalkyl, —$C_{1-6}$ alkylene-$C_{3-8}$ cycloalkyl, heterocyclyl, or $NR^h R^k$, where the alkyl, alkylene, cycloalkyl, and heterocyclyl groups are optionally substituted one or more times with substituents independently selected from $R^c$; or G is —CH$_2$Y$^3$, —CH$_2$CH$_2$Y$^3$, —CH$_2$CH$_2$CH$_2$Y$^3$, —CH(CH$_3$)CH$_2$Y$^3$, —CH$_2$CH(Y$^3$)CH$_3$, —CH(Y$^3$)CH$_3$, —CH$_2$C(Y$^3$)(CH$_3$)$_2$, —C(Y$^3$)(CH$_3$)$_2$, or

where Y$^3$ is -cyclopropyl, —CF$_3$, —OCF$_3$, —OCH$_3$, —OCH$_2$CH$_3$, —F, —Cl, —OH, —O(CH$_2$)$_2$—OH, —O(CH$_2$)$_2$—F, —SCH$_3$, —S(O)$_2$—CH$_3$, —SCH$_2$CH$_3$, —S(O)$_2$CH$_2$CH$_3$, —NH—CH$_3$, —NH—CH$_2$CH$_3$, —N(CH$_3$)$_2$, tetrahydropyran-4-yl, tetrahydrofuran-2-yl, morpholin-2-yl, morpholin-4-yl, piperidin-1-yl, 4-hydroxy-piperidin-1-yl, 3-hydroxy-piperidin-1-yl, —NH—C(O)—CH$_3$, —NH—C(O)—CH$_2$CH$_3$, tetrahydrofuran-2-yl-methyloxy, or —C(O)—Y$^4$, where Y$^4$ is —OH, —OCH$_3$, —OCH$_2$CH$_3$, —OC(CH$_3$)$_3$, —NH$_2$, —NH—CH$_3$, —NH—CH$_2$CH$_3$, —N(CH$_3$)$_2$, —N(CH$_2$CH$_3$)$_2$, morpholin-4-yl, 4-methyl-piperazin-1-yl, pyrrolidin-1-yl, or piperazin-1-yl;
L is —CH$_2$—C(O)N(R$^6$)—, —C(O)N(R$^6$)—, —C(O)—O—, —SO$_2$—, —C(O)—, or heterocyclylene optionally substituted one or more times with substituents independently selected from $R^x$; or the group -L-G is -cyano;
$R^1$ is hydrogen or $R^a$;
$R^c$ is
a) -halogen,
b) —$C_{1-6}$ alkyl,
c) —$C_{3-10}$ cycloalkyl,
d) -heterocyclyl,
e) -cyano,
f) —CF$_3$,
g) —OCF$_3$,
h) —O—$R^h$,
i) —S(O)$_w$—$R^h$,
j) —S(O)$_2$O—$R^h$,
k) —NR$^h$R$^k$,
l) —C(O)—$R^h$, m) —C(O)—O—$R^h$,
n) —OC(O)—$R^h$,
o) —C(O)N$R^h$ $R^k$,
p) —C(O)-heterocyclyl,
q) —N$R^h$ C(O)$R^k$,
r) —OC(O)N$R^h$ $R^k$,
s) —N$R^h$ C(O)O$R^k$,
t) —N$R^h$ C(O)N$R^h$ $R^k$, or
u) —O—($C_{1-4}$ alkylene)-O—($C_{1-4}$ alkylene)-N($R^h$)C(O)—O$R^k$,
where the alkylene, alkyl, cycloalkyl, and heterocyclyl groups are optionally substituted one or more times with substituents independently selected from $R^x$;
$R^h$ and $R^k$ are independently hydrogen, $C_{1-6}$ alkyl, or $C_{3-10}$ cycloalkyl, where the alkyl, and cycloalkyl groups are optionally substituted one or more times with substituents independently selected from $R^x$; or, if $R^h$ and $R^k$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, and azepano, where each ring is optionally substituted one or more times with substituents independently selected from $R^x$; and
$R^x$ is $R^y$.

Embodiment 45: A compound according to any one of embodiments 2 to 44, wherein
L-G is not -cyano.

Embodiment 46: A compound according to any one of embodiments 2 to 45, wherein
L-G is —C(O)N$R^h$ $R^k$.

Embodiment 47: A compound according to any one of embodiments 2 to 45, wherein
L is —C(O)N($R^6$)— or —C(O)—O—.

Embodiment 48: A compound according to any one of embodiments 2 to 45, wherein
L is —C(O)N($R^6$)—.

Embodiment 49: A compound according to any one of embodiments 2 to 45, wherein
L is not —$CH_2$—C(O)N($R^6$)—.

Embodiment 50: A compound according to any one of embodiments 2 to 45, wherein
L is —C(O)—O—.

Embodiment 51: A compound according to any one of embodiments 2 to 45, wherein
L is —C(O)—.

Embodiment 52: A compound according to any one of embodiments 2 to 45, wherein
L is —S(O)$_2$—.

Embodiment 53: A compound according to any one of embodiments 2 to 43, wherein
L is heteroarylene optionally substituted one or more times with substituents independently selected from $R^x$.

Embodiment 54: A compound according to any one of embodiments 2 to 53, wherein
$R^6$ is hydrogen.

Embodiment 55: A compound according to any one of embodiments 2 to 53, wherein
$R^6$ is hydrogen or -methyl.

Embodiment 56: A compound according to any one of embodiments 2 to 55, wherein
G is hydrogen, —$C_{1-8}$ alkyl, —$C_{3-10}$ cycloalkyl, or —$C_{1-6}$ alkylene-$C_{3-8}$ cycloalkyl, where the alkyl, cycloalkyl, and alkylene groups are optionally substituted one or more times with substituents independently selected from $R^x$.

Embodiment 57: A compound according to any one of embodiments 2 to 55, wherein
G is —H, -methyl, -ethyl, -n-propyl, -isopropyl, -isobutyl, —$CH_2Y^3$, —$CH_2CH_2Y^3$, —$CH_2CH_2CH_2Y^3$, —CH($CH_3$)$CH_2Y^3$, —$CH_2$CH($Y^3$)$CH_3$, —CH($Y^3$)$CH_3$, —$CH_2$C($Y^3$)($CH_3$)$_2$, or —C($Y^3$)($CH_3$)$_2$, where $Y^3$ is -cyclopropyl, —$CF_3$, —$OCF_3$, —$OCH_3$, —$OCH_2CH_3$, —F, —OH, —O($CH_2$)$_2$—OH, —O($CH_2$)$_2$—F, —$SCH_3$, —S(O)$_2$—$CH_3$, —$SCH_2CH_3$, —S(O)$_2$$CH_2CH_3$, —NH—$CH_3$, —NH—$CH_2CH_3$, —N($CH_3$)$_2$, —NH—C(O)—$CH_3$, —NH—C(O)—$CH_2CH_3$, or C(O)—$Y^4$, where $Y^4$ is —OH, —$OCH_3$, —$OCH_2CH_3$, —OC($CH_3$)$_3$, —$NH_2$, —NH—$CH_3$, —NH—$CH_2CH_3$, —N($CH_3$)$_2$, or —N($CH_2CH_3$)$_2$.

Embodiment 58: A compound according to any one of embodiments 2 to 55, wherein
G is -methyl, -ethyl, -n-propyl, -isopropyl, or -isobutyl, where each is optionally substituted one or more times with substituents independently selected from —$CF_3$, —$OCF_3$, —$OCH_3$, —$OCH_2CH_3$, —F, —OH, —O($CH_2$)$_2$—OH, —O($CH_2$)$_2$—F, —$SCH_3$, —$SCH_2CH_3$, —NH—$CH_3$, —NH—$CH_2CH_3$, and —N($CH_3$)$_2$.

Embodiment 59: A compound according to any one of embodiments 2 to 55, wherein
G is H.

Embodiment 60: A compound according to any one of embodiments 2 to 55, wherein
G is $C_{1-8}$ alkyl optionally substituted one or more times with halogen.

Embodiment 61: A compound according to any one of embodiments 2 to 55, wherein
G is $C_{3-10}$ cycloalkyl optionally substituted one or more times with halogen.

Embodiment 62: A compound according to any one of embodiments 2 to 55, wherein
G is heterocyclyl optionally substituted one or more times with halogen.

Embodiment 63: A compound according to any one of embodiments 2 to 55, wherein
G is —$C_{1-6}$ alkylene-$C_{3-10}$ cycloalkyl optionally substituted one or more times with halogen.

Embodiment 64: A compound according to any one of embodiments 2 to 55, wherein
G is N$R^h$ $R^k$.

Embodiment 65: A compound according to any one of embodiments 2 to 55, wherein
G is —$CH_2$—$R^c$.

Embodiment 66: A compound according to any one of embodiments 2 to 55, wherein
G is —$CH_2CH_2$—$R^c$.

Embodiment 67: A compound according to any one of embodiments 2 to 55, wherein
G is —$CH_2CH_2CH_2$—$R^c$.

Embodiment 68: A compound according to any one of embodiments 2 to 55, wherein
G is —CH($CH_3$)$CH_2R^c$.

Embodiment 69: A compound according to any one of embodiments 2 to 55, wherein
G is —$CH_2$CH($R^c$)$CH_3$.

Embodiment 70: A compound according to any one of embodiments 2 to 55, wherein
G is —CH($R^c$)$CH_3$.

Embodiment 71: A compound according to any one of embodiments 2 to 55, wherein
G is —CH$_2$C(R$^c$)(CH$_3$)$_2$.

Embodiment 72: A compound according to any one of embodiments 2 to 55, wherein
G is —C(R$^c$)(CH$_3$)$_2$.

Embodiment 73: A compound according to any one of embodiments 2 to 55, wherein
G is imidazol-2-yl, thiazol-2yl, oxazol-2-yl, pyrazol1-yl, furan-2yl, thiophen-2-yl, pyrrol-1-yl, 1H-1,2,4-triazolyl-3-yl, 5-methyl-1H-1,2,4-triazolyl-3-yl, —(CH2)$_{1-3}$-(imidazol-2-yl), —(CH$_2$)$_{1-3}$-(thiazol-2yl), —(CH$_2$)$_{1-3}$-(oxazol-2-yl), —(CH$_2$)$_{1-3}$-(pyrazol1-yl), —(CH$_2$)$_{1-3}$-(furan-2yl), —(CH$_2$)$_{1-3}$-(thiophen-2-yl), —(CH$_2$)$_{1-3}$-(pyrrol-1-yl), —(CH$_2$)$_{1-3}$-(1H-1,2,4-triazolyl-3-yl), or —(CH$_2$)$_{1-3}$-(5-methyl-1H-1,2,4-triazolyl-3-yl).

Embodiment 74: A compound according to any one of embodiments 2 to 73, wherein
the compound is in its free (non-salted) form.

Embodiment 75: A compound according to any one of embodiments 2 to 73, wherein
the compound is in the form of a pharmaceutically acceptable salt.

Embodiment 76: A compound according to any one of embodiments 1 to 75, wherein
any "heterocyclyl" group present in the compound is selected from the group consisting of: azetidin-1-yl, azetidin-2-yl, azetidin-3-yl, pyrrolidin-1-yl, pyrrolidin-2-yl, pyrrolidin-3-yl, tetrahydrofuran-2-yl, tetrahydrofuran-3-yl, tetrahydrothiophen-2-yl, tetrahydrothiophen-3-yl, pyrazolidin-1-yl, pyrazolidin-3-yl, pyrazolidin-4-yl, imidazolidin-1-yl, imidazolidin-2-yl, imidazolidin-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolodin-5-yl, isothiazolidin-2-yl, isothiazolidin-3-yl, isothiazolidin-4-yl, isothiazolodin-5-yl, 1,3-dioxolan-2-yl, 1,3-dioxolan-4-yl, 1,3-oxathiolan-2-yl, 1,3-oxathiolane-4-yl, 1,3-oxathiolan-5-yl, 1,2-dithiolan-3-yl, 1,2-dithiolan-4-yl, 1,3-dithiolan-2-yl, 1,3-dithiolan-4-yl, piperidin-1-yl, piperidin-2-yl, piperidin-3-yl, piperidin-4-yl, tetrahydropyran-2-yl, tetrahydropyran-3-yl, tetrahydropyran-4-yl, thian-2-yl, thian-3-yl, thian-4-yl, piperazin-1-yl, piperazin-2-yl, morpholin-2-yl, morpholin-3-yl, morpholin-4-yl, thiomorpholin-2-yl, thiomorpholin-3-yl, thiomorpholin-4-yl, 1,4-dioxan-2-yl, 1,3-dioxan-2-yl, 1,3-dioxan-4-yl, 1,3-dioxan-5-yl, 1,4-dithian-2-yl, 1,3-dithian-2-yl, 1,3-dithian-4-yl, 1,3-dithian-5-yl, 1,2-dithian-3-yl, 1,2-dithian-4-yl, azepan-1-yl, azepan-2-yl, azepan-3-yl, and azepan-4-yl, where each of these named rings may optionally be substituted one or more times with substituents independently selected from halogen, —NH$_2$, cyano, carboxy, C$_{1-4}$alkyl, C$_{3-10}$ cycloalkyl, hydroxyl, thiol, —CF$_3$, —OCF$_3$, —O—C$_{1-4}$alkyl, —NH—C$_{1-4}$ alkyl, —N(C$_{1-4}$ alkyl)$_2$, —S—C$_{1-4}$ alkyl, —S(O)$_2$—C$_{1-4}$ alkyl, —C(O)—C$_{1-4}$ alkyl, —C(O)O—C$_{1-4}$ alkyl, —C(O)NH$_2$, —C(O)NH—C$_{1-4}$ alkyl, and —C(O)N(C$_{1-4}$ alkyl)$_2$, and where any nitrogen atom in any of these named rings may optionally be oxidized when chemically feasible, and where any sulfur atom in any of these named rings may optionally be oxidized once or twice when chemically feasible.

Embodiment 77: A compound according to any one of embodiments 1 to 76, wherein
any "heteroaryl" group present in the compound is selected from the group consisting of: 1H-pyrrol-1-yl, 1H-pyrrol-2-yl, 1H-pyrrol-3-yl, furan-2-yl, furan-3-yl, thiophen-2-yl, thiophen-3-yl, 1H-imidazol-1-yl, 1H-imidazol-2-yl, 1H-imidazol-4-yl, 1H-imidazol-5-yl, 1H-pyrazol-1-yl, 1H-pyrazol-3-yl, 1H-pyrazol-4-yl, 1H-pyrazol-5-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, 1H-1,2,3-triazol-1-yl, 1H-1,2,3-triazol-4-yl, 1H-1,2,3-triazol-5-yl, 1H-1,2,4-triazol-1-yl, 1H-1,2,4-triazol-3-yl, 1H-1,2,4-triazol-5-yl, furazan-3-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1H-indol-1-yl, 1H-indol-2-yl, 1H-indol-3-yl, 2H-isoindol-1-yl, 2H-isoindol-2-yl, quinolin-2-yl, quinolin-3-yl, quinolin-4-yl, isoquinolin-1-yl, isoquinolin-3-yl, isoquinolin-4-yl, benzoxazol-2-yl, benzothiazol-2-yl, 1H-benzimidazol-1-yl, 1H-benzimidazol-2-yl, benzofuran-2-yl, benzofuran-3-yl, benzothiophen-2-yl, and benzothiophen-3-yl, where each of these named rings may optionally be substituted one or more times with substituents independently selected from halogen, —NH$_2$, cyano, carboxy, C$_{1-4}$alkyl, C$_{3-10}$ cycloalkyl, hydroxyl, thiol, —CF$_3$, —OCF$_3$, —O—C$_{1-4}$ alkyl, —NH—C$_{1-4}$ alkyl, —N(C$_{1-4}$ alkyl)$_2$, —S—C$_{1-4}$alkyl, —S(O)$_2$—C$_{1-4}$ alkyl, —C(O)—C$_{1-4}$alkyl, —C(O)O—C$_{1-4}$alkyl, —C(O)NH$_2$, —C(O)NH—C$_{1-4}$alkyl, —C(O)N(C$_{1-4}$alkyl)$_2$, and phenyl.

Embodiment 78: A compound according to any one of embodiments 1 to 77, wherein
any "heteroarylene" group present in the compound is selected from the group consisting of: 1H-pyrrol-2,5-diyl, furan-2,5-diyl, thiophen-2,5-diyl, 1H-imidazol-2,4-diyl, 1H-imidazol-2,5-diyl, oxazol-2,4-diyl, oxazol-2,5-diyl, thiazol-2,4-diyl, thiazol-2,5-diyl, 1H-1,2,4-triazol-3,5-diyl, and 2H-isoindol-1,3-diyl, where each of these named rings may optionally be substituted one or more times with substituents independently selected from halogen, —NH$_2$, cyano, carboxy, —C$_{1-4}$alkyl, —C$_{3-10}$ cycloalkyl, hydroxyl, thiol, —CF$_3$, —OCF$_3$, —O—C$_{1-4}$ alkyl, —NH—C$_{1-4}$ alkyl, —N(C$_{1-4}$ alkyl)$_2$, —S—C$_{1-4}$ alkyl, —S(O)$_2$—C$_{1-4}$ alkyl, —C(O)—C$_{1-4}$ alkyl, —C(O)O—C$_{1-4}$alkyl, —C(O)NH$_2$, —C(O)NH—C$_{1-4}$alkyl, —C(O)N(C$_{1-4}$alkyl)$_2$, and phenyl.

Embodiment 79: A compound according to embodiment 1.

Embodiment 80: A compound according to embodiment 79, wherein
R$^3$ is hydrogen.

Embodiment 81: A compound according to embodiment 79, wherein
R$^3$ is methyl.

Embodiment 82: A compound according to embodiment 79, wherein
R$^3$ is ethyl.

Embodiment 83: A compound according to embodiment 79, wherein
R$^3$ is isopropyl.

Embodiment 84: A compound according to any one of embodiments 79 to 83, wherein
X$^3$ is

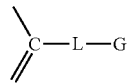

and $X^1$, $X^2$, and $X^4$ are

Embodiment 85: A compound according to any one of embodiments 79 to 83, wherein
$X^3$ is

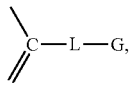

and $X^1$ and $X^4$ are

and $X^2$ is N.

Embodiment 86: A compound according to any one of embodiments 79 to 83, wherein
$X^3$ is

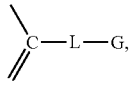

and $X^1$ and $X^2$ are

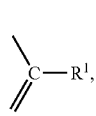

and $X^4$ is N.

Embodiment 87: A compound according to any one of embodiments 79 to 83, wherein
$X^3$ is

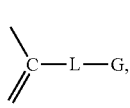

and $X^2$ and $X^4$ are

and $X^1$ is N.

Embodiment 88: A compound according to any one of embodiments 79 to 83, wherein
$X^2$ is

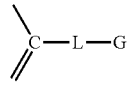

and $X^1$, $X^3$, and $X^4$ are

Embodiment 89: A compound according to any one of embodiments 79 to 83, wherein
$X^2$ is

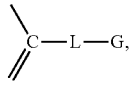

and $X^1$ and $X^4$ are

and $X^3$ is N.

Embodiment 90: A compound according to any one of embodiments 79 to 83, wherein
$X^2$ is

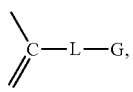

and $X^1$ and $X^3$ are

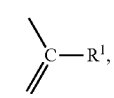

and $X^4$ is N.

Embodiment 91: A compound according to any one of embodiments 79 to 83, wherein
$X^2$ is

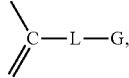

and $X^3$ and $X^4$ are

and $X^1$ is N.

Embodiment 92: A compound according to any one of embodiments 79 to 83, wherein
X² is

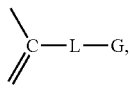

and two of X¹, X³, and X⁴ are N.

Embodiment 93: A compound according to any one of embodiments 79 to 83, wherein
X³ is

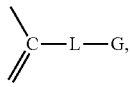

and two of X¹, X², and X⁴ are N.

Embodiment 94: A compound according to any one of embodiments 79 to 83, wherein
X² is

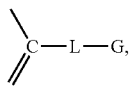

and X¹, X³, and X⁴ are N.

Embodiment 95: A compound according to any one of embodiments 79 to 83, wherein
X³ is

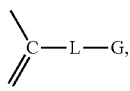

and X¹, X², and X⁴ are N.

Embodiment 96: A compound according to any one of embodiments 79 to 95, wherein
v is 0, 1 or 2.

Embodiment 97: A compound according to any one of embodiments 79 to 95, wherein
v is 1 or 2.

Embodiment 98: A compound according to any one of embodiments 79 to 95, wherein
v is 1.

Embodiment 99: A compound according to any one of embodiments 79 to 95, wherein
v is 1, and R² is attached at either the 5-position or the 6-position of the benzothiazole ring.

Embodiment 100: A compound according to any one of embodiments 79 to 95, wherein
v is 1, and R² is attached at the 6-position of the benzothiazole ring.

Embodiment 101: A compound according to any one of embodiments 79 to 95, wherein
v is 2, and one R² is attached at the 6-position of the benzothiazole ring.

Embodiment 102: A compound according to any one of embodiments 79 to 95, wherein
v is 2, and R² is attached at the 5-position and the 6-position of the benzothiazole ring.

Embodiment 103: A compound according to any one of embodiments 79 to 102, wherein
R² is -halogen, —$C_{1-6}$ alkyl, —$CF_3$, —$OCF_3$, —O—$R^f$, or —$S(O)_w$—$R^f$, where the alkyl group is optionally substituted one or more times with substituents independently selected from $R^z$.

Embodiment 104: A compound according to any one of embodiments 79 to 102, wherein
R² is -halogen, -methyl, ethyl, isopropyl, —$OCH_3$, —$OCH_2CH_3$, —$OCH(CH_3)_2$, —$CF_3$, —$OCF_3$, —$SCF_3$, —$S(O)_2$—$CH_3$, —O-phenyl, —O-(2-pyridyl), —O-(3-pyridyl), or —O-(4-pyridyl).

Embodiment 105: A compound according to any one of embodiments 79 to 102, wherein
R² is -halogen, -methyl, ethyl, isopropyl, —$OCH_3$, —$OCH_2CH_3$, —$OCH(CH_3)_2$, —$CF_3$, —$OCF_3$, —$SCF_3$, —$S(O)_2$—$CH_3$, or —O-(3-pyridyl).

Embodiment 106: A compound according to any one of embodiments 79 to 102, wherein
R² is —Cl, —F, —$CF_3$, or —$OCF_3$.

Embodiment 107: A compound according to any one of embodiments 79 to 102, wherein
R² is —$OCF_3$.

Embodiment 108: A compound according to any one of embodiments 79 to 102, wherein
R² is —$CF_3$.

Embodiment 109: A compound according to any one of embodiments 79 to 102, wherein
R² is —F.

Embodiment 110: A compound according to any one of embodiments 79 to 102, wherein
R² is —Cl.

Embodiment 111: A compound according to any one of embodiments 79 to 102, wherein
R² is —$SO_2CH_3$.

Embodiment 112: A compound according to any one of embodiments 79 to 102, wherein
R² is methyl, ethyl, or isopropyl.

Embodiment 113: A compound according to any one of embodiments 79 to 102, wherein
R² is methyl.

Embodiment 114: A compound according to any one of embodiments 79 to 102, wherein
R² is —$OCH_2CH_3$.

Embodiment 115: A compound according to any one of embodiments 79 to 102, wherein
R² is —O-phenyl.

Embodiment 116: A compound according to any one of embodiments 79 to 102, wherein
R² is —O-(2-pyridyl), —O-(3-pyridyl), or —O-(4-pyridyl).

Embodiment 117: A compound according to any one of embodiments 79 to 102, wherein
R² is —O-(3-pyridyl).

Embodiment 118: A compound according to any one of embodiments 79 to 117, wherein
R⁴ is -methyl, -ethyl, -n-propyl, -isopropyl, -n-butyl, -sec-butyl, -isobutyl, -tert-butyl, —$(CH_2)_{1-2}$—$OCH_3$, —$(CH_2)_{1-2}$—F, —$(CH_2)_{1-2}$—Cl, —$(CH_2)_{1-2}$—$OCF_3$, —$(CH_2)_{1-2}$—$NH_2$, —$(CH_2)_{1-2}$—CN, —$(CH_2)_{1-2}$—OH, —$(CH_2)_{1-2}$—$CF_3$, —$(CH_2)_{1-2}$—$CO_2H$, —$(CH_2)_{1-2}$—SH, —$(CH_2)_{1-2}$—$SCH_3$, —$(CH_2)_{1-2}$—$S(O)_2CH_3$, —$(CH_2)_{1-2}$—$OCH_2CH_3$, —$(CH_2)_{1-2}$—$SCH_2CH_3$, —$(CH_2)_{1-2}$—$S(O)_2CH_2CH_3$, —$(CH_2)_{1-2}$—NH—$CH_3$, or —$(CH_2)_{1-2}$—$N(CH_3)_2$.

Embodiment 119: A compound according to any one of embodiments 79 to 117, wherein
$R^4$ is -methyl, -ethyl, -isopropyl, -isobutyl, —$CH_2CH_2$—$OCH_3$, —$CH_2CH_2$—F, —$CH_2CH_2$—$NH_2$, or —$CH_2CH_2$—NH—$CH_3$.

Embodiment 120: A compound according to any one of embodiments 79 to 117, wherein
$R^4$ is -methyl, -ethyl, -isopropyl, or -isobutyl.

Embodiment 121: A compound according to any one of embodiments 79 to 117, wherein
$R^4$ is methyl.

Embodiment 122: A compound according to any one of embodiments 79 to 117, wherein
$R^4$ is -ethyl.

Embodiment 123: A compound according to any one of embodiments 79 to 117, wherein
$R^4$ is -isopropyl.

Embodiment 124: A compound according to any one of embodiments 79 to 117, wherein
$R^4$ is -isobutyl.

Embodiment 125: A compound according to any one of embodiments 79 to 117, wherein
$R^4$ is —$CH_2CH_2$—$OCH_3$.

Embodiment 126: A compound according to any one of embodiments 79 to 117, wherein
$R^4$ is —$CH_2CH_2$—F.

Embodiment 127: A compound according to any one of embodiments 79 to 117, wherein
$R^4$ is —$CH_2CH_2$—$NH_2$.

Embodiment 128: A compound according to any one of embodiments 79 to 117, wherein
$R^4$ is —$CH_2CH_2$—NH—$CH_3$.

Embodiment 129: A compound according to any one of embodiments 79 to 128, wherein
$R^1$ is independently hydrogen, —$OCH_3$, —F, —Cl, —$NH_2$, -cyano, —OH, —$CF_3$, —$OCF_3$, —SH, —S—$C_{1-6}$ alkyl, —$S(O)_2$—$C_{1-6}$ alkyl, —$CO_2H$, —NH—$C_{1-6}$ alkyl, —N($C_{1-6}$ alkyl)$_2$, or —NH—$C_{1-6}$ alkyl.

Embodiment 130: A compound according to any one of embodiments 79 to 128, wherein
$R^1$ is independently —$OCH_3$, —F, —$CF_3$, —$OCF_3$, —N($CH_3$)$_2$, —N($CH_2CH_3$)$_2$, or —N($CH_3$)($CH_2CH_3$).

Embodiment 131: A compound according to any one of embodiments 79 to 128, wherein
$R^1$ is independently hydrogen, —$OCH_3$, or —F.

Embodiment 132: A compound according to any one of embodiments 79 to 128, wherein
$R^1$ is hydrogen.

Embodiment 133: A compound according to any one of embodiments 79 to 128, wherein
$R^1$ is —F.

Embodiment 134: A compound according to any one of embodiments 79 to 128, wherein
$R^1$ is —$OCH_3$.

Embodiment 135: A compound according to any one of embodiments 79 to 128, wherein
$R^1$ is —N($CH_2CH_3$)$_2$.

Embodiment 136: A compound according to any one of embodiments 79 to 135, wherein
no more than one $R^1$ substituent is not hydrogen.

Embodiment 137: A compound according to any one of embodiments 79 to 136, wherein
G is hydrogen, —$C_{1-8}$ alkyl, —$C_{3-10}$ cycloalkyl, —$C_{1-6}$ alkylene-$C_{3-10}$ cycloalkyl, heterocyclyl, —$C_{1-6}$ alkylene-$C_{3-10}$ heterocyclyl, or $NR^h R^k$, where the alkyl, alkylene, cycloalkyl, and heterocyclyl groups are optionally substituted one or more times with substituents independently selected from $R^c$; or G is —$CH_2Y^3$, —$CH_2CH_2Y^3$, —$CH_2CH_2CH_2Y^3$, —$CH(CH_3)CH_2Y^3$, —$CH_2CH(Y^3)CH_3$, —$CH(Y^3)CH_3$, —$CH_2C(Y^3)(CH_3)_2$, —$C(Y^3)(CH_3)_2$, or

where $Y^3$ is cyclopropyl, —$CF_3$, —$OCF_3$, —$OCH_3$, —$OCH_2CH_3$, —F, —Cl, —OH, —$O(CH_2)_2$—OH, —$O(CH_2)_2$—F, —$SCH_3$, —$S(O)_2$—$CH_3$, —$SCH_2CH_3$, —$S(O)_2CH_2CH_3$, —NH—$CH_3$, —NH—$CH_2CH_3$, —N($CH_3$)$_2$, tetrahydropyran-4-yl, tetrahydrofuran-2-yl, morpholin-2-yl, morpholin-4-yl, piperidin-1-yl, 4-hydroxy-piperidin-1-yl, 3-hydroxy-piperidin-1-yl, —NH—C(O)—$CH_3$, —NH—C(O)—$CH_2CH_3$, tetrahydrofuran-2-yl-methyloxy, or —C(O)—$Y^4$, where $Y^4$ is —OH, —$OCH_3$, —$OCH_2CH_3$, —OC($CH_3$)$_3$, —$NH_2$, —NH—$CH_3$, —NH—$CH_2CH_3$, —N($CH_3$)$_2$, —N($CH_2CH_3$)$_2$, morpholin-4-yl, 4-methyl-piperazin-1-yl, pyrrolidin-1-yl, or piperazin-1-yl;

L is —$CH_2$—C(O)N($R^6$)—, —C(O)N($R^6$)—, —C(O)—O—, —$SO_2$—, —C(O)—, or heterocyclylene optionally substituted one or more times with substituents independently selected from $R^x$; or the group -L-G is -cyano;

$R^1$ is hydrogen or $R^a$;

$R^c$ is
a) -halogen,
b) —$C_{1-6}$ alkyl,
c) —$C_{3-10}$ cycloalkyl,
d) -heterocyclyl,
e) -cyano,
f) —$CF_3$,
g) —$OCF_3$,
h) —O—$R^h$,
i) —$S(O)_w$—$R^h$,
j) —$S(O)_2O$—$R^h$,
k) —$NR^hR^k$,
l) —C(O)—$R^h$,
m) —C(O)—O—$R^h$,
n) —OC(O)—$R^h$,
o) —C(O)$NR^h R^k$,
p) —C(O)-heterocyclyl,
q) —$NR^h$ C(O)$R^k$,
r) —OC(O)$NR^h R^k$,
s) —$NR^h$C(O)$OR^k$,
t) —$NR^h$C(O)$NR^h R^k$,
u) —$NR^h S(O)_w R^k$, or
v) —O—($C_{1-4}$ alkylene)-O—($C_{1-4}$ alkylene)-N($R^h$)C(O)—$OR^k$, where the alkylene, alkyl, cycloalkyl, and heterocyclyl groups are optionally substituted one or more times with substituents independently selected from $R^x$;

$R^h$ and $R^k$ independently are hydrogen, $C_{1-6}$ alkyl, $C_{3-10}$ cycloalkyl, or heterocyclyl, where the alkyl, cycloalkyl, and heterocyclyl groups are optionally substituted one or more times with substituents independently selected from $R^x$; or, if $R^h$ and $R^k$ are both attached to the same nitrogen atom, together with that nitrogen atom may optionally form a heterocyclic ring selected from azetidino, pyrrolidino, pyrazolidino, imidazolidino, oxazolidino, isoxazolidino, thiazolidino, isothiazolidino, piperidino, piperazino, morpholino, thiomorpholino, and azepano, where each ring is optionally substituted one or more times with substituents independently selected from $R^x$; and
$R^x$ is $R^y$.

Embodiment 137: A compound according to any one of embodiments 79 to 136, wherein
L-G is not -cyano.

Embodiment 138: A compound according to any one of embodiments 79 to 136, wherein
L is —C(O)N($R^6$)—.

Embodiment 139: A compound according to embodiment 138 wherein
$R^6$ is hydrogen.

Embodiment 140: A compound according to embodiment 138 wherein
$R^6$ is methyl.

Embodiment 141: A compound according to embodiment 140 wherein
G is —N(CH$_3$)$_2$.

Embodiment 142: A compound according to any one of embodiments 79 to 136, wherein
L-G is —C(O)N$R^h$ $R^k$.

Embodiment 143: A compound according to embodiment 142, wherein
N$R^h$ $R^k$ is pyrrolidino, piperidino, piperazino, 4-methyl-piperazino, or morpholino, where each of the foregoing is optionally substituted once with —(CH$_2$)$_{1-3}$—OH.

Embodiment 144: A compound according to embodiment 143, wherein
N$R^h$ $R^k$ is pyrrolidino, 4-(2-hydroxyethyl)-piperazino, or 4-(3-hydroxypropyl)-piperidino.

Embodiment 145: A compound according to embodiment 142, wherein
N$R^h$ $R^k$ is N[(CH$_2$)$_2$—OH]$_2$.

Embodiment 146: A compound according to any one of embodiments 79 to 137, wherein
L is not —CH$_2$—C(O)N($R^6$)—.

Embodiment 147: A compound according to any one of embodiments 79 to 146, wherein
L is not heterocyclylene.

Embodiment 148: A compound according to any one of embodiments 79 to 136, wherein
L is —S(O)$_2$—.

Embodiment 149: A compound according to embodiment 148, wherein
G is methyl or —CF$_3$.

Embodiment 150: A compound according to any one of embodiments 79 to 136, wherein
L is heteroarylene optionally substituted one or more times with substituents independently selected from $R^x$.

Embodiment 151: A compound according to embodiment 150, wherein
L-G is imidazol-2-yl, 1,2,4-triazol-3-yl, or 5-methyl-1,2,4-triazol-3-yl.

Embodiment 152: A compound according to any one of embodiments 79 to 136, wherein
L is —C(O)—O—.

Embodiment 153: A compound according to embodiment 152, wherein
G is hydrogen, or —C$_{1-8}$ alkyl, where the alkyl group is optionally substituted one or more times with substituents independently selected from $R^c$.

Embodiment 154: A compound according to embodiment 153, wherein
G is methyl or ethyl.

Embodiment 155: A compound according to embodiment 153, wherein
G is hydrogen.

Embodiment 156: A compound according to any one of embodiments 79 to 139, wherein
G is —C$_{1-8}$ alkyl, —C$_{3-10}$ cycloalkyl, —C$_{1-6}$ alkylene-C$_{3-10}$ cycloalkyl, heterocyclyl, or —C$_{1-6}$ alkylene-C$_{3-10}$ heterocyclyl, where the alkyl, alkylene, cycloalkyl, and heterocyclyl groups are optionally substituted one or more times with substituents independently selected from $R^c$.

Embodiment 157: A compound according to embodiment 156, wherein
G is —C$_{1-8}$ alkyl optionally substituted one or more times with substituents independently selected from $R^c$.

Embodiment 158: A compound according to embodiment 157, wherein
G is methyl, ethyl, isopropyl, n-propyl, n-butyl, sec-butyl, or isobutyl.

Embodiment 159: A compound according to embodiment 157, wherein
G is methyl, ethyl, or n-propyl.

Embodiment 160: A compound according to embodiment 157, wherein
G is 2-fluoroethyl, 2,2-difluoroethyl, or 2,2,2-trifluoroethyl.

Embodiment 161: A compound according to embodiment 157, wherein
G is 2-cyanoethyl.

Embodiment 162: A compound according to embodiment 157, wherein
G is —C$_{1-8}$ alkyl substituted once by —C(O)—O—$R^h$.

Embodiment 163: A compound according to embodiment 162, wherein
G is —CH$_2$—C(O)—O—$R^h$.

Embodiment 164: A compound according to embodiment 163, wherein
$R^h$ is hydrogen or methyl.

Embodiment 165: A compound according to embodiment 162, wherein
G is —CH$_2$CH$_2$—C(O)—O—$R^h$.

Embodiment 166: A compound according to embodiment 165, wherein
$R^h$ is hydrogen or methyl.

Embodiment 167: A compound according to embodiment 162, wherein
G is —C(CH$_3$)$_2$—C(O)—O—$R^h$.

Embodiment 168: A compound according to embodiment 167, wherein
$R^h$ is hydrogen or methyl.

Embodiment 169: A compound according to embodiment 162, wherein
G is —CH(CH$_3$)—C(O)—O—$R^h$.

Embodiment 170: A compound according to embodiment 169, wherein
$R^h$ is hydrogen or methyl.

Embodiment 171: A compound according to embodiment 157, wherein
G is —C$_{1-8}$alkyl substituted once by —C(O)N$R^h$ $R^k$.

Embodiment 172: A compound according to embodiment 171, wherein
G is CH$_2$—C(O)—N$R^h$ $R^k$.

Embodiment 173: A compound according to embodiment 172, wherein
N$R^h$ $R^k$ is methylamino, dimethylamino, or diethylamino.

Embodiment 174: A compound according to embodiment 172, wherein
N$R^h$ $R^k$ is thiomorpholino or 1,1-dioxothiomorpholino.

Embodiment 175: A compound according to embodiment 172, wherein
NR$^h$ R$^k$ is morpholino, pyrrolidino, piperidino, piperazino, or 4-methylpiperazino.

Embodiment 176: A compound according to embodiment 172, wherein
NR$^h$ R$^k$ is pyrrolidino, 3-hydroxy-pyrrolidino, 3-methoxy-pyrrolidino, 3-amino-pyrrolidino, 3-(methylamino)-pyrrolidino, 3-(dimethylamino)-pyrrolidino, 2-(hydroxymethyl)-pyrrolidino, 2-(dimethylaminocarbonyl)-pyrrolidino or 3,4-dihydroxy-pyrrolidino.

Embodiment 177: A compound according to embodiment 172, wherein
NR$^h$ R$^k$ is piperazino, 4-methylpiperazino, 4-(methylsulfonyl)-piperazino, or 4-(dimethylaminosulfonyl)-piperazino.

Embodiment 178: A compound according to embodiment 172, wherein
NR$^h$ R$^k$ is piperidino, 3-hydroxypiperidino, 4-hydroxypiperidino, 2-(hydroxymethyl)-piperidino, 3-(hydroxymethyl)-piperidino, 4-(hydroxymethyl)-piperidino, 3-methoxy-piperidino, 4-(methoxymethyl)-piperidino, 4-(fluoromethyl)-piperidino, 4-(trifluoromethyl)-piperidino, 4-cyano-piperidino, 4-carbamoyl-piperidino, 4-(methylamino)-piperidino, 4-(dimethylamino)-piperidino, 4-(methylaminomethyl)-piperidino, or 4-(dimethylaminomethyl)-piperidino.

Embodiment 179: A compound according to embodiment 172, wherein
NR$^h$ R$^k$ is NHR$^k$, where R$^k$ is 2-hydroxypropyl, 2-(methylsulfonyl)-ethyl, tetrahydrofuran-3-yl, tetrahydropyran-4-yl, 1-methylpiperidin-4-yl, piperidin-3-yl, or 1-methylpiperidin-3-yl.

Embodiment 180: A compound according to embodiment 172, wherein
NR$^h$ R$^k$ is N(CH$_3$)R$^k$, where R$^k$ is 2-hydroxyethyl, tetrahydropyran-4-yl, pyrrolidin-3-yl, 1-methylpyrrolidin-3-yl, or piperazin-3-yl.

Embodiment 181: A compound according to embodiment 172, wherein
NR$^h$ R$^k$ is N(CH$_2$CH$_2$OH)$_2$.

Embodiment 182: A compound according to embodiment 171, wherein
G is —(CH$_2$)$_{2-3}$—C(O)—N(CH$_3$)$_2$.

Embodiment 183: A compound according to embodiment 171, wherein
G is —(CH$_2$)$_3$—C(O)-(4-methylpiperazino).

Embodiment 184: A compound according to embodiment 171, wherein
G is —CH(CH$_3$)—C(O)—NR$^h$ R$^k$, where NR$^h$ R$^k$ is methylamino, dimethylamino, 4-methylpiperazino, or morpholino.

Embodiment 185: A compound according to embodiment 171, wherein
G is —C(CH$_3$)$_2$—C(O)—N(CH$_3$)$_2$.

Embodiment 186: A compound according to embodiment 157, wherein
G is —CH—[C(O)—N(CH$_3$)$_2$]—[CH$_2$OH], —CH—[C(O)—N(CH$_3$)$_2$]—[(CH$_2$)$_4$—NH$_2$], or —CH—[C(O)—N(CH$_3$)$_2$]—[(CH$_2$)$_4$—N(CH$_3$)$_2$].

Embodiment 187: A compound according to embodiment 157, wherein
G is —C$_{1-8}$ alkyl substituted once by —O—R$^h$.

Embodiment 188: A compound according to embodiment 187, wherein
G is —(CH$_2$)$_2$—O—R$^h$.

Embodiment 189: A compound according to embodiment 188, wherein
R$^h$ is hydrogen, methyl, or ethyl.

Embodiment 190: A compound according to embodiment 188, wherein
R$^h$ is trifluoromethyl, 2-fluoroethyl, 3-fluoropropyl, or 2,2-difluoroethyl.

Embodiment 191: A compound according to embodiment 188, wherein
R$^h$ is tetrahydrofuran-2-ylmethyl.

Embodiment 192: A compound according to embodiment 188, wherein
R$^h$ is 2-hydroxyethyl.

Embodiment 193: A compound according to embodiment 188, wherein
R$^h$ is 3-hydroxypropyl.

Embodiment 194: A compound according to embodiment 188, wherein
R$^h$ is 2-methoxyethyl.

Embodiment 195: A compound according to embodiment 188, wherein
R$^h$ is 2-(2-hydroxyethoxy)-ethyl.

Embodiment 196: A compound according to embodiment 188, wherein
R$^h$ is 2-hydroxypropyl or 1-hydroxyprop-2-yl.

Embodiment 197: A compound according to embodiment 188, wherein
R$^h$ is 2-cyanoethyl, 2-(methylcarbonylamino)-ethyl, or 2-(methylsulfonylamino)-ethyl.

Embodiment 198: A compound according to embodiment 188, wherein
R$^h$ is 2-aminoethyl, 2-(methylamino)-ethyl, or 2-(dimethylamino)-ethyl.

Embodiment 199: A compound according to embodiment 188, wherein
R$^h$ is carbamoylmethyl.

Embodiment 200: A compound according to embodiment 187, wherein
G is —(CH$_2$)$_3$—O—R$^h$.

Embodiment 201: A compound according to embodiment 200, wherein
R$^h$ is hydrogen, methyl, or ethyl.

Embodiment 202: A compound according to embodiment 200, wherein
R$^h$ is 2-hydroxyethyl.

Embodiment 203: A compound according to embodiment 187, wherein
G is —(CH2)$_4$—OH, —(CH2)$_5$—OH, —CH$_2$C(CH$_3$)$_2$—OH, —CH$_2$C(CH$_3$)$_2$—OCH$_3$, —CH$_2$C(CH$_3$)$_2$—CH$_2$—OH, —CH(CH$_3$)—CH$_2$—OCH$_3$, —(CH$_2$)$_3$C(CH$_3$)$_2$—CH$_2$—OH, —(CH$_2$)$_2$CH(CH$_3$)—CH$_2$—OH, or —(CH$_2$)$_2$CH(CH$_3$)—OH.

Embodiment 204: A compound according to embodiment 187, wherein
G is —CH$_2$CH(CH$_3$)—O—R$^h$.

Embodiment 205: A compound according to embodiment 204, wherein
R$^h$ is hydrogen, methyl, or ethyl.

Embodiment 206: A compound according to embodiment 157, wherein
G is —CH$_2$—CH(OH)—CH$_2$—OH.

Embodiment 207: A compound according to embodiment 157, wherein
G is —C$_{1-8}$ alkyl substituted once by —NR$^h$R$^k$.

Embodiment 208: A compound according to embodiment 207, wherein
G is —(CH$_2$)$_2$—NR$^h$R$^k$.

Embodiment 209: A compound according to embodiment 208, wherein
NR$^h$R$^k$ is amino, methylamino, or dimethylamino.
Embodiment 210: A compound according to embodiment 208, wherein
NR$^h$R$^k$ is methylcarbonylamino.
Embodiment 211: A compound according to embodiment 208, wherein
NR$^h$R$^k$ is (dimethylamino)methylcarbonylamino, hydroxymethylcarbonylamino, or 1-hydroxyethylcarbonylamino.
Embodiment 212: A compound according to embodiment 208, wherein
NR$^h$R$^k$ is methylsulfonylamino.
Embodiment 213: A compound according to embodiment 208, wherein
NR$^h$R$^k$ is piperidino, 4-hydroxypiperidino, or 3-hydroxypiperidino.
Embodiment 214: A compound according to embodiment 208, wherein
NR$^h$R$^k$ is piperidino, 4,4-difluoropiperidino, or 3,3-difluoropiperidino.
Embodiment 215: A compound according to embodiment 208, wherein
NR$^h$R$^k$ is 2-oxo-pyrrolidino, 2-oxo-imidazolidino, or 3-oxo-piperazino.
Embodiment 216: A compound according to embodiment 208, wherein
NR$^h$R$^k$ is piperazino, 4-methylpiperazino, morpholino, or 1,1-dioxo-thiomorpholino.
Embodiment 217: A compound according to embodiment 207, wherein
G is —(CH$_2$)$_3$—NR$^h$R$^k$.
Embodiment 218: A compound according to embodiment 217, wherein
NR$^h$R$^k$ is amino, dimethylamino, or diethylamino.
Embodiment 219: A compound according to embodiment 217, wherein
NR$^h$R$^k$ is piperidino, 4-methylpiperazino, or morpholino.
Embodiment 220: A compound according to embodiment 207, wherein
G is —(CH$_2$)$_4$—NR$^h$R$^k$.
Embodiment 221: A compound according to embodiment 220, wherein
NR$^h$R$^k$ is amino, dimethylamino, or diethylamino.
Embodiment 222: A compound according to embodiment 156, wherein
G is —C$_{1-6}$ alkylene-heterocyclyl, where the alkylene and heterocyclyl groups are optionally substituted one or more times with substituents independently selected from R$^c$.
Embodiment 223: A compound according to embodiment 222, wherein
G is —CH$_2$-heterocyclyl, where the heterocyclyl group is optionally substituted once with a substituent selected from R$^c$.
Embodiment 224: A compound according to embodiment 223, wherein
the heterocyclyl group is tetrahydropyran-4-yl, tetrahydrofuran-2-yl, 1,4-dioxan-2-yl, morpholin-2-yl, tetrahydropyran-2-yl, piperidin-4-yl, 1-(2-hydroxyethyl)-piperidin-4-yl, 1-(dimethylaminomethylcarbonyl)-piperidin-4-yl, piperazin-2-yl, or 1-methyl-piperazin-2-yl.
Embodiment 225: A compound according to embodiment 156, wherein
G is C$_{3-10}$ cycloalkyl optionally substituted one or more times with substituents independently selected from R$^c$.
Embodiment 226: A compound according to embodiment 225, wherein
G is 4-hydroxy-cyclohexyl, 4-carboxy-cyclohexyl, or 4-(dimethylaminocarbonyl)-cyclohexyl.
Embodiment 227: A compound according to embodiment 225, wherein
G is 1-carboxy-cyclopropyl, 1-(ethoxycarbonyl)-cyclopropyl, or 1-(dimethylamino-carbonyl)-cyclopropyl.
Embodiment 228: A compound according to embodiment 156, wherein
G is C$_{1-6}$ alkylene-C$_{3-10}$ cycloalkyl, where the alkylene and cycloalkyl groups are optionally substituted one or more times with substituents independently selected from R$^c$.
Embodiment 229: A compound according to embodiment 228, wherein
G is —CH$_2$-(4-hydroxy-cyclohexyl).
Embodiment 230: A compound according to embodiment 228, wherein
G is —(CH$_2$)$_2$-(4-hydroxy-cyclohexyl).
Embodiment 231: A compound according to embodiment 228, wherein
G is —CH$_2$-[4-(hydroxymethyl)-cyclohexyl].
Embodiment 232: A compound according to embodiment 156, wherein
G is heterocyclyl optionally substituted one or more times with substituents independently selected from R$^c$.
Embodiment 233: A compound according to embodiment 232, wherein
G is piperidin-4-yl, 1-methyl-piperidin-4-yl, 1-carboxy-piperidin-4-yl, 1-(methylsulfonyl)-piperidin-4-yl, 1-(2-hydroxyethyl)-piperidin-4-yl, 1-(dimethyl-aminocarbonyl)piperidin-4-yl, or 1-(dimethylaminomethylcarbonyl)-piperidin-4-yl.
Embodiment 234: A compound according to embodiment 232, wherein
G is piperidin-3-yl or 1-(dimethylaminomethylcarbonyl)-piperidin-3-yl.
Embodiment 235: A compound according to embodiment 232, wherein
G is 1,1-dioxo-tetrahydrothiophen-3-yl.
Embodiment 236: A compound according to embodiment 232, wherein
G is pyrrolidin-3-yl, 1-methyl-pyrrolidin-3-yl, 1-(2-hydroxyethyl)-pyrrolidin-3-yl, 1-(2-hydroxypropyl)-pyrrolidin-3-yl, 1-(2-hydroxy-2-methylpropyl)-pyrrolidin-3-yl, 1-(1-hydroxyethylcarbonyl)-pyrrolidin-3-yl, 1-(2-carboxyethyl)-pyrrolidin-3-yl, or 1-(2-methylsulfonylamino-ethyl)-pyrrolidin-3-yl.
Embodiment 237: A compound according to embodiment 157, wherein
G is —C$_{1-8}$ alkyl substituted once by —S—R$^h$.
Embodiment 238: A compound according to embodiment 237, wherein
G is —(CH$_2$)$_2$—S—R$^h$.
Embodiment 239: A compound according to embodiment 238, wherein
R$^h$ is methyl or ethyl.
Embodiment 240: A compound according to embodiment 238, wherein
R$^h$ is 2-hydroxyethyl.
Embodiment 241: A compound according to embodiment 237, wherein
G is —(CH$_2$)$_3$—S—R$^h$.

Embodiment 242: A compound according to embodiment 241, wherein
$R^h$ is methyl.
Embodiment 243: A compound according to embodiment 157, wherein
G is —$C_{1-8}$ alkyl substituted once by —$SO_2$—$R^h$.
Embodiment 244: A compound according to embodiment 243, wherein
G is —$(CH_2)_2$—$SO_2$—$R^h$.
Embodiment 245: A compound according to embodiment 244, wherein
$R^h$ is methyl or ethyl.
Embodiment 246: A compound according to embodiment 244, wherein
$R^h$ is 2-hydroxyethyl.
Embodiment 247: A compound according to embodiment 243, wherein
G is —$(CH_2)_3$—$SO_2$—$R^h$.
Embodiment 248: A compound according to embodiment 247, wherein
$R^h$ is methyl.
Embodiment 249: A compound according to embodiment 156 wherein
G is —$CH(CH_3)$—$NR^hR^k$, where $NR^hR^k$ is pyrrolidino, piperidino, 4-methyl-piperazino, morpholino, or dimethylamino.
Embodiment 250: A compound according to embodiment 156 wherein
G is 1-(2-hydroxypropyl)-pyrrolodin-3-yl or 1-(1-hydroxyethylcarbonyl)-pyrrolidin-3-yl.
Embodiment 251: A compound according to embodiment 156 wherein
G is 1-(dimethylaminomethylcarbonyl)-piperidin-4-yl.
Embodiment 252: A compound according to embodiment 156 wherein
G is —$(CH_2)_{3-5}$—OH.
Embodiment 253: A compound according to embodiment 156 wherein
G is 4-hydroxy-cyclohexylmethyl.
Embodiment 254: A compound according to embodiment 156 wherein
G is —$(CH_2)_2$—NHC(O)—$CH_2$—$N(CH_3)_2$.
Embodiment 255: A compound according to embodiment 156 wherein
G is 4-hydroxy-cyclohexylmethyl.
Embodiment 256: A compound according to embodiment 156 wherein
G is —$CH_2$—C(O)—$NR^hR^k$, where $NR^hR^k$ is 3-hydroxy-pyrrolidino or 3-(dimethyl-amino)-pyrrolidino.
Embodiment 257: A compound according to embodiment 156 wherein
G is —$CH_2$—C(O)—$NR^hR^k$, where $NR^hR^k$ is morpholino.
Embodiment 258: A compound according to embodiment 156 wherein G is —$CH_2$—C(O)—$NR^hR^k$, where $NR^hR^k$ is 4-hydroxy-piperidino, 4-methoxy-piperidino, 4-(hydroxymethyl)-piperidino, 3-hydroxy-piperidino, 3-methoxy-piperidino, 3-(hydroxymethyl)-piperidino, or 4,4-difluoropiperidino.
Embodiment 259: A compound according to embodiment 156 wherein
G is —$CH_2$—C(O)—$NR^hR^k$, where $NR^hR^k$ is dimethylamino.
Embodiment 260: A compound according to embodiment 156 wherein
G is —$(CH_2)_2$—O—$(CH_2)_2$—OH.
Embodiment 261: A compound according to embodiment 156 wherein
G is —$(CH_2)_2$—O—$(CH_2)_2$—$OCH_3$.
Embodiment 262: A compound according to embodiment 156 wherein G is —$CH_2$—$CH(CH_3)$—OH.
Embodiment 263: A compound according to any one of embodiments 79 to 136, wherein
L is C(O)NH, and G is $C_{1-3}$alkyl substituted once by a heteroaryl group, where the heteroaryl group is optionally substituted one or more times with substituents independently selected from $R^x$.
Embodiment 264: A compound according to embodiment 263, wherein
G is —$CH_2$-(2-furyl), —$CH_2$-(2-thienyl), —$CH_2$-(2-oxazolyl), or —$CH_2$-(2-thiazolyl).
Embodiment 265: A compound according to embodiment 263, wherein
G is —$(CH_2)_{2-3}$-(1-pyrrolyl), —$(CH_2)_{2-3}$-(1-pyrazolyl), or —$(CH_2)_{2-3}$-(1-imidazolyl).
Embodiment 266: A compound according to any one of embodiments 79 to 136, wherein
L is C(O)NH, and G is $C_{1-3}$alkyl substituted once by a phenyl group, where the phenyl group is optionally substituted one or more times with substituents independently selected from $R^x$.
Embodiment 267: A compound according to embodiment 266, wherein
G is —$(—CH_2)_{1-2}$-(4-hydroxyphenyl) or —$(—CH_2)_{1-2}$-(4-methoxy-3-hydroxyphenyl).
Embodiment 268: A compound according to any one of embodiments 79 to 136, wherein
L is C(O)NH, and G is —$CH_2$—C(O)NH—$CH_2$-(4-hydroxyphenyl).
Embodiment 269: A compound according to any one of embodiments 79 to 136, wherein
L is C(O)NH, and G is —$CH_2$—C(O)-[4-(pyrimidin-2-yloxy)-piperidino].
Embodiment 270: A compound according to any one of embodiments 1 to 269, wherein the compound is in the form of a free acid or a free base.
Embodiment 271: A compound according to any one of embodiments 1 to 269, wherein the compound is in the form of a pharmaceutically acceptable salt.

The routes in the Examples illustrate methods of synthesizing compounds of Formula (I), or a pharmaceutically acceptable salt thereof. The skilled artisan will appreciate that the compounds of the invention could be made by methods other than those specifically described herein, by adaptation of the methods described herein and/or adaptation thereof, for example by methods known in the art.

Examples of compounds of Formula (I) or pharmaceutically acceptable salts thereof having useful biological activity are listed the Examples section and in Table 1. The ability of compounds of Formula (I) or pharmaceutically acceptable salts thereof to increase levels or activity of HMOX1 was established using the Biological Assay described below. In the chemical structures shown below, standard chemical abbreviations are sometimes used. Including Me=methyl, Et=ethyl, OMe=methyoxy, OEt=ethyoxy, and the like. Note that, in some instances, the name may recite a salted form of the compound. In these instances, the salted form of the compound was made, even if the corresponding structure may not show the presence of the counterion. For compounds that were made in the form of a hydrochloride salt, no names or structures are intended to recite any particular stoichiometric relationship between counterions.

TABLE 1

| No. | Structure | Name |
|---|---|---|
| 1 | 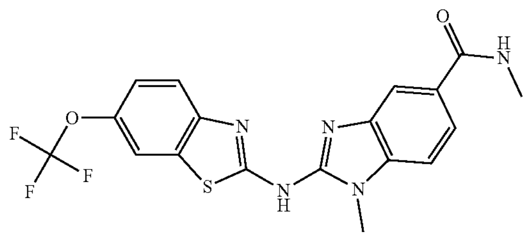 [SMILES: CNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid methyl amide |
| 2 | 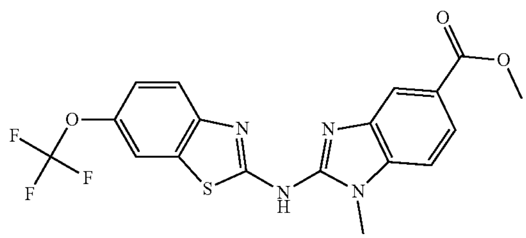 [SMILES: COC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid methyl ester |
| 3 | 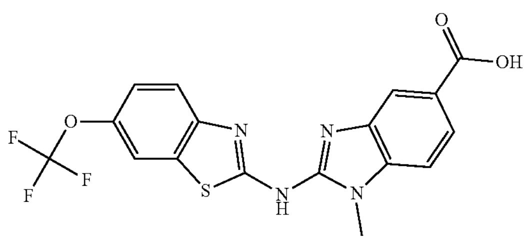 [SMILES: Cn1c(Nc2nc3ccc(OC(F)(F)F)cc3s2)nc2cc(C(=O)O)ccc21] | 1-Methyl-2-(6-trifluoromethoxy-benzothiazol-2-ylamino)-1H-benzoimidazole-5-carboxylic acid |
| 4 | 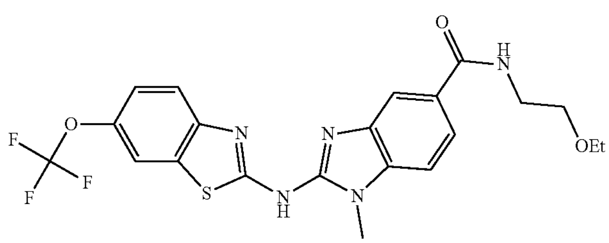 [SMILES: CCOCCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid (2-ethoxy-ethyl)-amide |
| 5 | 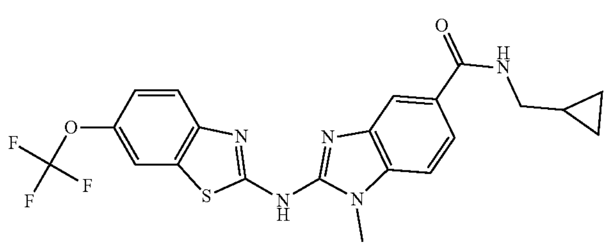 [SMILES: Cn1c(Nc2nc3ccc(OC(F)(F)F)cc3s2)nc2cc(C(=O)NCC3CC3)ccc21] | 1-Methyl-2-(6-trifluoromethoxy-benzothiazol-2-ylamino)-1H-benzoimidazole-5-carboxylic acid cyclopropylmethyl-amide |
| 6 | 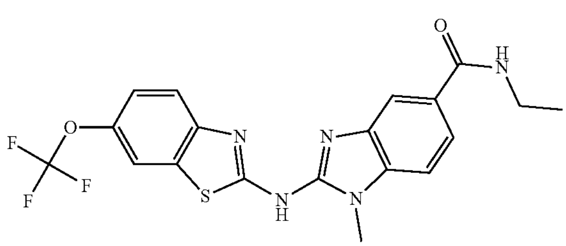 [SMILES: CCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid ethylamide |

TABLE 1-continued

| No. | Structure | Name |
|---|---|---|
| 7 | 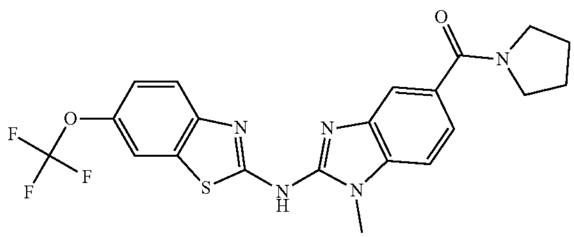 [SMILES: Cn1c(Nc2nc3ccc(OC(F)(F)F)cc3s2)nc2cc(C(=O)N3CCCC3)ccc21] | [1-Methyl-2-(6-trifluoromethoxy-benzothiazol-2-ylamino)-1H-benzoimidazol-5-yl]-pyrrolidin-1-yl-methanone |
| 8 | 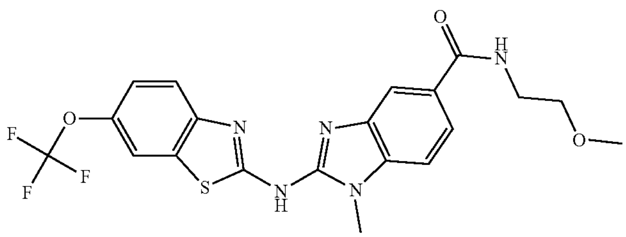 [SMILES: COCCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid (2-methoxy-ethyl)-amide |
| 9 | 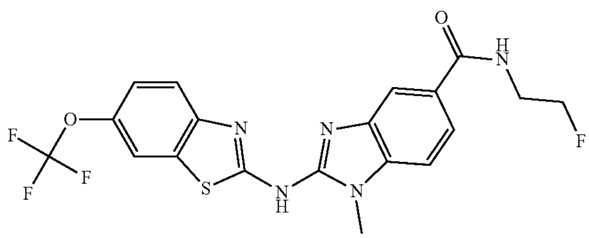 [SMILES: Cn1c(Nc2nc3ccc(OC(F)(F)F)cc3s2)nc2cc(C(=O)NCCF)ccc21] | 1-Methyl-2-(6-trifluoromethoxy-benzothiazol-2-ylamino)-1H-benzoimidazole-5-carboxylic acid (2-fluoro-ethyl)-amide |
| 10 | 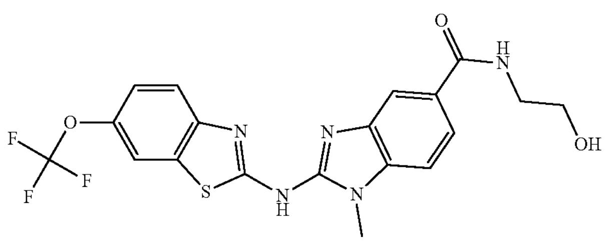 [SMILES: Cn1c(Nc2nc3ccc(OC(F)(F)F)cc3s2)nc2cc(C(=O)NCCO)ccc21] | 1-Methyl-2-(6-trifluoromethoxy-benzothiazol-2-ylamino)-1H-benzoimidazole-5-carboxylic acid (2-hydroxy-ethyl)-amide |
| 11 | 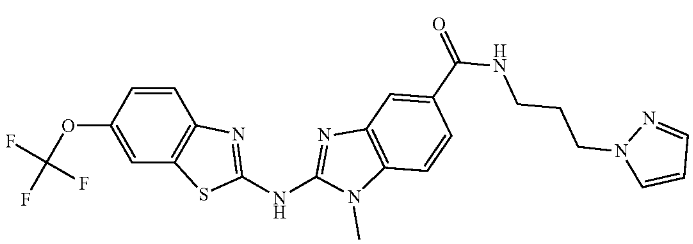 [SMILES: Cn1c(Nc2nc3ccc(OC(F)(F)F)cc3s2)nc2cc(C(=O)NCCCn3cccn3)ccc21] | 1-Methyl-2-(6-trifluoromethoxy-benzothiazol-2-ylamino)-1H-benzoimidazole-5-carboxylic acid (3-pyrazol-1-yl-propyl)-amide |
| 12 | 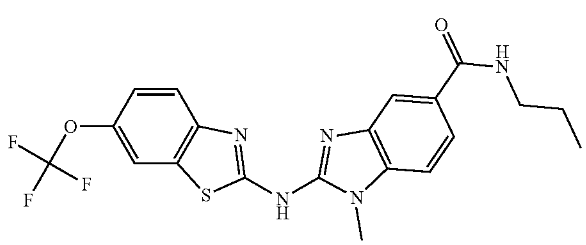 [SMILES: CCCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid propylamide |

TABLE 1-continued

| No. | Structure | Name |
|---|---|---|
| 13 | 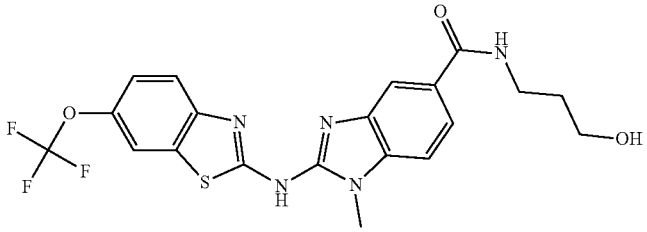 [SMILES: Cn1c(Nc2nc3ccc(OC(F)(F)F)cc3s2)nc2cc(C(=O)NCCCO)ccc21] | 1-Methyl-2-(6-trifluoromethoxy-benzothiazol-2-ylamino)-1H-benzoimidazole-5-carboxylic acid hydroxy-propyl)-amide |
| 14 | 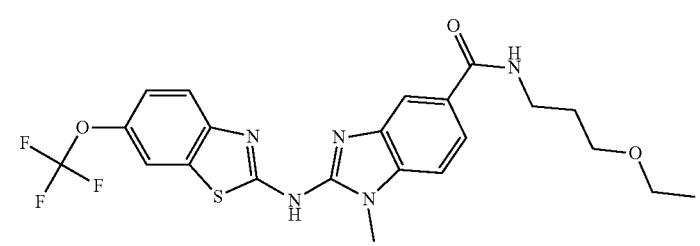 [SMILES: CCOCCCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid (3-ethoxy-propyl)-amide |
| 15 | 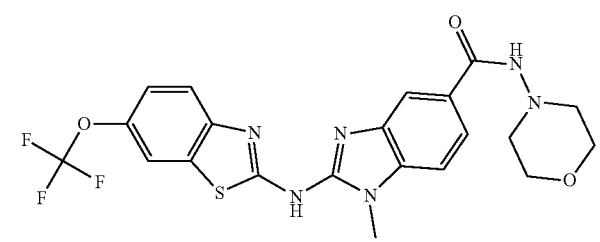 [SMILES: Cn1c(Nc2nc3ccc(OC(F)(F)F)cc3s2)nc2cc(C(=O)NN3CCOCC3)ccc21] | 1-Methyl-2-(6-trifluoromethoxy-benzothiazol-2-ylamino)-1H-benzoimidazole-5-carboxylic acid morpholin-4-ylamide |
| 16 | 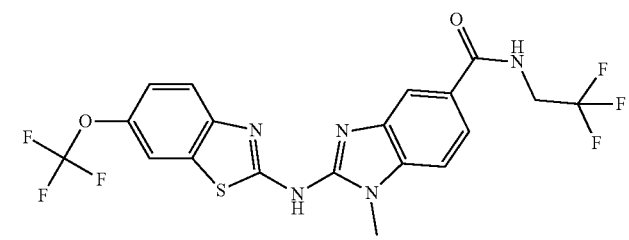 [SMILES: Cn1c(Nc2nc3ccc(OC(F)(F)F)cc3s2)nc2cc(C(=O)NCC(F)(F)F)ccc21] | 1-Methyl-2-(6-trifluoromethoxy-benzothiazol-2-ylamino)-1H-benzoimidazole-5-carboxylic acid (2,2,2-trifluoro-ethyl)-amide |
| 17 | 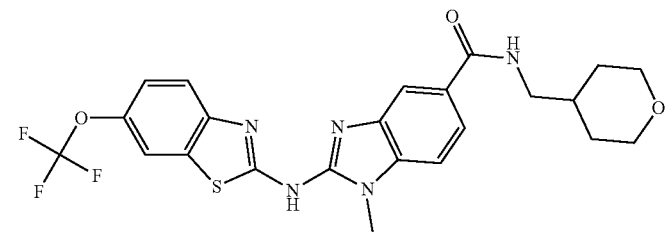 [SMILES: Cn1c(Nc2nc3ccc(OC(F)(F)F)cc3s2)nc2cc(C(=O)NCC3CCOCC3)ccc21] | 1-Methyl-2-(6-trifluoromethoxy-benzothiazol-2-ylamino)-1H-benzoimidazole-5-carboxylic acid (tetrahydro-pyran-4-ylmethyl)-amide |
| 18 | 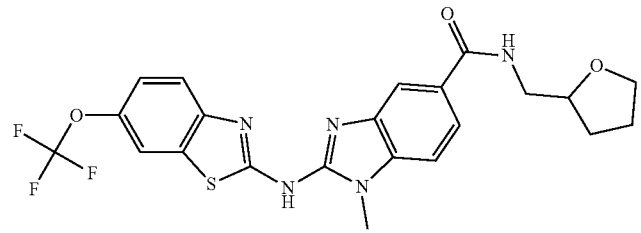 [SMILES: Cn1c(Nc2nc3ccc(OC(F)(F)F)cc3s2)nc2cc(C(=O)NCC3CCCO3)ccc21] | 1-Methyl-2-(6-trifluoromethoxy-benzothiazol-2-ylamino)-1H-benzoimidazole-5-carboxylic acid (tetrahydro-furan-2-ylmethyl)-amide |

TABLE 1-continued

| No. | Structure | Name |
|---|---|---|
| 19 | 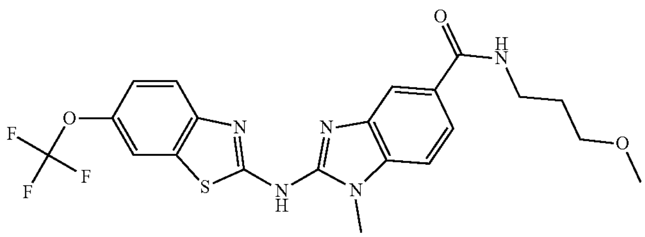 [SMILES: COCCCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid (3-methoxy-propyl)-amide |
| 20 | 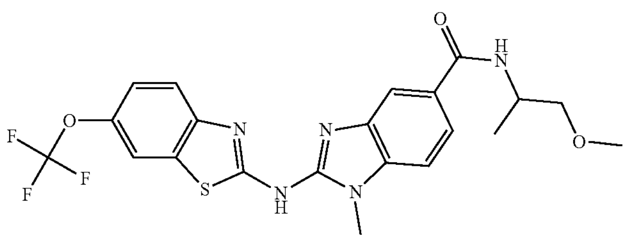 [SMILES: COCC(C)NC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid (2-methoxy-1-methyl-ethyl)-amide |
| 21 | 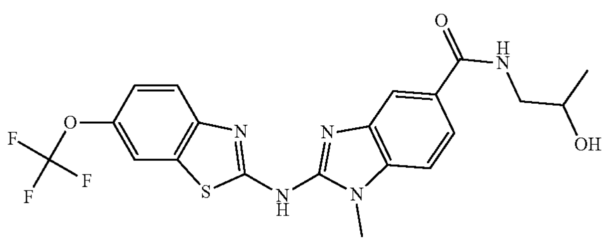 [SMILES: CC(O)CNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid (2-hydroxy-propyl)-amide |
| 22 | 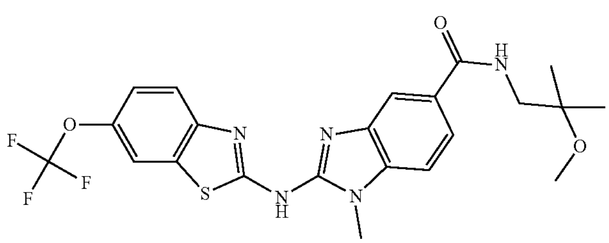 [SMILES: COC(C)(C)CNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid (2-methoxy-2-methyl-propyl)-amide |
| 23 | 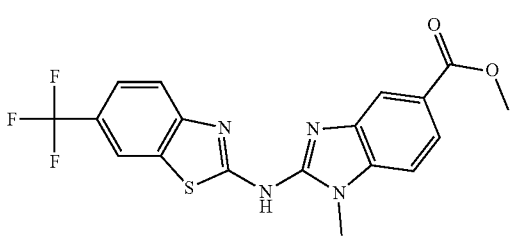 [SMILES: COC(=O)c1ccc2c(c1)nc(Nc1nc3ccc(C(F)(F)F)cc3s1)n2C] | 1-Methyl-2-(6-trifluoromethyl-benzothiazol-2-ylamino)-1H-benzoimidazole-5-carboxylic acid methyl ester |
| 24 | 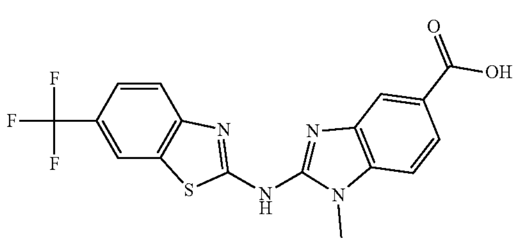 [SMILES: Cn1c(Nc2nc3ccc(C(F)(F)F)cc3s2)nc2cc(C(=O)O)ccc21] | 1-Methyl-2-(6-trifluoromethyl-benzothiazol-2-ylamino)-1H-benzoimidazole-5-carboxylic acid |

TABLE 1-continued

| No. | Structure | Name |
|---|---|---|
| 25 | 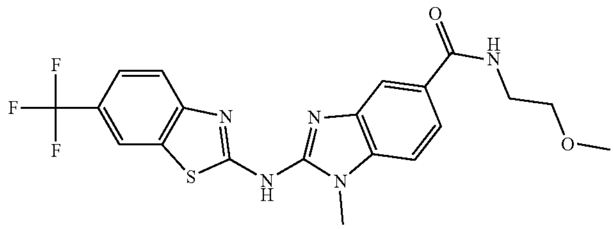 [SMILES: COCCNC(=O)c1ccc2c(c1)nc(Nc1nc3ccc(C(F)(F)F)cc3s1)n2C] | 1-Methyl-2-(6-trifluoromethyl-benzothiazol-2-ylamino)-1H-benzoimidazole-5-carboxylic acid (2-methoxy-ethyl)-amide |
| 26 | 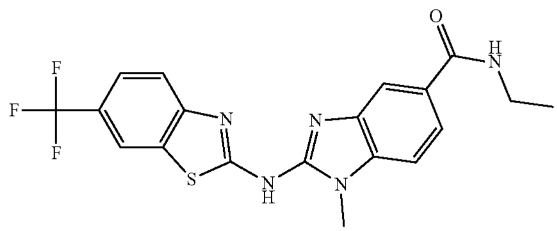 [SMILES: CCNC(=O)c1ccc2c(c1)nc(Nc1nc3ccc(C(F)(F)F)cc3s1)n2C] | 1-Methyl-2-(6-trifluoromethyl-benzothiazol-2-ylamino)-1H-benzoimidazole-5-carboxylic acid ethylamide |
| 27 | 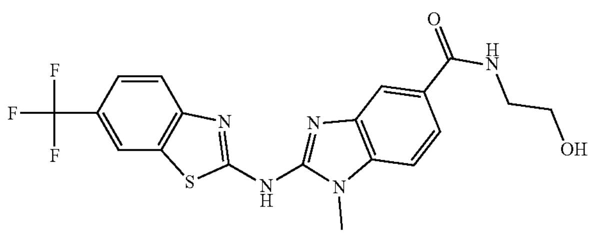 [SMILES: Cn1c(Nc2nc3ccc(C(F)(F)F)cc3s2)nc2cc(C(=O)NCCO)ccc21] | 1-Methyl-2-(6-trifluoromethyl-benzothiazol-2-ylamino)-1H-benzoimidazole-5-carboxylic acid (2-hydroxy-ethyl)-amide |
| 28 | 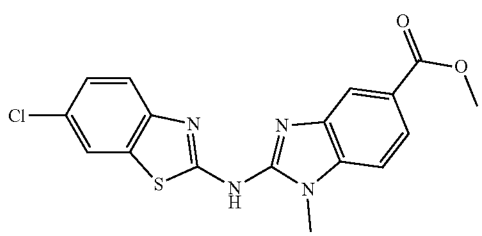 [SMILES: COC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid methyl ester |
| 29 | 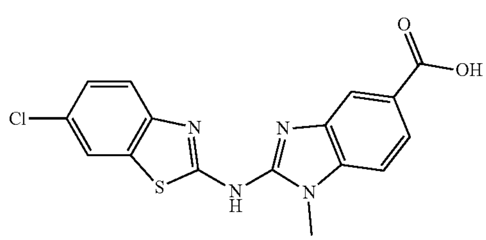 [SMILES: Cn1c(Nc2nc3ccc(Cl)cc3s2)nc2cc(C(=O)O)ccc21] | 2-(6-Chloro-benzothiazol-2-ylamino)-1-methyl-1H-benzoimidazole-5-carboxylic acid |
| 30 | 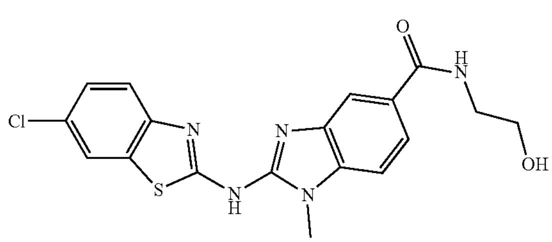 [SMILES: Cn1c(Nc2nc3ccc(Cl)cc3s2)nc2cc(C(=O)NCCO)ccc21] | 2-(6-Chloro-benzothiazol-2-ylamino)-1-methyl-1H-benzoimidazole-5-carboxylic acid (2-hydroxy-ethyl)-amide |

TABLE 1-continued

| No. | Structure | Name |
| --- | --- | --- |
| 31 | 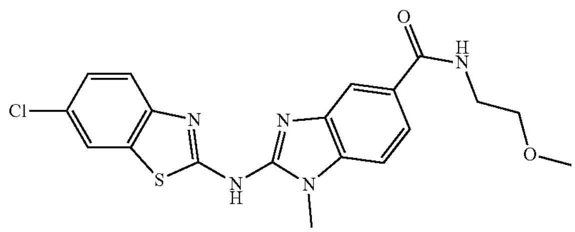 [SMILES: COCCNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid (2-methoxy-ethyl)-amide |
| 32 | 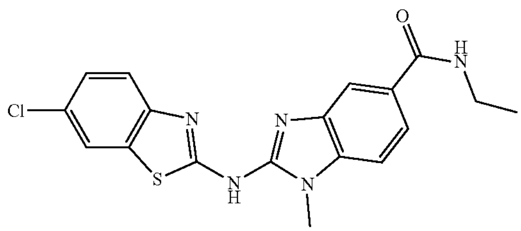 [SMILES: CCNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid ethylamide |
| 33 | 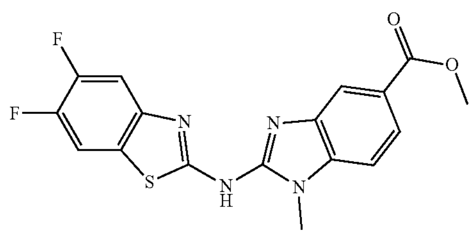 [SMILES: COC(=O)c1ccc2c(c1)nc(Nc1nc3cc(F)c(F)cc3s1)n2C] | 2-(5,6-Difluoro-benzothiazol-2-ylamino)-1-methyl-1H-benzoimidazole-5-carboxylic acid methyl ester |
| 34 | 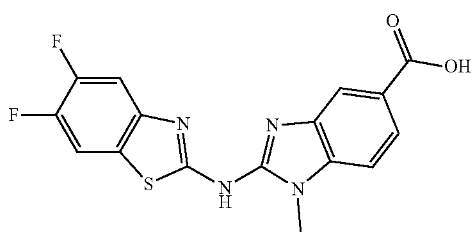 [SMILES: Cn1c(Nc2nc3cc(F)c(F)cc3s2)nc2cc(C(=O)O)ccc21] | 2-(5,6-Difluoro-benzothiazol-2-ylamino)-1-methyl-1H-benzoimidazole-5-carboxylic acid |
| 35 | 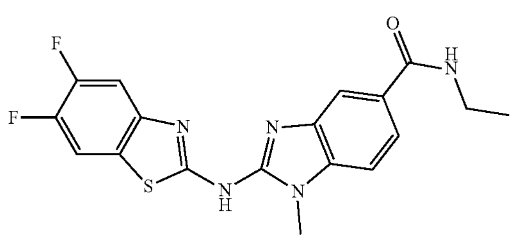 [SMILES: CCNC(=O)c1ccc2c(c1)nc(Nc1nc3cc(F)c(F)cc3s1)n2C] | 2-(5,6-Difluoro-benzothiazol-2-ylamino)-1-methyl-1H-benzoimidazole-5-carboxylic acid ethylamide |
| 36 | 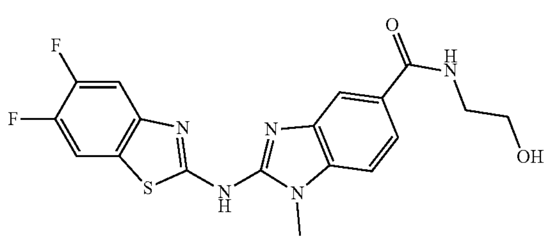 [SMILES: Cn1c(Nc2nc3cc(F)c(F)cc3s2)nc2cc(C(=O)NCCO)ccc21] | 2-(5,6-Difluoro-benzothiazol-2-ylamino)-1-methyl-1H-benzoimidazole-5-carboxylic acid (2-hydroxy-ethyl)-amide |

| No. | Structure | Name |
|---|---|---|
| 37 | 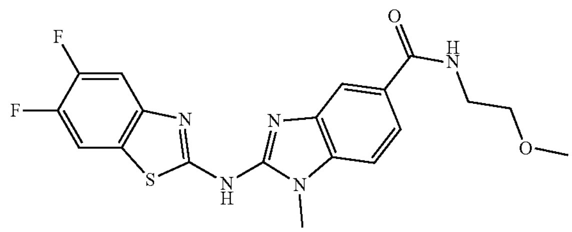 [SMILES: COCCNC(=O)c1ccc2c(c1)nc(Nc1nc3cc(F)c(F)cc3s1)n2C] | 2-(5,6-Difluoro-benzothiazol-2-ylamino)-1-methyl-1H-benzoimidazole-5-carboxylic acid (2-methoxy-ethyl)-amide |
| 38 | 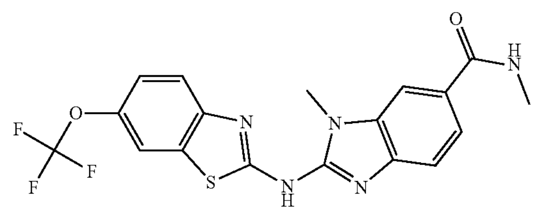 [SMILES: CNC(=O)c1ccc2nc(Nc3nc4ccc(OC(F)(F)F)cc4s3)n(C)c2c1] | 3-Methyl-2-(6-trifluoromethoxy-benzothiazol-2-ylamino)-3H-benzoimidazole-5-carboxylic acid methylamide |
| 39 | 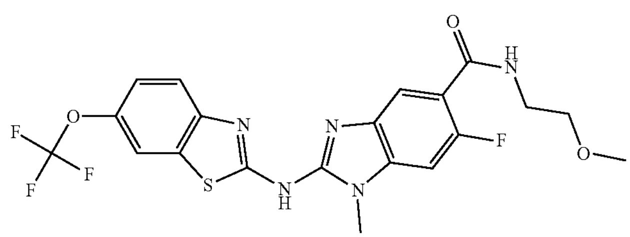 [SMILES: COCCNC(=O)c1cc2nc(Nc3nc4ccc(OC(F)(F)F)cc4s3)n(C)c2cc1F] | 6-Fluoro-1-methyl-2-(6-trifluoromethoxy-benzothiazol-2-ylamino)-1H-benzoimidazole-5-carboxylic acid (2-methoxy-ethyl)-amide |
| 40 | 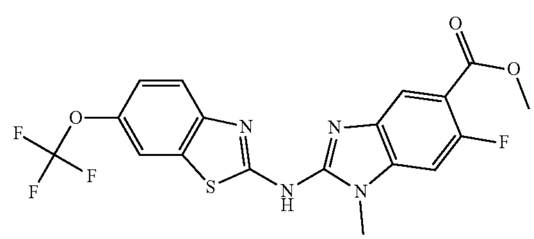 [SMILES: COC(=O)c1cc2nc(Nc3nc4ccc(OC(F)(F)F)cc4s3)n(C)c2cc1F] | 6-Fluoro-1-methyl-2-(6-trifluoromethoxy-benzothiazol-2-ylamino)-1H-benzoimidazole-5-carboxylic acid methyl ester |
| 41 | 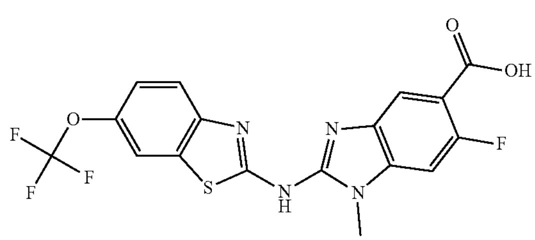 [SMILES: Cn1c(Nc2nc3ccc(OC(F)(F)F)cc3s2)nc2cc(C(=O)O)c(F)cc21] | 6-Fluoro-1-methyl-2-(6-trifluoromethoxy-benzothiazol-2-ylamino)-1H-benzoimidazole-5-carboxylic acid |
| 42 | 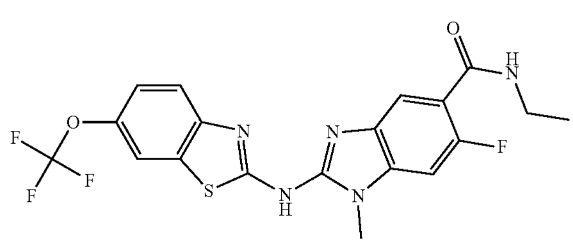 [SMILES: CCNC(=O)c1cc2nc(Nc3nc4ccc(OC(F)(F)F)cc4s3)n(C)c2cc1F] | 6-Fluoro-1-methyl-2-(6-trifluoromethoxy-benzothiazol-2-ylamino)-1H-benzoimidazole-5-carboxylic acid ethylamide |

TABLE 1-continued

| No. | Structure | Name |
|---|---|---|
| 43 | 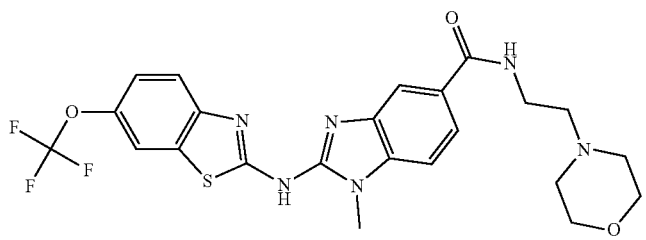 [SMILES: Cn1c(Nc2nc3ccc(OC(F)(F)F)cc3s2)nc2cc(C(=O)NCCN3CCOCC3)ccc21] | 1-Methyl-2-(6-trifluoromethoxy-benzothiazol-2-ylamino)-1H-benzoimidazole-5-carboxylic acid (2-morpholin-4-yl-ethyl)-amide |
| 44 | 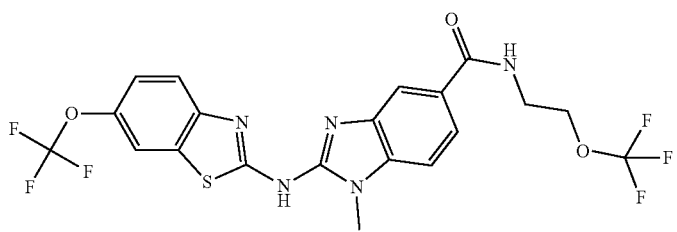 [SMILES: Cn1c(Nc2nc3ccc(OC(F)(F)F)cc3s2)nc2cc(C(=O)NCCOC(F)(F)F)ccc21] | 1-Methyl-2-(6-trifluoromethoxy-benzothiazol-2-ylamino)-1H-benzoimidazole-5-carboxylic acid (2-trifluoromethoxy-ethyl)-amide |
| 45 | 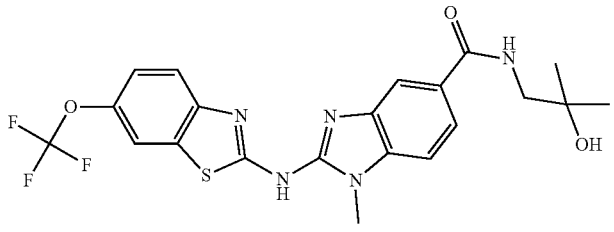 [SMILES: Cn1c(Nc2nc3ccc(OC(F)(F)F)cc3s2)nc2cc(C(=O)NCC(C)(C)O)ccc21] | 1-Methyl-2-(6-trifluoromethoxy-benzothiazol-2-ylamino)-1H-benzoimidazole-5-carboxylic acid (2-hydroxy-2-methyl-propyl)-amide |
| 46 | 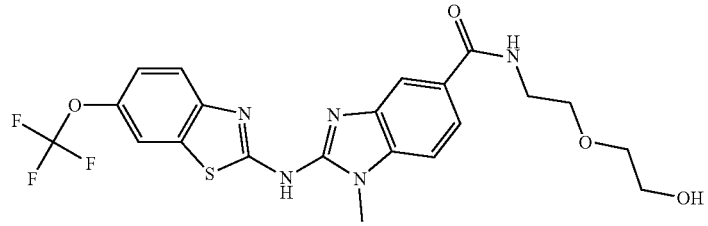 [SMILES: Cn1c(Nc2nc3ccc(OC(F)(F)F)cc3s2)nc2cc(C(=O)NCCOCCO)ccc21] | 1-Methyl-2-(6-trifluoromethoxy-benzothiazol-2-ylamino)-1H-benzoimidazole-5-carboxylic acid [2-(2-hydroxy-ethoxy)-ethyl]-amide |
| 47 | 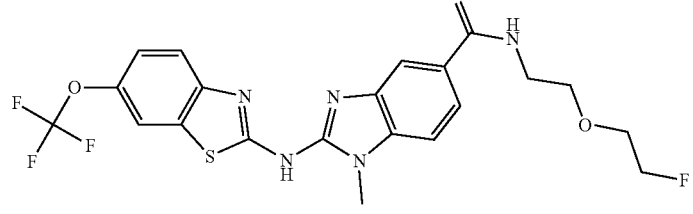 | 1-Methyl-2-(6-trifluoromethoxy-benzothiazol-2-ylamino)-1H-benzoimidazole-5-carboxylic acid [2-(2-fluoro-ethoxy)-ethyl]-amide |
| 48 | 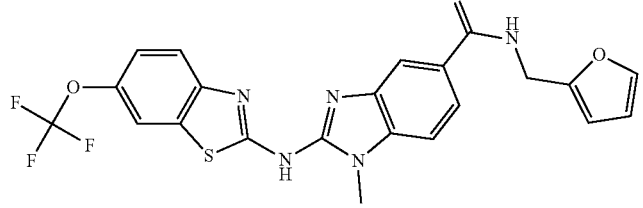 | 1-Methyl-2-(6-trifluoromethoxy-benzothiazol-2-ylamino)-1H-benzoimidazole-5-carboxylic acid (furan-2-ylmethyl)-amide |

TABLE 1-continued

| No. | Structure | Name |
|---|---|---|
| 49 | 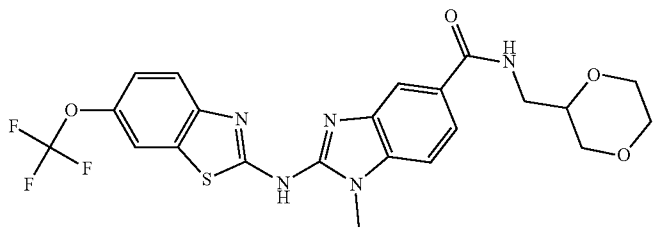 [SMILES: Cn1c(Nc2nc3ccc(OC(F)(F)F)cc3s2)nc2cc(C(=O)NCC3COCCO3)ccc21] | 1-Methyl-2-(6-trifluoromethoxy-benzothiazol-2-ylamino)-1H-benzoimidazole-5-carboxylic acid ([1,4]dioxan-2-ylmethyl)-amide |
| 50 | 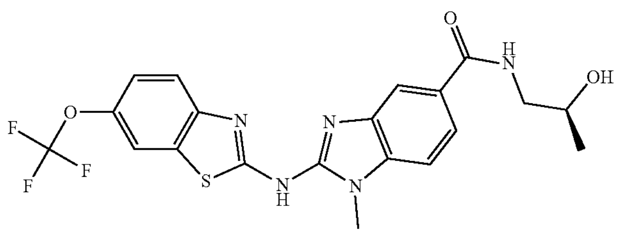 [SMILES: C[C@H](O)CNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid ((S)-2-hydroxy-propyl)-amide |
| 51 | 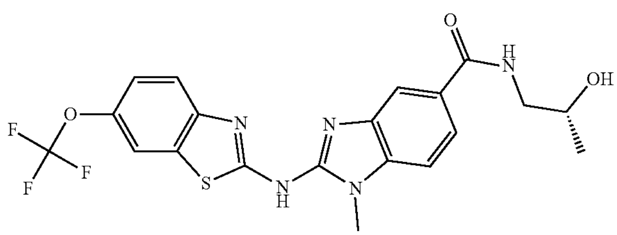 [SMILES: C[C@@H](O)CNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid ((R)-2-hydroxy-propyl)-amide |
| 52 | 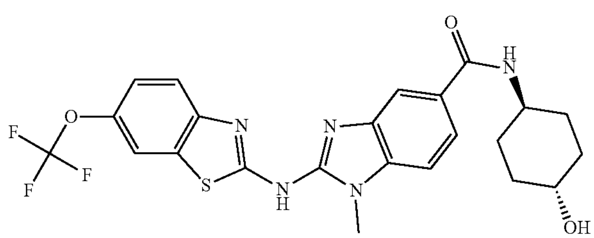 [SMILES: Cn1c(Nc2nc3ccc(OC(F)(F)F)cc3s2)nc2cc(C(=O)N[C@H]3CC[C@H](O)CC3)ccc21] | 1-Methyl-2-(6-trifluoromethoxy-benzothiazol-2-ylamino)-1H-benzoimidazole-5-carboxylic acid (trans-4-hydroxy-cyclohexyl)-amide |
| 53 | 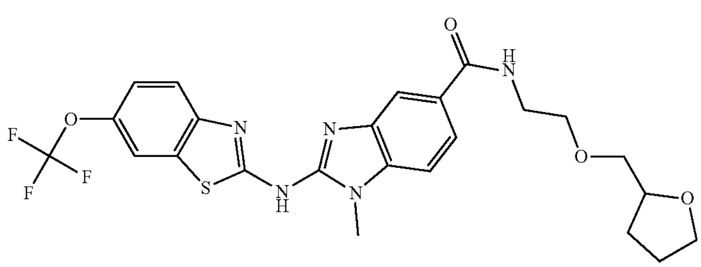 [SMILES: Cn1c(Nc2nc3ccc(OC(F)(F)F)cc3s2)nc2cc(C(=O)NCCOCC3CCCO3)ccc21] | 1-Methyl-2-(6-trifluoromethoxy-benzothiazol-2-ylamino)-1H-benzoimidazole-5-carboxylic acid [2-(tetrahydro-furan-2-ylmethoxy)-ethyl]-amide |
| 54 | 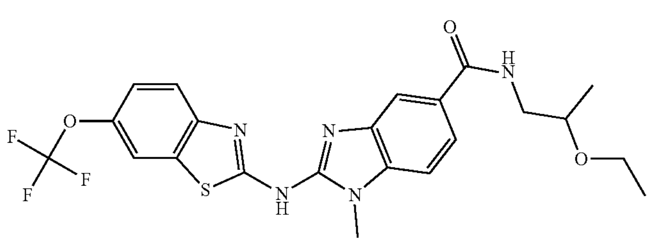 [SMILES: CCOC(C)CNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid (2-ethoxy-propyl)-amide |

TABLE 1-continued

| No. | Structure | Name |
|-----|-----------|------|
| 55 | 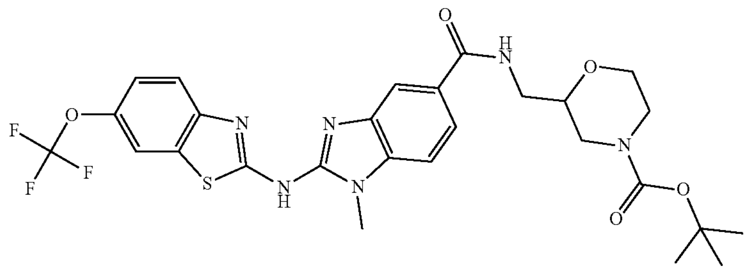 [SMILES: Cn1c(Nc2nc3ccc(OC(F)(F)F)cc3s2)nc2cc(C(=O)NCC3CN(C(=O)OC(C)(C)C)CCO3)ccc21] | 2-({[1-Methyl-2-(6-trifluoromethoxy-benzothiazol-2-ylamino)-1H-benzoimidazole-5-carbonyl]-amino}-methyl)-morpholine-4-carboxylic acid tert-butyl ester |
| 56 | 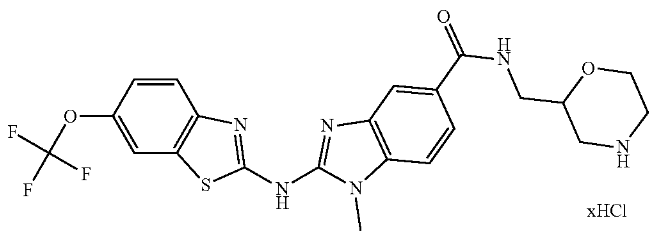 [SMILES: Cn1c(Nc2nc3ccc(OC(F)(F)F)cc3s2)nc2cc(C(=O)NCC3CNCCO3)ccc21] | 1-Methyl-2-(6-trifluoromethoxy-benzothiazol-2-ylamino)-1H-benzoimidazole-5-carboxylic acid (morpholin-2-ylmethyl)-amide hydrochloride |
| 57 | 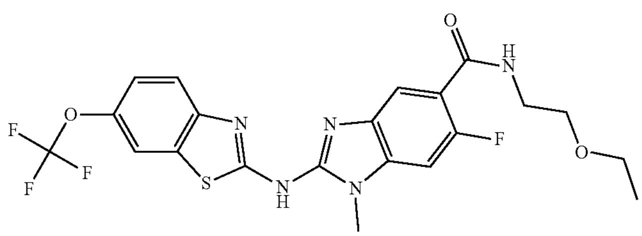 [SMILES: CCOCCNC(=O)c1cc2nc(Nc3nc4ccc(OC(F)(F)F)cc4s3)n(C)c2cc1F] | 6-Fluoro-1-methyl-2-(6-trifluoromethoxy-benzothiazol-2-ylamino)-1H-benzoimidazole-5-carboxylic acid (2-ethoxy-ethyl)-amide |
| 58 | 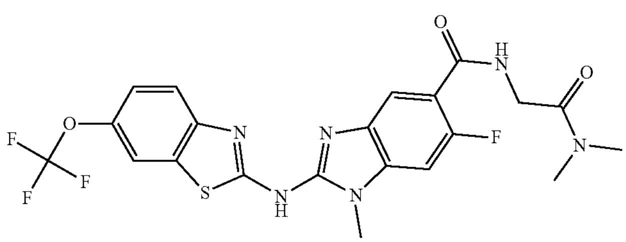 [SMILES: CN(C)C(=O)CNC(=O)c1cc2nc(Nc3nc4ccc(OC(F)(F)F)cc4s3)n(C)c2cc1F] | 6-Fluoro-1-methyl-2-(6-trifluoromethoxy-benzothiazol-2-ylamino)-1H-benzoimidazole-5-carboxylic acid dimethylcarbamoylmethyl-amide |
| 59 | 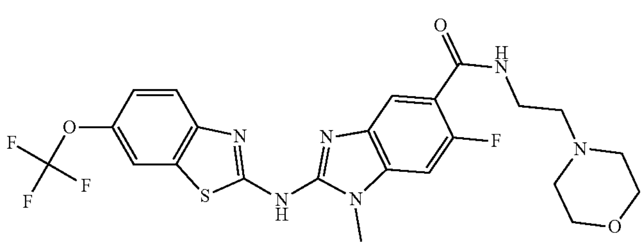 [SMILES: Cn1c(Nc2nc3ccc(OC(F)(F)F)cc3s2)nc2cc(C(=O)NCCN3CCOCC3)c(F)cc21] | 6-Fluoro-1-methyl-2-(6-trifluoromethoxy-benzothiazol-2-ylamino)-1H-benzoimidazole-5-carboxylic acid (2-morpholin-4-yl-ethyl)-amide |
| 60 | 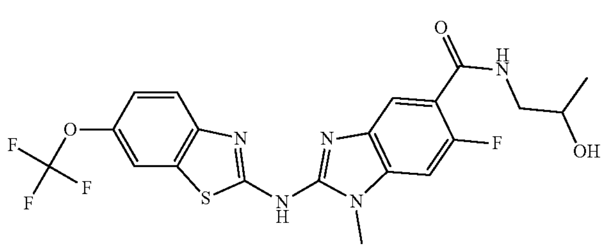 [SMILES: CC(O)CNC(=O)c1cc2nc(Nc3nc4ccc(OC(F)(F)F)cc4s3)n(C)c2cc1F] | 6-Fluoro-1-methyl-2-(6-trifluoromethoxy-benzothiazol-2-ylamino)-1H-benzoimidazole-5-carboxylic acid (2-hydroxy-propyl)-amide |

| No. | Structure | Name |
|---|---|---|
| 61 | 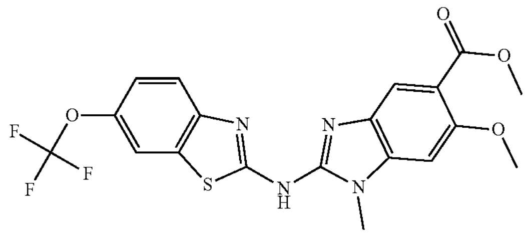 [SMILES: COC(=O)c1cc2nc(Nc3nc4ccc(OC(F)(F)F)cc4s3)n(C)c2cc1OC] | 6-Methoxy-1-methyl-2-(6-trifluoromethoxy-benzothiazol-2-ylamino)-1H-benzoimidazole-5-carboxylic acid methyl ester |
| 62 | 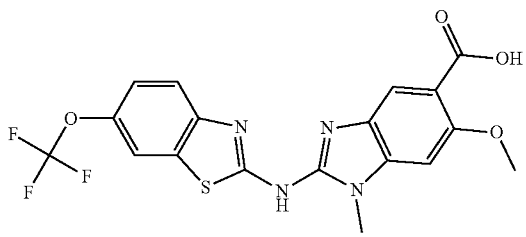 [SMILES: COc1cc2c(cc1C(=O)O)nc(Nc1nc3ccc(OC(F)(F)F)cc3s1)n2C] | 6-Methoxy-1-methyl-2-(6-trifluoromethoxy-benzothiazol-2-ylamino)-1H-benzoimidazole-5-carboxylic acid |
| 63 | 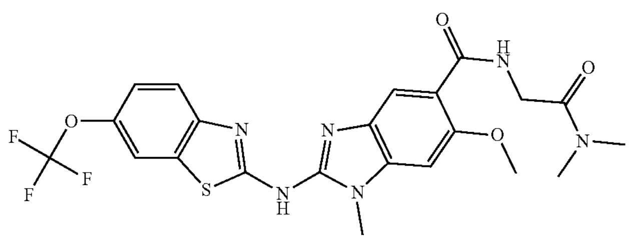 [SMILES: COc1cc2c(cc1C(=O)NCC(=O)N(C)C)nc(Nc1nc3ccc(OC(F)(F)F)cc3s1)n2C] | 6-Methoxy-1-methyl-2-(6-trifluoromethoxy-benzothiazol-2-ylamino)-1H-benzoimidazole-5-carboxylic acid dimethylcarbamoyl-methyl-amide |
| 64 | 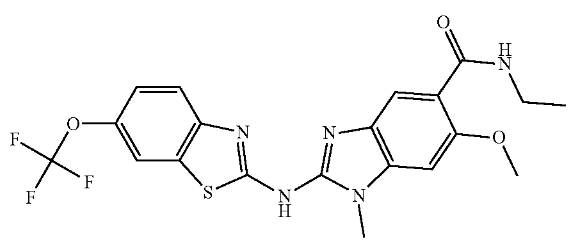 [SMILES: CCNC(=O)c1cc2nc(Nc3nc4ccc(OC(F)(F)F)cc4s3)n(C)c2cc1OC] | 6-Methoxy-1-methyl-2-(6-trifluoromethoxy-benzothiazol-2-ylamino)-1H-benzoimidazole-5-carboxylic acid ethylamide |
| 65 | 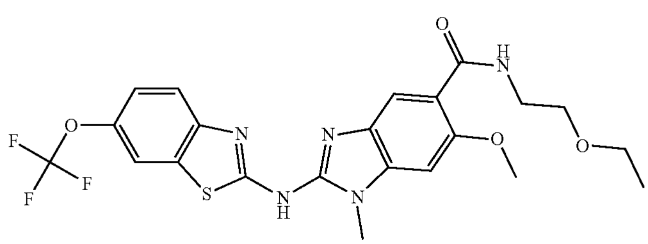 [SMILES: CCOCCNC(=O)c1cc2nc(Nc3nc4ccc(OC(F)(F)F)cc4s3)n(C)c2cc1OC] | 6-Methoxy-1-methyl-2-(6-trifluoromethoxy-benzothiazol-2-ylamino)-1H-benzoimidazole-5-carboxylic acid (2-ethoxy-ethyl)-amide |
| 66 | 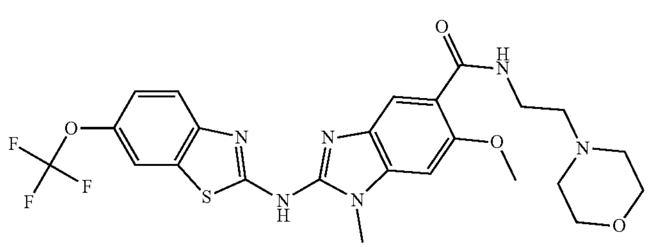 [SMILES: COc1cc2c(cc1C(=O)NCCN1CCOCC1)nc(Nc1nc3ccc(OC(F)(F)F)cc3s1)n2C] | 6-Methoxy-1-methyl-2-(6-trifluoromethoxy-benzothiazol-2-ylamino)-1H-benzoimidazole-5-carboxylic acid (2-morpholin-4-yl-ethyl)-amide |

TABLE 1-continued

| No. | Structure | Name |
|---|---|---|
| 67 | 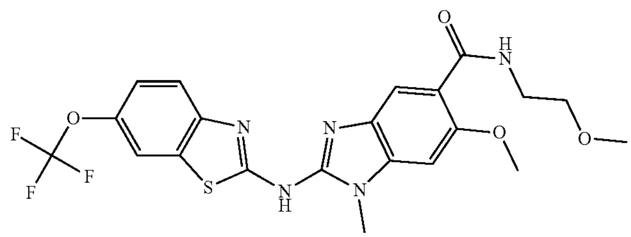 [SMILES: COCCNC(=O)c1cc2nc(Nc3nc4ccc(OC(F)(F)F)cc4s3)n(C)c2cc1OC] | 6-Methoxy-1-methyl-2-(6-trifluoromethoxy-benzothiazol-2-ylamino)-1H-benzoimidazole-5-carboxylic acid (2-methoxy-ethyl)-amide |
| 68 | 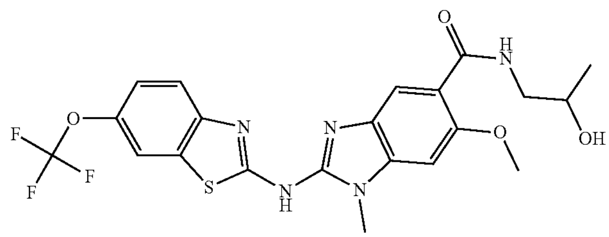 [SMILES: COc1cc2c(cc1C(=O)NCC(C)O)nc(Nc1nc3ccc(OC(F)(F)F)cc3s1)n2C] | 6-Methoxy-1-methyl-2-(6-trifluoromethoxy-benzothiazol-2-ylamino)-1H-benzoimidazole-5-carboxylic acid (2-hydroxy-propyl)-amide |
| 69 | 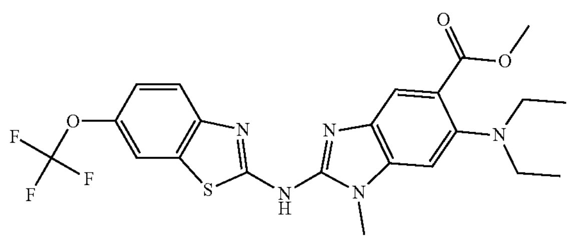 [SMILES: CCN(CC)c1cc2c(cc1C(=O)OC)nc(Nc1nc3ccc(OC(F)(F)F)cc3s1)n2C] | 6-Diehtylamino-1-methyl-2-(6-trifluoromethoxy-benzothiazol-2-ylamino)-1H-benzoimidazole-5-carboxylic acid methyl ester |
| 70 | 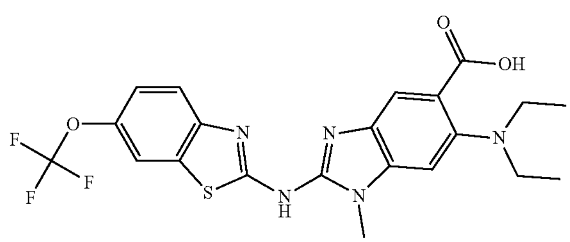 [SMILES: CCN(CC)c1cc2c(cc1C(=O)O)nc(Nc1nc3ccc(OC(F)(F)F)cc3s1)n2C] | 6-Diethylamino-1-methyl-2-(6-trifluoromethoxy-benzothiazol-2-ylamino)-1H-benzoimidazole-5-carboxylic acid |
| 71 | 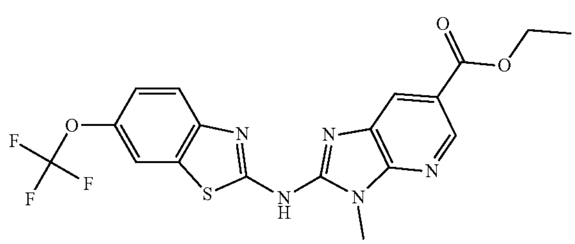 [SMILES: CCOC(=O)c1cnc2c(c1)nc(Nc1nc3ccc(OC(F)(F)F)cc3s1)n2C] | 3-Methyl-2-(6-trifluoromethoxy-benzothiazol-2-ylamino)-3H-imidazo[4,5-b]pyridine-6-carboxylic acid ethyl ester |
| 72 | 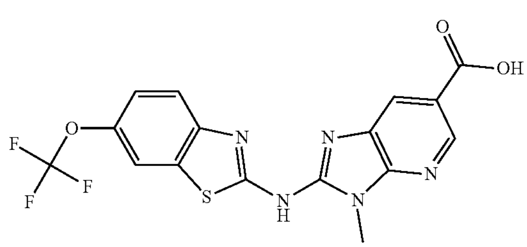 [SMILES: Cn1c(Nc2nc3ccc(OC(F)(F)F)cc3s2)nc2cc(C(=O)O)cnc21] | 3-Methyl-2-(6-trifluoromethoxy-benzothiazol-2-ylamino)-3H-imidazo[4,5-b]pyridine-6-carboxylic acid |

TABLE 1-continued

| No. | Structure | Name |
|---|---|---|
| 73 | 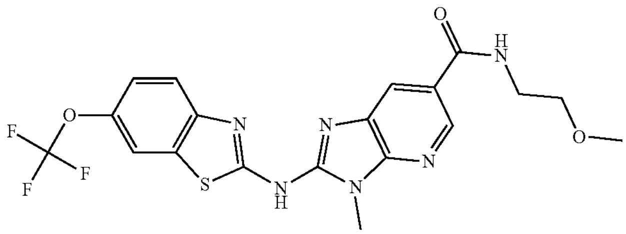 [SMILES: COCCNC(=O)c1cnc2c(c1)nc(Nc1nc3ccc(OC(F)(F)F)cc3s1)n2C] | 3-Methyl-2-(6-trifluoromethoxy-benzothiazol-2-ylamino)-3H-imidazo[4,5-b]pyridine-6-carboxylic acid (2-methoxy-ethyl)-amide |
| 74 | 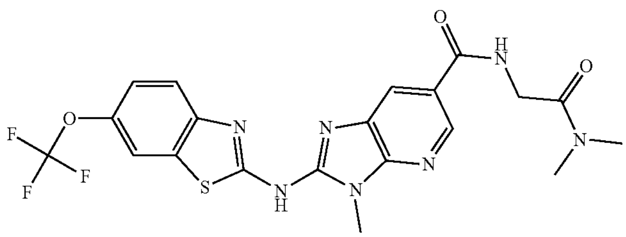 [SMILES: CN(C)C(=O)CNC(=O)c1cnc2c(c1)nc(Nc1nc3ccc(OC(F)(F)F)cc3s1)n2C] | 3-Methyl-2-(6-trifluoromethoxy-benzothiazol-2-ylamino)-3H-imidazo[4,5-b]pyridine-6-carboxylic acid dimethylcarbamoylmethyl-amide |
| 75 | 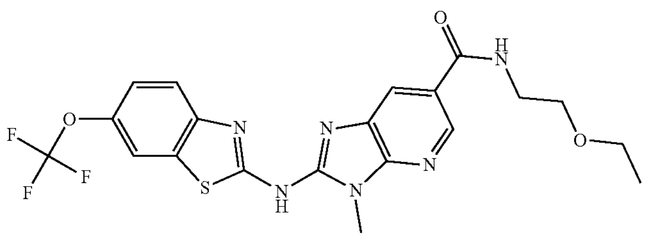 [SMILES: CCOCCNC(=O)c1cnc2c(c1)nc(Nc1nc3ccc(OC(F)(F)F)cc3s1)n2C] | 3-Methyl-2-(6-trifluoromethoxy-benzothiazol-2-ylamino)-3H-imidazo[4,5-b]pyridine-6-carboxylic acid (2-ethoxy-ethyl)-amide |
| 76 | 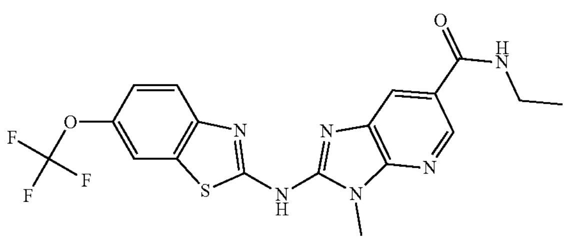 [SMILES: CCNC(=O)c1cnc2c(c1)nc(Nc1nc3ccc(OC(F)(F)F)cc3s1)n2C] | 3-Methyl-2-(6-trifluoromethoxy-benzothiazol-2-ylamino)-3H-imidazo[4,5-b]pyridine-6-carboxylic acid ethylamide |
| 77 | 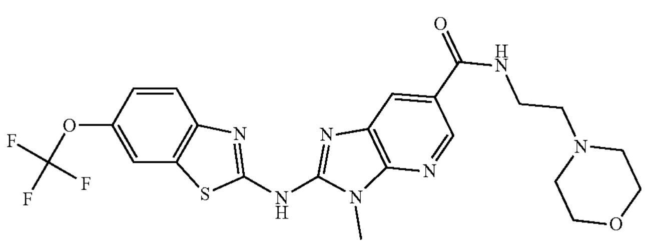 [SMILES: Cn1c(Nc2nc3ccc(OC(F)(F)F)cc3s2)nc2cc(C(=O)NCCN3CCOCC3)cnc21] | 3-Methyl-2-(6-trifluoromethoxy-benzothiazol-2-ylamino)-3H-imidazo[4,5-b]pyridine-6-carboxylic acid (2-morpholin-4-yl-ethyl)-amide |
| 78 | 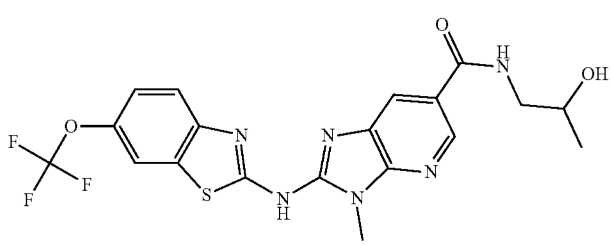 [SMILES: CC(O)CNC(=O)c1cnc2c(c1)nc(Nc1nc3ccc(OC(F)(F)F)cc3s1)n2C] | 3-Methyl-2-(6-trifluoromethoxy-benzothiazol-2-ylamino)-3H-imidazo[4,5-b]pyridine-6-carboxylic acid (2-hydroxy-propyl)-amide |

TABLE 1-continued

| No. | Structure | Name |
|---|---|---|
| 79 | 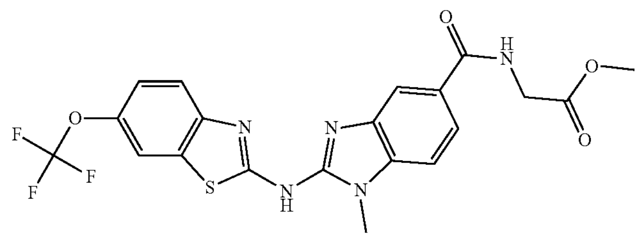 [SMILES: COC(=O)CNC(=O)c1ccc2c(c1)nc(Nc1nc3ccc(OC(F)(F)F)cc3s1)n2C] | {[1-Methyl-2-(6-trifluoromethoxy-benzothiazol-2-ylamino)-1H-benzoimidazole-5-carbonyl]-amino}-acetic acid methyl ester |
| 80 | 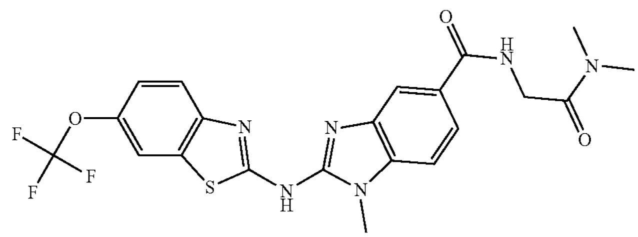 [SMILES: CN(C)C(=O)CNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid dimethylcarbamoylmethyl-amide |
| 81 | 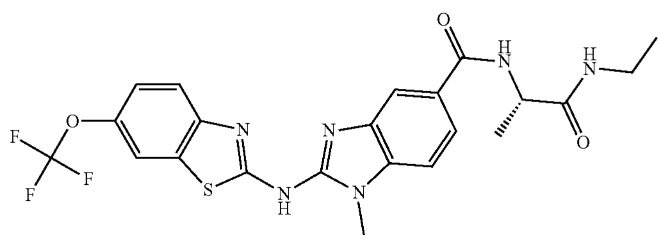 [SMILES: CCNC(=O)[C@H](C)NC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid ((S)-1-ethylcarbamooyl-ethyl)-amide |
| 82 | 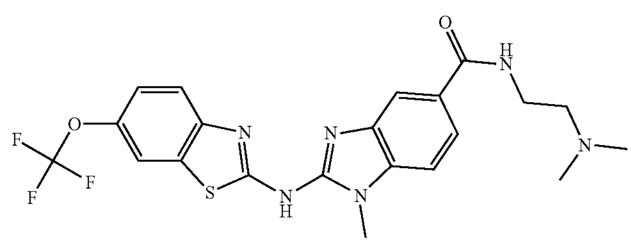 [SMILES: CN(C)CCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid (2-dimethylamino-ethyl)-amide |
| 83 | 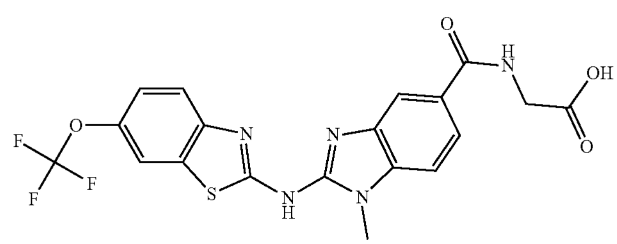 [SMILES: Cn1c(Nc2nc3ccc(OC(F)(F)F)cc3s2)nc2cc(C(=O)NCC(=O)O)ccc21] | {[1-Methyl-2-(6-trifluoromethoxy-benzothiazol-2-ylamino)-1H-benzoimidazole-5-carbonyl]-amino}-acetic acid |
| 84 | 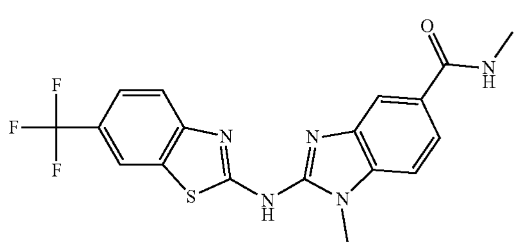 [SMILES: CNC(=O)c1ccc2c(c1)nc(Nc1nc3ccc(C(F)(F)F)cc3s1)n2C] | 1-Methyl-2-(6-trifluoromethyl-benzothiazol-2-ylamino)-1H-benzoimidazole-5-carboxylic acid methylamide |

TABLE 1-continued

| No. | Structure | Name |
|---|---|---|
| 85 | 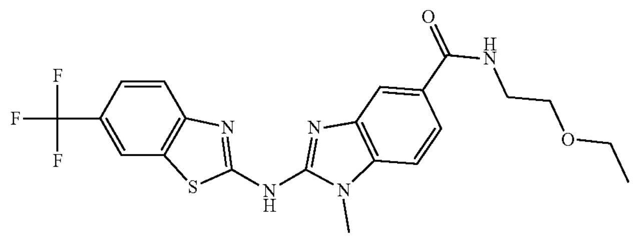 [SMILES: CCOCCNC(=O)c1ccc2c(c1)nc(Nc1nc3ccc(C(F)(F)F)cc3s1)n2C] | 1-Methyl-2-(6-trifluoromethyl-benzothiazol-2-ylamino)-1H-benzoimidazole-5-carboxylic acid (2-ethoxy-ethyl)-amide |
| 86 | 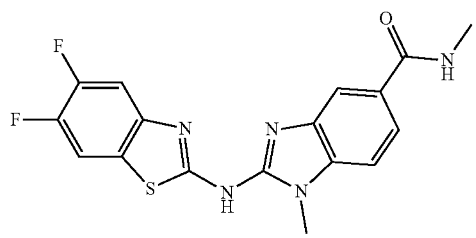 [SMILES: CNC(=O)c1ccc2c(c1)nc(Nc1nc3cc(F)c(F)cc3s1)n2C] | 2-(5,6-Difluoro-benzothiazol-2-ylamino)-1-methyl-1H-benzoimidazole-5-carboxylic acid methylamide |
| 87 | 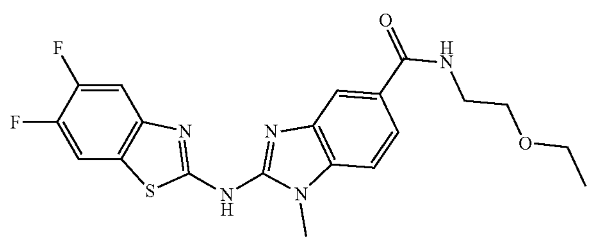 [SMILES: CCOCCNC(=O)c1ccc2c(c1)nc(Nc1nc3cc(F)c(F)cc3s1)n2C] | 2-(5,6-Difluoro-benzothiazol-2-ylamino)-1-methyl-1H-benzoimidazole-5-carboxylic acid (2-ethoxy-ethyl)-amide |
| 88 | 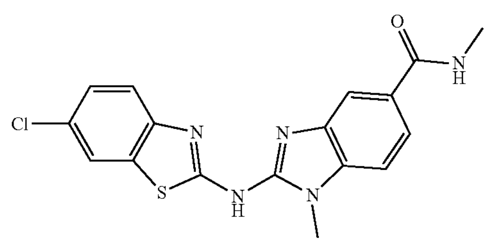 [SMILES: CNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid methylamide |
| 89 | 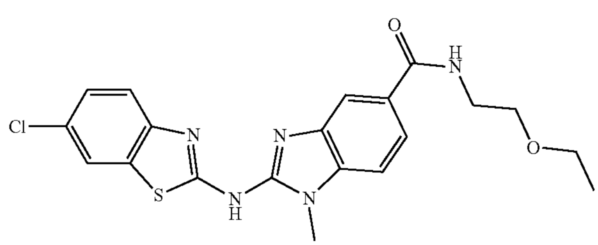 [SMILES: CCOCCNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid (2-ethoxy-ethyl)-amide |
| 90 | 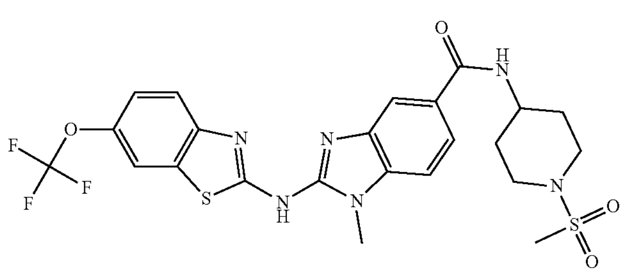 [SMILES: Cn1c(Nc2nc3ccc(OC(F)(F)F)cc3s2)nc2cc(C(=O)NC3CCN(S(C)(=O)=O)CC3)ccc21] | 1-Methyl-2-(6-trifluoromethoxy-benzothiazol-2-ylamino)-1H-benzoimidazole-5-carboxylic acid (1-methanesulfonyl-piperidin-4-yl)-amide |

TABLE 1-continued

| No. | Structure | Name |
|---|---|---|
| 91 | 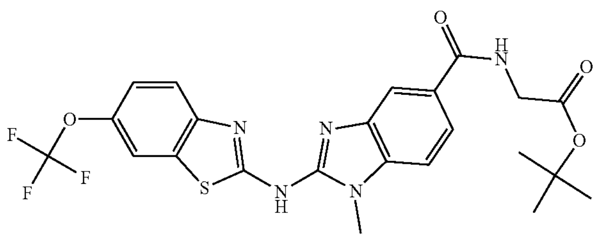 [SMILES: Cn1c(Nc2nc3ccc(OC(F)(F)F)cc3s2)nc2cc(C(=O)NCC(=O)OC(C)(C)C)ccc21] | {[1-Methyl-2-(6-trifluoromethoxy-benzothiazol-2-ylamino)-1H-benzoimidazole-5-carbonyl]-amino}-acetic acid tert-butyl ester |
| 92 | 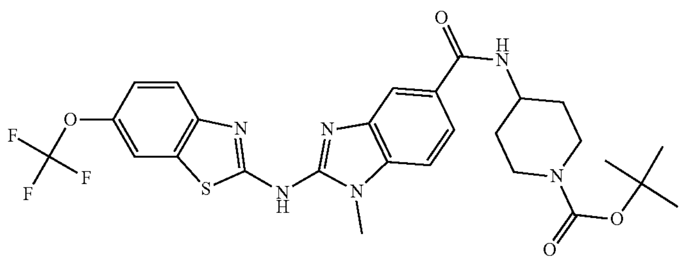 [SMILES: Cn1c(Nc2nc3ccc(OC(F)(F)F)cc3s2)nc2cc(C(=O)NC3CCN(C(=O)OC(C)(C)C)CC3)ccc21] | 4-{[1-Methyl-2-(6-trifluoromethoxy-benzothiazol-2-ylamino)-1H-benzoimidazole-5-carbonyl]-amino}-piperidine-1-carboxylic acid tert-butyl ester |
| 93 | 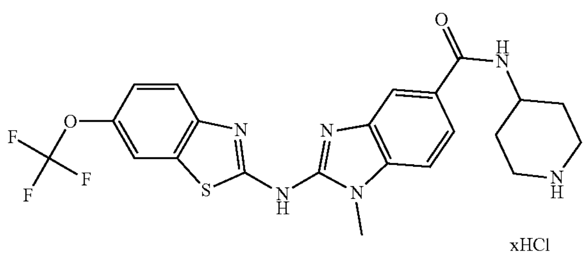 [SMILES: Cn1c(Nc2nc3ccc(OC(F)(F)F)cc3s2)nc2cc(C(=O)NC3CCNCC3)ccc21] | 1-Methyl-2-(6-trifluoromethoxy-benzothiazol-2-ylamino)-1H-benzoimidazole-5-carboxylic acid piperidin-4-ylamide hydrochloride |
| 94 | 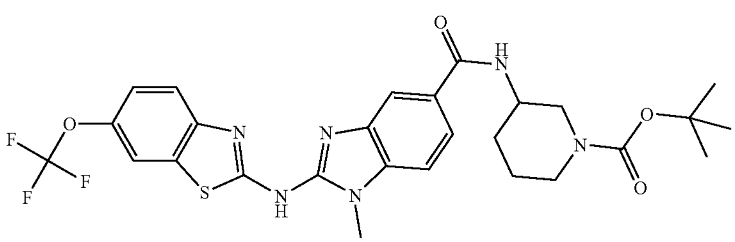 [SMILES: Cn1c(Nc2nc3ccc(OC(F)(F)F)cc3s2)nc2cc(C(=O)NC3CCCN(C(=O)OC(C)(C)C)C3)ccc21] | 3-{[1-Methyl-2-(6-trifluoromethoxy-benzothiazol-2-ylamino)-1H-benzoimidazole-5-carbonyl]-amino}-piperidine-1-carboxylic acid tert-butyl ester |
| 95 | 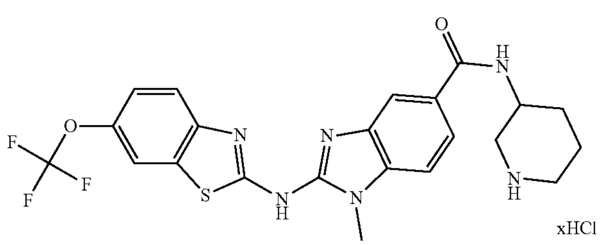 [SMILES: Cn1c(Nc2nc3ccc(OC(F)(F)F)cc3s2)nc2cc(C(=O)NC3CCCNC3)ccc21] | 1-Methyl-2-(6-trifluoromethoxy-benzothiazol-2-ylamino)-1H-benzoimidazole-5-carboxylic acid piperidin-3-ylamide hydrochloride |
| 96 | 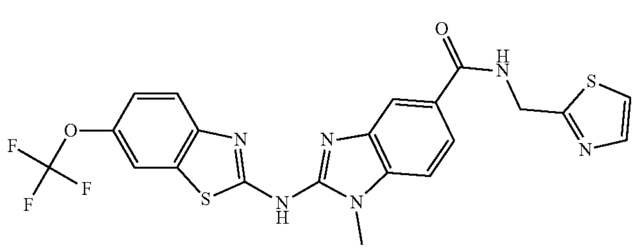 [SMILES: Cn1c(Nc2nc3ccc(OC(F)(F)F)cc3s2)nc2cc(C(=O)NCc3nccs3)ccc21] | 1-Methyl-2-(6-trifluoromethoxy-benzothiazol-2-ylamino)-1H-benzoimidazole-5-carboxylic acid (thiazol-2-ylmethyl)-amide |

TABLE 1-continued

| No. | Structure | Name |
|---|---|---|
| 97 | 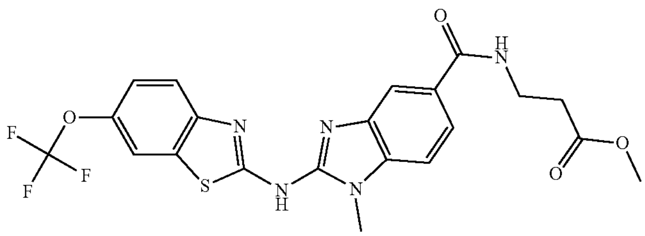 [SMILES: COC(=O)CCNC(=O)c1ccc2c(c1)nc(Nc1nc3ccc(OC(F)(F)F)cc3s1)n2C] | 3-{[1-Methyl-2-(6-trifluoromethoxy-benzothiazol-2-ylamino)-1H-benzoimidazole-5-carbonyl]-amino}-propionic acid methyl ester |
| 98 | 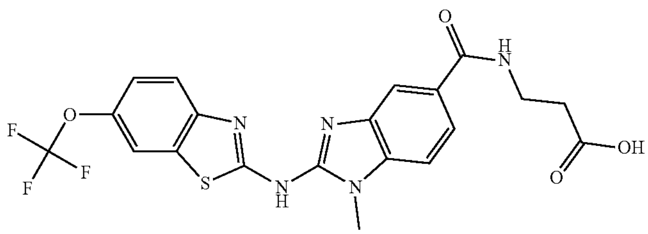 [SMILES: Cn1c(Nc2nc3ccc(OC(F)(F)F)cc3s2)nc2cc(C(=O)NCCC(=O)O)ccc21] | 3-{[2-(6-Trifluoromethoxy-benzothiazol-2-ylamino)-1-methyl-1H-benzimidazole-5-carbonyl]-amino}-propionic acid |
| 99 | 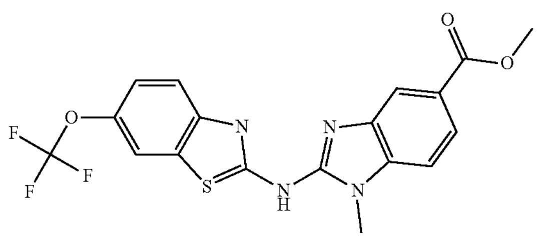 | 1-Methyl-2-(5-trifluoromethoxy-benzothiazol-2-ylamino)-1H-benzoimidazole-5-carboxylic acid methyl ester |
| 100 | 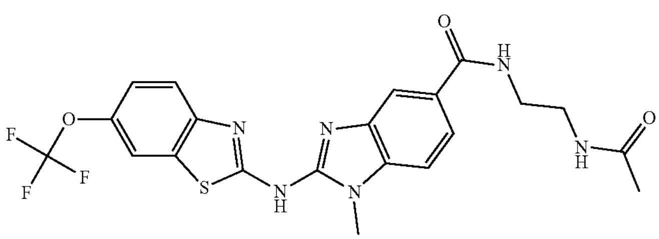 [SMILES: CC(=O)NCCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid (2-acetylamino-ethyl)-amide |
| 101 | 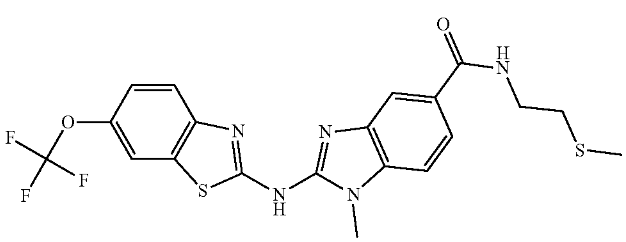 [SMILES: CSCCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid (2-methylsulfanyl-ethyl)-amide |
| 102 | 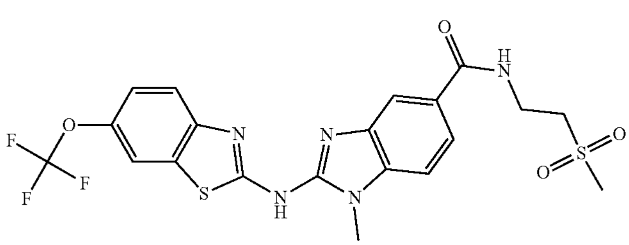 [SMILES: Cn1c(Nc2nc3ccc(OC(F)(F)F)cc3s2)nc2cc(C(=O)NCCS(C)(=O)=O)ccc21] | 1-Methyl-2-(6-trifluoromethoxy-benzothiazol-2-ylamino)-1H-benzoimidazole-5-carboxylic acid (2-methanesulfonyl-ethyl)-amide |

TABLE 1-continued

| No. | Structure | Name |
|---|---|---|
| 103 | 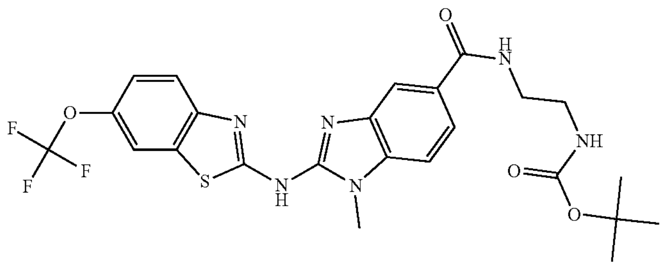 [SMILES: Cn1c(Nc2nc3ccc(OC(F)(F)F)cc3s2)nc2cc(C(=O)NCCNC(=O)OC(C)(C)C)ccc21] | (2-{[1-Methyl-2-(6-trifluoromethoxy-benzothiazol-2-ylamino)-1H-benzoimidazole-5-carbonyl]-amino}-ethyl)-carbamic acid tert-butyl ester |
| 104 | xHCl | 1-Methyl-2-(6-trifluoromethoxy-benzothiazol-2-ylamino)-1H-benzoimidazole-5-carboxylic acid (2-amino-ethyl)-amide hydrochloride |
| 105 | 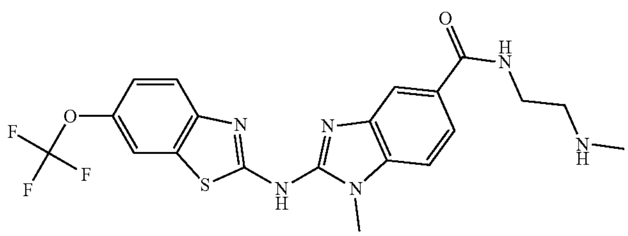 | 1-Methyl-2-(6-trifluoromethoxy-benzothiazol-2-ylamino)-1H-benzoimidazole-5-carboxylic acid (2-methylamino-ethyl)-amide |
| 106 | 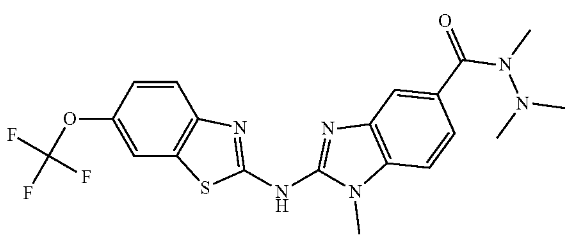 [SMILES: CN(C)N(C)C(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid trimethylhydrazide |
| 107 | 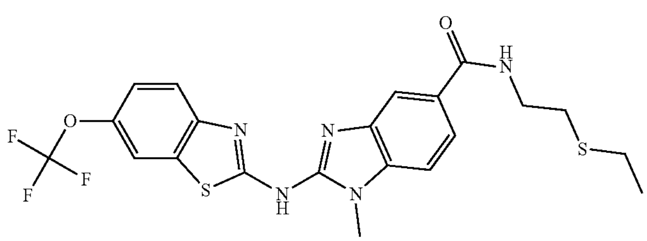 [SMILES: CCSCCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid (2-ethylsulfanyl-ethyl)-amide |
| 108 | 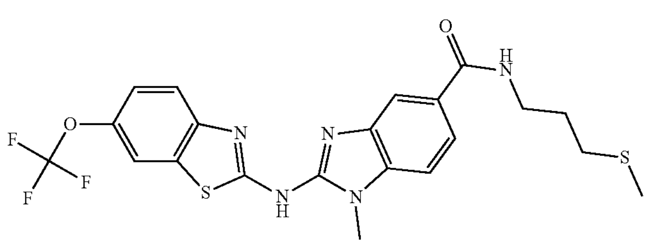 [SMILES: CSCCCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid (3-methylsulfanyl-propyl)-amide |

TABLE 1-continued

| No. | Structure | Name |
|---|---|---|
| 109 | 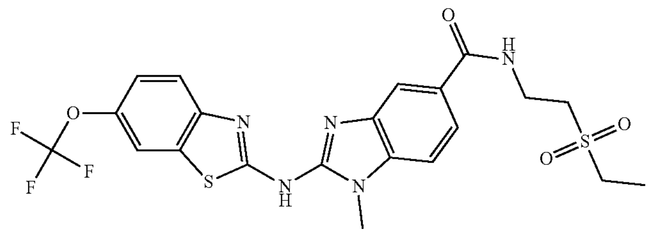 [SMILES: CCS(=O)(=O)CCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid (2-ethanesulfonyl-ethyl)-amide |
| 110 | 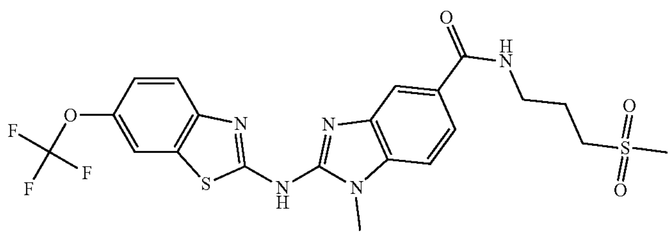 [SMILES: Cn1c(Nc2nc3ccc(OC(F)(F)F)cc3s2)nc2cc(C(=O)NCCCS(C)(=O)=O)ccc21] | 1-Methyl-2-(6-trifluoromethoxy-benzothiazol-2-ylamino)-1H-benzoimidazole-5-carboxylic acid (3-methanesulfonyl-propyl)-amide |
| 111 | 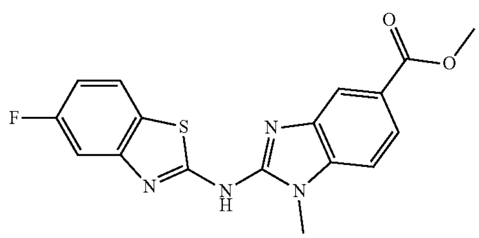 [SMILES: COC(=O)c1ccc2c(c1)nc(Nc1nc3cc(F)ccc3s1)n2C] | 2-(5-Fluoro-benzothiazol-2-ylamino)-1-methyl-1H-benzoimidazole-5-carboxylic acid methyl ester |
| 112 | 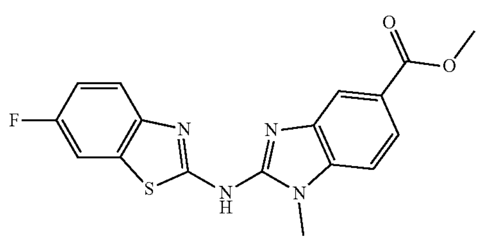 [SMILES: COC(=O)c1ccc2c(c1)nc(Nc1nc3ccc(F)cc3s1)n2C] | 2-(6-Fluoro-benzothiazol-2-ylamino)-1-methyl-1H-benzoimidazole-5-carboxylic acid methyl ester |
| 113 | 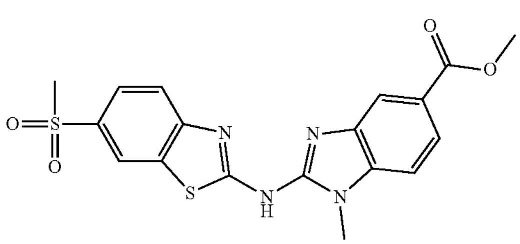 [SMILES: COC(=O)c1ccc2c(c1)nc(Nc1nc3ccc(S(C)(=O)=O)cc3s1)n2C] | 2-(6-Methanesulfonyl-benzothiazol-2-ylamino)-1-methyl-1H-benzoimidazole-5-carboxylic acid methyl ester |
| 114 | 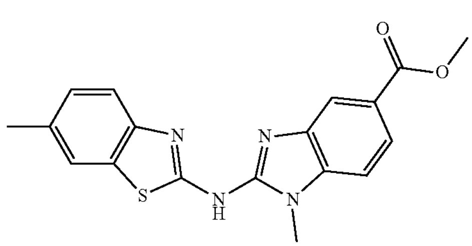 | 1-Methyl-2-(6-methyl-benzothiazol-2-ylamino)-1H-benzoimidazole-5-carboxylic acid methyl ester |

TABLE 1-continued

| No. | Structure | Name |
|---|---|---|
| 115 | 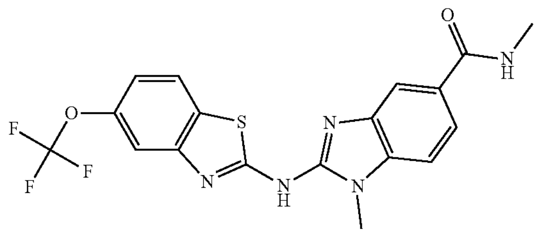 | 1-Methyl-2-(5-trifluoromethoxy-benzothiazol-2-ylamino)-1H-benzoimidazole-5-carboxylic acid methylamide |
| 116 | 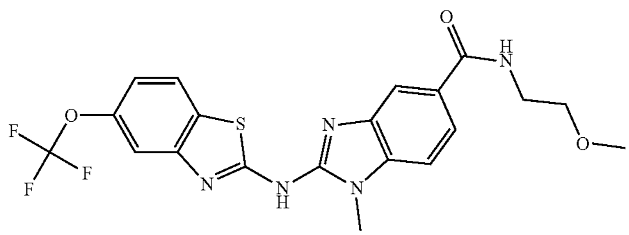 [SMILES: COCCNC(=O)c1ccc2c(c1)nc(Nc1nc3cc(OC(F)(F)F)ccc3s1)n2C] | 1-Methyl-2-(5-trifluoromethoxy-benzothiazol-2-ylamino)-1H-benzoimidazole-5-carboxylic acid (2-methoxy-ethyl)-amide |
| 117 | 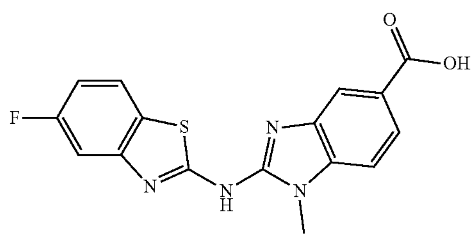 [SMILES: Cn1c(Nc2nc3cc(F)ccc3s2)nc2cc(C(=O)O)ccc21] | 2-(5-Fluoro-benzothiazol-2-ylamino)-1-methyl-1H-benzimidazole-5-carboxylic acid |
| 118 | 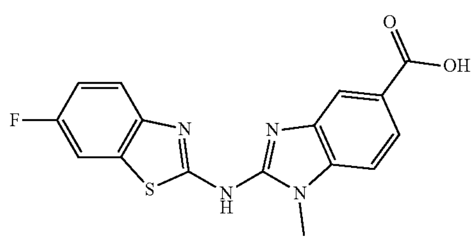 [SMILES: Cn1c(Nc2nc3ccc(F)cc3s2)nc2cc(C(=O)O)ccc21] | 2-(6-Fluoro-benzothiazol-2-ylamino)-1-methyl-1H-benzoimidazole-5-carboxylic acid |
| 119 | 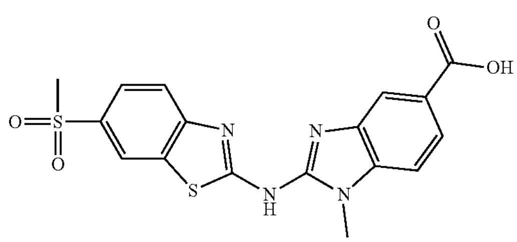 [SMILES: Cn1c(Nc2nc3ccc(S(C)(=O)=O)cc3s2)nc2cc(C(=O)O)ccc21] | 2-(6-Methanesulfonyl-benzothiazol-2-ylamino)-1-methyl-1H-benzimidazole-5-carboxylic acid |
| 120 | 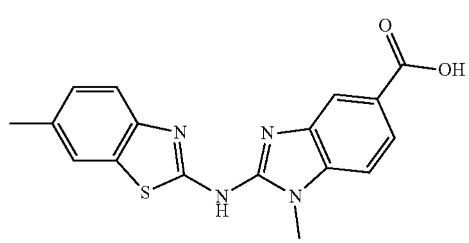 [SMILES: Cc1ccc2nc(Nc3nc4cc(C(=O)O)ccc4n3C)sc2c1] | 1-Methyl-2-(6-methyl-benzothiazol-2-ylamino)-1H-benzimidazole-5-carboxylic acid |

TABLE 1-continued

| No. | Structure | Name |
|---|---|---|
| 121 | 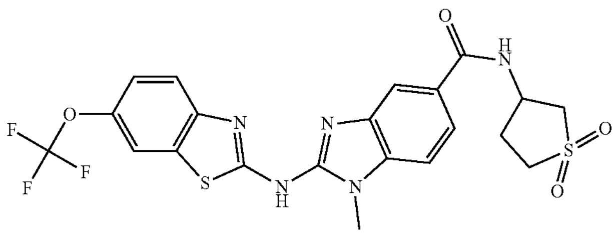 [SMILES: Cn1c(Nc2nc3ccc(OC(F)(F)F)cc3s2)nc2cc(C(=O)NC3CCS(=O)(=O)C3)ccc21] | 1-Methyl-2-(6-trifluoromethoxy-benzothiazol-2-ylamino)-1H-benzoimidazole-5-carboxylic acid (1,1-dioxo-tetrahydro-1λ$^6$-thiophen-3-yl)-amide |
| 122 | 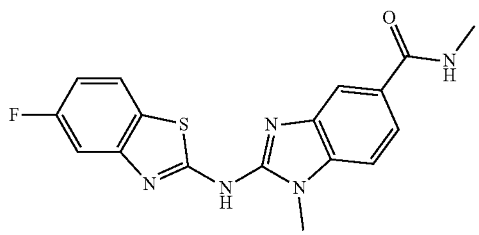 [SMILES: CNC(=O)c1ccc2c(c1)nc(Nc1nc3cc(F)ccc3s1)n2C] | 2-(5-Fluoro-benzothiazol-2-ylamino)-1-methyl-1H-benzimidazole-5-carboxylic acid methylamide |
| 123 | 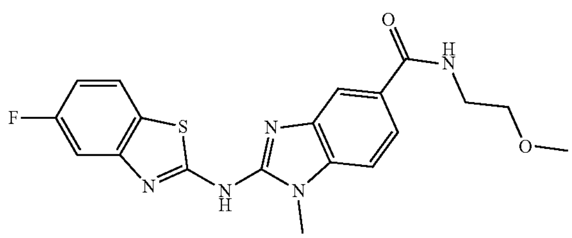 [SMILES: COCCNC(=O)c1ccc2c(c1)nc(Nc1nc3cc(F)ccc3s1)n2C] | 2-(5-Fluoro-benzothiazol-2-ylamino)-1-methyl-1H-benzimidazole-5-carboxylic acid (2-methoxy-ethyl)-amide |
| 124 | 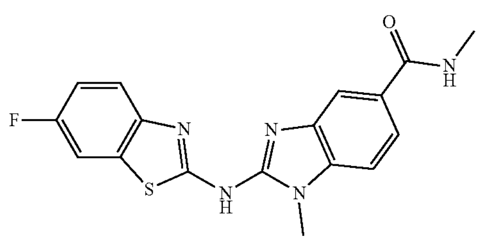 [SMILES: CNC(=O)c1ccc2c(c1)nc(Nc1nc3ccc(F)cc3s1)n2C] | 2-(6-Fluoro-benzothiazol-2-ylamino)-1-methyl-1H-benzimidazole-5-carboxylic acid methylamide |
| 125 | 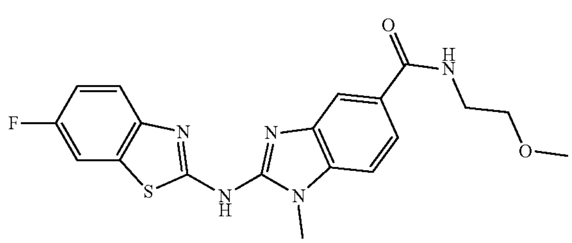 [SMILES: COCCNC(=O)c1ccc2c(c1)nc(Nc1nc3ccc(F)cc3s1)n2C] | 2-(6-Fluoro-benzothiazol-2-ylamino)-1-methyl-1H-benzimidazole-5-carboxylic acid (2-methoxy-ethyl)-amide |
| 126 | 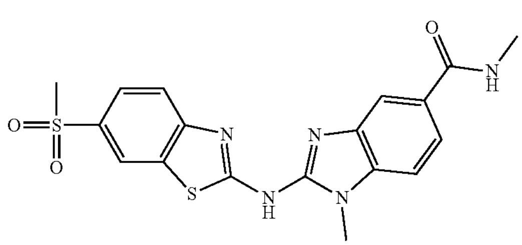 [SMILES: CNC(=O)c1ccc2c(c1)nc(Nc1nc3ccc(S(C)(=O)=O)cc3s1)n2C] | 2-(6-Methanesulfonyl-benzothiazol-2-ylamino)-1-methyl-1H-benzimidazole-5-carboxylic acid methylamide |

TABLE 1-continued

| No. | Structure | Name |
|---|---|---|
| 127 | 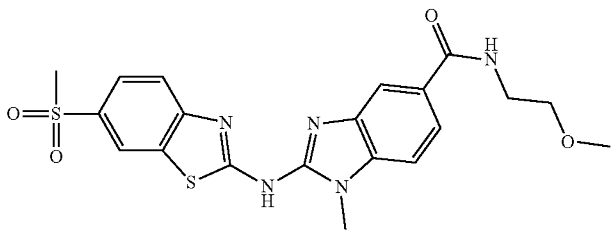 [SMILES: COCCNC(=O)c1ccc2c(c1)nc(Nc1nc3ccc(S(C)(=O)=O)cc3s1)n2C] | 2-(6-Methanesulfonyl-benzothiazol-2-ylamino)-1-methyl-1H-benzimidazole-5-carboxylic acid (2-methoxy-ethyl)-amide |
| 128 | 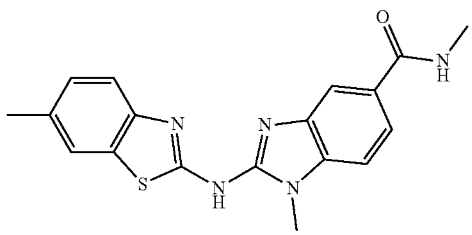 | 2-(6-Methyl-benzothiazol-2-ylamino)-1-methyl-1H-benzimidazole-5-carboxylic acid methylamide |
| 129 | 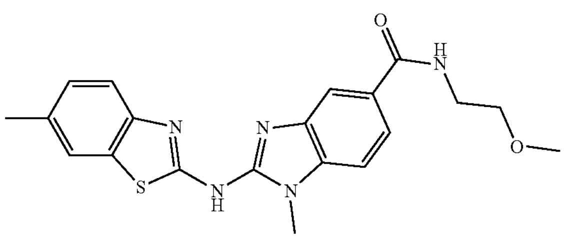 | 2-(6-Methyl-benzothiazol-2-ylamino)-1-methyl-1H-benzimidazole-5-carboxylic acid (2-methoxy-ethyl)-amide |
| 130 | 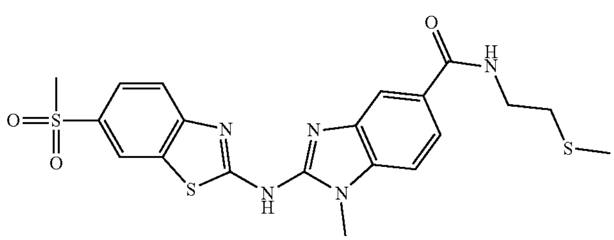 [SMILES: CSCCNC(=O)c1ccc2c(c1)nc(Nc1nc3ccc(S(C)(=O)=O)cc3s1)n2C] | 2-(6-Methanesulfonyl-benzothiazol-2-ylamino)-1-methyl-1H-benzimidazole-5-carboxylic acid (2-methylsulfanyl-ethyl)-amide |
| 131 | 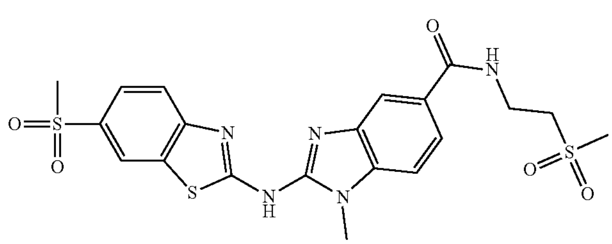 [SMILES: Cn1c(Nc2nc3ccc(S(C)(=O)=O)cc3s2)nc2cc(C(=O)NCCS(C)(=O)=O)ccc21] | 2-(6-Methanesulfonyl-benzothiazol-2-ylamino)-1-methyl-1H-benzimidazole-5-carboxylic acid (2-methylsulfonyl-ethyl)-amide |
| 132 | 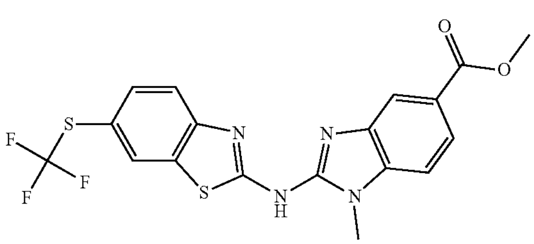 [SMILES: COC(=O)c1ccc2c(c1)nc(Nc1nc3ccc(SC(F)(F)F)cc3s1)n2C] | 1-Methyl-2-(6-trifluoromethylsulfanyl-benzothiazol-2-ylamino)-1H-benzimidazole-5-carboxylic acid methyl ester |

TABLE 1-continued

| No. | Structure | Name |
|---|---|---|
| 133 | 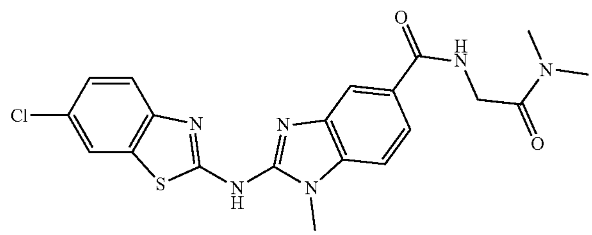 [SMILES: CN(C)C(=O)CNC(=O)c1ccc2c(c1)nc(Nc1nc3ccc(Cl)cc3s1)n2C] | 2-(6-Chloro-benzothiazol-2-ylamino)-1-methyl-1H-benzimidazole-5-carboxylic acid dimethylcarbamoylmethyl-amide |
| 134 | 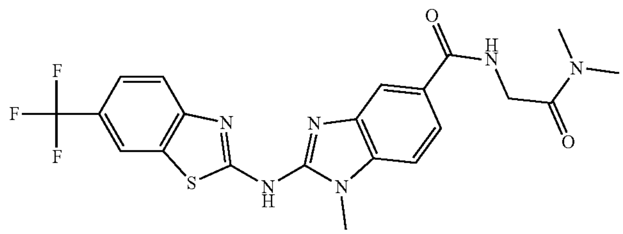 [SMILES: CN(C)C(=O)CNC(=O)c1ccc2c(c1)nc(Nc1nc3ccc(C(F)(F)F)cc3s1)n2C] | 1-Methyl-2-(6-trifluoromethyl-benzothiazol-2-ylamino)-1H-benzimidazole-5-carboxylic acid dimethylcarbamoylmethyl-amide |
| 135 | 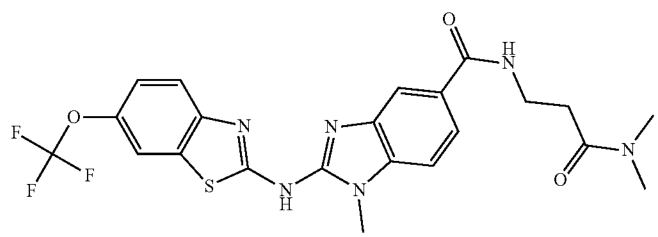 [SMILES: CN(C)C(=O)CCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid (2-dimethylcarbamoyl-ethyl)-amide |
| 136 | 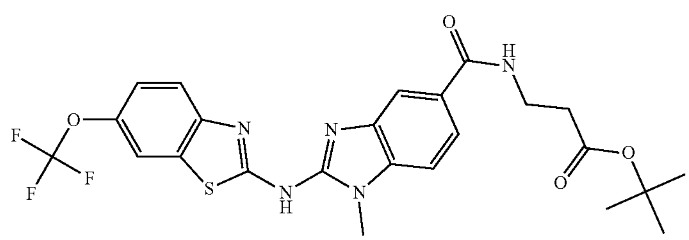 [SMILES: Cn1c(Nc2nc3ccc(OC(F)(F)F)cc3s2)nc2cc(C(=O)NCCC(=O)OC(C)(C)C)ccc21] | 3-{[1-Methyl-2-(6-trifluoromethoxy-benzothiazol-2-ylamino)-1H-benzimidazole-5-carbony]-amino}-propionic acid tert-butyl ester |
| 137 | 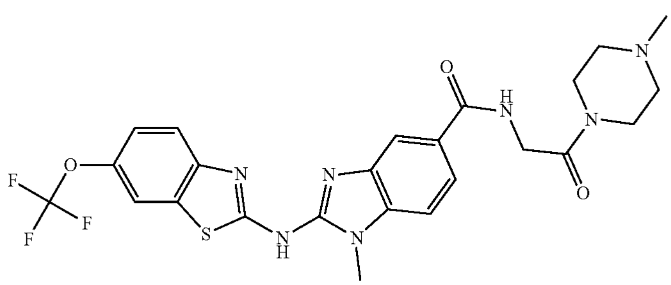 [SMILES: CN1CCN(C(=O)CNC(=O)c2ccc3c(c2)nc(Nc2nc4ccc(OC(F)(F)F)cc4s2)n3C)CC1] | 1-Methyl-2-(6-trifluoromethoxy-benzothiazol-2-ylamino)-1H-benzoimidazole-5-carboxylic acid [2-(4-methyl-piperazin-1-yl)-2-oxo-ethyl]-amide |
| 138 | 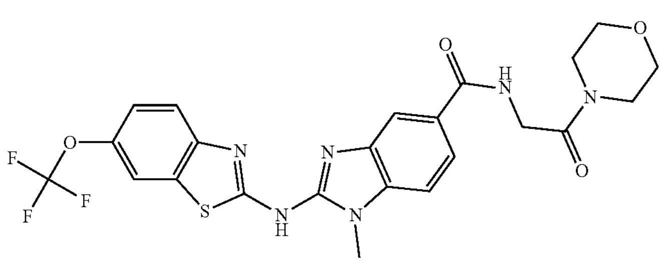 [SMILES: Cn1c(Nc2nc3ccc(OC(F)(F)F)cc3s2)nc2cc(C(=O)NCC(=O)N3CCOCC3)ccc21] | 1-Methyl-2-(6-trifluoromethoxy-benzothiazol-2-ylamino)-1H-benzoimidazole-5-carboxylic acid (2-morpholin-4-yl-2-oxo-ethyl)-amide |

TABLE 1-continued

| No. | Structure | Name |
|---|---|---|
| 139 | 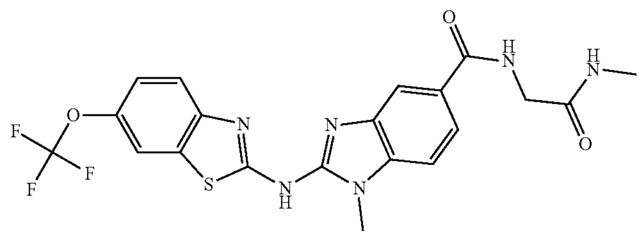 [SMILES: CNC(=O)CNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid methylcarbamoylmethyl-amide |
| 140 | 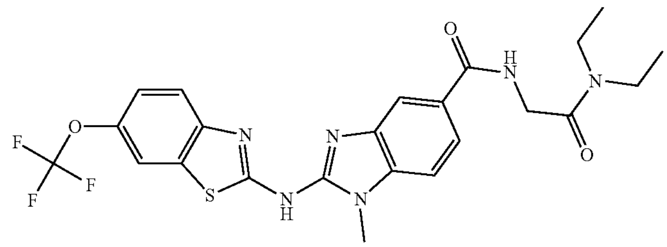 [SMILES: CCN(CC)C(=O)CNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid diethylcarbamoylmethyl-amide |
| 141 | 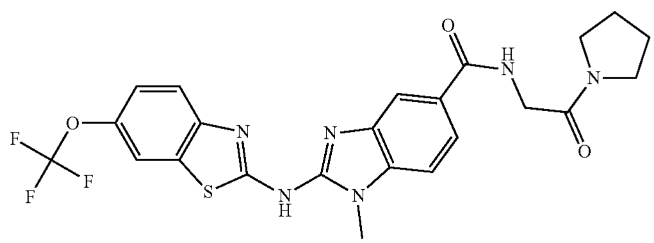 [SMILES: Cn1c(Nc2nc3ccc(OC(F)(F)F)cc3s2)nc2cc(C(=O)NCC(=O)N3CCCC3)ccc21] | 1-Methyl-2-(6-trifluoromethoxy-benzothiazol-2-ylamino)-1H-benzoimidazole-5-carboxylic acid (2-oxo-2-pyrrolidin-1-yl-ethyl)-amide |
| 142 | 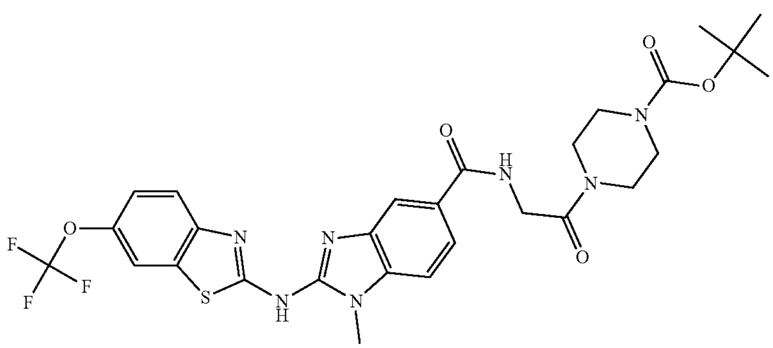 [SMILES: Cn1c(Nc2nc3ccc(OC(F)(F)F)cc3s2)nc2cc(C(=O)NCC(=O)N3CCN(C(=O)OC(C)(C)C)CC3)ccc21] | 4-(2-{[1-Methyl-2-(6-trifluoromethoxy-benzothiazol-2-ylamino)-1H-benzimidazole-5-carbonyl]-amino}-acetyl)-piperazine-1-carboxylic acid tert-butyl ester |
| 143 | 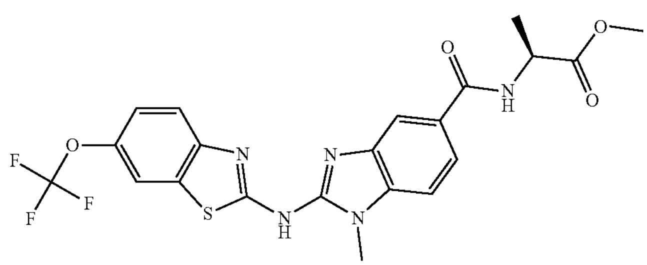 [SMILES: COC(=O)[C@H](C)NC(=O)c1ccc2c(c1)nc(Nc1nc3ccc(OC(F)(F)F)cc3s1)n2C] | (S)-2-{[1-Methyl-2-(6-trifluoromethoxy-benzothiazol-2-ylamino)-1H-benzimidazole-5-carbonyl]-amino}-propionic acid methyl ester |
| 144 | 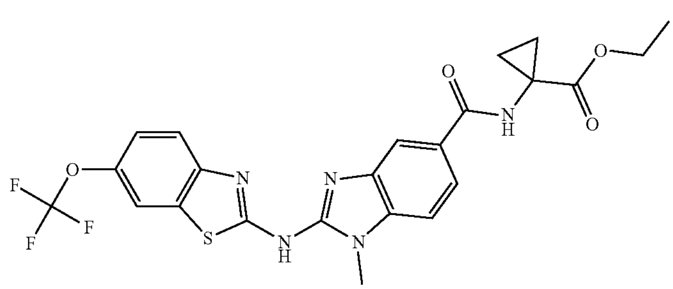 [SMILES: CCOC(=O)C1(NC(=O)c2ccc3c(c2)nc(Nc2nc4ccc(OC(F)(F)F)cc4s2)n3C)CC1] | 1-{[1-Methyl-2-(6-trifluoromethoxy-benzothiazol-2-ylamino)-1H-benzimidazole-5-carbonyl]-amino}-cyclopropanecarboxylic acid ethyl ester |

TABLE 1-continued

| No. | Structure | Name |
|---|---|---|
| 145 | 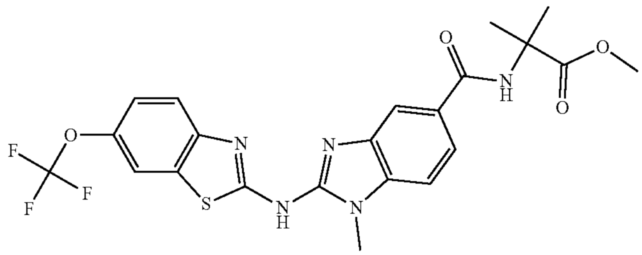 [SMILES: COC(=O)C(C)(C)NC(=O)c1ccc2c(c1)nc(Nc1nc3ccc(OC(F)(F)F)cc3s1)n2C] | 2-Methyl-2-{[1-methyl-2-(6-trifluoromethoxy-benzothiazol-2-ylamino)-1H-benzimidazole-5-carbonyl]-amino}-propionic acid methyl ester |
| 146 | 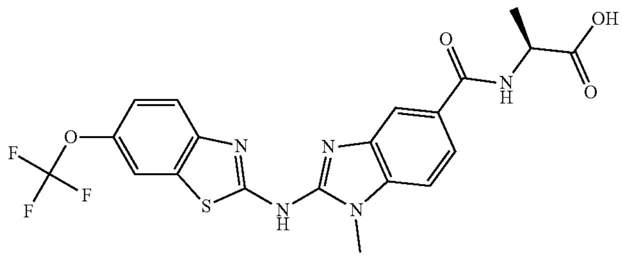 [SMILES: C[C@H](NC(=O)c1ccc2c(c1)nc(Nc1nc3ccc(OC(F)(F)F)cc3s1)n2C)C(=O)O] | (S)-2-{[1-Methyl-2-(6-trifluoromethoxy-benzothiazol-2-ylamino)-1H-benzimidazole-5-carbonyl]-amino}-propionic acid |
| 147 | 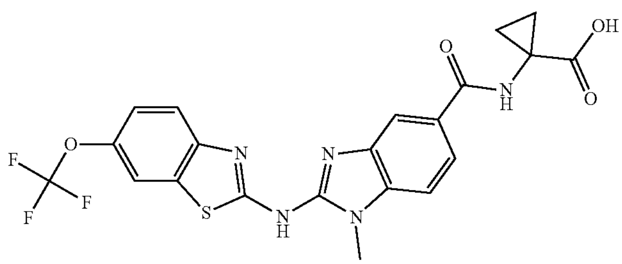 [SMILES: Cn1c(Nc2nc3ccc(OC(F)(F)F)cc3s2)nc2cc(C(=O)NC3(C(=O)O)CC3)ccc21] | 1-{[1-Methyl-2-(6-trifluoromethoxy-benzothiazol-2-ylamino)-1H-benzimidazole-5-carbonyl]-amino}-cyclopropanecarboxylic acid |
| 148 | 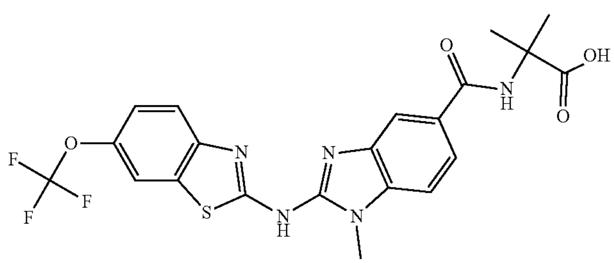 [SMILES: Cn1c(Nc2nc3ccc(OC(F)(F)F)cc3s2)nc2cc(C(=O)NC(C)(C)C(=O)O)ccc21] | 2-Methyl-2-{[1-methyl-2-(6-trifluoromethoxy-benzothiazol-2-ylamino)-1H-benzimidazole-5-carbonyl]-amino}-propionic acid |
| 149 | 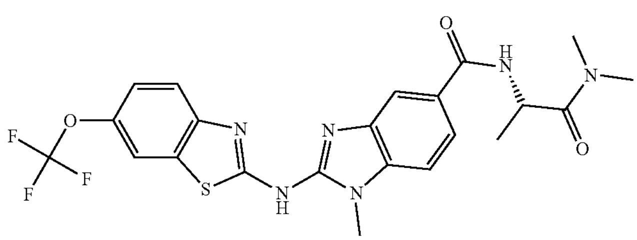 | 1-Methyl-2-(6-trifluoromethoxy-benzothiazol-2-ylamino)-1H-benzoimidazole-5-carboxylic acid ((S)-1-dimethylcarbamoyl-ethyl)-amide |
| 150 | 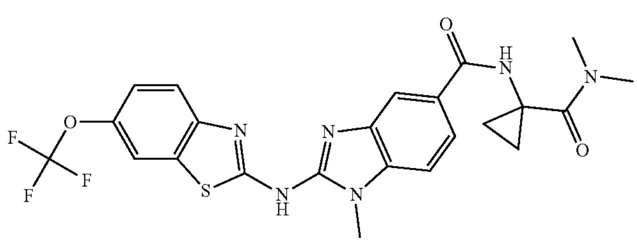 [SMILES: CN(C)C(=O)C1(NC(=O)c2ccc3c(c2)nc(Nc2nc4ccc(OC(F)(F)F)cc4s2)n3C)CC1] | 1-Methyl-2-(6-trifluoromethoxy-benzothiazol-2-ylamino)-1H-benzoimidazole-5-carboxylic acid (1-dimethylcarbamoyl-cyclopropyl)-amide |

TABLE 1-continued

| No. | Structure | Name |
|---|---|---|
| 151 | 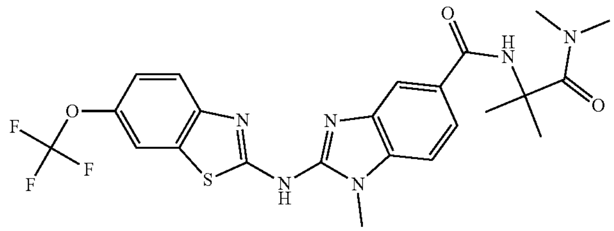 [SMILES: CN(C)C(=O)C(C)(C)NC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid (1-dimethylcarbamoyl-1-methyl-ethyl)-amide |
| 152 | xHCl | 1-Methyl-2-(6-trifluoromethoxy-benzothiazol-2-ylamino)-1H-benzoimidazole-5-carboxylic acid (2-oxo-2-piperazin-1-yl-ethyl)-amide hydrochloride |
| 153 | 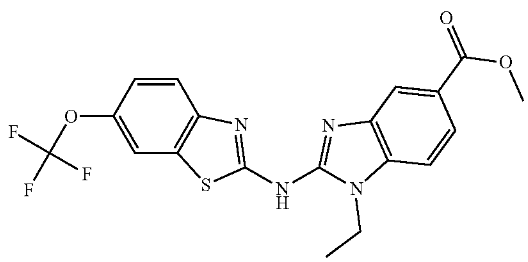 [SMILES: CCn1c(Nc2nc3ccc(OC(F)(F)F)cc3s2)nc2cc(C(=O)OC)ccc21] | 1-Ethyl-2-(6-trifluoromethoxy-benzothiazol-2-ylamino)-1H-benzoimidazole-5-carboxylic acid methyl ester |
| 154 | 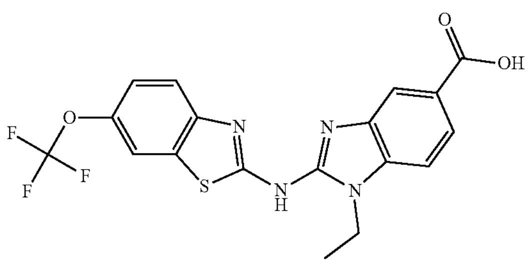 [SMILES: CCn1c(Nc2nc3ccc(OC(F)(F)F)cc3s2)nc2cc(C(=O)O)ccc21] | 1-Ethyl-2-(6-trifluoromethoxy-benzothiazol-2-ylamino)-1H-benzoimidazole-5-carboxylic acid |
| 155 | 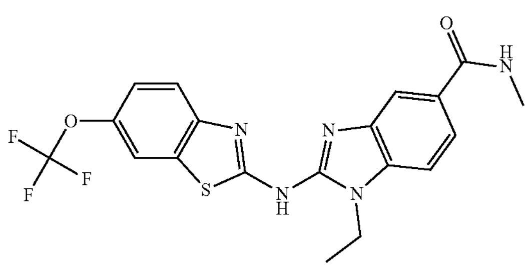 [SMILES: CCn1c(Nc2nc3ccc(OC(F)(F)F)cc3s2)nc2cc(C(=O)NC)ccc21] | 1-Ethyl-2-(6-trifluoromethoxy-benzothiazol-2-ylamino)-1H-benzoimidazole-5-carboxyic acid methylamide |
| 156 | 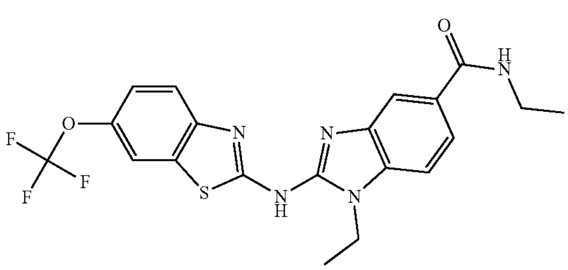 [SMILES: CCNC(=O)c1ccc2c(c1)nc(Nc1nc3ccc(OC(F)(F)F)cc3s1)n2CC] | 1-Ethyl-2-(6-trifluoromethoxy-benzothiazol-2-ylamino)-1H-benzoimidazole-5-carboxylic acid ethylamide |

TABLE 1-continued

| No. | Structure | Name |
|---|---|---|
| 157 | 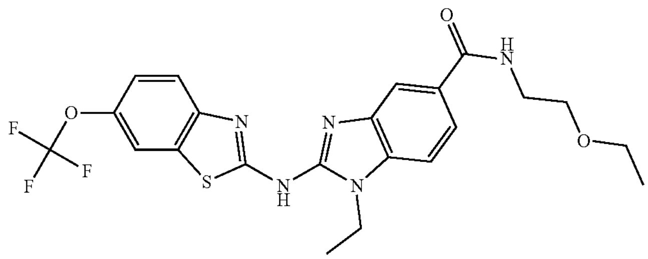 [SMILES: CCOCCNC(=O)c1ccc2c(c1)nc(Nc1nc3ccc(OC(F)(F)F)cc3s1)n2CC] | 1-Ethyl-2-(6-trifluoromethoxy-benzothiazol-2-ylamino)-1H-benzoimidazole-5-carboxylic acid (2-ethoxy-ethyl)-amide |
| 158 | 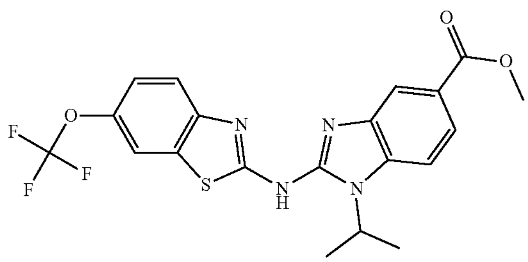 [SMILES: COC(=O)c1ccc2c(c1)nc(Nc1nc3ccc(OC(F)(F)F)cc3s1)n2C(C)C] | 1-Isopropyl-2-(6-trifluoromethoxy-benzothiazol-2-ylamino)-1H benzoimidazole-5-carboxylic acid methyl ester |
| 159 | 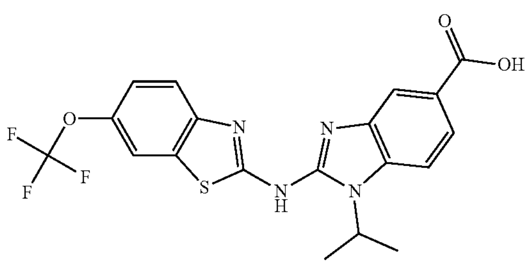 [SMILES: CC(C)n1c(Nc2nc3ccc(OC(F)(F)F)cc3s2)nc2cc(C(=O)O)ccc21] | 1-Isopropyl-2-(6-trifluoromethoxy-benzothiazol-2-ylamino)-1H-benzoimidazole-5-carboxylic acid |
| 160 | 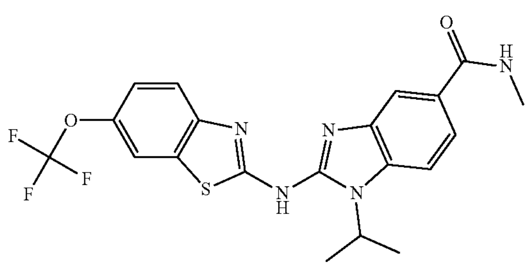 [SMILES: CNC(=O)c1ccc2c(c1)nc(Nc1nc3ccc(OC(F)(F)F)cc3s1)n2C(C)C] | 1-Isopropyl-2-(6-trifluoromethoxy-benzothiazol-2-ylamino)-1H-benzoimidazole-5-carboxylic acid methylamide |
| 161 | 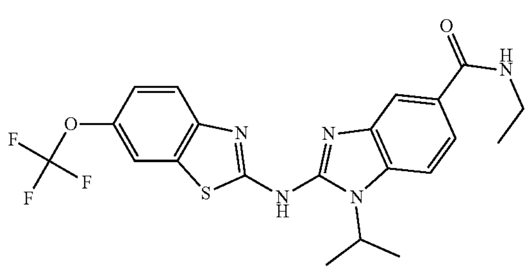 [SMILES: CCNC(=O)c1ccc2c(c1)nc(Nc1nc3ccc(OC(F)(F)F)cc3s1)n2C(C)C] | 1-Isopropyl-2-(6-trifluoromethoxy-benzothiazol-2-ylamino)-1H-benzoimidazole-5-carboxylic acid ethylamide |
| 162 | 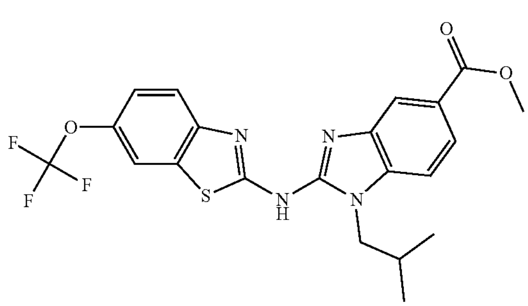 [SMILES: COC(=O)c1ccc2c(c1)nc(Nc1nc3ccc(OC(F)(F)F)cc3s1)n2CC(C)C] | 1-Isobutyl-2-(6-trifluoromethoxy-benzothiazol-2-ylamino)-1H-benzoimidazole-5-carboxylic acid methyl ester |

TABLE 1-continued

| No. | Structure | Name |
|---|---|---|
| 163 | 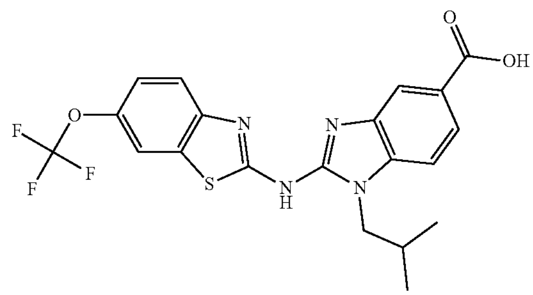 [SMILES: CC(C)Cn1c(Nc2nc3ccc(OC(F)(F)F)cc3s2)nc2cc(C(=O)O)ccc21] | 1-Isobutyl-2-(6-trifluoromethoxy-benzothiazol-2-ylamino)-1H-benzoimidazole-5-carboxylic acid |
| 164 | 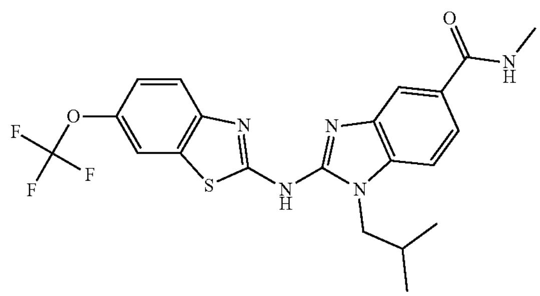 [SMILES: CNC(=O)c1ccc2c(c1)nc(Nc1nc3ccc(OC(F)(F)F)cc3s1)n2CC(C)C] | 1-Isobutyl-2-(6-trifluoromethoxy-benzothiazol-2-ylamino)-1H-benzoimidazole-5-carboxylic acid methylamide |
| 165 | 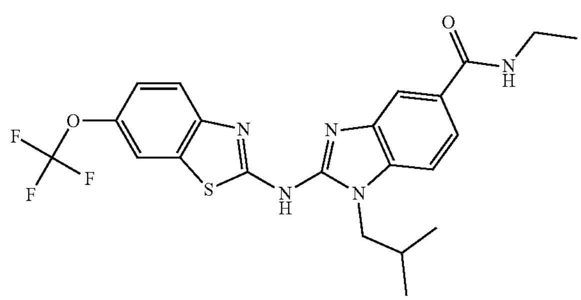 [SMILES: CCNC(=O)c1ccc2c(c1)nc(Nc1nc3ccc(OC(F)(F)F)cc3s1)n2CC(C)C] | 1-Isobutyl-2-(6-trifluoromethoxy-benzothiazol-2-ylamino)-1H-benzoimidazole-5-carboxylic acid ethylamide |
| 166 | 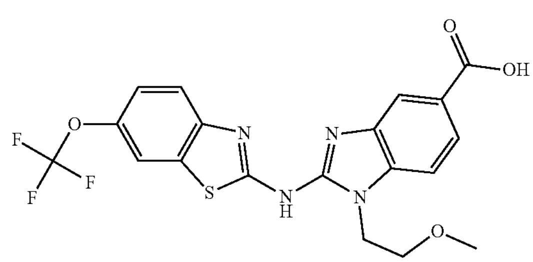 [SMILES: COCCn1c(Nc2nc3ccc(OC(F)(F)F)cc3s2)nc2cc(C(=O)O)ccc21] | 1-(2-Methoxy-ethyl)-2-(6-trifluoromethoxy-benzothiazol-2-ylamino)-1H-benzoimidazole-5-carboxylic acid |
| 167 | 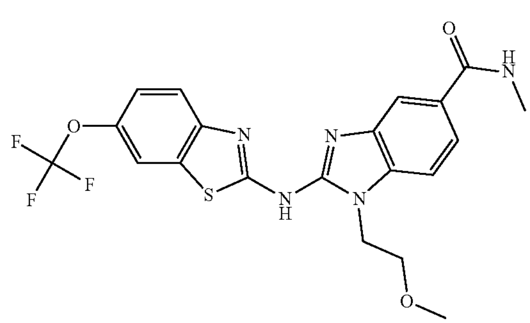 [SMILES: CNC(=O)c1ccc2c(c1)nc(Nc1nc3ccc(OC(F)(F)F)cc3s1)n2CCOC] | 1-(2-Methoxy-ethyl)-2-(6-trifluoromethoxy-benzothiazol-2-ylamino)-1H-benzoimidazole-5-carboxylic acid methylamide |

TABLE 1-continued

| No. | Structure | Name |
|---|---|---|
| 168 | 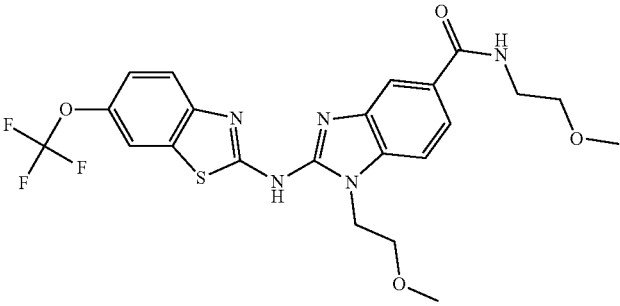 [SMILES: COCCNC(=O)c1ccc2c(c1)nc(Nc1nc3ccc(OC(F)(F)F)cc3s1)n2CCOC] | 1-(2-Methoxy-ethyl)-2-(6-trifluoromethoxy-benzothiazol-2-ylamino)-1H-benzoimidazole-5-carboxylic acid (2-methoxy-ethyl)-amide |
| 169 | 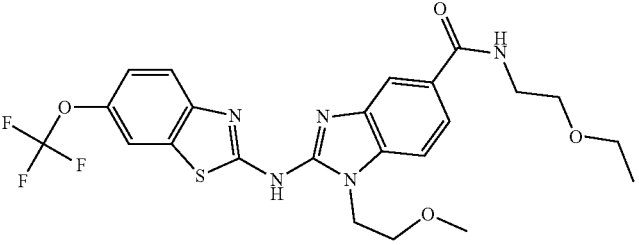 [SMILES: CCOCCNC(=O)c1ccc2c(c1)nc(Nc1nc3ccc(OC(F)(F)F)cc3s1)n2CCOC] | 1-(2-Methoxy-ethyl)-2-(6-trifluoromethoxy-benzothiazol-2-ylamino)-1H-benzoimidazole-5-carboxylic acid (2-ethoxy-ethyl)-amide |
| 170 | 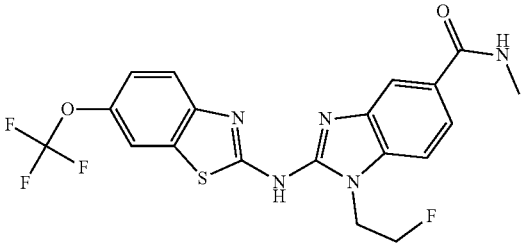 [SMILES: CNC(=O)c1ccc2c(c1)nc(Nc1nc3ccc(OC(F)(F)F)cc3s1)n2CCF] | 1-(2-Fluoro-ethyl)-2-(6-trifluoromethoxy-benzothiazol-2-ylamino)-1H-benzoimidazole-5-carboxylic acid methylamide |
| 171 | 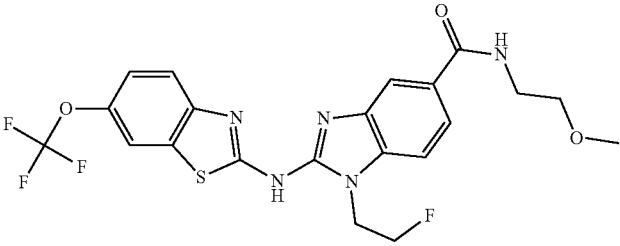 [SMILES: COCCNC(=O)c1ccc2c(c1)nc(Nc1nc3ccc(OC(F)(F)F)cc3s1)n2CCF] | 1-(2-Fluoro-ethyl)-2-(6-trifluoromethoxy-benzothiazol-2-ylamino)-1H-benzoimidazole-5-carboxylic acid (2-methoxy-ethyl)-amide |
| 172 | 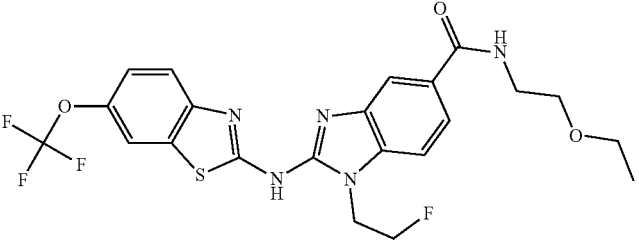 [SMILES: CCOCCNC(=O)c1ccc2c(c1)nc(Nc1nc3ccc(OC(F)(F)F)cc3s1)n2CCF] | 1-(2-Fluoro-ethyl)-2-(6-trifluoromethoxy-benzothiazol-2-ylamino)-1H-benzoimidazole-5-carboxylic acid (2-ethoxy-ethyl)-amide |
| 173 | 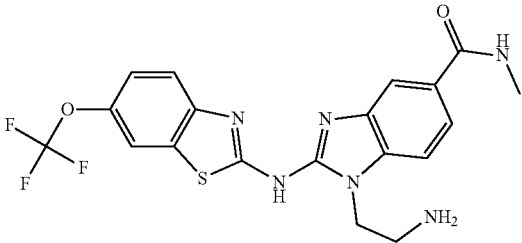 [SMILES: CNC(=O)c1ccc2c(c1)nc(Nc1nc3ccc(OC(F)(F)F)cc3s1)n2CCN] | 1-(2-Amino-ethyl)-2-(6-trifluoromethoxy-benzothiazol-2-ylamino)-1H-benzoimidazole-5-carboxylic acid methylamide hydrochloride |

TABLE 1-continued

| No. | Structure | Name |
|---|---|---|
| 174 | 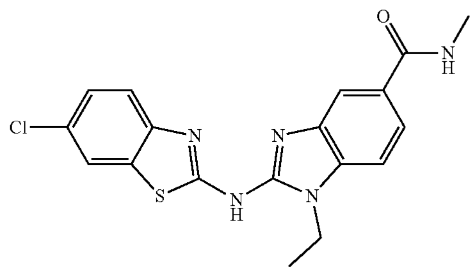 [SMILES: CCn1c(Nc2nc3ccc(Cl)cc3s2)nc2cc(C(=O)NC)ccc21] | 2-(6-Chloro-benzothiazol-2-ylamino)-1-ethyl-1H-benzoimidazole-5-carboxylic acid methylamide |
| 175 | 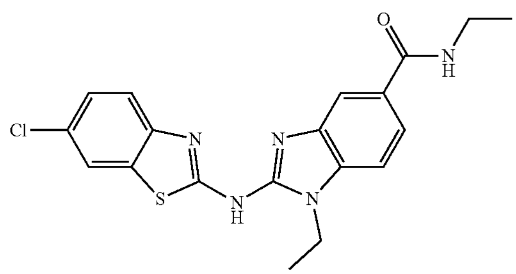 [SMILES: CCNC(=O)c1ccc2c(c1)nc(Nc1nc3ccc(Cl)cc3s1)n2CC] | 2-(6-Chloro-benzothiazol-2-ylamino)-1-ethyl-1H-benzoimidazole-5-carboxylic acid ethylamide |
| 176 | 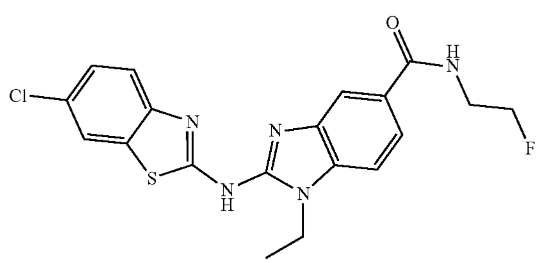 [SMILES: CCn1c(Nc2nc3ccc(Cl)cc3s2)nc2cc(C(=O)NCCF)ccc21] | 2-(6-Chloro-benzothiazol-2-ylamino)-1-ethyl-1H-benzoimidazole-5-carboxylic acid (2-fluoro-ethyl)-amide |
| 177 | 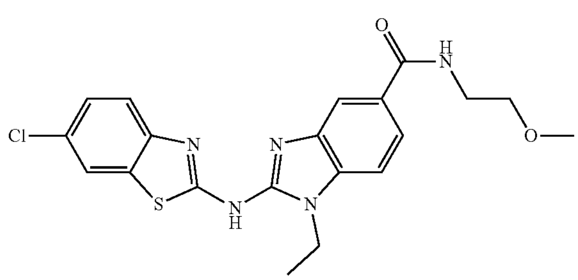 [SMILES: CCn1c(Nc2nc3ccc(Cl)cc3s2)nc2cc(C(=O)NCCOC)ccc21] | 2-(6-Chloro-benzothiazol-2-ylamino)-1-ethyl-1H-benzoimidazole-5-carboxylic acid (2-methoxy-ethyl)-amide |
| 178 | 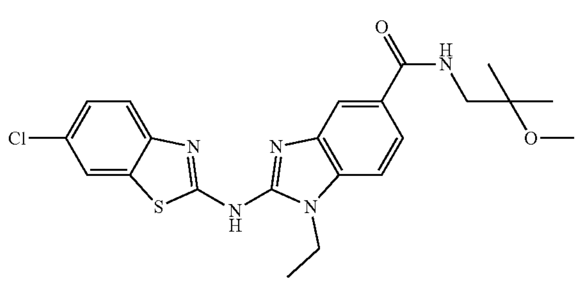 [SMILES: CCn1c(Nc2nc3ccc(Cl)cc3s2)nc2cc(C(=O)NCC(C)(C)OC)ccc21] | 2-(6-Chloro-benzothiazol-2-ylamino)-1-ethyl-1H-benzoimidazole-5-carboxylic acid (2-methoxy-2-methyl-propyl)-amide |

TABLE 1-continued

| No. | Structure | Name |
|---|---|---|
| 179 | 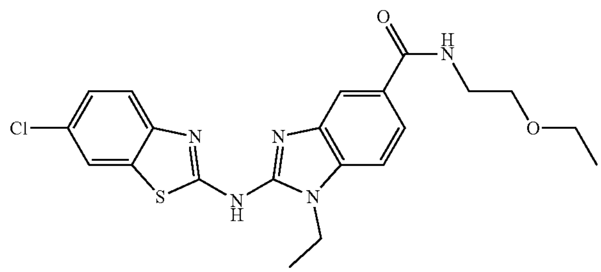 [SMILES: CCOCCNC(=O)c1ccc2c(c1)nc(Nc1nc3ccc(Cl)cc3s1)n2CC] | 2-(6-Chloro-benzothiazol-2-ylamino)-1-ethyl-1H-benzoimidazole-5-carboxylic acid (2-ethoxy-ethyl)-amide |
| 180 | 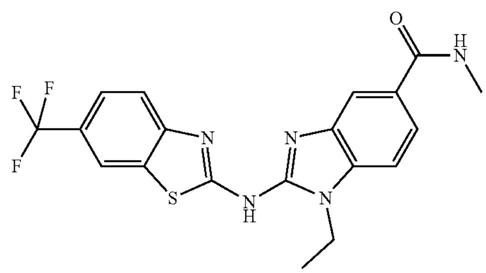 [SMILES: CCn1c(Nc2nc3ccc(C(F)(F)F)cc3s2)nc2cc(C(=O)NC)ccc21] | 1-Ethyl-2-(6-trifluoromethyl-benzothiazol-2-ylamino)-1H-benzoimidazole-5-carboxylic acid methylamide |
| 181 | 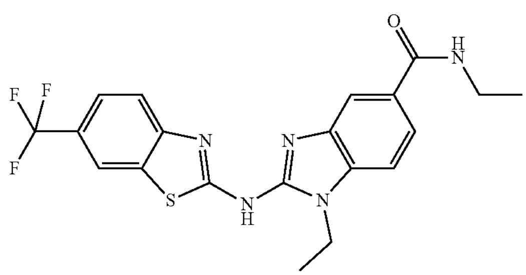 [SMILES: CCNC(=O)c1ccc2c(c1)nc(Nc1nc3ccc(C(F)(F)F)cc3s1)n2CC] | 1-Ethyl-2-(6-trifluoromethyl-benzothiazol-2-ylamino)-1H-benzoimidazole-5-carboxylic acid ethylamide |
| 182 | 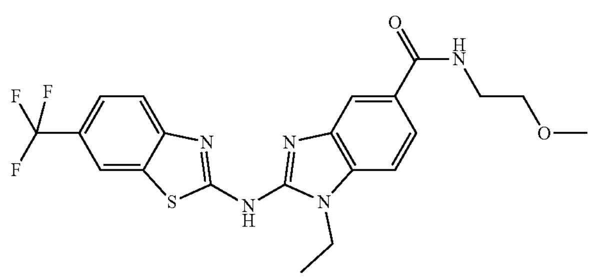 [SMILES: CCn1c(Nc2nc3ccc(C(F)(F)F)cc3s2)nc2cc(C(=O)NCCOC)ccc21] | 1-Ethyl-2-(6-trifluoromethyl-benzothiazol-2-ylamino)-1H-benzoimidazole-5-carboxylic acid (2-methoxy-ethyl)-amide |
| 183 | 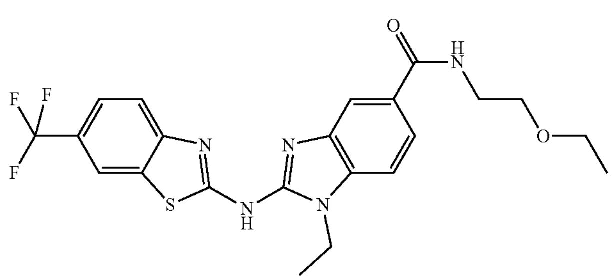 [SMILES: CCOCCNC(=O)c1ccc2c(c1)nc(Nc1nc3ccc(C(F)(F)F)cc3s1)n2CC] | 1-Ethyl-2-(6-trifluoromethyl-benzothiazol-2-ylamino)-1H-benzoimidazole-5-carboxylic acid (2-ethoxy-ethyl)-amide |

TABLE 1-continued

| No. | Structure | Name |
|---|---|---|
| 184 | 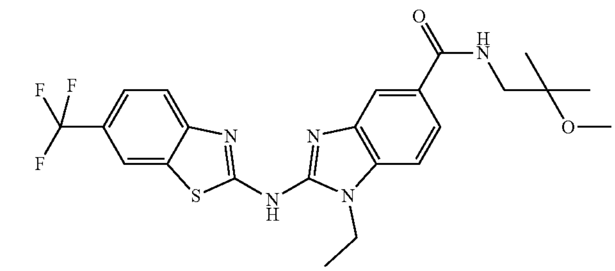 [SMILES: CCn1c(Nc2nc3ccc(C(F)(F)F)cc3s2)nc2cc(C(=O)NCC(C)(C)OC)ccc21] | 1-Ethyl-2-(6-trifluoromethyl-benzothiazol-2-ylamino)-1H-benzoimidazole-5-carboxylic acid (2-methoxy-2-methyl-propyl)-amide |
| 185 | 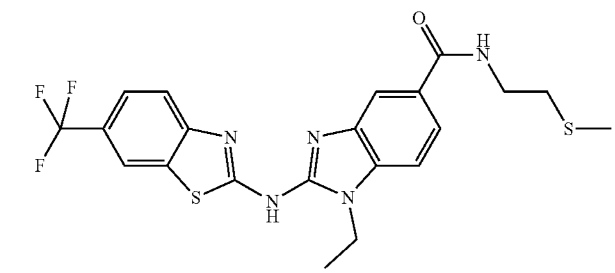 [SMILES: CCn1c(Nc2nc3ccc(C(F)(F)F)cc3s2)nc2cc(C(=O)NCCSC)ccc21] | 1-Ethyl-2-(6-trifluoromethyl-benzothiazol-2-ylamino)-1H-benzoimidazole-5-carboxylic acid (2-methylsulfanyl-ethyl)-amide |
| 186 | 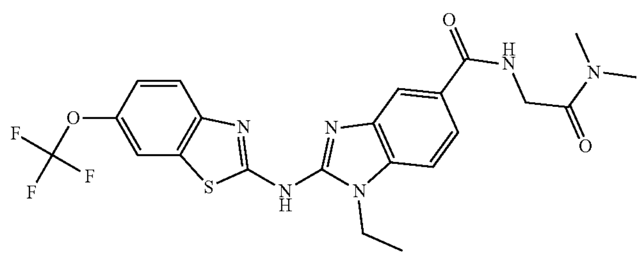 [SMILES: CCn1c(Nc2nc3ccc(OC(F)(F)F)cc3s2)nc2cc(C(=O)NCC(=O)N(C)C)ccc21] | 1-Ethyl-2-(6-trifluoromethoxy-benzothiazol-2-ylamino)-1H-benzoimidazole-5-carboxylic acid dimethylcarbamoylmethyl-amide |
| 187 | 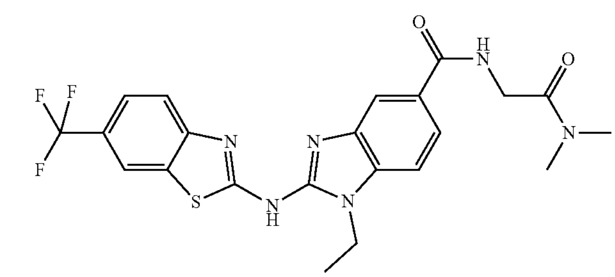 [SMILES: CCn1c(Nc2nc3ccc(C(F)(F)F)cc3s2)nc2cc(C(=O)NCC(=O)N(C)C)ccc21] | 1-Ethyl-2-(6-trifluoromethyl-benzothiazol-2-ylamino)-1H-benzoimidazole-5-carboxylic acid dimethylcarbamoylmethyl-amide |
| 188 | 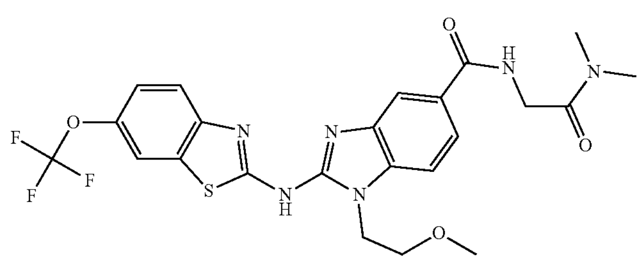 [SMILES: COCCn1c(Nc2nc3ccc(OC(F)(F)F)cc3s2)nc2cc(C(=O)NCC(=O)N(C)C)ccc21] | 1-(2-Methoxy-ethyl)-2-(6-trifluoromethoxy-benzothiazol-2-ylamino)-1H-benzoimidazole-5-carboxylic acid dimethylcarbamoylmethyl-amide |
| 189 | 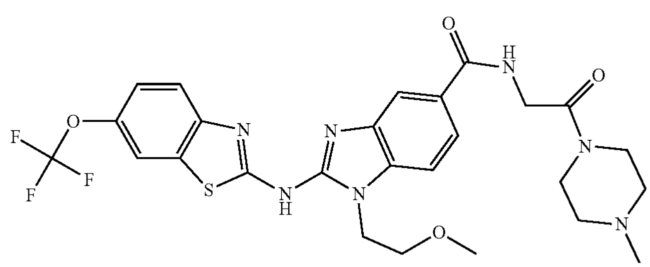 [SMILES: COCCn1c(Nc2nc3ccc(OC(F)(F)F)cc3s2)nc2cc(C(=O)NCC(=O)N3CCN(C)CC3)ccc21] | 1-(2-Methoxy-ethyl)-2-(6-trifluoromethoxy-benzothiazol-2-ylamino)-1H-benzoimidazole-5-carboxylic acid [2-(4-methyl-piperazin-1-yl)-2-oxo-ethyl]-amide |

TABLE 1-continued

| No. | Structure | Name |
|---|---|---|
| 190 | 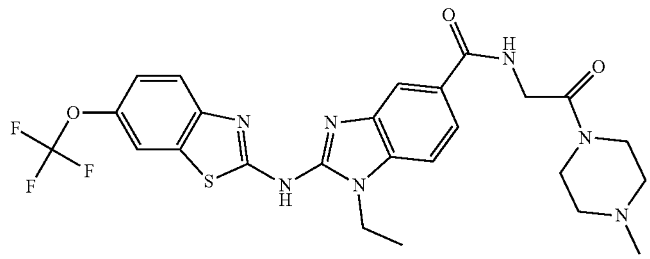 [SMILES: CCn1c(Nc2nc3ccc(OC(F)(F)F)cc3s2)nc2cc(C(=O)NCC(=O)N3CCN(C)CC3)ccc21] | 1-Ethyl-2-(6-trifluoromethoxy-benzothiazol-2-ylamino)-1H-benzoimidazole-5-carboxylic acid [2-(4-methyl-piperazin-1-yl)-2-oxo-ethyl]-amide |
| 191 | 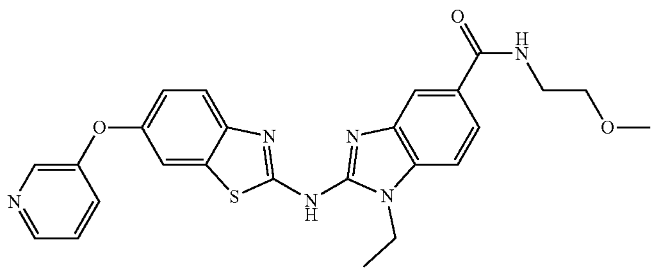 [SMILES: CCn1c(Nc2nc3ccc(Oc4cccnc4)cc3s2)nc2cc(C(=O)NCCOC)ccc21] | 1-Ethyl-2-[6-(pyridin-3-yloxy)-benzothiazol-2-ylamino]-1H-benzoimidazole-5-carboxylic acid (2-methoxy-ethyl)-amide |
| 192 | 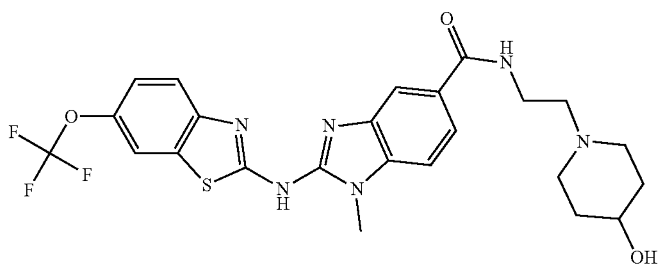 [SMILES: Cn1c(Nc2nc3ccc(OC(F)(F)F)cc3s2)nc2cc(C(=O)NCCN3CCC(O)CC3)ccc21] | 1-Methyl-2-(6-trifluoromethoxy-benzothiazol-2-ylamino)-1H-benzoimidazole-5-carboxylic acid [2-(4-hydroxy-piperidin-1-yl)-ethyl]-amide |
| 193 | 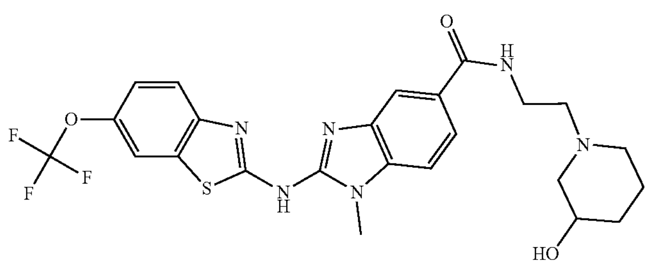 [SMILES: Cn1c(Nc2nc3ccc(OC(F)(F)F)cc3s2)nc2cc(C(=O)NCCN3CCCC(O)C3)ccc21] | 1-Methyl-2-(6-trifluoromethoxy-benzothiazol-2-ylamino)-1H-benzoimidazole-5-carboxylic acid [2-(3-hydroxy-piperidin-1-yl)-ethyl]-amide |
| 194 | 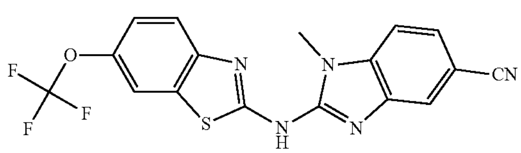 [SMILES: Cn1c(Nc2nc3ccc(OC(F)(F)F)cc3s2)nc2cc(C#N)ccc21] | 1-Methyl-2-(6-trifluoromethoxy-benzothiazol-2-ylamino)-1H-benzoimidazole-5-carbonitrile |
| 195 | 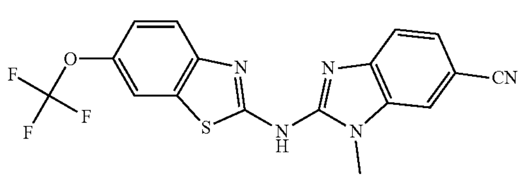 [SMILES: Cn1c(Nc2nc3ccc(OC(F)(F)F)cc3s2)nc2ccc(C#N)cc21] | 1-Methyl-2-(6-trifluoromethoxy-benzothiazol-2-ylamino)-1H-benzoimidazole-6-carbonitrile |

TABLE 1-continued

| No. | Structure | Name |
|---|---|---|
| 196 | 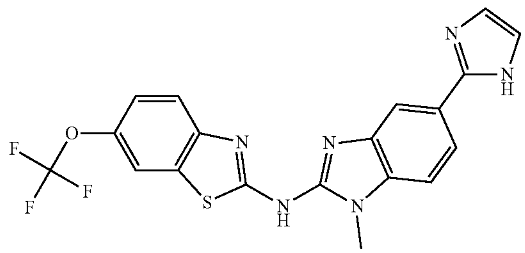 [SMILES: Cn1c(Nc2nc3ccc(OC(F)(F)F)cc3s2)nc2cc(-c3ncc[nH]3)ccc21] | [5-(1H-Imidazol-2-yl)-1-methyl-1H-benzimidazol-2-yl]-(6-trifluoromethoxy-benzothiazol-2-yl)-amine |
| 197 | 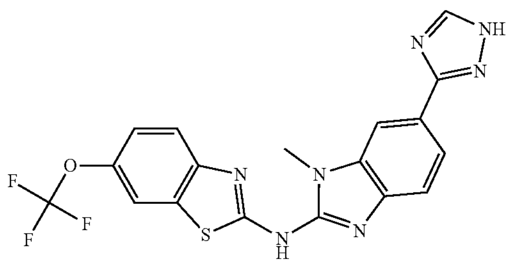 [SMILES: Cn1c(Nc2nc3ccc(OC(F)(F)F)cc3s2)nc2ccc(-c3nc[nH]n3)cc21] | [1-Methyl-6-(1H-1,2,4-triazol-3-yl)-1H-benzimdiazol-2-yl]-(6-trifluoromethoxy-benzothiazol-2-yl)-amine |
| 198 | 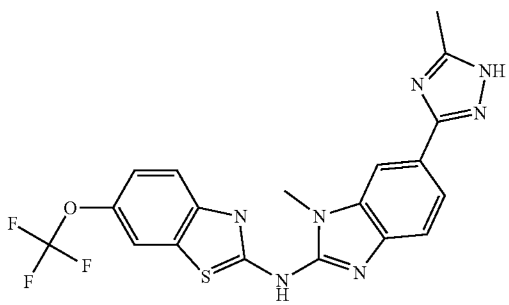 | [1-Methyl-6-(5-methyl-1H-1,2,4-triazol-3-yl)-1H-benzimidazol-2-yl]-(5-trifluoromethoxy-benzothiazol-2-yl)-amine |
| 199 | 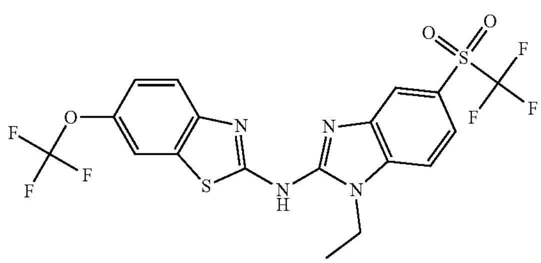 [SMILES: CCn1c(Nc2nc3ccc(OC(F)(F)F)cc3s2)nc2cc(S(=O)(=O)C(F)(F)F)ccc21] | (1-Ethyl-5-trifluoromethanesulfonyl-1H-benzoimidazol-2-yl)-(6-trifluoromethoxy-benzothiazol-2-yl)-amine |
| 200 | 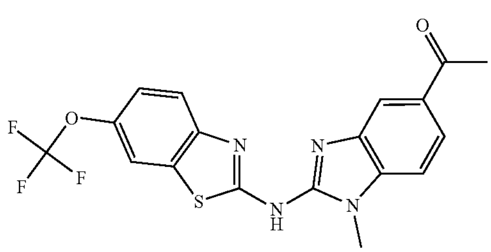 [SMILES: CC(=O)c1ccc2c(c1)nc(Nc1nc3ccc(OC(F)(F)F)cc3s1)n2C] | 1-[1-Methyl-2-(6-trifluoromethoxy-benzothiazol-2-ylamino)-1H-benzoimidazol-5-yl]-ethanone |
| 201 | 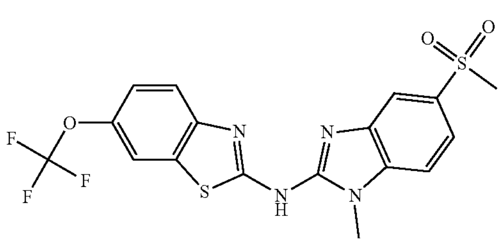 [SMILES: Cn1c(Nc2nc3ccc(OC(F)(F)F)cc3s2)nc2cc(S(C)(=O)=O)ccc21] | (5-Methanesulfonyl-1-methyl-1H-benzoimidazol-2-yl)-(6-trifluoromethoxy-benzothiazol-2-yl)-amine |

TABLE 1-continued

| No. | Structure | Name |
|---|---|---|
| 202 | 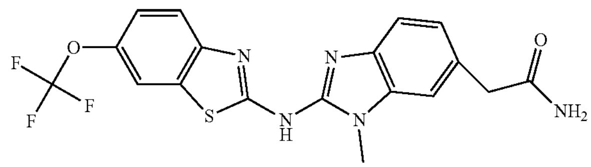 [SMILES: Cn1c(Nc2nc3ccc(OC(F)(F)F)cc3s2)nc2ccc(CC(N)=O)cc21] | 2-[1-Methyl-2-(6-trifluoromethoxy-benzothiazol-2-ylamino)-1H-benzoimidazol-6-yl]-acetamide |
| 203 | 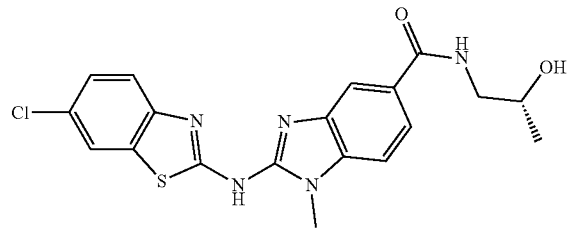 [SMILES: C[C@@H](O)CNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid ((R)-2-hydroxy-propyl)-amide |
| 204 | 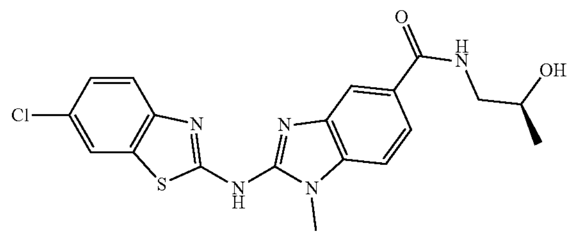 [SMILES: C[C@H](O)CNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid ((S)-2-hydroxy-propyl)-amide |
| 205 | 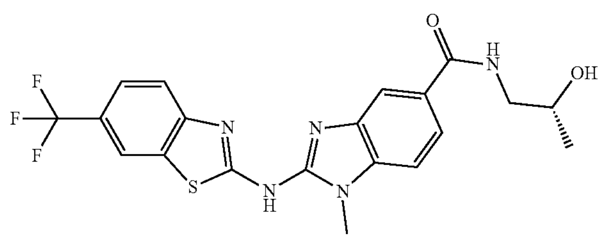 [SMILES: C[C@@H](O)CNC(=O)c1ccc2c(c1)nc(Nc1nc3ccc(C(F)(F)F)cc3s1)n2C] | 1-Methyl-2-(6-trifluoromethyl-benzothiazol-2-ylamino)-1H-benzoimidazole-5-carboxylic acid ((R)-2-hydroxy-propyl)-amide |
| 206 | 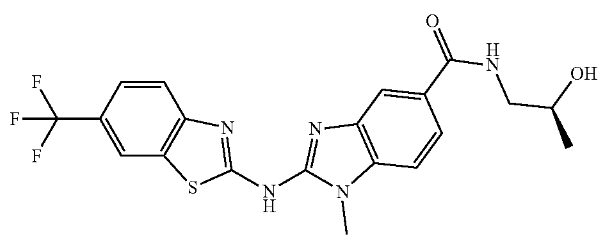 [SMILES: C[C@H](O)CNC(=O)c1ccc2c(c1)nc(Nc1nc3ccc(C(F)(F)F)cc3s1)n2C] | 1-Methyl-2-(6-trifluoromethyl-benzothiazol-2-ylamino)-1H-benzoimidazole-5-carboxylic acid ((S)-2-hydroxy-propyl)-amide |
| 207 | 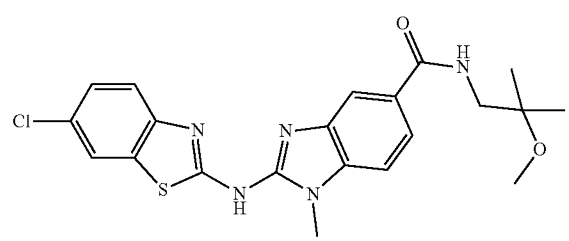 [SMILES: COC(C)(C)CNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid (2-methoxy-2-methyl-propyl)-amide |
| 208 | 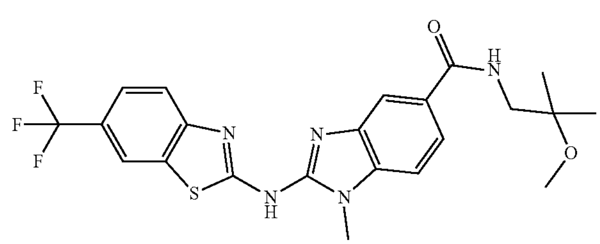 [SMILES: COC(C)(C)CNC(=O)c1ccc2c(c1)nc(Nc1nc3ccc(C(F)(F)F)cc3s1)n2C] | 1-Methyl-2-(6-trifluoromethyl-benzothiazol-2-ylamino)-1H-benzoimidazole-5-carboxylic acid (2-methoxy-2-methyl-propyl)-amide |

TABLE 1-continued

| No. | Structure | Name |
|---|---|---|
| 209 | 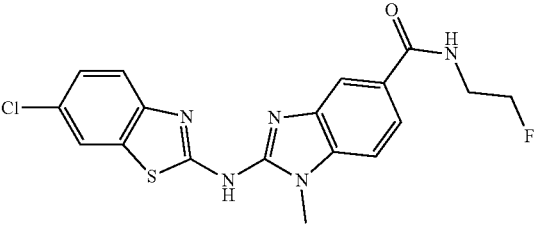 [SMILES: Cn1c(Nc2nc3ccc(Cl)cc3s2)nc2cc(C(=O)NCCF)ccc21] | 2-(6-Chloro-benzothiazol-2-ylamino)-1-methyl-1H-benzoimidazole-5-carboxylic acid (2-fluoro-ethyl)-amide |
| 210 | 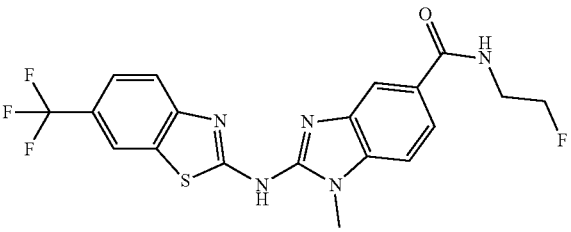 [SMILES: Cn1c(Nc2nc3ccc(C(F)(F)F)cc3s2)nc2cc(C(=O)NCCF)ccc21] | 1-Methyl-2-(6-trifluoromethyl-benzothiazol-2-ylamino)-1H-benzoimidazole-5-carboxylic acid (2-fluoro-ethyl)-amide |
| 211 | 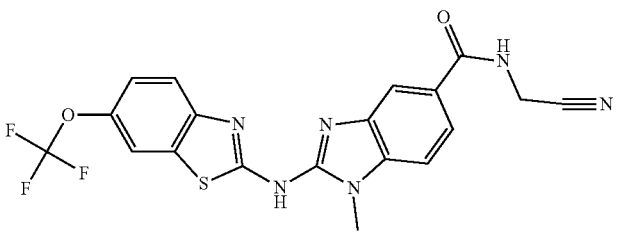 [SMILES: Cn1c(Nc2nc3ccc(OC(F)(F)F)cc3s2)nc2cc(C(=O)NCC#N)ccc21] | 1-Methyl-2-(6-trifluoromethoxy-benzothiazol-2-ylamino)-1H-benzoimidazole-5-carboxylic acid cyanomethyl-amide |
| 212 | 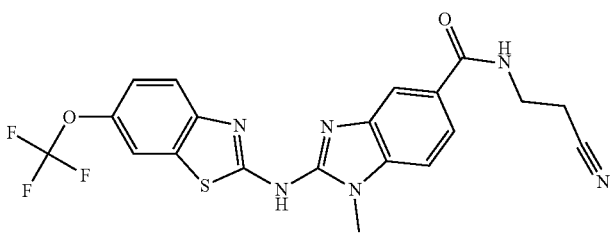 [SMILES: Cn1c(Nc2nc3ccc(OC(F)(F)F)cc3s2)nc2cc(C(=O)NCCC#N)ccc21] | 1-Methyl-2-(6-trifluoromethoxy-benzothiazol-2-ylamino)-1H-benzoimidazole-5-carboxylic acid (2-cyano-ethyl)-amide |
| 213 | 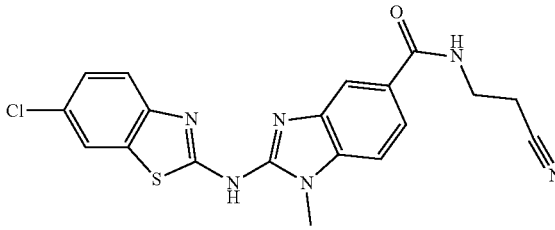 | 2-(6-Chloro-benzothiazol-2-ylamino)-1-methyl-1H-benzoimidazole-5-carboxylic acid (2-cyano-ethyl)-amide |
| 214 | 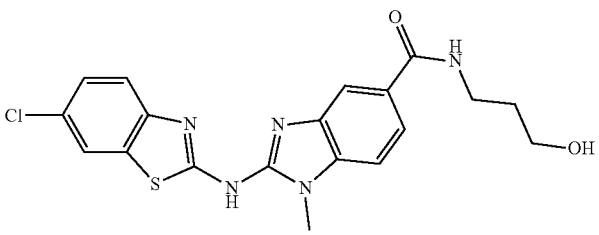 [SMILES: Cn1c(Nc2nc3ccc(Cl)cc3s2)nc2cc(C(=O)NCCCO)ccc21] | 2-(6-Chloro-benzothiazol-2-ylamino)-1-methyl-1H-benzoimidazole-5-carboxylic acid (3-hydroxy-propyl)-amide |

TABLE 1-continued

| No. | Structure | Name |
|-----|-----------|------|
| 215 | 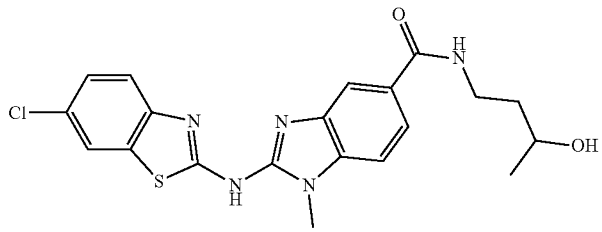 [SMILES: CC(O)CCNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid (3-hydroxy-butyl)-amide |
| 216 | 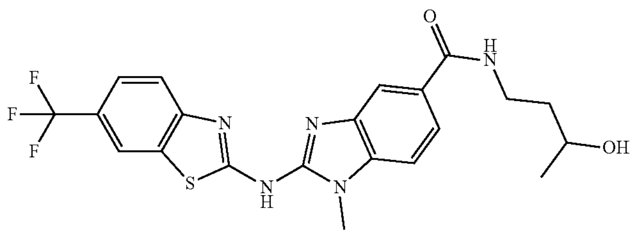 [SMILES: CC(O)CCNC(=O)c1ccc2c(c1)nc(Nc1nc3ccc(C(F)(F)F)cc3s1)n2C] | 1-Methyl-2-(6-trifluoromethyl-benzothiazol-2-ylamino)-1H-benzoimidazole-5-carboxylic acid (3-hydroxy-butyl)-amide |
| 217 | 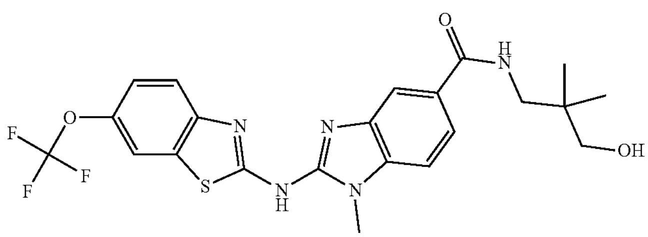 [SMILES: Cn1c(Nc2nc3ccc(OC(F)(F)F)cc3s2)nc2cc(C(=O)NCC(C)(C)CO)ccc21] | 1-Methyl-2-(6-trifluoromethoxy-benzothiazol-2-ylamino)-1H-benzoimidazole-5-carboxylic acid (3-hydroxy-2,2-dimethyl-propyl)-amide |
| 218 | 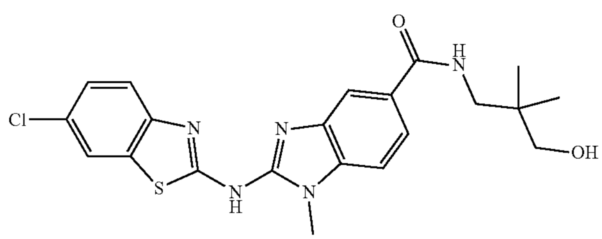 [SMILES: Cn1c(Nc2nc3ccc(Cl)cc3s2)nc2cc(C(=O)NCC(C)(C)CO)ccc21] | 2-(6-Chloro-benzothiazol-2-ylamino)-1-methyl-1H-benzoimidazole-5-carboxylic acid (3-hydroxy-2,2-dimethyl-propyl)-amide |
| 219 | 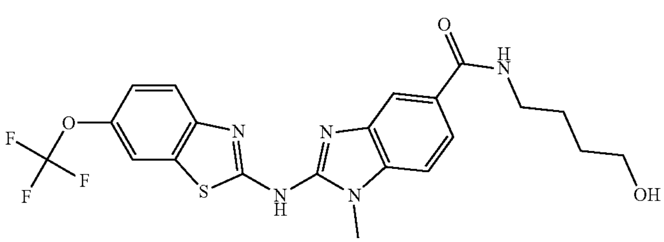 [SMILES: Cn1c(Nc2nc3ccc(OC(F)(F)F)cc3s2)nc2cc(C(=O)NCCCCO)ccc21] | 1-Methyl-2-(6-trifluoromethoxy-benzothiazol-2-ylamino)-1H-benzoimidazole-5-carboxylic acid (4-hydroxy-butyl)-amide |
| 220 | 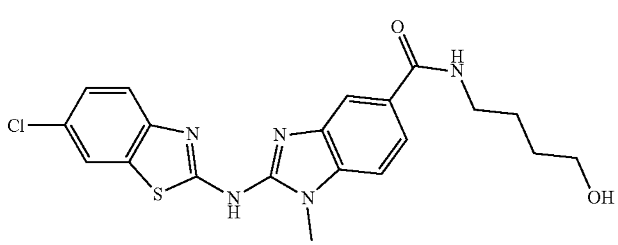 [SMILES: Cn1c(Nc2nc3ccc(Cl)cc3s2)nc2cc(C(=O)NCCCCO)ccc21] | 2-(6-Chloro-1H-benzoimidazol-2-ylamino)-1-methyl-1H-benzoimidazole-5-carboxylic acid (4-hydroxy-butyl)-amide |

| No. | Structure | Name |
|---|---|---|
| 221 | 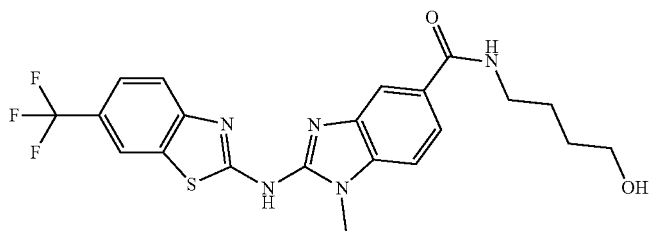 [SMILES: Cn1c(Nc2nc3ccc(C(F)(F)F)cc3s2)nc2cc(C(=O)NCCCCO)ccc21] | 1-Methyl-2-(6-trifluoromethyl-benzothiazol-2-ylamino)-1H-benzoimidazole-5-carboxylic acid (4-hydroxy-butyl)-amide |
| 222 | 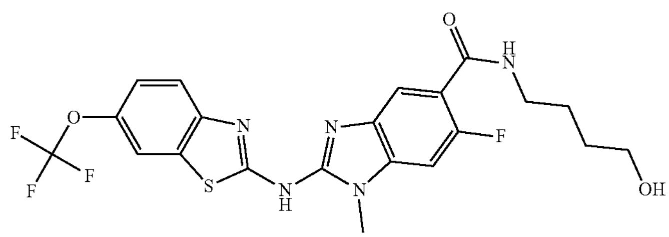 [SMILES: Cn1c(Nc2nc3ccc(OC(F)(F)F)cc3s2)nc2cc(C(=O)NCCCCO)c(F)cc21] | 6-Fluoro-1-methyl-2-(6-trifluoromethoxy-benzothiazol-2-ylamino)-1H-benzoimidazole-5-carboxylic acid (4-hydroxy-butyl)-amide |
| 223 | 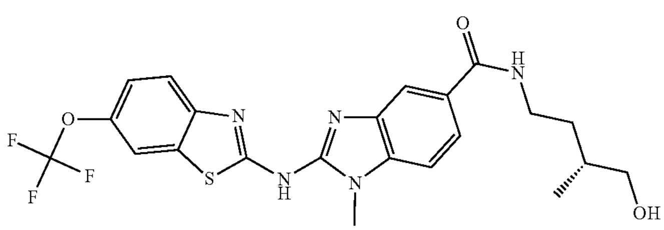 [SMILES: C[C@@H](CO)CCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid ((R)-4-hydroxy-3-methyl-butyl)-amide |
| 224 | 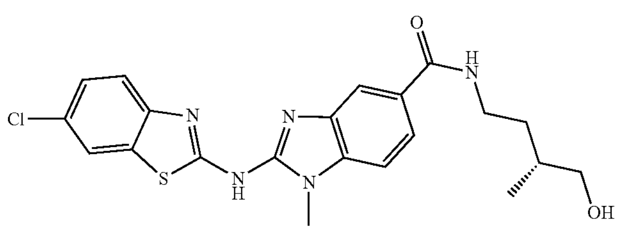 [SMILES: C[C@@H](CO)CCNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid ((R)-4-hydroxy-3-methyl-butyl)-amide |
| 225 | 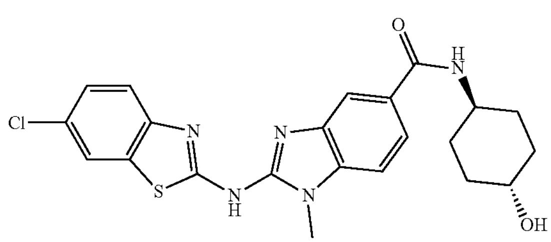 [SMILES: Cn1c(Nc2nc3ccc(Cl)cc3s2)nc2cc(C(=O)N[C@H]3CC[C@H](O)CC3)ccc21] | 2-(6-Chloro-benzothiazol-2-ylamino)-1-methyl-1H-benzoimidazole-5-carboxylic acid (trans-4-hydroxy-cyclohexyl)-amide |
| 226 | 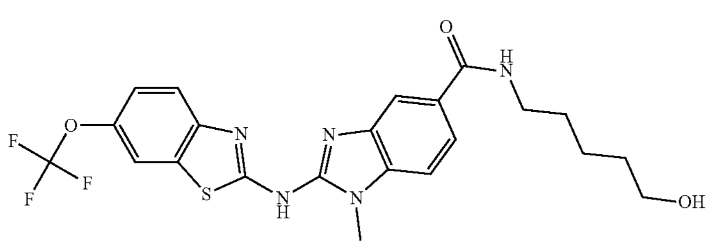 [SMILES: Cn1c(Nc2nc3ccc(OC(F)(F)F)cc3s2)nc2cc(C(=O)NCCCCCO)ccc21] | 1-Methyl-2-(6-trifluoromethoxy-benzothiazol-2-ylamino)-1H-benzoimidazole-5-carboxylic acid (5-hydroxy-pentyl)-amide |

TABLE 1-continued

| No. | Structure | Name |
|---|---|---|
| 227 | 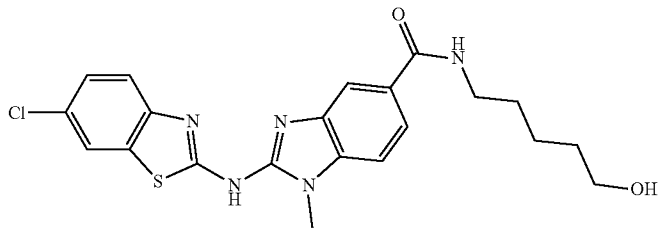 [SMILES: Cn1c(Nc2nc3ccc(Cl)cc3s2)nc2cc(C(=O)NCCCCCO)ccc21] | 2-(6-Chloro-benzothiazol-2-ylamino)-1-methyl-1H-benzoimidazole-5-carboxylic acid (5-hydroxy-pentyl)-amide |
| 228 | 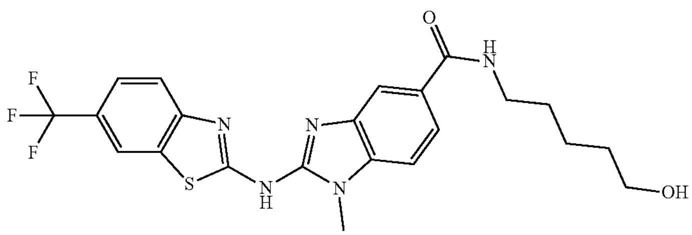 [SMILES: Cn1c(Nc2nc3ccc(C(F)(F)F)cc3s2)nc2cc(C(=O)NCCCCCO)ccc21] | 1-Methyl-2-(6-trifluoromethyl-benzothiazol-2-ylamino)-1H-benzoimidazole-5-carboxylic acid (5-hydroxy-pentyl)-amide |
| 229 | 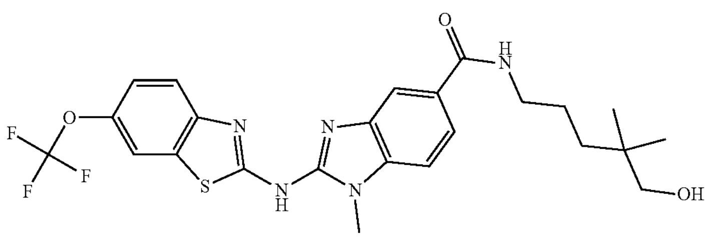 [SMILES: Cn1c(Nc2nc3ccc(OC(F)(F)F)cc3s2)nc2cc(C(=O)NCCCC(C)(C)CO)ccc21] | 1-Methyl-2-(6-trifluoromethoxy-benzothiazol-2-ylamino)-1H-benzoimidazole-5-carboxylic acid (5-hydroxy-4,4-dimethyl-pentyl)-amide |
| 230 | 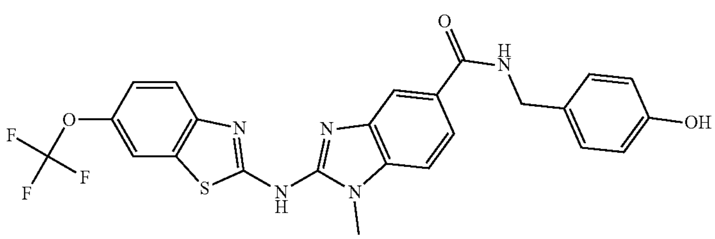 [SMILES: Cn1c(Nc2nc3ccc(OC(F)(F)F)cc3s2)nc2cc(C(=O)NCc3ccc(O)cc3)ccc21] | 1-Methyl-2-(6-trifluoromethoxy-benzothiazol-2-ylamino)-1H-benzoimidazole-5-carboxylic acid 4-hydroxy-benzylamide |
| 231 | 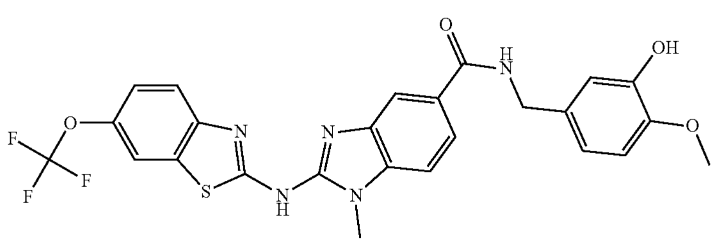 [SMILES: COc1ccc(CNC(=O)c2ccc3c(c2)nc(Nc2nc4ccc(OC(F)(F)F)cc4s2)n3C)cc1O] | 1-Methyl-2-(6-trifluoromethoxy-benzothiazol-2-ylamino)-1H-benzoimidazole-5-carboxylic acid 3-hydroxy-4-methoxy-benzylamide |
| 232 | 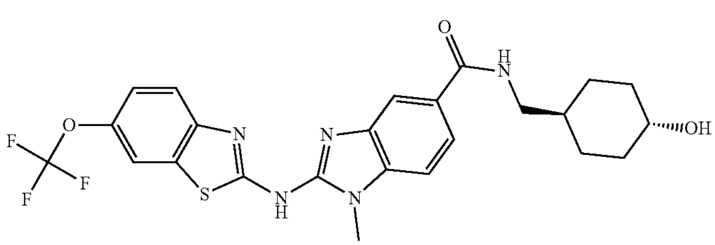 [SMILES: Cn1c(Nc2nc3ccc(OC(F)(F)F)cc3s2)nc2cc(C(=O)NC[C@H]3CC[C@H](O)CC3)ccc21] | 1-Methyl-2-(6-trifluoromethoxy-benzothiazol-2-ylamino)-1H-benzoimidazole-5-carboxylic acid (trans-4-hydroxy-cyclohexylmethyl)-amide |

| No. | Structure | Name |
|---|---|---|
| 233 | 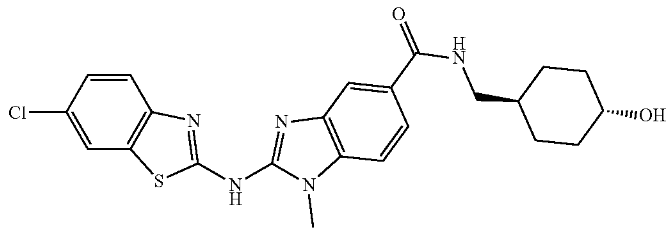 [SMILES: Cn1c(Nc2nc3ccc(Cl)cc3s2)nc2cc(C(=O)NC[C@H]3CC[C@H](O)CC3)ccc21] | 2-(6-Chloro-benzothiazol-2-ylamino)-1-methyl-1H-benzoimidazole-5-carboxylic acid (trans-4-hydroxy-cyclohexylmethyl)-amide |
| 234 | 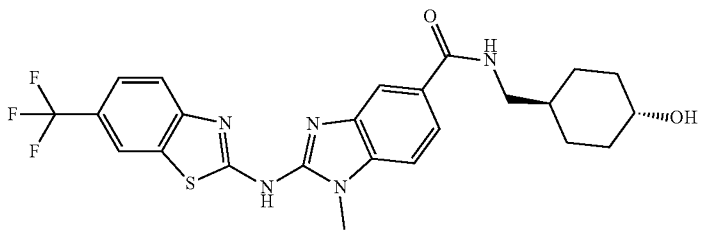 [SMILES: Cn1c(Nc2nc3ccc(C(F)(F)F)cc3s2)nc2cc(C(=O)NC[C@H]3CC[C@H](O)CC3)ccc21] | 1-Methyl-2-(6-trifluoromethyl-benzothiazol-2-ylamino)-1H-benzoimidazole-5-carboxylic acid (trans-4-hydroxy-cyclohexylmethyl)-amide |
| 235 | 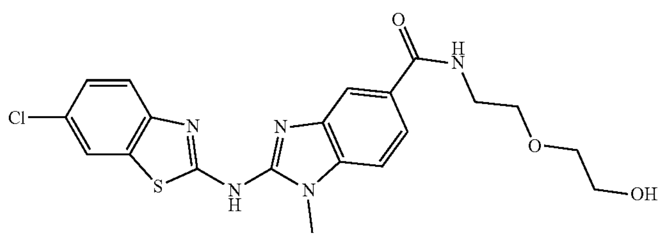 [SMILES: Cn1c(Nc2nc3ccc(Cl)cc3s2)nc2cc(C(=O)NCCOCCO)ccc21] | 2-(6-Chloro-benzothiazol-2-ylamino)-1-methyl-1H-benzoimidazole-5-carboxylic acid [2-(2-hydroxy-ethoxy)-ethyl]-amide |
| 236 | 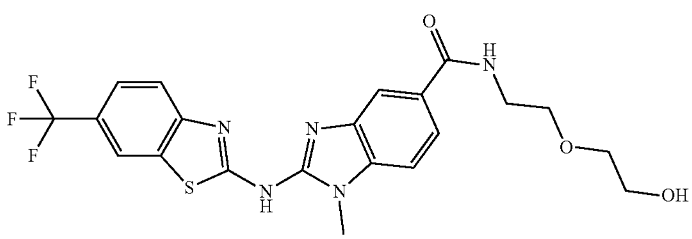 | 1-Methyl-2-(6-trifluoromethyl-benzothiazol-2-ylamino)-1H-benzoimidazole-5-carboxylic acid [2-(2-hydroxy-ethoxy)-ethyl]-amide |
| 237 | 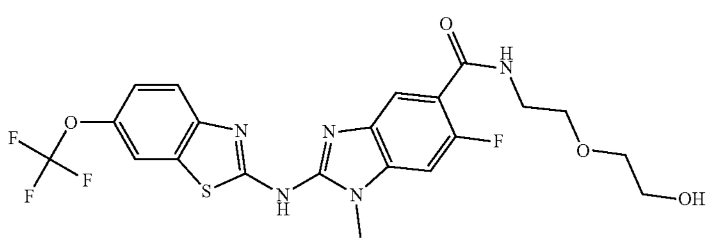 [SMILES: Cn1c(Nc2nc3ccc(OC(F)(F)F)cc3s2)nc2cc(C(=O)NCCOCCO)c(F)cc21] | 6-Fluoro-1-methyl-2-(6-trifluoromethoxy-benzothiazol-2-ylamino)-1H-benzoimidazole-5-carboxylic acid [2-(2-hydroxy-ethoxy)-ethyl]-amide |
| 238 | 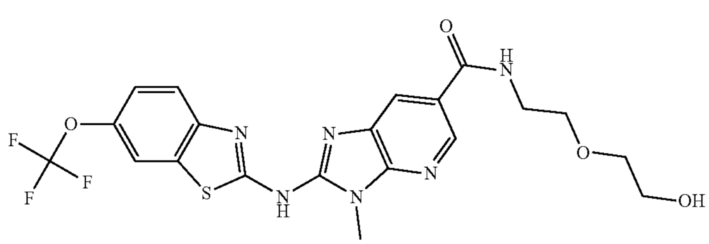 [SMILES: Cn1c(Nc2nc3ccc(OC(F)(F)F)cc3s2)nc2cc(C(=O)NCCOCCO)cnc21] | 3-Methyl-2-(6-trifluoromethoxy-benzothiazol-2-ylamino)-3H-imidazo[4,5-b]pyridine-6-carboxylic acid [2-(2-hydroxy-ethoxy)-ethyl]-amide |

TABLE 1-continued

| No. | Structure | Name |
|---|---|---|
| 239 | 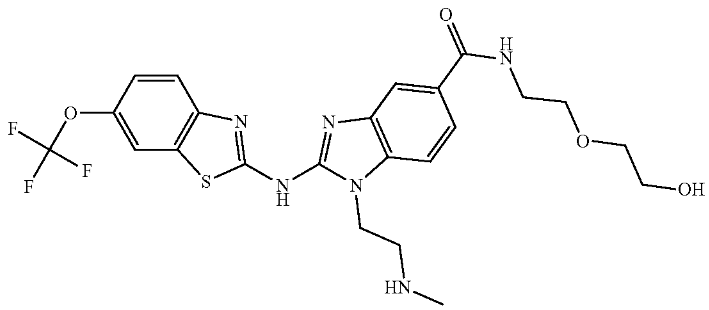 [SMILES: CNCCn1c(Nc2nc3ccc(OC(F)(F)F)cc3s2)nc2cc(C(=O)NCCOCCO)ccc21] | 1-(2-Methylamino-ethyl)-2-(6-trifluoromethoxy-benzothiazol-2 ylamino)-1H-benzoimidazole-5-carboxylic acid [2-(2-hydroxy-ethoxy)-ethyl]-amide hydrochloride |
| 240 | 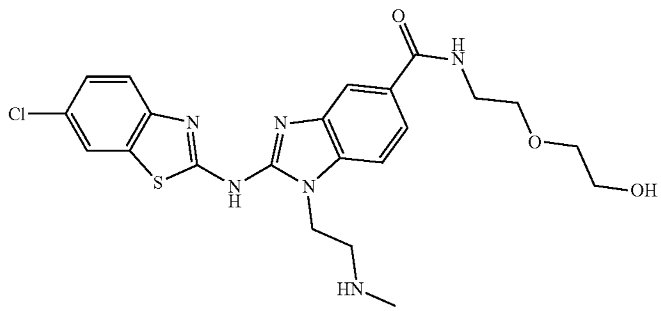 [SMILES: CNCCn1c(Nc2nc3ccc(Cl)cc3s2)nc2cc(C(=O)NCCOCCO)ccc21] | 2-(6-Chloro-benzothiazol-2-ylamino)-1-(2-methylamino-ethyl)-1H-benzoimidazole-5-carboxylic acid [2-(2-hydroxy-ethoxy)-ethyl]-amide hydrochloride |
| 241 | 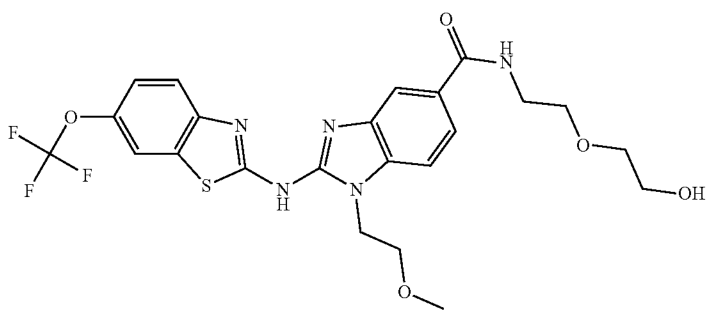 [SMILES: COCCn1c(Nc2nc3ccc(OC(F)(F)F)cc3s2)nc2cc(C(=O)NCCOCCO)ccc21] | 1-(2-Methoxy-ethyl)-2-(6-trifluoromethoxy-benzothiazol-2-ylamino)-1H-benzoimidazole-5-carboxylic acid [2-(2-hydroxy-ethoxy)-ethyl]-amide |
| 242 | 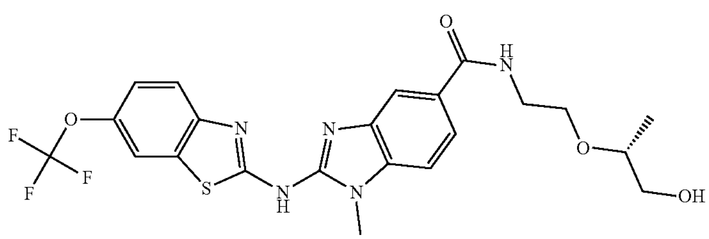 [SMILES: C[C@H](CO)OCCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid [2-((R)-2-hydroxy-1-methyl-ethoxy)-ethyl]-amide |
| 243 | 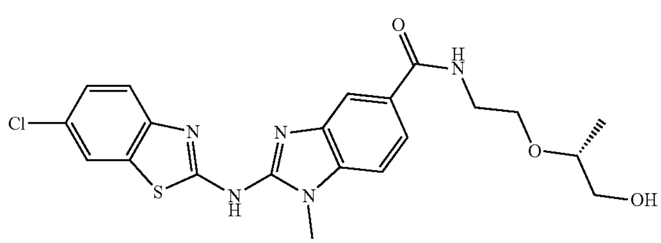 [SMILES: C[C@H](CO)OCCNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid [2-((R)-2-hydroxy-1-methyl-ethoxy)-ethyl]-amide |

TABLE 1-continued

| No. | Structure | Name |
|---|---|---|
| 244 | 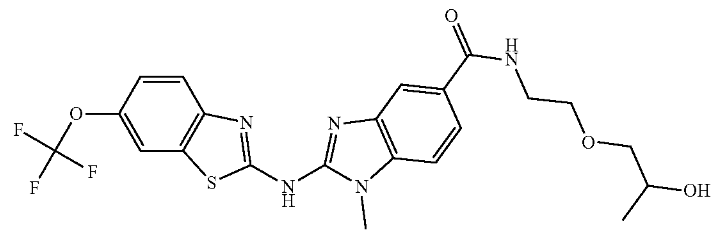 [SMILES: CC(O)COCCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid [2-(2-hydroxy-propoxy)-ethyl]-amide |
| 245 | 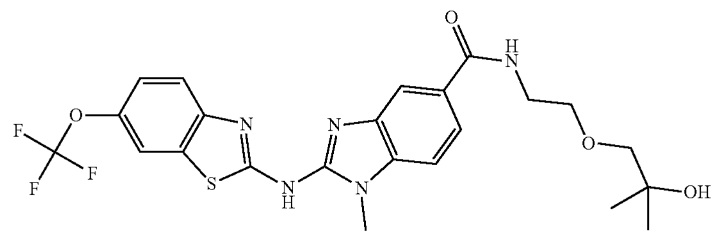 [SMILES: Cn1c(Nc2nc3ccc(OC(F)(F)F)cc3s2)nc2cc(C(=O)NCCOCC(C)(C)O)ccc21] | 1-Methyl-2-(6-trifluoromethoxy-benzothiazol-2-ylamino)-1H-benzoimidazole-5-carboxylic acid [2-(2-hydroxy-2-methyl-propoxy)-ethyl]-amide |
| 246 | 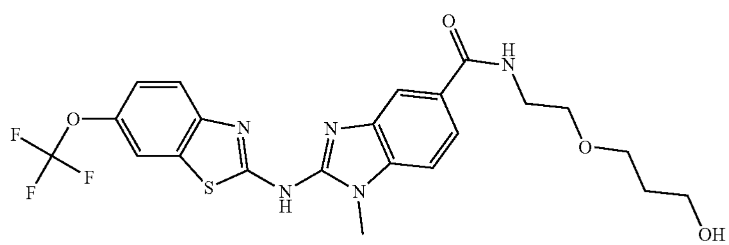 [SMILES: Cn1c(Nc2nc3ccc(OC(F)(F)F)cc3s2)nc2cc(C(=O)NCCOCCCO)ccc21] | 1-Methyl-2-(6-trifluoromethoxy-benzothiazol-2-ylamino)-1H-benzoimidazole-5-carboxylic acid [2-(3-hydroxy-propoxy)-ethyl]-amide |
| 247 | 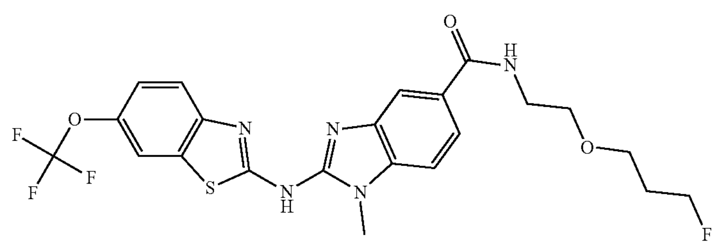 [SMILES: Cn1c(Nc2nc3ccc(OC(F)(F)F)cc3s2)nc2cc(C(=O)NCCOCCCF)ccc21] | 1-Methyl-2-(6-trifluoromethoxy-benzothiazol-2-ylamino)-1H-benzoimidazole-5-carboxylic acid [2-(3-fluoro-propoxy)-ethyl]-amide |
| 248 | 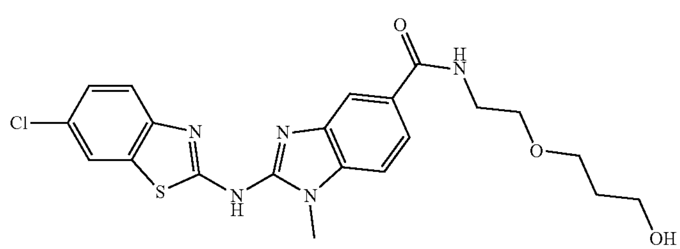 [SMILES: Cn1c(Nc2nc3ccc(Cl)cc3s2)nc2cc(C(=O)NCCOCCCO)ccc21] | 2-(6-Chloro-benzothiazol-2-ylamino)-1-methyl-1H-benzoimidazole-5-carboxylic acid [2-(3-hydroxy-propoxy)-ethyl]-amide |
| 249 | 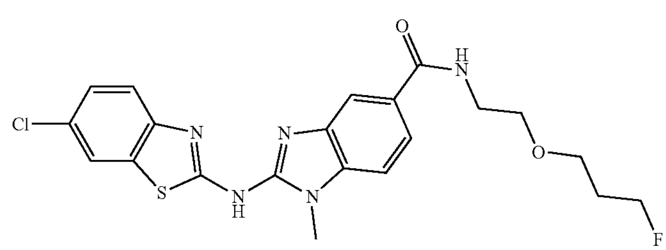 [SMILES: Cn1c(Nc2nc3ccc(Cl)cc3s2)nc2cc(C(=O)NCCOCCCF)ccc21] | 2-(6-Chloro-benzothiazol-2-ylamino)-1-methyl-1H-benzoimidazol-5-carboxylic acid [2-(3-fluoro-propoxy)-ethyl]-amide |

| No. | Structure | Name |
|---|---|---|
| 250 | 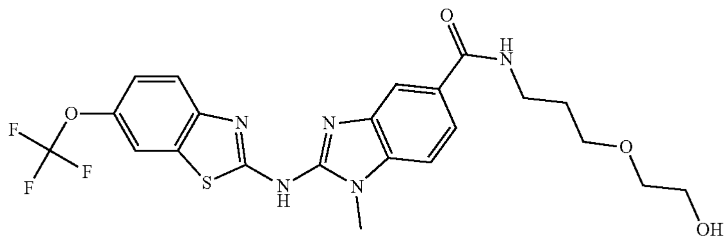 [SMILES: Cn1c(Nc2nc3ccc(OC(F)(F)F)cc3s2)nc2cc(C(=O)NCCCOCCO)ccc21] | 1-Methyl-2-(6-trifluoromethoxy-benzothiazol-2-ylamino)-1H-benzoimidazole-5-carboxylic acid [3-(2-hydroxy-ethoxy)-propyl]-amide |
| 251 | 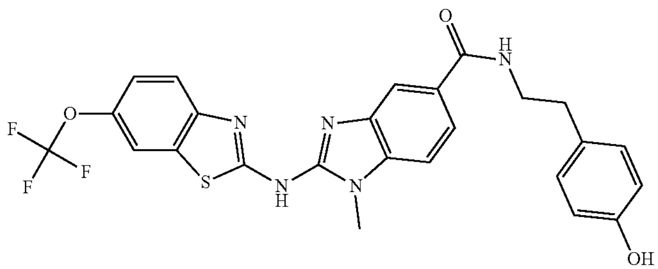 [SMILES: Cn1c(Nc2nc3ccc(OC(F)(F)F)cc3s2)nc2cc(C(=O)NCCc3ccc(O)cc3)ccc21] | 1-Methyl-2-(6-trifluoromethoxy-benzothiazol-2-ylamino)-1H-benzoimidazole-5-carboxylic acid [2-(4-hydroxy-phenyl)-ethyl]-amide |
| 252 | 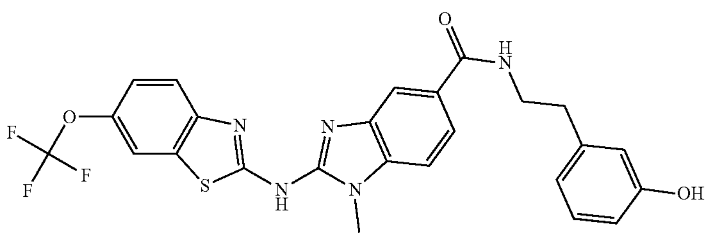 [SMILES: Cn1c(Nc2nc3ccc(OC(F)(F)F)cc3s2)nc2cc(C(=O)NCCc3cccc(O)c3)ccc21] | 1-Methyl-2-(6-trifluoromethoxy-benzothiazol-2-ylamino)-1H-benzoimidazole-5-carboxylic acid [2-(3-hydroxy-phenyl)-ethyl]-amide |
| 253 | 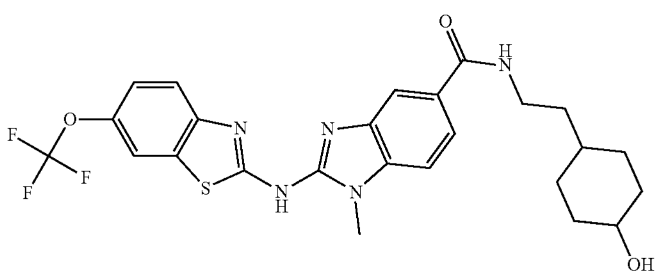 [SMILES: Cn1c(Nc2nc3ccc(OC(F)(F)F)cc3s2)nc2cc(C(=O)NCCC3CCC(O)CC3)ccc21] | 1-Methyl-2-(6-trifluoromethoxy-benzothiazol-2-ylamino)-1H-benzoimidazole-5-carboxylic acid [2-(4-hydroxy-cyclohexyl)-ethyl]-amide |
| 254 | 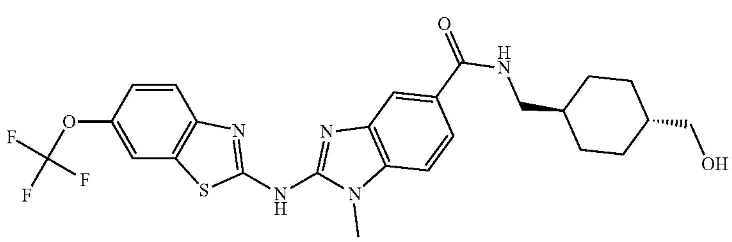 [SMILES: Cn1c(Nc2nc3ccc(OC(F)(F)F)cc3s2)nc2cc(C(=O)NC[C@H]3CC[C@H](CO)CC3)ccc21] | 1-Methyl-2-(6-trifluoromethoxy-benzothiazol-2-ylamino)-1H-benzoimidazole-5-carboxylic acid (trans-4-hydroxymethyl-cyclohexylmethyl)-amide |
| 255 | 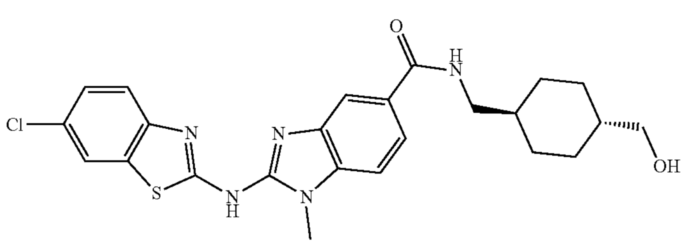 [SMILES: Cn1c(Nc2nc3ccc(Cl)cc3s2)nc2cc(C(=O)NC[C@H]3CC[C@H](CO)CC3)ccc21] | 2-(6-Chloro-benzothiazol-2-ylamino)-1-methyl-1H-benzoimidazole-5-carboxylic acid (trans-4-hydroxymethyl-cyclohexylmethyl)-amide |

TABLE 1-continued

| No. | Structure | Name |
|---|---|---|
| 256 | 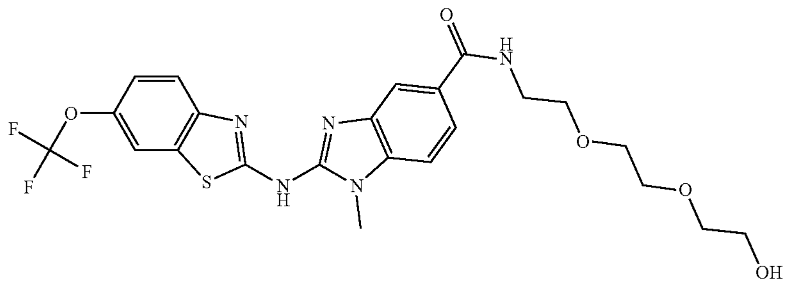 [SMILES: Cn1c(Nc2nc3ccc(OC(F)(F)F)cc3s2)nc2cc(C(=O)NCCOCCOCCO)ccc21] | 1-Methyl-2-(6-trifluoromethoxy-benzothiazol-2-ylamino)-1H-benzoimidazole-5-carboxylic acid {2-[2-(2-hydroxy-ethoxy)-ethoxy]-ethyl}-amide |
| 257 | 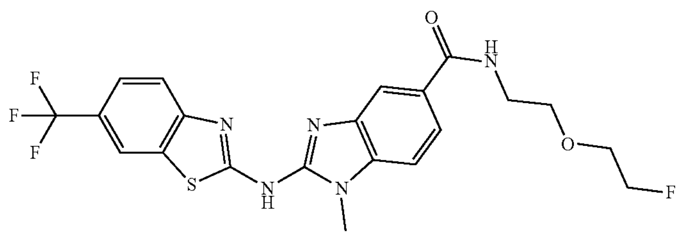 [SMILES: Cn1c(Nc2nc3ccc(C(F)(F)F)cc3s2)nc2cc(C(=O)NCCOCCF)ccc21] | 1-Methyl-2-(6-trifluoromethyl-benzothiazol-2-ylamino)-1H-benzoimidazole-5-carboxylic acid [2-(2-fluoro-ethoxy)-ethyl]-amide |
| 258 | 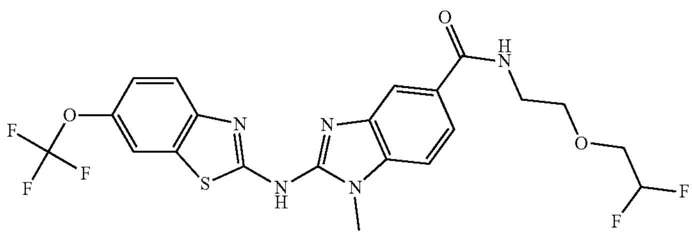 [SMILES: Cn1c(Nc2nc3ccc(OC(F)(F)F)cc3s2)nc2cc(C(=O)NCCOCC(F)F)ccc21] | 1-Methyl-2-(6-trifluoromethoxy-benzothiazol-2-ylamino)-1H-benzoimidazole-5-carboxylic acid [2-(2,2-difluoro-ethoxy)-ethyl]-amide |
| 259 | 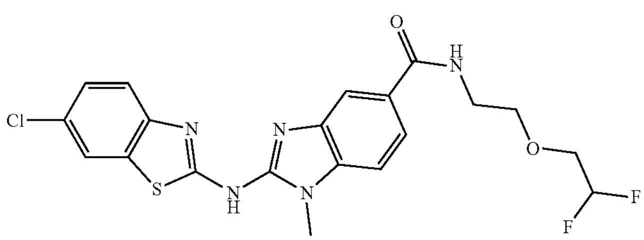 [SMILES: Cn1c(Nc2nc3ccc(Cl)cc3s2)nc2cc(C(=O)NCCOCC(F)F)ccc21] | 2-(6-Chloro-benzothiazol-2-ylamino)-1-methyl-1H-benzoimidazole-5-carboxylic acid [2-(2,2-difluoro-ethoxy)-ethyl]-amide |
| 260 | 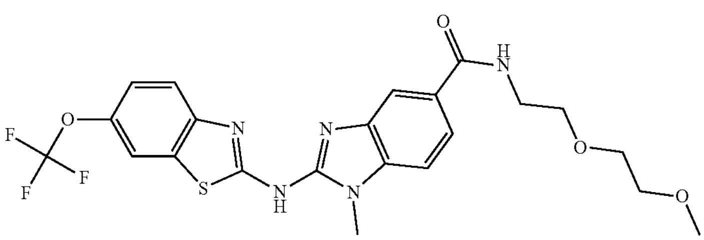 [SMILES: COCCOCCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid [2-(2-methoxy-ethoxy)-ethyl]-amide |
| 261 | 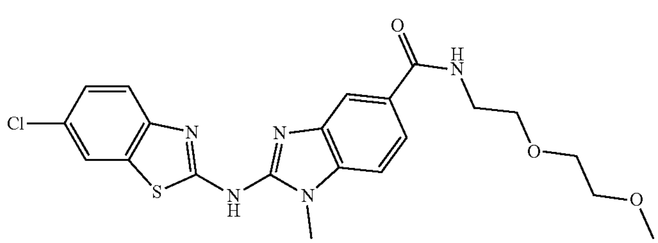 [SMILES: COCCOCCNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid [2-(2-methoxy-ethoxy)-ethyl]-amide |

TABLE 1-continued

| No. | Structure | Name |
|---|---|---|
| 262 | 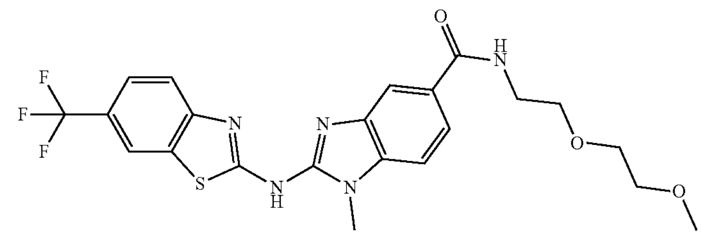 [SMILES: COCCOCCNC(=O)c1ccc2c(c1)nc(Nc1nc3ccc(C(F)(F)F)cc3s1)n2C] | 1-Methyl-2-(6-trifluoromethyl-benzothiazol-2-ylamino)-1H-benzoimidazole-5-carboxylic acid [2-(2-methoxy-ethoxy)-ethyl]-amide |
| 263 | 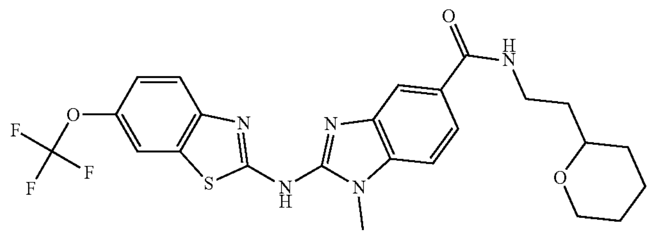 [SMILES: Cn1c(Nc2nc3ccc(OC(F)(F)F)cc3s2)nc2cc(C(=O)NCCC3CCCCO3)ccc21] | 1-Methyl-2-(6-trifluoromethoxy-benzothiazol-2-ylamino)-1H-benzoimidazole-5-carboxylic acid [2-(tetrahydro-pyran-2-yl)-ethyl]-amide |
| 264 | 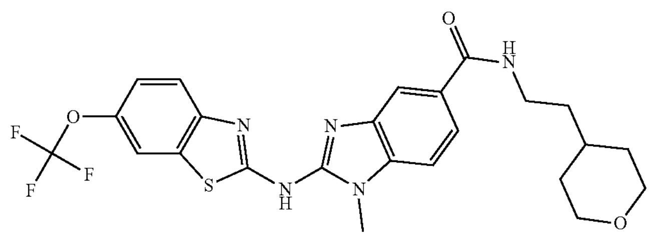 [SMILES: Cn1c(Nc2nc3ccc(OC(F)(F)F)cc3s2)nc2cc(C(=O)NCCC3CCOCC3)ccc21] | 1-Methyl-2-(6-trifluoromethoxy-benzothiazol-2-ylamino)-1H-benzoimidazole-5-carboxylic acid [2-(tetrahydro-pyran-4-yl)-ethyl]-amide |
| 265 | 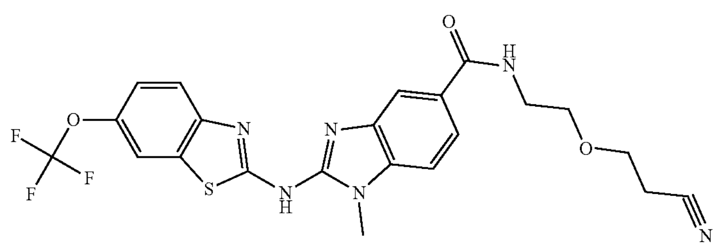 [SMILES: Cn1c(Nc2nc3ccc(OC(F)(F)F)cc3s2)nc2cc(C(=O)NCCOCCC#N)ccc21] | 1-Methyl-2-(6-trifluoromethoxy-benzothiazol-2-ylamino)-1H-benzoimidazole-5-carboxylic acid [2-(2-cyano-ethoxy)-ethyl]-amide |
| 266 | 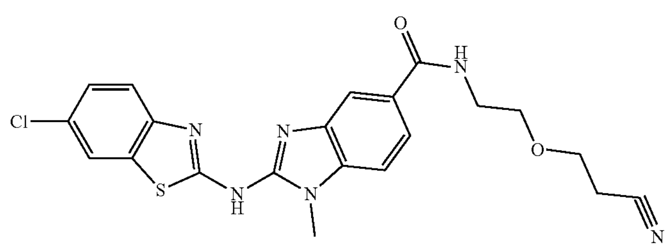 [SMILES: Cn1c(Nc2nc3ccc(Cl)cc3s2)nc2cc(C(=O)NCCOCCC#N)ccc21] | 2-(6-Chloro-benzothiazol-2-ylamino)-1-methyl-1H-benzoimidazole-5-carboxylic acid [2-(2-cyano-ethoxy)-ethyl]-amide |
| 267 | 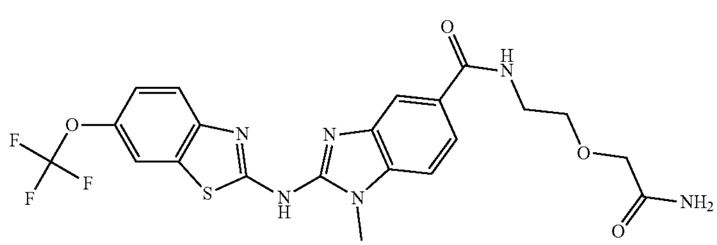 [SMILES: Cn1c(Nc2nc3ccc(OC(F)(F)F)cc3s2)nc2cc(C(=O)NCCOCC(N)=O)ccc21] | 1-Methyl-2-(6-trifluoromethoxy-benzothiazol-2-ylamino)-1H-benzoimidazole-5-carboxylic acid (2-carbamoylmethoxy-ethyl)-amide |

TABLE 1-continued

| No. | Structure | Name |
|---|---|---|
| 268 | 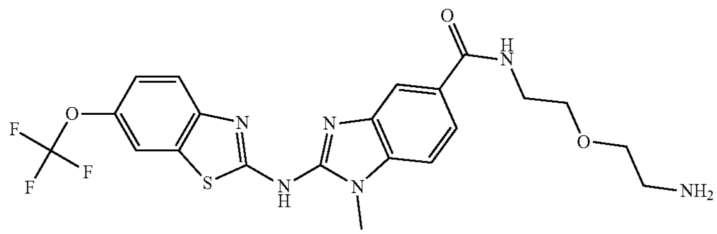 [SMILES: Cn1c(Nc2nc3ccc(OC(F)(F)F)cc3s2)nc2cc(C(=O)NCCOCCN)ccc21] | 1-Methyl-2-(6-trifluoromethoxy-benzothiazol-2-ylamino)-1H benzoimidazole-5-carboxylic acid [2-(2-amino-ethoxy)-ethyl]-amide |
| 269 | 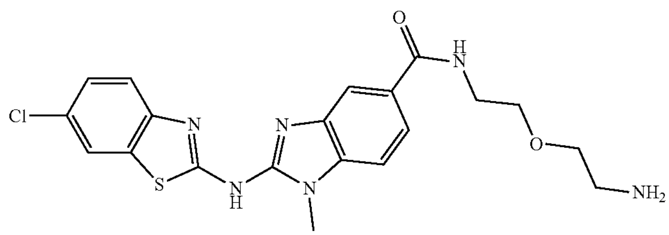 [SMILES: Cn1c(Nc2nc3ccc(Cl)cc3s2)nc2cc(C(=O)NCCOCCN)ccc21] | 2-(6-Chloro-benzothiazol-2-ylamino)-1-methyl-1H-benzoimidazole-5-carboxylic acid [2-(2-amino-ethoxy)-ethyl]-amide |
| 270 | 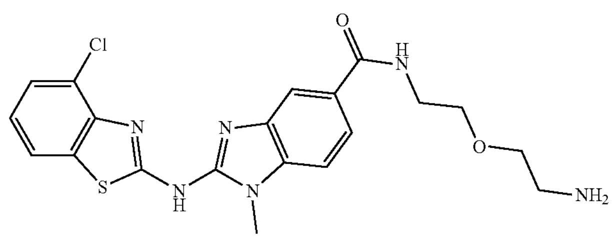 [SMILES: Cn1c(Nc2nc3c(Cl)cccc3s2)nc2cc(C(=O)NCCOCCN)ccc21] | 2-(4-Chloro-benzothiazol-2-ylamino)-1-methyl-1H-benzoimidazole-5-carboxylic acid [2-(2-amino-ethoxy)-ethyl]-amide |
| 271 | 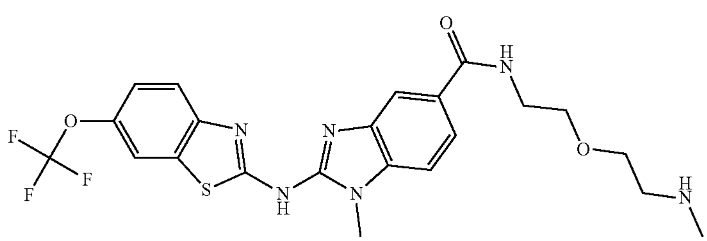 [SMILES: CNCCOCCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid [2-(2-methylamino-ethoxy)-ethyl]-amide hydrochloride |
| 272 | 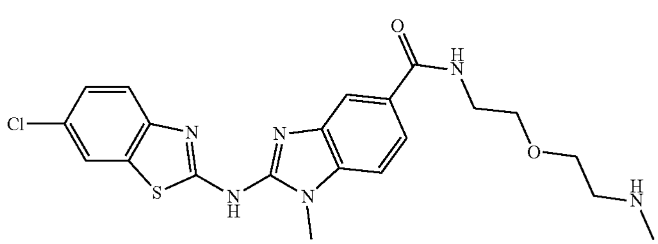 [SMILES: CNCCOCCNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid [2-(2-methylamino-ethoxy)-ethyl]-amide hydrochloride |
| 273 | 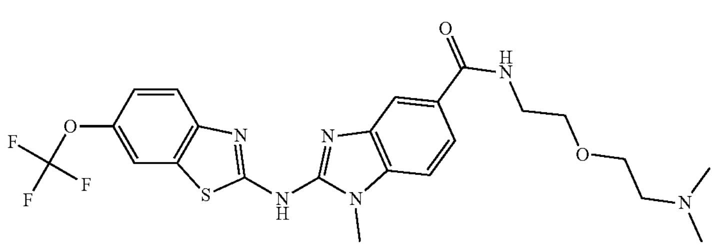 [SMILES: CN(C)CCOCCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid [2-(2-dimethylamino-ethoxy)-ethyl]-amide |

TABLE 1-continued

| No. | Structure | Name |
|---|---|---|
| 274 | 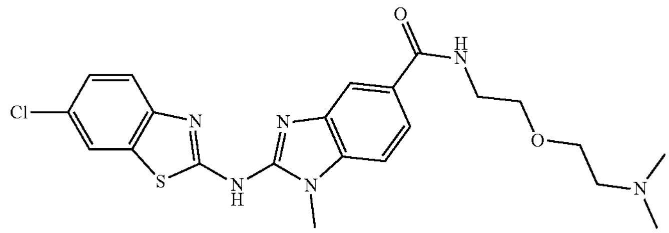 [SMILES: CN(C)CCOCCNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid [2-(2-dimethylamino-ethoxy)-ethyl]-amide |
| 275 | 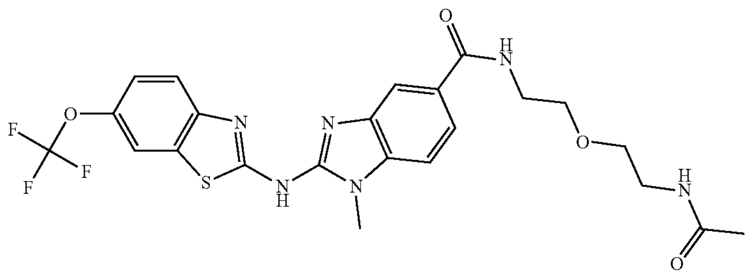 [SMILES: CC(=O)NCCOCCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid [2-(2-acetylamino-ethoxy)-ethyl]-amide |
| 276 | 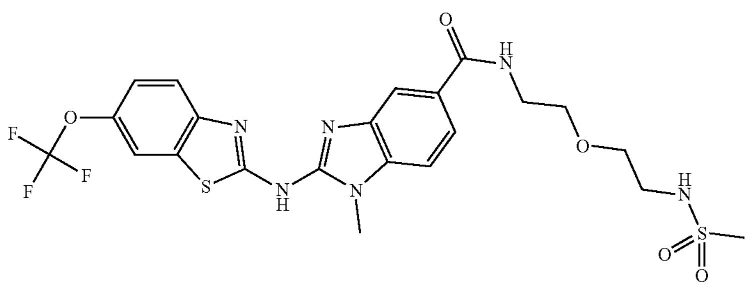 [SMILES: Cn1c(Nc2nc3ccc(OC(F)(F)F)cc3s2)nc2cc(C(=O)NCCOCCNS(C)(=O)=O)ccc21] | 1-Methyl-2-(6-trifluoromethoxy-benzothiazol-2-ylamino)-1H-benzoimidazole-5-carboxylic acid [2-(2-methanesulfonylamino-ethoxy)-ethyl]-amide |
| 277 | 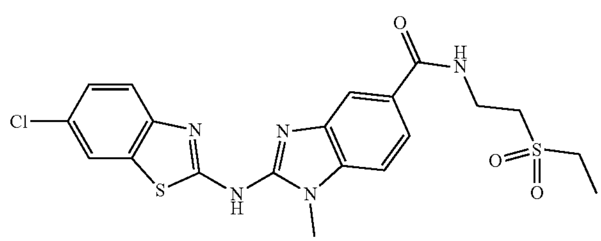 [SMILES: CCS(=O)(=O)CCNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid (2-ethanesulfonyl-ethyl)-amide |
| 278 | 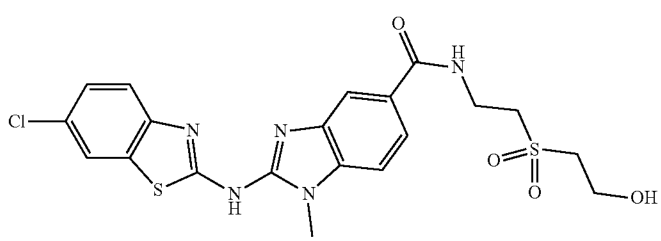 [SMILES: Cn1c(Nc2nc3ccc(Cl)cc3s2)nc2cc(C(=O)NCCS(=O)(=O)CCO)ccc21] | 2-(6-Chloro-benzothiazol-2-ylamino)-1-methyl-1H-benzoimidazole-5-carboxylic acid [2-(2-hydroxy-ethanesulfonyl)-ethyl]-amide |
| 279 | 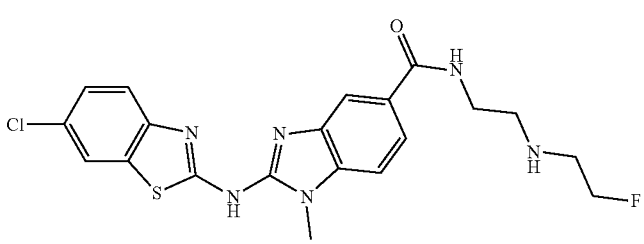 [SMILES: Cn1c(Nc2nc3ccc(Cl)cc3s2)nc2cc(C(=O)NCCNCCF)ccc21] | 2-(6-Chloro-benzothiazol-2-ylamino)-1-methyl-1H-benzoimidazole-5-carboxylic acid [2-(2-fluoro-ethylamino)-ethyl]-amide hydrochloride |

TABLE 1-continued

| No. | Structure | Name |
|---|---|---|
| 280 | 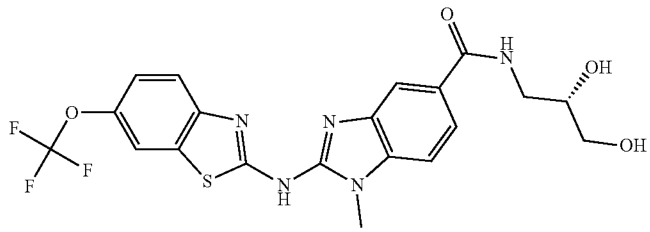 [SMILES: Cn1c(Nc2nc3ccc(OC(F)(F)F)cc3s2)nc2cc(C(=O)NC[C@H](O)CO)ccc21] | 1-Methyl-2-(6-trifluoromethoxy-benzothiazol-2-ylamino)-1H-benzoimidazole-5-carboxylic acid ((S)-2,3-dihydroxy-propyl)-amide |
| 281 | 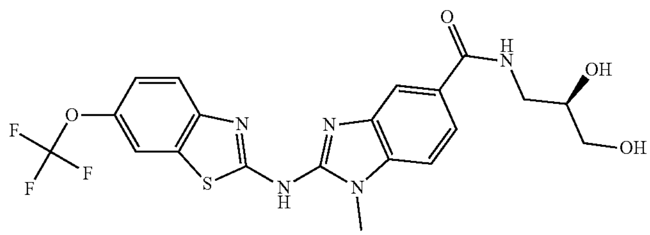 [SMILES: Cn1c(Nc2nc3ccc(OC(F)(F)F)cc3s2)nc2cc(C(=O)NC[C@@H](O)CO)ccc21] | 1-Methyl-2-(6-trifluoromethoxy-benzothiazol-2-ylamino)-1H-benzoimidazole-5-carboxylic acid ((R)-2,3-dihydroxy-propyl)-amide |
| 282 | 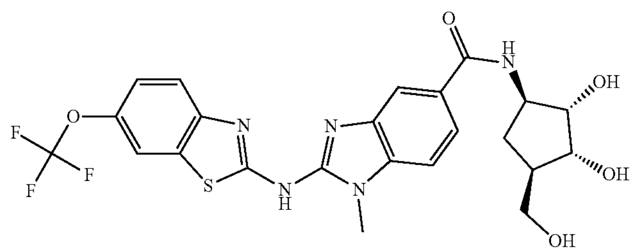 [SMILES: Cn1c(Nc2nc3ccc(OC(F)(F)F)cc3s2)nc2cc(C(=O)N[C@@H]3C[C@H](CO)[C@@H](O)[C@H]3O)ccc21] | 1-Methyl-2-(6-trifluoromethoxy-benzothiazol-2-ylamino)-1H-benzoimidazole-5-carboxylic acid ((1R,2S,3R,4R)-2,3-dihydroxy-4-hydroxymethyl-cyclopentyl)-amide |
| 283 | 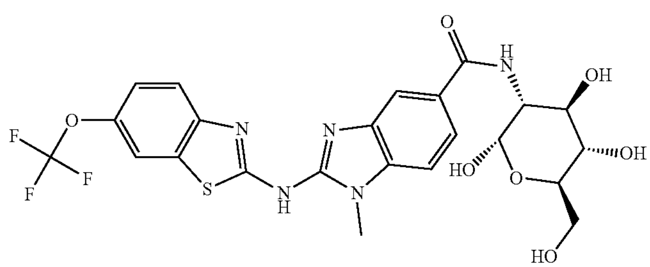 [SMILES: Cn1c(Nc2nc3ccc(OC(F)(F)F)cc3s2)nc2cc(C(=O)N[C@@H]3[C@@H](O)[C@H](O)[C@@H](CO)O[C@@H]3O)ccc21] | 1-Methyl-2-(6-trifluoromethoxy-benzothiazol-2-ylamino)-1H-benzoimidazole-5-carboxylic acid ((2S,3R,4R,5S,6R)-2,4,5-trihydroxy-6-hydroxymethyl-tetrahydro-pyran-3-yl)-amide |
| 284 | 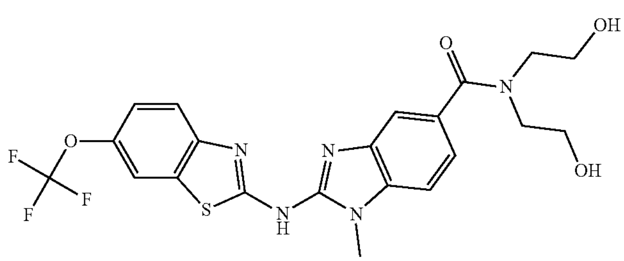 [SMILES: Cn1c(Nc2nc3ccc(OC(F)(F)F)cc3s2)nc2cc(C(=O)N(CCO)CCO)ccc21] | 1-Methyl-2-(6-trifluoromethoxy-benzothiazol-2-ylamino)-1H-benzoimidazole-5-carboxylic acid bis-(2-hydroxy-ethyl)-amide |
| 285 | 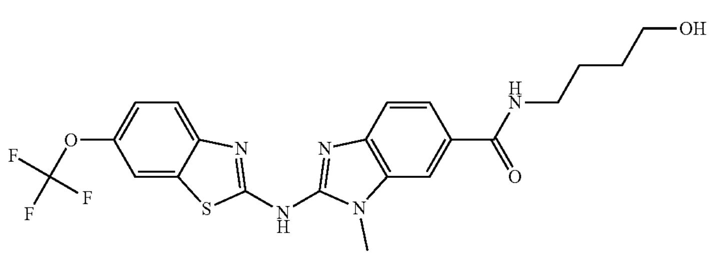 [SMILES: Cn1c(Nc2nc3ccc(OC(F)(F)F)cc3s2)nc2ccc(C(=O)NCCCCO)cc21] | 1-Methyl-2-(6-trifluoromethoxy-benzothiazol-2-ylamino)-1H-benzoimidazole-5-carboxylic acid (4-hydroxy-butyl)-amide |

| No. | Structure | Name |
|---|---|---|
| 286 | 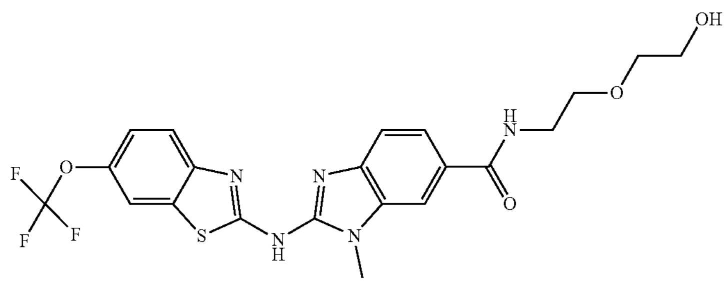 [SMILES: Cn1c(Nc2nc3ccc(OC(F)(F)F)cc3s2)nc2ccc(C(=O)NCCOCCO)cc21] | 1-Methyl-2-(6-trifluoromethoxy-benzothiazol-2-ylamino)-1H-benzoimidazole-5-carboxylic acid [2-(2-hydroxy-ethoxy)-ethyl]-amide |
| 287 | 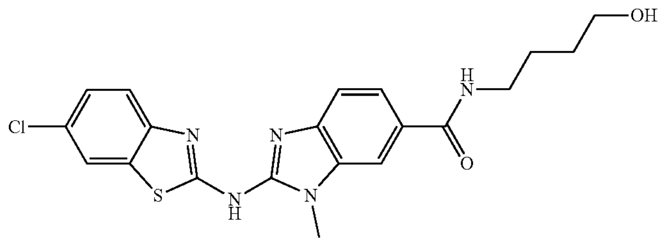 [SMILES: Cn1c(Nc2nc3ccc(Cl)cc3s2)nc2ccc(C(=O)NCCCCO)cc21] | 2-(6-Chloro-benzothiazol-2-ylamino)-1-methyl-1H-benzoimidazole-5-carboxylic acid (4-hydroxy-butyl)-amide |
| 288 | 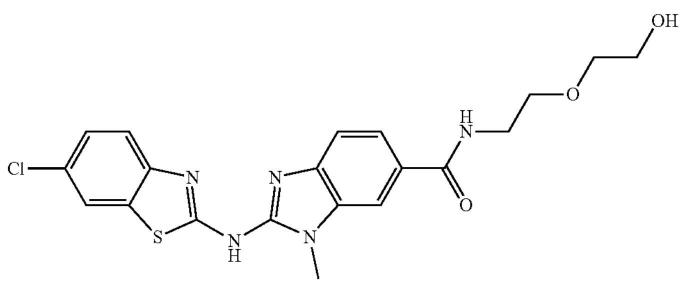 [SMILES: Cn1c(Nc2nc3ccc(Cl)cc3s2)nc2ccc(C(=O)NCCOCCO)cc21] | 2-(6-Chloro-benzothiazol-2-ylamino)-1-methyl-1H-benzoimidazole-5-carboxylic acid [2-(2-hydroxy-ethoxy)-ethyl]-amide |
| 289 | 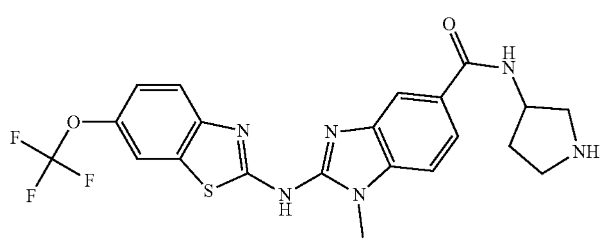 [SMILES: Cn1c(Nc2nc3ccc(OC(F)(F)F)cc3s2)nc2cc(C(=O)NC3CCNC3)ccc21] | 1-Methyl-2-(6-trifluoromethoxy-benzothiazol-2-ylamino)-1H-benzoimidazole-5-carboxylic acid pyrrolidin-3-ylamide hydrochloride |
| 290 | 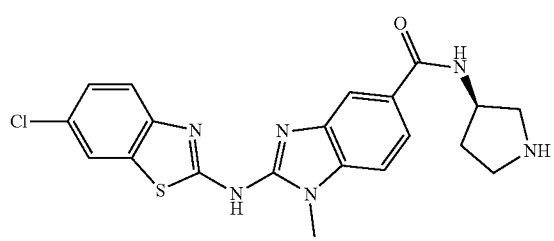 [SMILES: Cn1c(Nc2nc3ccc(Cl)cc3s2)nc2cc(C(=O)N[C@@H]3CCNC3)ccc21] | 2-(6-Chloro-benzothiazol-2-ylamino)-1-methyl-1H-benzoimidazole-5-carboxylic acid (R)-pyrrolidin-3-ylamide hydrochloride |
| 291 | 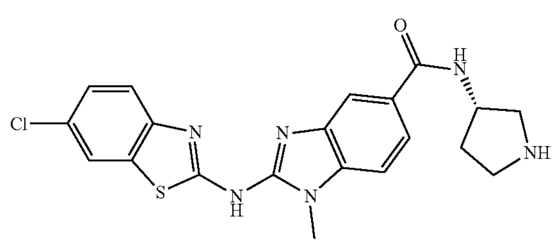 [SMILES: Cn1c(Nc2nc3ccc(Cl)cc3s2)nc2cc(C(=O)N[C@H]3CCNC3)ccc21] | 2-(6-Chloro-benzothiazol-2-ylamino)-1-methyl-1H-benzoimidazole-5-carboxylic acid (S)-pyrrolidin-3-ylamide hydrochloride |

TABLE 1-continued

| No. | Structure | Name |
|---|---|---|
| 292 | 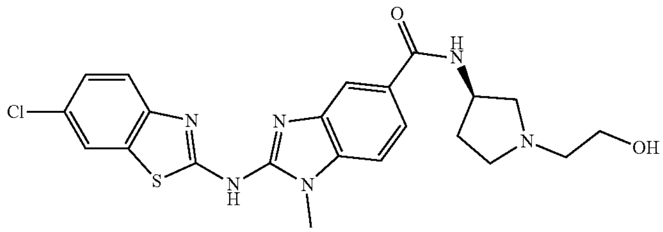 [SMILES: Cn1c(Nc2nc3ccc(Cl)cc3s2)nc2cc(C(=O)N[C@@H]3CCN(CCO)C3)ccc21] | 2-(6-Chloro-benzothiazol-2-ylamino)-1-methyl-1H-benzoimidazole-5-carboxylic acid [(R)-1-(2-hydroxy-ethyl)-pyrrolidin-3-yl]-amide |
| 293 | 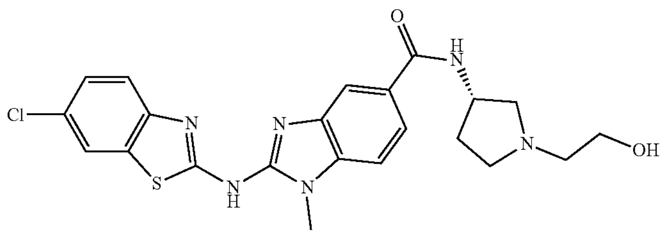 [SMILES: Cn1c(Nc2nc3ccc(Cl)cc3s2)nc2cc(C(=O)N[C@H]3CCN(CCO)C3)ccc21] | 2-(6-Chloro-benzothiazol-2-ylamino)-1-methyl-1H-benzoimidazole-5-carboxylic acid [(S)-1-(2-hydroxy-ethyl)-pyrrolidin-3-yl]-amide |
| 294 | 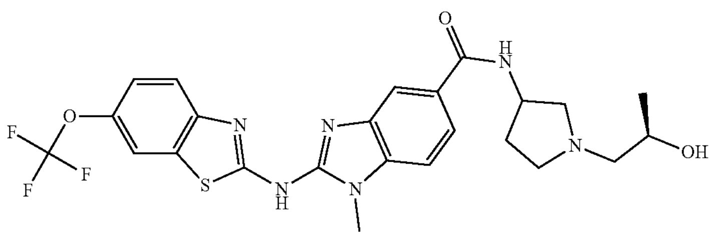 [SMILES: C[C@@H](O)CN1CCC(NC(=O)c2ccc3c(c2)nc(Nc2nc4ccc(OC(F)(F)F)cc4s2)n3C)C1] | 1-Methyl-2-(6-trifluoromethoxy-benzothiazol-2-ylamino)-1H-benzoimidazole-5-carboxylic acid [1-((R)-2-hydroxy-propyl)-pyrrolidin-3-yl]-amide |
| 295 | 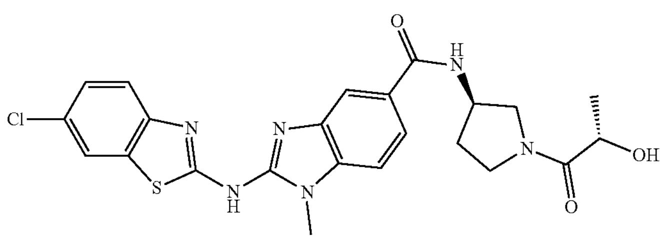 [SMILES: C[C@H](O)C(=O)N1CC[C@@H](NC(=O)c2ccc3c(c2)nc(Nc2nc4ccc(Cl)cc4s2)n3C)C1] | 2-(6-Chloro-benzothiazol-2-ylamino)-1-methyl-1H-benzoimidazole-5-carboxylic acid [(R)-1-((S)-2-hydroxy-propionyl)-pyrrolidin-3-yl]-amide |
| 296 | 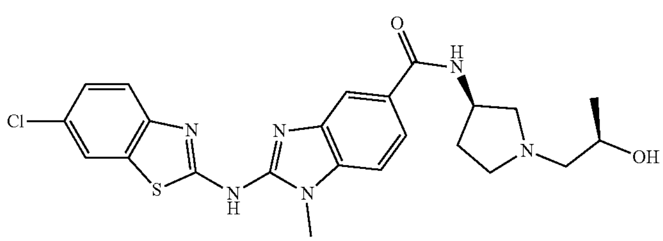 [SMILES: C[C@@H](O)CN1CC[C@@H](NC(=O)c2ccc3c(c2)nc(Nc2nc4ccc(Cl)cc4s2)n3C)C1] | 2-(6-Chloro-benzothiazol-2-ylamino)-1-methyl-1H-benzoimidazole-5-carboxylic acid [(R)-1-((R)-2-hydroxy-propyl)-pyrrolidin-3-yl]-amide |
| 297 | 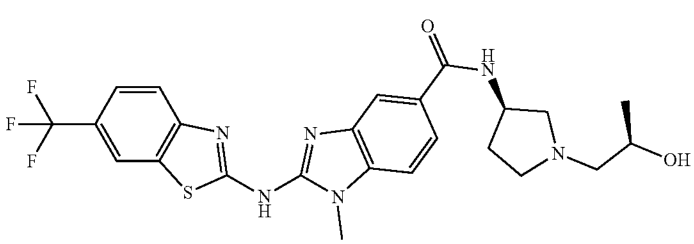 [SMILES: C[C@@H](O)CN1CC[C@@H](NC(=O)c2ccc3c(c2)nc(Nc2nc4ccc(C(F)(F)F)cc4s2)n3C)C1] | 1-Methyl-2-(6-trifluoromethyl-benzothiazol-2-ylamino)-1H-benzoimidazole-5-carboxylic acid [(R)-1-((R)-2-hydroxy-propyl)-pyrrolidin-3-yl]-amide |

TABLE 1-continued

| No. | Structure | Name |
|---|---|---|
| 298 | 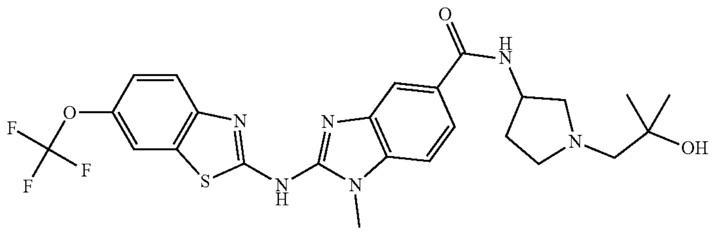 [SMILES: Cn1c(Nc2nc3ccc(OC(F)(F)F)cc3s2)nc2cc(C(=O)NC3CCN(CC(C)(C)O)C3)ccc21] | 1-Methyl-2-(6-trifluoromethoxy-benzothiazol-2-ylamino)-1H-benzoimidazole-5-carboxylic acid [1-(2-hydroxy-2-methyl-propyl)-pyrrolidin-3-yl]-amide |
| 299 | 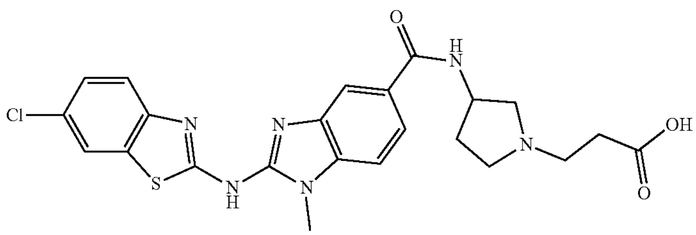 [SMILES: Cn1c(Nc2nc3ccc(Cl)cc3s2)nc2cc(C(=O)NC3CCN(CCC(=O)O)C3)ccc21] | 3-(3-{[2-(6-Chloro-benzothiazol-2-ylamino)-1-methyl-1H-benzoimidazole-5-carbonyl]-amino}-pyrrolidin-1-yl)-propionic acid |
| 300 | 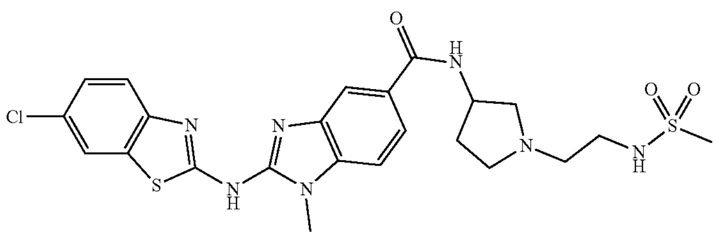 [SMILES: Cn1c(Nc2nc3ccc(Cl)cc3s2)nc2cc(C(=O)NC3CCN(CCNS(C)(=O)=O)C3)ccc21] | 2-(6-Chloro-benzothiazol-2-ylamino)-1-methyl-1H-benzoimidazole-5-carboxylic acid [1-(2-methanesulfonylamino-ethyl)-pyrrolidin-3-yl]-amide |
| 301 | 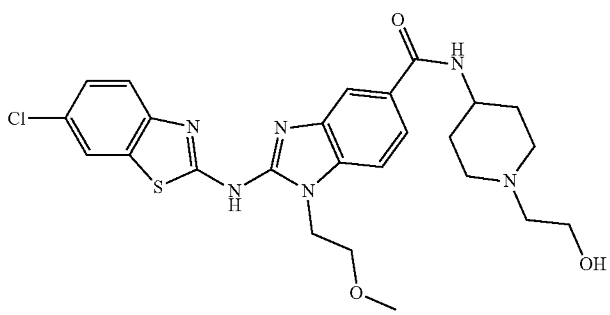 [SMILES: COCCn1c(Nc2nc3ccc(Cl)cc3s2)nc2cc(C(=O)NC3CCN(CCO)CC3)ccc21] | 2-(6-Chloro-benzothiazol-2-ylamino)-1-(2-methoxy-ethyl)-1H-benzoimidazole-5-carboxylic acid [1-(2-hydroxy-ethyl)-piperidin-4-yl]-amide |
| 302 | 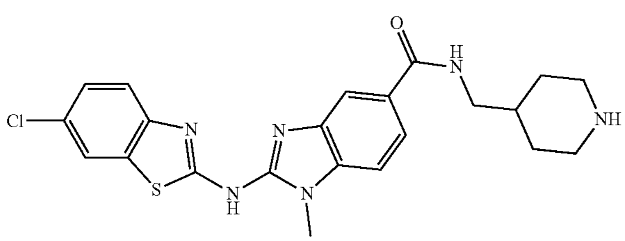 [SMILES: Cn1c(Nc2nc3ccc(Cl)cc3s2)nc2cc(C(=O)NCC3CCNCC3)ccc21] | 2-(6-Chloro-benzothiazol-2-ylamino)-1-methyl-1H-benzoimidazole-5-carboxylic acid (piperidin-4-ylmethyl)-amide hydrochloride |
| 303 | 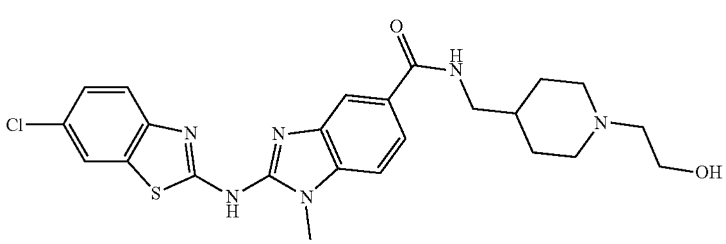 [SMILES: Cn1c(Nc2nc3ccc(Cl)cc3s2)nc2cc(C(=O)NCC3CCN(CCO)CC3)ccc21] | 2-(6-Chloro-benzothiazol-2-ylamino)-1-methyl-1H-benzoimidazole-5-carboxylic acid [1-(2-hydroxy-ethyl)-piperidin-4-ylmethyl]-amide |

TABLE 1-continued

| No. | Structure | Name |
|---|---|---|
| 304 | 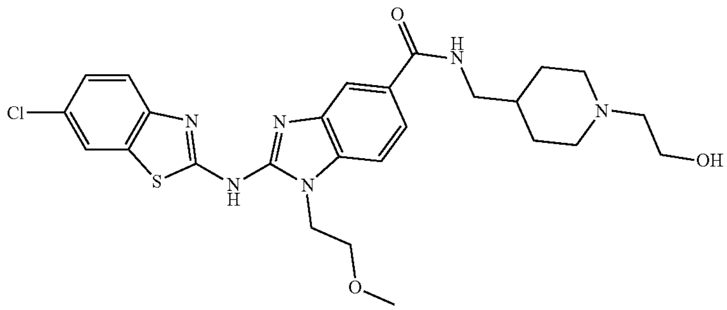 [SMILES: COCCn1c(Nc2nc3ccc(Cl)cc3s2)nc2cc(C(=O)NCC3CCN(CCO)CC3)ccc21] | 2-(6-Chloro-benzothiazol-2-ylamino)-1-(2-methoxy-ethyl)-1H-benzoimidazole-5-carboxylic acid [1-(2-hydroxy-ethyl)-piperidin-4-ylmethyl]-amide |
| 305 | 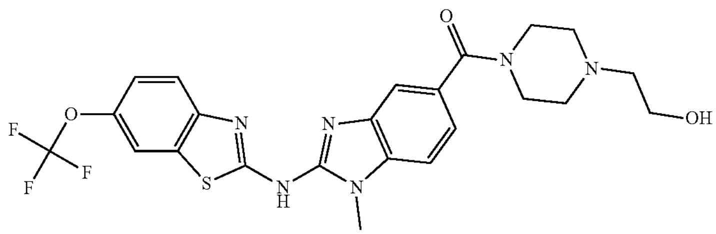 [SMILES: Cn1c(Nc2nc3ccc(OC(F)(F)F)cc3s2)nc2cc(C(=O)N3CCN(CCO)CC3)ccc21] | [4-(2-Hydroxy-ethyl)-piperazin-1-yl]-[1-methyl-2-(6-trifluoromethoxy-benzothiazol-2-ylamino)-1H-benzoimidazol-5-yl]-methanone |
| 306 | 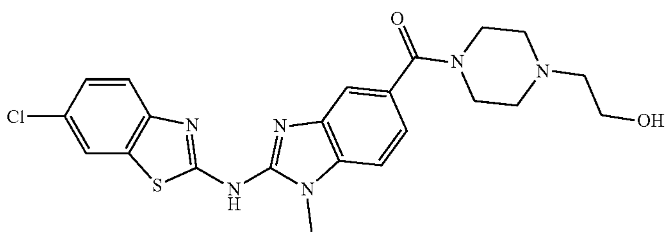 [SMILES: Cn1c(Nc2nc3ccc(Cl)cc3s2)nc2cc(C(=O)N3CCN(CCO)CC3)ccc21] | [2-(6-Chloro-benzothiazol-2-ylamino)-1-methyl-1H-benzoimidazol-5-yl]-[4-(2-hydroxy-ethyl)-piperazin-1-yl]-methanone |
| 307 | 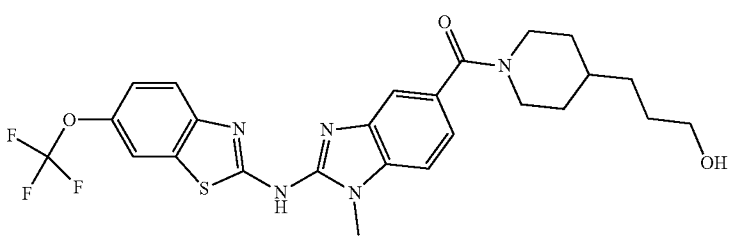 [SMILES: Cn1c(Nc2nc3ccc(OC(F)(F)F)cc3s2)nc2cc(C(=O)N3CCC(CCCO)CC3)ccc21] | [4-(3-Hydroxy-propyl)-piperidin-1-yl]-[1-methyl-2-(6-trifluoromethoxy-benzothiazol-2-ylamino)-1H benzoimidazol-5-yl]-methanone |
| 308 | 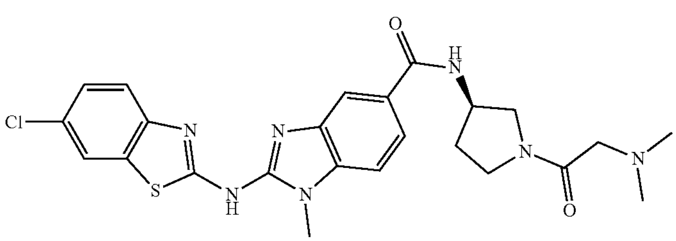 [SMILES: CN(C)CC(=O)N1CC[C@@H](NC(=O)c2ccc3c(c2)nc(Nc2nc4ccc(Cl)cc4s2)n3C)C1] | 2-(6-Chloro-benzothiazol-2-ylamino)-1-methyl-1H-benzoimidazole-5-carboxylic acid [(R)-1-(2-dimethylamino-acetyl)-pyrrolidin-3-yl]-amide |
| 309 | 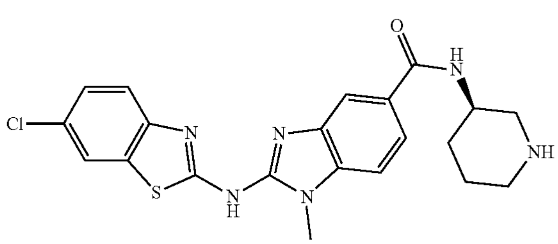 [SMILES: Cn1c(Nc2nc3ccc(Cl)cc3s2)nc2cc(C(=O)N[C@@H]3CCCNC3)ccc21] | 2-(6-Chloro-benzothiazol-2-ylamino)-1-methyl-1H-benzoimidazole-5-carboxylic acid (R)-piperidin-3-ylamide hydrochloride |

TABLE 1-continued

| No. | Structure | Name |
|---|---|---|
| 310 | 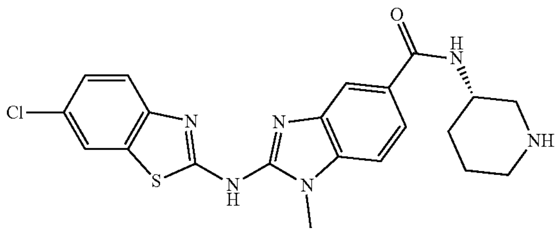 [SMILES: Cn1c(Nc2nc3ccc(Cl)cc3s2)nc2cc(C(=O)N[C@H]3CCCNC3)ccc21] | 2-(6-Chloro-benzothiazol-2-ylamino)-1-methyl-1H-benzoimidazole-5-carboxylic acid (S)-piperidin-3-ylamide hydrochloride |
| 311 | 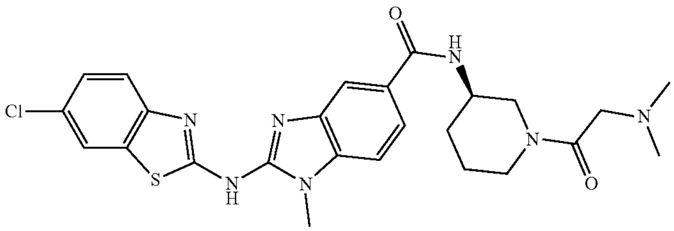 [SMILES: CN(C)CC(=O)N1CCC[C@@H](NC(=O)c2ccc3c(c2)nc(Nc2nc4ccc(Cl)cc4s2)n3C)C1] | 2-(6-Chloro-benzothiazol-2-ylamino)-1-methyl-1H-benzoimidazole-5-carboxylic acid [(R)-1-(2-dimethylamino-acetyl)-piperidin-3-yl]-amide |
| 312 | 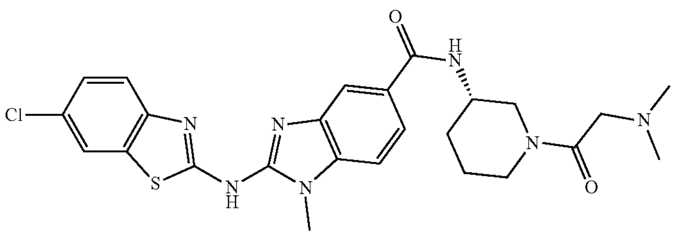 [SMILES: CN(C)CC(=O)N1CCC[C@H](NC(=O)c2ccc3c(c2)nc(Nc2nc4ccc(Cl)cc4s2)n3C)C1] | 2-(6-Chloro-benzothiazol-2-ylamino)-1-methyl-1H-benzoimidazole-5-carboxylic acid [(S)-1-(2-dimethylamino-acetyl)-piperidin-3-yl]-amide |
| 313 | 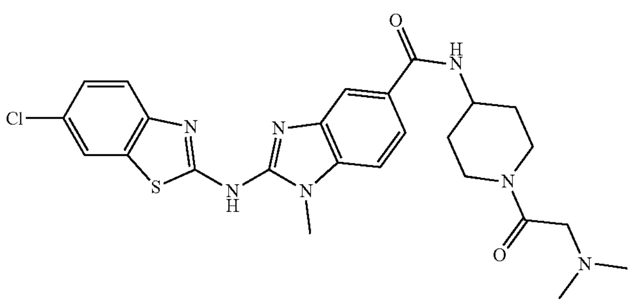 [SMILES: CN(C)CC(=O)N1CCC(NC(=O)c2ccc3c(c2)nc(Nc2nc4ccc(Cl)cc4s2)n3C)CC1] | 2-(6-Chloro-benzothiazol-2-ylamino)-1-methyl-1H-benzoimidazole-5-carboxylic acid [1-(2-dimethylamino-acetyl)-piperidin-4-yl]-amide |
| 314 | 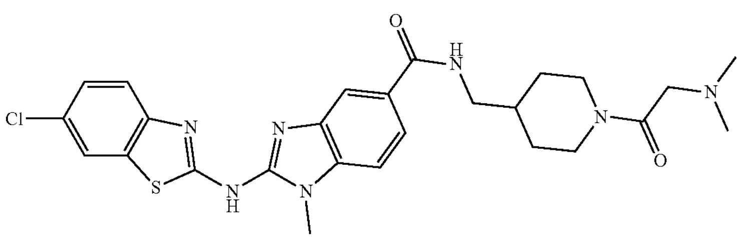 [SMILES: CN(C)CC(=O)N1CCC(CNC(=O)c2ccc3c(c2)nc(Nc2nc4ccc(Cl)cc4s2)n3C)CC1] | 2-(6-Chloro-benzothiazol-2-ylamino)-1-methyl-1H-benzoimidazole-5-carboxylic acid [1-(2-dimethylamino-acetyl)-piperidin-4-ylmethyl]-amide |
| 315 | 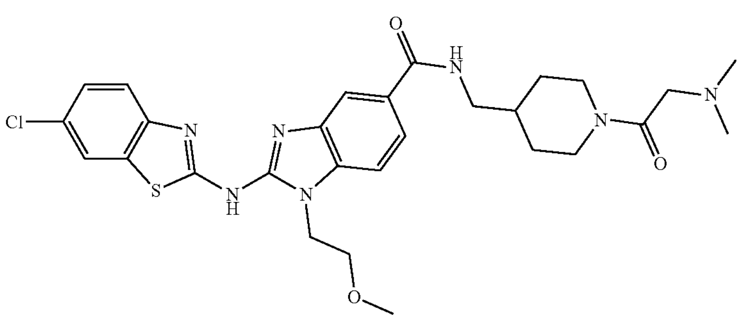 [SMILES: COCCn1c(Nc2nc3ccc(Cl)cc3s2)nc2cc(C(=O)NCC3CCN(C(=O)CN(C)C)CC3)ccc21] | 2-(6-Chloro-benzothiazol-2-ylamino)-1-(2-methoxy-ethyl)-1H-benzoimidazole-5-carboxylic acid [1-(2-dimethylamino-acetyl)-piperidin-4-ylmethyl]-amide |

TABLE 1-continued

| No. | Structure | Name |
|---|---|---|
| 316 | 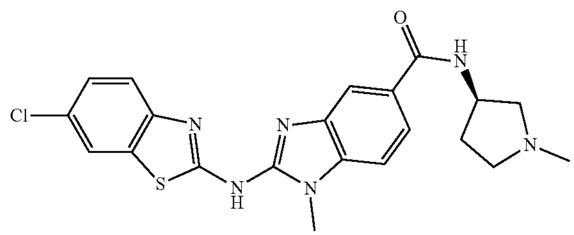 [SMILES: CN1CC[C@@H](NC(=O)c2ccc3c(c2)nc(Nc2nc4ccc(Cl)cc4s2)n3C)C1] | 2-(6-Chloro-benzothiazol-2-ylamino)-1-methyl-1H benzoimidazole-5-carboxylic acid ((R)-1-methyl-pyrrolidin-3-yl)-amide |
| 317 | 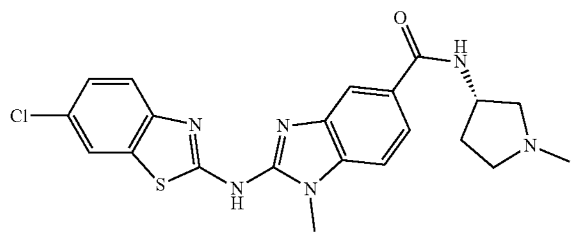 [SMILES: CN1CC[C@H](NC(=O)c2ccc3c(c2)nc(Nc2nc4ccc(Cl)cc4s2)n3C)C1] | 2-(6-Chloro-benzothiazol-2 ylamino)-1-methyl-1H-benzoimidazole-5-carboxylic acid ((S)-1-methyl-pyrrolidin-3-yl)-amide |
| 318 | 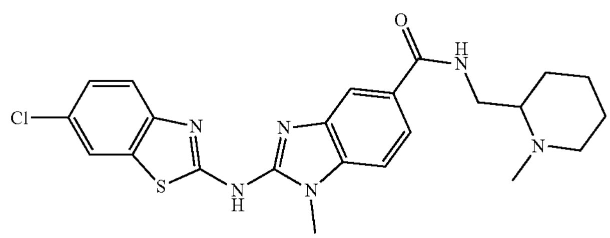 [SMILES: CN1CCCCC1CNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid (1-methyl-piperidin-2-ylmethyl)-amide |
| 319 | 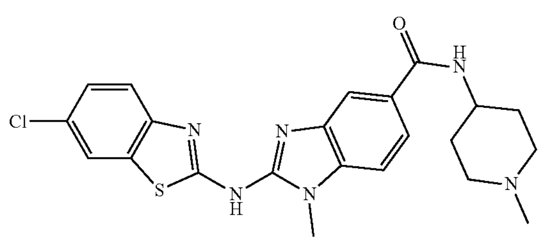 [SMILES: CN1CCC(NC(=O)c2ccc3c(c2)nc(Nc2nc4ccc(Cl)cc4s2)n3C)CC1] | 2-(6-Chloro-benzothiazol-2-ylamino)-1-methyl-1H-benzoimidazole-5-carboxylic acid (1-methyl-piperidin-4-yl)-amide |
| 320 | 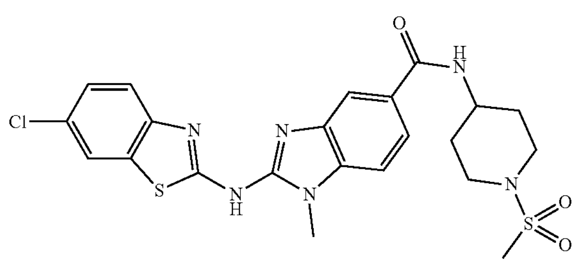 [SMILES: Cn1c(Nc2nc3ccc(Cl)cc3s2)nc2cc(C(=O)NC3CCN(S(C)(=O)=O)CC3)ccc21] | 2-(6-Chloro-benzothiazol-2-ylamino)-1-methyl-1H-benzoimidazole-5-carboxylic acid (1-methanesulfonyl-piperidin-4-yl)-amide |
| 321 | 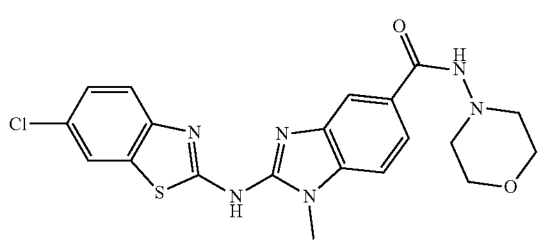 [SMILES: Cn1c(Nc2nc3ccc(Cl)cc3s2)nc2cc(C(=O)NN3CCOCC3)ccc21] | 2-(6-Chloro-benzothiazol-2-ylamino)-1-methyl-1H-benzoimidazole-5-carboxylic acid morpholin-4-ylamide |

TABLE 1-continued

| No. | Structure | Name |
|---|---|---|
| 322 | 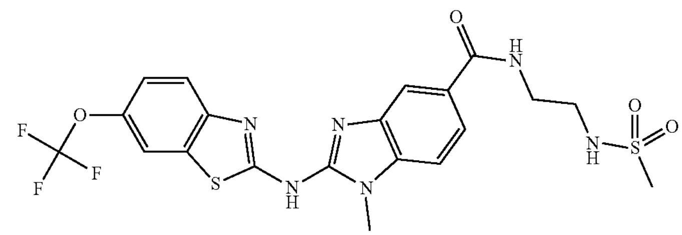 [SMILES: Cn1c(Nc2nc3ccc(OC(F)(F)F)cc3s2)nc2cc(C(=O)NCCNS(C)(=O)=O)ccc21] | 1-Methyl-2-(6-trifluoromethoxy-benzothiazol-2-ylamino)-1H-benzoimidazole-5-carboxylic acid (2-methanesulfonylamino-ethyl)-amide |
| 323 | 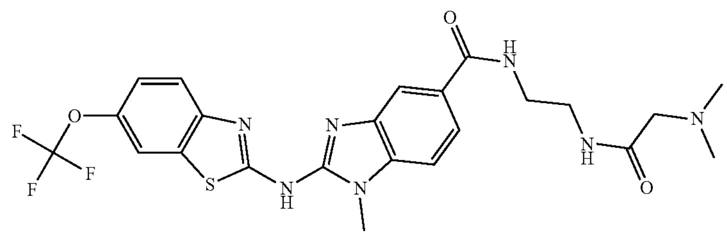 [SMILES: CN(C)CC(=O)NCCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid [2-(2-dimethylamino-acetylamino)-ethyl]-amide |
| 324 | 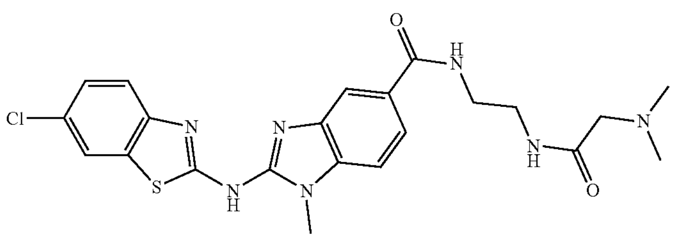 [SMILES: CN(C)CC(=O)NCCNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid [2-(2-dimethylamino-acetylamino)-ethyl]-amide |
| 325 | 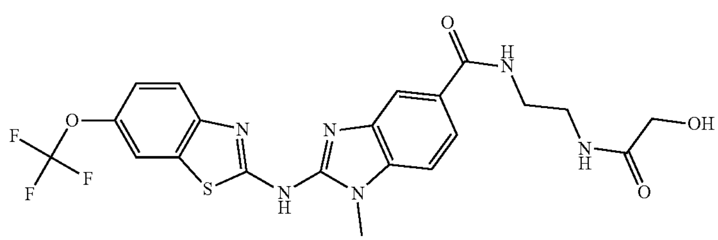 [SMILES: Cn1c(Nc2nc3ccc(OC(F)(F)F)cc3s2)nc2cc(C(=O)NCCNC(=O)CO)ccc21] | 1-Methyl-2-(6-trifluoromethoxy-benzothiazol-2-ylamino)-1H-benzoimidazole-5-carboxylic acid [2-(2-hydroxy-acetylamino)-ethyl]-amide |
| 326 | 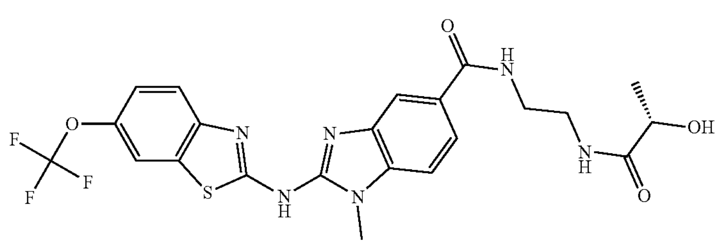 [SMILES: C[C@H](O)C(=O)NCCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid [2-((S)-2-hydroxy-propionylamino)-ethyl]-amide |
| 327 | 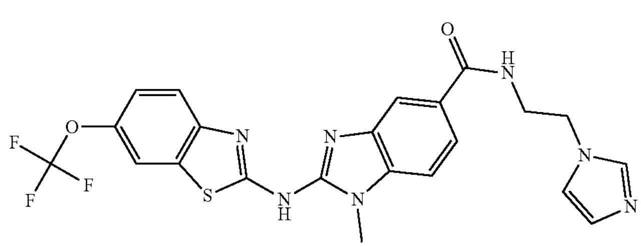 [SMILES: Cn1c(Nc2nc3ccc(OC(F)(F)F)cc3s2)nc2cc(C(=O)NCCn3ccnc3)ccc21] | 1-Methyl-2-(6-trifluoromethoxy-benzothiazol-2-ylamino)-1H-benzoimidazole-5-carboxylic acid (2-imidazol-1-yl-ethyl)-amide |

TABLE 1-continued

| No. | Structure | Name |
|---|---|---|
| 328 | 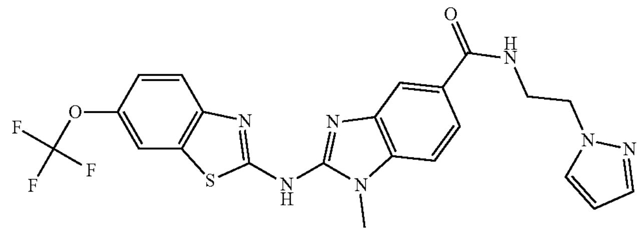 [SMILES: Cn1c(Nc2nc3ccc(OC(F)(F)F)cc3s2)nc2cc(C(=O)NCCn3cccn3)ccc21] | 1-Methyl-2-(6-trifluoromethoxy-benzothiazol-2-ylamino)-1H-benzoimidazole-5-carboxylic acid (2-pyrazol-1-yl-ethyl)-amide |
| 329 | 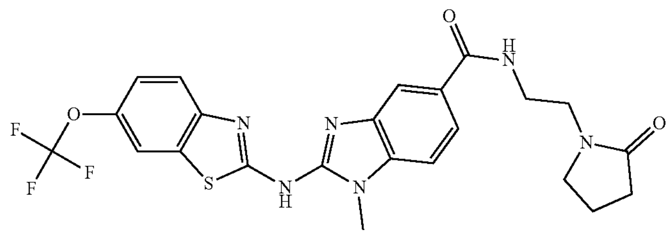 [SMILES: Cn1c(Nc2nc3ccc(OC(F)(F)F)cc3s2)nc2cc(C(=O)NCCN3CCCC3=O)ccc21] | 1-Methyl-2-(6-trifluoromethoxy-benzothiazol-2-ylamino)-1H-benzoimidazole-5-carboxylic acid [2-(2-oxo-pyrrolidin-1-yl)-ethyl]-amide |
| 330 | 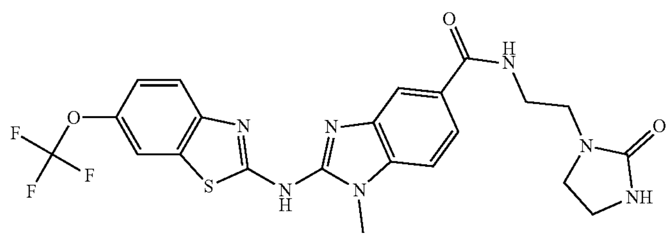 [SMILES: Cn1c(Nc2nc3ccc(OC(F)(F)F)cc3s2)nc2cc(C(=O)NCCN3CCNC3=O)ccc21] | 1-Methyl-2-(6-trifluoromethoxy-benzothiazol-2-ylamino)-1H-benzoimidazole-5-carboxylic acid [2-(2-oxo-imidazolidin-1-yl)-ethyl]-amide |
| 331 | 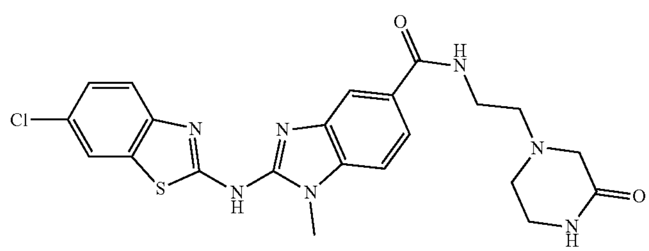 [SMILES: Cn1c(Nc2nc3ccc(Cl)cc3s2)nc2cc(C(=O)NCCN3CCNC(=O)C3)ccc21] | 2-(6-Chloro-benzothiazol-2-ylamino)-1-methyl-1H-benzoimidazole-5-carboxylic acid [2-(3-oxo-piperazin-1-yl)-ethyl]-amide |
| 332 | 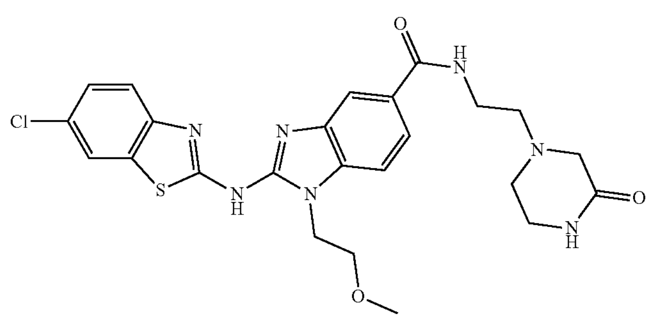 [SMILES: COCCn1c(Nc2nc3ccc(Cl)cc3s2)nc2cc(C(=O)NCCN3CCNC(=O)C3)ccc21] | 2-(6-Chloro-benzothiazol-2-ylamino)-1-(2-methoxy-ethyl)-1H-benzoimidazole-5-carboxylic acid [2-(3-oxo-piperazin-1-yl)-ethyl]-amide |
| 333 | 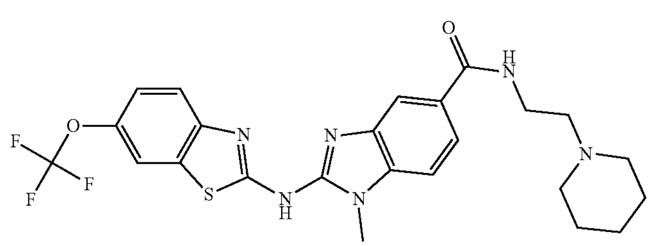 | 1-Methyl-2-(6-trifluoromethoxy-benzothiazol-2-ylamino)-1H-benzoimidazole-5-carboxylic acid (2-piperidin-1-yl-ethyl)-amide |

TABLE 1-continued

| No. | Structure | Name |
|---|---|---|
| 334 | 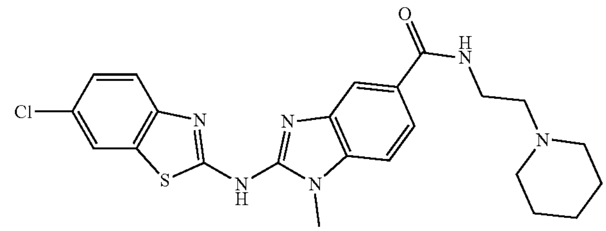 [SMILES: Cn1c(Nc2nc3ccc(Cl)cc3s2)nc2cc(C(=O)NCCN3CCCCC3)ccc21] | 2-(6-Chloro-benzothiazol-2-ylamino)-1-methyl-1H-benzoimidazole-5-carboxylic acid (2-piperidin-1-yl-ethyl)-amide |
| 335 | 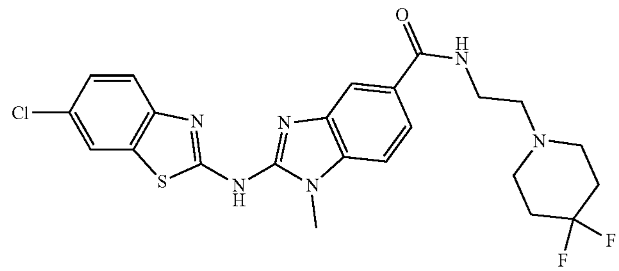 [SMILES: Cn1c(Nc2nc3ccc(Cl)cc3s2)nc2cc(C(=O)NCCN3CCC(F)(F)CC3)ccc21] | 2-(6-Chloro-benzothiazol-2-ylamino)-1-methyl-1H-benzoimidazole-5-carboxylic acid [2-(4,4-difluoro-piperidin-1-yl)-ethyl]-amide |
| 336 | 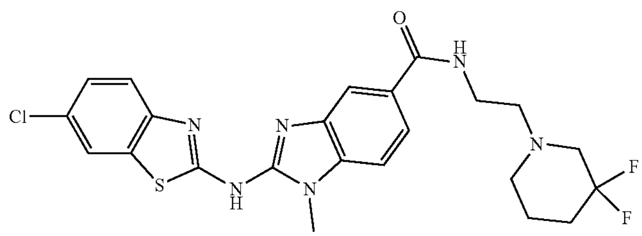 [SMILES: Cn1c(Nc2nc3ccc(Cl)cc3s2)nc2cc(C(=O)NCCN3CCCC(F)(F)C3)ccc21] | 2-(6-Chloro-benzothiazol-2-ylamino)-1-methyl-1H-benzoimidazole-5-carboxylic acid [2-(3,3-difluoro-piperidin-1-yl)-ethyl]-amide |
| 337 | 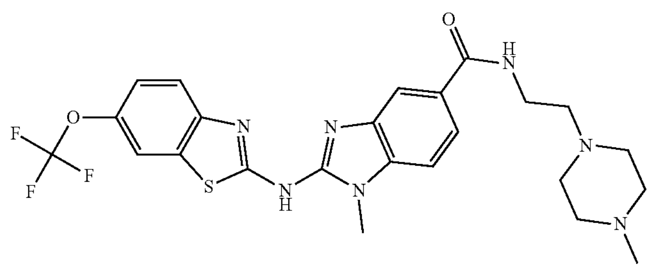 [SMILES: CN1CCN(CCNC(=O)c2ccc3c(c2)nc(Nc2nc4ccc(OC(F)(F)F)cc4s2)n3C)CC1] | 1-Methyl-2-(6-trifluoromethoxy-benzothiazol-2-ylamino)-1H-benzoimidazole-5-carboxylic acid [2-(4-methyl-piperazin-1-yl)-ethyl]-amide |
| 338 | 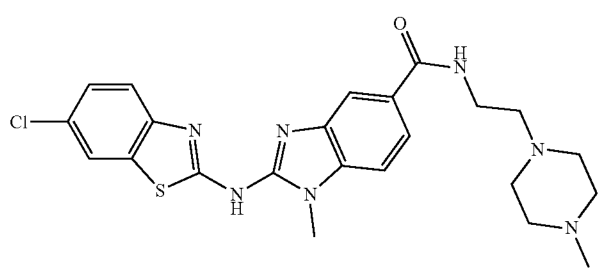 [SMILES: CN1CCN(CCNC(=O)c2ccc3c(c2)nc(Nc2nc4ccc(Cl)cc4s2)n3C)CC1] | 2-(6-Chloro-benzothiazol-2-ylamino)-1-methyl-1H-benzoimidazole-5-carboxylic acid [2-(4-methyl-piperazin-1-yl)-ethyl]-amide |
| 339 | 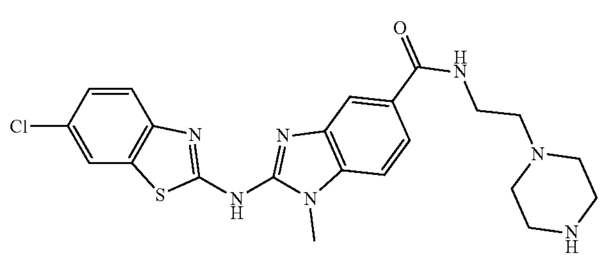 [SMILES: Cn1c(Nc2nc3ccc(Cl)cc3s2)nc2cc(C(=O)NCCN3CCNCC3)ccc21] | 2-(6-Chloro-benzothiazol-2-ylamino)-1-methyl-1H-benzoimidazole-5-carboxylic acid (2-piperazin-1-yl-ethyl)-amide hydrochloride |

TABLE 1-continued

| No. | Structure | Name |
|---|---|---|
| 340 | 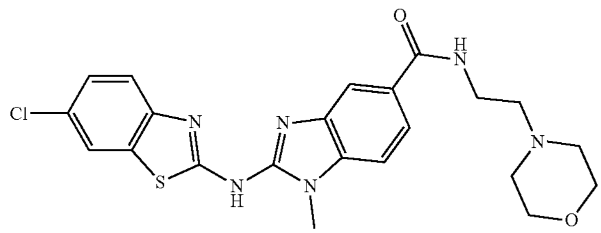 [SMILES: Cn1c(Nc2nc3ccc(Cl)cc3s2)nc2cc(C(=O)NCCN3CCOCC3)ccc21] | 2-(6-Chloro-benzothiazol-2-ylamino)-1-methyl-1H-benzoimidazole-5-carboxylic acid (2-morpholin-4-yl-ethyl)-amide |
| 341 | 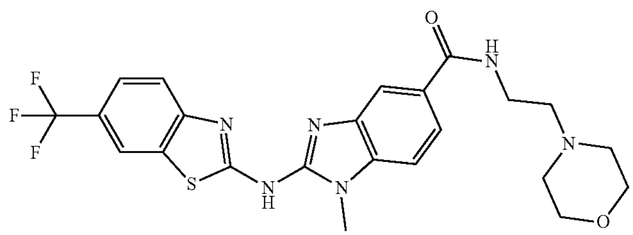 [SMILES: Cn1c(Nc2nc3ccc(C(F)(F)F)cc3s2)nc2cc(C(=O)NCCN3CCOCC3)ccc21] | 1-Methyl-2-(6-trifluoromethyl-benzothiazol-2-ylamino)-1H-benzoimidazole-5-carboxylic acid (2-morpholin-4-yl-ethyl)-amide |
| 342 | 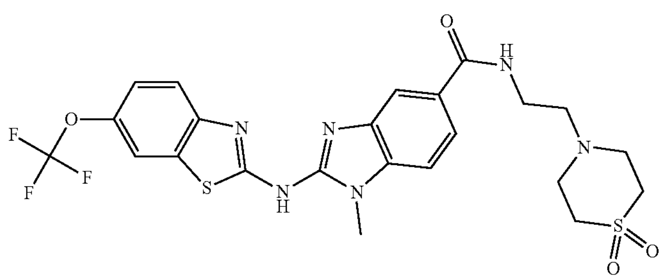 [SMILES: Cn1c(Nc2nc3ccc(OC(F)(F)F)cc3s2)nc2cc(C(=O)NCCN3CCS(=O)(=O)CC3)ccc21] | 1-Methyl-2-(6-trifluoromethoxy-benzothiazol-2-ylamino)-1H-benzoimidazole-5-carboxylic acid [2-(1,1-dioxo-thiomorpholin-4-yl)-ethyl]-amide |
| 343 | 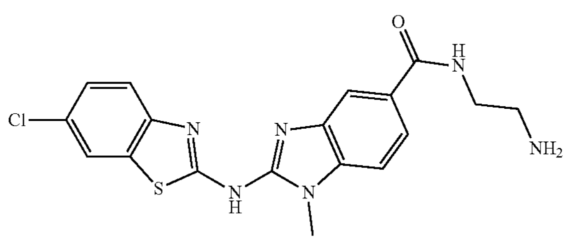 [SMILES: Cn1c(Nc2nc3ccc(Cl)cc3s2)nc2cc(C(=O)NCCN)ccc21] | 2-(6-Chloro-benzothiazol-2-ylamino)-1-methyl-1H-benzoimidazole-5-carboxylic acid (2-amino-ethyl)-amide hydrochloride |
| 344 | 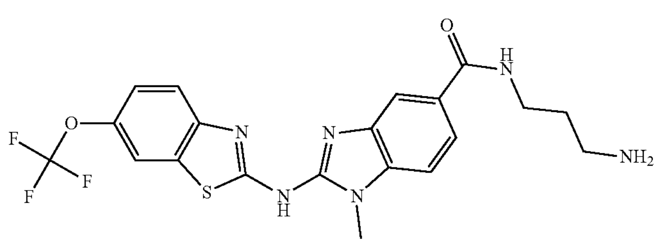 [SMILES: Cn1c(Nc2nc3ccc(OC(F)(F)F)cc3s2)nc2cc(C(=O)NCCCN)ccc21] | 1-Methyl-2-(6-trifluoromethoxy-benzothiazol-2-ylamino)-1H-benzoimidazole-5-carboxylic acid (3-amino-propyl)-amide hydrochloride |
| 345 | 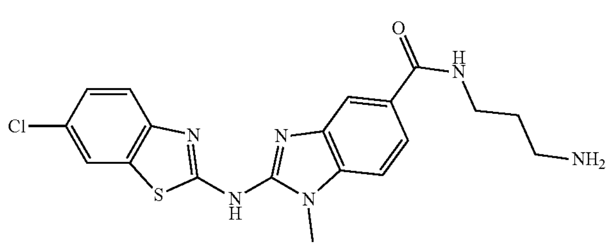 [SMILES: Cn1c(Nc2nc3ccc(Cl)cc3s2)nc2cc(C(=O)NCCCN)ccc21] | 2-(6-Chloro-benzothiazol-2-ylamino)-1-methyl-1H-benzoimidazole-5-carboxylic acid (3-amino-propyl)-amide hydrochloride |

| No. | Structure | Name |
|---|---|---|
| 346 | 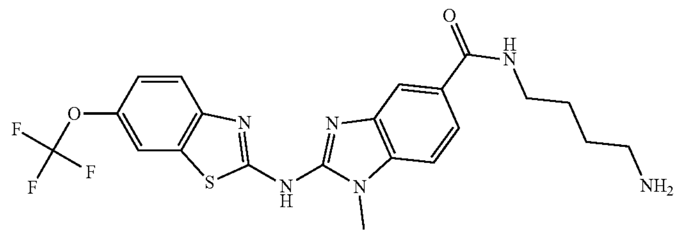 [SMILES: Cn1c(Nc2nc3ccc(OC(F)(F)F)cc3s2)nc2cc(C(=O)NCCCCN)ccc21] | 1-Methyl-2-(6-trifluoromethoxy-benzothiazol-2-ylamino)-1H-benzoimidazole-5-carboxylic acid (4-amino-butyl)-amide hydrochloride |
| 347 | 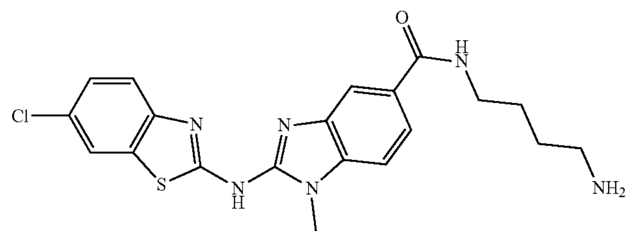 [SMILES: Cn1c(Nc2nc3ccc(Cl)cc3s2)nc2cc(C(=O)NCCCCN)ccc21] | 2-(6-Chloro-benzothiazol-2-ylamino)-1-methyl-1H-benzoimidazole-5-carboxylic acid (4-amino-butyl)-amide hydrochloride |
| 348 | 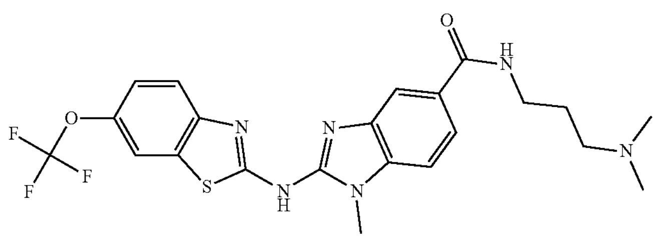 [SMILES: CN(C)CCCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid (3-dimethylamino-propyl)-amide |
| 349 | 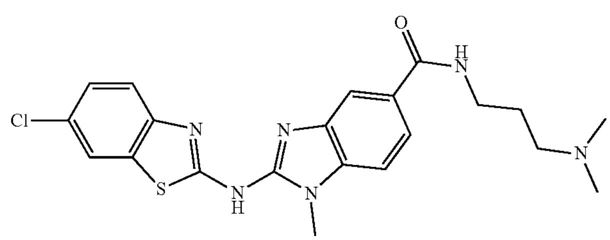 [SMILES: CN(C)CCCNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid (3-dimethylamino-propyl)-amide |
| 350 | 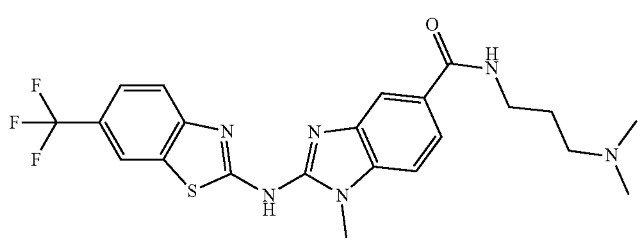 [SMILES: CN(C)CCCNC(=O)c1ccc2c(c1)nc(Nc1nc3ccc(C(F)(F)F)cc3s1)n2C] | 1-Methyl-2-(6-trifluoromethyl-benzothiazol-2-ylamino)-1H-benzoimidazole-5-carboxylic acid (3-dimethylamino-propyl)-amide |
| 351 | 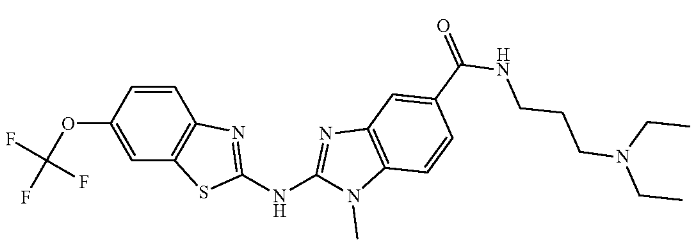 [SMILES: CCN(CC)CCCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid (3-diethylamino-propyl)-amide |

TABLE 1-continued

| No. | Structure | Name |
|---|---|---|
| 352 | 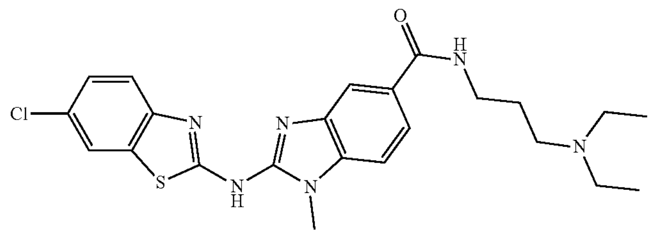 [SMILES: CCN(CC)CCCNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid (3-diethylamino-propyl)-amide |
| 353 | 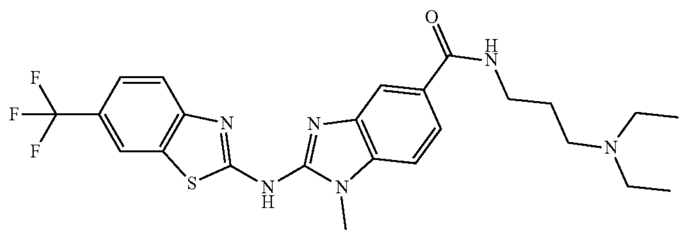 [SMILES: CCN(CC)CCCNC(=O)c1ccc2c(c1)nc(Nc1nc3ccc(C(F)(F)F)cc3s1)n2C] | 1-Methyl-2-(6-trifluoromethyl-benzothiazol-2-ylamino)-1H-benzoimidazole-5-carboxylic acid (3-diethylamino-propyl)-amide |
| 354 | 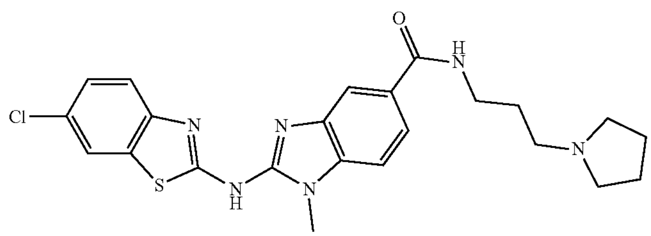 [SMILES: Cn1c(Nc2nc3ccc(Cl)cc3s2)nc2cc(C(=O)NCCCN3CCCC3)ccc21] | 2-(6-Chloro-benzothiazol-2-ylamino)-1-methyl-1H-benzoimidazole-5-carboxylic acid (3-pyrrolidin-1-yl-propyl)-amide |
| 355 | 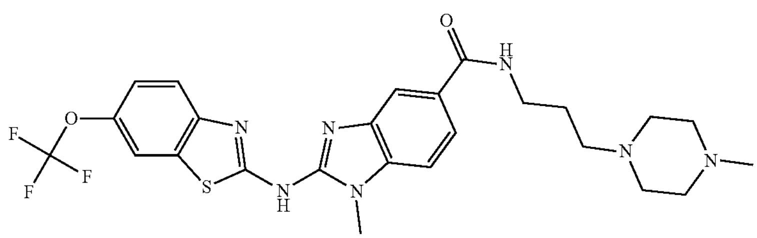 [SMILES: CN1CCN(CCCNC(=O)c2ccc3c(c2)nc(Nc2nc4ccc(OC(F)(F)F)cc4s2)n3C)CC1] | 1-Methyl-2-(6-trifluoromethoxy-benzothiazol-2-ylamino)-1H-benzoimidazole-5-carboxylic acid [3-(4-methyl-piperazin-1-yl)-propyl]-amide |
| 356 | 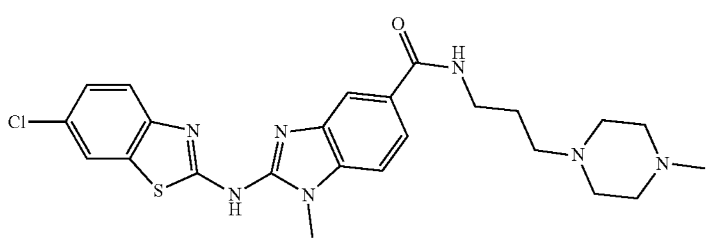 [SMILES: CN1CCN(CCCNC(=O)c2ccc3c(c2)nc(Nc2nc4ccc(Cl)cc4s2)n3C)CC1] | 2-(6-Chloro-benzothiazol-2-ylamino)-1-methyl-1H-benzoimidazole-5-carboxylic acid [3-(4-methyl-piperazin-1-yl)-propyl]-amide |
| 357 | 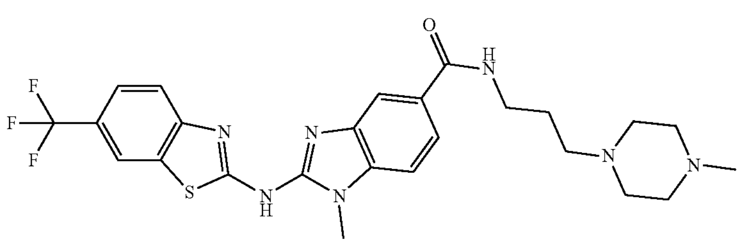 [SMILES: CN1CCN(CCCNC(=O)c2ccc3c(c2)nc(Nc2nc4ccc(C(F)(F)F)cc4s2)n3C)CC1] | 1-Methyl-2-(6-trifluoromethyl-benzothiazol-2-ylamino)-1H-benzoimidazole-5-carboxylic acid [3-(4-methyl-piperazin-1-yl)-propyl]-amide |

TABLE 1-continued

| No. | Structure | Name |
|---|---|---|
| 358 | 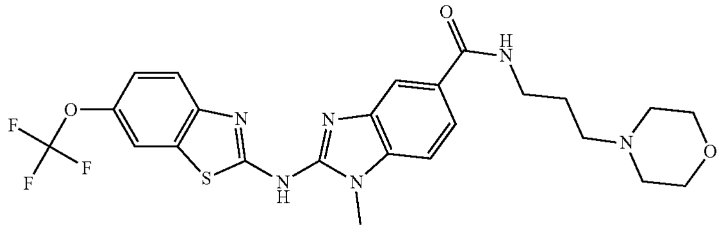 [SMILES: Cn1c(Nc2nc3ccc(OC(F)(F)F)cc3s2)nc2cc(C(=O)NCCCN3CCOCC3)ccc21] | 1-Methyl-2-(6-trifluoromethoxy-benzothiazol-2-ylamino)-1H-benzoimidazole-5-carboxylic acid (3-morpholin-4-yl-propyl)-amide |
| 359 | 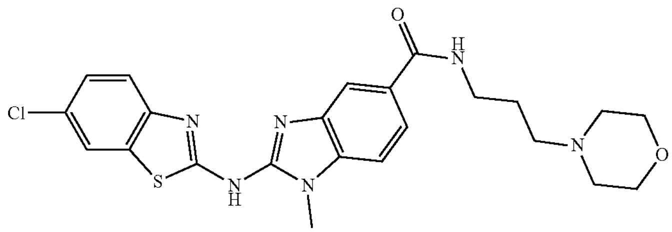 [SMILES: Cn1c(Nc2nc3ccc(Cl)cc3s2)nc2cc(C(=O)NCCCN3CCOCC3)ccc21] | 2-(6-Chloro-benzothiazol-2-ylamino)-1-methyl-1H-benzoimidazole-5-carboxylic acid (3-morpholin-4-yl-propyl)-amide |
| 360 | 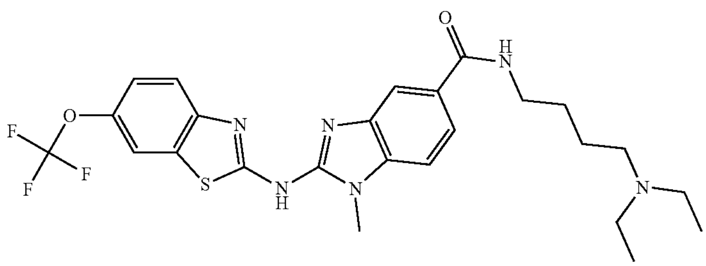 [SMILES: CCN(CC)CCCCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid (4-diethylamino-butyl)-amide |
| 361 | 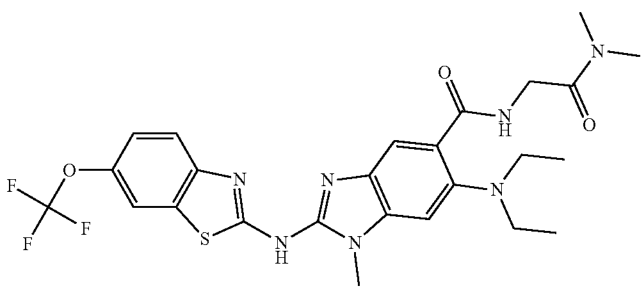 [SMILES: CCN(CC)c1cc2c(cc1C(=O)NCC(=O)N(C)C)nc(Nc1nc3ccc(OC(F)(F)F)cc3s1)n2C] | 6-Diethylamino-1-methyl-2-(6-trifluoromethoxy-benzothiazol-2-ylamino)-1H-benzoimidazole-5-carboxylic acid dimethylcarbamoylmethyl-amide |
| 362 | 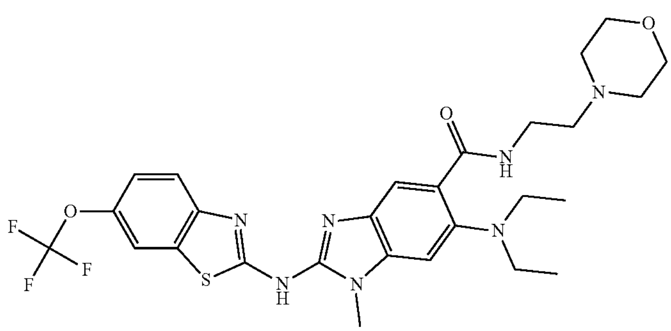 [SMILES: CCN(CC)c1cc2c(cc1C(=O)NCCN1CCOCC1)nc(Nc1nc3ccc(OC(F)(F)F)cc3s1)n2C] | 6-Diethylamino-1-methyl-2-(6-trifluoromethoxy-benzothiazol-2-ylamino)-1H-benzoimidazole-5-carboxylic acid (2-morpholin-4-yl-ethyl)-amide |
| 363 | 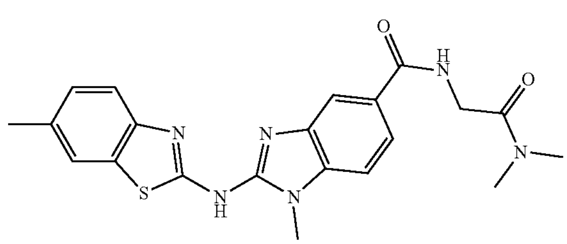 | 1-Methyl-2-(6-methyl-benzothiazol-2-ylamino)-1H-benzoimidazole-5-carboxylic acid dimethylcarbamoylmethyl-amide |

TABLE 1-continued

| No. | Structure | Name |
|---|---|---|
| 364 | 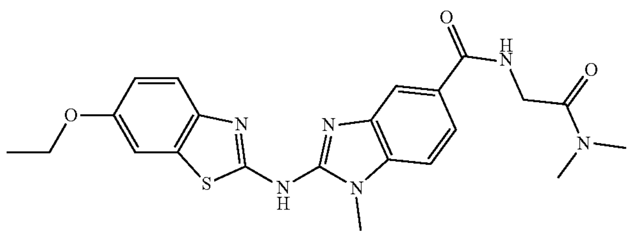 [SMILES: CCOc1ccc2nc(Nc3nc4cc(C(=O)NCC(=O)N(C)C)ccc4n3C)sc2c1] | 2-(6-Ethoxy-benzothiazol-2-ylamino)-1-methyl-1H-benzoimidazole-5-carboxylic acid dimethylcarbamoylmethyl-amide |
| 365 | 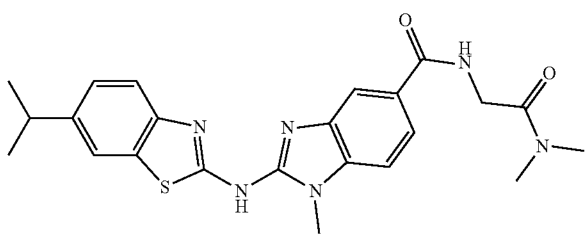 [SMILES: CC(C)c1ccc2nc(Nc3nc4cc(C(=O)NCC(=O)N(C)C)ccc4n3C)sc2c1] | 2-(6-Isopropyl-benzothiazol-2-ylamino)-1-methyl-1H-benzoimidazole-5-carboxylic acid dimethylcarbamoylmethyl-amide |
| 366 | 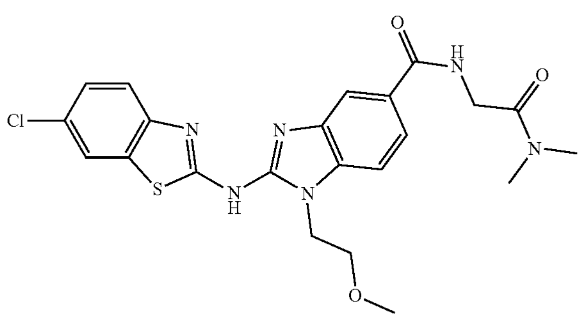 [SMILES: COCCn1c(Nc2nc3ccc(Cl)cc3s2)nc2cc(C(=O)NCC(=O)N(C)C)ccc21] | 2-(6-Chloro-benzothiazol-2-ylamino)-1-(2-methoxy-ethyl)-1H-benzoimidazole-5-carboxylic acid dimethylcarbamoylmethyl-amide |
| 367 | 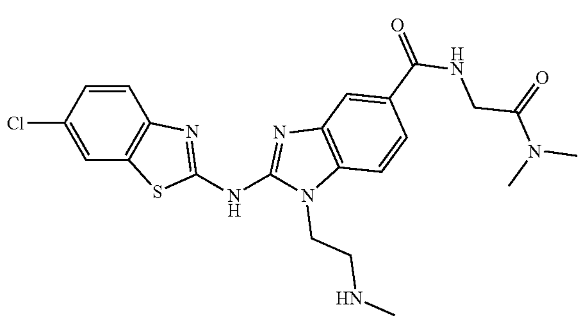 [SMILES: CNCCn1c(Nc2nc3ccc(Cl)cc3s2)nc2cc(C(=O)NCC(=O)N(C)C)ccc21] | 2-(6-Chloro-benzothiazol-2-ylamino)-1-(2-methylamino-ethyl)-1H-benzoimidazole-5-carboxylic acid dimethylcarbamoylmethyl-amide hydrochloride |
| 368 | 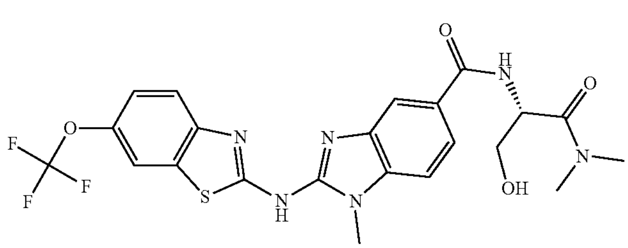 [SMILES: CN(C)C(=O)[C@H](CO)NC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid ((S)-1-dimethylcarbamoyl-2-hydroxy-ethyl)-amide |

TABLE 1-continued

| No. | Structure | Name |
|---|---|---|
| 369 | 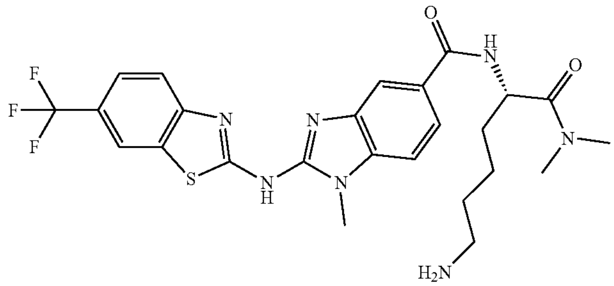 [SMILES: CN(C)C(=O)[C@H](CCCCN)NC(=O)c1ccc2c(c1)nc(Nc1nc3ccc(C(F)(F)F)cc3s1)n2C] | 1-Methyl-2-(6-trifluoromethyl-benzothiazol-2-ylamino)-1H-benzoimidazole-5-carboxylic acid ((S)-2-amino-1-dimethylcarbamoyl-pentyl)-amide hydrochloride |
| 370 | 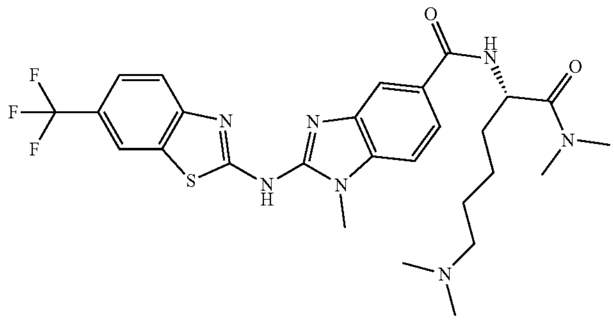 [SMILES: CN(C)CCCC[C@H](NC(=O)c1ccc2c(c1)nc(Nc1nc3ccc(C(F)(F)F)cc3s1)n2C)C(=O)N(C)C] | 1-Methyl-2-(6-trifluoromethyl-benzothiazol-2-ylamino)-1H-benzoimidazole-5-carboxylic acid ((S)-5-dimethylamino-1-dimethylcarbamoyl-pentyl)-amide |
| 371 | 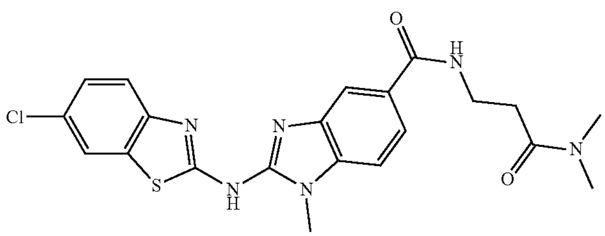 [SMILES: CN(C)C(=O)CCNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid (2-dimethylcarbamoyl-ethyl)-amide |
| 372 | 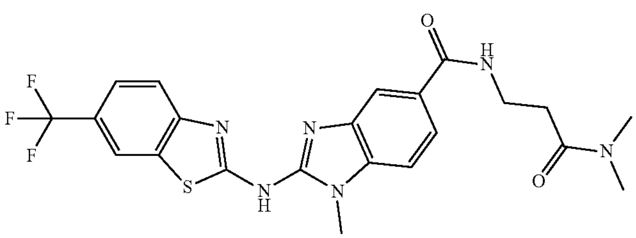 [SMILES: CN(C)C(=O)CCNC(=O)c1ccc2c(c1)nc(Nc1nc3ccc(C(F)(F)F)cc3s1)n2C] | 1-Methyl-2-(6-trifluoromethyl-benzothiazol-2-ylamino)-1H-benzoimidazole-5-carboxylic acid (2-dimethylcarbamoyl-ethyl)-amide |
| 373 | 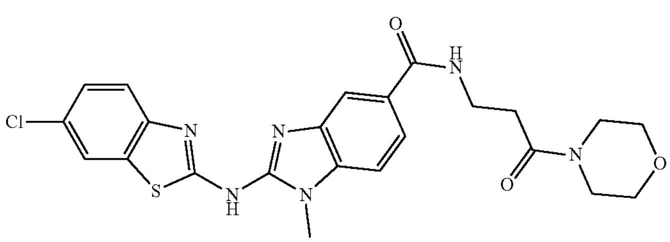 [SMILES: Cn1c(Nc2nc3ccc(Cl)cc3s2)nc2cc(C(=O)NCCC(=O)N3CCOCC3)ccc21] | 2-(6-Chloro-benzothiazol-2-ylamino)-1-methyl-1H-benzoimidazole-5-carboxylic acid (3-morpholin-4-yl-3-oxo-propyl)-amide |
| 374 | 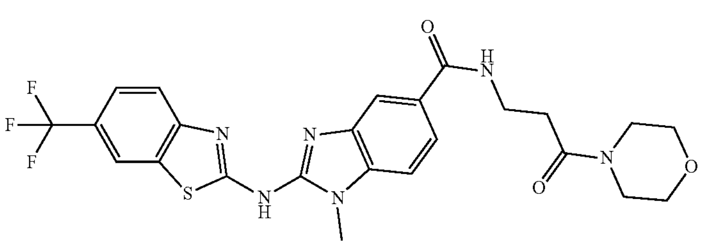 [SMILES: Cn1c(Nc2nc3ccc(C(F)(F)F)cc3s2)nc2cc(C(=O)NCCC(=O)N3CCOCC3)ccc21] | 1-Methyl-2-(6-trifluoromethyl-benzothiazol-2-ylamino)-1H-benzoimidazole-5-carboxylic acid (3-morpholin-4-yl-3-oxo-propyl)-amide |

TABLE 1-continued

| No. | Structure | Name |
|---|---|---|
| 375 | 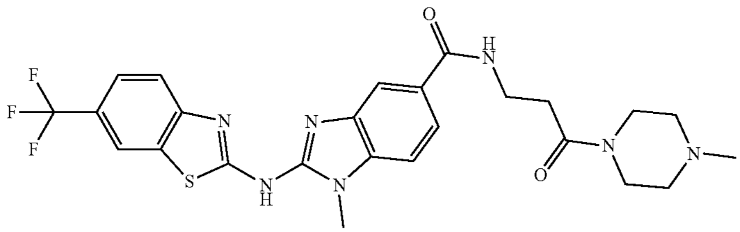 [SMILES: CN1CCN(C(=O)CCNC(=O)c2ccc3c(c2)nc(Nc2nc4ccc(C(F)(F)F)cc4s2)n3C)CC1] | 1-Methyl-2-(6-trifluoromethyl-benzothiazol-2-ylamino)-1H-benzoimidazole-5-carboxylic acid [3-(4-methyl-piperazin-1-yl)-3-oxo-propyl]-amide |
| 376 | 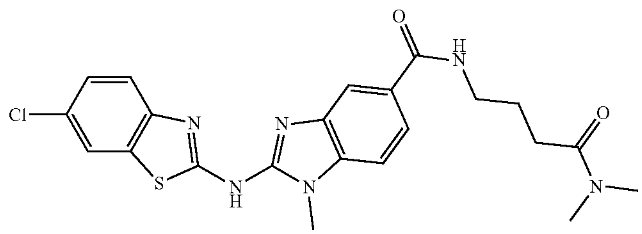 [SMILES: CN(C)C(=O)CCCNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid (3-dimethylcarbamoyl-propyl)-amide |
| 377 | 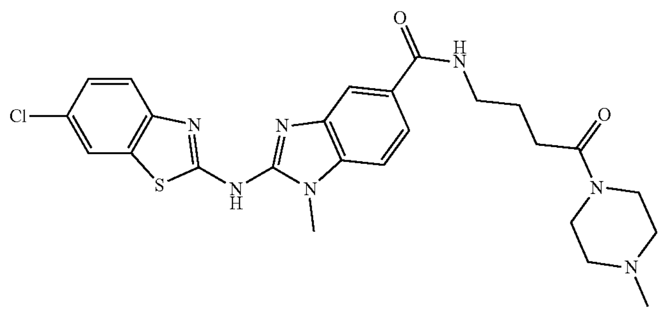 [SMILES: CN1CCN(C(=O)CCCNC(=O)c2ccc3c(c2)nc(Nc2nc4ccc(Cl)cc4s2)n3C)CC1] | 2-(6-Chloro-benzothiazol-2-ylamino)-1-methyl-1H-benzoimidazole-5-carboxylic acid [4-(4-methyl-piperazin-1-yl)-4-oxo-butyl]-amide |
| 378 | 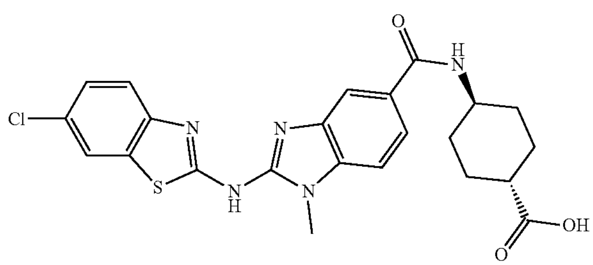 [SMILES: Cn1c(Nc2nc3ccc(Cl)cc3s2)nc2cc(C(=O)N[C@H]3CC[C@H](C(=O)O)CC3)ccc21] | 4-{[2-(6-Chloro-benzothiazol-2-ylamino)-1-methyl-1H-benzoimidazole-5-carbonyl]-amino}-trans-cyclohexanecarboxylic acid |
| 379 | 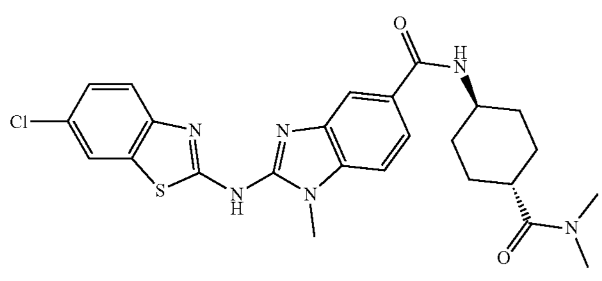 [SMILES: CN(C)C(=O)[C@H]1CC[C@H](NC(=O)c2ccc3c(c2)nc(Nc2nc4ccc(Cl)cc4s2)n3C)CC1] | 2-(6-Chloro-benzothiazol-2-ylamino)-1-methyl-1H-benzoimidazole-5-carboxylic acid (4-trans-dimethylcarbamoyl-cyclohexyl)-amide |
| 380 | 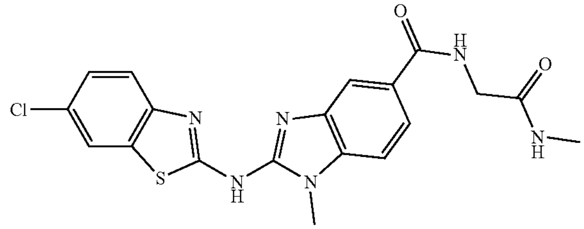 [SMILES: CNC(=O)CNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid methylcarbamoylmethyl-amide |

TABLE 1-continued

| No. | Structure | Name |
|---|---|---|
| 381 | 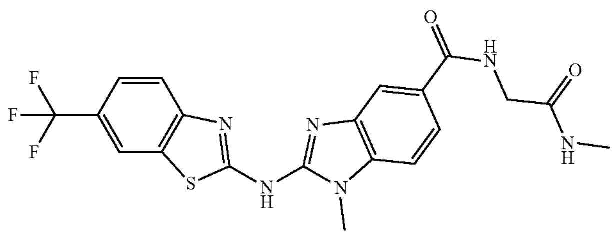 [SMILES: CNC(=O)CNC(=O)c1ccc2c(c1)nc(Nc1nc3ccc(C(F)(F)F)cc3s1)n2C] | 1-Methyl-2-(6-trifluoromethyl-benzothiazol-2-ylamino)-1H-benzoimidazole-5-carboxylic acid methylcarbamoylmethyl-amide |
| 382 | 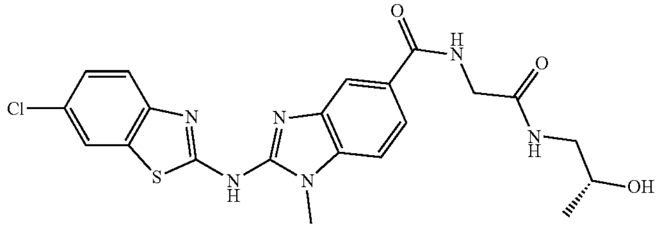 [SMILES: C[C@@H](O)CNC(=O)CNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid [((R)-2-hydroxy-propylcarbamoyl)-methyl]-amide |
| 383 | 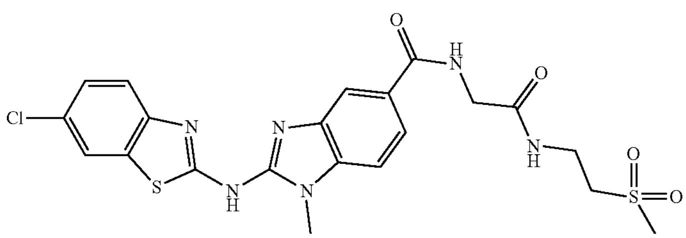 [SMILES: Cn1c(Nc2nc3ccc(Cl)cc3s2)nc2cc(C(=O)NCC(=O)NCCS(C)(=O)=O)ccc21] | 2-(6-Chloro-benzothiazol-2-ylamino)-1-methyl-1H-benzoimidazole-5-carboxylic acid [(2-methanesulfonyl-ethylcarbamoyl)-methyl]-amide |
| 384 | 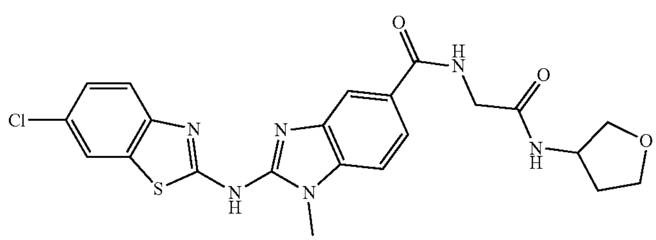 [SMILES: Cn1c(Nc2nc3ccc(Cl)cc3s2)nc2cc(C(=O)NCC(=O)NC3CCOC3)ccc21] | 2-(6-Chloro-benzothiazol-2-ylamino)-1-methyl-1H-benzoimidazole-5-carboxylic acid [(tetrahydro-furan-3-ylcarbamoyl)-methyl]-amide |
| 385 | 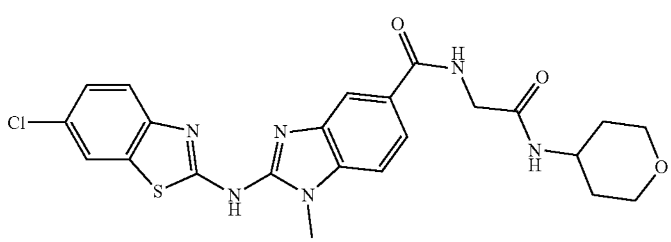 | 2-(6-Chloro-benzothiazol-2-ylamino)-1-methyl-1H-benzoimidazole-5-carboxylic acid [(tetrahydro-pyran-4-ylcarbamoyl)-methyl]-amide |
| 386 | 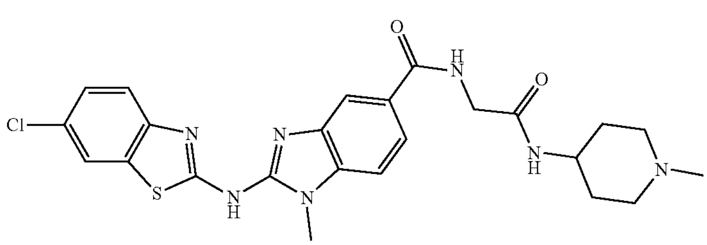 [SMILES: CN1CCC(NC(=O)CNC(=O)c2ccc3c(c2)nc(Nc2nc4ccc(Cl)cc4s2)n3C)CC1] | 2-(6-Chloro-benzothiazol-2-ylamino)-1-methyl-1H-benzoimidazole-5-carboxylic acid [(1-methyl-piperidin-4-ylcarbamoyl)-methyl]-amide |

TABLE 1-continued

| No. | Structure | Name |
|---|---|---|
| 387 | 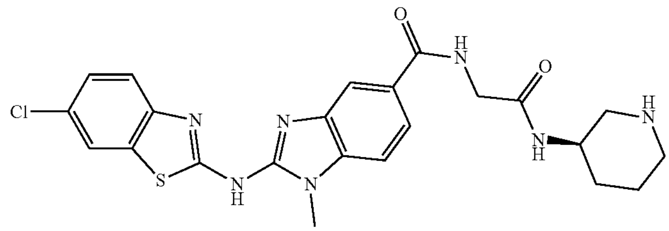 [SMILES: Cn1c(Nc2nc3ccc(Cl)cc3s2)nc2cc(C(=O)NCC(=O)N[C@@H]3CCCNC3)ccc21] | 2-(6-Chloro-benzothiazol-2-ylamino)-1-methyl-1H-benzoimidazole-5-carboxylic acid ((R)-piperidin-3-ylcarbamoylmethyl)-amide hydrochloride |
| 388 | 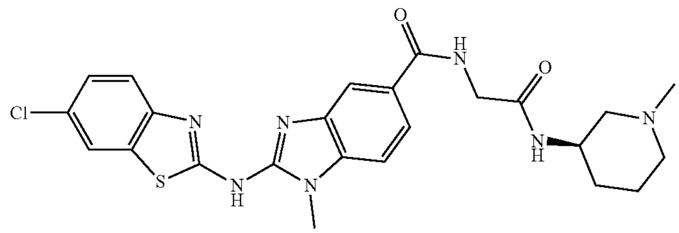 [SMILES: CN1CCC[C@@H](NC(=O)CNC(=O)c2ccc3c(c2)nc(Nc2nc4ccc(Cl)cc4s2)n3C)C1] | 2-(6-Chloro-benzothiazol-2-ylamino)-1-methyl-1H-benzoimidazole-5-carboxylic acid [((R)-1-methyl-piperidin-3-ylcarbamoyl)-methyl]-amide |
| 389 | 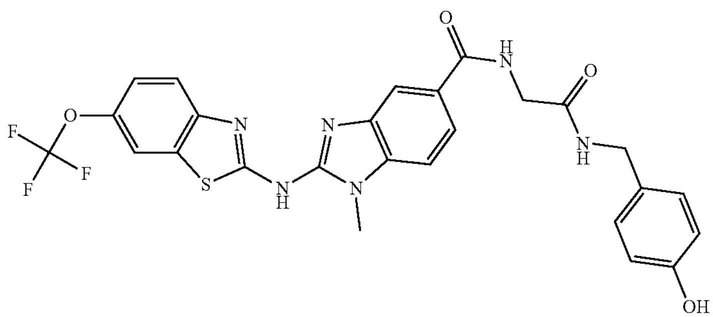 [SMILES: Cn1c(Nc2nc3ccc(OC(F)(F)F)cc3s2)nc2cc(C(=O)NCC(=O)NCc3ccc(O)cc3)ccc21] | 1-Methyl-2-(6-trifluoromethoxy-benzothiazol-2-ylamino)-1H-benzoimidazole-5-carboxylic acid [(4-hydroxy-benzylcarbamoyl)-methyl]-amide |
| 390 | 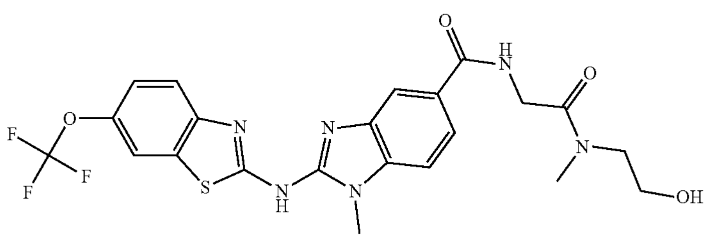 [SMILES: CN(CCO)C(=O)CNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid {[(2-hydroxy-ethyl)-methyl-carbamoyl]-methyl}-amide |
| 391 | 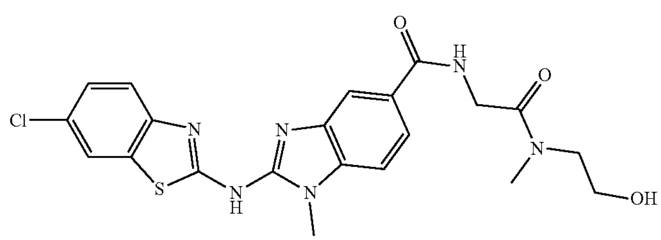 [SMILES: CN(CCO)C(=O)CNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid {[(2-hydroxy-ethyl)-methyl-carbamoyl]-methyl}-amide |
| 392 | 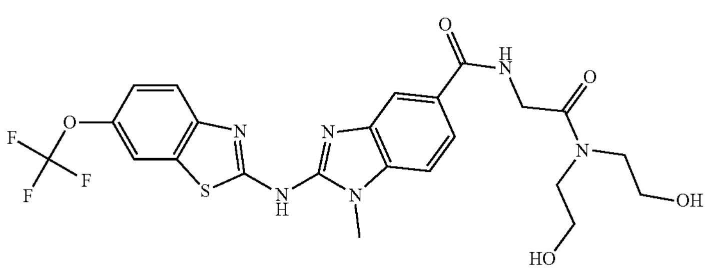 [SMILES: Cn1c(Nc2nc3ccc(OC(F)(F)F)cc3s2)nc2cc(C(=O)NCC(=O)N(CCO)CCO)ccc21] | 1-Methyl-2-(6-trifluoromethoxy-benzothiazol-2-ylamino)-1H-benzoimidazole-5-carboxylic acid {[bis-(2-hydroxy-ethyl)-carbamoyl]-methyl}-amide |

| No. | Structure | Name |
|---|---|---|
| 393 | 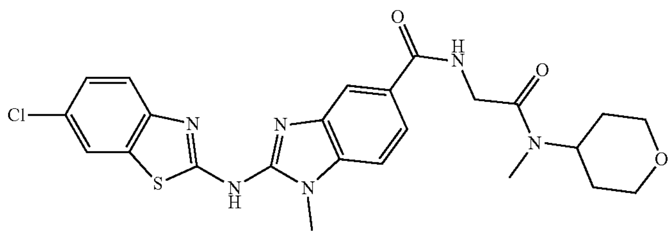 [SMILES: CN(C(=O)CNC(=O)c1ccc2c(c1)nc(Nc1nc3ccc(Cl)cc3s1)n2C)C1CCOCC1] | 2-(6-Chloro-benzothiazol-2-ylamino)-1-methyl-1H-benzoimidazole-5-carboxylic acid {[methyl-(tetrahydro-pyran-4-yl)-carbamoyl]-methyl}-amide |
| 394 | 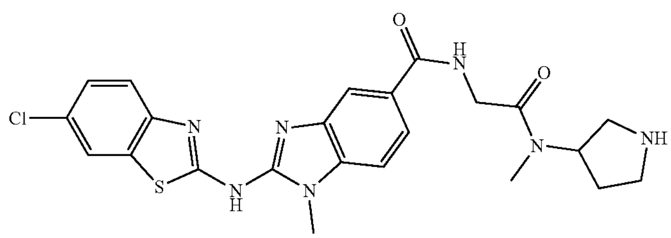 [SMILES: CN(C(=O)CNC(=O)c1ccc2c(c1)nc(Nc1nc3ccc(Cl)cc3s1)n2C)C1CCNC1] | 2-(6-Chloro-benzothiazol-2-ylamino)-1-methyl-1H-benzoimidazole-5-carboxylic acid [(methyl-pyrrolidin-3-yl-carbamoyl)-methyl]-amide hydrochloride |
| 395 | 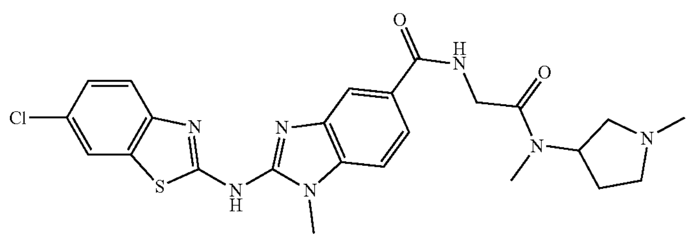 [SMILES: CN1CCC(N(C)C(=O)CNC(=O)c2ccc3c(c2)nc(Nc2nc4ccc(Cl)cc4s2)n3C)C1] | 2-(6-Chloro-benzothiazol-2-ylamino)-1-methyl-1H-benzoimidazole-5-carboxylic acid {[methyl-(1-methyl-pyrrolidin-3-yl)-carbamoyl]-methyl}-amide |
| 396 | 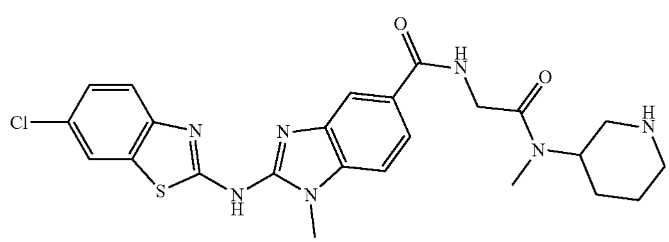 [SMILES: CN(C(=O)CNC(=O)c1ccc2c(c1)nc(Nc1nc3ccc(Cl)cc3s1)n2C)C1CCCNC1] | 2-(6-Chloro-benzothiazol-2-ylamino)-1-methyl-1H-benzoimidazole-5-carboxylic acid [(methyl-piperidin-3-yl-carbamoyl)-methyl]-amide hydrochloride |
| 397 | 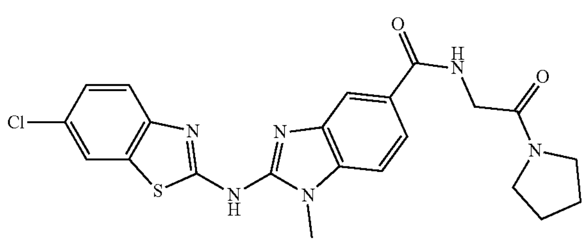 [SMILES: Cn1c(Nc2nc3ccc(Cl)cc3s2)nc2cc(C(=O)NCC(=O)N3CCCC3)ccc21] | 2-(6-Chloro-benzothiazol-2-ylamino)-1-methyl-1H-benzoimidazole-5-carboxylic acid (2-oxo-2-pyrrolidin-1-yl-ethyl)-amide |
| 398 | 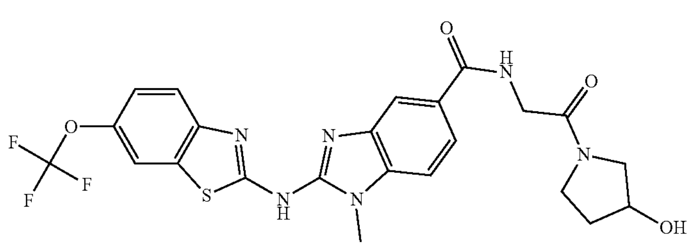 [SMILES: Cn1c(Nc2nc3ccc(OC(F)(F)F)cc3s2)nc2cc(C(=O)NCC(=O)N3CCC(O)C3)ccc21] | 1-Methyl-2-(6-trifluoromethoxy-benzothiazol-2-ylamino)-1H-benzoimidazole-5-carboxylic acid [2-(3-hydroxy-pyrrolidin-1-yl)-2-oxo-ethyl]-amide |

TABLE 1-continued

| No. | Structure | Name |
|---|---|---|
| 399 | 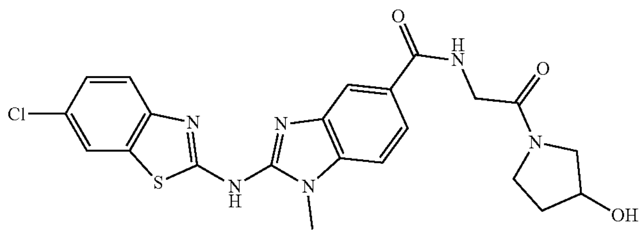 [SMILES: Cn1c(Nc2nc3ccc(Cl)cc3s2)nc2cc(C(=O)NCC(=O)N3CCC(O)C3)ccc21] | 2-(6-Chloro-benzothiazol-2-ylamino)-1-methyl-1H-benzoimidazole-5-carboxylic acid [2-(3-hydroxy-pyrrolidin-1-yl)-2-oxo-ethyl]-amide |
| 400 | 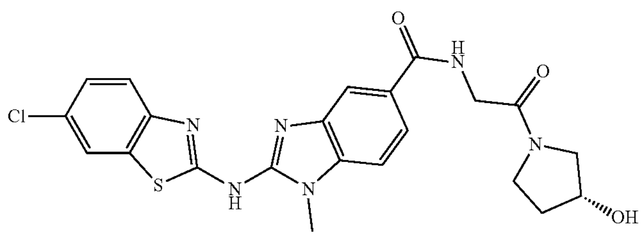 [SMILES: Cn1c(Nc2nc3ccc(Cl)cc3s2)nc2cc(C(=O)NCC(=O)N3CC[C@@H](O)C3)ccc21] | 2-(6-Chloro-benzothiazol-2-ylamino)-1-methyl-1H-benzoimidazole-5-carboxylic acid [2-((R)-3-hydroxy-pyrrolidin-1-yl)-2-oxo-ethyl]-amide |
| 401 | 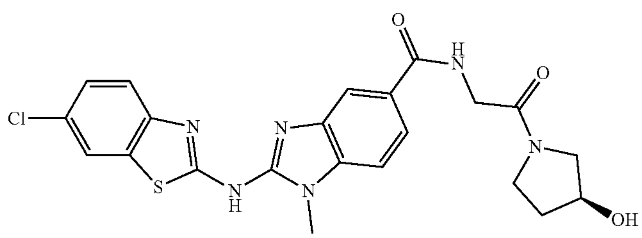 [SMILES: Cn1c(Nc2nc3ccc(Cl)cc3s2)nc2cc(C(=O)NCC(=O)N3CC[C@H](O)C3)ccc21] | 2-(6-Chloro-benzothiazol-2-ylamino)-1-methyl-1H-benzoimidazole-5-carboxylic acid [2-((S)-3-hydroxy-pyrrolidin-1-yl)-2-oxo-ethyl]-amide |
| 402 | 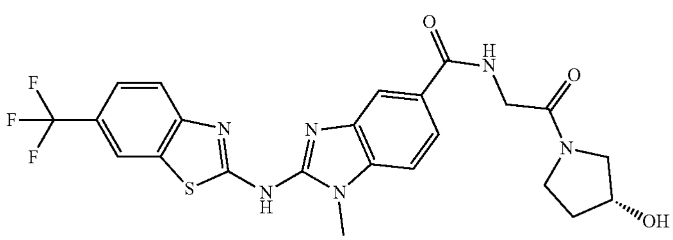 [SMILES: Cn1c(Nc2nc3ccc(C(F)(F)F)cc3s2)nc2cc(C(=O)NCC(=O)N3CC[C@@H](O)C3)ccc21] | 1-Methyl-2-(6-trifluoromethyl-benzothiazol-2-ylamino)-1H-benzoimidazole-5-carboxylic acid [2-((R)-3-hydroxy-pyrrolidin-1-yl)-2-oxo-ethyl]-amide |
| 403 | 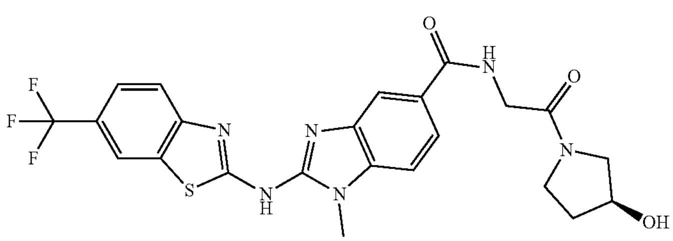 [SMILES: Cn1c(Nc2nc3ccc(C(F)(F)F)cc3s2)nc2cc(C(=O)NCC(=O)N3CC[C@H](O)C3)ccc21] | 1-Methyl-2-(6-trifluoromethyl-benzothiazol-2-ylamino)-1H-benzoimidazole-5-carboxylic acid [2-((S)-3-hydroxy-pyrrolidin-1-yl)-2-oxo-ethyl]-amide |
| 404 | 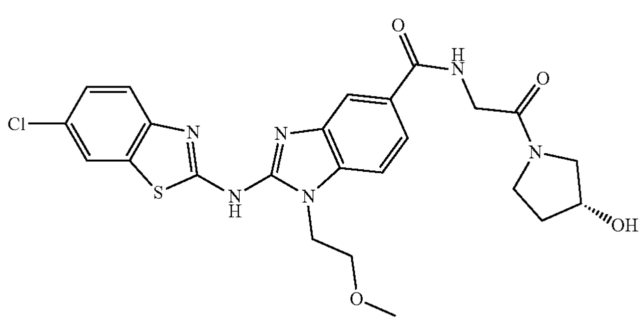 [SMILES: COCCn1c(Nc2nc3ccc(Cl)cc3s2)nc2cc(C(=O)NCC(=O)N3CC[C@@H](O)C3)ccc21] | 2-(6-Chloro-benzothiazol-2-ylamino)-1-(2-methoxy-ethyl)-1H-benzoimidazole-5-carboxylic acid [2-((R)-3-hydroxy-pyrrolidin-1-yl)-2-oxo-ethyl]-amide |

TABLE 1-continued

| No. | Structure | Name |
|---|---|---|
| 405 | 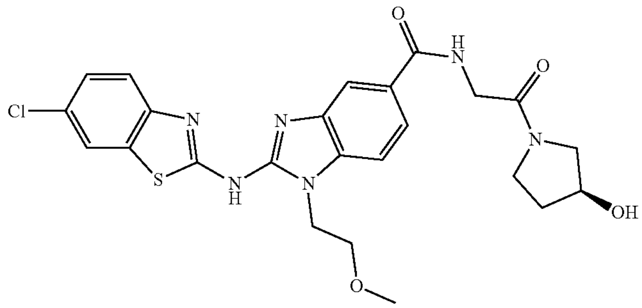 [SMILES: COCCn1c(Nc2nc3ccc(Cl)cc3s2)nc2cc(C(=O)NCC(=O)N3CC[C@H](O)C3)ccc21] | 2-(6-Chloro-benzothiazol-2-ylamino)-1-(2-methoxy-ethyl)-1H-benzoimidazole-5-carboxylic acid [2-((S)-3-hydroxy-pyrrolidin-1-yl)-2-oxo-ethyl]-amide |
| 406 | 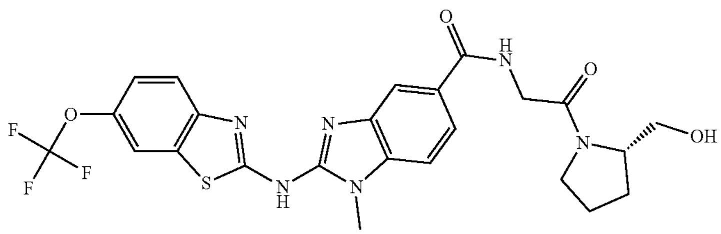 [SMILES: Cn1c(Nc2nc3ccc(OC(F)(F)F)cc3s2)nc2cc(C(=O)NCC(=O)N3CCC[C@H]3CO)ccc21] | 1-Methyl-2-(6-trifluoromethoxy-benzothiazol-2-ylamino)-1H-benzoimidazole-5-carboxylic acid [2-((S)-2-hydroxymethyl-pyrrolidin-1-yl)-2-oxo-ethyl]-amide |
| 407 | 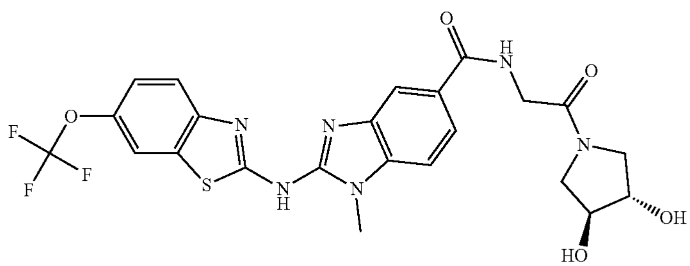 [SMILES: Cn1c(Nc2nc3ccc(OC(F)(F)F)cc3s2)nc2cc(C(=O)NCC(=O)N3C[C@H](O)[C@@H](O)C3)ccc21] | 1-Methyl-2-(6-trifluoromethoxy-benzothiazol-2-ylamino)-1H-benzoimidazole-5-carboxylic acid [2-((3S,4S)-3,4-dihydroxy-pyrrolidin-1-yl)-2-oxo-ethyl]-amide |
| 408 | 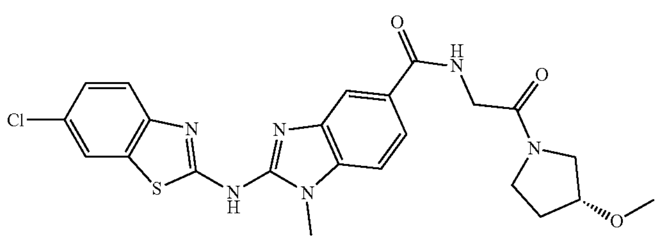 [SMILES: CO[C@@H]1CCN(C(=O)CNC(=O)c2ccc3c(c2)nc(Nc2nc4ccc(Cl)cc4s2)n3C)C1] | 2-(6-Chloro-benzothiazol-2-ylamino)-1-methyl-1H-benzoimidazole-5-carboxylic acid [2-((R)-3-methoxy-pyrrolidin-1-yl)-2-oxo-ethyl]-amide |
| 409 | 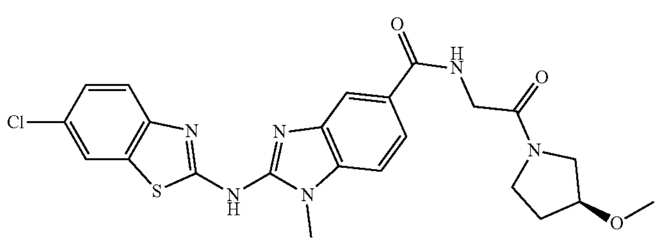 [SMILES: CO[C@H]1CCN(C(=O)CNC(=O)c2ccc3c(c2)nc(Nc2nc4ccc(Cl)cc4s2)n3C)C1] | 2-(6-Chloro-benzothiazol-2-ylamino)-1-methyl-1H-benzoimidazole-5-carboxylic acid [2-((S)-3-methoxy-pyrrolidin-1-yl)-2-oxo-ethyl]-amide |
| 410 | 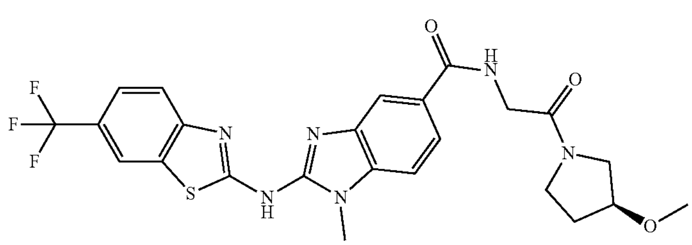 [SMILES: CO[C@H]1CCN(C(=O)CNC(=O)c2ccc3c(c2)nc(Nc2nc4ccc(C(F)(F)F)cc4s2)n3C)C1] | 1-Methyl-2-(6-trifluoromethyl-benzothiazol-2-ylamino)-1H-benzoimidazole-5-carboxylic acid [2-((S)-3-methoxy-pyrrolidin-1-yl)-2-oxo-ethyl]-amide |

TABLE 1-continued

| No. | Structure | Name |
|---|---|---|
| 411 | 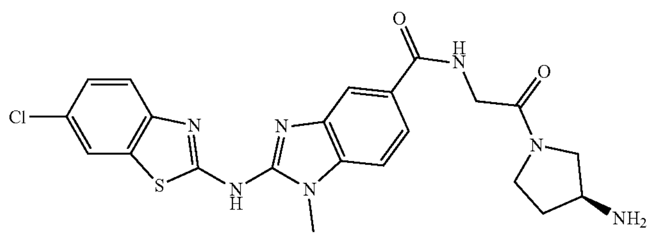 [SMILES: Cn1c(Nc2nc3ccc(Cl)cc3s2)nc2cc(C(=O)NCC(=O)N3CC[C@H](N)C3)ccc21] | 2-(6-Chloro-benzothiazol-2-ylamino)-1-methyl-1H-benzoimidazole-5-carboxylic acid [2-((S)-3-amino-pyrrolidin-1-yl)-2-oxo-ethyl]-amide hydrochloride |
| 412 | 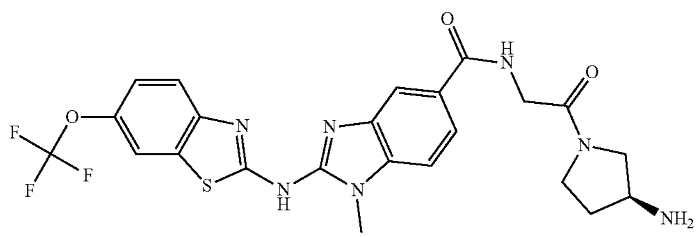 [SMILES: Cn1c(Nc2nc3ccc(OC(F)(F)F)cc3s2)nc2cc(C(=O)NCC(=O)N3CC[C@H](N)C3)ccc21] | 1-Methyl-2-(6-trifluoromethoxy-benzothiazol-2-ylamino)-1H-benzoimidazole-5-carboxylic acid [2-((S)-3-amino-pyrrolidin-1-yl)-2-oxo-ethyl]-amide hydrochloride |
| 413 | 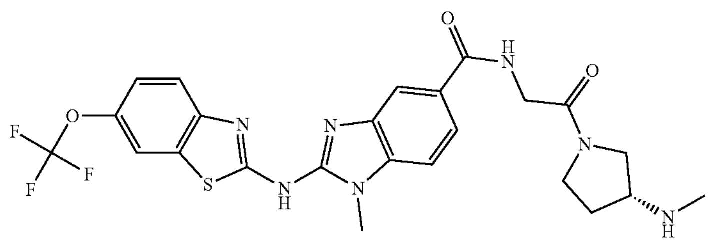 [SMILES: CN[C@@H]1CCN(C(=O)CNC(=O)c2ccc3c(c2)nc(Nc2nc4ccc(OC(F)(F)F)cc4s2)n3C)C1] | 1-Methyl-2-(6-trifluoromethoxy-benzothiazol-2-ylamino)-1H-benzoimidazole-5-carboxylic acid [2-((R)-3-methylamino-pyrrolidin-1-yl)-2-oxo-ethyl]-amide hydrochloride |
| 414 | 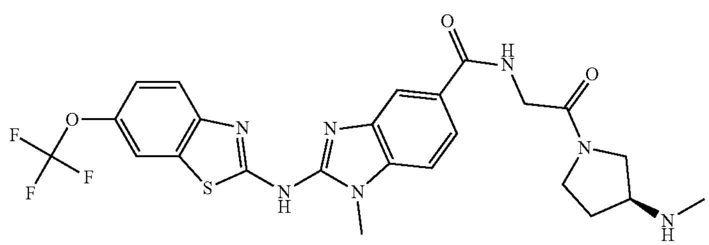 [SMILES: CN[C@H]1CCN(C(=O)CNC(=O)c2ccc3c(c2)nc(Nc2nc4ccc(OC(F)(F)F)cc4s2)n3C)C1] | 1-Methyl-2-(6-trifluoromethoxy-benzothiazol-2-ylamino)-1H-benzoimidazole-5-carboxylic acid [2-((S)-3-methylamino-pyrrolidin-1-yl)-2-oxo-ethyl]-amide hydrochloride |
| 415 | 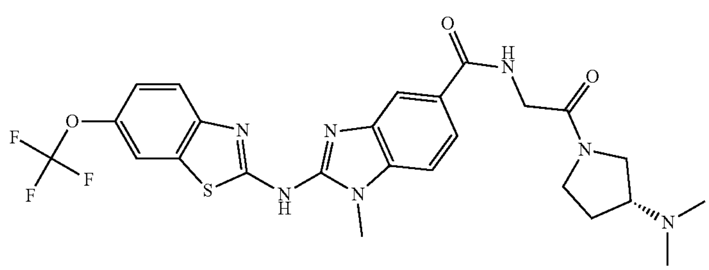 [SMILES: CN(C)[C@@H]1CCN(C(=O)CNC(=O)c2ccc3c(c2)nc(Nc2nc4ccc(OC(F)(F)F)cc4s2)n3C)C1] | 1-Methyl-2-(6-trifluoromethoxy-benzothiazol-2-ylamino)-1H-benzoimidazole-5-carboxylic acid [2-((R)-3-dimethylamino-pyrrolidin-1-yl)-2-oxo-ethyl]-amide |
| 416 | 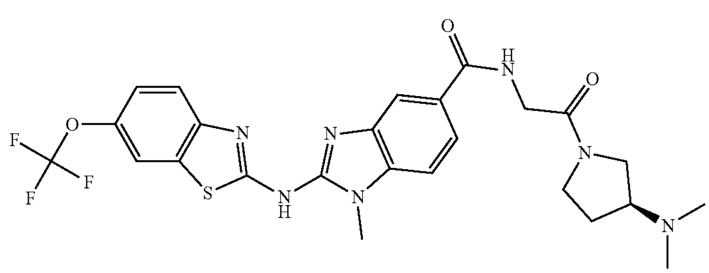 [SMILES: CN(C)[C@H]1CCN(C(=O)CNC(=O)c2ccc3c(c2)nc(Nc2nc4ccc(OC(F)(F)F)cc4s2)n3C)C1] | 1-Methyl-2-(6-trifluoromethoxy-benzothiazol-2-ylamino)-1H-benzoimidazole-5-carboxylic acid [2-((S)-3-dimethylamino-pyrrolidin-1-yl)-2-oxo-ethyl]-amide |

TABLE 1-continued

| No. | Structure | Name |
|---|---|---|
| 417 | 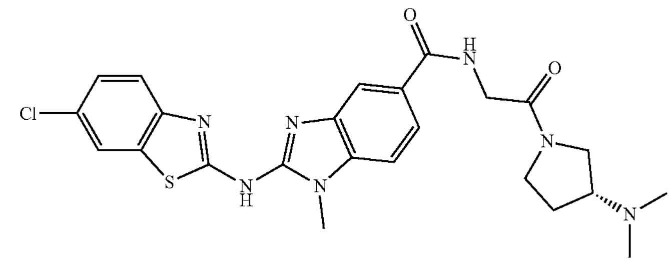 [SMILES: CN(C)[C@@H]1CCN(C(=O)CNC(=O)c2ccc3c(c2)nc(Nc2nc4ccc(Cl)cc4s2)n3C)C1] | 2-(6-Chloro-benzothiazol-2-ylamino)-1-methyl-1H-benzoimidazole-5-carboxylic acid [2-((R)-3-dimethylamino-pyrrolidin-1-yl)-2-oxo-ethyl]-amide |
| 418 | 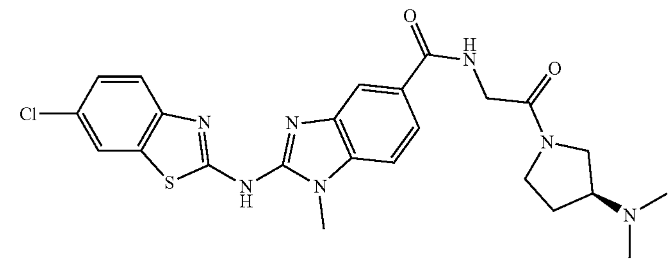 [SMILES: CN(C)[C@H]1CCN(C(=O)CNC(=O)c2ccc3c(c2)nc(Nc2nc4ccc(Cl)cc4s2)n3C)C1] | 2-(6-Chloro-benzothiazol-2-ylamino)-1-methyl-1H-benzoimidazole-5-carboxylic acid [2-((S)-3-dimethylamino-pyrrolidin-1-yl)-2-oxo-ethyl]-amide |
| 419 | 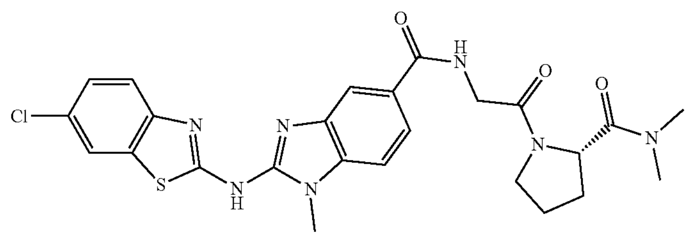 [SMILES: CN(C)C(=O)[C@@H]1CCCN1C(=O)CNC(=O)c1ccc2c(c1)nc(Nc1nc3ccc(Cl)cc3s1)n2C] | 2-(6-Chloro-benzothiazol-2-ylamino)-1-methyl-1H-benzoimidazole-5-carboxylic acid [2-((S)-2-dimethylcarbamoyl-pyrrolidin-1-yl)-2-oxo-ethyl]-amide |
| 420 | 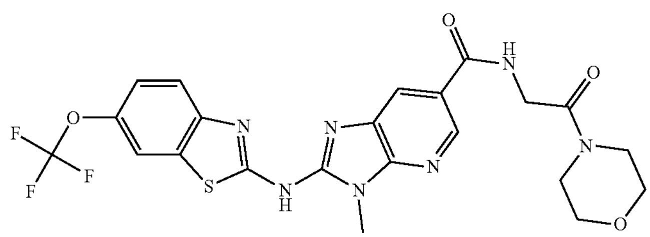 [SMILES: Cn1c(Nc2nc3ccc(OC(F)(F)F)cc3s2)nc2cc(C(=O)NCC(=O)N3CCOCC3)cnc21] | 3-Methyl-2-(6-trifluoromethoxy-benzothiazol-2-ylamino)-3H-imidazol[4,5-b]pyridine-6-carboxylic acid (2-morpholin-4-yl-2-oxo-ethyl)-amide |
| 421 | 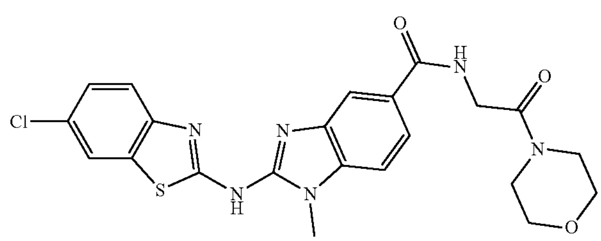 [SMILES: Cn1c(Nc2nc3ccc(Cl)cc3s2)nc2cc(C(=O)NCC(=O)N3CCOCC3)ccc21] | 2-(6-Chloro-benzothiazol-2-ylamino)-1-methyl-1H-benzoimidazole-5-carboxylic acid (2-morpholin-4-yl-2-oxo-ethyl)-amide |
| 422 | 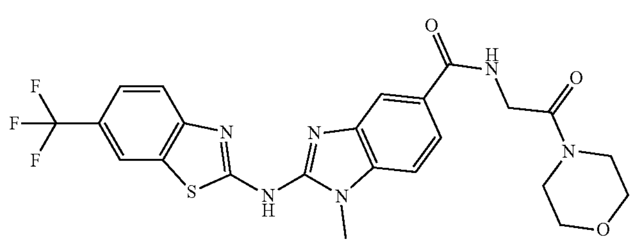 [SMILES: Cn1c(Nc2nc3ccc(C(F)(F)F)cc3s2)nc2cc(C(=O)NCC(=O)N3CCOCC3)ccc21] | 1-Methyl-2-(6-trifluoromethyl-benzothiazol-2-ylamino)-1H-benzimidazole-5-carboxylic acid (2-morpholin-4-yl-2-oxo-ethyl)-amide |

TABLE 1-continued

| No. | Structure | Name |
|---|---|---|
| 423 | 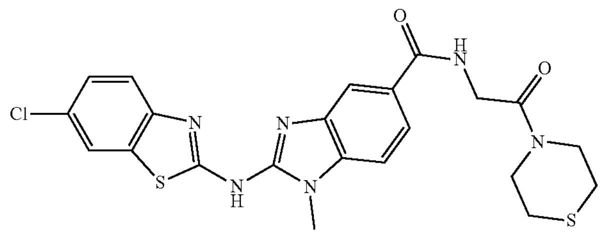 | 2-(6-Chloro-benzothiazol-2-ylamino)-1-methyl-1H-benzoimidazole-5-carboxylic acid (2-oxo-2-thiomorpholin-4-yl-ethyl)-amide |
| 424 | 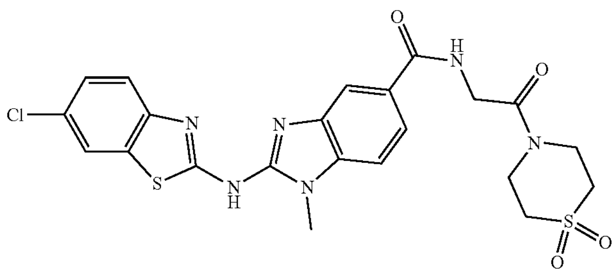 [SMILES: Cn1c(Nc2nc3ccc(Cl)cc3s2)nc2cc(C(=O)NCC(=O)N3CCS(=O)(=O)CC3)ccc21] | 2-(6-Chloro-benzothiazol-2-ylamino)-1-methyl-1H-benzoimidazole-5-carboxylic acid [2-(1,1-dioxo-thiomorpholin-4-yl)-2-oxo-ethyl]-amide |
| 425 | 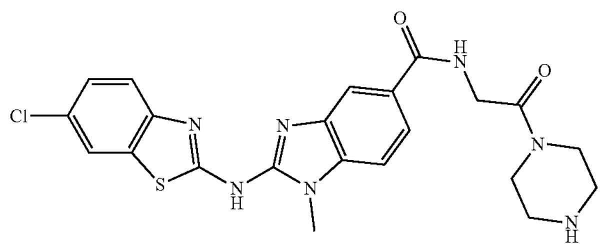 [SMILES: Cn1c(Nc2nc3ccc(Cl)cc3s2)nc2cc(C(=O)NCC(=O)N3CCNCC3)ccc21] | 2-(6-Chloro-benzothiazol-2-ylamino)-1-methyl-1H-benzoimidazole-5-carboxylic acid (2-oxo-2-piperazin-1-yl-ethyl)-amide hydrochloride |
| 426 | 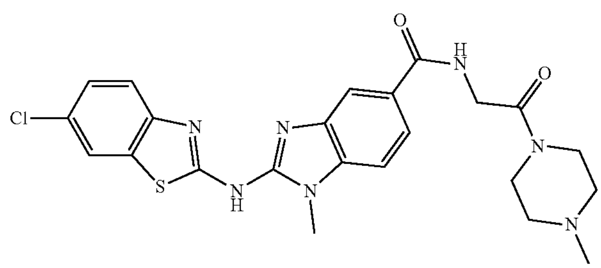 [SMILES: CN1CCN(C(=O)CNC(=O)c2ccc3c(c2)nc(Nc2nc4ccc(Cl)cc4s2)n3C)CC1] | 2-(6-Chloro-benzothiazol-2-ylamino)-1-methyl-1H-benzoimidazol-5-carboxylic acid [2-(4-methyl-piperazin-1-yl)-2-oxo-ethyl]-amide |
| 427 | 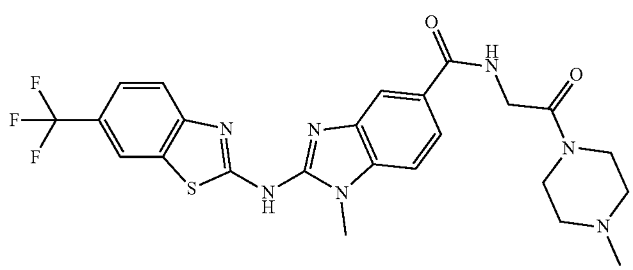 [SMILES: CN1CCN(C(=O)CNC(=O)c2ccc3c(c2)nc(Nc2nc4ccc(C(F)(F)F)cc4s2)n3C)CC1] | 1-Methyl-2-(6-trifluoromethyl-benzothiazol-2-ylamino)-1H-benzoimidazole-5-carboxylic acid [2-(4-methyl-piperazin-1-yl)-2-oxo-ethyl]-amide |
| 428 | 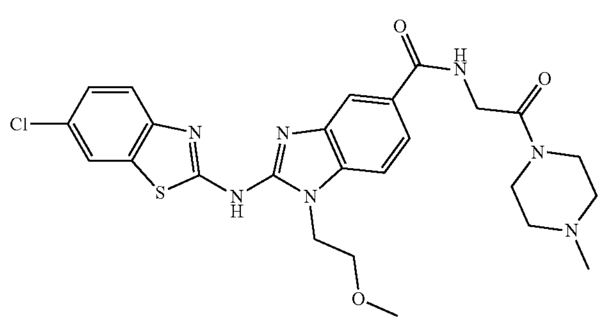 [SMILES: COCCn1c(Nc2nc3ccc(Cl)cc3s2)nc2cc(C(=O)NCC(=O)N3CCN(C)CC3)ccc21] | 2-(6-Chloro-benzothiazol-2-ylamino)-1-(2-methoxy-ethyl)-1H-benzoimidazole-5-carboxylic acid [2-(4-methyl-piperazin-1-yl)-2-oxo-ethyl]-amide |

TABLE 1-continued

| No. | Structure | Name |
|---|---|---|
| 429 | 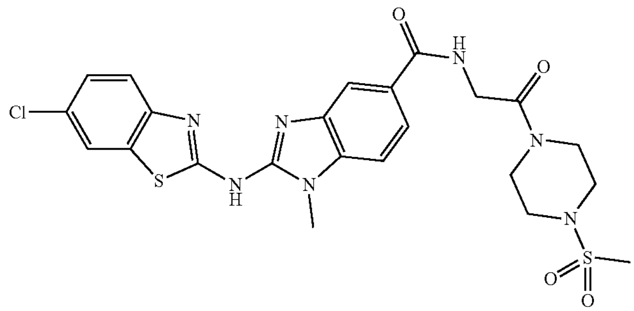 [SMILES: Cn1c(Nc2nc3ccc(Cl)cc3s2)nc2cc(C(=O)NCC(=O)N3CCN(S(C)(=O)=O)CC3)ccc21] | 2-(6-Chloro-benzothiazol-2-ylamino)-1-methyl-1H-benzoimidazole-5-carboxylic acid [2-(4-methanesulfonyl-piperazin-1-yl)-2-oxo-ethyl]-amide |
| 430 | 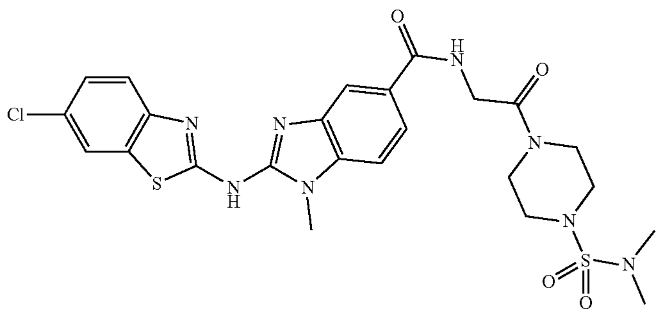 [SMILES: CN(C)S(=O)(=O)N1CCN(C(=O)CNC(=O)c2ccc3c(c2)nc(Nc2nc4ccc(Cl)cc4s2)n3C)CC1] | 2-(6-Chloro-benzothiazol-2-ylamino)-1-methyl-1H-benzoimidazole-5-carboxylic acid [2-(4-dimethylsulfamoyl-piperazin-1-yl)-2-oxo-ethyl]-amide |
| 431 | 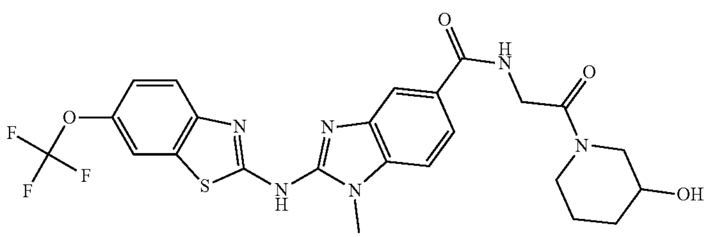 [SMILES: Cn1c(Nc2nc3ccc(OC(F)(F)F)cc3s2)nc2cc(C(=O)NCC(=O)N3CCCC(O)C3)ccc21] | 1-Methyl-2-(6-trifluoromethoxy-benzothiazol-2-ylamino)-1H-benzoimidazole-5-carboxylic acid [2-(3-hydroxy-piperidin-1-yl)-2-oxo-ethyl]-amide |
| 432 | 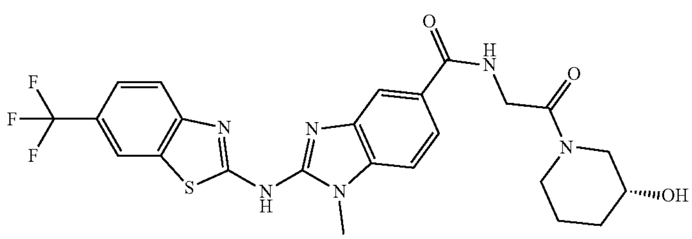 [SMILES: Cn1c(Nc2nc3ccc(C(F)(F)F)cc3s2)nc2cc(C(=O)NCC(=O)N3CCC[C@@H](O)C3)ccc21] | 1-Methyl-2-(6-trifluoromethyl-benzothiazol-2-ylamino)-1H-benzoimidazole-5-carboxylic acid [2-((R)-3-hydroxy-piperidin-1-yl)-2-oxo-ethyl]-amide |
| 433 | 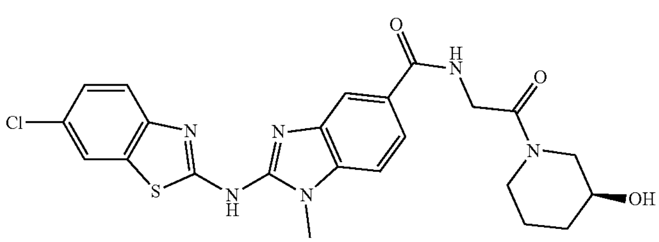 [SMILES: Cn1c(Nc2nc3ccc(Cl)cc3s2)nc2cc(C(=O)NCC(=O)N3CCC[C@H](O)C3)ccc21] | 2-(6-Chloro-benzothiazol-2-ylamino)-1-methyl-1H-benzoimidazole-5-carboxylic acid [2-((S)-3-hydroxy-piperidin-1-yl)-2-oxo-ethyl]-amide |
| 434 | 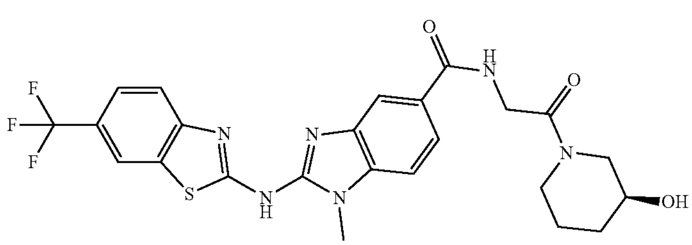 [SMILES: Cn1c(Nc2nc3ccc(C(F)(F)F)cc3s2)nc2cc(C(=O)NCC(=O)N3CCC[C@H](O)C3)ccc21] | 1-Methyl-2-(6-trifluoromethyl-benzothiazol-2-ylamino)-1H-benzoimidazole-5-carboxylic acid [2-((S)-3-hydroxy-piperidin-1-yl)-2-oxo-ethyl]-amide |

TABLE 1-continued

| No. | Structure | Name |
|---|---|---|
| 435 | 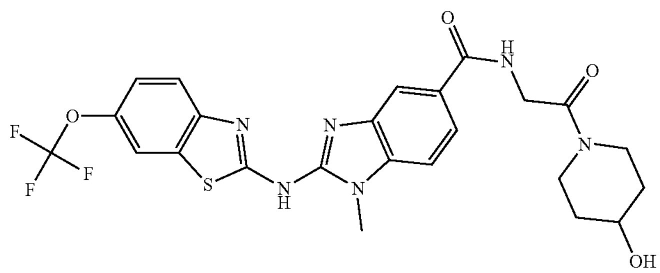 [SMILES: Cn1c(Nc2nc3ccc(OC(F)(F)F)cc3s2)nc2cc(C(=O)NCC(=O)N3CCC(O)CC3)ccc21] | 1-Methyl-2-(6-trifluoromethoxy-benzothiazol-2-ylamino)-1H-benzoimidazole-5-carboxylic acid [2-(4-hydroxy-piperidin-1-yl)-2-oxo-ethyl]-amide |
| 436 | 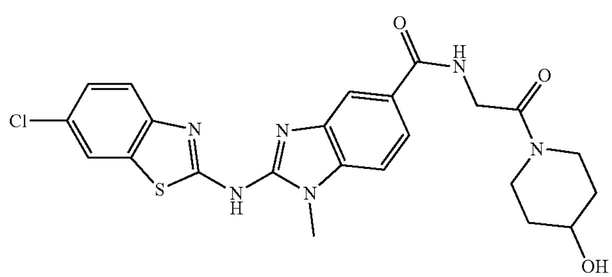 [SMILES: Cn1c(Nc2nc3ccc(Cl)cc3s2)nc2cc(C(=O)NCC(=O)N3CCC(O)CC3)ccc21] | 2-(6-Chloro-benzothiazol-2-ylamino)-1-methyl-1H-benzoimidazole-5-carboxylic acid [2-(4-hydroxy-piperidin-1-yl)-2-oxo-ethyl]-amide |
| 437 | 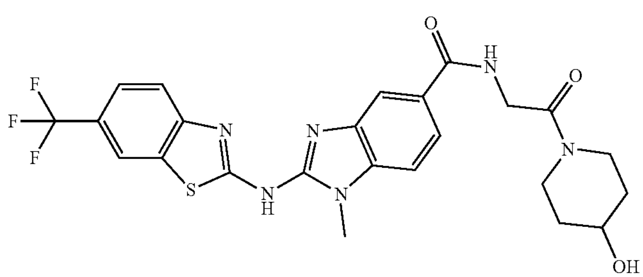 [SMILES: Cn1c(Nc2nc3ccc(C(F)(F)F)cc3s2)nc2cc(C(=O)NCC(=O)N3CCC(O)CC3)ccc21] | 1-Methyl-2-(6-trifluoromethyl-benzothiazol-2-ylamino)-1H-benzoimidazole-5-carboxylic acid [2-(4-hydroxy-piperidin-1-yl)-2-oxo-ethyl]-amide |
| 438 | 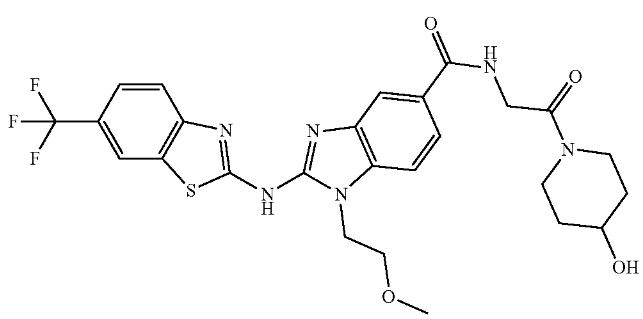 [SMILES: COCCn1c(Nc2nc3ccc(C(F)(F)F)cc3s2)nc2cc(C(=O)NCC(=O)N3CCC(O)CC3)ccc21] | 2-(6-Chloro-benzothiazol-2-ylamino)-1-(2-methoxy-ethyl)-1H-benzoimidazole-5-carboxylic acid [2-(4-hydroxy-piperidin-1-yl)-2-oxo-ethyl]-amide |
| 439 | 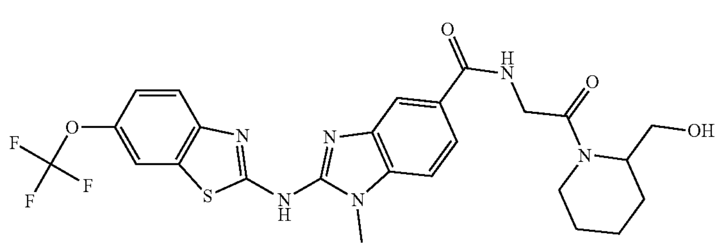 [SMILES: Cn1c(Nc2nc3ccc(OC(F)(F)F)cc3s2)nc2cc(C(=O)NCC(=O)N3CCCCC3CO)ccc21] | 1-Methyl-2-(6-trifluoromethoxy-benzothiazol-2-ylamino)-1H-benzoimidazole-5-carboxylic acid [2-(2-hydroxymethyl-piperidin-1-yl)-2-oxo-ethyl]-amide |

TABLE 1-continued

| No. | Structure | Name |
|---|---|---|
| 440 | 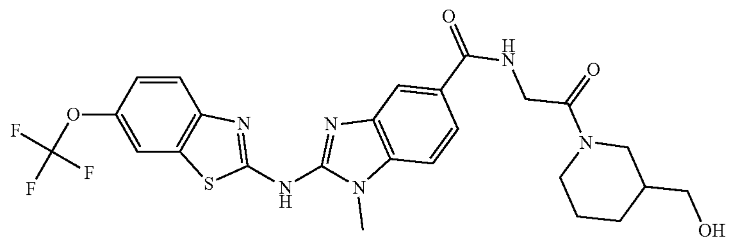 [SMILES: Cn1c(Nc2nc3ccc(OC(F)(F)F)cc3s2)nc2cc(C(=O)NCC(=O)N3CCCC(CO)C3)ccc21] | 1-Methyl-2-(6-trifluoromethoxy-benzothiazol-2-ylamino)-1H-benzoimidazole-5-carboxylic acid [2-(3-hydroxymethyl-piperidin-1-yl)-2-oxo-ethyl]-amide |
| 441 | 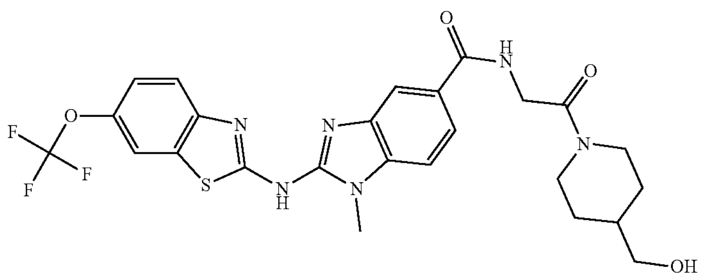 [SMILES: Cn1c(Nc2nc3ccc(OC(F)(F)F)cc3s2)nc2cc(C(=O)NCC(=O)N3CCC(CO)CC3)ccc21] | 1-Methyl-2-(6-trifluoromethoxy-benzothiazol-2-ylamino)-1H-benzoimidazole-5-carboxylic acid [2-(4-hydroxymethyl-piperidin-1-yl)-2-oxo-ethyl]-amide |
| 442 | 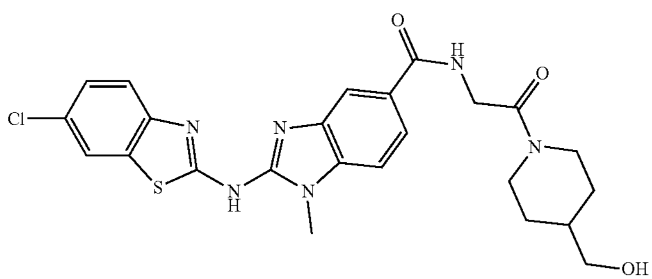 [SMILES: Cn1c(Nc2nc3ccc(Cl)cc3s2)nc2cc(C(=O)NCC(=O)N3CCC(CO)CC3)ccc21] | 2-(6-Chloro-benzothiazol-2-ylamino)-1-methyl-1H-benzoimidazole-5-carboxylic acid [2-(4-hydroxymethyl-piperidin-1-yl)-2-oxo-ethyl]-amide |
| 443 | 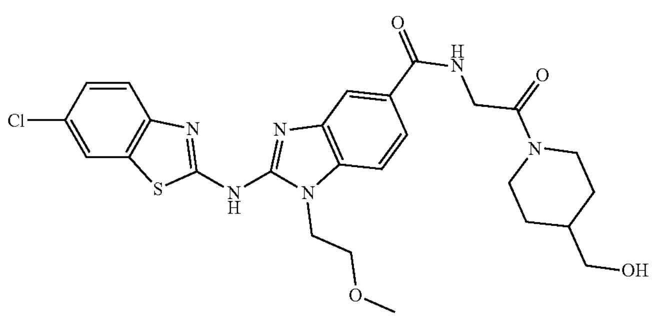 [SMILES: COCCn1c(Nc2nc3ccc(Cl)cc3s2)nc2cc(C(=O)NCC(=O)N3CCC(CO)CC3)ccc21] | 2-(6-Chloro-benzothiazol-2-ylamino)-1-(2-methoxy-ethyl)-1H-benzoimidazole-5-carboxylic acid [2-(4-hydroxymethyl-piperidin-1-yl)-2-oxo-ethyl]-amide |
| 444 | 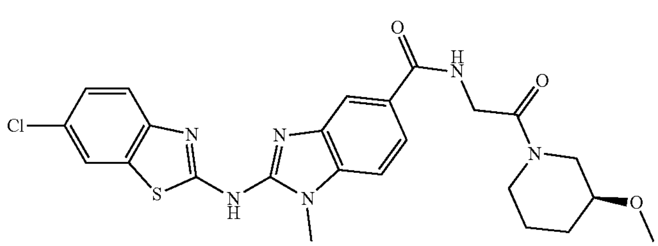 [SMILES: CO[C@H]1CCCN(C(=O)CNC(=O)c2ccc3c(c2)nc(Nc2nc4ccc(Cl)cc4s2)n3C)C1] | 2-(6-Chloro-benzothiazol-2-ylamino)-1-methyl-1H-benzoimidazole-5-carboxylic acid [2-((S)-3-methoxy-piperidin-1-yl)-2-oxo-ethyl]-amide |
| 445 | 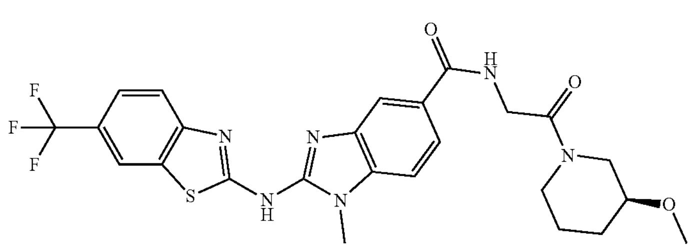 [SMILES: CO[C@H]1CCCN(C(=O)CNC(=O)c2ccc3c(c2)nc(Nc2nc4ccc(C(F)(F)F)cc4s2)n3C)C1] | 1-Methyl-2-(6-trifluoromethyl-benzothiazol-2-ylamino)-1H-benzoimidazole-5-carboxylic acid [2-((S)-3-methoxy-piperidin-1-yl)-2-oxo-ethyl]-amide |

TABLE 1-continued

| No. | Structure | Name |
|---|---|---|
| 446 | 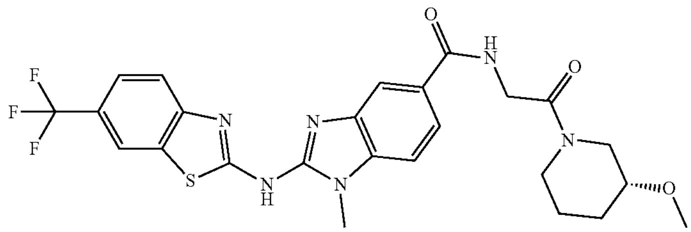 [SMILES: CO[C@@H]1CCCN(C(=O)CNC(=O)c2ccc3c(c2)nc(Nc2nc4ccc(C(F)(F)F)cc4s2)n3C)C1] | 1-Methyl-2-(6-trifluoromethyl-benzothiazol-2-ylamino)-1H-benzoimidazole-5-carboxylic acid [2-((R)-3-methoxy-piperidin-1-yl)-2-oxo-ethyl]-amide |
| 447 | 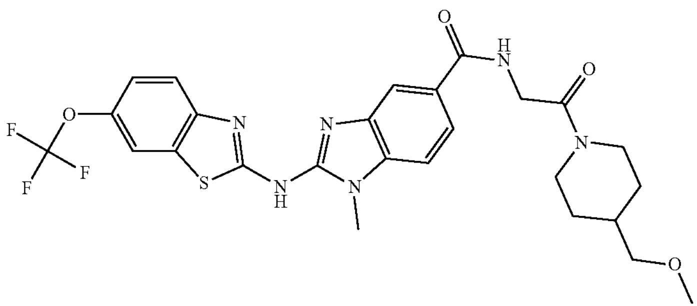 [SMILES: COCC1CCN(C(=O)CNC(=O)c2ccc3c(c2)nc(Nc2nc4ccc(OC(F)(F)F)cc4s2)n3C)CC1] | 1-Methyl-2-(6-trifluoromethoxy-benzothiazol-2-ylamino)-1H-benzoimidazole-5-carboxylic acid [2-(4-methoxymethyl-piperidin-1-yl)-2-oxo-ethyl]-amide |
| 448 | 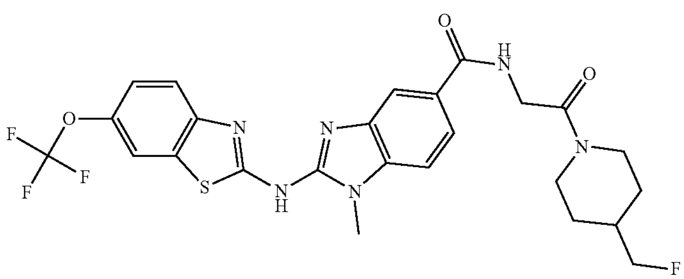 [SMILES: Cn1c(Nc2nc3ccc(OC(F)(F)F)cc3s2)nc2cc(C(=O)NCC(=O)N3CCC(CF)CC3)ccc21] | 1-Methyl-2-(6-trifluoromethoxy-benzothiazol-2-ylamino)-1H-benzoimidazole-5-carboxylic acid [2-(4-fluoromethyl-piperidin-1-yl)-2-oxo-ethyl]-amide |
| 449 | 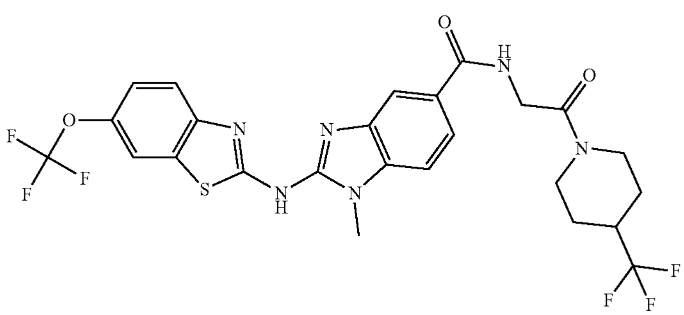 [SMILES: Cn1c(Nc2nc3ccc(OC(F)(F)F)cc3s2)nc2cc(C(=O)NCC(=O)N3CCC(C(F)(F)F)CC3)ccc21] | 1-Methyl-2-(6-trifluoromethoxy-benzothiazol-2-ylamino)-1H-benzoimidazole-5-carboxylic acid [2-oxo-2-(4-trifluoromethyl-piperidin-1-yl)-ethyl]-amide |
| 450 | 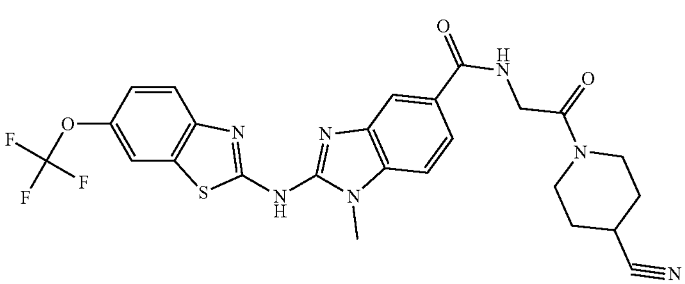 [SMILES: Cn1c(Nc2nc3ccc(OC(F)(F)F)cc3s2)nc2cc(C(=O)NCC(=O)N3CCC(C#N)CC3)ccc21] | 1-Methyl-2-(6-trifluoromethoxy-benzothiazol-2-ylamino)-1H-benzoimidazole-5-carboxylic acid [2-(4-cyano-piperidin-1-yl)-2-oxo-ethyl]-amide |

TABLE 1-continued

| No. | Structure | Name |
|---|---|---|
| 451 | 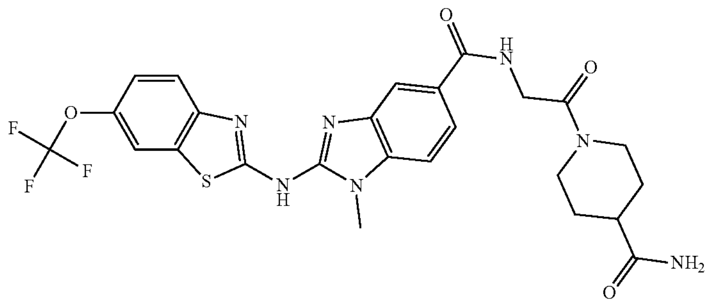 [SMILES: Cn1c(Nc2nc3ccc(OC(F)(F)F)cc3s2)nc2cc(C(=O)NCC(=O)N3CCC(C(N)=O)CC3)ccc21] | 1-Methyl-2-(6-trifluoromethoxy-benzothiazol-2-ylamino)-1H-benzoimidazole-5-carboxylic acid [2-(4-carbamoyl-piperidin-1-yl)-2-oxo-ethyl]-amide |
| 452 | 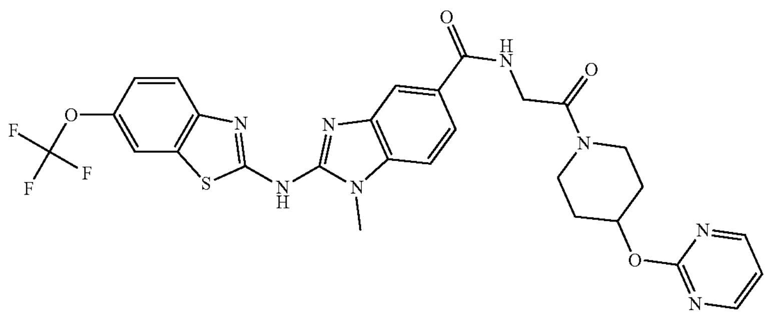 [SMILES: Cn1c(Nc2nc3ccc(OC(F)(F)F)cc3s2)nc2cc(C(=O)NCC(=O)N3CCC(Oc4ncccn4)CC3)ccc21] | 1-Methyl-2-(6-trifluoromethoxy-benzothiazol-2-ylamino)-1H-benzoimidazole-5-carboxylic acid {2-oxo-2-[4-(pyrimidin-2-yloxy)-piperidin-1-yl]-ethyl}-amide |
| 453 | 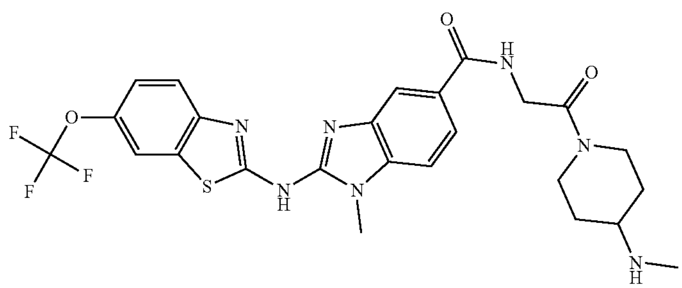 [SMILES: CNC1CCN(C(=O)CNC(=O)c2ccc3c(c2)nc(Nc2nc4ccc(OC(F)(F)F)cc4s2)n3C)CC1] | 1-Methyl-2-(6-trifluoromethoxy-benzothiazol-2-ylamino)-1H-benzoimidazole-5-carboxylic acid [2-(4-methylamino-piperidin-1-yl)-2-oxo-ethyl]-amide hydrochloride |
| 454 | 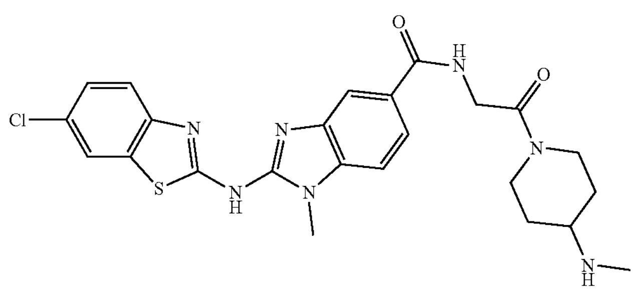 [SMILES: CNC1CCN(C(=O)CNC(=O)c2ccc3c(c2)nc(Nc2nc4ccc(Cl)cc4s2)n3C)CC1] | 2-(6-Chloro-benzothiazol-2-ylamino-1-methyl-1H-benzoimidazole-5-carboxylic acid [2-(4-methylamino-piperidin-1-yl)-2-oxo-ethyl]-amide hydrochloride |
| 455 | 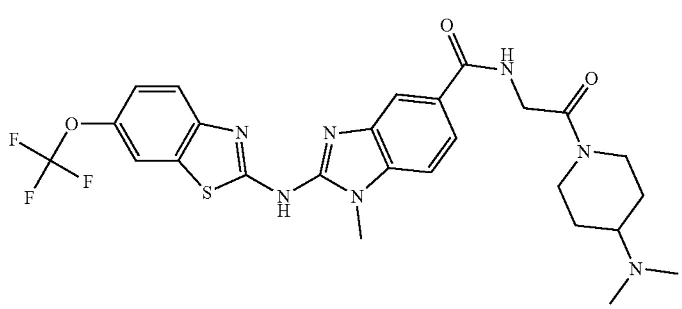 [SMILES: CN(C)C1CCN(C(=O)CNC(=O)c2ccc3c(c2)nc(Nc2nc4ccc(OC(F)(F)F)cc4s2)n3C)CC1] | 1-Methyl-2-(6-trifluoromethoxy-benzothiazol-2-ylamino)-1H-benzoimidazole-5-carboxylic acid [2-(4-dimethylamino-piperidin-1-yl)-2-oxo-ethyl]-amide |

| No. | Structure | Name |
|---|---|---|
| 456 | 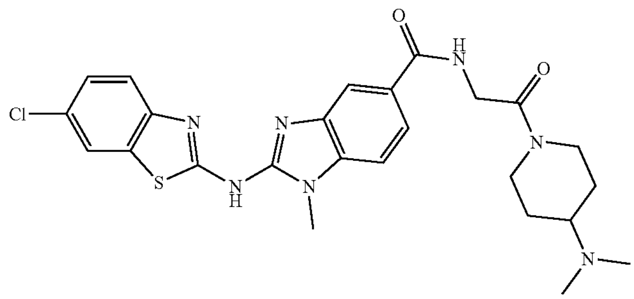 [SMILES: CN(C)C1CCN(C(=O)CNC(=O)c2ccc3c(c2)nc(Nc2nc4ccc(Cl)cc4s2)n3C)CC1] | 2-(6-Chloro-benzothiazol-2-ylamino)-1-methyl-1H-benzoimidazole-5-carboxylic acid [2-(4-dimethylamino-piperidin-1-yl)-2-oxo-ethyl]-amide |
| 457 | 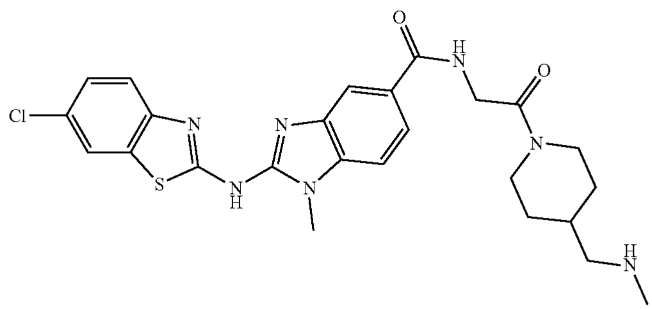 [SMILES: CNCC1CCN(C(=O)CNC(=O)c2ccc3c(c2)nc(Nc2nc4ccc(Cl)cc4s2)n3C)CC1] | 2-(6-Chloro-benzothiazol-2-ylamino)-1-methyl-1H-benzoimidazole-5-carboxylic acid [2-(4-methylaminomethyl-piperidin-1-yl)-2-oxo-ethyl]-amide hydrochloride |
| 458 | 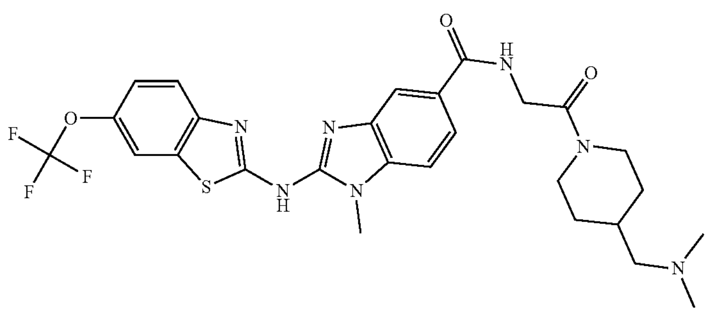 [SMILES: CN(C)CC1CCN(C(=O)CNC(=O)c2ccc3c(c2)nc(Nc2nc4ccc(OC(F)(F)F)cc4s2)n3C)CC1] | 1-Methyl-2-(6-trifluoromethoxy-benzothiazol-2-ylamino)-1H-benzoimidazole-5-carboxylic acid [2-(4-dimethylaminomethyl-piperidin-1-yl)-2-oxo-ethyl]-amide |
| 459 | 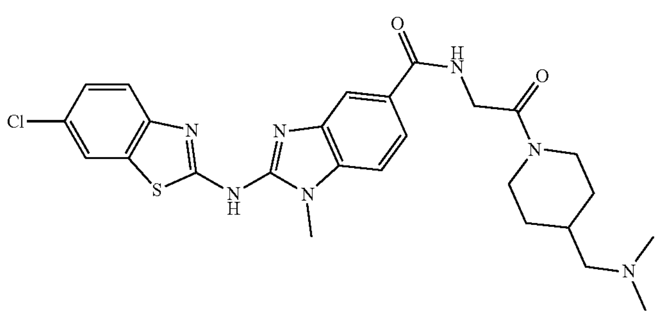 [SMILES: CN(C)CC1CCN(C(=O)CNC(=O)c2ccc3c(c2)nc(Nc2nc4ccc(Cl)cc4s2)n3C)CC1] | 2-(6-Chloro-benzothiazol-2-ylamino)-1-methyl-1H-benzoimidazole-5-carboxylic acid [2-(4-dimethylaminomethyl-piperidin-1-yl)-2-oxo-ethyl]-amide |
| 460 | 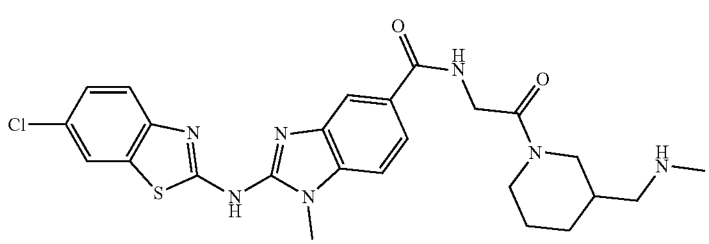 [SMILES: CNCC1CCCN(C(=O)CNC(=O)c2ccc3c(c2)nc(Nc2nc4ccc(Cl)cc4s2)n3C)C1] | 2-(6-Chloro-benzothiazol-2-ylamino)-1-methyl-1H-benzoimidazole-5-carboxylic acid [2-(3-methylaminomethyl-piperidin-1-yl)-2-oxo-ethyl]-amid hydrochloride |

TABLE 1-continued

| No. | Structure | Name |
|---|---|---|
| 461 | 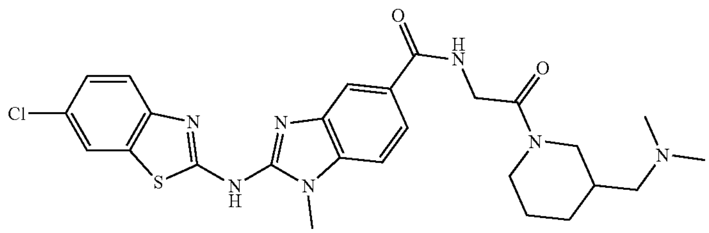 [SMILES: CN(C)CC1CCCN(C(=O)CNC(=O)c2ccc3c(c2)nc(Nc2nc4ccc(Cl)cc4s2)n3C)C1] | 2-(6-Chloro-benzothiazol-2-ylamino)-1-methyl-1H-benzoimidazole-5-carboxylic acid [2-(3-dimethylaminomethyl-piperidin-1-yl)-2-oxo-ethyl]-amide |
| 462 | 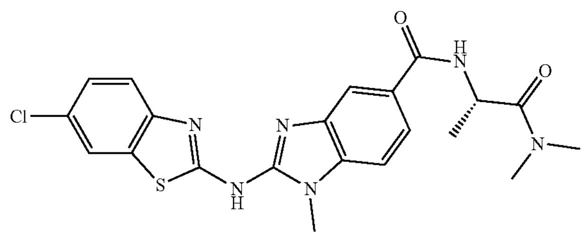 [SMILES: C[C@H](NC(=O)c1ccc2c(c1)nc(Nc1nc3ccc(Cl)cc3s1)n2C)C(=O)N(C)C] | 2-(6-Chloro-benzothiazol-2-ylamino)-1-methyl-1H-benzoimidazole-5-carboxylic acid ((S)-1-dimethylcarbamoyl-ethyl)-amide |
| 463 | 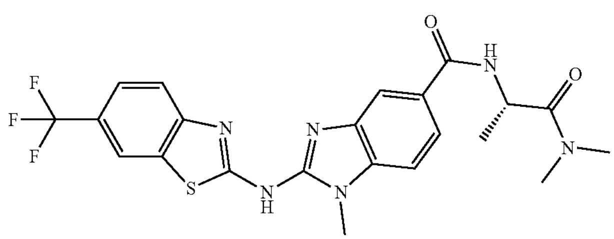 [SMILES: C[C@H](NC(=O)c1ccc2c(c1)nc(Nc1nc3ccc(C(F)(F)F)cc3s1)n2C)C(=O)N(C)C] | 1-Methyl-2-(6-trifluoromethyl-benzothiazol-2-ylamino)-1H-benzoimidazole-5-carboxylic acid ((S)-1-dimethylcarbamoyl-ethyl)-amide |
| 464 | 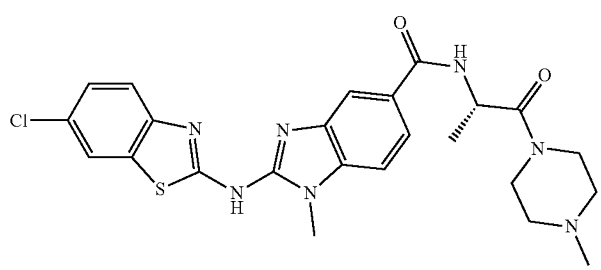 [SMILES: C[C@H](NC(=O)c1ccc2c(c1)nc(Nc1nc3ccc(Cl)cc3s1)n2C)C(=O)N1CCN(C)CC1] | 2-(6-Chloro-benzothiazol-2-ylamino)-1-methyl-1H-benzoimidazole-5-carboxylic acid [(S)-1-methyl-2-(4-methyl-piperazin-1-yl)-2-oxo-ethyl]-amide |
| 465 | 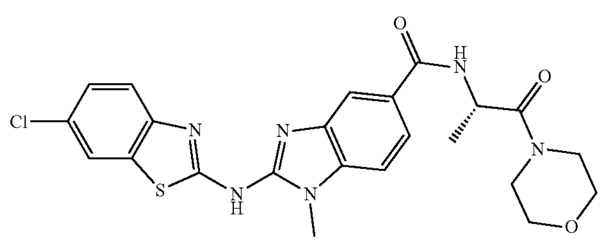 [SMILES: C[C@H](NC(=O)c1ccc2c(c1)nc(Nc1nc3ccc(Cl)cc3s1)n2C)C(=O)N1CCOCC1] | 2-(6-Chloro-benzothiazol-2-ylamino)-1-methyl-1H-benzoimidazole-5-carboxylic acid ((S)-1-methyl-2-morpholin-4-yl-2-oxo-ethyl)-amide |
| 466 | 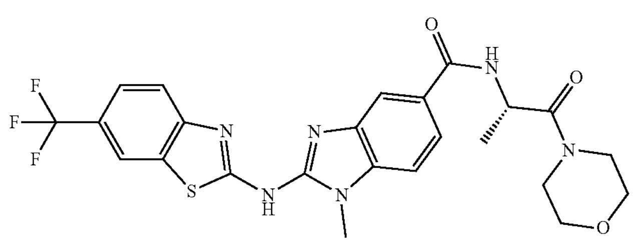 [SMILES: C[C@H](NC(=O)c1ccc2c(c1)nc(Nc1nc3ccc(C(F)(F)F)cc3s1)n2C)C(=O)N1CCOCC1] | 1-Methyl-2-(6-trifluoromethyl-benzothiazol-2-ylamino)-1H-benzoimidazole-5-carboxylic acid ((S)-1-methyl-2-morpholin-4-yl-2-oxo-ethyl)-amide |

TABLE 1-continued

| No. | Structure | Name |
|---|---|---|
| 467 | 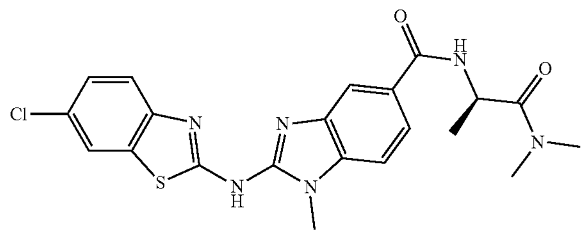 [SMILES: C[C@@H](NC(=O)c1ccc2c(c1)nc(Nc1nc3ccc(Cl)cc3s1)n2C)C(=O)N(C)C] | 2-(6-Chloro-benzothiazol-2-ylamino)-1-methyl-1H-benzoimidazole-5-carboxylic acid ((R)-1-dimethylcarbamoyl-ethyl)-amide |
| 468 | 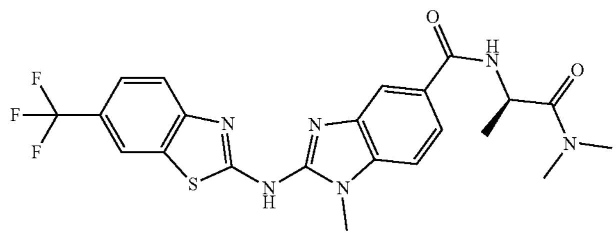 [SMILES: C[C@@H](NC(=O)c1ccc2c(c1)nc(Nc1nc3ccc(C(F)(F)F)cc3s1)n2C)C(=O)N(C)C] | 1-Methyl-2-(6-trifluoromethyl-benzothiazol-2-ylamino)-1H-benzoimidazole-5-carboxylic acid ((R)-1-dimethylcarbamoyl-ethyl)-amide |
| 469 | 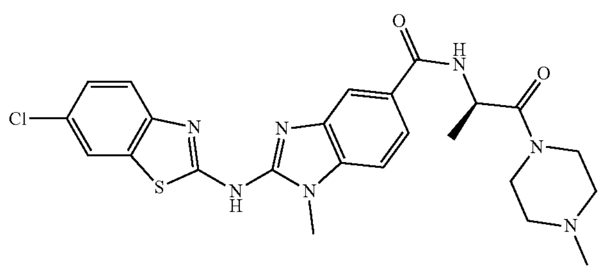 [SMILES: C[C@@H](NC(=O)c1ccc2c(c1)nc(Nc1nc3ccc(Cl)cc3s1)n2C)C(=O)N1CCN(C)CC1] | 2-(6-Chloro-benzothiazol-2-ylamino)-1-methyl-1H-benzoimidazole-5-carboxylic acid [(R)-1-methyl-2-(4-methyl-piperazin-1-yl)-2-oxo-ethyl]-amide |
| 470 | 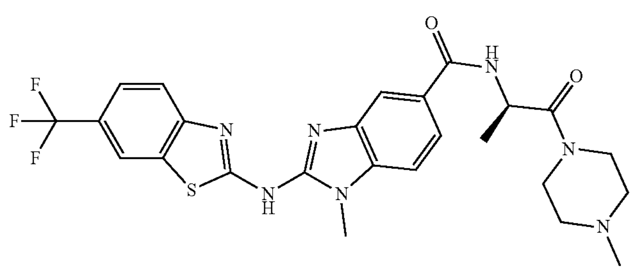 [SMILES: C[C@@H](NC(=O)c1ccc2c(c1)nc(Nc1nc3ccc(C(F)(F)F)cc3s1)n2C)C(=O)N1CCN(C)CC1] | 1-Methyl-2-(6-trifluoromethyl-benzothiazol-2-ylamino)-1H-benzoimidazole-5-carboxylic acid [(R)-1-methyl-2-(4-methyl-piperazin-1-yl)-2-oxo-ethyl]-amide |
| 471 | 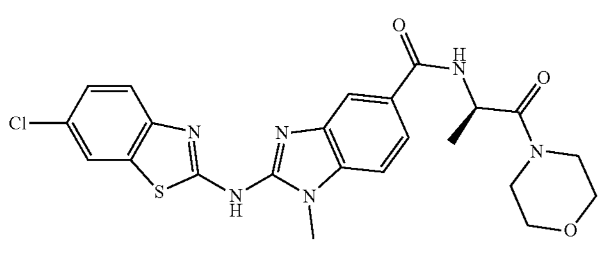 [SMILES: C[C@@H](NC(=O)c1ccc2c(c1)nc(Nc1nc3ccc(Cl)cc3s1)n2C)C(=O)N1CCOCC1] | 2-(6-Chloro-benzothiazol-2-ylamino)-1-methyl-1H-benzoimidazole-5-carboxylic acid ((R)-1-methyl-2-morpholin-4-yl-2-oxo-ethyl)-amide |
| 472 | 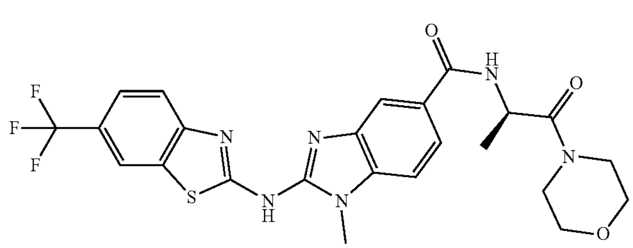 [SMILES: C[C@@H](NC(=O)c1ccc2c(c1)nc(Nc1nc3ccc(C(F)(F)F)cc3s1)n2C)C(=O)N1CCOCC1] | 1-Methyl-2-(6-trifluoromethyl-benzothiazol-2-ylamino)-1H-benzoimidazole-5-carboxylic acid ((R)-1-methyl-2-morpholin-4-yl-2-oxo-ethyl)-amide |

Compounds that increase levels or activity of HMOX1 are potentially useful in treating diseases or conditions that may be associated at least in part with oxidative stress such as, but not limited to, fibrotic diseases, neurodegenerative disease, cardiovascular disease, renal disease, inflammatory disease, liver disease, eye disease, thyroid disease, viral infection, osteoporosis, pregnancy disorders, endometriosis, diabetes, and cancer. As used herein, the diseases or conditions associated with oxidative stress also include chronic effects (e.g., tissue damage, chronic inflammation) associated with persistent or long-term increases in oxidative stress due to the diseases or conditions described herein.

Fibrotic diseases associated with oxidative stress include, but are not limited to, fibrotic diseases of the lung such as COPD, idiopathic pulmonary fibrosis, and sarcoidosis; fibrotic diseases of the liver including those caused by alcoholic cirrhosis, steatosis, cholestasis, drug side effect, and viral infection; and fibrotic diseases of the skin including autoimmune diseases such as scleroderma and psoriasis.

Neurodegenerative diseases associated with oxidative stress include, but are not limited to, Friedreich's ataxia, Alzheimer's disease, Parkinson's disease, amyotrophic lateral sclerosis, multiple sclerosis, and Charcot-Marie-Tooth syndrome.

Cardiovascular diseases associated with oxidative stress include, but are not limited to, hypertension, heart failure, hypercholesterolaemia, atherosclerosis, acute coronary thrombosis, deep vein thrombosis, peripheral vascular disease, congestive heart failure, acute coronary syndrome, failure of arterial fistula for dialysis, and primary pulmonary hypertension.

Renal diseases associated with oxidative stress include, but are not limited to, diabetic nephropathy, glomerular nephritis, and acute tubular necrosis.

Inflammatory diseases associated with oxidative stress include, but are not limited to, asthma, chronic obstructive pulmonary disease, idiopathic pulmonary fibrosis, inflammatory bowel syndrome, Crohn's disease, celiac disease, scleroderma, systemic lupus erythematosus, and rheumatoid arthritis.

Liver diseases associated with oxidative stress include, but are not limited to, drug induced liver toxicity, nonalcoholic steatohepatitis, and hepatitis C infection.

Eye diseases and conditions associated with oxidative stress include, but are not limited to, glaucoma, uveitis, wound healing (e.g., after surgery such as LASIK), eye trauma, corneal grafts, macular degeneration, cataracts, light retinopathy, and retinopathy of prematurity, as well as inflammation and tissue damage associated with these diseases.

Thyroid diseases associated with oxidative stress include, but are not limited to, Graves' disease, follicular adenoma, and papillary and follicular carcinomas.

Viral infections associated with oxidative stress include both viral replication of viruses, as well as tissue damage (e.g., fibrosis) due to oxidative stress resulting from chronic viral infection, for viruses including but are not limited to, human immunodeficiency virus, hepatitis B, hepatitis C, and herpesvirus.

Diabetic conditions include, but are not limited to, type 1 diabetes mellitus, type 2 diabetes mellitus, gestational diabetes, pre-diabetes, hyperglycemia, and metabolic syndrome as well as secondary conditions resulting from diabetic conditions (e.g., congestive heart failure and nephropathy).

The compounds of Formula (I) or pharmaceutically acceptable salts thereof may therefore be useful in the treatment of one or more of these diseases.

In one embodiment, the present invention provides a pharmaceutical composition comprising the compound of Formula (I) or a pharmaceutically acceptable salt thereof. In another embodiment, the present invention provides a pharmaceutical composition comprising a compound of any one of embodiments 1 to 271 (recited above). In another embodiment, the pharmaceutical composition comprises a compound of any one of embodiments 1 to 271 and a pharmaceutically acceptable carrier, excipient, diluent, or a mixture thereof.

In an embodiment, the pharmaceutical compositions containing a compound of Formula (I) or a pharmaceutically acceptable salt thereof may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and U.S. Pat. No. 4,265,874, to form osmotic therapeutic tablets for controlled release.

In another embodiment, formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

In another embodiment, the composition may comprise an aqueous suspension. Aqueous suspensions may contain the active compounds in an admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Also, oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

In another embodiment, the pharmaceutical compositions of the present invention may comprise a syrup or elixir. Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The pharmaceutical compositions of the present invention may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

In an embodiment, for topical use, creams, ointments, jellies, solutions of suspensions, etc., containing the compounds of the invention may be employed. For the purpose of this application, topical applications shall include mouth washes and gargles.

In an embodiment, the compounds of Formula (I) and pharmaceutically acceptable salts thereof may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

Pharmaceutically-acceptable salts of compounds of Formula (I), where a basic or acidic group is present in the structure, are also included within the scope of the invention. The term "pharmaceutically acceptable salts" refers to salts of the compounds of this invention which are not biologically or otherwise undesirable and are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxalate, maleate, pyruvate, malonate, succinate, citrate, tartarate, fumarate, mandelate, benzoate, cinnamate, methanesulfonate, ethanesulfonate, picrate and the like, and include acids related to the pharmaceutically-acceptable salts recited in Stephen M. Berge, et al., *J. Pharm. Sci.*, Vol 66(1), pp. 1-19 (1977).

Thus, in another embodiment, the invention provides a pharmaceutical composition comprising a compound of Formula (I) or a pharmaceutically acceptable salt thereof, and one or more pharmaceutically acceptable carriers, excipients, or diluents. In another embodiment, the invention provides a pharmaceutical composition comprising a compound of any one of embodiments 1 to 271 and one or more pharmaceutically acceptable carriers, excipients, or diluents.

In another embodiment, the present invention provides a compound of Formula (I) or a pharmaceutically acceptable salt thereof for use in medicine. In another embodiment, the invention provides a compound of any one of embodiments 1 to 271 for use in medicine.

The present invention further provides for the use of a compound of Formula (I), or a pharmaceutically acceptable salt thereof, in combination with one or more medically effective active compounds for simultaneous, subsequent, or sequential administration. The invention also provides for the use of a compound of any one of embodiments 1 to 271 in combination with one or more medically effective active compounds for simultaneous, subsequent, or sequential administration. Examples of such medically effective active ingredients include, but are not limited to, Nrf2 activators, antioxidants, detoxification agents, anti-inflammatory agents, and antidiabetic agents, e.g., metformin. In one embodiment, the invention provides a pharmaceutical composition comprising a compound of any one of embodiments 1 to 271 and at least one other medically effective active ingredient selected from Nrf2 activators, antioxidants, detoxification agents, anti-inflammatory agents, and antidiabetic agents, e.g., metformin. In another embodiment, the invention provides for the use of a compound of any one of embodiments 1 to 271 in combination with at least one other medically effective active ingredient selected from Nrf2 activators, antioxidants, detoxification agents, anti-inflammatory agents, and antidiabetic agents, e.g., metformin for simultaneous, subsequent, or sequential administration.

Examples of the Nrf2 activators include sulforaphane, avicins, 15dPGJ$_2$, xanthohumol, curcumin, carnosol, zerumbone, isothiocyanate, α-lipoic acid, oltipraz (4-methyl-5-[2-pyrazinyl]-1,2-dithiole-3-thione), 1,2-dithiole-3-thione, and 2,3-butyl-4-hydroxyanisole.

Examples of the antioxidants include vitamin C, vitamin E, carotenoids, retinolds, polyphenols, flavonoids, lignan, selenium, butylated hydroxyanisole, ethylene diamine tetraacetate, calcium disodium, acetylcysteine, probucol, and tempo.

Examples of the detoxification agents include dimethyl caprol, glutathione, acetylcysteine, methionine, sodium hydrogen carbonate, deferoxamine mesylate, calcium disodium edetate, trientine hydrochloride, penicillamine, and pharmaceutical charcoal.

The anti-inflammatory agents include steroidal anti-inflammatory agents and non-steroidal anti-inflammatory agents. Examples of the steroidal anti-inflammatory agents include cortisone acetate, hydrocortisone, paramethasone acetate, prednisolone, prednisolone, methylprednine, dexamethasone, triamcinolone, and betamethasone. Examples of the non-steroidal anti-inflammatory agents include salicylic acid non-steroidal anti-inflammatory agents such as aspirin, difiunisal, aspirin+ascorbic acid, and aspirin dialuminate; aryl acid non-steroidal anti-inflammatory agents such as diclofenac sodium, sulindac, fenbufen, indomethacin, indomethacin farnesyl, acemetacin, proglumetacin maleate, anfenac sodium, nabmeton, mofezolac, and etodorag; fenamic acid non-steroidal anti-inflammatory agents such as mefenamic acid, flufenamic acid aluminum, tolfenamic acid, and floctafenine; propionic acid non-steroidal anti-inflammatory agents such as ibuprofen, flurbiprofen, ketoprofen, naproxen, pranoprofen, fenoprofen calcium, thiaprofen, oxaprozin, loxoprofen sodium, alminoprofen, and zaltoprofen; oxicam non-steroldal anti-inflammatory agents such as piroxicam, ampiroxicam, tenoxicam, lornoxicam, and meloxicam; and basic non-steroidal anti-inflammatory agents such as tiaramide hydrochloride, epirizole, and emorfazone.

Methods of Use

A compound of Formula (I) or pharmaceutically acceptable salt thereof, or a pharmaceutical composition comprising a compound of Formula (I) or pharmaceutically acceptable salt thereof may be used for the treatment of a disease or condition which is treatable by activation of transcription factor Nrf2, by increasing the activity and/or the amount of HMOX1, or by reducing amounts of ROS in a subject. The treatment can be systemic or targeted, for example targeted to an inducible heme-oxygenase found in monocytes and macrophages in the human body.

Examples of a disease or condition which may be treatable by activation of transcription factor Nrf2, by increasing the activity and/or the amount of HMOX1, or by reducing amounts of ROS in a subject, include cerebral nerve degenerative diseases, eye diseases, skin diseases, asthma, cancer, arteriosclerosis and diseases or conditions related thereto. Examples of the cerebral nerve degenerative diseases include Alzheimer's disease, Parkinson's disease, and amyotrophic lateral sclerosis. Further, examples of the eye diseases include age-related macular degeneration, cataracts, light retinopathy, and retinopathy of prematurity. Specific examples of the chronic inflammatory diseases include vasculitis, pulmonary bronchitis, rheumatoid arthritis, osteoarthritis, hepatitis, pancreatitis, dermatitis, esophagitis, ulcerative colitis, Crohn's disease, and conjunctivitis. Further examples of conditions that may be treatable include thrombosis and diseases of the kidney.

Examples of a disease or condition which may be treatable by activation of transcription factor Nrf2, by increasing the activity and/or the amount of HMOX1, or by reducing amounts of ROS in a subject, include, but are not limited to, fibrotic diseases, neurodegenerative disease, cardiovascular disease, renal disease, inflammatory disease, liver disease, eye disease, thyroid disease, viral infection, osteoporosis, pregnancy disorders, endometriosis, diabetes, and cancer. As used herein, the diseases or conditions associated with oxidative stress also include chronic effects (e.g., tissue damage, chronic inflammation) associated with persistent or long-term increases in oxidative stress due to the diseases or conditions described herein.

Fibrotic diseases associated with oxidative stress include, but are not limited to, fibrotic diseases of the lung such as COPD, idiopathic pulmonary fibrosis, and sarcoidosis; fibrotic diseases of the liver including those caused by alcoholic cirrhosis, steatosis, cholestasis, drug side effect, and viral infection; and fibrotic diseases of the skin including autoimmune diseases such as scleroderma and psoriasis.

Neurodegenerative diseases associated with oxidative stress include, but are not limited to, Friedreich's ataxia, Alzheimer's disease, Parkinson's disease, amyotrophic lateral sclerosis, multiple sclerosis, and Charcot-Marie-Tooth syndrome.

Cardiovascular diseases associated with oxidative stress include, but are not limited to, hypertension, heart failure, hypercholesterolaemia, atherosclerosis, acute coronary thrombosis, deep vein thrombosis, peripheral vascular disease, congestive heart failure, acute coronary syndrome, failure of arterial fistula for dialysis, and primary pulmonary hypertension.

Renal diseases associated with oxidative stress include, but are not limited to, diabetic nephropathy, glomerular nephritis, and acute tubular necrosis.

Inflammatory diseases associated with oxidative stress include, but are not limited to, asthma, chronic obstructive pulmonary disease, idiopathic pulmonary fibrosis, inflammatory bowel syndrome, Crohn's disease, celiac disease, scleroderma, systemic lupus erythematosus, and rheumatoid arthritis.

Liver diseases associated with oxidative stress include, but are not limited to, drug induced liver toxicity, nonalcoholic steatohepatitis, and hepatitis C infection.

Eye diseases and conditions associated with oxidative stress include, but are not limited to, glaucoma, uveitis, wound healing (e.g., after surgery such as LASIK), eye trauma, corneal grafts, macular degeneration, cataracts, light retinopathy, and retinopathy of prematurity, as well as inflammation and tissue damage associated with these diseases.

Thyroid diseases associated with oxidative stress include, but are not limited to, Graves' disease, follicular adenoma, and papillary and follicular carcinomas.

Viral infections associated with oxidative stress include both viral replication of viruses, as well as tissue damage (e.g., fibrosis) due to oxidative stress resulting from chronic viral infection, for viruses including but are not limited to human immunodeficiency virus, hepatitis B, hepatitis C, and herpesvirus.

Diabetic conditions include, but are not limited to, type 1 diabetes mellitus, type 2 diabetes mellitus, gestational diabetes, pre-diabetes, hyperglycemia, and metabolic syndrome as well as secondary conditions resulting from diabetic conditions (e.g., congestive heart failure and nephropathy).

Thus the present invention provides a method of treatment comprising administering to a subject a compound of Formula (I) or a pharmaceutically acceptable salt thereof so as to treat at least one of the diseases or conditions listed above.

In one embodiment, the invention provides a method of treatment comprising administering a compound of any one of embodiments 1 to 271 to a human. In another embodiment, the invention provides a method of treatment comprising administering at least 0.1 milligrams of a compound of any one of embodiments 1 to 271 to a human.

In another embodiment, the invention provides a method of treatment comprising administering a compound of any one of embodiments 1 to 271 to a human, so as to treat chronic inflammation. In a further embodiment, the invention provides a method of treatment comprising administering a compound of any one of embodiments 1 to 271 to a human, so as to treat a disease or condition selected from rheumatoid arthritis, a chronic inflammatory bowel disease, multiple sclerosis, asthma, airways inflammatory disease, tendonitis, and chronic inflammation in the brain.

In another embodiment, the invention provides a compound of any one of embodiments 1 to 271 for use in medicine. In another embodiment, the invention provides a compound of any one of embodiments 1 to 271 for use in the treatment of chronic inflammation. In another embodiment, the invention provides a compound of any one of embodiments 1 to 271 for use in the prevention of chronic inflammation. In another embodiment, the invention provides a compound of any one of embodiments 1 to 271 for use in the treatment of a disease or condition selected from rheumatoid arthritis, a chronic inflammatory bowel disease, multiple sclerosis, asthma, airways inflammatory disease, tendonitis, and chronic inflammation in the brain. In another embodiment, the invention provides a compound of any one of embodiments 1 to 271 for use in the prevention of a disease or condition selected from rheumatoid arthritis, a chronic inflammatory bowel disease, multiple sclerosis, asthma, airways inflammatory disease, tendonitis, and chronic inflammation in the brain.

In another embodiment, the invention provides the use of a compound of any one of embodiments 1 to 271 for the preparation of a medicament for the treatment of chronic inflammation. In another embodiment, the invention provides the use of a compound of any one of embodiments 1 to 271 for the preparation of a medicament for the prevention of chronic inflammation. In another embodiment, the invention provides the use of a compound of any one of embodiments 1 to 271 for the preparation of a medicament for the treatment of a disease or condition selected from rheumatoid arthritis, a chronic inflammatory bowel disease, multiple sclerosis, asthma, airways inflammatory disease, tendonitis, and chronic inflammation in the brain. In a further embodiment, the invention provides the use of a compound of any one of embodiments 1 to 271 for the preparation of a medicament for the prevention of a disease or condition selected from rheumatoid arthritis, a chronic inflammatory bowel disease, multiple sclerosis, asthma, airways inflammatory disease, tendonitis, and chronic inflammation in the brain. In another embodiment, the invention provides the use of a compound of any one of embodiments 1 to 271 for the preparation of a medicament for the prevention of a disease or condition selected from rheumatoid arthritis, a chronic inflammatory bowel disease, multiple sclerosis, asthma, airways inflammatory disease, tendonitis, and chronic inflammation in the brain. In a further embodiment, the invention provides the use of a compound of any one of embodiments 1 to 271 for the preparation of a medicament for the prevention of a disease or condition selected from rheumatoid arthritis, a chronic inflammatory bowel disease, multiple sclerosis, asthma, airways inflammatory disease, tendonitis, and chronic inflammation in the brain.

In another embodiment, the invention provides a method of treatment comprising administering to a human a compound of any one of embodiments 1 to 271 so as to increase the activity or amount of HMOX1 in a subject. In a further embodiment, the invention provides for the use of a compound of any one of embodiments 1 to 271 for the preparation of a medicament for increasing the activity or amount of HMOX1 in a human.

In another embodiment, the invention provides a method of treatment comprising administering a compound of any one of embodiments 1 to 271 to a human, so as to treat a disease or condition selected from: cardiovascular disease including arteriosclerosis, peripheral vascular disease, thrombosis, ischemia-reperfusion events, congestive heart failure, primary and secondary pulmonary arterial hypertension and hypertension; renal diseases such as acute tubular necrosis; glomerulonephritis, including diabetic related complications including glomerular nephropathy and supportive care for dialysis including maintenance of arterial fistulas; pulmonary diseases including bronchitis, bronchiecstasis, chronic obstructive pulmonary disease, pulmonary edema, asthma, emphysema, sarcoidosis; liver disease including those leading to scarring and fibrosis such as cholestasis, hepatitis B and C infection, cirrhosis; autoimmune diseases and their complications including rheumatoid arthritis, ankylosing spondylosis, systemic lupus erthyamatosus, scleroderma and psoriasis; cerebral nerve degenerative diseases including Alzheimers disease, Parkinsons disease, ALS (amyotrophic lateral sclerosis) and multiple sclerosis; skin diseases; eye diseases including macular degeneration, cataracts, light retinopathy, and retinopathy of diabetes, prematurity; and cancer; supportive care for transplantation including graft viability and reduction of ischemic damage.

In another embodiment, the invention provides a compound of any one of embodiments 1 to 271 for use in the treatment of a disease or condition selected from: cardiovascular disease including arteriosclerosis, peripheral vascular disease, thrombosis, ischemia-reperfusion events, congestive heart failure, primary and secondary pulmonary arterial hypertension and hypertension; renal diseases such as acute tubular necrosis; glomerulonephritis, including diabetic related complications including glomerular nephropathy and supportive care for dialysis including maintenance of arterial fistulas; pulmonary diseases including bronchitis, bronchiecstasis, chronic obstructive pulmonary disease, pulmonary edema, asthma, emphysema, sarcoidosis; liver disease including those leading to scarring and fibrosis such as cholestasis, hepatitis B and C infection, cirrhosis; autoimmune diseases and their complications including rheumatoid arthritis, ankylosing spondylosis, systemic lupus erthyamatosus, scleroderma and psoriasis; cerebral nerve degenerative diseases including Alzheimers disease, Parkinsons disease, ALS (amyotrophic lateral sclerosis) and multiple sclerosis; skin diseases; eye diseases including macular degeneration, cataracts, light retinopathy, and retinopathy of diabetes, prematurity; and cancer; supportive care for transplantation including graft viability and reduction of ischemic damage.

In another embodiment, the invention provides a compound of any one of embodiments 1 to 271 for use in the prevention of a disease or condition selected from: cardiovascular disease including arteriosclerosis, peripheral vascular disease, thrombosis, ischemia-reperfusion events, congestive heart failure, primary and secondary pulmonary arterial hypertension and hypertension; renal diseases such as acute tubular necrosis; glomerulonephritis, including diabetic related complications including glomerular nephropathy and supportive care for dialysis including maintenance of arterial fistulas; pulmonary diseases including bronchitis, bronchiecstasis, chronic obstructive pulmonary disease, pulmonary edema, asthma, emphysema, sarcoidosis; liver disease including those leading to scarring and fibrosis such as cholestasis, hepatitis B and C infection, cirrhosis; autoimmune diseases and their complications including rheumatoid arthritis, ankylosing spondylosis, systemic lupus erthyamatosus, scleroderma and psoriasis; cerebral nerve degenerative diseases including Alzheimers disease, Parkinsons disease, ALS (amyotrophic lateral sclerosis) and multiple sclerosis; skin diseases; eye diseases including macular degeneration, cataracts, light retinopathy, and retinopathy of diabetes, prematurity; and cancer; supportive care for transplantation including graft viability and reduction of ischemic damage.

In another embodiment, the invention provides for the use of a compound of any one of embodiments 1 to 271 for the preparation of a medicament for the treatment of a disease or condition selected from: cardiovascular disease including arteriosclerosis, peripheral vascular disease, thrombosis, ischemia-reperfusion events, congestive heart failure, primary and secondary pulmonary arterial hypertension and hypertension; renal diseases such as acute tubular necrosis; glomerulonephritis, including diabetic related complications including glomerular nephropathy and supportive care for dialysis including maintenance of arterial fistulas; pulmonary diseases including bronchitis, bronchiecstasis, chronic obstructive pulmonary disease, pulmonary edema, asthma, emphysema, sarcoidosis; liver disease including those leading to scarring and fibrosis such as cholestasis, hepatitis B and C infection, cirrhosis; autoimmune diseases and their complications including rheumatoid arthritis, ankylosing spondylosis, systemic lupus erthyamatosus, scleroderma and psoriasis; cerebral nerve degenerative diseases including Alzheimers disease, Parkinsons disease, ALS (amyotrophic lateral sclerosis) and multiple sclerosis; skin diseases; eye diseases including macular degeneration, cataracts, light retinopathy, and retinopathy of diabetes, prematurity; and cancer; supportive care for transplantation including graft viability and reduction of ischemic damage.

In another embodiment, the invention provides for the use of a compound of any one of embodiments 1 to 271 for the preparation of a medicament for the prevention of a disease or condition selected from: cardiovascular disease including arteriosclerosis, peripheral vascular disease, thrombosis, ischemia-reperfusion events, congestive heart failure, primary and secondary pulmonary arterial hypertension and hypertension; renal diseases such as acute tubular necrosis; glomerulonephritis, including diabetic related complications including glomerular nephropathy and supportive care for dialysis including maintenance of arterial fistulas; pulmonary diseases including bronchitis, bronchiecstasis, chronic obstructive pulmonary disease, pulmonary edema, asthma, emphysema, sarcoidosis; liver disease including those leading to scarring and fibrosis such as cholestasis, hepatitis B and C infection, cirrhosis; autoimmune diseases and their complications including rheumatoid arthritis, ankylosing spondylosis, systemic lupus erthyamatosus, scleroderma and psoriasis; cerebral nerve degenerative diseases including Alzheimers disease, Parkinsons disease, ALS (amyotrophic lateral sclerosis) and multiple sclerosis; skin diseases; eye diseases including macular degeneration, cataracts, light retinopathy, and retinopathy of diabetes, prematurity; and cancer; supportive care for transplantation including graft viability and reduction of ischemic damage.

In each of the methods or uses described above, a compound of any of embodiments 1 to 271 may be administered to a subject as part of a pharmaceutically formulation, as described above.

EXAMPLES

The general procedures used in the methods to prepare the compounds of the present invention are described below.
General Experimental Section LC-MS data are obtained using gradient elution on a parallel MUX™ system, running four Waters® 1525 binary HPLC pumps, equipped with a Mux-UV 2488 multichannel UV-Vis detector (recording at 215 and 254 nM) and a Leap Technologies HTS PAL Auto sampler using a Sepax GP-C18, 4.6×50 mm; 5 micron particle-size column. In general, a three minute gradient is run from 25% B (97.5% acetonitrile, 2.5% water, 0.05% TFA) and 75% A (97.5% water, 2.5% acetonitrile, 0.05% TFA) to 100% B. The system is interfaced with a Waters Micromass ZQ mass spectrometer using electrospray ionization. MassLynx software is employed. All MS data were obtained in the positive mode unless otherwise noted. The reported m/z data are generally accurate within about ±1 for the M+ ion.

$^1$H NMR data were obtained on a Varian® Mercury 400 MHz spectrometer and chemical shifts were referenced using either the residual solvent proton signal (e.g., residual $CHCl_3$ in $CDCl_3$) or the TMS signal as an internal reference. Microwave heating procedures were used in some experiments and, in these cases, a Discover® microwave synthesis system (CEM, Matthews, N.C., USA) was used which included the use of pressurized glass reaction vessels at elevated temperatures.

All reagents and solvents including anhydrous solvents were commercially available and were used as received unless described otherwise. Any solutions of Grignard reagents and organolithium reagents were commercially available and were used as received and at the concentrations listed on their labels. Reactions are stirred using a magnetic stirring apparatus and magnetic stir bar in most cases. All reactions using air-sensitive reagents were run under inert gas. For reactions not heated using a microwave-generating apparatus, the reaction temperatures reported in the experimental section refer to the temperatures of an oil bath or cooling bath placed around a reaction vessel. For reactions performed using a microwave-generating apparatus, the temperatures refer to the temperatures reported by the microwave apparatus.

Abbreviations

Below are definitions of some common abbreviations that are used in the specification. The specification may also employ other abbreviations whose meanings are well known in the relevant art.

AcOH=acetic acid
DCM=dichloromethane
DIEA=diisopropylethylamine
DMAP=N,N'-dimethylamino pyridine
DME=1,2-dimethoxyethane
DMF=N,N'-dimethylformamide
DMSO=dimethylsulfoxide
DPPA=diphenylphosphoryl azide
EDC=1-ethyl-3-(3-dimethylaminopropyl)carbodiimide
EtOAc=ethyl acetate
EtOH=ethanol
$^1$H NMR=proton NMR analysis
HBTU=2-(1H-benzotriazol-1-yl)-1,1,3,3-tetramethyluronium hexafluorophosphate
HCl=hydrochloric acid
LC/MS=liquid chromatography-mass spectrometry analysis
MeOH=methanol
OAc=acetate
THF=tetrahydrofuran
thioCDI=1,1'-thiocarbonyldiimidazole
TLC=thin layer chromatography
rt or RT=room temperature
h=hour
min=minutes
M=molar concentration
N=normal concentration
uL=ul=microliters
mL=ml=milliliters
ug=micrograms
mg=milligrams
g=grams General Procedure A: Ipso substitution of o- or p-nitrohaloarene To a DMF solution of a nitrohaloarene would be added an amine or sodium alkoxide, and the reaction mixture would be stirred at room temperature for 16 h. It would be poured into water and extracted with ethyl acetate. The combined organic extracts would be washed with water, washed with brine, dried over sodium sulfate, filtered, and concentrated under vacuum to give the product, which would not be purified further and would be used directly in the next step.

General Procedure B: Reduction of Nitro Group to Amine

10% Pd/C would be added to a solution of the nitro compound in methanol. The resulting mixture would be stirred at room temperature under a $H_2$ atmosphere for 16 h. The contents would then be filtered through a pad of Celite or silica gel and the solid would be washed with portions of methanol. The filtrate and washings would be combined and evaporated to afford the corresponding amine, which would not be purified further and used directly in the next step.

General Procedure C: Formation of Aminobenzothiazoles

To a suspension of the aniline in acetic acid would be added potassium isothiocyanate and the reaction mixture was allowed to stir at room temperature for 10 min. A solution of bromine (1.5 mL in acetic acid (20 mL) would then be added over 20 min. The reaction mixture would be stirred at room temperature for 24 h then poured onto ice-cold water, made alkaline with 28% aqueous ammonium hydroxide and the resulting precipitate would be filtered, washed with water, and dried under reduced pressure to give the desired substituted aminobenzothiazoles. The product would be used in the next step without further purification.

General Procedure D: Thiourea Formation and its Conversion to Aminobenzimidazole 1,1'-Thiocarbonylimidazole would be added to a solution of amine in DMF (10 mL) and the reaction mixture would be stirred at 90-100° C. (1-24 h). To this reaction mixture at room temperature would be added EDC and stirred at 60° C. for 5 min. To this reaction mixture at room temperature would be added substituted phenylenediamine and would be stirred at 90° C. for 16 h. The reaction mixture would then be cooled to room temperature, poured into ice-cold water and the solid would be collected by filtration. The crude product thus obtained would be purified by trituration with DCM-methanol (9:1).

General Procedure E: Hydrolysis of Benzoate Ester

A solution of LiOH in water would be added to a solution of ester in 1:1 THF/MeOH and the resulting mixture would be stirred at 60° C. for 16 h. After completion of the reaction, the mixture would be concentrated under vacuum. The pH of the resulting suspension would be adjusted by the dropwise addition of 6 N HCl to pH ~3 and the precipitate would be collected by filtration, washed with water and dried under vacuum. The desired carboxylic acid would be used without purification.

General Procedure F: Amide Formation Using HBTU as Coupling Reagent

To a solution of a carboxylic acid in dry DMF (5-10 mL) would be added DIEA followed by HBTU and the reaction mixture was stirred at room temperature for 30 min. An amine would then be added, and the reaction would be stirred at room temperature for 16 h. The contents would be diluted with ice-water and the product would be precipitated. The pure product would be isolated after filtration either with subsequent washings with water and DCM/Methanol or through silica gel chromatography using hexanes/ethyl acetate (from 80:20 to 60:40) as an eluent system.

General Procedure G: Alkylnitrile Reduction

Lithium aluminum hydride would be suspended in dry ether (50 mL) and cooled to 0° C. under a nitrogen atmosphere. The nitrile in dry ether (12.5 mL) would be added dropwise, and the reaction mixture would be stirred overnight at room temperature. With cooling and vigorous stirring, water (3 mL), sodium hydroxide (20%, 3 mL), and water (10 mL) would be added. The ether solution would be decanted and the residue would be washed with ether (2×12.5 mL). The ether portions would be combined, dried over anhydrous sodium sulfate, filtered, and concentrated in vacuo.

General Procedure H: Fluorination of an Alcohol

To a DCM suspension of the alcohol, cooled to 0° C., would be added bis(2-methoxyethyl)aminosulfur trifluoride dropwise. The reaction would be allowed to return to room temperature and stirred for 6 h. It would then be cooled to 0° C., and water (3 mL) would be added dropwise. The aqueous phase would be extracted with DCM (2×3 mL). The combined organics would be dried over anhydrous sodium sulfate, filtered, and concentrated in vacuo.

General Procedure I: Imidazole Formation

Step 1: The arylnitrile (product which was obtained following the general procedure D) would be dissolved in absolute ethanol (25 mL) and to this solution hydrochloric acid gas would carefully be cannulated at −10° C. within 30 min. The reaction mixture would be sealed and stirred at room temperature for 16 h to give aryl ethylimidate. This crude product would then be used in next step without further purification.

Step 2: To a solution of aryl ethylimidate in EtOH (10 mL) would be added aminoacetaldehyde diethylacetal and AcOH. This mixture would then be heated to 60° C. and stirred for 2 h. The reaction mixture would then be cooled down and concentrated under vacuum. This crude material would again be dissolved in EtOH (10 ml) and hydrochloric acid (0.2 mL, 6N in water) added to the mixture and refluxed at 85° C. for 16 h. After completion of the reaction, the mixture would then be concentrated under vacuum and basified with triethylamine and purified with silica gel chromatography using DCM:MeOH (95:5 to 80:20) to give desired imidazoles. (53-76% yields).

General Procedure J: Triazole Formation

Method A: To a solution of benzamide in toluene (10 mL) would be added N,N-dimethylformamide diethylacetal and heated to 110° C. and refluxed for 3 h. The reaction mixture would then be cooled down and concentrated under vacuum. This residue would then be dissolved in AcOH (2 mL) and hydrazine (1.0 M solution in THF) was added, and the solution would be heated to 100° C. and stirred at this temperature for 4 h. After completion of the reaction, the mixture would be concentrated and poured into cold saturated sodium bicarbonate solution (25 mL) and extracted with ethyl acetate (2×25 mL). The combined organic extracts would be washed with water (25 mL) and brine (25 mL), dried over sodium sulfate, and concentrated under vacuum. This residue would then be purified with silica gel chromatography using DCM:ethyl acetate (70:30 to 50:50) as an eluent system to give the desired triazoles (58-66% yields).

Method B: To a solution of aryl ethylimidate in EtOH (10 mL) would be added formic or acetic hydrazide. The reaction mixture would then be refluxed for 4 h. The mixture would be concentrated under vacuum and purified with silica gel chromatography using DCM:ethyl acetate (70:30 to 40:60) to give desired triazoles (47-61% yields).

General Procedure K: Methyl Ester Formation

To a methanol solution of the benzoic acid cooled to 0° C. using an ice bath, would be added thionyl chloride dropwise. The reaction mixture would then be heated at 50° C. for 5 h. The solvent would be evaporated, and ethyl acetate and saturated aqueous sodium bicarbonate would be added. The phases would be separated, and the aqueous phase would be extracted twice with ethyl acetate. The combined organics would be dried over sodium sulfate and then filtered. The solvent would be evaporated to give the pure methyl ester.

General Procedure L: Removal of t-Boc Group to Give Arylamines

A solution of aryl amino-tert-butylester in DCM (10 mL) would be added to hydrochloric acid (3 eq., and 4.0 N solution in dioxane) at room temperature and stirred for 3 h. After completion of the reaction, the mixture would be concentrated under vacuum and the residue would be washed with ether (10 ml) to remove unwanted organic impurities, and then triturated with DCM:hexanes (2:8) to give the desired amines as hydrochloric acid salts (77-85% yields).

General Procedure M: Formation of Alkylsulfones from Alkylsulfides

A solution of alkylsulfide in DCM would be added peracetic acid (2 eq., 32 wt % solution in acetic acid) at −10° C. Then the reaction mixture would be stirred at room temperature for 2-6 h. After completion of the reaction, the mixture would be poured into saturated sodium bicarbonate solution (25 mL) and extracted with DCM (25 mL), dried over sodium sulfate and concentrated under vacuum. The residue would then be triturated with DCM:hexanes (2:8) to give the desired sulfones. If necessary, the residue would be purified with silica gel chromatography using DCM:ethyl acetate (80:20 to 60:40) as eluent system to provide the desired sulfones (88-96% yields).

General Procedure N: Amide Formation Using DPPA as Coupling Reagent

To a solution of a carboxylic acid in dry DMF would be added DIEA followed by DPPA and the reaction mixture would be stirred at room temperature for 30 min. The amine would then be added, and the reaction would be stirred at room temperature for 2 h. The contents would be diluted with ice-water and the product would be precipitated. The pure product would be isolated after filtration either with subsequent washings with water and DCM/Methanol or through silica gel chromatography using hexanes/ethyl acetate as eluent.

General Procedure O: Fmoc Deprotection

To a DMF solution of fluroenylmethyl carbamate of an amine at room temperature would be added 20% (v/v) piperidine. The reaction mixture would then be stirred for 2 h. The reaction mixture would be added to ethyl acetate and saturated aqueous sodium bicarbonate. The phases would be separated, and the aqueous phase would be extracted twice with ethyl acetate. The combined organics would be dried over sodium sulfate and then filtered. The solvent would be evaporated and crude compound would be purified by flash chromatography using DCM:methanol as eluent.

General Procedure P: Reductive Amination

To a DCM solution of amine at room temperature would be added aldehyde and sodium triacetoxyborohydride. The reaction mixture would then be stirred for 2-8 h. The reaction would be added to DCM and saturated aqueous sodium bicarbonate. The phases would be separated, and the aqueous phase would be extracted twice with DCM. The combined organics would be dried over sodium sulfate and then filtered. The solvent would be evaporated and crude compound would be purified by flash chromatography using DCM:methanol as eluent.

General Procedure Q: Sulfonamide Formation

To a DCM solution of amine at 0° C. would be added triethylamine followed by dropwise addition of sulfonyl chloride. The reaction mixture would then be stirred at 0° C. for 20 min and then at room temperature for 30 min. The reaction would be added to DCM and saturated aqueous sodium bicarbonate. The phases would be separated, and the aqueous phase would be extracted twice with DCM. The combined organics would be dried over sodium sulfate and then filtered. The solvent would be evaporated and crude compound would be purified by flash chromatography using DCM:methanol as eluent.

General Procedure R: Amide Formation

To a DCM solution of amine at 0° C. would be added triethylamine followed by dropwise addition of acyl chloride. The reaction mixture would then be stirred at 0° C. for 20 min and then at room temperature for 30 min. The reaction would be added to DCM and saturated aqueous sodium bicarbonate. The phases would be separated, and the aqueous phase would be extracted twice with DCM. The combined organics would be dried over sodium sulfate and then filtered. The solvent would be evaporated and crude compound would be purified by flash chromatography using DCM:methanol as eluent.

General Procedure S: Alkylation of Alcohol/Amine

To a dioxane or DMF solution of alcohol/amine at room temperature would be added dibenzyl-(2-chloro-ethyl)-amine followed by 50% (w/w) aqueous KOH solution or DIEA and catalytic amount of tetrabutylammonium bromide. The reaction mixture would be stirred at 55° C. for 8 h. The reaction would be added to saturated sodium chloride solution and extracted with ethyl acetate. The phases would be separated, and the combined organics would be dried over sodium sulfate and then filtered. The solvent would be evaporated and crude compound would be purified by flash chromatography using hexane:ethyl acetate as eluent.

General Procedure T: Debenzylation of Amine

To a methanol solution of dibenzyl amine at room temperature would be added Pd—C 20% by weight. The reaction mixture would be subjected to hydrogen atmosphere at 60 PSI at room temperature for 12-24 h. The reaction mixture would be filtered through celite and washed with methanol. The filtrate would be evaporated to isolate pure compound.

General Procedure U: Conversion of Alkyl Halide to Azide

To a solution of alkyl bromide in dry DMF would be added sodium azide, and the reaction mixture would be stirred at room temperature for 16 h. After completion of the reaction, the contents would be diluted with ethyl acetate and washed with water, dried over anhydrous sodium sulfate, filtered, and concentrated in vacuo.

General Procedure V: Conversion of Alcohol to Tosylate

To a solution of alcohol in pyridine would be added DMAP, and the reaction mixture would be cooled to 0° C. p-Toluenesulfonyl chloride would be added, and the reaction mixture would continue to stir at 0° C. for 3 h. After completion of the reaction, the contents would be diluted with ethyl acetate and washed with 1 N HCl, with saturated aqueous sodium bicarbonate, and then with water. It would then be dried over anhydrous sodium sulfate, filtered, and concentrated in vacuo.

General Procedure W: Reaction of Tosylate and Alcohol

To a solution of alcohol and tosylate in toluene would be added a 50% aqueous NaOH solution and tetrabutylammonium hydrogen sulfate. The reaction mixture would be stirred at 80° C. for 3 h then stirred at 50° C. for 16 h. After completion of the reaction, an aqueous ammonium chloride solution would be added, and the reaction mixture would be further diluted with ethyl acetate. The phases would be separated, and the aqueous phase would be extracted with ethyl acetate. The combined organic phases would be dried over anhydrous sodium sulfate, filtered, and concentrated in vacuo.

General Procedure X: Epoxide Opening with an Alcohol

To a solution of alcohol and epoxide in dry DMF would be added potassium hydroxide, and the reaction mixture would be stirred at room temperature for 16 h then at 60° C. for another 24 h. After completion of the reaction, the contents would be concentrated in vacuo. The pure product would be isolated through silica gel chromatography.

Example 1

1-Methyl-2-(6-trifluoromethoxy-benzothiazol-2-ylamino)-1H-benzoimidazole-5-carboxylic acid methyl amide 4-Methylamino-3-nitro-benzoic acid (825 mg) was prepared by following General Procedure A starting from 4-fluoro-3-nitro-benzoic acid (1.0 g) and methylamine (2 M in THF, 8.1 mL) in THF. The crude product was used in the next step without further purification.

Synthesis of N-methyl-4-methylamino-3-nitro-benzamide (375 mg) was prepared by following General Procedure F starting from 4-methylamino-3-nitro-benzoic acid (500 mg), HBTU (1.45 g), DIEA (0.89 mL), and methylamine (2 M in THF, 8.1 mL). Purification was carried out using silica gel chromatography using hexanes/ethyl acetate as an eluent.

3-Amino-N-methyl-4-methylamino-benzamide (460 mg) was prepared by following General Procedure B starting from N-methyl-4-methylamino-3-nitro-benzamide (535 mg) and Pd/C (10% by weight, 54 mg). The crude product was used in the next step without further purification.

1-Methyl-2-(6-trifluoromethoxy-benzothiazol-2-ylamino)-1H-benzoimidazole-5-carboxylic acid methyl amide (74 mg) was prepared by following General Procedure D starting from 3-amino-N-methyl-4-methylamino-benzamide (460 mg), 2-amino-6-(trifluoromethoxy)benzothiazole (499 mg), 1,1'-thiocarbonyl-diimidazole (454 mg), and EDC (611 mg). LC/MS: m/z 423.0. $^1$H NMR (DMSO-$d_6$, 400 MHz): δ 12.39 (bs, 1H), 8.42 (s, 1H), 8.09 (s, 1H), 7.93 (s, 1H), 7.75 (d, 2H), 7.50 (d, 1H), 7.36 (d, 1H), 3.68 (bs, 3H), 2.81 (d, 3H).

Example 2

1-Methyl-2-(6-trifluoromethoxy-benzothiazol-2-ylamino)-1H-benzoimidazole-5-carboxylic acid methyl ester 4-Methylamino-3-nitro-benzoic acid methyl ester (822 mg) was prepared by following General Procedure A starting from methyl 4-chloro-3-nitrobenzoate (1.0 g) and methylamine (2 M in THF, 6.95 mL) in DMF. The crude product was used in the next step without further purification.

3-amino-4-methylamino-benzoic acid methyl ester (677 mg) was prepared by following General Procedure B starting from 4-methylamino-3-nitro-benzoic acid methyl ester (822 mg) and Pd/C (10% by weight, 82 mg). The crude product was used in the next step without further purification.

1-Methyl-2-(6-trifluoromethoxy-benzothiazol-2-ylamino)-1H-benzoimidazole-5-carboxylic acid methyl ester (1.47 g) was prepared by following General Procedure D starting from 3-amino-4-methylamino-benzoic acid methyl ester (1.5 g), 2-amino-6-(trifluoromethoxy)benzothiazole (1.62 g), 1,1'-thiocarbonyl-diimidazole (1.48 g), and EDC (1.99 g). LC/MS: m/z 423.8. $^1$H NMR (DMSO-$d_6$, 400 MHz): δ 8.20 (s, 1H), 7.92 (s, 1H), 7.85 (bs, 1H), 7.78-7.63 (m, 1H), 7.51 (d, 1H), 7.35 (d, 2H), 3.86 (s, 3H), 3.63 (bs, 3H).

Example 3

1-Methyl-2-(6-trifluoromethoxy-benzothiazol-2-ylamino)-1H-benzoimidazole-5-carboxylic acid 1-Methyl-2-(6-trifluoromethoxy-benzothiazol-2-ylamino)-1H-benzoimidazole-5-carboxylic acid (185 mg) was prepared by following General Procedure E starting from 1-methyl-2-(6-trifluoromethoxy-benzothiazol-2-ylamino)-1H-benzoimidazole-5-carboxylic acid methyl ester (200 mg) and lithium hydroxide (80 mg). LC/MS: m/z 409.9. $^1$H NMR (DMSO-$d_6$, 400 MHz): δ 8.16 (s, 1H), 7.95 (s, 1H), 7.86 (d, 1H), 7.78-7.61 (m, 2H), 7.51 (d, 1H), 7.37 (d, 1H), 3.67 (s, 3H), —COO$\underline{H}$ proton signal was not observed.

Example 4

1-Methyl-2-(6-trifluoromethoxy-benzothiazol-2-ylamino)-1H-benzoimidazole-5-carboxylic acid (2-ethoxy-ethyl)-amide 1-Methyl-2-(6-trifluoromethoxy-benzothiazol-2-ylamino)-1H-benzoimidazole-5-carboxylic acid (2-ethoxyethyl)-amide (27 mg) was prepared by following General Procedure N starting from 1-methyl-2-(6-trifluoromethoxy-benzothiazol-2-ylamino)-1H-benzoimidazole-5-carboxylic acid (90 mg), 2-ethoxyethylamine (20 mg), DPPA (61 mg), and DIEA (28 mg). LC/MS: m/z 481.0. $^1$H NMR (DMSO-$d_6$, 400 MHz): δ 12.37 (bs, 1H), 8.47 (s, 1H), 8.07 (s, 1H), 7.90 (s, 1H), 7.76 (d, 1H), 7.71 (d, 1H), 7.47 (d, 1H), 7.35 (s, 1H), 3.62 (bs, 3H), 3.54-3.37 (m, 6H), 1.11 (t, 3H).

Example 5

1-Methyl-2-(6-trifluoromethoxy-benzothiazol-2-ylamino)-1H-benzoimidazole-5-carboxylic acid cyclopropylmethyl-amide 1-Methyl-2-(6-trifluoromethoxy-benzothiazol-2-ylamino)-1H-benzoimidazole-5-carboxylic acid cyclopropylmethyl-amide (24 mg) was prepared by following General Procedure N starting from 1-methyl-2-(6-trifluoromethoxy-benzothiazol-2-ylamino)-1H-benzoimidazole-5-carboxylic acid (90 mg), cyclopropanemethylamine (16 mg), DPPA (48 uL), and DIEA (39 uL). LC/MS: m/z 462.9. $^1$H NMR (DMSO-$d_6$, 400 MHz): δ 12.16 (bs, 1H), 8.30 (s, 1H), 7.87 (s, 1H), 7.68 (s, 1H), 7.55 (d, 1H), 7.50 (d, 1H), 7.26 (d, 1H), 7.12 (d, 1H), 3.40 (bs, 3H), 2.94 (t, 2H), 0.89-0.78 (m, 1H), 0.21 (d, 2H), 0.02 (d, 2H).

Example 6

1-Methyl-2-(6-trifluoromethoxy-benzothiazol-2-ylamino)-1H-benzoimidazole-5-carboxylic acid ethylamide 1-Methyl-2-(6-trifluoromethoxy-benzothiazol-2-ylamino)-1H-benzoimidazole-5-carboxylic acid ethylamide (17 mg) was prepared by following General Procedure N starting from 1-methyl-2-(6-trifluoromethoxy-benzothiazol-2-ylamino)-1H-benzoimidazole-5-carboxylic acid (100 mg), ethylamine (2 M in THF, 123 uL), DPPA (53 uL), and DIEA (43 uL). LC/MS: 436.9 m/z (M+1)$^+$. $^1$H NMR (DMSO-$d_6$, 400 MHz): δ 8.43 (s, 1H), 8.07 (s, 1H), 7.89 (s, 1H), 7.79-7.65 (m, 2H), 7.46 (d, 1H), 7.35 (s, 1H), 3.62 (bs, 3H), 3.30-3.23 (m, 2H), 1.13 (t, 3H), —NH proton signal was not observed.

Example 7

[1-Methyl-2-(6-trifluoromethoxy-benzothiazol-2-ylamino)-1H-benzoimidazol-5-yl]-pyrrolidin-1-yl-methanone

[1-Methyl-2-(6-trifluoromethoxy-benzothiazol-2-ylamino)-1H-benzoimidazol-5-yl]-pyrrolidin-1-yl-methanone (34 mg) was prepared by following General Procedure N starting from 1-methyl-2-(6-trifluoromethoxy-benzothiazol-2-ylamino)-1H-benzoimidazole-5-carboxylic acid (100 mg), pyrrolidine (17 mg), DPPA (53 uL), and DIEA (43 uL). LC/MS: m/z 462.9. $^1$H NMR (DMSO-$d_6$, 400 MHz): δ 12.28 (bs, 1H), 7.90 (s, 1H), 7.80-7.56 (m, 2H), 7.42 (s, 2H), 7.33 (d, 1H), 3.63 (s, 3H), 3.55-3.33 (m, 4H), 1.95-1.74 (m, 4H).

Example 8

1-Methyl-2-(6-trifluoromethoxy-benzothiazol-2-ylamino)-1H-benzoimidazole-5-carboxylic acid (2-methoxy-ethyl)-amide 1-Methyl-2-(6-trifluoromethoxy-benzothiazol-2-ylamino)-1H-benzo-imidazole-5-carboxylic acid (2-methoxy-ethyl)-amide (22 mg) was prepared by following General Procedure N starting from 1-methyl-2-(6-trifluoromethoxy-benzothiazol-2-ylamino)-1H-benzoimidazole-5-carboxylic acid (100 mg), 2-methoxy-ethylamine (18 mg), DPPA (53 uL), and DIEA (43 uL). LC/MS: m/z 466.9. $^1$H NMR (DMSO-$d_6$, 400 MHz): δ 12.36 (bs, 1H), 8.47 (s, 1H), 8.08 (s, 1H), 7.89 (s, 1H), 7.76 (s, 1H), 7.71 (d, 1H), 7.47 (d, 1H), 7.34 (d, 1H), 3.62 (bs, 3H), 3.53-3.38 (m, 4H), 3.27 (s, 3H).

Example 9

1-Methyl-2-(6-trifluoromethoxy-benzothiazol-2-ylamino)-1H-benzoimidazole-5-carboxylic acid (2-fluoro-ethyl)-amide 1-Methyl-2-(6-trifluoromethoxy-benzothiazol-2-ylamino)-1H-benzoimidazole-5-carboxylic acid (2-fluoro-ethyl)-amide (31 mg) was prepared by following General Procedure N starting from 1-methyl-2-(6-trifluoromethoxy-benzothiazol-2-ylamino)-1H-benzoimidazole-5-carboxylic acid (100 mg), 2-fluoroethylamine hydrochloride (24 mg), DPPA (53 uL), and DIEA (43 uL). LC/MS: m/z 454.8. $^1$H NMR (DMSO-$d_6$, 400 MHz): δ 12.37 (bs, 1H), 8.67 (s, 1H), 8.10 (s, 1H), 7.90 (s, 1H), 7.79 (d, 1H), 7.71 (d, 1H), 7.49 (d, 1H), 7.34 (d, 1H), 4.61 (t, 1H), 4.49 (t, 1H), 3.62 (bs, 3H), 3.58-3.48 (m, 2H).

Example 10

1-Methyl-2-(6-trifluoromethoxy-benzothiazol-2-ylamino)-1H-benzoimidazole-5-carboxylic acid (2-hydroxy-ethyl)-amide 1-Methyl-2-(6-trifluoromethoxy-benzothiazol-2-ylamino)-1H-benzoimidazole-5-carboxylic acid (2-hydroxy-ethyl)-amide (27 mg) was prepared by following General Procedure N starting from 1-methyl-2-(6-trifluoromethoxy-benzothiazol-2-ylamino)-1H-benzoimidazole-5-carboxylic acid (100 mg), ethanolamine (15 mg), DPPA (53 uL), and DIEA (43 uL). LC/MS: m/z 452.9. $^1$H NMR (DMSO-$d_6$, 400 MHz): δ 8.37 (s, 1H), 8.07 (s, 1H), 7.91 (s, 1H), 7.81-7.56 (m, 2H), 7.46 (d, 1H), 7.34 (d, 1H), 4.72 (s, 1H), 3.64 (s, 3H), 3.58-3.48 (m, 2H), 3.40-3.32 (m, 2H), —NH proton signal was not observed.

Example 11

1-Methyl-2-(6-trifluoromethoxy-benzothiazol-2-ylamino)-1H-benzoimidazole-5-carboxylic acid (3-pyrazol-1-yl-propyl)-amide 1-Methyl-2-(6-trifluoromethoxy-benzothiazol-2-ylamino)-1H-benzoimidazole-5-carboxylic acid (3-pyrazol-1-yl-propyl)-amide (99 mg) was prepared by following General Procedure F starting from 1-methyl-2-(6-trifluoromethoxy-benzothiazol-2-ylamino)-1H-benzoimidazole-5-carboxylic acid (100 mg), 3-(1H-pyrazol-1-yl)propan-1-amine dihydrochloride (50 mg), HBTU (111 mg), and DIEA (64 uL). LC/MS: m/z 517.0. $^1$H NMR (DMSO-$d_6$, 400 MHz): δ 12.36 (bs, 1H), 8.48 (s, 1H), 8.07 (s, 1H), 7.90 (s, 1H), 7.81-7.63 (m, 3H), 7.47 (d, 1H), 7.43 (d, 1H), 7.35 (d, 1H), 6.22 (t, 1H), 4.18 (t, 2H), 3.62 (bs, 3H), 3.26 (q, 2H), 2.09-1.97 (m, 2H).

Example 12

1-Methyl-2-(6-trifluoromethoxy-benzothiazol-2-ylamino)-1H-benzoimidazole-5-carboxylic acid propylamide 1-Methyl-2-(6-trifluoromethoxy-benzothiazol-2-ylamino)-1H-benzoimidazole-5-carboxylic acid propylamide (86 mg) was prepared by following General Procedure F starting from 1-methyl-2-(6-trifluoromethoxy-benzothiazol-2-ylamino)-1H-benzo-imidazole-5-carboxylic acid (100 mg), propylamine (16 mg), HBTU (111 mg), and DIEA (64 uL). LC/MS: m/z 450.9. $^1$H NMR (DMSO-$d_6$, 400 MHz): δ 12.38 (bs, 1H), 8.42 (s, 1H), 8.07 (s, 1H), 7.90 (s, 1H), 7.75 (d, 1H), 7.72 (d, 1H), 7.46 (d, 1H), 7.34 (d, 1H), 3.62 (bs, 3H), 3.22 (q, 2H), 1.60-1.45 (m, 2H), 0.90 (t, 3H).

Example 13

1-Methyl-2-(6-trifluoromethoxy-benzothiazol-2-ylamino)-1H-benzoimidazole-5-carboxylic acid (3-hydroxy-propyl)-amide 1-Methyl-2-(6-trifluoromethoxy-benzothiazol-2-ylamino)-1H-benzoimidazole-5-carboxylic acid (3-hydroxy-propyl)-amide (98 mg) was prepared by following General Procedure F starting from 1-methyl-2-(6-trifluoromethoxy-benzothiazol-2-ylamino)-1H-benzoimidazole-5-carboxylic acid (100 mg), 3-amino-1-propanol (20 mg), HBTU (111 mg), and DIEA (64 uL). LC/MS: m/z 466.8. $^1$H NMR (DMSO-$d_6$, 400 MHz): δ 12.40 (bs, 1H), 8.39 (s, 1H), 8.05 (s, 1H), 7.90 (s, 1H), 7.78-7.60 (m, 2H), 7.45 (d, 1H), 7.34 (d, 1H), 4.48 (s, 1H), 3.63 (bs, 3H), 3.48 (q, 2H), 3.38-3.30 (m, 2H), 1.76-1.64 (m, 2H).

Example 14

1-Methyl-2-(6-trifluoromethoxy-benzothiazol-2-ylamino)-1H-benzoimidazole-5-carboxylic acid (3-ethoxy-propyl)-amide 1-Methyl-2-(6-trifluoromethoxy-benzothiazol-2-ylamino)-1H-benzoimidazole-5-carboxylic acid (3-ethoxy-propyl)-amide (97 mg) was prepared by following General Procedure F starting from 1-methyl-2-(6-trifluoromethoxy-benzothiazol-2-ylamino)-1H-benzoimidazole-5-carboxylic acid (100 mg), 3-ethoxy-propylamine (28 mg), HBTU (111 mg), and DIEA (64 uL). LC/MS: m/z 494.9. $^1$H NMR (DMSO-$d_6$, 400 MHz): δ 12.36 (bs, 1H), 8.41 (s, 1H), 8.06 (s, 1H), 7.89 (s, 1H), 7.78-7.64 (m, 2H), 7.46 (d, 1H), 7.34 (d, 1H), 3.62 (bs, 3H), 3.45-3.37 (m, 4H), 3.36-3.31 (m, 2H), 1.83-1.70 (m, 2H), 1.10 (t, 3H).

Example 15

1-Methyl-2-(6-trifluoromethoxy-benzothiazol-2-ylamino)-1H-benzoimidazole-5-carboxylic acid morpholin-4-ylamide 1-Methyl-2-(6-trifluoromethoxy-benzothiazol-2-ylamino)-1H-benzoimidazole-5-carboxylic acid morpholin-4-ylamide (100 mg) was prepared by following General Procedure F starting from 1-methyl-2-(6-trifluoromethoxy-benzothiazol-2-ylamino)-1H-benzoimidazole-5-carboxylic acid (100 mg), 4-aminomorpholine (28 mg), HBTU (111 mg), and DIEA (64 uL). LC/MS: m/z 493.9. $^1$H NMR (DMSO-$d_6$, 400 MHz): δ 12.40 (bs, 1H), 9.49 (s, 1H), 8.02 (s, 1H), 7.90 (s, 1H), 7.78-7.59 (m, 2H), 7.47 (d, 1H), 7.34 (d, 1H), 3.78-3.56 (m, 7H), 2.93-2.84 (m, 4H).

Example 16

1-Methyl-2-(6-trifluoromethoxy-benzothiazol-2-ylamino)-1H-benzoimidazole-5-carboxylic acid (2,2,2-trifluoro-ethyl)-amide 1-Methyl-2-(6-trifluoromethoxy-benzothiazol-2-ylamino)-1H-benzoimidazole-5-carboxylic acid (2,2,2-trifluoro-ethyl)-amide (102 mg) was prepared by following General Procedure F starting from 1-methyl-2-(6-trifluoromethoxy-benzothiazol-2-ylamino)-1H-benzoimidazole-5-carboxylic acid (100 mg), 2,2,2-trifluoroethylamine (27 mg), HBTU (111 mg), and DIEA (64 uL). LC/MS: m/z 490.9. $^1$H NMR (DMSO-$d_6$, 400 MHz): δ 12.40 (bs, 1H), 9.05 (s, 1H), 8.12 (s, 1H), 7.90 (s, 1H), 7.81 (d, 1H), 7.72 (d, 1H), 7.51 (d, 1H), 7.34 (d, 1H), 4.18-4.01 (m, 2H), 3.62 (bs, 3H).

Example 17

1-Methyl-2-(6-trifluoromethoxy-benzothiazol-2-ylamino)-1H-benzoimidazole-5-carboxylic acid (tetrahydro-pyran-4-ylmethyl)-amide 1-Methyl-2-(6-trifluoromethoxy-benzothiazol-2-ylamino)-1H-benzoimidazole-5-carboxylic acid (tetrahydro-pyran-4-ylmethyl)-amide (91 mg) was prepared by following General Procedure F starting from 1-methyl-2-(6-trifluoromethoxy-benzo-thiazol-2-ylamino)-1H-benzoimidazole-5-carboxylic acid (100 mg), 4-amino-methyltetrahydropyran hydrochloride (41 mg), HBTU (111 mg), and DIEA (64 uL). LC/MS: m/z 507.0. $^1$H NMR (DMSO-$d_6$, 400 MHz): δ 8.47 (s, 1H), 8.08 (s, 1H), 7.91 (s, 1H), 7.77 (d, 1H), 7.73 (d, 1H), 7.48 (d, 1H), 7.35 (d, 1H), 3.86 (d, 2H), 3.63 (bs, 3H), 3.28 (t, 2H), 3.18 (t, 2H), 1.91-1.62 (m, 1H), 3.28 (d, 2H), 1.30-1.14 (m, 2H), —NH proton signal was not observed.

Example 18

1-Methyl-2-(6-trifluoromethoxy-benzothiazol-2-ylamino)-1H-benzoimidazole-5-carboxylic acid (tetrahydro-furan-2-ylmethyl)-amide 1-Methyl-2-(6-trifluoromethoxy-benzothiazol-2-ylamino)-1H-benzoimidazole-5-carboxylic acid (tetrahydro-furan-2-ylmethyl)-amide (73 mg) was prepared by following General Procedure F starting from 1-methyl-2-(6-trifluoromethoxy-benzo-thiazol-2-ylamino)-1H-benzoimidazole-5-carboxylic acid (100 mg), tetrahydrofurfurylamine (27 mg), HBTU (111 mg), and DIEA (64 uL). LC/MS: m/z 492.9. $^1$H NMR (DMSO-$d_6$, 400 MHz): δ 12.37 (bs, 1H), 8.47 (s, 1H), 8.07 (s, 1H), 7.90 (s, 1H), 7.77 (d, 1H), 7.72 (d, 1H), 7.47 (d, 1H), 7.34 (d, 1H), 4.03-3.94 (m, 1H), 3.78 (q, 1H), 3.74-3.57 (m, 5H), 3.38-3.31 (m, 1H), 2.00-1.73 (m, 3H), 1.68-1.53 (m, 1H).

Example 19

1-Methyl-2-(6-trifluoromethoxy-benzothiazol-2-ylamino)-1H-benzoimidazole-5-carboxylic acid (3-methoxy-propyl)-amide 1-Methyl-2-(6-trifluoromethoxy-benzothiazol-2-ylamino)-1H-benzoimidazole-5-carboxylic acid (3-methoxy-propyl)-amide (91 mg) was prepared by following General Procedure F starting from 1-methyl-2-(6-trifluoromethoxy-benzothiazol-2-ylamino)-1H-benzoimidazole-5-carboxylic acid (100 mg), 3-methoxy-propylamine (24 mg), HBTU (111 mg), and DIEA (64 uL). LC/MS: m/z 480.9. $^1$H NMR (DMSO-d$_6$, 400 MHz): δ 12.37 (bs, 1H), 8.42 (s, 1H), 8.06 (s, 1H), 7.90 (s, 1H), 7.78-7.63 (m, 2H), 7.46 (d, 1H), 7.34 (d, 1H), 3.62 (bs, 3H), 3.38 (t, 2H), 3.34-3.27 (m, 2H), 3.24 (s, 3H), 1.82-1.71 (m, 2H).

Example 20

1-Methyl-2-(6-trifluoromethoxy-benzothiazol-2-ylamino)-1H-benzoimidazole-5-carboxylic acid (2-methoxy-1-methyl-ethyl)-amide 1-Methyl-2-(6-trifluoromethoxy-benzothiazol-2-ylamino)-1H-benzoimidazole-5-carboxylic acid (2-methoxy-1-methyl-ethyl)-amide (86 mg) was prepared by following General Procedure F starting from 1-methyl-2-(6-trifluoromethoxy-benzo-thiazol-2-ylamino)-1H-benzoimidazole-5-carboxylic acid (100 mg), 1-methoxy-2-propylamine (24 mg), HBTU (111 mg), and DIEA (64 uL). LC/MS: m/z 480.9. $^1$H NMR (DMSO-d$_6$, 400 MHz): δ 12.39 (bs, 1H), 8.18 (s, 1H), 8.07 (s, 1H), 7.90 (s, 1H), 7.76 (d, 1H), 7.71 (d, 1H), 7.46 (d, 1H), 7.34 (d, 1H), 4.30-4.15 (m, 1H), 3.62 (bs, 3H), 3.42 (dd, 1H), 3.29 (dd, 1H), 3.27 (s, 3H), 1.14 (d, 3H).

Example 21

1-Methyl-2-(6-trifluoromethoxy-benzothiazol-2-ylamino)-1H-benzoimidazole-5-carboxylic acid (2-hydroxy-propyl)-amide 1-Methyl-2-(6-trifluoromethoxy-benzothiazol-2-ylamino)-1H-benzoimidazole-5-carboxylic acid (2-hydroxy-propyl)-amide (67 mg) was prepared by following General Procedure F starting from 1-methyl-2-(6-trifluoromethoxy-benzothiazol-2-ylamino)-1H-benzoimidazole-5-carboxylic acid (100 mg), 1-amino-2-propanol (20 mg), HBTU (111 mg), and DIEA (64 uL). LC/MS: m/z 466.9. $^1$H NMR (DMSO-d$_6$, 400 MHz): δ 12.40 (bs, 1H), 8.35 (s, 1H), 8.09 (s, 1H), 7.92 (s, 1H), 7.86-7.66 (m, 2H), 7.48 (d, 1H), 7.36 (d, 1H), 4.77 (d, 1H), 3.87-3.77 (m, 1H), 3.64 (bs, 3H), 3.29-3.17 (m, 2H), 1.09 (d, 3H).

Example 22

1-Methyl-2-(6-trifluoromethoxy-benzothiazol-2-ylamino)-1H-benzoimidazole-5-carboxylic acid (2-methoxy-2-methyl-propyl)-amide 1-Methyl-2-(6-trifluoromethoxy-benzothiazol-2-ylamino)-1H-benzoimidazole-5-carboxylic acid (2-methoxy-2-methyl-propyl)-amide (68 mg) was prepared by following General Procedure F starting from 1-methyl-2-(6-trifluoromethoxy-benzo-thiazol-2-ylamino)-1H-benzoimidazole-5-carboxylic acid (100 mg), 2-methoxy-2-methyl-propylamine (58 mg), HBTU (111 mg), and DIEA (64 uL). LC/MS: m/z 494.9. $^1$H NMR (DMSO-d$_6$, 400 MHz): δ 12.40 (bs, 1H), 8.17 (t, 1H), 8.08 (s, 1H), 7.92 (s, 1H), 7.78 (d, 1H), 7.73 (d, 1H), 7.48 (d, 1H), 7.36 (d, 1H), 3.64 (bs, 3H), 3.36 (d, 2H), 3.18 (s, 3H), 1.14 (d, 6H).

Example 23

1-Methyl-2-(6-trifluoromethyl-benzothiazol-2-ylamino)-1H-benzoimidazole-5-carboxylic acid methyl ester 1-Methyl-2-(6-trifluoromethyl-benzothiazol-2-ylamino)-1H-benzoimidazole-5-carboxylic acid methyl ester (765 mg) was prepared by following General Procedure D starting from 3-amino-4-methylamino-benzoic acid methyl ester (991 mg), 2-amino-6-(trifluoromethyl)benzothiazole (1.0 g), 1,1'-thiocarbonyldiimidazole (1.09 g), and EDC (1.32 g). LC/MS: m/z 407.9. $^1$H NMR (DMSO-d$_6$, 400 MHz): δ 12.37 (bs, 1H), 8.15 (s, 1H), 7.97 (d, 1H), 7.95 (d, 1H), 7.85 (d, 1H), 7.62-7.43 (m, 2H), 3.86 (s, 3H), 3.62 (bs, 3H).

Example 24

1-Methyl-2-(6-trifluoromethyl-benzothiazol-2-ylamino)-1H-benzoimidazole-5-carboxylic acid 1-Methyl-2-(6-trifluoromethyl-benzothiazol-2-ylamino)-1H-benzoimidazole-5-carboxylic acid (434 mg) was prepared by following General Procedure E starting from 1-methyl-2-(6-trifluoromethyl-benzothiazol-2-ylamino)-1H-benzoimidazole-5-carboxylic acid methyl ester (765 mg) and lithium hydroxide (316 mg). LC/MS: m/z 393.9. $^1$H NMR (DMSO-d$_6$, 400 MHz): δ 12.77 (bs, 1H), 12.49 (bs, 1H), 8.34-8.14 (m, 2H), 7.93-7.73 (m, 2H), 7.67 (d, 1H), 7.52 (d, 1H), 3.64 (bs, 3H).

Example 25

1-Methyl-2-(6-trifluoromethyl-benzothiazol-2-ylamino)-1H-benzoimidazole-5-carboxylic acid (2-methoxy-ethyl)-amide 1-Methyl-2-(6-trifluoromethyl-benzothiazol-2-ylamino)-1H-benzoimidazole-5-carboxylic acid (2-methoxy-ethyl)-amide (78 mg) was prepared by following General Procedure F starting from 1-methyl-2-(6-trifluoromethyl-benzothiazol-2-ylamino)-1H-benzoimidazole-5-carboxylic acid (100 mg), 2-methoxy-ethylamine (21 mg), HBTU (116 mg), and DIEA (67 uL). LC/MS: m/z 450.9. $^1$H NMR (DMSO-d$_6$, 400 MHz): δ 12.45 (bs, 1H), 8.47 (s, 1H), 8.24 (s, 1H), 8.09 (s, 1H), 7.78 (s, 2H), 7.67 (d, 1H), 7.48 (d, 1H), 3.66 (bs, 3H), 3.51-3.39 (m, 4H), 3.27 (s, 3H).

Example 26

1-Methyl-2-(6-trifluoromethyl-benzothiazol-2-ylamino)-1H-benzoimidazole-5-carboxylic acid ethylamide 1-Methyl-2-(6-trifluoromethyl-benzothiazol-2-ylamino)-1H-benzoimidazole-5-carboxylic acid ethylamide (77 mg) was prepared by following General Procedure F starting from 1-methyl-2-(6-trifluoromethyl-benzothiazol-2-ylamino)-1H-benzo-imidazole-5-carboxylic acid (100 mg), ethylamine (2 M in THF, 254 uL), HBTU (116 mg), and DIEA (67 uL). LC/MS: m/z 421.0. $^1$H NMR (DMSO-d$_6$, 400 MHz): δ 12.46 (bs, 1H), 8.42 (s, 1H), 8.24 (s, 1H), 8.08

(s, 1H), 7.74 (s, 2H), 7.64 (d, 1H), 7.48 (d, 1H), 3.66 (bs, 3H), 3.30 (q, 2H), 1.13 (t, 3H).

Example 27

1-Methyl-2-(6-trifluoromethyl-benzothiazol-2-ylamino)-1H-benzoimidazole-5-carboxylic acid (2-hydroxy-ethyl)-amide 1-Methyl-2-(6-trifluoromethyl-benzothiazol-2-ylamino)-1H-benzoimidazole-5-carboxylic acid (2-hydroxy-ethyl)-amide (91 mg) was prepared by following General Procedure F starting from 1-methyl-2-(6-trifluoromethyl-benzothiazol-2-ylamino)-1H-benzoimidazole-5-carboxylic acid (100 mg), ethanolamine (17 mg), HBTU (116 mg), and DIEA (67 uL). LC/MS: m/z 436.9. $^1$H NMR (DMSO-$d_6$, 400 MHz): δ 12.46 (bs, 1H), 8.38 (s, 1H), 8.24 (s, 1H), 8.09 (s, 1H), 7.77 (s, 2H), 7.67 (d, 1H), 7.48 (d, 1H), 4.72 (t, 1H), 3.65 (bs, 3H), 3.52 (q, 2H), 3.34 (q, 2H).

Example 28

2-(6-Chloro-benzothiazol-2-ylamino)-1-methyl-1H-benzoimidazole-5-carboxylic acid methyl ester 2-(6-Chloro-benzothiazol-2-ylamino)-1-methyl-1H-benzoimidazole-5-carboxylic acid methyl ester (842 mg) was prepared by following General Procedure D starting from 3-amino-4-methylamino-benzoic acid methyl ester (650 mg), 2-amino-6-chloro-benzothiazole (556 mg), 1,1'-thiocarbonyldiimidazole (715 mg), and EDC (865 mg). LC/MS: m/z 373.7. $^1$H NMR (DMSO-$d_6$, 400 MHz): δ 12.39 (bs, 1H), 8.19 (s, 1H), 7.92 (s, 1H), 7.84 (s, 1H), 7.64 (s, 1H), 7.50 (d, 1H), 7.38 (d, 1H), 3.86 (s, 3H), 3.62 (bs, 3H).

Example 29

2-(6-Chloro-benzothiazol-2-ylamino)-1-methyl-1H-benzoimidazole-5-carboxylic acid 2-(6-Chloro-benzothiazol-2-ylamino)-1-methyl-1H-benzoimidazole-5-carboxylic acid (250 mg) was prepared by following General Procedure E starting from 2-(6-chloro-benzothiazol-2-ylamino)-1-methyl-1H-benzoimidazole-5-carboxylic acid methyl ester (842 mg) and lithium hydroxide (379 mg). LC/MS: m/z 359.9. $^1$H NMR (DMSO-$d_6$, 400 MHz): δ 8.12 (s, 1H), 7.92 (d, 1H), 7.83 (d, 1H), 7.55 (s, 1H), 7.48 (d, 1H), 7.38 (dd, 1H), 3.65 (s, 3H), —COO$\underline{H}$ and —N$\underline{H}$ proton signal was not observed.

Example 30

2-(6-Chloro-benzothiazol-2-ylamino)-1-methyl-1H-benzoimidazole-5-carboxylic acid (2-hydroxy-ethyl)-amide 2-(6-Chloro-benzothiazol-2-ylamino)-1-methyl-1H-benzoimidazole-5-carboxylic acid (2-hydroxy-ethyl)-amide (9 mg) was prepared by following General Procedure F starting from 2-(6-chloro-benzothiazol-2-ylamino)-1-methyl-1H-benzoimidazole-5-carboxylic acid (90 mg), ethanolamine (17 mg), HBTU (114 mg), and DIEA (66 uL). LC/MS: m/z 402.9. $^1$H NMR (DMSO-$d_6$, 400 MHz): δ 12.35 (bs, 1H), 8.36 (s, 1H), 8.06 (s, 1H), 7.91 (s, 1H), 7.74 (s, 1H), 7.63 (s, 1H), 7.45 (d, 1H), 7.37 (dd, 1H), 4.72 (t, 1H), 3.63 (bs, 3H), 3.52 (q, 2H), 3.34 (q, 2H).

Example 31

2-(6-Chloro-benzothiazol-2-ylamino)-1-methyl-1H-benzoimidazole-5-carboxylic acid (2-methoxy-ethyl)-amide 2-(6-Chloro-benzothiazol-2-ylamino)-1-methyl-1H-benzoimidazole-5-carboxylic acid (2-methoxy-ethyl)-amide (51 mg) was prepared by following General Procedure F starting from 2-(6-chloro-benzothiazol-2-ylamino)-1-methyl-1H-benzo-imidazole-5-carboxylic acid (90 mg), 2-methoxyethylamine (21 mg), HBTU (114 mg), and DIEA (66 uL). LC/MS: m/z 416.8. $^1$H NMR (DMSO-$d_6$, 400 MHz): δ 12.36 (bs, 1H), 8.46 (s, 1H), 8.06 (s, 1H), 7.91 (s, 1H), 7.75 (s, 1H), 7.64 (s, 1H), 7.46 (d, 1H), 7.38 (dd, 1H), 3.62 (bs, 3H), 3.50-3.39 (m, 4H), 3.27 (s, 3H).

Example 32

2-(6-Chloro-benzothiazol-2-ylamino)-1-methyl-1H-benzoimidazole-5-carboxylic acid ethylamide 2-(6-Chloro-benzothiazol-2-ylamino)-1-methyl-1H-benzoimidazole-5-carboxylic acid ethylamide (64 mg) was prepared by following General Procedure F starting from 2-(6-chloro-benzothiazol-2-ylamino)-1-methyl-1H-benzoimidazole-5-carboxylic acid (90 mg), ethylamine (2 M in THF, 251 uL), HBTU (114 mg), and DIEA (66 uL). LC/MS: m/z 386.9. $^1$H NMR (DMSO-$d_6$, 400 MHz): δ 12.38 (bs, 1H), 8.40 (s, 1H), 8.05 (s, 1H), 7.90 (s, 1H), 7.72 (d, 1H), 7.57 (bs, 1H), 7.44 (d, 1H), 7.37 (dd, 1H), 3.64 (bs, 3H), 3.30 (q, 2H), 1.13 (t, 3H).

Example 33

2-(5,6-Difluoro-benzothiazol-2-ylamino)-1-methyl-1H-benzoimidazole-5-carboxylic acid methyl ester 2-(5,6-Difluoro-benzothiazol-2-ylamino)-1-methyl-1H-benzoimidazole-5-carboxylic acid methyl ester (579 mg) was prepared by following General Procedure D starting from 3-amino-4-methylamino-benzoic acid methyl ester (650 mg), 2-amino-5,6-difluorobenzothiazole (560 mg), 1,1'-thiocarbonyldiimidazole (715 mg), and EDC (865 mg). LC/MS: m/z 375.8. $^1$H NMR (DMSO-$d_6$, 400 MHz): δ 12.51 (bs, 1H), 8.25 (s, 1H), 8.19 (s, 1H), 7.85 (s, 1H), 7.68 (d, 1H), 7.52 (d, 1H), 3.86 (s, 3H), 3.67 (bs, 3H).

Example 34

2-(5,6-Difluoro-benzothiazol-2-ylamino)-1-methyl-1H-benzoimidazole-5-carboxylic acid 2-(5,6-Difluoro-benzothiazol-2-ylamino)-1-methyl-1H-benzoimidazole-5-carboxylic acid (265 mg) was prepared by following General Procedure E starting from 2-(5,6-difluoro-benzothiazol-2-ylamino)-1-methyl-1H-benzoimidazole-5-carboxylic acid methyl ester (579 mg) and lithium hydroxide (260 mg). LC/MS: m/z 361.9. $^1$H NMR (DMSO-$d_6$, 400 MHz): δ 12.75 (bs, 1H), 12.35 (bs, 1H), 8.15 (s, 1H), 7.96 (t, 1H), 7.85 (d, 1H), 7.57 (s, 1H), 7.48 (d, 1H), 3.62 (bs, 3H).

Example 35

2-(5,6-Difluoro-benzothiazol-2-ylamino)-1-methyl-1H-benzoimidazole-5-carboxylic acid ethylamide 2-(5,6-Difluoro-benzothiazol-2-ylamino)-1-methyl-1H-benzoimidazole-5-carboxylic acid ethylamide (55 mg) was prepared by following General Procedure F starting from 2-(5,6-difluoro-benzothiazol-2-ylamino)-1-methyl-1H-benzoimidazole-5-carboxylic acid (90 mg), ethylamine (2 M in THF, 250 uL), HBTU (114 mg), and DIEA (65 uL). LC/MS: m/z 388.9. $^1$H NMR (DMSO-$d_6$, 400 MHz): δ 12.34 (bs, 1H), 8.42 (s, 1H), 8.04 (s, 1H), 7.95 (dd, 1H), 7.74 (d, 1H), 7.55 (s, 1H), 7.45 (d, 1H), 3.62 (s, 3H), 3.30 (q, 2H), 1.13 (t, 3H).

Example 36

2-(5,6-Difluoro-benzothiazol-2-ylamino)-1-methyl-1H-benzoimidazole-5-carboxylic acid (2-hydroxy-ethyl)-amide 2-(5,6-Difluoro-benzothiazol-2-ylamino)-1-methyl-1H-benzoimidazole-5-carboxylic acid (2-hydroxy-ethyl)-amide (71 mg) was prepared by following General Procedure F starting from 2-(5,6-difluoro-benzothiazol-2-ylamino)-1-methyl-1H-benzoimidazole-5-carboxylic acid (90 mg), ethanolamine (17 mg), HBTU (114 mg), and DIEA (65 uL). LC/MS: m/z 404.8. $^1$H NMR (DMSO-$d_6$, 400 MHz): δ 12.34 (bs, 1H), 8.38 (s, 1H), 8.05 (s, 1H), 7.95 (t, 1H), 7.76 (s, 1H), 7.56 (s, 1H), 7.46 (d, 1H), 4.72 (t, 1H), 3.62 (bs, 3H), 3.52 (q, 2H), 3.34 (q, 2H).

Example 37

2-(5,6-Difluoro-benzothiazol-2-ylamino)-1-methyl-1H-benzoimidazole-5-carboxylic acid (2-methoxy-ethyl)-amide 2-(5,6-Difluoro-benzothiazol-2-ylamino)-1-methyl-1H-benzoimidazole-5-carboxylic acid (2-methoxy-ethyl)-amide (60 mg) was prepared by following General Procedure F starting from 2-(5,6-difluoro-benzothiazol-2-ylamino)-1-methyl-1H-benzoimidazole-5-carboxylic acid (90 mg), 2-methoxyethylamine (21 mg), HBTU (114 mg), and DIEA (65 uL). LC/MS: m/z 418.9. $^1$H NMR (DMSO-$d_6$, 400 MHz): δ 12.34 (bs, 1H), 8.48 (t, 1H), 8.05 (s, 1H), 7.95 (dd, 1H), 7.77 (d 1H), 7.58 (dd, 1H), 7.47 (d, 1H), 3.61 (bs, 3H), 3.50-3.39 (m, 4H), 3.27 (s, 3H).

Example 38

3-Methyl-2-(6-trifluoromethoxy-benzothiazol-2-ylamino)-3H-benzoimidazole-5-carboxylic acid methylamide 3-Methylamino-4-nitro-benzoic acid (1.1 g) was prepared by following General Procedure A starting from 3-chloro-4-nitro-benzoic acid (1.0 g) and methylamine (2 M in THF, 8.1 mL) in THF. The crude product was used in the next step without further purification.
N-Methyl-3-methylamino-4-nitro-benzamide (407 mg) was prepared by following General Procedure N starting from 3-methylamino-4-nitro-benzoic acid (500 mg), DPPA (550 uL), DIEA (445 uL), and methylamine (2 M in THF, 2.55 mL).
4-Amino-N-methyl-3-methylamino-benzamide (298 mg, 86%) was prepared by following General Procedure B starting from N-Methyl-3-methylamino-4-nitro-benzamide (407 mg) and Pd/C (10% by weight, 40 mg). The crude product was used directly in the next step.
3-Methyl-2-(6-trifluoromethoxy-benzothiazol-2-ylamino)-3H-benzoimidazole-5-carboxylic acid methylamide (11 mg) was prepared by following General Procedure D starting from 4-amino-N-methyl-3-methylamino-benzamide (298 mg), 2-amino-6-(trifluoromethoxy)benzothiazole (303 mg), 1,1'-thiocarbonyl-diimidazole (329 mg), and EDC (398 mg). LC/MS: m/z 422.9. $^1$H NMR (DMSO-$d_6$, 400 MHz): δ 8.39 (s, 1H), 8.01 (s, 1H), 7.88 (s, 1H), 7.69 (s, 1H), 7.54 (d, 1H), 7.45 (s, 1H), 7.33 (d, 1H), 6.73 (d, 1H), 3.63 (bs, 3H), 3.46 (s, 3H).

Example 39

6-Fluoro-1-methyl-2-(6-trifluoromethoxy-benzothiazol-2-ylamino)-1H-benzoimidazole-5-carboxylic acid (2-methoxy-ethyl)-amide 2-Fluoro-4-methylamino-5-nitro-benzoic acid (750 mg) was prepared by following General Procedure A starting from 2,4-difluoro-5-nitro-benzoic acid (1.0 g) and methylamine (2 M in THF, 2.46 mL) in THF.
2-Fluoro-N-(2-methoxy-ethyl)-4-methylamino-5-nitro-benzamide was prepared by following General Procedure F starting from 2-fluoro-4-methylamino-5-nitro-benzoic acid (75 mg), HBTU (159 mg), DIEA (92 uL), and 2-methoxy-ethylamine (26 mg). The crude product was used directly in the next step without further purification.
5-Amino-2-fluoro-N-(2-methoxy-ethyl)-4-methylamino-benzamide (72 mg) was prepared by following General Procedure B starting from 2-fluoro-N-(2-methoxy-ethyl)-4-methylamino-5-nitro-benzamide and Pd/C (10% by weight, 10 mg). The crude product was used in the next step without further purification.
6-Fluoro-1-methyl-2-(6-trifluoromethoxy-benzothiazol-2-ylamino)-1H-benzoimidazole-5-carboxylic acid (2-methoxy-ethyl)-amide (41 mg) was prepared by following General Procedure D starting from 5-amino-2-fluoro-N-(2-methoxy-ethyl)-4-methylamino-benzamide (72 mg), 2-amino-6-(trifluoromethoxy)-benzothiazole (59 mg), 1,1'-thiocarbonyldiimidazole (64 mg), and EDC (77 mg). LC/MS: m/z 484.8. $^1$H NMR (DMSO-$d_6$, 400 MHz): δ 12.35 (bs, 1H), 8.16 (s, 1H), 7.91 (d, 1H), 7.88 (s, 1H), 7.73 (d, 1H), 7.50 (d, 1H), 7.36 (d, 1H), 3.61 (bs, 3H), 3.51-3.40 (m, 4H), 3.30 (s, 3H).

Example 40

6-Fluoro-1-methyl-2-(6-trifluoromethoxy-benzothiazol-2-ylamino)-1H-benzoimidazole-5-carboxylic acid methyl ester 2,4-Difluoro-5-nitro-benzoic acid methyl ester (440 mg) was prepared by following General Procedure K starting from 2,4-difluoro-5-nitro-benzoic acid (500 mg) and thionyl chloride (233 uL).
2-Fluoro-4-methylamino-5-nitro-benzoic acid (375 mg) was prepared by following General Procedure A starting from 2,4-difluoro-5-nitro-benzoic acid methyl ester (440 mg) and methylamine (2 M in THF, 1.01 mL) in DMF.
5-Amino-2-fluoro-4-methylamino-benzoic acid methyl ester (115 mg) was prepared by following General Procedure B starting from 2-fluoro-4-methylamino-5-nitro-benzoic acid methyl ester (150 mg) and Pd/C (10% by weight, 15 mg). The crude product was used in the next step without further purification.
6-Fluoro-1-methyl-2-(6-trifluoromethoxy-benzothiazol-2-ylamino)-1H-benzoimidazole-5-carboxylic acid methyl ester (140 mg) was prepared by following General Procedure D starting from 5-amino-2-fluoro-4-methylamino-benzoic acid methyl ester (115 mg), 2-amino-6-(trifluo-

Example 41

6-Fluoro-1-methyl-2-(6-trifluoromethoxy-benzothiazol-2-ylamino)-1H-benzoimidazole-5-carboxylic acid 6-Fluoro-1-methyl-2-(6-trifluoromethoxy-benzothiazol-2-ylamino)-1H-benzoimidazole-5-carboxylic acid (121 mg) was prepared by following General Procedure E starting from 6-fluoro-1-methyl-2-(6-trifluoromethoxy-benzothiazol-2-ylamino)-1H-benzoimidazole-5-carboxylic acid methyl ester (140 mg) and lithium hydroxide (53 mg). LC/MS: m/z 427.8. $^1$H NMR (DMSO-d$_6$, 400 MHz): δ 8.01 (d, 1H), 7.95 (s, 1H), 7.61 (d, 1H), 7.48 (d, 1H), 7.38 (d, 1H), 3.65 (s, 3H), —COO$\underline{H}$ and —N$\underline{H}$ proton signal was not observed.

Example 42

6-Fluoro-1-methyl-2-(6-trifluoromethoxy-benzothiazol-2-ylamino)-1H-benzoimidazole-5-carboxylic acid ethylamide 6-Fluoro-1-methyl-2-(6-trifluoromethoxy-benzothiazol-2-ylamino)-1H-benzo-imidazole-5-carboxylic acid ethylamide (65 mg) was prepared by following General Procedure F starting from 6-fluoro-1-methyl-2-(6-trifluoromethoxy-benzothiazol-2-ylamino)-1H-benzoimidazole-5-carboxylic acid (100 mg), ethylamine (2 M in THF, 235 uL), HBTU (107 mg), and DIEA (62 uL). LC/MS: m/z 454.8. $^1$H NMR (DMSO-d$_6$, 400 MHz): δ 12.34 (bs, 1H), 8.17 (s, 1H), 7.93 (s, 1H), 7.85 (s, 1H), 7.73 (s, 1H), 7.48 (s, 1H), 7.36 (d, 1H), 3.61 (bs, 3H), 3.33-3.21 (m, 2H), 1.14 (t, 3H).

Example 43

1-Methyl-2-(6-trifluoromethoxy-benzothiazol-2-ylamino)-1H-benzoimidazole-5-carboxylic acid (2-morpholin-4-yl-ethyl)-amide 1-Methyl-2-(6-trifluoromethoxy-benzothiazol-2-ylamino)-1H-benzoimidazole-5-carboxylic acid (2-morpholin-4-yl-ethyl)-amide (92 mg) was prepared by following General Procedure F starting from 1-methyl-2-(6-trifluoromethoxy-benzothiazol-2-ylamino)-1H-benzoimidazole-5-carboxylic acid (100 mg), 4-(2-amino-ethyl)morpholine (36 uL), HBTU (112 mg), and DIEA (65 uL). LC/MS: m/z 521.9. $^1$H NMR (DMSO-d$_6$, 400 MHz): δ 12.40 (bs, 1H), 8.11 (s, 1H), 7.95 (s, 1H), 7.92 (s, 1H), 7.79 (d, 1H), 7.73 (d, 1H), 7.52 (d, 1H), 7.36 (d, 1H), 3.85-3.48 (m, 7H), 2.89 (s, 2H), 2.73 (s, 2H), 2.51-2.48 (m, 4H).

Example 44

1-Methyl-2-(6-trifluoromethoxy-benzothiazol-2-ylamino)-1H-benzoimidazole-5-carboxylic acid (2-trifluoromethoxy-ethyl)-amide 1-Methyl-2-(6-trifluoromethoxy-benzothiazol-2-ylamino)-1H-benzoimidazole-5-carboxylic acid (2-trifluoromethyl-ethyl)-amide (87 mg) was prepared by following General Procedure F starting from 1-methyl-2-(6-trifluoromethoxy-benzothiazol-2-ylamino)-1H-benzoimidazole-5-carboxylic acid (100 mg), 2-(trifluoromethoxy)ethylamine hydrochloride (45 mg), HBTU (112 mg), and DIEA (65 uL). LC/MS: m/z 520.8. $^1$H NMR (DMSO-d$_6$, 400 MHz): δ 12.41 (bs, 1H), 8.72 (s, 1H), 8.10 (s, 1H), 7.92 (s, 1H), 7.78 (d, 1H), 7.74 (d, 1H), 7.51 (d, 1H), 7.36 (d, 1H), 4.23 (t, 2H), 3.81-3.55 (m, 5H).

Example 45

1-Methyl-2-(6-trifluoromethoxy-benzothiazol-2-ylamino)-1H-benzoimidazole-5-carboxylic acid (2-hydroxy-2-methyl-propyl)-amide 1-Amino-2-methyl-propan-2-ol (244 mg) was prepared by following General Procedure G starting from acetone cyanohydrin (3.34 g) and lithium aluminum hydride (3.13 g).

1-Methyl-2-(6-trifluoromethoxy-benzothiazol-2-ylamino)-1H-benzoimidazole-5-carboxylic acid (2-hydroxy-2-methyl-propyl)-amide (97 mg) was prepared by following General Procedure F starting from 1-methyl-2-(6-trifluoromethoxy-benzothiazol-2-ylamino)-1H-benzoimidazole-5-carboxylic acid (100 mg), 1-amino-2-methyl-propan-2-ol (24 mg), HBTU (112 mg), and DIEA (65 uL). LC/MS: m/z 480.9. $^1$H NMR (DMSO-d$_6$, 400 MHz): δ 12.39 (bs, 1H), 8.18 (t, 1H), 8.10 (s, 1H), 7.92 (s, 1H), 7.80 (d, 1H), 7.73 (d, 1H), 7.49 (d, 1H), 7.36 (d, 1H), 4.60 (s, 1H), 3.64 (s, 3H), 3.29 (d, 2H), 1.14 (s, 6H).

Example 46

1-Methyl-2-(6-trifluoromethoxy-benzothiazol-2-ylamino)-1H-benzoimidazole-5-carboxylic acid [2-(2-hydroxy-ethoxy)-ethyl]-amide 1-Methyl-2-(6-trifluoromethoxy-benzothiazol-2-ylamino)-1H-benzoimidazole-5-carboxylic acid [2-(2-hydroxy-ethoxy)-ethyl]-amide (220 mg) was prepared by following General Procedure F starting from 1-methyl-2-(6-trifluoromethoxy-benzothiazol-2-ylamino)-1H-benzoimidazole-5-carboxylic acid (250 mg), 2-(2-aminoethoxy)ethanol (71 mg), HBTU (279 mg), and DIEA (160 uL). LC/MS: m/z 496.8. $^1$H NMR (DMSO-d$_6$, 400 MHz): δ 12.39 (bs, 1H), 8.47 (t, 1H), 8.09 (s, 1H), 7.91 (s, 1H), 7.78 (d, 1H), 7.73 (d, 1H), 7.49 (d, 1H), 7.36 (d, 1H), 4.61 (t, 1H), 3.64 (s, 3H), 3.57 (t, 2H), 3.51 (t, 2H), 3.49-3.41 (m, 4H).

Example 47

1-Methyl-2-(6-trifluoromethoxy-benzothiazol-2-ylamino)-1H-benzoimidazole-5-carboxylic acid [2-(2-fluoro-ethoxy)-ethyl]-amide 1-Methyl-2-(6-trifluoromethoxy-benzothiazol-2-ylamino)-1H-benzoimidazole-5-carboxylic acid [2-(2-fluoro-ethoxy)-ethyl]-amide (53 mg) was prepared by following General Procedure H starting from 1-methyl-2-(6-trifluoromethoxy-benzothiazol-2-ylamino)-1H-benzoimidazole-5-carboxylic acid [2-(2-hydroxy-ethoxy)-ethyl]-amide (50 mg) and bis(2-methoxyethyl)aminosulfur trifluoride (47 uL). LC/MS: m/z 498.9. $^1$H NMR (DMSO-d$_6$, 400 MHz): δ 12.39 (bs, 1H), 8.51 (s, 1H), 8.09 (s, 1H), 7.93 (s, 1H), 7.86-7.62 (m, 2H), 7.49 (d, 1H), 7.36 (d, 1H), 4.63-4.46 (m, 1H), 3.80-3.69 (m, 2H), 3.68-3.52 (m, 6H), 3.46 (q, 2H).

Example 48

1-Methyl-2-(6-trifluoromethoxy-benzothiazol-2-ylamino)-1H-benzoimidazole-5-carboxylic acid (furan-2-ylmethyl)-amide 1-Methyl-2-(6-trifluoromethoxy-benzothiazol-2-ylamino)-1H-benzoimidazole-5-carboxylic acid (furan-2-ylmethyl)-amide (108 mg) was prepared by following General Procedure F starting from 1-methyl-2-(6-trifluoromethoxy-benzothiazol-2-ylamino)-1H-benzoimidazole-5-carboxylic acid (100 mg), furfurylamine (26 mg), HBTU (111 mg), and DIEA (64 uL). LC/MS: m/z 489.0. $^1$H NMR (DMSO-$d_6$, 400 MHz): δ 12.37 (bs, 1H), 8.92 (s, 1H), 8.09 (s, 1H), 7.90 (s, 1H), 7.79 (d, 1H), 7.71 (d, 1H), 7.57 (s, 1H), 7.47 (d, 1H), 7.34 (d, 1H), 6.39 (dd, 1H), 6.27 (d, 1H), 4.48 (d, 2H), 3.62 (s, 3H).

Example 49

1-Methyl-2-(6-trifluoromethoxy-benzothiazol-2-ylamino)-1H-benzoimidazole-5-carboxylic acid ([1,4]dioxan-2-ylmethyl)-amide 1-Methyl-2-(6-trifluoromethoxy-benzothiazol-2-ylamino)-1H-benzoimidazole-5-carboxylic acid ([1,4]dioxan-2-ylmethyl)-amide (88 mg) was prepared by following General Procedure F starting from 1-methyl-2-(6-trifluoromethoxy-benzothiazol-2-ylamino)-1H-benzoimidazole-5-carboxylic acid (100 mg), c-[1,4]dioxan-2-yl-methylamine (32 mg), HBTU (111 mg), and DIEA (64 uL). LC/MS: m/z 508.8. $^1$H NMR (DMSO-$d_6$, 400 MHz): δ 12.38 (bs, 1H), 8.52 (s, 1H), 8.09 (s, 1H), 7.93 (s, 1H), 7.87-7.61 (m, 2H), 7.49 (d, 1H), 7.37 (d, 1H), 3.85-3.21 (m, 12H).

Example 50

1-Methyl-2-(6-trifluoromethoxy-benzothiazol-2-ylamino)-1H-benzoimidazole-5-carboxylic acid ((S)-2-hydroxy-propyl)-amide 1-Methyl-2-(6-trifluoromethoxy-benzothiazol-2-ylamino)-1H-benzoimidazole-5-carboxylic acid ((S)-2-hydroxy-propyl)-amide (70 mg) was prepared by following General Procedure F starting from 1-methyl-2-(6-trifluoromethoxy-benzothiazol-2-yl-amino)-1H-benzoimidazole-5-carboxylic acid (100 mg), (S)-(+)-1-amino-2-propanol (20 mg), HBTU (111 mg), and DIEA (64 uL). LC/MS: m/z 466.8. $^1$H NMR (DMSO-$d_6$, 400 MHz): δ 12.39 (s, 1H), 8.36 (s, 1H), 8.10 (s, 1H), 7.92 (s, 1H), 7.80 (d, 1H), 7.73 (d, 1H), 7.49 (d, 1H), 7.36 (d, 1H), 4.77 (d, 1H), 3.87-3.78 (m, 1H), 3.64 (bs, 3H), 3.27-3.20 (m, 2H), 1.09 (d, 3H).

Example 51

1-Methyl-2-(6-trifluoromethoxy-benzothiazol-2-ylamino)-1H-benzoimidazole-5-carboxylic acid ((R)-2-hydroxy-propyl)-amide 1-Methyl-2-(6-trifluoromethoxy-benzothiazol-2-ylamino)-1H-benzoimidazole-5-carboxylic acid ((R)-2-hydroxy-propyl)-amide (78 mg) was prepared by following General Procedure F starting from 1-methyl-2-(6-trifluoromethoxy-benzothiazol-2-yl-amino)-1H-benzoimidazole-5-carboxylic acid (100 mg), (R)-(−)-1-amino-2-propanol (20 mg), HBTU (111 mg), and DIEA (64 uL). LC/MS: m/z 466.8. $^1$H NMR (DMSO-$d_6$, 400 MHz): δ 12.39 (s, 1H), 8.36 (s, 1H), 8.09 (s, 1H), 7.92 (s, 1H), 7.86-7.65 (m, 2H), 7.48 (d, 1H), 7.36 (d, 1H), 4.77 (d, 1H), 3.89-3.77 (m, 1H), 3.64 (bs, 3H), 3.26-3.19 (m, 2H), 1.09 (d, 3H).

Example 52

1-Methyl-2-(6-trifluoromethoxy-benzothiazol-2-ylamino)-1H-benzoimidazole-5-carboxylic acid (trans-4-hydroxy-cyclohexyl)-amide 1-Methyl-2-(6-trifluoromethoxy-benzothiazol-2-ylamino)-1H-benzoimidazole-5-carboxylic acid (trans-4-hydroxy-cyclohexyl)-amide (42 mg) was prepared by following General Procedure F starting from 1-methyl-2-(6-trifluoromethoxy-benzothiazol-2-ylamino)-1H-benzoimidazole-5-carboxylic acid (75 mg), trans-4-amino-cyclohexanol (23 mg), HBTU (84 mg), and DIEA (48 uL). LC/MS: m/z 506.8. $^1$H NMR (DMSO-$d_6$, 400 MHz): δ 12.40 (s, 1H), 8.17 (s, 1H), 8.08 (s, 1H), 7.92 (s, 1H), 7.82-7.64 (m, 2H), 7.47 (d, 1H), 7.36 (d, 1H), 4.57 (d, 1H), 3.81-3.68 (m, 1H), 3.64 (bs, 3H), 3.46-3.35 (m, 1H), 1.92-1.78 (m, 4H), 1.39 (q, 2H), 1.26 (q, 2H).

Example 53

1-Methyl-2-(6-trifluoromethoxy-benzothiazol-2-ylamino)-1H-benzoimidazole-5-carboxylic acid [2-(tetrahydro-furan-2-ylmethoxy)-ethyl]-amide 1-Methyl-2-(6-trifluoromethoxy-benzothiazol-2-ylamino)-1H-benzoimidazole-5-carboxylic acid [2-(tetrahydro-furan-2-ylmethoxy)-ethyl]-amide (21 mg) was prepared by following General Procedure F starting from 1-methyl-2-(6-trifluoromethoxy-benzothiazol-2-ylamino)-1H-benzoimidazole-5-carboxylic acid (75 mg), 2-(tetrahydro-furan-2-ylmethoxy)-ethylamine (29 mg), HBTU (84 mg), and DIEA (48 uL). LC/MS: m/z 536.8. $^1$H NMR (DMSO-$d_6$, 400 MHz): δ 12.39 (s, 1H), 8.46 (s, 1H), 8.09 (s, 1H), 7.92 (s, 1H), 7.83-7.65 (m, 2H), 7.49 (d, 1H), 7.36 (d, 1H), 3.98-3.90 (m, 1H), 3.79-3.68 (m, 2H), 3.64 (bs, 3H), 3.61-3.52 (m, 2H), 3.49-3.38 (m, 5H), 1.94-1.68 (m, 2H), 1.60-1.47 (m, 1H).

Example 54

1-Methyl-2-(6-trifluoromethoxy-benzothiazol-2-ylamino)-1H-benzoimidazole-5-carboxylic acid (2-ethoxy-propyl)-amide 1-Methyl-2-(6-trifluoromethoxy-benzothiazol-2-ylamino)-1H-benzoimidazole-5-carboxylic acid (2-ethoxy-propyl)-amide (31 mg) was prepared by following General Procedure F starting from 1-methyl-2-(6-trifluoromethoxy-benzothiazol-2-ylamino)-1H-benzoimidazole-5-carboxylic acid (75 mg), 2-ethoxy-propylamine (21 mg), HBTU (84 mg), and DIEA (48 uL). LC/MS: m/z 494.7. $^1$H NMR (DMSO-$d_6$, 400 MHz): δ 12.39 (s, 1H), 8.43 (s, 1H), 8.08 (s, 1H), 7.92 (s, 1H), 7.83-7.66 (m, 2H), 7.48 (d, 1H), 7.36 (d, 1H), 3.79-3.43 (m, 5H), 3.41-3.30 (m, 2H), 3.29-3.18 (m, 1H), 1.14-1.08 (m, 6H).

Example 55

2-({[1-Methyl-2-(6-trifluoromethoxy-benzothiazol-2-ylamino)-1H-benzoimidazole-5-carbonyl]-amino}-methyl)-morpholine-4-carboxylic acid tert-butyl ester 2-({[1-Methyl-2-(6-trifluoromethoxy-benzothiazol-2-ylamino)-1H-benzoimidazole-5-carbonyl]-amino}-methyl)- morpholine-4-carboxylic acid tert-butyl ester (76 mg) was prepared by following General Procedure F starting from 1-methyl-2-(6-trifluoro-methoxy-benzothiazol-2-ylamino)-1H-benzoimidazole-5-carboxylic acid (75 mg), 2-aminomethyl-morpholine-4-carboxylic acid tert-butyl ester (44 mg), HBTU (84 mg), and DIEA (48 uL). LC/MS: m/z 607.9. $^1$H NMR (DMSO-$d_6$, 400 MHz): δ 12.41 (s, 1H), 8.59 (s, 1H), 8.09 (s, 1H), 7.92 (s, 1H), 7.85-7.63 (m, 2H), 7.50 (d, 1H), 7.37 (d, 1H), 3.95-3.78 (m, 2H), 3.76-3.58 (m, 5H), 3.56-3.45 (m, 1H), 3.44-3.35 (m, 4H), 1.22 (s, 9H).

Example 56

1-Methyl-2-(6-trifluoromethoxy-benzothiazol-2-ylamino)-1H-benzoimidazole-5-carboxylic acid (morpholin-2-ylmethyl)-amide hydrochloride 1-Methyl-2-(6-trifluoromethoxy-benzothiazol-2-ylamino)-1H-benzoimidazole-5-carboxylic acid (morpholin-2-ylmethyl)-amide dihydrochloride (57 mg) was prepared by following General Procedure L starting from 2-({[1-methyl-2-(6-trifluoro-methoxy-benzothiazol-2-ylamino)-1H-benzoimidazole-5-carbonyl]-amino}-methyl)-morpholine-4-carboxylic acid tert-butyl ester (63 mg) and HCl (4 M in dioxanes, 260 uL). LC/MS: m/z 507.7. $^1$H NMR (DMSO-$d_6$, 400 MHz): δ 9.37 (bs, 2H), 8.68 (t, 1H), 8.11 (s, 1H), 7.95 (s, 1H), 7.80 (d, 1H), 7.64 (d, 1H), 7.52 (d, 1H), 7.38 (d, 1H), 4.04-3.86 (m, 2H), 3.76 (t, 1H), 3.69 (s, 3H), 3.52-3.31 (m, 2H), 3.28 (d, 1H), 3.18 (d, 1H), 3.06-2.90 (m, 1H), 2.80 (q, 1H).

Example 57

6-Fluoro-1-methyl-2-(6-trifluoromethoxy-benzothiazol-2-ylamino)-1H-benzoimidazole-5-carboxylic acid (2-ethoxy-ethyl)-amide 6-Fluoro-1-methyl-2-(6-trifluoromethoxy-benzothiazol-2-ylamino)-1H-benzo-imidazole-5-carboxylic acid (2-ethoxy-ethyl)-amide (52 mg) was prepared by following General Procedure F starting from 6-fluoro-1-methyl-2-(6-trifluoromethoxy-benzothiazol-2-ylamino)-1H-benzoimidazole-5-carboxylic acid (75 mg), 2-ethoxyethylamine (17 mg), HBTU (80 mg), and DIEA (46 uL). LC/MS: m/z 498.7. $^1$H NMR (DMSO-$d_6$, 400 MHz): δ 12.35 (bs, 1H), 8.14 (d, 1H), 7.92 (s, 1H), 7.89 (d, 1H), 7.73 (d, 1H), 7.50 (d, 1H), 7.37 (s, 1H), 3.60 (bs, 3H), 3.56-3.41 (m, 6H), 1.14 (t, 3H).

Example 58

6-Fluoro-1-methyl-2-(6-trifluoromethoxy-benzothiazol-2-ylamino)-1H-benzoimidazole-5-carboxylic acid dimethylcarbamoylmethyl-amide 6-Fluoro-1-methyl-2-(6-trifluoromethoxy-benzothiazol-2-ylamino)-1H-benzoimidazole-5-carboxylic acid dimethylcarbamoylmethyl-amide (32 mg) was prepared by following General Procedure F starting from 6-fluoro-1-methyl-2-(6-trifluoromethoxy-benzothiazol-2-ylamino)-1H-benzoimidazole-5-carboxylic acid (75 mg), glycine dimethylamide acetate (32 mg), HBTU (80 mg), and DIEA (46 uL). LC/MS: m/z 511.7. $^1$H NMR (DMSO-$d_6$, 400 MHz): δ 12.39 (bs, 1H), 8.19-8.00 (m, 2H), 7.93 (s, 1H), 7.74 (d, 1H), 7.54 (d, 1H), 7.36 (d, 1H), 4.18 (d, 2H), 3.61 (bs, 3H), 3.01 (s, 3H), 2.89 (s, 3H).

Example 59

6-Fluoro-1-methyl-2-(6-trifluoromethoxy-benzothiazol-2-ylamino)-1H-benzoimidazole-5-carboxylic acid (2-morpholin-4-yl-ethyl)-amide 6-Fluoro-1-methyl-2-(6-trifluoromethoxy-benzothiazol-2-ylamino)-1H-benzoimidazole-5-carboxylic acid (2-morpholin-4-yl-ethyl)-amide (21 mg) was prepared by following General Procedure F starting from 6-fluoro-1-methyl-2-(6-trifluoro-methoxy-benzothiazol-2-ylamino)-1H-benzoimidazole-5-carboxylic acid (75 mg), 4-(2-aminoethyl)morpholine (25 mg), HBTU (80 mg), and DIEA (46 uL). LC/MS: m/z 539.7. $^1$H NMR (DMSO-$d_6$, 400 MHz): δ 12.38 (bs, 1H), 9.54 (s, 1H), 8.41 (s, 1H), 7.95 (s, 1H), 7.74 (s, 1H), 7.56 (s, 1H), 7.36 (d, 1H), 4.01 (d, 2H), 3.80-3.51 (m, 7H), 3.25-3.09 (m, 2H), 2.53-2.49 (m, 4H).

Example 60

6-Fluoro-1-methyl-2-(6-trifluoromethoxy-benzothiazol-2-ylamino)-1H-benzoimidazole-5-carboxylic acid (2-hydroxy-propyl)-amide 6-Fluoro-1-methyl-2-(6-trifluoromethoxy-benzothiazol-2-ylamino)-1H-benzoimidazole-5-carboxylic acid (2-hydroxy-propyl)-amide (52 mg) was prepared by following General Procedure F starting from 6-fluoro-1-methyl-2-(6-trifluoromethoxy-benzothiazol-2-ylamino)-1H-benzoimidazole-5-carboxylic acid (75 mg), 1-amino-2-propanol (15 mg), HBTU (80 mg), and DIEA (46 uL). LC/MS: m/z 484.7. $^1$H NMR (DMSO-$d_6$, 400 MHz): δ 12.93 (bs, 1H), 12.35 (bs, 1H), 8.02 (s, 1H), 7.93 (s, 1H), 7.73 (d, 1H), 7.51 (d, 1H), 7.36 (d, 1H), 4.79 (s, 1H), 3.86-3.75 (m, 1H), 3.61 (bs, 3H), 3.29-3.17 (m, 2H), 1.10 (d, 3H).

Example 61

6-Methoxy-1-methyl-2-(6-trifluoromethoxy-benzothiazol-2-ylamino)-1H-benzoimidazole-5-carboxylic acid methyl ester 2-Methoxy-4-methylamino-5-nitro-benzoic acid methyl ester (120 mg) was prepared by following General Procedure A starting from 2-Fluoro-4-methylamino-5-nitro-benzoic acid methyl ester (200 mg) and sodium methoxide (190 mg) in DMF.

5-Amino-2-methoxy-4-methylamino-benzoic acid methyl ester (95 mg) was prepared by following General Procedure B starting from 2-methoxy-4-methylamino-5-nitro-benzoic acid methyl ester (120 mg) and Pd/C (10% by weight, 12 mg). The crude product was used in the next step without further purification.

6-Methoxy-1-methyl-2-(6-trifluoromethoxy-benzothiazol-2-ylamino)-1H-benzoimidazole-5-carboxylic acid methyl ester (80 mg) was prepared by following General Procedure D starting from 5-amino-2-methoxy-4-methylamino-benzoic acid methyl ester (95 mg), 2-amino-6-(trifluoromethoxy)benzothiazole (82 mg), 1,1'-thiocarbonyldiimidazole (90 mg), and EDC (108 mg). LC/MS: m/z 453.8. $^1$H NMR (DMSO-$d_6$, 400 MHz): δ 12.24, (s, 1H), 7.97 (s, 1H), 7.92 (s, 1H), 7.71 (d, 1H), 7.36 (d, 1H), 7.24 (s, 1H), 3.90 (s, 3H), 3.80 (s, 3H), 3.64 (s, 3H).

Example 62

6-Methoxy-1-methyl-2-(6-trifluoromethoxy-benzothiazol-2-ylamino)-1H-benzoimidazole-5-carboxylic acid 6-Methoxy-1-methyl-2-(6-trifluoromethoxy-benzothiazol-2-ylamino)-1H-benzoimidazole-5-carboxylic acid (60 mg) was prepared by following General Procedure E starting from 6-methoxy-1-methyl-2-(6-trifluoromethoxy-benzothiazol-2-ylamino)-1H-benzoimidazole-5-carboxylic acid methyl ester (80 mg) and lithium hydroxide (30 mg). LC/MS: m/z 439.8.

Example 63

6-Methoxy-1-methyl-2-(6-trifluoromethoxy-benzothiazol-2-ylamino)-1H-benzoimidazole-5-carboxylic acid dimethylcarbamoylmethyl-amide 6-Methoxy-1-methyl-2-(6-trifluoromethoxy-benzothiazol-2-ylamino)-1H-benzoimidazole-5-carboxylic acid dimethylcarbamoylmethyl-amide (37 mg) was prepared by following General Procedure F starting from 6-methoxy-1-methyl-2-(6-trifluoromethoxy-benzothiazol-2-ylamino)-1H-benzoimidazole-5-carboxylic acid (60 mg), glycine dimethylamide acetate (25 mg), HBTU (63 mg), and DIEA (36 uL). LC/MS: m/z 523.7. $^1$H NMR (DMSO-$d_6$, 400 MHz): δ 12.29 (bs, 1H), 8.84 (t, 1H), 8.26 (s, 1H), 7.90 (s, 1H), 7.72 (d, 1H), 7.35 (d, 1H), 7.30 (s, 1H), 4.21 (d, 2H), 4.04 (s, 3H), 3.65 (s, 3H), 3.00 (s, 3H), 2.91 (s, 3H).

Example 64

6-Methoxy-1-methyl-2-(6-trifluoromethoxy-benzothiazol-2-ylamino)-1H-benzoimidazole-5-carboxylic acid ethylamide 6-Methoxy-1-methyl-2-(6-trifluoromethoxy-benzothiazol-2-ylamino)-1H-benzoimidazole-5-carboxylic acid ethylamide (37 mg) was prepared by following General Procedure F starting from 6-methoxy-1-methyl-2-(6-trifluoromethoxy-benzo-thiazol-2-ylamino)-1H-benzoimidazole-5-carboxylic acid (75 mg), ethylamine (2 M in THF, 171 uL), HBTU (78 mg), and DIEA (45 uL). LC/MS: m/z 466.7. $^1$H NMR (DMSO-$d_6$, 400 MHz): δ 12.25 (s, 1H), 8.22 (t, 1H), 8.10 (s, 1H), 7.90 (s, 1H), 7.71 (d, 1H), 7.34 (d, 1H), 7.24 (s, 1H), 3.98 (s, 3H), 3.64 (s, 3H), 3.39-3.30 (m, 2H), 1.14 (t, 3H).

Example 65

6-Methoxy-1-methyl-2-(6-trifluoromethoxy-benzothiazol-2-ylamino)-1H-benzoimidazole-5-carboxylic acid (2-ethoxy-ethyl)-amide 6-Methoxy-1-methyl-2-(6-trifluoromethoxy-benzothiazol-2-ylamino)-1H-benzoimidazole-5-carboxylic acid (2-ethoxy-ethyl)-amide (72 mg) was prepared by following General Procedure F starting from 6-methoxy-1-methyl-2-(6-trifluoromethoxy-benzothiazol-2-ylamino)-1H-benzoimidazole-5-carboxylic acid (75 mg), 2-ethoxyethylamine (17 mg), HBTU (78 mg), and DIEA (45 uL). LC/MS: m/z 510.7. $^1$H NMR (DMSO-$d_6$, 400 MHz): δ 12.27 (s, 1H), 8.34 (t, 1H), 8.16 (s, 1H), 7.90 (s, 1H), 7.71 (d, 1H), 7.35 (d, 1H), 7.26 (s, 1H), 4.0 (s, 3H), 3.64 (s, 3H), 3.56-3.43 (m, 6H), 1.16 (t, 3H).

Example 66

6-Methoxy-1-methyl-2-(6-trifluoromethoxy-benzothiazol-2-ylamino)-1H-benzoimidazole-5-carboxylic acid (2-morpholin-4-yl-ethyl)-amide 6-Methoxy-1-methyl-2-(6-trifluoromethoxy-benzothiazol-2-ylamino)-1H-benzoimidazole-5-carboxylic acid (2-morpholin-4-yl-ethyl)-amide (69 mg) was prepared by following General Procedure F starting from 6-methoxy-1-methyl-2-(6-trifluoro-methoxy-benzothiazol-2-ylamino)-1H-benzoimidazole-5-carboxylic acid (75 mg), 4-(2-aminoethyl)morpholine (25 mg), HBTU (78 mg), and DIEA (45 uL). LC/MS: m/z 551.7. $^1$H NMR (DMSO-$d_6$, 400 MHz): δ 12.27 (bs, 1H), 8.50 (bs, 1H), 8.18 (s, 1H), 7.90 (s, 1H), 7.71 (d, 1H), 7.35 (d, 1H), 7.28 (s, 1H), 4.02 (s, 3H), 3.76-3.55 (m, 7H), 3.38-3.27 (m, 4H), 2.52-2.49 (m, 4H).

Example 67

6-Methoxy-1-methyl-2-(6-trifluoromethoxy-benzothiazol-2-ylamino)-1H-benzoimidazole-5-carboxylic acid (2-methoxy-ethyl)-amide 6-Methoxy-1-methyl-2-(6-trifluoromethoxy-benzothiazol-2-ylamino)-1H-benzoimidazole-5-carboxylic acid (2-methoxy-ethyl)-amide (55 mg) was prepared by following General Procedure F starting from 6-methoxy-1-methyl-2-(6-trifluoro-methoxy-benzothiazol-2-ylamino)-1H-benzoimidazole-5-carboxylic acid (75 mg), 2-methoxyethylamine (14 mg), HBTU (78 mg), and DIEA (45 uL). LC/MS: m/z 496.7. $^1$H NMR (DMSO-$d_6$, 400 MHz): δ 12.26 (s, 1H), 8.32 (s, 1H), 8.15 (s, 1H), 7.90 (s, 1H), 7.71 (d, 1H), 7.34 (s, 1H), 7.26 (s, 1H), 4.00 (s, 3H), 3.64 (s, 3H), 3.51-3.47 (m, 4H), 3.31 (s, 3H).

Example 68

6-Methoxy-1-methyl-2-(6-trifluoromethoxy-benzothiazol-2-ylamino)-1H-benzoimidazole-5-carboxylic acid (2-hydroxy-propyl)-amide 6-Methoxy-1-methyl-2-(6-trifluoromethoxy-benzothiazol-2-ylamino)-1H-benzo-imidazole-5-carboxylic acid (2-hydroxy-propyl)-amide (56 mg) was prepared by following General Procedure F starting from 6-methoxy-1-methyl-2-(6-trifluoromethoxy-benzothiazol-2-ylamino)-1H-benzoimidazole-5-carboxylic acid (75 mg), 1-amino-2-propanol (14 mg), HBTU (78 mg), and DIEA (45 uL). LC/MS: m/z 496.6. $^1$H NMR (DMSO-$d_6$, 400 MHz): δ 12.27 (s, 1H), 8.32 (t, 1H), 8.16 (s, 1H), 7.90 (s, 1H), 7.71 (d, 1H), 7.35 (d, 1H), 7.26 (s, 1H), 4.85 (d, 1H), 4.00 (s, 3H), 3.85-3.76 (m, 1H), 3.64 (s, 3H), 3.43-3.34 (m, 1H), 3.24-3.14 (m, 1H), 1.10 (d, 3H).

Example 69

6-Diethylamino-1-methyl-2-(6-trifluoromethoxy-benzothiazol-2-ylamino)-1H-benzoimidazole-5-carboxylic acid methyl ester 2-Diethylamino-4-methylamino-5-nitro-benzoic acid methyl ester (1.2 g) was prepared by following General Procedure A starting from 2-fluoro-4-methylamino-5-nitro-benzoic acid methyl ester (1.0 g) and diethylamine (683 uL) in DMF.

5-Amino-2-diethylamino-4-methylamino-benzoic acid methyl ester (1.015 g) was prepared by following General Procedure B starting from 2-diethylamino-4-methylamino-5-nitro-benzoic acid methyl ester (1.2 g) and Pd/C (10% by weight, 120 mg). The crude product was used in the next step without further purification.

6-Diethylamino-1-methyl-2-(6-trifluoromethoxy-benzothiazol-2-ylamino)-1H-benzoimidazole-5-carboxylic acid methyl ester (1.26 g) was prepared by following General Procedure D starting from 5-amino-2-diethylamino-4-methylamino-benzoic acid methyl ester (1.015 mg), 2-amino-6-(trifluoromethoxy)benzothiazole (656 mg), 1,1'-thiocarbonyldiimidazole (714 mg), and EDC (865 mg). LC/MS: m/z 494.9. $^1$H NMR (DMSO-d$_6$, 400 MHz): δ 12.21 (bs, 1H), 7.90 (s, 1H), 7.80-7.56 (m, 2H), 7.34 (d, 1H), 7.25 (s, 1H), 3.81 (s, 3H), 3.62 (s, 3H), 3.13-2.97 (m, 4H), 0.96 (t, 6H).

Example 70

6-Diethylamino-1-methyl-2-(6-trifluoromethoxy-benzothiazol-2-ylamino)-1H-benzoimidazole-5-carboxylic acid 6-Diethylamino-1-methyl-2-(6-trifluoromethoxy-benzothiazol-2-ylamino)-1H-benzoimidazole-5-carboxylic acid (175 mg) was prepared by following General Procedure E starting from 6-diethylamino-1-methyl-2-(6-trifluoromethoxy-benzothiazol-2-ylamino)-1H-benzoimidazole-5-carboxylic acid methyl ester (300 mg) and lithium hydroxide (102 mg). LC/MS: m/z 480.9. $^1$H NMR (DMSO-d$_6$, 400 MHz): δ 12.45 (bs, 1H), 8.25 (bs, 1H), 7.96 (s, 1H), 7.85 (s, 1H), 7.80-7.62 (m, 1H), 7.38 (d, 1H), 3.68 (s, 3H), 3.41-3.25 (m, 4H), 0.94 (t, 6H), —COO$\underline{H}$ proton signal was not observed Example 71

3-Methyl-2-(6-trifluoromethoxy-benzothiazol-2-ylamino)-3H-imidazo[4,5-b]pyridine-6-carboxylic acid ethyl ester 6-Methylamino-5-nitro-nicotinic acid ethyl ester (911 mg) was prepared by following General Procedure A starting from 6-chloro-5-nitro-nicotinic acid ethyl ester (1.0 g) and methylamine (2 M in THF, 3.25 mL) in DMF.

5-Amino-6-methylamino-nicotinic acid ethyl ester (723 mg) was prepared by following General Procedure B starting from 6-methylamino-5-nitro-nicotinic acid ethyl ester (911 mg) and Pd/C (10% by weight, 90 mg). The crude product was used in the next step without further purification.

3-Methyl-2-(6-trifluoromethoxy-benzothiazol-2-ylamino)-3H-imidazo[4,5-b]pyridine-6-carboxylic acid ethyl ester (560 mg) was prepared by following General Procedure D starting from 5-amino-6-methylamino-nicotinic acid ethyl ester (723 mg), 2-amino-6-(trifluoromethoxy)benzothiazole (735 mg), 1,1'-thiocarbonyldiimidazole (802 mg), and EDC (969 mg). LC/MS: m/z 437.8. $^1$H NMR (DMSO-d$_6$, 400 MHz): δ 12.44 (s, 1H), 7.94 (s, 1H), 7.89 (s, 1H), 7.74 (s, 1H), 7.52 (d, 1H), 7.37 (d, 1H), 4.33 (q, 2H), 3.65 (s, 3H), 1.36 (t, 3H).

Example 72

3-Methyl-2-(6-trifluoromethoxy-benzothiazol-2-ylamino)-3H-imidazo[4,5-b]pyridine-6-carboxylic acid 3-Methyl-2-(6-trifluoromethoxy-benzothiazol-2-ylamino)-3H-imidazo[4,5-b]pyridine-6-carboxylic acid (58 mg, 62%) was prepared by following General Procedure E starting from 3-methyl-2-(6-trifluoromethoxy-benzothiazol-2-ylamino)-3H-imidazo[4,5-b]pyridine-6-carboxylic acid ethyl ester (100 mg) and lithium hydroxide (38 mg). LC/MS: m/z 409.7. $^1$H NMR (DMSO-d$_6$, 400 MHz): δ 13.00 (s, 1H), 8.16 (s, 1H), 7.95 (d, 1H), 7.86 (dd, 1H), 7.65 (d, 1H), 7.52 (d, 1H), 7.37 (d, 1H), 3.68 (s, 3H).

Example 73

3-Methyl-2-(6-trifluoromethoxy-benzothiazol-2-ylamino)-3H-imidazo[4,5-b]pyridine-6-carboxylic acid (2-methoxy-ethyl)-amide 3-Methyl-2-(6-trifluoromethoxy-benzothiazol-2-ylamino)-3H-imidazo[4,5-b]pyridine-6-carboxylic acid (2-methoxy-ethyl)-amide (38 mg) was prepared by following General Procedure F starting from 3-methyl-2-(6-trifluoromethoxy-benzothiazol-2-ylamino)-3H-imidazo[4,5-b]pyridine-6-carboxylic acid (58 mg), 2-methoxyethylamine (12 mg), HBTU (65 mg), and DIEA (37 uL). LC/MS: m/z 466.8. $^1$H NMR (DMSO-d$_6$, 400 MHz): δ 8.49 (t, 1H), 8.09 (s, 1H), 7.94 (s, 1H), 7.78 (d, 1H), 7.64 (d, 1H), 7.50 (d, 1H), 7.37 (d, 1H), 3.67 (s, 3H), 3.54-3.40 (m, 4H), 3.29 (s, 3H).

Example 74

3-Methyl-2-(6-trifluoromethoxy-benzothiazol-2-ylamino)-3H-imidazo[4,5-b]pyridine-6-carboxylic acid dimethylcarbamoylmethyl-amide 3-Methyl-2-(6-trifluoromethoxy-benzothiazol-2-ylamino)-3H-imidazo[4,5-b]pyridine-6-carboxylic acid dimethylcarbamoylmethyl-amide (25 mg) was prepared by following General Procedure F starting from 3-methyl-2-(6-trifluoromethoxy-benzothiazol-2-ylamino)-3H-imidazo[4,5-b]pyridine-6-carboxylic acid (48 mg), glycine dimethylamide acetate (21 mg), HBTU (53 mg), and DIEA (31 uL). LC/MS: m/z 493.8. $^1$H NMR (DMSO-d$_6$, 400 MHz): δ 8.46 (t, 1H), 8.12 (s, 1H), 7.93 (s, 1H), 7.81 (s, 1H), 7.73 (s, 1H), 7.51 (d, 1H), 7.36 (d, 1H), 4.13 (d, 2H), 3.65 (bs, 3H), 3.03 (s, 3H), 2.87 (s, 3H).

Example 75

3-Methyl-2-(6-trifluoromethoxy-benzothiazol-2-ylamino)-3H-imidazo[4,5-b]pyridine-6-carboxylic acid (2-ethoxy-ethyl)-amide 3-Methyl-2-(6-trifluoromethoxy-benzothiazol-2-ylamino)-3H-imidazo[4,5-b]pyridine-6-carboxylic acid (2-ethoxy-ethyl)-amide (52 mg) was prepared by following General Procedure F starting from 3-methyl-2-(6-trifluoromethoxy-benzothiazol-2-ylamino)-3H-imidazo[4,5-b]pyridine-6-carboxylic acid (75 mg), 2-ethoxyethylamine (18 mg), HBTU (83 mg), and DIEA (48 uL). LC/MS: m/z 480.7. $^1$H NMR (DMSO-d$_6$, 400 MHz): δ 12.41 (bs, 1H), 8.47 (t, 1H), 8.09 (s, 1H), 7.93 (s, 1H), 7.76 (d, 1H), 7.48 (d, 1H), 7.36 (d, 1H), 3.66 (s, 3H), 3.56-3.39 (m, 6H), 1.13 (t, 3H).

Example 76

3-Methyl-2-(6-trifluoromethoxy-benzothiazol-2-ylamino)-3H-imidazo[4,5-b]pyridine-6-carboxylic acid ethylamide 3-Methyl-2-(6-trifluoromethoxy-benzothiazol-2-ylamino)-3H-imidazo[4,5-b]pyridine-6-carboxylic acid ethylamide (58 mg) was prepared by following General Procedure F starting from 3-methyl-2-(6-trifluoromethoxy-benzothiazol-2-ylamino)-3H-imidazo[4,5-b]pyridine-6-carboxylic acid (75 mg), 2-ethylamine (2 M in THF, 183 uL), HBTU (83 mg), and DIEA (48 uL). LC/MS: m/z 436.6. $^1$H NMR (DMSO-d$_6$, 400 MHz): δ 12.39 (bs, 1H), 8.44 (s, 1H), 8.09 (s, 1H), 7.92 (s, 1H), 7.81-7.65 (m, 1H), 7.48 (d, 1H), 7.36 (d, 1H), 3.64 (s, 3H), 3.40-3.23 (m, 2H), 1.15 (t, 3H).

Example 77

3-Methyl-2-(6-trifluoromethoxy-benzothiazol-2-ylamino)-3H-imidazo[4,5-b]pyridine-6-carboxylic acid (2-morpholin-4-yl-ethyl)-amide 3-Methyl-2-(6-trifluoromethoxy-benzothiazol-2-ylamino)-3H-imidazo[4,5-b]pyridine-6-carboxylic acid (2-morpholin-4-yl-ethyl)-amide (28 mg) was prepared by following General Procedure F starting from 3-methyl-2-(6-trifluoromethoxy-benzo-thiazol-2-ylamino)-3H-imidazo[4,5-b]pyridine-6-carboxylic acid (75 mg), 4-(2-aminoethyl)morpholine (26 mg), HBTU (83 mg), and DIEA (48 uL). LC/MS: m/z 466.8. $^1$H NMR (DMSO-d$_6$, 400 MHz): δ 12.39 (bs, 1H), 8.48 (bs, 1H), 8.09 (s, 1H), 7.94 (d, 1H), 7.81-7.66 (m, 1H), 7.51 (d, 1H), 7.35 (d, 1H), 3.83-3.23 (m, 11H), 2.51-2.48 (m, 4H).

Example 78

3-Methyl-2-(6-trifluoromethoxy-benzothiazol-2-ylamino)-3H-imidazo[4,5-b]pyridine-6-carboxylic acid (2-hydroxy-propyl)-amide 3-Methyl-2-(6-trifluoromethoxy-benzothiazol-2-ylamino)-3H-imidazo[4,5-b]pyridine-6-carboxylic acid (2-hydroxy-propyl)-amide (56 mg) was prepared by following General Procedure F starting from 3-methyl-2-(6-trifluoromethoxy-benzothiazol-2-ylamino)-3H-imidazo[4,5-b]pyridine-6-carboxylic acid (75 mg), 1-amino-2-propanol (15 mg), HBTU (83 mg), and DIEA (48 uL). LC/MS: m/z 466.7. $^1$H NMR (DMSO-d$_6$, 400 MHz): δ 8.36 (s, 1H), 8.10 (s, 1H), 7.92 (s, 1H), 7.80 (d, 1H), 7.73 (d, 1H), 7.49 (d, 1H), 7.36 (d, 1H), 4.77 (d, 1H), 3.89-3.77 (m, 1H), 3.64 (s, 3H), 3.27-3.16 (m, 2H), 1.10 (d, 3H).

Example 79

{[1-Methyl-2-(6-trifluoromethoxy-benzothiazol-2-ylamino)-1H-benzoimidazole-5-carbonyl]-amino}-acetic acid methyl ester {[1-Methyl-2-(6-trifluoromethoxy-benzothiazol-2-ylamino)-1H-benzoimidazole-5-carbonyl]-amino}-acetic acid methyl ester (36 mg) was prepared by following General Procedure F using 1-methyl-2-(6-trifluoromethoxy-benzothiazol-2-ylamino)-1H-benzimidazole-5-carboxylic acid (41 mg), glycine methyl ester (27 mg), HBTU (38 mg), and DIEA (0.1 ml). LC/MS: m/z 481. $^1$H NMR (DMSO-d$_6$, 400 MHz): δ 8.85 (br, 1H), 8.08 (s, 1H), 7.91 (m, 2H), 7.81-7.70 (m, 2H), 7.49 (d, 1H), 7.35 (d, 1H), 4.03 (d, 2H), 3.65 (s, 3H), and 3.62 (s, 3H).

Example 80

1-Methyl-2-(6-trifluoromethoxy-benzothiazol-2-ylamino)-1H-benzoimidazole-5-carboxylic acid dimethylcarbamoylmethyl-amide 1-Methyl-2-(6-trifluoromethoxy-benzothiazol-2-ylamino)-1H-benzoimidazole-5-carboxylic acid dimethylcarbamoylmethyl-amide (41 mg) was prepared by following General Procedure F using 1-methyl-2-(6-trifluoromethoxy-benzothiazol-2-ylamino)-1H-benzimidazole-5-carboxylic acid (41 mg), 2-amino-N,N-dimethyl-acetamide (0.33 ml), HBTU (38 mg), and DIEA (0.1 ml). LC/MS: m/z 494. $^1$H NMR (DMSO-d$_6$, 400 MHz): δ 8.42 (t, 1H), 8.09 (s, 1H), 7.90 (m, 1H), 7.78 (br, 1H), 7.72 (br, 1H), 7.48 (d, 1H), 7.44 (d, 1H), 7.34 (m, 1H), 4.11 (d, 2H), 3.63 (s, 3H), and 3.00 (d, 6H).

Example 81

1-Methyl-2-(6-trifluoromethoxy-benzothiazol-2-ylamino)-1H-benzoimidazole-5-carboxylic acid ((S)-1-ethylcarbamoyl-ethyl)-amide 1-Methyl-2-(6-trifluoromethoxy-benzothiazol-2-ylamino)-1H-benzoimidazole-5-carboxylic acid ((S)-1-ethylcarbamoyl-ethyl)-amide (37 mg) was prepared by following General Procedure F using 1-methyl-2-(6-trifluoromethoxy-benzothiazol-2-ylamino)-1H-benzimidazole-5-carboxylic acid (41 mg), (S)-2-amino-N-ethyl-propionamide (0.37 ml), HBTU (38 mg), and DIEA (0.1 ml). LC/MS: m/z 508. $^1$H NMR (DMSO-d$_6$, 400 MHz): δ 8.38 (d, 1H), 8.13 (s, 1H), 7.92 (s, 2H), 7.86 (br, 1H), 7.73 (br, 1H), 7.48 (d, 1H), 7.36 (d, 1H), 4.46 (p, 1H), 3.66 (s, 3H), 3.12-3.09 (m, 2H), 1.34 (d, 3H), and 1.04 (t, 3H), NH proton signal was not observed Example 82

1-Methyl-2-(6-trifluoromethoxy-benzothiazol-2-ylamino)-1H-benzoimidazole-5-carboxylic acid (2-dimethylamino-ethyl)-amide 1-Methyl-2-(6-trifluoromethoxy-benzothiazol-2-ylamino)-1H-benzoimidazole-5-carboxylic acid (2-dimethylamino-ethyl)-amide (42 mg) was prepared by following General Procedure F using 1-methyl-2-(6-trifluoromethoxy-benzothiazol-2-ylamino)-1H-benzimidazole-5-carboxylic acid (41 mg), N,N-dimethyl-ethylenediamine (0.29 ml), HBTU (38 mg), and DIEA (0.1 ml). LC/MS: m/z 480. $^1$H NMR (DMSO-d$_6$, 400 MHz): δ 8.16 (t, 1H), 7.81 (s, 1H), 7.61 (d, 1H), 7.49 (d, 1H), 7.29 (d, 1H), 7.15 (d, 1H), 7.07 (d, 1H), 3.56 (s, 3H), 3.32 (m, 2H), 2.85 (m, 2H), 2.41 (t, 1H), 2.17 (s, 6H).

Example 83

{[1-Methyl-2-(6-trifluoromethoxy-benzothiazol-2-ylamino)-1H-benzoimidazole-5-carbonyl]-amino}-acetic acid {[1-Methyl-2-(6-trifluoromethoxy-benzothiazol-2-ylamino)-1H-benzoimidazole-5-carbonyl]-amino}-acetic acid (211 mg) was prepared by following General Procedure E starting from {[1-Methyl-2-(6-trifluoromethoxy-benzothiazol-2-ylamino)-1H-benzoimidazole-5-carbonyl]-amino}-acetic acid methyl ester (240 mg), and LiOH (1.0 ml, 2.0 N solution in water). LC/MS: m/z 467.

Example 84

1-Methyl-2-(6-trifluoromethyl-benzothiazol-2-ylamino)-1H-benzoimidazole-5-carboxylic acid methylamide 1-Methyl-2-(6-trifluoromethyl-benzothiazol-2-ylamino)-1H-benzoimidazole-5-carboxylic acid methylamide (29 mg) was prepared by following General Procedure F using 1-methyl-2-(6-trifluoromethyl-benzothiazol-2-ylamino)-1H-benzoimidazole-5-carboxylic acid (39 mg), methylamine (0.2 ml, 2.0 M solution in THF), HBTU (38 mg), and DIEA (0.2 ml). LCMS: m/z 407; and $^1$H NMR (DMSO-$d_6$, 400 MHz): δ 8.52 (d, 1H), 7.93 (s, 1H), 7.85 (s, 1H), 7.70 (d, 1H), 7.54 (d, 1H), 7.30 (d, 1H), 7.22-7.16 (m, 2H), 3.57 (s, 3H), and 2.87 (d, 3H).

Example 85

1-Methyl-2-(6-trifluoromethyl-benzothiazol-2-ylamino)-1H-benzoimidazole-5-carboxylic acid (2-ethoxy-ethyl)-amide 1-Methyl-2-(6-trifluoromethyl-benzothiazol-2-ylamino)-1H-benzoimidazole-5-carboxylic acid (2-ethoxy-ethyl)-amide (36 mg) was prepared by following General Procedure F using 1-methyl-2-(6-trifluoromethyl-benzothiazol-2-ylamino)-1H-benzo-imidazole-5-carboxylic acid (39 mg), 2-ethoxy-ethylamine (0.1 ml), HBTU (38 mg), and DIEA (0.1 ml). LCMS: m/z 465; and $^1$H NMR (DMSO-$d_6$, 400 MHz): δ 8.40 (t, 1H), 7.99 (s, 1H), 7.82 (d, 1H), 7.66 (d, 1H), 7.44 (br, 2H), 7.36 (d, 1H), 7.30 (dd, 1H), 3.61 (s, 3H), 3.46 (q, 2H), 3.41 (t, 2H), 2.82 (m 2H), and 1.07 (t, 3H).

Example 86

2-(5,6-Difluoro-benzothiazol-2-ylamino)-1-methyl-1H-benzoimidazole-5-carboxylic acid methylamide 2-(5,6-Difluoro-benzothiazol-2-ylamino)-1-methyl-1H-benzoimidazole-5-carboxylic acid methylamide (26 mg) was prepared by following General Procedure F using 2-(5,6-Difluoro-benzothiazol-2-ylamino)-1-methyl-1H-benzoimidazole-5-carboxylic acid (36 mg), methylamine (0.2 ml, 2.0 M solution in THF), HBTU (38 mg), and DIEA (0.2 ml). LCMS: m/z 375; and $^1$H NMR (DMSO-$d_6$, 400 MHz): δ 8.30 (d, 1H), 8.04 (s, 1H), 7.93 (d, 1H), 7.60 (d, 1H), 7.49 (m, 2H), 7.29 (d, 1H), 3.62 (s, 3H), and 2.80 (d, 3H).

Example 87

2-(5,6-Difluoro-benzothiazol-2-ylamino)-1-methyl-1H-benzoimidazole-5-carboxylic acid (2-ethoxy-ethyl)-amide 2-(5,6-Difluoro-benzothiazol-2-ylamino)-1-methyl-1H-benzoimidazole-5-carboxylic acid (2-ethoxy-ethyl)-amide (31 mg) was prepared by following General Procedure F using 2-(5,6-Difluoro-benzothiazol-2-ylamino)-1-methyl-1H-benzoimidazole-5-carboxylic acid (36 mg), 2-ethoxy-ethyl amine (0.1 ml), HBTU (38 mg), and DIEA (0.2 ml). LCMS: m/z 433; and $^1$H NMR (DMSO-$d_6$, 400 MHz): δ 8.46 (m, 1H), 8.21 (s, 1H), 8.06 (s, 1H), 7.76 (m, 1H), 7.65 (d, 1H), 7.48 (m, 2H), 3.66 (s, 3H), 3.47 (t, 2H), 2.88 (m, 4H), and 1.09 (t, 3H).

Example 88

2-(6-Chloro-benzothiazol-2-ylamino)-1-methyl-1H-benzoimidazole-5-carboxylic acid methylamide 1-Methyl-2-(6-chloro-benzothiazol-2-ylamino)-1H-benzoimidazole-5-carboxylic acid methylamide (30 mg) was prepared by following General Procedure F using 1-methyl-2-(6-chloro-benzothiazol-2-ylamino)-1H-benzoimidazole-5-carboxylic acid (36 mg), methylamine (0.2 ml, 2.0 M solution in THF), HBTU (38 mg), and DIEA (0.2 ml). LCMS: m/z 373; and $^1$H NMR (DMSO-$d_6$, 400 MHz): δ 9.63 (d, 1H), 8.24 (d, 1H), 7.84 (m, 1H), 7.71 (t, 1H) 7.52 (d, 1H), 7.22 (m 2H), 5.24 (m, 1H), 3.65 (s, 3H), and 2.81 (d, 3H).

Example 89

2-(6-Chloro-benzothiazol-2-ylamino)-1-methyl-1H-benzoimidazole-5-carboxylic acid (2-ethoxy-ethyl)-amide 1-Methyl-2-(6-chloro-benzothiazol-2-ylamino)-1H-benzoimidazole-5-carboxylic acid (2-ethoxy-ethyl)-amide (33 mg) was prepared by following General Procedure F using 1-methyl-2-(6-chloro-benzothiazol-2-ylamino)-1H-benzoimidazole-5-carboxylic acid (36 mg), 2-ethoxy-ethylamine (0.1 ml), HBTU (38 mg), and DIEA (0.1 ml). LCMS: m/z 431; and $^1$H NMR (DMSO-$d_6$, 400 MHz): δ 8.26 (t, 1H), 7.80 (s, 1H), 7.65 (t, 1H), 7.56 (br, 2H), 7.48 (d, 1H), 7.18 (m, 1H), 7.14 (d, 1H), 3.54 (s, 3H), 3.46 (q, 2H), 3.38 (m 2H), 3.24 (t, 2H), and 1.08 (t, 3H).

Example 90

1-Methyl-2-(6-trifluoromethoxy-benzothiazol-2-ylamino)-1H-benzoimidazole-5-carboxylic acid (1-methanesulfonyl-piperidin-4-yl)-amide 1-Methyl-2-(6-trifluoromethoxy-benzothiazol-2-ylamino)-1H-benzoimidazole-5-carboxylic acid (1-methanesulfonyl-piperidin-4-yl)-amide (42 mg) was prepared by following General Procedure F using 1-methyl-2-(6-trifluoromethoxy-benzothiazol-2-ylamino)-1H-benzimidazole-5-carboxylic acid (41 mg), 1-methanesulfonyl-piperidin-4-ylamine (60 mg), HBTU (38 mg), and DIEA (0.1 ml). LC/MS: m/z 570. $^1$H NMR (DMSO-$d_6$, 400 MHz): δ 8.32 (br, 1H), 8.07 (s, 1H), 7.89 (s, 1H), 7.74 (br, 1H), 7.46 (d, 1H), 7.34 (d, 1H), 3.92 (br, 1H), 3.63 (s, 3H), 3.58 (m, 2H), 2.87 (s, 3H), 2.82 (m, 2H), 1.83 (m, 2H), and 1.62 (m, 2H), 2 —NH proton signals were not observed.

Example 91

{[1-Methyl-2-(6-trifluoromethoxy-benzothiazol-2-ylamino)-1H-benzoimidazole-5-carbonyl]-amino}-acetic acid tert-butyl ester {[1-Methyl-2-(6-trifluoromethoxy-benzothiazol-2-ylamino)-1H-benzoimidazole-5-carbonyl]-amino}-acetic acid tert-butyl ester (41 mg) was prepared by following General Procedure F using 1-methyl-2-(6-trifluoromethoxybenzothiazol-2-ylamino)-1H-benzimidazole-5-carboxylic acid (41 mg), glycine-tert-butyl ester (44 mg), HBTU (38 mg), and DIEA (0.1 ml). LC/MS: m/z 523. $^1$H NMR (DMSO-d$_6$, 400 MHz): δ 8.76 (t, 1H), 8.20 (br, 1H), 8.12 (m, 1H), 8.05 (s, 1H), 7.88 (d, 1H), 7.73 (d, 1H), 7.46 (d, 1H), 7.31 (d, 1H), 3.90 (d, 2H), 3.65 (s, 3H), and 1.42 (s, 9H).

Example 92

4-{[1-Methyl-2-(6-trifluoromethoxy-benzothiazol-2-ylamino)-1H-benzoimidazole-5-carbonyl]-amino}-piperidine-1-carboxylic acid tert-butyl ester 4-{[1-Methyl-2-(6-trifluoromethoxy-benzothiazol-2-ylamino)-1H-benzoimidazole-5-carbonyl]-amino}-piperidine-1-carboxylic acid tert-butyl ester (46 mg) was prepared by following General Procedure F using 1-methyl-2-(6-trifluoromethoxy-benzothiazol-2-ylamino)-1H-benzimidazole-5-carboxylic acid (41 mg), 4-amino-piperidine-1-carboxylic acid tert-butyl ester (67 mg), HBTU (38 mg), and DIEA (0.1 ml). LC/MS: m/z 592. $^1$H NMR (DMSO-d$_6$, 400 MHz): δ 8.26 (d, 1H), 8.08 (s, 1H), 7.91 (s, 1H), 7.74 (br, 1H), 7.47 (d, 1H), 7.35 (d, 1H), 3.97 (br, 1H), 3.91 (m, 2H), 3.66 (s, 3H), 2.82 (m, 2H), 1.81 (m, 2H), 1.42 (s, 9H), and 1.41 (m, 2H), 2 —NH proton signals were not observed.

Example 93

1-Methyl-2-(6-trifluoromethoxy-benzothiazol-2-ylamino)-1H-benzoimidazole-5-carboxylic acid piperidin-4-ylamide hydrochloride 1-Methyl-2-(6-trifluoromethoxy-benzothiazol-2-ylamino)-1H-benzoimidazole-5-carboxylic acid piperidin-4-ylamide hydrochloride (15 mg) was prepared by following General Procedure L using 4-{[1-methyl-2-(6-trifluoromethoxy-benzothiazol-2-ylamino)-1H-benzoimidazole-5-carbonyl]-amino}-piperidine-1-carboxylic acid tert-butyl ester (30 mg), and hydrochloric acid (0.1 ml, 4.0 N solution in dioxane). LC/MS: m/z 492. $^1$H NMR (DMSO-d$_6$, 400 MHz): δ 9.21 (br, 1H), 9.00 (br, 1H), 8.42 (m, 1H), 8.06 (s, 1H), 7.90 (s, 1H), 7.72 (br, 1H), 7.45 (d, 1H), 7.36 (d, 1H), 3.52 (s, 3H), 3.32 (m, 4H), 2.92 (q, 4H), and 1.79 (m, 2H).

Example 94

3-{[1-Methyl-2-(6-trifluoromethoxy-benzothiazol-2-ylamino)-1H-benzoimidazole-5-carbonyl]-amino}-piperidine-1-carboxylic acid tert-butyl ester 3-{[1-Methyl-2-(6-trifluoromethoxy-benzothiazol-2-ylamino)-1H-benzoimidazole-5-carbonyl]-amino}-piperidine-1-carboxylic acid tert-butyl ester (44 mg) was prepared by following General Procedure F using 1-methyl-2-(6-trifluoromethoxy-benzothiazol-2-ylamino)-1H-benzimidazole-5-carboxylic acid (41 mg), 3-amino-piperidine-1-carboxylic acid tert-butyl ester (67 mg), HBTU (38 mg), and DIEA (0.1 ml). LC/MS: m/z 592. $^1$H NMR (DMSO-d$_6$, 400 MHz): δ 8.22 (m, 1H), 8.06 (s, 1H), 7.87 (s, 1H), 7.73 (br, 1H), 7.53 (br, 1H), 7.43 (d, 1H), 7.32 (d, 1H), 3.82 (br, 1H), 3.65 (s, 3H), 3.20 (m, 2H), 2.80 (m, 2H), 1.81 (m, 1H), 1.39 (s, 9H) and 1.03 (d, 4H).

Example 95

1-Methyl-2-(6-trifluoromethoxy-benzothiazol-2-ylamino)-1H-benzoimidazole-5-carboxylic acid piperidin-3-ylamide hydrochloride 1-Methyl-2-(6-trifluoromethoxy-benzothiazol-2-ylamino)-1H-benzoimidazole-5-carboxylic acid piperidin-3-ylamide hydrochloride (13 mg) was prepared by following General Procedure L using 3-{[1-methyl-2-(6-trifluoromethoxy-benzothiazol-2-ylamino)-1H-benzoimidazole-5-carbonyl]-amino}-piperidine-1-carboxylic acid tert-butyl ester (30 mg), and hydrochloric acid (0.1 ml, 4.0 N solution dioxane). LC/MS: m/z 492.

Example 96

1-Methyl-2-(6-trifluoromethoxy-benzothiazol-2-ylamino)-1H-benzoimidazole-5-carboxylic acid (thiazol-2-ylmethyl)-amide 1-Methyl-2-(6-trifluoromethoxy-benzothiazol-2-ylamino)-1H-benzoimidazole-5-carboxylic acid (thiazol-2-ylmethyl)-amide (44 mg) was prepared by following General Procedure F using 1-methyl-2-(6-trifluoromethoxy-benzothiazol-2-ylamino)-1H-benzimidazole-5-carboxylic acid (41 mg), 2-aminomethyl-thiazole (38 mg), HBTU (38 mg), and DIEA (0.1 ml). LC/MS: m/z 506. $^1$H NMR (DMSO-d$_6$, 400 MHz): δ 9.36 (br, 1H), 8.13 (s, 1H), 7.93 (s, 1H), 7.82 (br, 1H), 7.75 (d, 1H), 7.63 (d, 1H), 7.54 (d, 1H), 7.36 (d, 1H), 4.77 (d, 2H), and 3.67 (s, 3H).

Example 97

3-{[1-Methyl-2-(6-trifluoromethoxy-benzothiazol-2-ylamino)-1H-benzoimidazole-5-carbonyl]-amino}-propionic acid methyl ester 3-{[1-Methyl-2-(6-trifluoromethoxy-benzothiazol-2-ylamino)-1H-benzoimidazole-5-carbonyl]-amino}-propionic acid methyl ester (33 mg) was prepared by following General Procedure F using 1-methyl-2-(6-trifluoromethoxy-benzothiazol-2-ylamino)-1H-benz-imidazole-5-carboxylic acid (41 mg), 3-amino-propionic acid methyl ester (35 mg), HBTU (38 mg), and DIEA (0.1 ml). LC/MS: m/z 495. $^1$H NMR (DMSO-d$_6$, 400 MHz): δ 8.53 (t, 1H), 8.12 (br, 1H), 8.08 (s, 1H), 7.91 (s, 1H), 7.42 (m, 2H), 7.48 (d, 1H), 7.38 (d, 1H), 3.65 (s, 3H), 3.62 (s, 3H), 3.04 (m, 2H), and 2.62 (t, 2H).

Example 98

3-{[2-(6-Trifluoromethoxy-benzothiazol-2-ylamino)-1-methyl-1H-benzimidazole-5-carbonyl]-amino}-propionic acid 3-{[2-(6-Trifluoromethoxy-benzothiazol-2-ylamino)-1-methyl-1H-benzimidazole-5-carbonyl]-amino}-propionic acid (200 mg) was prepared by following General Procedure E starting from 3-{[2-(6-trifluoromethoxy-benzothiazol-2-ylamino)-1-methyl-1H-benz-imidazole-5-carbonyl]-amino}-propionic acid methyl ester (247 mg), and LiOH (1.0 ml, 2.0 N solution in water). LC/MS: m/z 481. $^1$H NMR (DMSO-d$_6$, 400 MHz): δ 8.51 (t, 1H), 8.10 (br, 1H), 8.06 (s, 1H), 7.92 (s, 1H), 7.75 (d, 1H), 7.64 (br, 1H), 7.46 (d, 1H), 7.34 (d, 1H), 3.63 (s, 3H), 3.46 (m, 2H), and 2.58 (t, 2H), —COO$\underline{H}$ proton signal was not observed.

Example 99

1-Methyl-2-(5-trifluoromethoxy-benzothiazol-2-ylamino)-1H-benzoimidazole-5-carboxylic acid methyl ester 4-Methylamino-3-nitro-benzoic acid methyl ester (822 mg) was prepared by following General Procedure A starting from methyl 4-chloro-3-nitrobenzoate (1.0 g) and methylamine (2 M in THF, 6.95 mL) in DMF. The crude product was used in the next step without further purification.

3-amino-4-methylamino-benzoic acid methyl ester (677 mg) was prepared by following General Procedure B starting from 4-methylamino-3-nitro-benzoic acid methyl ester (822 mg) and Pd/C (10% by weight, 82 mg). The crude product was used in the next step without further purification.

1-Methyl-2-(5-trifluoromethoxy-benzothiazol-2-ylamino)-1H-benzoimidazole-5-carboxylic acid methyl ester (1.35 g) was prepared by following General Procedure D starting from 3-amino-4-methylamino-benzoic acid methyl ester (0.9 g), 2-amino-5-(trifluoromethoxy)benzothiazole (1.17 g), 1,1'-thiocarbonyldiimidazole (1.07 g), and EDC (1.15 g). LC/MS: m/z 424. $^1$H NMR (DMSO-$d_6$, 400 MHz): δ 8.16 (s, 1H), 7.92 (s, 1H), 7.85 (br, 1H), 7.78-7.63 (m, 1H), 7.50 (d, 1H), 7.36 (d, 2H), 3.66 (s, 3H), and 3.58 (s, 3H).

Example 100

1-Methyl-2-(6-trifluoromethoxy-benzothiazol-2-ylamino)-1H-benzoimidazole-5-carboxylic acid (2-acetylamino-ethyl)-amide 1-Methyl-2-(6-trifluoromethoxy-benzothiazol-2-ylamino)-1H-benzoimidazole-5-carboxylic acid (2-acetylamino-ethyl)-amide (44 mg) was prepared by following General Procedure F using 1-methyl-2-(6-trifluoromethoxy-benzothiazol-2-ylamino)-1H-benzimidazole-5-carboxylic acid (41 mg), N-(2-amino-ethyl)-acetamide (34 mg), HBTU (38 mg), and DIEA (0.1 ml). LC/MS: m/z 494. $^1$H NMR (DMSO-$d_6$, 400 MHz): δ 8.40 (s, 1H), 7.98 (m, 2H), 7.81 (s, 1H), 7.64 (d, 1H), 7.51 (br, 1H), 7.35 (m, 1H), 7.25 (d, 1H), 3.62 (s, 3H), 3.22 (t, 4H), and 1.81 (s, 3H), —N$\underline{H}$ proton signal was not observed.

Example 101

1-Methyl-2-(6-trifluoromethoxy-benzothiazol-2-ylamino)-1H-benzoimidazole-5-carboxylic acid (2-methylsulfanyl-ethyl)-amide 1-Methyl-2-(6-trifluoromethoxy-benzothiazol-2-ylamino)-1H-benzoimidazole-5-carboxylic acid (2-methylsulfanyl-ethyl)-amide (82 mg) was prepared by following General Procedure F using 1-methyl-2-(6-trifluoromethoxy-benzothiazol-2-ylamino)-1H-benzimidazole-5-carboxylic acid (82 mg), 2-methylthio-ethylamine (30 mg), HBTU (76 mg), and DIEA (0.2 ml). LC/MS: m/z 483. $^1$H NMR (DMSO-$d_6$, 400 MHz): δ 8.58 (s, 1H), 8.09 (s, 1H), 7.91 (m, 1H), 7.47 (m, 2H), 7.48 (d, 1H), 7.37 (d, 1H), 3.64 (s, 3H), 3.48 (q, 2H), 2.68 (t, 2H), and 2.12 (s, 3H), —N$\underline{H}$ proton signal was not observed.

Example 102

1-Methyl-2-(6-trifluoromethoxy-benzothiazol-2-ylamino)-1H-benzoimidazole-5-carboxylic acid (2-methanesulfonyl-ethyl)-amide 1-Methyl-2-(6-trifluoromethoxy-benzothiazol-2-ylamino)-1H-benzoimidazole-5-carboxylic acid (2-methylsulfonyl-ethyl)-amide (37 mg) was prepared by following General Procedure M using 1-methyl-2-(6-trifluoromethoxy-benzothiazol-2-ylamino)-1H-benzoimidazole-5-carboxylic acid (2-methylsulfanyl-ethyl)-amide (48 mg), and peracetic acid (0.1 ml, 32 wt % solution in acetic acid). LC/MS: m/z 515. $^1$H NMR (DMSO-$d_6$, 400 MHz): δ 8.68 (t, 1H), 8.09 (s, 1H), 7.92 (s, 1H), 7.75 (m, 2H), 7.52 (d, 1H), 7.44 (d, 1H), 7.37 (d, 1H), 3.72 (m, 2H), 3.63 (s, 3H), 3.40 (t, 2H), and 3.06 (s, 3H).

Example 103

(2-{[1-Methyl-2-(6-trifluoromethoxy-benzothiazol-2-ylamino)-1H-benzoimidazole-5-carbonyl]-amino}-ethyl)-carbamic acid tert-butyl ester (2-{[1-Methyl-2-(6-trifluoromethoxy-benzothiazol-2-ylamino)-1H-benzoimidazole-5-carbonyl]-amino}-ethyl)-carbamic acid tert-butyl ester (92 mg) was prepared by following General Procedure F using 1-methyl-2-(6-trifluoromethoxy-benzothiazol-2-ylamino)-1H-benzimidazole-5-carboxylic acid (82 mg), (2-amino-ethyl)-carbamic acid tert-butyl ester (64 mg), HBTU (76 mg), and DIEA (0.2 ml). LC/MS: m/z 552. $^1$H NMR (DMSO-$d_6$, 400 MHz): δ 8.40 (br, 1H), 8.06 (s, 1H), 7.91 (s, 1H), 7.73 (m, 2H), 7.46 (d, 1H), 7.34 (d, 1H), 6.91 (t, 1H), 4.24 (t, 2H), 3.64 (s, 3H), 3.14-3.09 (q, 2H), and 1.36 (s, 9H), —N$\underline{H}$ proton signal was not observed.

Example 104

1-Methyl-2-(6-trifluoromethoxy-benzothiazol-2-ylamino)-1H-benzoimidazole-5-carboxylic acid (2-amino-ethyl)-amide hydrochloride 1-Methyl-2-(6-trifluoromethoxy-benzothiazol-2-ylamino)-1H-benzoimidazole-5-carboxylic acid (2-amino-ethyl)-amide hydrochloride (27 mg) was prepared by following General Procedure L using (2-{[1-methyl-2-(6-trifluoromethoxy-benzothiazol-2-ylamino)-1H-benzoimidazole-5-carbonyl]-amino}-ethyl)-carbamic acid tert-butyl ester (55 mg), and hydrochloric acid (0.1 ml, 4.0 N solution dioxane). LC/MS: m/z 452. $^1$H NMR (DMSO-$d_6$, 400 MHz): δ 8.63 (br, 1H), 8.42 (br, 1H), 8.07 (s, 1H), 7.90 (s, 1H), 7.71 (m, 2H), 7.44 (d, 1H), 7.35 (d, 1H), 4.19 (t, 2H), 3.64 (s, 3H), and 3.08 (m, 2H), 2 —N$\underline{H}$ proton signals were not observed.

Example 105

1-Methyl-2-(6-trifluoromethoxy-benzothiazol-2-ylamino)-1H-benzoimidazole-5-carboxylic acid (2-methylamino-ethyl)-amide 1-Methyl-2-(6-trifluoromethoxy-benzothiazol-2-ylamino)-1H-benzoimidazole-5-carboxylic acid (2-methylamino-ethyl)-amide (28 mg) was prepared by following General Procedure F using 1-methyl-2-(6-trifluoromethoxy-benzothiazol-2-ylamino)-1H-benzimidazole-5-carboxylic acid (41 mg), N-methyl-ethylendiamine (25 mg), HBTU (38 mg), and DIEA (0.1 ml). LC/MS: m/z 466. $^1$H NMR (DMSO-d$_6$, 400 MHz): δ 8.43 (br, 1H), 8.20 (br, 1H), 7.95 (s, 1H), 7.88 (m, 1H), 7.69 (m, 2H), 7.56 (d, 1H), 7.38 (d, 1H), 7.23 (d, 1H), 3.59 (s, 3H), 3.44 (m, 2H), 2.98 (m, 2H), and 2.70 (d, 3H).

Example 106

1-Methyl-2-(6-trifluoromethoxy-benzothiazol-2-ylamino)-1H-benzimidazole-5-carboxylic acid trimethylhydrazide 1-Methyl-2-(6-trifluoromethoxy-benzothiazol-2-ylamino)-1H-benzimidazole-5-carboxylic acid trimethylhydrazide (33 mg) was prepared by following General Procedure F using 1-methyl-2-(6-trifluoromethoxy-benzothiazol-2-ylamino)-1H-benzimidazole-5-carboxylic acid (41 mg), N,N,N'-trimethylhydrazine dihydrochloride (49 mg), HBTU (38 mg), and DIEA (0.1 ml). LC/MS: m/z 466.

Example 107

1-Methyl-2-(6-trifluoromethoxy-benzothiazol-2-ylamino)-1H-benzoimidazole-5-carboxylic acid (2-ethylsulfanyl-ethyl)-amide 1-Methyl-2-(6-trifluoromethoxy-benzothiazol-2-ylamino)-1H-benzoimidazole-5-carboxylic acid (2-ethylsulfanyl-ethyl)-amide (72 mg) was prepared by following General Procedure F using 1-methyl-2-(6-trifluoromethoxy-benzothiazol-2-ylamino)-1H-benz-imidazole-5-carboxylic acid (82 mg), 2-ethylthio-ethylamine (34 mg), HBTU (76 mg), and DIEA (0.2 ml). LC/MS: m/z 497.

Example 108

1-Methyl-2-(6-trifluoromethoxy-benzothiazol-2-ylamino)-1H-benzoimidazole-5-carboxylic acid (3-methylsulfanyl-propyl)-amide 1-Methyl-2-(6-trifluoromethoxy-benzothiazol-2-ylamino)-1H-benzoimidazole-5-carboxylic acid (3-methylsulfanyl-propyl)-amide (69 mg) was prepared by following General Procedure F using 1-methyl-2-(6-trifluoromethoxy-benzothiazol-2-ylamino)-1H-benzimidazole-5-carboxylic acid (82 mg), 3-methylthio-propylamine (38 mg), HBTU (76 mg), and DIEA (0.2 ml). LC/MS: m/z 497.

Example 109

1-Methyl-2-(6-trifluoromethoxy-benzothiazol-2-ylamino)-1H-benzimidazole-5-carboxylic acid (2-ethanesulfonyl-ethyl)-amide 1-Methyl-2-(6-trifluoromethoxy-benzothiazol-2-ylamino)-1H-benzoimidazole-5-carboxylic acid (2-ethylsulfonyl-ethyl)-amide (36 mg) was prepared by following General Procedure M using 1-methyl-2-(6-trifluoromethoxy-benzothiazol-2-ylamino)-1H-benzo-imidazole-5-carboxylic acid (2-ethylsulfanyl-ethyl)-amide (50 mg), and peracetic acid (0.1 ml, 32 wt % solution in acetic acid). LC/MS: m/z 529. $^1$H NMR (DMSO-d$_6$, 400 MHz): δ 8.72 (br, 1H), 8.09 (d, 1H), 7.92 (m, 1H), 7.75 (t, 2H), 7.50 (m, 1H), 7.37 (d, 1H), 3.72 (m, 1H), 3.63 (s, 3H), 3.50 (m, 2H), 3.40 (t, 2H), 3.16 (q, 2H), and 1.24 (t, 3H).

Example 110

1-Methyl-2-(6-trifluoromethoxy-benzothiazol-2-ylamino)-1H-benzimidazole-5-carboxylic acid (3-methanesulfonyl-propyl)-amide 1-Methyl-2-(6-trifluoromethoxy-benzothiazol-2-ylamino)-1H-benzoimidazole-5-carboxylic acid (3-methanesulfonyl-propyl)-amide (37 mg) was prepared by following General Procedure M using 1-methyl-2-(6-trifluoromethoxy-benzothiazol-2-ylamino)-1H-benzoimidazole-5-carboxylic acid (3-methylsulfanyl-propyl)-amide (48 mg), and peracetic acid (0.1 ml, 32 wt % solution in acetic acid). LC/MS: m/z 529. $^1$H NMR (DMSO-d$_6$, 400 MHz): δ 12.40 (br, 1H), 8.56 (t, 1H), 8.10 (d, 1H), 7.91 (s, 1H), 7.79 (d, 1H), 7.73 (d, 1H), 7.50 (d, 1H), 7.37 (d, 1H), 3.64 (s, 3H), 3.19 (t, 2H), 2.99 (s, 3H), 1.99 (t, 2H), and 1.31 (t, 2H).

Example 111

2-(5-Fluoro-benzothiazol-2-ylamino)-1-methyl-1H-benzoimidazole-5-carboxylic acid methyl ester 4-Methylamino-3-nitro-benzoic acid methyl ester (822 mg) was prepared by following General Procedure A using methyl 4-chloro-3-nitrobenzoate (1.0 g) and methylamine (2 M in THF, 6.95 mL, 13.9) in DMF (5 mL). The crude product was used in the next step without further purification.

3-amino-4-methylamino-benzoic acid methyl ester (677 mg) was prepared by following General Procedure B starting from 4-methylamino-3-nitro-benzoic acid methyl ester (822 mg) and Pd/C (10% by weight). The crude product was used in the next step without further purification.

1-Methyl-2-(5-fluoro-benzothiazol-2-ylamino)-1H-benzoimidazole-5-carboxylic acid methyl ester (1.16 g) was prepared by following General Procedure D starting from 3-amino-4-methylamino-benzoic acid methyl ester (0.9 g), 2-amino-5-fluoro-benzothiazole (0.84 g), 1,1'-thiocarbonyldiimidazole (1.07 g), and EDC (1.15 g). LC/MS: m/z 358.

Example 112

2-(6-Fluoro-benzothiazol-2-ylamino)-1-methyl-1H-benzoimidazole-5-carboxylic acid methyl ester 4-Methylamino-3-nitro-benzoic acid methyl ester (822 mg) was prepared by following General Procedure A using methyl 4-chloro-3-nitrobenzoate (1.0 g) and methylamine (2 M in THF, 6.95 mL) in DMF (5 mL). The crude product was used in the next step without further purification.

3-amino-4-methylamino-benzoic acid methyl ester (677 mg) was prepared by following General Procedure B starting from 4-methylamino-3-nitro-benzoic acid methyl ester (822 mg) and Pd/C (10% by weight, 82 mg). The crude product was used in the next step without further purification.

1-Methyl-2-(6-fluoro-benzothiazol-2-ylamino)-1H-benzoimidazole-5-carboxylic acid methyl ester (1.26 g) was prepared by following General Procedure D starting from 3-amino-4-methylamino-benzoic acid methyl ester (0.9 g), 2-amino-6-fluoro-benzo-thiazole (0.84 g), 1,1'-thiocarbonyldiimidazole (1.07 g), and EDC (1.15 g). LC/MS: m/z 358.

Example 113

2-(6-Methanesulfonyl-benzothiazol-2-ylamino)-1-methyl-1H-benzoimidazole-5-carboxylic acid methyl ester 4-Methylamino-3-nitro-benzoic acid methyl ester (822 mg) was prepared by following General Procedure A using methyl 4-chloro-3-nitrobenzoate (1.0 g) and methylamine (2 M in THF, 6.95 mL) in DMF (5 mL). The crude product was used in the next step without further purification.

3-amino-4-methylamino-benzoic acid methyl ester (677 mg) was prepared by following General Procedure B starting from 4-methylamino-3-nitro-benzoic acid methyl ester (822 mg) and Pd/C (10% by weight, 82 mg). The crude product was used in the next step without further purification.

2-(6-Methanesulfonyl-benzothiazol-2-ylamino)-1-methyl-1H-benzoimidazole-5-carboxylic acid methyl ester (1.64 g) was prepared by following General Procedure D starting from 3-amino-4-methylamino-benzoic acid methyl ester (0.9 g), 2-amino-6-methanesulfonyl-benzothiazole (1.14 g), 1,1'-thiocarbonyldiimidazole (1.07 g), and EDC (1.15 g). LC/MS: m/z 418.

Example 114

1-Methyl-2-(6-methyl-benzothiazol-2-ylamino)-1H-benzoimidazole-5-carboxylic acid methyl ester 4-Methylamino-3-nitro-benzoic acid methyl ester (822 mg) was prepared by following General Procedure A using methyl 4-chloro-3-nitrobenzoate (1.0 g) and methylamine (2 M in THF, 6.95 mL) in DMF (5 mL). The crude product was used in the next step without further purification.

3-amino-4-methylamino-benzoic acid methyl ester (677 mg) was prepared by following General Procedure B starting from 4-methylamino-3-nitro-benzoic acid methyl ester (822 mg) and Pd/C (10% by weight, 82 mg). The crude product was used in the next step without further purification.

1-Methyl-2-(6-methyl-benzothiazol-2-ylamino)-1H-benzoimidazole-5-carboxylic acid methyl ester (1.47 g) was prepared by following General Procedure D starting from 3-amino-4-methylamino-benzoic acid methyl ester (0.9 g), 2-amino-6-methyl-benzothiazole (0.82 g), 1,1'-thiocarbonyldiimidazole (1.07 g), and EDC (1.15 g). LC/MS: m/z 354.

Example 115

1-Methyl-2-(5-trifluoromethoxy-benzothiazol-2-ylamino)-1H-benzimidazole-5-carboxylic acid methylamide 1-Methyl-2-(5-trifluoromethoxy-benzothiazol-2-ylamino)-1H-benzimidazole-5-carboxylic acid methylamide (27 mg) was prepared by following General Procedure F using 1-methyl-2-(5-trifluoromethoxy-benzothiazol-2-ylamino)-1H-benz-imidazole-5-carboxylic acid (41 mg), methylamine (0.2 ml, 2.0 M solution in THF), HBTU (38 mg), and DIEA (0.1 ml). LCMS: m/z 423.

Example 116

1-Methyl-2-(5-trifluoromethoxy-benzothiazol-2-ylamino)-1H-benzimidazole-5-carboxylic acid (2-methoxy-ethyl)-amide 1-Methyl-2-(5-trifluoromethoxy-benzothiazol-2-ylamino)-1H-benzimidazole-5-carboxylic acid (2-methoxy-ethyl)-amide (35 mg) was prepared by following General Procedure F using 1-methyl-2-(5-trifluoromethoxy-benzothiazol-2-ylamino)-1H-benz-imidazole-5-carboxylic acid (41 mg), 2-methoxy-ethylamine (0.1 ml), HBTU (38 mg), and DIEA (0.1 ml). LCMS: m/z 467.

Example 117

2-(5-Fluoro-benzothiazol-2-ylamino)-1-methyl-1H-benzimidazole-5-carboxylic acid 2-(5-Fluoro-benzothiazol-2-ylamino)-1-methyl-1H-benzimidazole-5-carboxylic acid (1.53 g) was prepared by following General Procedure E starting from 2-(5-fluoro-benzothiazol-2-ylamino)-1-methyl-1H-benzimidazole-5-carboxylic acid methyl ester (1.78 g), and LiOH (10.0 ml, 2.0 N solution in water). LC/MS: m/z 344.

Example 118

2-(6-Fluoro-benzothiazol-2-ylamino)-1-methyl-1H-benzimidazole-5-carboxylic acid 2-(6-Fluoro-benzothiazol-2-ylamino)-1-methyl-1H-benzimidazole-5-carboxylic acid (1.49 g) was prepared by following General Procedure E starting from 2-(6-fluoro-benzothiazol-2-ylamino)-1-methyl-1H-benzimidazole-5-carboxylic acid methyl ester (1.78 g), and LiOH (10.0 ml, 2.0 N solution in water). LC/MS: m/z 344.

Example 119

2-(6-Methanesulfonyl-benzothiazol-2-ylamino)-1-methyl-1H-benzimidazole-5-carboxylic acid 2-(6-Methanesulfonyl-benzothiazol-2-ylamino)-1-methyl-1H-benzimidazole-5-carboxylic acid (1.75 g) was prepared by following General Procedure E starting from 2-(6-methanesulfonyl-benzothiazol-2-ylamino)-1-methyl-1H-benzimidazole-5-carboxylic acid methyl ester (2.08 g), and LiOH (10.0 ml, 2.0 N solution in water). LC/MS: m/z 404.

Example 120

1-Methyl-2-(6-methyl-benzothiazol-2-ylamino)-1H-benzimidazole-5-carboxylic acid

1-Methyl-2-(6-methyl-benzothiazol-2-ylamino)-1H-benzimidazole-5-carboxylic acid (1.55 g) was prepared by following General Procedure E starting from 1-methyl-2-(6-methyl-benzothiazol-2-ylamino)-1H-benzimidazole-5-carboxylic acid methyl ester (1.76 g), and LiOH (10.0 ml, 2.0 N solution in water). LC/MS: m/z 340.

Example 121

1-Methyl-2-(6-trifluoromethoxy-benzothiazol-2-ylamino)-1H-benzimidazole-5-carboxylic acid (1,1-dioxo-tetrahydro-1λ6-thiophen-3-yl)-amide

1-Methyl-2-(6-trifluoromethoxy-benzothiazol-2-ylamino)-1H-benzimidazole-5-carboxylic acid (1,1-dioxo-tetrahydro-1$\lambda^6$-thiophen-3-yl)-amide (39 mg) was prepared by following General Procedure F using 1-methyl-2-(6-trifluoromethoxy-benzothiazol-2-ylamino)-1H-benzimidazole-5-carboxylic acid (41 mg), 1,1-dioxo-tetrahydro-1$\lambda^6$-thiophen-3-ylamine (30 mg), HBTU (38 mg), and DIEA (0.1 ml). LCMS: m/z 527; and $^1$H NMR (DMSO-$d_6$, 400 MHz): δ 8.72 (br, 1H), 8.09 (d, 1H), 7.92 (d, 1H), 7.78-7.63 (m, 2H), 7.48 (d, 1H), 7.34 (d, 1H), 4.72 (m, 1H), 3.62 (s, 3H), 3.52 (m, 1H), 3.38 (m, 1H), 3.20 (m, 1H), 3.08 (m, 1H), 2.43 (t, 2H), and 2.25 (m, 1H).

Example 122

2-(5-Fluoro-benzothiazol-2-ylamino)-1-methyl-1H-benzimidazole-5-carboxylic acid methylamide

2-(5-Fluoro-benzothiazol-2-ylamino)-1-methyl-1H-benzimidazole-5-carboxylic acid methylamide (24 mg) was prepared by following General Procedure F using 2-(5-fluoro-benzothiazol-2-ylamino)-1-methyl-1H-benzimidazole-5-carboxylic acid (34 mg), methylamine (0.2 ml, 2.0 M solution in THF), HBTU (38 mg), and DIEA (0.1 ml). LCMS: m/z 357.

Example 123

2-(5-Fluoro-benzothiazol-2-ylamino)-1-methyl-1H-benzimidazole-5-carboxylic acid (2-methoxy-ethyl)-amide

2-(5-Fluoro-benzothiazol-2-ylamino)-1-methyl-1H-benzimidazole-5-carboxylic acid (2-methoxy-ethyl)-amide (32 mg) was prepared by following General Procedure F using 2-(5-fluoro-benzothiazol-2-ylamino)-1-methyl-1H-benzimidazole-5-carboxylic acid (34 mg), 2-methoxy-ethylamine (0.1 ml), HBTU (38 mg), and DIEA (0.1 ml). LCMS: m/z 401; and $^1$H NMR (DMSO-$d_6$, 400 MHz): δ 8.46 (t, 1H), 8.05 (d, 1H), 7.95 (s, 1H), 7.79-7.71 (m, 2H), 7.42 (d, 1H), 7.30 (d, 1H), 6.99 (t, 1H), 3.65 (s, 3H), 3.51-3.42 (m, 2H), 0.3.36 (d, 2H), and 2.73 (s, 3H).

Example 124

2-(6-Fluoro-benzothiazol-2-ylamino)-1-methyl-1H-benzimidazole-5-carboxylic acid methylamide

2-(6-Fluoro-benzothiazol-2-ylamino)-1-methyl-1H-benzimidazole-5-carboxylic acid methylamide (26 mg) was prepared by following General Procedure F using 2-(6-fluoro-benzothiazol-2-ylamino)-1-methyl-1H-benzimidazole-5-carboxylic acid (34 mg), methylamine (0.2 ml, 2.0 M solution in THF), HBTU (38 mg), and DIEA (0.1 ml). LCMS: m/z 357. $^1$H NMR (DMSO-$d_6$, 400 MHz): δ 8.31 (m, 1H), 7.93 (d, 1H), 7.63 (d, 2H), 7.50-7.42 (m, 1H), 7.38-7.28 (m, 1H), 7.12 (t, 2H), 3.60 (s, 3H), and 2.78 (d, 3H).

Example 125

2-(6-Fluoro-benzothiazol-2-ylamino)-1-methyl-1H-benzimidazole-5-carboxylic acid (2-methoxy-ethyl)-amide

2-(6-Fluoro-benzothiazol-2-ylamino)-1-methyl-1H-benzimidazole-5-carboxylic acid (2-methoxy-ethyl)-amide (29 mg) was prepared by following General Procedure F using 2-(6-fluoro-benzothiazol-2-ylamino)-1-methyl-1H-benzimidazole-5-carboxylic acid (34 mg), 2-methoxy-ethylamine (0.1 ml), HBTU (38 mg), and DIEA (0.1 ml). LCMS: m/z 401; and $^1$H NMR (DMSO-$d_6$, 400 MHz): δ 8.44 (m, 1H), 8.06 (br, 1H), 7.76-7.70 (m, 2H), 7.66 (br, 1H), 7.45 (d, 1H), 7.20 (t, 1H), 3.61 (s, 3H), 3.44 (m, 4H), and 3.26 (s, 3H), —NH proton signal was not observed.

Example 126

2-(6-Methanesulfonyl-benzothiazol-2-ylamino)-1-methyl-1H-benzimidazole-5-carboxylic acid methylamide

2-(6-Methanesulfonyl-benzothiazol-2-ylamino)-1-methyl-1H-benzimidazole-5-carboxylic acid methylamide (34 mg) was prepared by following General Procedure F using 2-(6-methanosulfonyl-benzothiazol-2-ylamino)-1-methyl-1H-benzimidazole-5-carboxylic acid (40 mg), methylamine (0.2 ml, 2.0 M solution in THF), HBTU (38 mg), and DIEA (0.1 ml). LCMS: m/z 417; and $^1$H NMR (DMSO-$d_6$, 400 MHz): δ 8.45 (m, 1H), 8.04 (br, 1H), 8.00 (m, 1H), 7.93 (s, 1H), 7.71 (t, 2H), 7.43 (d, 1H), 7.18 (t, 1H), 3.63 (s, 3H), 3.27 (s, 3H), and 2.87 (s, 3H).

Example 127

2-(6-Methanesulfonyl-benzothiazol-2-ylamino)-1-methyl-1H-benzimidazole-5-carboxylic acid (2-methoxy-ethyl)-amide

2-(6-Methanesulfonyl-benzothiazol-2-ylamino)-1-methyl-1H-benzimidazole-5-carboxylic acid (2-methoxy-ethyl)-amide (33 mg) was prepared by following General Procedure F using 2-(6-methanesulfonyl-benzothiazol-2-ylamino)-1-methyl-1H-benz-imidazole-5-carboxylic acid (40 mg), 2-methoxy-ethylamine (0.1 ml), HBTU (38 mg), and DIEA (0.1 ml). LCMS: m/z 461; and $^1$H NMR (DMSO-$d_6$, 400 MHz): δ 8.36 (t, 1H), 8.14 (br, 1H), 7.94 (d, 2H), 7.66 (d, 1H), 7.59 (d, 1H), 7.44 (d, 1H), 7.25 (d, 1H), 3.61 (s, 3H), 3.45 (m, 4H), 3.27 (s, 3H), and 2.87 (s, 3H).

Example 128

2-(6-Methyl-benzothiazol-2-ylamino)-1-methyl-1H-benzimidazole-5-carboxylic acid methylamide

2-(6-Methyl-benzothiazol-2-ylamino)-1-methyl-1H-benzimidazole-5-carboxylic acid methylamide (26 mg) was prepared by following General Procedure F using 2-(6-methyl-benzothiazol-2-ylamino)-1-methyl-1H-benzimidazole-5-carboxylic acid (34 mg), methylamine (0.2 ml, 2.0 M solution in THF), HBTU (38 mg), and DIEA (0.1 ml). LCMS: m/z 353. $^1$H NMR (DMSO-$d_6$, 400 MHz): δ 8.32 (m, 1H), 8.00 (br, 1H), 7.66 (d, 1H), 7.55 (s, 2H), 7.38 (m, 2H), 7.14 (d, 1H), 3.63 (s, 3H), 2.87 (d, 3H), and 2.35 (s, 3H).

Example 129

2-(6-Methyl-benzothiazol-2-ylamino)-1-methyl-1H-benzimidazole-5-carboxylic acid (2-methoxy-ethyl)-amide 2-(6-Methyl-benzothiazol-2-ylamino)-1-methyl-1H-benzimidazole-5-carboxylic acid (2-methoxy-ethyl)-amide (29 mg) was prepared by following General Procedure F using 2-(6-methyl-benzothiazol-2-ylamino)-1-methyl-1H-benzimidazole-5-carboxylic acid (34 mg), 2-methoxy-ethylamine (0.1 ml), HBTU (38 mg), and DIEA (0.1 ml). LCMS: m/z 397.

Example 130

2-(6-Methanesulfonyl-benzothiazol-2-ylamino)-1-methyl-1H-benzimidazole-5-carboxylic acid (2-methylsulfanyl-ethyl)-amide 2-(6-Methanesulfonyl-benzothiazol-2-ylamino)-1-methyl-1H-benzimidazole-5-carboxylic acid (2-methylsulfanyl-ethyl)-amide (41 mg) was prepared by following General Procedure F using 2-(6-methanesulfonyl-benzothiazol-2-ylamino)-1-methyl-1H-benzimidazole-5-carboxylic acid (80 mg), 2-methylthio-ethylamine (0.2 ml), HBTU (76 mg), and DIEA (0.2 ml). LCMS: m/z 477.

Example 131

2-(6-Methanesulfonyl-benzothiazol-2-ylamino)-1-methyl-1H-benzimidazole-5-carboxylic acid (2-methylsulfonyl-ethyl)-amide 2-(6-Methanesulfonyl-benzothiazol-2-ylamino)-1-methyl-1H-benzimidazole-5-carboxylic acid (2-methylsulfonyl-ethyl)-amide (36 mg) was prepared by following General Procedure M using 2-(6-methanesulfonyl-benzothiazol-2-ylamino)-1-methyl-1H-benzimidazole-5-carboxylic acid (2-methylsulfanyl-ethyl)-amide (48 mg), and peracetic acid (0.1 ml, 32 wt % solution in acetic acid). LC/MS: m/z 509. $^1$H NMR (DMSO-$d_6$, 400 MHz): δ 8.68 (m, 2H), 8.35 (s 1H), 8.08 (br, 1H), 7.93 (s, 1H), 7.84 (m, 2H), 7.76 (br, 1H), 3.70 (m, 2H), 3.66 (s, 3H), 3.40 (t, 2H), 3.20 (s, 3H), and 2.87 (d, 3H).

Example 132

1-Methyl-2-(6-trifluoromethylsulfanyl-benzothiazol-2-ylamino)-1H-benzoimidazole-5-carboxylic acid methyl ester 4-Methylamino-3-nitro-benzoic acid methyl ester (822 mg) was prepared by following General Procedure A starting from methyl 4-chloro-3-nitrobenzoate (1.0 g) and methylamine (2.0 M in THF, 6.95 mL) in DMF (5 mL). The crude product was used in the next step without further purification.

3-amino-4-methylamino-benzoic acid methyl ester (677 mg) was prepared by following General Procedure B starting from 4-methylamino-3-nitro-benzoic acid methyl ester (822 mg) and Pd/C (10% by weight). The crude product was used in the next step without further purification.

1-Methyl-2-(6-trifluoromethylsulfanyl-benzothiazol-2-ylamino)-1H-benzo-imidazole-5-carboxylic acid methyl ester (1.43 g) was prepared by following General Procedure D starting from 3-amino-4-methylamino-benzoic acid methyl ester (0.9 g), 6-trifluoromethylsulfanyl-benzothiazol-2-ylamine (1.25 g), 1,1'-thiocarbonyldiimidazole (1.07 g), and EDC (1.15 g). LC/MS: m/z 440. $^1$H NMR (DMSO-$d_6$, 400 MHz): δ 8.23 (s, 2H), 7.89 (br, 1H), 7.76 (br, 1H), 7.69 (d, 2H), 7.54 (d, 1H), 3.88 (s, 3H), and 3.68 (s, 3H).

Example 133

2-(6-Chloro-benzothiazol-2-ylamino)-1-methyl-1H-benzimidazole-5-carboxylic acid dimethylcarbamoylmethyl-amide 2-(6-Chloro-benzothiazol-2-ylamino)-1-methyl-1H-benzimidazole-5-carboxylic acid dimethylcarbamoylmethyl-amide (33 mg) was prepared by following General Procedure F using 2-(6-chloro-benzothiazol-2-ylamino)-1-methyl-1H-benzimidazole-5-carboxylic acid (36 mg), 2-amino-N,N-dimethyl-acetamide acetic acid salt (48 mg), HBTU (38 mg), and DIEA (0.1 ml). LC/MS: m/z 444. $^1$H NMR (DMSO-$d_6$, 400 MHz): δ 11.70 (br, 1H), 8.44 (t, 1H), 8.11 (s, 1H), 7.94 (m, 1H), 7.80 (m, 1H), 7.66 (br, 1H), 7.50 (d, 1H), 7.38 (d, 1H), 4.12 (d, 2H), 3.61 (s, 3H), 3.03 (s, 3H), and 2.87 (s, 3H).

Example 134

1-Methyl-2-(6-trifluoromethyl-benzothiazol-2-ylamino)-1H-benzimidazole-5-carboxylic acid dimethylcarbamoylmethyl-amide 1-Methyl-2-(6-trifluoromethyl-benzothiazol-2-ylamino)-1H-benzimidazole-5-carboxylic acid dimethylcarbamoylmethyl-amide (38 mg) was prepared by following General Procedure F using 1-methyl-2-(6-trifluoromethyl-benzothiazol-2-ylamino)-1H-benzimidazole-5-carboxylic acid (39 mg), 2-amino-N,N-dimethyl-acetamide acetic acid salt (48 mg), HBTU (38 mg), and DIEA (0.1 ml). LC/MS: m/z 478. $^1$H NMR (DMSO-$d_6$, 400 MHz): δ 12.49 (br, 1H), 8.46 (t, 1H), 8.25 (s, 1H), 8.14 (s, 1H), 7.82 (m, 2H), 7.68 (m, 1H), 7.53 (d, 1H), 4.13 (d, 2H), 3.66 (s, 3H), 3.04 (s, 3H), and 2.87 (s, 3H).

Example 135

1-Methyl-2-(6-trifluoromethoxy-benzothiazol-2-ylamino)-1H-benzimidazole-5-carboxylic acid (2-dimethylcarbamoyl-ethyl)-amide 1-Methyl-2-(6-trifluoromethoxy-benzothiazol-2-ylamino)-1H-benzimidazole-5-carboxylic acid (2-dimethylcarbamoyl-ethyl)-amide (38 mg) was prepared by following General Procedure F using 3-{[1-methyl-2-(6-trifluoromethoxy-benzothiazol-2-ylamino)-1H-benzimidazole-5-carbonyl]-amino}-propionic acid (48 mg), dimethyl amine (0.3 ml, 1.0 M solution in THF), HBTU (38 mg), and DIEA (0.1 ml). LC/MS: m/z 508. $^1$H NMR (DMSO-$d_6$, 400 MHz): δ 8.41 (t, 1H), 8.05 (s, 1H), 7.91 (s, 1H), 7.73 (m, 2H), 7.46 (m, 1H), 7.35 (d, 1H), 7.34 (m, 1H), 3.66 (s, 3H), 3.51-3.46 (q, 2H), 2.98 (s, 3H), 2.84 (s, 3H), and 2.62 (t, 2H).

Example 136

3-{[1-Methyl-2-(6-trifluoromethoxy-benzothiazol-2-ylamino)-1H-benzimidazole-5-carbonyl]-amino}-propionic acid tert-butyl ester 3-{[1-Methyl-2-(6-trifluoromethoxy-benzothiazol-2-ylamino)-1H-benzimidazole-5-carbonyl]-amino}-propionic acid tert-butyl ester (38 mg) was prepared by following General Procedure F using 1-methyl-2-(6-trifluoromethyl-benzothiazol-2-ylamino)-1H-benzimidazole-5-carboxylic acid (39 mg), β-alanine tert-butyl ester (42 mg), HBTU (38 mg), and DIEA (0.1 ml). LC/MS: m/z 537.

Example 137

1-Methyl-2-(6-trifluoromethoxy-benzothiazol-2-ylamino)-1H-benzimidazole-5-carboxylic acid [2-(4-methyl-piperazin-1-yl)-2-oxo-ethyl]-amide 1-Methyl-2-(6-trifluoromethoxy-benzothiazol-2-ylamino)-1H-benzimidazole-5-carboxylic acid [2-(4-methyl-piperazin-1-yl)-2-oxo-ethyl]-amide (41 mg) was prepared by following General Procedure F using 1-methyl-2-(6-trifluoromethoxy-benzothiazol-2-ylamino)-1H-benzimidazole-5-carboxylic acid (41 mg), 2-amino-1-(4-methyl-piperazin-1-yl)-ethanone (0.30 ml), HBTU (38 mg), and DIEA (0.1 ml). LC/MS: m/z 549. $^1$H NMR (DMSO-$d_6$, 400 MHz): δ 8.48 (t, 1H), 8.10 (s, 1H), 7.96 (s, 1H), 7.91 (d, 1H), 7.78 (d, 1H), 7.64 (br, 1H), 7.48 (d, 1H), 7.36 (d, 1H), 4.14 (d, 2H), 3.67 (s, 3H), 3.61 (m, 2H), 3.48 (m, 4H), 2.89 (s, 3H), and 2.32 (m, 2H).

Example 138

1-Methyl-2-(6-trifluoromethoxy-benzothiazol-2-ylamino)-1H-benzimidazole-5-carboxylic acid (2-morpholin-4-yl-2-oxo-ethyl)-amide 1-Methyl-2-(6-trifluoromethoxy-benzothiazol-2-ylamino)-1H-benzimidazole-5-carboxylic acid (2-morpholin-4-yl-2-oxo-ethyl)-amide (39 mg) was prepared by following General Procedure F using 1-methyl-2-(6-trifluoromethoxy-benzothiazol-2-ylamino)-1H-benzimidazole-5-carboxylic acid (41 mg), 2-amino-1-morpholin-4-yl-ethanone (0.28 ml), HBTU (38 mg), and DIEA (0.1 ml). LC/MS: m/z 536. $^1$H NMR (DMSO-$d_6$, 400 MHz): δ 8.50 (t, 1H), 8.10 (s, 1H), 7.92 (m, 1H), 7.79 (br, 1H), 7.74 (br, 1H), 7.50 (d, 2H), 7.38 (m, 1H), 4.16 (d, 2H), 3.66 (s, 3H), 3.62 (m, 2H), 3.58 (t, 2H), 3.52 (t, 2H), and 3.48 (t, 2H).

Example 139

1-Methyl-2-(6-trifluoromethoxy-benzothiazol-2-ylamino)-1H-benzimidazole-5-carboxylic acid methylcarbamoylmethyl-amide 1-Methyl-2-(6-trifluoromethoxy-benzothiazol-2-ylamino)-1H-benzimidazole-5-carboxylic acid methylcarbamoylmethyl-amide (47 mg) was prepared by following General Procedure F using {[1-methyl-2-(6-trifluoromethoxy-benzothiazol-2-ylamino)-1H-benzimidazole-5-carbonyl]-amino}-acetic acid (47 mg), methylamine (0.2 ml, 1.0 M solution in THF), HBTU (38 mg), and DIEA (0.1 ml), with a minor modification of General Procedure F where DIEA was slowly added to the reaction mixture at last while stirring at 0° C. LC/MS: m/z 480.

Example 140

1-Methyl-2-(6-trifluoromethoxy-benzothiazol-2-ylamino)-1H-benzimidazole-5-carboxylic acid diethylcarbamoylmethyl-amide 1-Methyl-2-(6-trifluoromethoxy-benzothiazol-2-ylamino)-1H-benzimidazole-5-carboxylic acid diethylcarbamoylmethyl-amide (48 mg) was prepared by following General Procedure F using {[1-methyl-2-(6-trifluoromethoxy-benzothiazol-2-ylamino)-1H-benzimidazole-5-carbonyl]-amino}-acetic acid (47 mg), diethylamine (0.2 ml), HBTU (38 mg), and DIEA (0.1 ml), with a minor modification of General Procedure F where DIEA was slowly added to the reaction mixture at last while stirring at 0° C. LC/MS: m/z 522. $^1$H NMR (DMSO-$d_6$, 400 MHz): δ 8.45 (t, 1H), 8.08 (s, 1H), 7.90 (m, 2H), 7.78 (br, 1H), 7.66 (br, 1H), 7.48 (d, 1H), 7.34 (d, 1H), 4.13 (d, 2H), 3.66 (s, 3H), 3.38-3.28 (m, 4H), and 1.05 (t, 6H).

Example 141

1-Methyl-2-(6-trifluoromethoxy-benzothiazol-2-ylamino)-1H-benzimidazole-5-carboxylic acid (2-oxo-2-pyrrolidin-1-yl-ethyl)-amide 1-Methyl-2-(6-trifluoromethoxy-benzothiazol-2-ylamino)-1H-benzimidazole-5-carboxylic acid (2-oxo-2-pyrrolidin-1-yl-ethyl)-amide (46 mg) was prepared by following General Procedure F using {[1-methyl-2-(6-trifluoromethoxy-benzothiazol-2-ylamino)-1H-benzimidazole-5-carbonyl]-amino}-acetic acid (47 mg), pyrrolidine (0.14 ml), HBTU (38 mg), and DIEA (0.1 ml), with a minor modification of General Procedure F where DIEA was slowly added to the reaction mixture at last while stirring at 0° C. LC/MS: m/z 520. $^1$H NMR (DMSO-$d_6$, 400 MHz): δ 8.32 (t, 1H), 7.82 (s, 1H), 7.61 (m, 2H), 7.52 (d, 1H), 7.28 (m, 1H), 7.17 (m, 1H), 7.09 (m, 1H), 4.02 (d, 2H), 3.57 (s, 3H), 3.49 (t, 2H), 3.34 (m 2H), 1.91 (p, 2H), and 1.79 (p, 2H).

Example 142

4-(2-{[1-Methyl-2-(6-trifluoromethoxy-benzothiazol-2-ylamino)-1H-benzimidazole-5-carbonyl]-amino}-acetyl)-piperazine-1-carboxylic acid tert-butyl ester 4-(2-{[1-Methyl-2-(6-trifluoromethoxy-benzothiazol-2-ylamino)-1H-benzimidazole-5-carbonyl]-amino}-acetyl)-piperazine-1-carboxylic acid tert-butyl ester (58 mg) was prepared by following General Procedure F using {[1-methyl-2-(6-trifluoromethoxy-benzothiazol-2-ylamino)-1H-benzimidazole-5-carbonyl]-amino}-acetic acid (47 mg), piperazine-1-carboxylic acid tert-butyl ester (34 mg), HBTU (38 mg), and DIEA (0.1 ml), with a minor modification of General Procedure F where DIEA was slowly added to the reaction mixture at last while stirring at 0° C. LC/MS: m/z 635.

Example 143

(S)-2-{[1-Methyl-2-(6-trifluoromethoxy-benzothiazol-2-ylamino)-1H-benzoimidazole-5-carbonyl]-amino}-propionic acid methyl ester (S)-2-{[1-Methyl-2-(6-trifluoromethoxy-benzothiazol-2-ylamino)-1H-benzoimidazole-5-carbonyl]-amino}-propionic acid methyl ester (39 mg) was prepared by following General Procedure F using 1-methyl-2-(6-trifluoromethyl-benzothiazol-2-ylamino)-1H-benzimidazole-5-carboxylic acid (41 mg), L-alanine methyl ester hydrochloride (42 mg), HBTU (38 mg), and DIEA (0.1 ml). LC/MS: m/z 495.

Example 144

1-{[1-Methyl-2-(6-trifluoromethoxy-benzothiazol-2-ylamino)-1H-benzimidazole-5-carbonyl]-amino}-cyclopropanecarboxylic acid ethyl ester 1-{[1-Methyl-2-(6-trifluoromethoxy-benzothiazol-2-ylamino)-1H-benzimidazole-5-carbonyl]-amino}-cyclopropanecarboxylic acid ethyl ester (45 mg) was prepared by following General Procedure F using 1-methyl-2-(6-trifluoromethyl-benzothiazol-2-ylamino)-1H-benzimidazole-5-carboxylic acid (41 mg), 1-amino-cyclopropanecarboxylic acid ethyl ester hydrochloride (50 mg), HBTU (38 mg), and DIEA (0.1 ml). LC/MS: m/z 521.

Example 145

2-Methyl-2-{[1-methyl-2-(6-trifluoromethoxy-benzothiazol-2-ylamino)-1H-benzimidazole-5-carbonyl]-amino}-propionic acid methyl ester 2-Methyl-2-{[1-methyl-2-(6-trifluoromethoxy-benzothiazol-2-ylamino)-1H-benzimidazole-5-carbonyl]-amino}-propionic acid methyl ester (43 mg) was prepared by following General Procedure F using 1-methyl-2-(6-trifluoromethyl-benzothiazol-2-ylamino)-1H-benzimidazole-5-carboxylic acid (41 mg), 2-amino-2-methyl-propionic acid methyl ester hydrochloride (46 mg), HBTU (38 mg), and DIEA (0.1 ml). LC/MS: m/z 509.

Example 146

(S)-2-{[1-Methyl-2-(6-trifluoromethoxy-benzothiazol-2-ylamino)-1H-benzoimidazole-5-carbonyl]-amino}-propionic acid (S)-2-{[1-Methyl-2-(6-trifluoromethoxy-benzothiazol-2-ylamino)-1H-benzo-imidazole-5-carbonyl]-amino}-propionic acid (83 mg) was prepared by following General Procedure E starting from (S)-2-{[1-methyl-2-(6-trifluoromethoxy-benzothiazol-2-ylamino)-1H-benzoimidazole-5-carbonyl]-amino}-propionic acid methyl ester (99 mg), and LiOH (0.5 ml, 2.0 N solution in water). LC/MS: m/z 481.

Example 147

1-{[1-Methyl-2-(6-trifluoromethoxy-benzothiazol-2-ylamino)-1H-benzimidazole-5-carbonyl]-amino}-cyclopropanecarboxylic acid 1-{[1-Methyl-2-(6-trifluoromethoxy-benzothiazol-2-ylamino)-1H-benzimidazole-5-carbonyl]-amino}-cyclopropanecarboxylic acid (91 mg) was prepared by following General Procedure E starting from 1-{[1-methyl-2-(6-trifluoromethoxy-benzothiazol-2-ylamino)-1H-benzimidazole-5-carbonyl]-amino}-cyclopropanecarboxylic acid ethyl ester (104 mg), and LiOH (0.5 ml, 2.0 N solution in water). LC/MS: m/z 493.

Example 148

2-Methyl-2-{[1-methyl-2-(6-trifluoromethoxy-benzothiazol-2-ylamino)-1H-benzimidazole-5-carbonyl]-amino}-propionic acid 2-Methyl-2-{[1-methyl-2-(6-trifluoromethoxy-benzothiazol-2-ylamino)-1H-benzimidazole-5-carbonyl]-amino}-propionic acid (88 mg) was prepared by following General Procedure E starting from 2-methyl-2-{[1-methyl-2-(6-trifluoromethoxy-benzothiazol-2-ylamino)-1H-benzimidazole-5-carbonyl]-amino}-propionic acid methyl ester (102 mg), and LiOH (0.5 ml, 2.0 N solution in water). LC/MS: m/z 495.

Example 149

1-Methyl-2-(6-trifluoromethoxy-benzothiazol-2-ylamino)-1H-benzoimidazole-5-carboxylic acid ((S)-1-dimethylcarbamoyl-ethyl)-amide 1-Methyl-2-(6-trifluoromethoxy-benzothiazol-2-ylamino)-1H-benzoimidazole-5-carboxylic acid ((S)-1-dimethylcarbamoyl-ethyl)-amide (46 mg) was prepared by following General Procedure F using (S)-2-{[1-methyl-2-(6-trifluoromethoxy-benzothiazol-2-ylamino)-1H-benzimidazole-5-carbonyl]-amino}-propionic acid (48 mg), dimethyl amine (0.3 ml, 1.0 M solution in THF), HBTU (38 mg), and DIEA (0.1 ml), with a minor modification of General Procedure F where DIEA was slowly added to the reaction mixture at last while stirring at 0° C. LC/MS: m/z 508. $^1$H NMR (DMSO-$d_6$, 400 MHz): δ 8.39 (d, 1H), 7.98 (s, 1H), 7.95 (s, 1H), 7.76 (m, 1H), 7.66 (m, 1H), 7.45 (br, 1H), 7.30 (m, 1H), 7.22 (d, 1H), 4.93 (p, 1H), 3.62 (s, 3H), 2.87 (d, 6H), and 1.31 (d, 3H).

Example 150

1-Methyl-2-(6-trifluoromethoxy-benzothiazol-2-ylamino)-1H-benzimidazole-5-carboxylic acid (1-dimethylcarbamoyl-cyclopropyl)-amide 1-Methyl-2-(6-trifluoromethoxy-benzothiazol-2-ylamino)-1H-benzimidazole-5-carboxylic acid (1-dimethylcarbamoyl-cyclopropyl)-amide (48 mg) was prepared by following General Procedure F using 1-{[1-methyl-2-(6-trifluoromethoxy-benzothiazol-2-ylamino)-1H-benzimidazole-5-carbonyl]-amino}-cyclopropanecarboxylic acid (49 mg), dimethyl amine (0.3 ml, 1.0 M solution in THF), HBTU (38 mg), and DIEA (0.1 ml), with a minor modification of General Procedure F where DIEA was slowly added to the reaction mixture at last while stirring at 0° C. LC/MS: m/z 520 [M+2]. $^1$H NMR (DMSO-$d_6$, 400 MHz): δ 8.92 (s, 1H), 8.06 (s, 1H), 7.91 (m, 1H), 7.72 (d, 1H), 7.60 (br, 1H), 7.46 (d, 1H), 7.33 (d, 1H), 7.24 (m, 1H), 3.66 (s, 3H), 2.87 (d, 6H), 1.26 (t, 2H), and 1.01 (t, 2H).

Example 151

1-Methyl-2-(6-trifluoromethoxy-benzothiazol-2-ylamino)-1H-benzimidazole-5-carboxylic acid (1-dimethylcarbamoyl-1-methyl-ethyl)-amide 1-Methyl-2-(6-trifluoromethoxy-benzothiazol-2-ylamino)-1H-benzimidazole-5-carboxylic acid (1-dimethylcarbamoyl-1-methyl-ethyl)-amide (47 mg) was prepared by following General Procedure F using 2-methyl-2-{[1-methyl-2-(6-trifluoromethoxy-benzo-thiazol-2-ylamino)-1H-benzimidazole-5-carbonyl]-amino}-propionic acid (49 mg), dimethyl amine (0.3 ml, 1.0 M solution in THF), HBTU (38 mg), and DIEA (0.1 ml), with a minor modification of General Procedure F where DIEA was slowly added to the reaction mixture at last while stirring at 0° C. LC/MS: m/z 522. $^1$H NMR (DMSO-$d_6$, 400 MHz): δ 8.54 (s, 1H), 8.09 (s, 1H), 7.92 (s, 1H), 7.78 (d, 1H), 7.64 (br, 1H), 7.47 (d, 1H), 7.36 (d, 1H), 3.67 (s, 3H), 2.87 (d, 6H), and 1.49 (s, 6H), —N$\underline{H}$ proton signals was not observed.

Example 152

1-Methyl-2-(6-trifluoromethoxy-benzothiazol-2-ylamino)-1H-benzimidazole-5-carboxylic acid (2-oxo-2-piperazin-1-yl-ethyl)-amide hydrochloride 1-Methyl-2-(6-trifluoromethoxy-benzothiazol-2-ylamino)-1H-benzimidazole-5-carboxylic acid (2-oxo-2-piperazin-1-yl-ethyl)-amide dihydrochloride (42 mg) was prepared by following General Procedure L using 4-(2-{[1-methyl-2-(6-trifluoromethoxy-benzothiazol-2-ylamino)-1H-benzimidazole-5-carbonyl]-amino}-acetyl)-piperazine-1-carboxylic acid tert-butyl ester (63 mg), and hydrochloric acid (0.25 ml, 4.0 N solution dioxane). LC/MS: m/z 535. $^1$H NMR (DMSO-d$_6$, 400 MHz): δ 9.55 (br, 1H), 9.48 (br, 1H), 8.64 (t, 1H), 8.13 (s, 1H), 7.98 (s, 1H), 7.84 (d, 1H), 7.66 (d, 1H), 7.57 (d, 1H), 7.40 (d, 1H), 4.21 (d, 2H), 3.79 (m, 2H), 3.73 (m, 2H), 3.71 (s, 3H), 3.16 (m, 2H), and 3.07 (m, 2H).

Example 153

1-Ethyl-2-(6-trifluoromethoxy-benzothiazol-2-ylamino)-1H-benzoimidazole-5-carboxylic acid methyl ester 4-Ethylamino-3-nitro-benzoic acid methyl ester (4.0 g) was prepared by following General Procedure A starting from methyl 4-chloro-3-nitrobenzoate (5.0 g) in ethylamine (2.0 M in THF, 50 mL). The crude product was used in the next step without further purification.

3-Amino-4-ethylamino-benzoic acid methyl ester (3.2 g) was prepared by following General Procedure B starting from 4-ethylamino-3-nitro-benzoic acid methyl ester (4.0 g) and Pd/C (20% by weight, 800.0 mg) in MeOH:EtOAc (1:1, 30.0 mL). The crude product was used in the next step without further purification.

1-Ethyl-2-(6-trifluoromethoxy-benzothiazol-2-ylamino)-1H-benzoimidazole-5-carboxylic acid methyl ester (3.70 g) was prepared by following General Procedure D starting from 3-amino-4-ethylamino-benzoic acid methyl ester (3.0 g), 2-amino-6-(trifluoromethoxy)benzothiazole (4.4 g), 1,1'-thiocarbonyldiimidazole (3.5 g), and EDC (3.6 g). LCMS: m/z 438; and $^1$H NMR (DMSO-d$_6$, 400 MHz): δ 8.25 and 8.05 (0.59 and 0.53, 1H, m), 7.93 (2H, m), 7.75 (1H, m), 7.59 (1H, m), 7.38-7.37 (1H, m), 4.25-4.23 (2H, m), 3.88 (3H, s), 1.35-1.31 (3H, t), —N$\underline{H}$ proton signal was not observed.

Example 154

1-Ethyl-2-(6-trifluoromethoxy-benzothiazol-2-ylamino)-1H-benzoimidazole-5-carboxylic acid 1-Ethyl-2-(6-trifluoromethoxy-benzothiazol-2-ylamino)-1H-benzoimidazole-5-carboxylic acid (2.1 g) was prepared by following General Procedure E starting from 1-ethyl-2-(6-trifluoromethoxy-benzothiazol-2-ylamino)-1H-benzo-imidazole-5-carboxylic acid methyl ester (3.5 g) and sodium hydroxide (2.0 N solution, 8.0 mL). LCMS: m/z 424; and $^1$H NMR (DMSO-d$_6$, 400 MHz): δ 8.17 (1H, m), 7.96 (1H, m), 7.75 (1H, m), 7.88-7.85 (1H, m), 7.65-7.63 (1H, m), 7.59-7.57 (1H, m), 7.40-7.37 (1H, m), 4.26-4.25 (2H, q), 1.35-1.32 (3H, t) —COO$\underline{H}$ proton signal was not observed.

Example 155

1-Ethyl-2-(6-trifluoromethoxy-benzothiazol-2-ylamino)-1H-benzoimidazole-5-carboxylic acid methylamide 1-Ethyl-2-(6-trifluoromethoxy-benzothiazol-2-ylamino)-1H-benzoimidazole-5-carboxylic acid methylamide (50.0 mg) was prepared by following General Procedure F starting from 1-ethyl-2-(6-trifluoromethoxy-benzothiazol-2-ylamino)-1H-benzoimidazole-5-carboxylic acid (100.0 mg), methylamine (2.0 M solution in THF, 1 mL), DPPA (82.0 mg), and DIEA (0.1 mL) in DMF (1.0 mL). LCMS: m/z 437; and $^1$H NMR (CD$_3$OD, 400 MHz): δ 7.93 (1H, d), 7.73-7.70 (2H, m), 7.64-7.63 (1H, d), 7.40-7.38 (1H, m), 7.25-7.22 (1H, m), 4.25-4.23 (2H, q), 2.95 (3H, s), 1.41-1.38 (3H, t), 2 —N$\underline{H}$ proton signals were not observed.

Example 156

1-Ethyl-2-(6-trifluoromethoxy-benzothiazol-2-ylamino)-1H-benzoimidazole-5-carboxylic acid ethylamide 1-Ethyl-2-(6-trifluoromethoxy-benzothiazol-2-ylamino)-1H-benzo-imidazole-5-carboxylic acid ethylamide (53.0 mg) was prepared by following General Procedure F starting from 1-methyl-2-(6-trifluoromethoxy-benzothiazol-2-ylamino)-1H-benzo-imidazole-5-carboxylic acid (100.0 mg), ethylamine (2.0 M solution in THF, 1 mL), DPPA (85.0 mg), and DIEA (0.1 mL) in DMF (1.0 mL). LCMS: m/z 451; and $^1$H NMR (CD$_3$OD, 400 MHz): δ 7.95 (1H, d), 7.75-7.73 (2H, m), 7.65-7.64 (1H, d), 7.42-7.40 (1H, m), 7.26-7.24 (1H, m), 4.27-4.25 (2H, q), 3.47-3.42 (2H, q), 1.42-1.39 (3H, t), 1.27-1.24 (3H, t) 2 —N$\underline{H}$ proton signals were not observed.

Example 157

1-Ethyl-2-(6-trifluoromethoxy-benzothiazol-2-ylamino)-1H-benzoimidazole-5-carboxylic acid (2-ethoxy-ethyl)-amide 1-Ethyl-2-(6-trifluoromethoxy-benzothiazol-2-ylamino)-1H-benzo-imidazole-5-carboxylic acid (2-ethoxy-ethyl)-amide (60.0 mg) was prepared by following General Procedure F starting from 1-ethyl-2-(6-trifluoromethoxy-benzothiazol-2-ylamino)-1H-benzoimidazole-5-carboxylic acid (100.0 mg), 2-ethoxy-ethylamine (30.0 mg), DPPA (85.0 mg), and DIEA (0.1 mL) in DMF (1.0 mL). LCMS: m/z 495; and $^1$H NMR (CD$_3$OD, 400 MHz): δ 7.96 (1H, d), 7.77-7.75 (2H, m), 7.65 (1H, d), 7.43-7.41 (1H, m), 7.26-7.24 (1H, m), 4.27-4.26 (2H, q), 3.66-3.64 (2H, m), 3.59-3.55 (4H, m), 1.43-1.39 (3H, t), 1.23-1.20 (3H, t), 2 —N$\underline{H}$ proton signals were not observed.

Example 158

1-Isopropyl-2-(6-trifluoromethoxy-benzothiazol-2-ylamino)-1H benzoimidazole-5-carboxylic acid methyl ester 4-Isopropylamino-3-nitro-benzoic acid methyl ester (900.0 mg) was prepared by following General Procedure A starting from methyl 4-chloro-3-nitrobenzoate (1.0 g) and isopropyl amine (325.0 mg) in DMF (10.0 mL). The crude product was used in the next step without further purification.

3-Amino-4-isopropylamino-benzoic acid methyl ester (700.0 mg) was prepared by following General Procedure B starting from 4-isopropylamino-3-nitro-benzoic acid methyl ester (900.0 mg) and Pd/C (20% by weight, 180.0 mg) in MeOH:EtOAc (1:1, 10.0 mL). The crude product was used in the next step without further purification.

1-Isopropyl-2-(6-trifluoromethoxy-benzothiazol-2-ylamino)-1H-benzoimidazole-5-carboxylic acid methyl ester (580.0 mg) was prepared by following General Procedure D starting from 3-amino-4-isopropylamino-benzoic acid methyl ester (700.0 mg), 2-amino-6-(trifluoromethoxy) benzothiazole (930.0 mg), 1,1'-thiocarbonyldiimidazole (700.0 mg), and EDC (770.0 mg) in DMF (8.0 mL). LCMS: m/z 452; and $^1$H NMR (DMSO-$d_6$, 400 MHz): δ 8.27 and 8.05 (0.6 and 0.47, 1H, m), 7.93 (1H, m), 7.84 (1H, m), 7.73 (2H, m), 7.37 (1H, m), 5.15 (1H, m), 3.88 (3H, s), 1.58-1.57 (6H, d), —NH proton signal was not observed.

Example 159

1-Isopropyl-2-(6-trifluoromethoxy-benzothiazol-2-ylamino)-1H-benzoimidazole-5-carboxylic acid 1-Isopropyl-2-(6-trifluoromethoxy-benzothiazol-2-ylamino)-1H-benzoimid azole-5-carboxylic acid (500.0 mg) was prepared by following General Procedure E starting from 1-isopropyl-2-(6-trifluoromethoxy-benzothiazol-2-ylamino)-1H-benzoimidazole-5-carboxylic acid methyl ester (580.0 mg) and lithium hydroxide (2.0 N solution, 3.0 mL), MeOH (2.0 mL) and THF (2.0 mL). LCMS: m/z 438; and $^1$H NMR (DMSO-$d_6$, 400 MHz): δ 8.17 (1H, m), 7.96 (1H, m), 7.84-7.82 (1H, m), 7.72-7.70 (1H, m), 7.64-7.61 (1H, m), 7.40-7.37 (1H, m), 5.16-5.13 (1H, m), 1.59-1.58 (6H, d), —NH proton and —COOH signals were not observed.

Example 160

1-Isopropyl-2-(6-trifluoromethoxy-benzothiazol-2-ylamino)-1H-benzoimidazole-5-carboxylic acid methylamide 1-Isopropyl-2-(6-trifluoromethoxy-benzothiazol-2-ylamino)-1H-benzoimidazole-5-carboxylic acid methylamide (44.0 mg) was prepared by following General Procedure F starting from 1-isopropyl-2-(6-trifluoromethoxy-benzothiazol-2-ylamino)-1H-benzo-imidazole-5-carboxylic acid (100.0 mg), methylamine (2.0 M solution in THF, 0.5 mL), HBTU (130.0 mg) and DIEA (0.1 mL) in DMF (1.0 mL). LCMS: m/z 451; and $^1$H NMR (DMSO-$d_6$, 400 MHz): δ 8.40 (1H, m), 8.10 (1H, m), 7.92 (1H, m), 7.75-7.68 (2H, m), 7.37-7.35 (1H, m), 5.17-5.12 (1H, m), 2.82-2.80 (3H, s), 1.58-1.57 (6H, d), 2 —NH proton signals were not observed.

Example 161

1-Isopropyl-2-(6-trifluoromethoxy-benzothiazol-2-ylamino)-1H-benzoimidazole-5-carboxylic acid ethylamide 1-Isopropyl-2-(6-trifluoromethoxy-benzothiazol-2-ylamino)-1H-benzoimidazole-5-carboxylic acid ethylamide (50.0 mg) was prepared by following General Procedure F starting from 1-isopropyl-2-(6-trifluoromethoxy-benzothiazol-2-ylamino)-1H-benzo-imidazole-5-carboxylic acid (100.0 mg), ethylamine (2.0 M solution in THF, 0.5 mL), HBTU (130.0 mg) and DIEA (0.1 mL) in DMF (1.0 mL). LCMS: m/z 465; and $^1$H NMR (DMSO-$d_6$, 400 MHz): δ 8.43 (1H, m), 8.11 (1H, m), 7.92 (1H, m), 7.71-7.67 (2H, m), 7.36-7.35 (1H, m), 5.15-5.12 (1H, m), 3.32 (2H, m), 1.58-1.57 (6H, d), 1.16-1.13 (3H, t), 2 —NH proton signals were not observed.

Example 162

1-Isobutyl-2-(6-trifluoromethoxy-benzothiazol-2-ylamino)-1H-benzoimidazole-5-carboxylic acid methyl ester 4-Isobutylamino-3-nitro-benzoic acid methyl ester (950.0 mg) was prepared by following General Procedure A starting from methyl 4-chloro-3-nitrobenzoate (1.0 g) and isobutyl amine (402.0 mg) in DMF (10.0 mL). The crude product was used in the next step without further purification.

3-Amino-4-isobutylamino-benzoic acid methyl ester (790.0 mg) was prepared by following General Procedure B starting from 4-isobutylamino-3-nitro-benzoic acid methyl ester (950.0 mg) and Pd/C (20% by weight, 190.0 mg) in MeOH:EtOAc (1:1, 10.0 mL). The crude product was used in the next step without further purification.

1-Isobutyl-2-(6-trifluoromethoxy-benzothiazol-2-ylamino)-1H-benzoimidazole-5-carboxylic acid methyl ester (660.0 mg) was prepared by following General Procedure D starting from 3-amino-4-isobutylamino-benzoic acid methyl ester (790.0 g), 2-amino-6-(trifluoromethoxy) benzothiazole (930.0 mg), 1,1'-thiocarbonyldiimidazole (700.0 mg), and EDC (770.0 mg) in DMF (8.0 mL). LCMS: m/z 466; and $^1$H NMR (DMSO-$d_6$, 400 MHz): δ 8.25 and 8.05 (0.6 and 0.46, 1H, m), 7.98-7.88 (2H, m), 7.75-7.73 (1H, m), 7.60-7.58 (1H, m), 7.38-7.37 (1H, m), 4.00-3.98 (2H, m), 3.88 (3H, s), 2.29-2.28 (1H, m), 0.92-0.86 (6H, m), —NH proton signal was not observed.

Example 163

1-Isobutyl-2-(6-trifluoromethoxy-benzothiazol-2-ylamino)-1H-benzoimidazole-5-carboxylic acid 1-Isobutyl-2-(6-trifluoromethoxy-benzothiazol-2-ylamino)-1H-benzoimidazole-5-carboxylic acid (570.0 mg) was prepared by following General Procedure E starting from 1-isobutyl-2-(6-trifluoromethoxy-benzothiazol-2-ylamino)-1H-benzoimidazole-5-carboxylic acid methyl ester (660.0 mg) and lithium hydroxide (2.0 N solution, 3.0 mL) MeOH (1.0 mL) and THF (3.0 mL). LCMS: m/z 452; and $^1$H NMR (DMSO-$d_6$, 400 MHz): δ 8.16 (1H, m), 7.97-7.94 (1H, m), 7.85-7.82 (1H, m), 7.57-7.55 (2H, m), 7.39-7.37 (1H, m), 4.03-4.01 (2H, d), 2.29-2.24 (1H, m), 0.93-0.91 (6H, d), 2 —NH proton signals were not observed.

Example 164

1-Isobutyl-2-(6-trifluoromethoxy-benzothiazol-2-ylamino)-1H-benzoimidazole-5-carboxylic acid methylamide 1-Isobutyl-2-(6-trifluoromethoxy-benzothiazol-2-ylamino)-1H-benzoimidazole-5-carboxylic acid methylamide (40.0 mg) was prepared by following General Procedure F starting from 1-isobutyl-2-(6-trifluoromethoxy-benzothi-azol-2-ylamino)-1H-benzo-imidazole-5-carboxylic acid (100.0 mg), methylamine (2.0 M solution in THF, 0.5 mL), HBTU (130.0 mg) and DIEA (0.1 mL) in DMF (1.0 mL). LCMS: m/z 465; and $^1$H NMR (DMSO-d$_6$, 400 MHz): δ 8.40 (1H, m), 8.09 (1H, m), 7.91 (1H, m), 7.72 (1H, m), 7.54 (1H, m), 7.35 (1H, m), 4.00-3.99 (2H, m), 2.81-2.80 (3H, d), 1.23 (1H, m), 0.95-0.92 (6H, m), 2 —NH proton signals were not observed.

Example 165

1-Isobutyl-2-(6-trifluoromethoxy-benzothiazol-2-ylamino)-1H-benzoimidazole-5-carboxylic acid ethylamide 1-Isobutyl-2-(6-trifluoromethoxy-benzothiazol-2-ylamino)-1H-benzoimidazole-5-carboxylic acid ethylamide (47.0 mg) was prepared by following General Procedure F starting from 1-isobutyl-2-(6-trifluoromethoxy-benzothiazol-2-ylamino)-1H-benzo-imidazole-5-carboxylic acid (100.0 mg), ethylamine (2.0 M solution in THF, 0.5 mL), HBTU (130.0 mg) and DIEA (0.1 mL) in DMF (1.0 mL). LCMS: m/z 479 and $^1$H NMR (DMSO-d$_6$, 400 MHz): δ 8.43 (1H, m), 8.09 (1H, m), 7.91 (1H, m), 7.73 (1H, m), 7.54 (1H, m), 7.37-7.35 (1H, m), 4.04-4.00 (2H, m), 3.32 (2H, m), 2.28 (1H, m), 1.16-1.13 (3H, t), 0.95-0.91 (6H, m), 2 —NH proton signals were not observed.

Example 166

1-(2-Methoxy-ethyl)-2-(6-trifluoromethoxy-benzothiazol-2-ylamino)-1H-benzoimidazole-5-carboxylic acid 4-(2-Methoxy-ethylamino)-3-nitro-benzoic acid methyl ester (960.0 mg) was prepared by following General Procedure A starting from methyl 4-chloro-3-nitrobenzoate (1.0 g) and 2-methoxy-ethylamine (413.0 mg) in DMF (10.0 mL). The crude product was used in the next step without further purification.

3-Amino-4-(2-methoxy-ethylamino)-benzoic acid methyl ester (800.0 mg) was prepared by following General Procedure B starting from 4-(2-methoxy-ethylamino)-3-nitrobenzoic acid methyl ester (960.0 mg) and Pd/C (20% by weight, 190.0 mg) in MeOH:EtOAc (1:1, 10.0 mL). The crude product was used in the next step without further purification.

1-(2-Methoxy-ethyl)-2-(6-trifluoromethoxy-benzothiazol-2-ylamino)-1H-benzoimidazole-5-carboxylic acid methyl ester (829.0 mg) was prepared by following General Procedure D starting from 3-amino-4-(2-methoxy-ethylamino)-benzoic acid methyl ester (800.0 mg), 2-amino-6-(trifluoromethoxy)benzothiazole (930.0 mg), 1,1'-thiocarbonyldiimidazole (700.0 mg), and EDC (770.0 mg) in DMF (8.0 mL).

1-(2-Methoxy-ethyl)-2-(6-trifluoromethoxy-benzothiazol-2-ylamino)-1H-benzoimidazole-5-carboxylic acid (723.0 mg) was prepared by following General Procedure E starting from 1-(2-methoxy-ethyl)-2-(6-trifluoromethoxy-benzothiazol-2-ylamino)-1H-benzoimidazole-5-carboxylic acid methyl ester (829.0 mg) and sodium hydroxide (2.0 N solution, 3.0 mL) MeOH (1.0 mL) and THF (3.0 mL). LCMS: m/z 454; and $^1$H NMR (DMSO-d$_6$, 400 MHz): δ 8.14 (1H, s), 7.95 (1H, m), 7.84-7.82 (1H, m), 7.63 (1H, br. m), 7.51 (1H, m), 7.55-7.52 (1H, m), 7.39-7.36 (1H, m), 4.39-4.36 (2H, t), 3.74-3.71 (2H, t), 3.24 (3H, s), —COOH proton signal was not observed.

Example 167

1-(2-Methoxy-ethyl)-2-(6-trifluoromethoxy-benzothiazol-2-ylamino)-1H-benzoimidazole-5-carboxylic acid methylamide 1-(2-Methoxy-ethyl)-2-(6-trifluoromethoxy-benzothiazol-2-ylamino)-1H-benzoimidazole-5-carboxylic acid methylamide (46.0 mg) was prepared by following General Procedure F starting from 1-(2-methoxy-ethyl)-2-(6-trifluoromethoxy-benzo-thiazol-2-ylamino)-1H-benzoimidazole-5-carboxylic acid (100.0 mg), methylamine (2.0 M solution in THF, 0.5 mL), HBTU (130.0 mg) and DIEA (0.1 mL) in DMF (1.0 mL). LCMS: m/z 467; and $^1$H NMR (DMSO-d$_6$, 400 MHz): δ 8.39 (1H, br. s), 8.07 (1H, br. s), 7.92 (1H, br. s), 7.74-7.72 (1H, br. m), 7.51-7.49 (1H, m), 7.37-7.35 (1H, m), 4.35 (4H, br. s), 3.73-3.72 (2H, br. t), 3.24 (3H, s), 2.82-2.80 (3H, d).

Example 168

1-(2-Methoxy-ethyl)-2-(6-trifluoromethoxy-benzothiazol-2-ylamino)-1H-benzoimidazole-5-carboxylic acid (2-methoxy-ethyl)-amide 1-(2-Methoxy-ethyl)-2-(6-trifluoromethoxy-benzothiazol-2-ylamino)-1H-benzoimidazole-5-carboxylic acid (2-methoxy-ethyl)-amide (42.0 mg) was prepared by following General Procedure F starting from 1-(2-methoxy-ethyl)-2-(6-trifluoromethoxy-benzothiazol-2-ylamino)-1H-benzoimidazole-5-carboxylic acid (100.0 mg), 2-methoxy-ethylamine (26.0 mg), HBTU (130.0 mg) and DIEA (0.1 mL) in DMF (1.0 mL). LCMS: m/z 511; and $^1$H NMR (DMSO-d$_6$, 400 MHz): δ 8.47 (1H, br. s), 8.08 (1H, br. s), 7.93 (1H, br. s), 7.74-7.72 (1H, br. m), 7.51 (1H, m), 7.37-7.35 (1H, m), 4.35 (2H, br. s), 3.73-3.72 (2H, br. t), 3.53-3.43 (4H, m), 3.29 (3H, s), 3.24 (3H, s), 2 —NH proton signals were not observed.

Example 169

1-(2-Methoxy-ethyl)-2-(6-trifluoromethoxy-benzothiazol-2-ylamino)-1H-benzoimidazole-5-carboxylic acid (2-ethoxy-ethyl)-amide 1-(2-Methoxy-ethyl)-2-(6-trifluoromethoxy-benzothiazol-2-ylamino)-1H-benzoimidazole-5-carboxylic acid (2-ethoxy-ethyl)-amide (49.0 mg) was prepared by following General Procedure F starting from 1-(2-methoxy-ethyl)-2-(6-trifluoromethoxy-benzothiazol-2-ylamino)-1H-benzoimidazole-5-carboxylic acid (100.0 mg), 2-ethoxy-ethylamine (30.0 mg), HBTU (130.0 mg) and DIEA (0.1 mL) in DMF (1.0 mL). LCMS: m/z 525; and $^1$H NMR (DMSO-d$_6$, 400 MHz): δ 8.44 (1H, br. s), 8.06 (1H, br. s), 7.91 (1H, br. s), 7.71 (1H, br. m), 7.49-7.47 (1H, m), 7.35-7.34 (1H, m), 4.34 (2H, br. s), 3.72-3.69 (2H, br. t), 3.52-3.40 (6H, m), 3.22 (3H, s), 1.13-1.09 (3H, t), 2 —NH proton signals were not observed.

Example 170

1-(2-Fluoro-ethyl)-2-(6-trifluoromethoxy-benzothiazol-2-ylamino)-1H-benzoimidazole-5-carboxylic acid methylamide 4-(2-Fluoro-ethylamino)-3-nitro-benzoic acid methyl ester (854.0 mg) was prepared by following General Procedure A starting from methyl 4-chloro-3-nitrobenzoate (1.0 g), DIEA (2.0 mL) and 2-fluoro-ethylamine (335.0 mg) in DMF (10.0 mL). The crude product was used in the next step without further purification.

3-Amino-4-(2-fluoro-ethylamino)-benzoic acid methyl ester (657.0 mg) was prepared by following General Procedure B starting from 4-(2-fluoro-ethylamino)-3-nitro-benzoic acid methyl ester (854.0 mg) and Pd/C (20% by weight, 170.0 mg) in MeOH:EtOAc (1:1, 10.0 mL). The crude product was used in the next step without further purification.

1-(2-Fluoro-ethyl)-2-(6-trifluoromethoxy-benzothiazol-2-ylamino)-1H-benzoimidazole-5-carboxylic acid methyl ester (550.0 mg) was prepared by following General Procedure D starting from 3-amino-4-(2-fluoro-ethylamino)-benzoic acid methyl ester (657.0 mg), 2-amino-6-(trifluoromethoxy)benzothiazole (819.0 mg), 1,1'-thiocarbonyldiimidazole (623.0 mg), and EDC (670.0 mg) in DMF (6.0 mL).

1-(2-Fluoro-ethyl)-2-(6-trifluoromethoxy-benzothiazol-2-ylamino)-1H-benzoimidazole-5-carboxylic acid (475.0 mg) was prepared by following General Procedure E starting from 1-(2-fluoro-ethyl)-2-(6-trifluoromethoxy-benzothiazol-2-ylamino)-1H-benzoimidazole-5-carboxylic acid methyl ester (550.0 mg) and sodium hydroxide (2.0 N solution, 3.0 mL) MeOH (1.0 mL) and THF (3.0 mL). LCMS: m/z 441 (M+2)$^+$ and $^1$H NMR (CD$_3$OD, 400 MHz): δ 8.16 (1H, m), 8.06-8.03 (1H, m), 7.96 (1H, m), 7.86-7.84 (1H, m), 7.57-7.52 (1H, m), 7.44-7.37 (2H, m), 4.89-4.75 (2H, m), 4.59-4.51 (2H, m) (—COO$\underline{H}$ proton signal was not observed).

1-(2-Fluoro-ethyl)-2-(6-trifluoromethoxy-benzothiazol-2-ylamino)-1H-benzoimidazole-5-carboxylic acid methylamide (39.0 mg) was prepared by following General Procedure F starting from 1-(2-fluoro-ethyl)-2-(6-trifluoromethoxy-benzothiazol-2-ylamino)-1H-benzoimidazole-5-carboxylic acid (100.0 mg), methylamine (2.0 M solution in THF, 0.5 mL), HBTU (130.0 mg) and DIEA (0.1 mL) in DMF (1.0 mL). LCMS: m/z 455; and $^1$H NMR (DMSO-d$_6$, 400 MHz): δ 8.35-8.34 (1H, m), 8.13-8.08 (1H, m), 8.02-8.01 (1H, m), 7.90-7.80 (1H, m), 7.74-7.68 (1H, m), 7.51-7.36 (2H, m), 4.87-4.83 (1H, m), 4.51-4.45 (1H, m), 3.30 (3H, s), 2.80-2.79 (2H, d), —N$\underline{H}$ proton signal was not observed.

Example 171

1-(2-Fluoro-ethyl)-2-(6-trifluoromethoxy-benzothiazol-2-ylamino)-1H-benzoimidazole-5-carboxylic acid (2-methoxy-ethyl)-amide 1-(2-Fluoro-ethyl)-2-(6-trifluoromethoxy-benzothiazol-2-ylamino)-1H-benzoimidazole-5-carboxylic acid (2-methoxy-ethyl)-amide (49.0 mg) was prepared by following General Procedure F starting from 1-(2-fluoro-ethyl)-2-(6-trifluoromethoxy-benzothiazol-2-ylamino)-1H-benzoimidazole-5-carboxylic acid (100.0 mg), 2-methoxy-ethylamine (26.0 mg), HBTU (130.0 mg) and DIEA (0.1 mL) in DMF (1.0 mL). LCMS: m/z 499.

Example 172

1-(2-Fluoro-ethyl)-2-(6-trifluoromethoxy-benzothiazol-2-ylamino)-1H-benzoimidazole-5-carboxylic acid (2-ethoxy-ethyl)-amide 1-(2-Fluoro-ethyl)-2-(6-trifluoromethoxy-benzothiazol-2-ylamino)-1H-benzo-imidazole-5-carboxylic acid (2-ethoxy-ethyl)-amide (50.0 mg) was prepared by following General Procedure F starting from 1-(2-fluoro-ethyl)-2-(6-trifluoromethoxy-benzothiazol-2-ylamino)-1H-benzoimidazole-5-carboxylic acid (100.0 mg), 2-ethoxy-ethylamine (31.0 mg), HBTU (130.0 mg) and DIEA (0.1 mL) in DMF (1.0 mL). LCMS: m/z 513.

Example 173

1-(2-Amino-ethyl)-2-(6-trifluoromethoxy-benzothiazol-2-ylamino)-1H-benzoimidazole-5-carboxylic acid methylamide hydrochloride 4-(2-tert-Butoxycarbonylamino-ethylamino)-3-nitro-benzoic acid methyl ester (650.0 mg) was prepared by following General Procedure A starting from methyl 4-chloro-3-nitrobenzoate (542.0 mg) and (2-amino-ethyl)-carbamic acid tert-butyl ester (500.0 mg) in DMF (3.0 mL). The crude product was used in the next step without further purification.

3-Amino-4-(2-tert-butoxycarbonylamino-ethylamino)-benzoic acid methyl ester (525.0 mg) was prepared by following General Procedure B starting from 4-(2-tert-butoxycarbonylamino-ethylamino)-3-nitro-benzoic acid methyl ester (650.0 mg) and Pd/C (20% by weight, 130.0 mg) in MeOH:EtOAc (1:1, 6.0 mL). The crude product was used in the next step without further purification.

1-(2-tert-Butoxycarbonylamino-ethyl)-2-(6-trifluoromethoxy-benzothiazol-2-ylamino)-1H-benzoimidazole-5-carboxylic acid methyl ester (374.0 mg) was prepared by following General Procedure D starting from 3-amino-4-(2-tert-butoxycarbonylamino-ethylamino)-benzoic acid methyl ester (525.0 mg), 2-amino-6-(trifluoromethoxy)-benzothiazole (585.0 mg), 1,1'-thiocarbonyldiimidazole (445.0 mg), and EDC (480.0 mg) in DMF (2.0 mL).

1-(2-tert-Butoxycarbonylamino-ethyl)-2-(6-trifluoromethoxy-benzothiazol-2-ylamino)-1H-benzoimidazole-5-carboxylic acid (327.0 mg) was prepared by following General Procedure E starting from 1-(2-tert-butoxycarbonylamino-ethyl)-2-(6-trifluoromethoxy-benzothiazol-2-ylamino)-1H-benzoimidazole-5-carboxylic acid methyl ester (374.0 mg) and sodium hydroxide (2.0 N solution, 1.0 mL) MeOH (0.5 mL) and THF (2.0 mL).

{2-[5-Methylcarbamoyl-2-(6-trifluoromethoxy-benzothiazol-2-ylamino)-benzoimidazol-1-yl]-ethyl}-carbamic acid tert-butyl ester (39.0 mg) was prepared by following General Procedure F starting from 1-(2-tert-butoxycarbonylamino-ethyl)-2-(6-trifluoromethoxy-benzothiazol-2-ylamino)-1H-benzoimidazole-5-carboxylic acid (75.0 mg), methylamine (2.0 M solution in THF, 0.5 mL), HBTU (80.0 mg) and DIEA (0.05 mL) in DMF (1.0 mL).

1-(2-Amino-ethyl)-2-(6-trifluoromethoxy-benzothiazol-2-ylamino)-1H-benzo-imidazole-5-carboxylic acid methylamide hydrochloride (16.0 mg) was prepared using 4.0 M HCl-dioxane:DCM (2:1, 1.0 mL). LCMS: m/z 452; and $^1$H NMR (CD$_3$OD, 400 MHz): δ 8.35-8.34 (1H, m), 8.06-8.05 (1H, m), 7.89-7.62 (5H, m), 7.42-7.37 (2H, m), 4.63-4.60 (2H, m), 3.50 (1H, m), 2.98-2.96 (3H, d), 2.89-2.85 (2H, m).

Example 174

2-(6-Chloro-benzothiazol-2-ylamino)-1-ethyl-1H-benzoimidazole-5-carboxylic acid methylamide 4-Ethylamino-3-nitro-benzoic acid methyl ester (8.3 g) was prepared by following General Procedure A starting from methyl 4-chloro-3-nitrobenzoate (10.0 g), DIEA (1.6 mL) and ethylamine hydrochloride salt (4.5 g) in DMF (50.0 mL). The crude product was used in the next step without further purification.

3-Amino-4-ethylamino-benzoic acid methyl ester (6.4 g) was prepared by following General Procedure B starting from 4-ethylamino-3-nitro-benzoic acid methyl ester (8.3 g) and Pd/C (20% by weight, 170 mg) in MeOH:EtOAc (1:1, 50.0 mL). The crude product was used in the next step without further purification.

2-(6-Chloro-benzothiazol-2-ylamino)-1-ethyl-1H-benzoimidazole-5-carboxylic acid methyl ester (926.0 mg) was prepared by following General Procedure D starting from 3-amino-4-ethylamino-benzoic acid methyl ester (1.06 g), 2-amino-6-chloro-benzothiazole (1.0 g), 1,1'-thiocarbonyl-diimidazole (979.0 mg), and EDC (1.05 g) in DMF (5.0 mL).

2-(6-Chloro-benzothiazol-2-ylamino)-1-ethyl-1H-benzoimidazole-5-carboxylic acid (803.0 mg) was prepared by following General Procedure E starting from 2-(6-chloro-benzothiazol-2-ylamino)-1-ethyl-1H-benzoimidazole-5-carboxylic acid methyl ester (926.0 mg) and sodium hydroxide (2.0 N solution, 2.0 mL) MeOH (1.0 mL) and THF (2.0 mL).

2-(6-Chloro-benzothiazol-2-ylamino)-1-ethyl-1H-benzoimidazole-5-carboxylic acid methylamide (77.0 mg) was prepared by following General Procedure F starting from 2-(6-chloro-benzothiazol-2-ylamino)-1-ethyl-1H-benzoimidazole-5-carboxylic acid (150.0 mg), methylamine (2.0 M solution in THF, 1.0 mL), HBTU (190 mg) and DIEA (0.2 mL) in DMF (1.0 mL). LCMS: m/z 387; and $^1$H NMR (DMSO-$d_6$, 400 MHz): δ 8.40 (1H, br. s), 8.08 (1H, br. s), 7.95 (1H, m), 7.73 (2H, m), 7.51 (1H, m), 7.41-7.38 (1H, m), 4.21 (1H, bs. s), 2.82-2.80 (3H, d), 1.34-1.30 (3H, t), 2 —N$\underline{H}$ proton signals were not observed.

Example 175

2-(6-Chloro-benzothiazol-2-ylamino)-1-ethyl-1H-benzoimidazole-5-carboxylic acid ethylamide 2-(6-Chloro-benzothiazol-2-ylamino)-1-ethyl-1H-benzoimidazole-5-carboxylic acid ethylamide (70.0 mg) was prepared by following General Procedure F starting from 2-(6-chloro-benzothiazol-2-ylamino)-1-ethyl-1H-benzoimidazole-5-carboxylic acid (150.0 mg), ethylamine (2.0 M solution in THF, 1.0 mL), HBTU (190.0 mg) and DIEA (0.2 mL) in DMF (1.0 mL). LCMS: m/z 401; and $^1$H NMR (DMSO-$d_6$, 400 MHz): δ 8.44 (1H, m), 8.08 (1H, m), 7.95-7.92 (1H, m), 7.75-7.64 (2H, m), 7.53-7.51 (1H, m), 7.41-7.38 (1H, m), 4.21-4.19 (2H, m), 3.32-3.28 (2H, m), 1.34-1.32 (3H, t), 1.17-1.13 (3H, t), —N$\underline{H}$ proton signal was not observed.

Example 176

2-(6-Chloro-benzothiazol-2-ylamino)-1-ethyl-1H-benzoimidazole-5-carboxylic acid (2-fluoro-ethyl)-amide 2-(6-Chloro-benzothiazol-2-ylamino)-1-ethyl-1H-benzoimidazole-5-carboxylic acid (2-fluoro-ethyl)-amide (75.0 mg) was prepared by following General Procedure F starting from 2-(6-chloro-benzothiazol-2-ylamino)-1-ethyl-1H-benzoimidazole-5-carboxylic acid (150.0 mg), 2-fluoro-ethylamine (38.0 mg), HBTU (190.0 mg) and DIEA (0.2 mL) in DMF (1.0 mL). LCMS: m/z 419$^+$.

Example 177

2-(6-Chloro-benzothiazol-2-ylamino)-1-ethyl-1H-benzoimidazole-5-carboxylic acid (2-methoxy-ethyl)-amide 2-(6-Chloro-benzothiazol-2-ylamino)-1-ethyl-1H-benzoimidazole-5-carboxylic acid (2-methoxy-ethyl)-amide (68.0 mg) was prepared by following General Procedure F starting from 2-(6-chloro-benzothiazol-2-ylamino)-1-ethyl-1H-benzoimidazole-5-carboxylic acid (150.0 mg), 2-methoxy-ethylamine (45.0 mg), HBTU (190.0 mg) and DIEA (0.2 mL) in DMF (1.0 mL). LCMS: m/z 431; and $^1$H NMR (DMSO-$d_6$, 400 MHz): δ 8.46 (1H, br. s), 8.08 (1H, br. s), 7.92 (1H, br. s), 7.76-7.65 (2H, m), 7.51 (1H, m), 7.40-7.38 (1H, m), 4.22 (2H, br. s), 3.50-3.43 (4H, m), 3.29 (3H, s), 1.33-1.30 (3H, t), —N$\underline{H}$ proton signal was not observed.

Example 178

2-(6-Chloro-benzothiazol-2-ylamino)-1-ethyl-1H-benzoimidazole-5-carboxylic acid (2-methoxy-2-methyl-propyl)-amide 2-(6-Chloro-benzothiazol-2-ylamino)-1-ethyl-1H-benzoimidazole-5-carboxylic acid (2-methoxy-2-methyl-propyl)-amide (73.0 mg) was prepared by following General Procedure F starting from 2-(6-chloro-benzothiazol-2-ylamino)-1-ethyl-1H-benzo-imidazole-5-carboxylic acid (150.0 mg), 2-methoxy-2-methyl-propylamine (61.0 mg), HBTU (190.0 mg) and DIEA (0.2 mL) in DMF (1.0 mL). LCMS: m/z 459; and $^1$H NMR (DMSO-$d_6$, 400 MHz): δ 8.18-8.16 (1H, m), 8.08 (1H, m), 7.92-7.91 (1H, m), 7.79-7.77 (1H, m), 7.67-7.65 (1H, m), 7.54-7.52 (1H, m), 7.40-7.37 (1H, m), 4.21-4.20 (2H, m), 3.37-3.35 (2H, d), 3.18 (3H, s), 1.34-1.30 (3H, t), 1.14 (6H, s), —N$\underline{H}$ proton signal was not observed.

Example 179

2-(6-Chloro-benzothiazol-2-ylamino)-1-ethyl-1H-benzoimidazole-5-carboxylic acid (2-ethoxy-ethyl)-amide 2-(6-Chloro-benzothiazol-2-ylamino)-1-ethyl-1H-benzoimidazole-5-carboxylic acid (2-ethoxy-ethyl)-amide (79.0 mg) was prepared by following General Procedure F starting from 2-(6-chloro-benzothiazol-2-ylamino)-1-ethyl-1H-benzoimidazole-5-carboxylic acid (150.0 mg), 2-ethoxy-ethylamine (53.0 mg), HBTU (190.0 mg) and DIEA (0.2 mL) in DMF (1.0 mL). LCMS: m/z 445; and $^1$H NMR (DMSO-$d_6$, 400 MHz): δ 8.47 (1H, br. s), 8.08 (1H, br. s), 7.92 (1H, br. s), 7.76-7.63 (2H, m), 7.52 (1H, m), 7.40-7.38 (1H, m), 4.22 (2H, m), 3.53-3.41 (6H, m), 1.34-1.30 (3H, t), 1.14-1.11 (3H, t), —N$\underline{H}$ proton signal was not observed.

Example 180

1-Ethyl-2-(6-trifluoromethyl-benzothiazol-2-ylamino)-1H-benzoimidazole-5-carboxylic acid methylamide 4-Ethylamino-3-nitro-benzoic acid methyl ester (8.3 g) was prepared by following General Procedure A starting from methyl 4-chloro-3-nitrobenzoate (10.0 g), DIEA (1.6 mL) and ethylamine hydrochloride salt (4.5 g) in DMF (50.0 mL). The crude product was used in the next step without further purification.

3-Amino-4-ethylamino-benzoic acid methyl ester (6.4 g) was prepared by following General Procedure B starting from 4-ethylamino-3-nitro-benzoic acid methyl ester (8.3 g) and Pd/C (20% by weight, 170 mg) in MeOH:EtOAc (1:1, 50.0 mL). The crude product was used in the next step without further purification.

1-Ethyl-2-(6-trifluoromethyl-benzothiazol-2-ylamino)-1H-benzoimidazole-5-carboxylic acid methyl ester (840.0 mg) was prepared by following General Procedure D starting from 3-amino-4-ethylamino-benzoic acid methyl ester (970.0 mg), 6-trifluoromethyl-benzothiazol-2-ylamine (1.0 g), 1,1'-thiocarbonyldiimidazole (890.0 mg), and EDC (970.0 mg) in DMF (5.0 mL).

1-Ethyl-2-(6-trifluoromethyl-benzothiazol-2-ylamino)-1H-benzoimidazole-5-carboxylic acid (770.0 mg) was prepared by following General Procedure E starting from 1-ethyl-2-(6-trifluoromethyl-benzothiazol-2-ylamino)-1H-benzoimidazole-5-carboxylic acid methyl ester (840.0 mg) and sodium hydroxide (2.0 N solution, 2.0 mL) MeOH (1.0 mL) and THF (2.0 mL).

1-Ethyl-2-(6-trifluoromethyl-benzothiazol-2-ylamino)-1H-benzoimidazole-5-carboxylic acid methylamide (75.0 mg) was prepared by following General Procedure F starting from 1-ethyl-2-(6-trifluoromethyl-benzothiazol-2-ylamino)-1H-benzoimidazole-5-carboxylic acid (150.0 mg), methylamine (2.0 M solution in THF, 1.0 mL), HBTU (200.0 mg) and DIEA (0.2 mL) in DMF (1.0 mL). LCMS: m/z 421.

Example 181

1-Ethyl-2-(6-trifluoromethyl-benzothiazol-2-ylamino)-1H-benzoimidazole-5-carboxylic acid ethylamide 1-Ethyl-2-(6-trifluoromethyl-benzothiazol-2-ylamino)-1H-benzoimidazole-5-carboxylic acid ethylamide (70.0 mg) was prepared by following General Procedure F starting from 1-ethyl-2-(6-trifluoromethyl-benzothiazol-2-ylamino)-1H-benzoimidazole-5-carboxylic acid (150.0 mg), ethylamine (2.0 M solution in THF, 1.0 mL), HBTU (200.0 mg) and DIEA (0.2 mL) in DMF (1.0 mL). LCMS: m/z 435; and $^1$H NMR (DMSO-$d_6$, 400 MHz): δ 8.45-8.39 (1H, m), 8.29-8.25 (1H, m), 8.12-8.08 (1H, m), 7.82-7.67 (3H, m), 7.57-7.50 (1H, m), 4.26-4.22 (2H, m), 3.31-3.29 (2H, m), 1.35-1.32 (3H, t), 1.17-1.13 (3H, t), —N$\underline{H}$ proton signal was not observed.

Example 182

1-Ethyl-2-(6-trifluoromethyl-benzothiazol-2-ylamino)-1H-benzoimidazole-5-carboxylic acid (2-methoxy-ethyl)-amide 1-Ethyl-2-(6-trifluoromethyl-benzothiazol-2-ylamino)-1H-benzoimidazole-5-carboxylic acid (2-methoxy-ethyl)-amide (64.0 mg) was prepared by following General Procedure F starting from 1-ethyl-2-(6-trifluoromethyl-benzothiazol-2-ylamino)-1H-benzoimidazole-5-carboxylic acid (150.0 mg), 2-methoxy-ethylamine (38.0 mg), HBTU (200.0 mg) and DIEA (0.2 mL) in DMF (1.0 mL). LCMS: m/z 465; and $^1$H NMR (DMSO-$d_6$, 400 MHz): δ 8.50 (1H, m), 8.25 (1H, br. s), 8.12 (1H, br., s), 7.82-7.78 (2H, m), 7.70-7.68 (1H, m), 7.57-7.54 (1H, m), 4.24 (2H, m), 3.51-3.43 (4H, m), 3.29 (3H, s), 1.35-1.31 (3H, t), —N$\underline{H}$ proton signal was not observed.

Example 183

1-Ethyl-2-(6-trifluoromethyl-benzothiazol-2-ylamino)-1H-benzoimidazole-5-carboxylic acid (2-ethoxy-ethyl)-amide 1-Ethyl-2-(6-trifluoromethyl-benzothiazol-2-ylamino)-1H-benzoimidazole-5-carboxylic acid (2-ethoxy-ethyl)-amide (66.0 mg) was prepared by following General Procedure F starting from 1-ethyl-2-(6-trifluoromethyl-benzothiazol-2-ylamino)-1H-benzoimidazole-5-carboxylic acid (150.0 mg), 2-ethoxy-ethylamine (45.0 mg), HBTU (200.0 mg) and DIEA (0.2 mL) in DMF (1.0 mL). LCMS: m/z 479.

Example 184

1-Ethyl-2-(6-trifluoromethyl-benzothiazol-2-ylamino)-1H-benzoimidazole-5-carboxylic acid (2-methoxy-2-methyl-propyl)-amide 1-Ethyl-2-(6-trifluoromethyl-benzothiazol-2-ylamino)-1H-benzoimidazole-5-carboxylic acid (2-methoxy-2-methyl-propyl)-amide (78.0 mg) was prepared by following General Procedure F starting from 1-ethyl-2-(6-trifluoromethyl-benzothiazol-2-ylamino)-1H-benzoimidazole-5-carboxylic acid (150.0 mg), 2-methoxy-2-methyl-propylamine (50.0 mg), HBTU (200.0 mg) and DIEA (0.2 mL) in DMF (1.0 mL). LCMS: m/z 493; and $^1$H NMR (DMSO-$d_6$, 400 MHz): δ 8.25 (1H, br. s), 8.20-8.17 (1H, m), 8.11 (1H, br., s), 7.81 (1H, m), 7.70 (1H, m), 7.57 (1H, m), 4.25 (2H, m), 3.37-3.35 (2H, d), 3.32 (2H, s), 3.18 (3H, s), 1.35-1.32 (3H, t), 1.14 (6H. s).

Example 185

1-Ethyl-2-(6-trifluoromethyl-benzothiazol-2-ylamino)-1H-benzoimidazole-5-carboxylic acid (2-methylsulfanyl-ethyl)-amide 1-Ethyl-2-(6-trifluoromethyl-benzothiazol-2-ylamino)-1H-benzoimidazole-5-carboxylic acid (2-methylsulfanyl-ethyl)-amide (67.0 mg) was prepared by following General Procedure F starting from 1-ethyl-2-(6-trifluoromethyl-benzothiazol-2-ylamino)-1H-benzoimidazole-5-carboxylic acid (150.0 mg), 2-methylsulfanyl-ethylamine (45.0 mg), HBTU (200.0 mg) and DIEA (0.2 mL) in DMF (1.0 mL). LCMS: m/z 481; and $^1$H NMR (DMSO-$d_6$, 400 MHz): δ 8.59 (1H, br. s), 8.26 (1H, br. s), 8.11 (1H, br., s), 7.76-7.68 (2H, m), 7.56 (1H, m), 4.25 (2H, bs. s), 3.51-3.46 (2H, q), 3.32 (2H, s), 2.70-2.66 (2H, t), 2.12 (3H, s), 1.35-1.32 (3H, t).

Example 186

1-Ethyl-2-(6-trifluoromethoxy-benzothiazol-2-ylamino)-1H-benzoimidazole-5-carboxylic acid dimethylcarbamoylmethyl-amide 1-Ethyl-2-(6-trifluoromethoxy-benzothiazol-2-ylamino)-1H-benzoimidazole-5-carboxylic acid dimethylcarbamoyl-methyl-amide (45.0 mg) was prepared by following General Procedure F starting from 1-ethyl-2-(6-trifluoromethoxy-benzothiazol-2-ylamino)-1H-benzoimidazole-5-carboxylic acid (100.0 mg), 2-amino-N,N-dimethyl-acetamide (25.0 mg), HBTU (190.0 mg) and DIEA (0.2 mL) in DMF (1.0 mL). LCMS: m/z 508; and $^1$H NMR (DMSO-$d_6$, 400 MHz): δ 8.19 (1H, br. s), 7.88 (1H, br. s), 7.68 (1H, br., s), 7.55 (1H, br., s), 7.34-7.24 (2H, m), 7.13 (1H, m), 4.19-4.16 (2H, m), 4.12-4.10 (2H, d), 3.03 (3H, s), 2.88 (3H, s), 1.31-1.27 (3H, t), —N$\underline{\text{H}}$ proton signal was not observed.

Example 187

1-Ethyl-2-(6-trifluoromethyl-benzothiazol-2-ylamino)-1H-benzoimidazole-5-carboxylic acid dimethylcarbamoylmethyl-amide 1-Ethyl-2-(6-trifluoromethyl-benzothiazol-2-ylamino)-1H-benzoimidazole-5-carboxylic acid dimethylcarbamoylmethyl-amide (40.0 mg) was prepared by following General Procedure F starting from 1-ethyl-2-(6-trifluoromethyl-benzothiazol-2-ylamino)-1H-benzoimidazole-5-carboxylic acid (100.0 mg), 2-amino-N,N-dimethyl-acetamide (25.0 mg), HBTU (190.0 mg) and DIEA (0.2 mL) in DMF (1.0 mL). LCMS: m/z 492; and $^1$H NMR (DMSO-$d_6$, 400 MHz): δ 8.25 (1H, m), 7.88-7.84 (2H, m), 7.51-7.49 (1H, m), 7.37-7.28 (2H, m), 7.19-7.18 (1H, m), 4.18-4.15 (2H, m), 4.11-4.09 (2H, m), 3.03 (3H, s), 2.87 (3H, s), 1.29-1.23 (3H, t), —N$\underline{\text{H}}$ proton signal was not observed.

Example 188

1-(2-Methoxy-ethyl)-2-(6-trifluoromethoxy-benzothiazol-2-ylamino)-1H-benzoimidazole-5-carboxylic acid dimethylcarbamoylmethyl-amide 1-(2-Methoxy-ethyl)-2-(6-trifluoromethoxy-benzothiazol-2-ylamino)-1H-benzoimidazole-5-carboxylic acid dimethylcarbamoylmethyl-amide (35.0 mg) was prepared by following General Procedure F starting from 1-(2-methoxy-ethyl)-2-(6-trifluoromethoxy-benzothiazol-2-ylamino)-1H-benzoimidazole-5-carboxylic acid (100.0 mg), 2-amino-N,N-dimethyl-acetamide (25.0 mg), HBTU (190.0 mg) and DIEA (0.2 mL) in DMF (1.0 mL). LCMS: m/z 537.6; and $^1$H NMR (DMSO-$d_6$, 400 MHz): δ 8.59 (1H, m), 7.90 (1H, br. s), 7.72 (1H, br., s), 7.56-7.54 (1H, m), 7.38-7.31 (2H, m), 7.18 (1H, m), 4.30-4.27 (2H, t), 4.11-4.10 (2H, d), 3.70-3.67 (2H, t), 3.25 (3H, s), 3.03 (3H, s), 2.87 (3H, s), —N$\underline{\text{H}}$ proton signal was not observed.

Example 189

1-(2-Methoxy-ethyl)-2-(6-trifluoromethoxy-benzothiazol-2-ylamino)-1H-benzoimidazole-5-carboxylic acid [2-(4-methyl-piperazin-1-yl)-2-oxo-ethyl]-amide 1-(2-Methoxy-ethyl)-2-(6-trifluoromethoxy-benzothiazol-2-ylamino)-1H-benzoimidazole-5-carboxylic acid [2-(4-methyl-piperazin-1-yl)-2-oxo-ethyl]-amide (45.0 mg) was prepared by following General Procedure F starting from 1-(2-methoxy-ethyl)$_2$-(6-trifluoromethoxy-benzothiazol-2-ylamino)-1H-benzoimidazole-5-carboxylic acid (100.0 mg), 2-amino-1-(4-methyl-piperazin-1-yl)-ethanone (40.0 mg), HBTU (190.0 mg) and DIEA (0.2 mL) in DMF (1.0 mL). LCMS: m/z 593; and $^1$H NMR (DMSO-$d_6$, 400 MHz): δ 8.49-8.46 (1H, m), 8.09 (1H, br. s), 7.95-7.93 (2H, m), 7.74 (1H, m), 7.53-7.50 (1H, m), 7.37-7.34 (1H, m), 4.37-4.36 (2H, m), 4.16-4.14 (2H, d), 3.74-3.71 (2H, t), 3.48-3.46 (4H, m), 3.24 (3H, s), 2.36-2.28 (4H, m), 2.20 (3H, s), —N$\underline{\text{H}}$ proton signal was not observed.

Example 190

1-Ethyl-2-(6-trifluoromethoxy-benzothiazol-2-ylamino)-1H-benzoimidazole-5-carboxylic acid [2-(4-methyl-piperazin-1-yl)-2-oxo-ethyl]-amide 1-Ethyl-2-(6-trifluoromethoxy-benzothiazol-2-ylamino)-1H-benzoimidazole-5-carboxylic acid [2-(4-methyl-piperazin-1-yl)-2-oxo-ethyl]-amide (50.0 mg) was prepared by following General Procedure F starting from 1-ethyl-2-(6-trifluoromethoxybenzo-thiazol-2-ylamino)-1H-benzoimidazole-5-carboxylic acid (100.0 mg), 2-amino-1-(4-methyl-piperazin-1-yl)-ethanone (40.0 mg), HBTU (190.0 mg) and DIEA (0.2 mL) in DMF (1.0 mL). LCMS: m/z 563; and $^1$H NMR (DMSO-$d_6$, 400 MHz): δ 8.51-8.48 (1H, m), 8.12 (1H, br. s), 7.93 (1H, br., s), 7.74-7.71 (2H, m), 7.55 (1H, m), 7.37 (1H, m), 4.26 (2H, bs. s), 4.16-4.15 (2H, m), 3.51-3.50 (4H, m), 2.40-2.33 (4H, m), 2.24 (3H, s), 1.35-1.31 (3H, t), —N$\underline{\text{H}}$ proton signal was not observed.

Example 191

1-Ethyl-2-[6-(pyridin-3-yloxy)-benzothiazol-2-ylamino]-1H-benzoimidazole-5-carboxylic acid (2-methoxy-ethyl)-amide 6-(Pyridin-3-yloxy)-benzothiazol-2-ylamine (2.1 g) was prepared using 4-(pyridin-3-yloxy)-phenylamine (2.0 g) and KCNS (3.3 g) in acetic acid (45.0 ml). The reaction was stirred at room temperature for 20 min. Bromine (0.3 mL) in 3.0 ml acetic acid was added slowly and the reaction was stirred at room temperature for 8-10 h. The reaction mixture was diluted with water (100.0 ml), and the precipitate was filtered and dried. The precipitate was washed with saturated sodium bicarbonate solution and the crude product was used in the next step without further purification.

1-Ethyl-2-[6-(pyridin-3-yloxy)-benzothiazol-2-ylamino]-1H-benzoimidazole-5-carboxylic acid methyl ester (155.0 mg) was prepared by following General Procedure D starting from 3-amino-4-ethylamino-benzoic acid methyl ester (160.0 mg), 6-(pyridin-3-yloxy)-benzothiazol-2-ylamine (200.0 mg), 1,1'-thiocarbonyldiimidazole (200.0 mg), and EDC (200.0 mg) in DMF (2.0 mL).

1-Ethyl-2-[6-(pyridin-3-yloxy)-benzothiazol-2-ylamino]-1H-benzoimidazole-5-carboxylic acid (133.0 mg) was prepared by following General Procedure E starting from 1-ethyl-2-[6-(pyridin-3-yloxy)-benzothiazol-2-ylamino]-1H-benzoimidazole-5-carboxylic acid methyl ester (155.0 mg) and sodium hydroxide (2.0 N solution, 1.0 mL) MeOH (0.5 mL) and THF (1.0 mL).

1-Ethyl-2-[6-(pyridin-3-yloxy)-benzothiazol-2-ylamino]-1H-benzoimidazole-5-carboxylic acid (2-methoxy-ethyl)-amide (61.0 mg) was prepared by following General Procedure F starting from 1-ethyl-2-[6-(pyridin-3-yloxy)-benzothiazol-2-ylamino]-1H-benzoimidazole-5-carboxylic acid (133.0 mg), 2-methoxy-ethylamine (38.0 mg), HBTU (200.0 mg) and DIEA (0.2 mL) in DMF (1.0 mL). LCMS: m/z 490. $^1$H NMR (DMSO-$d_6$, 400 MHz): δ 8.44 (1H, m), 8.38-8.32 (2H, m), 8.07 (1H, m), 7.76-7.68 (2H, m), 7.51-7.45 (1H, m), 7.40-7.39 (2H, m), 7.12-7.10 (1H, m), 4.20-4.17 (2H, m), 3.48-3.42 (3H, m), 3.26 (3H, s), 1.48-1.46 (1H, m), 1.32-1.28 (3H, t), 2 —N$\underline{\text{H}}$ proton signals were not observed.

Example 192

1-Methyl-2-(6-trifluoromethoxy-benzothiazol-2-ylamino)-1H-benzoimidazole-5-carboxylic acid [2-(4-hydroxy-piperidin-1-yl)-ethyl]-amide 1-Methyl-2-(6-trifluoromethoxy-benzothiazol-2-ylamino)-1H-benzoimidazole-5-carboxylic acid [2-(4-hydroxy-piperidin-1-yl)-ethyl]-amide (50.0 mg) was prepared by following General Procedure F starting from 1-methyl-2-(6-trifluoromethoxy-benzothiazol-2-ylamino)-1H-benzoimidazole-5-carboxylic acid (100.0 mg), 1-(2-amino-ethyl)-piperidin-4-ol (72.0 mg), HBTU (200.0 mg) and DIEA (0.2 mL) in DMF (1.0 mL). LCMS: m/z 421. $^1$H NMR (DMSO-$d_6$, 400 MHz): δ 8.00 (1H, m), 7.80-7.77 (1H, m), 7.65 (1H, m), 7.41-7.39 (1H, m), 7.26-7.24 (1H, m), 3.90 (1H, m), 3.75-3.72 (2H, t), 3.69 (3H, s), 3.37 (1H, m), 3.18 (2H, m), 2.07-2.02 (2H, m), 1.83-1.78 (2H, m), 1.32-1.29 (2H, m), 0.90-0.87 (2H, m), 2 —N$\underline{H}$ and —O$\underline{H}$ proton signals were not observed.

Example 193

1-Methyl-2-(6-trifluoromethoxy-benzothiazol-2-ylamino)-1H-benzoimidazole-5-carboxylic acid [2-(3-hydroxy-piperidin-1-yl)-ethyl]-amide 1-Methyl-2-(6-trifluoromethoxy-benzothiazol-2-ylamino)-1H-benzoimidazole-5-carboxylic acid [2-(3-hydroxy-piperidin-1-yl)-ethyl]-amide (38.0 mg) was prepared by following General Procedure F starting from 1-methyl-2-(6-trifluoromethoxy-benzo-thiazol-2-ylamino)-1H-benzoimidazole-5-carboxylic acid (100.0 mg), 1-(2-amino-ethyl)-piperidin-3-ol (72.0 mg), HBTU (200.0 mg) and DIEA (0.2 mL) in DMF (1.0 mL). LCMS: m/z 536. $^1$H NMR (DMSO-$d_6$, 400 MHz): δ 7.90 (1H, m), 7.72-7.65 (2H, m), 7.61 (1H, m), 7.33-7.30 (1H, m), 7.23-7.21 (1H, m), 3.78-3.74 (1H, m), 3.64 (3H, s), 3.60-3.56 (2H, t), 2.99-2.96 (1H, m), 2.81-2.78 (1H, m), 2.72-2.69 (2H, t), 2.30-2.22 (2H, m), 1.92-1.83 (2H, m), 1.63-1.58 (1H, m), 1.37-1.34 (1H, m), 2 —N$\underline{H}$ and —O$\underline{H}$ proton signals were not observed.

Example 194

1-Methyl-2-(6-trifluoromethoxy-benzothiazol-2-ylamino)-1H-benzoimidazole-5-carbonitrile 4-Methylamino-3-nitro-benzonitrile (1.69 mg) was prepared by following General Procedure A starting from methyl 4-fluoro-3-nitrobenzonitrile (1.66 g) and methylamine (2 M in THF, 10.0 mL) in DMF. The crude product was used in the next step without further purification.

3-Amino-4-methylamino-benzonitrile (1.23 mg) was prepared by following General Procedure B starting from 4-methylamino-3-nitro-benzonitrile (1.33 g) and Pd/C (10% by weight, 133 mg). The crude product was used in the next step without further purification.

1-Methyl-2-(6-trifluoromethoxy-benzothiazol-2-ylamino)-1H-benzoimidazole-5-carbonitrile (2.12 g) was prepared by following General Procedure D starting from 3-amino-4-methylamino-benzonitrile (1.1 g), 2-amino-6-(trifluoromethoxy)-benzothiazole (1.75 g), 1,1'-thiocarbonyldiimidazole (1.78 g), and EDC (1.9 g). LC/MS: m/z 391. $^1$H NMR (DMSO-$d_6$, 400 MHz): δ 7.97 (s, 1H), 7.89 (s, 1H), 7.78 (br, 1H), 7.60 (d, 2H), 7.55 (br, 1H), 7.39 (d, 1H), and 3.72 (s, 3H).

Example 195

1-Methyl-2-(6-trifluoromethoxy-benzothiazol-2-ylamino)-1H-benzoimidazole-6-carbonitrile 3-Methylamino-4-nitro-benzonitrile (1.58 mg) was prepared by following General Procedure A starting from methyl 3-fluoro-4-nitrobenzonitrile (1.66 g) and methylamine (2 M in THF, 10.0 mL) in DMF. The crude product was used in the next step without further purification.

4-Amino-3-methylamino-benzonitrile (1.17 mg) was prepared by following General Procedure B starting from 3-methylamino-4-nitro-benzonitrile (1.33 g) and Pd/C (10% by weight, 133 mg). The crude product was used in the next step without further purification.

1-Methyl-2-(6-trifluoromethoxy-benzothiazol-2-ylamino)-1H-benzoimidazole-6-carbonitrile (2.27 g) was prepared by following General Procedure D starting from 4-amino-3-methylamino-benzonitrile (1.1 g), 2-amino-6-(trifluoromethoxy)-benzothiazole (1.75 g), 1,1'-thiocarbonyldiimidazole (1.78 g), and EDC (1.9 g). LC/MS: m/z 391.

Example 196

[5-(1H-Imidazol-2-yl)-1-methyl-1H-benzimidazol-2-yl]-(6-trifluoromethoxy-benzothiazol-2-yl)-amine 1-Methyl-2-(6-trifluoromethoxy-benzothiazol-2-ylamino)-1H-benzoimidazole-5-carbonitrile (2.27 g) was prepared by following General Procedure D starting from 4-amino-3-methylamino-benzonitrile (1.1 g), 2-amino-6-(trifluoromethoxy)benzothiazole (1.75 g), 1,1'-thiocarbonyl-diimidazole (1.78 g), and EDC (1.9 g). This product was triturated with DCM-methanol (9:1) before being used in the next step.

1-Methyl-2-(6-trifluoromethoxy-benzothiazol-2-ylamino)-1H-benzimidazole-5-carboximidic acid ethyl ester (630 mg) was prepared from 1-methyl-2-(6-trifluoromethoxy-benzothiazol-2-ylamino)-1H-benzoimidazole-5-carbonitrile (778 mg) and aminoacetaldehyde diethylacetal (0.53 ml) and AcOH (0.6 ml) by following Step 1 of General Procedure I. The crude product was used in the next step without further purification.

[5-(1H-Imidazol-2-yl)-1-methyl-1H-benzimidazol-2-yl]-(6-trifluoromethoxy-benzothiazol-2-yl)-amine (316 mg) was prepared by following Step 2 of General Procedure I starting from 1-methyl-2-(6-trifluoromethoxy-benzothiazol-2-ylamino)-1H-benzimidazole-5-carboximidic acid ethyl ester (435 mg), AcOH (0.5 ml), and dilute hydrochloric acid (5.0 ml, 1.0 N solution in water). LC/MS: m/z 432.

Example 197

[1-Methyl-6-(1H-1,2,4-triazol-3-yl)-1H-benzimidazol-2-yl]-(6-trifluoromethoxy-benzothiazol-2-yl)-amine

[1-Methyl-6-(1H-1,2,4-triazol-3-yl)-1H-benzimidazol-2-yl]-(6-trifluoromethoxy-benzothiazol-2-yl)-amine (106 mg) was prepared by following Method B of General Procedure J using 1-methyl-2-(6-trifluoromethoxy-benzothiazol-2-ylamino)-1H-benz-imidazole-5-carboximidic acid ethyl ester (218 mg) and formic hydrazide (18 mg). LC/MS: m/z 433. $^1$H NMR (DMSO-$d_6$, 400 MHz): δ 9.06 (br, 1H), 8.12 (s, 1H), 7.99 (m, 2H), 7.88 (d, 2H), 7.46 (d, 1H), 4.48 (br, 1H), and 3.63 (s, 3H), —N$\underline{H}$ proton signal was not observed.

Example 198

[1-Methyl-6-(5-methyl-1H-1,2,4-triazol-3-yl)-1H-benzimidazol-2-yl]-(5-trifluoromethoxy-benzothiazol-2-yl)-amine

[1-Methyl-6-(5-methyl-1H-1,2,4-triazol-3-yl)-1H-benzimidazol-2-yl]-(5-trifluoromethoxy-benzothiazol-2-yl)-amine (112 mg) was prepared by following Method B of General Procedure J using 1-methyl-2-(6-trifluoromethoxy-benzothiazol-2-ylamino)-1H-benzimidazole-5-carboximidic acid ethyl ester (218 mg) and acetic hydrazide (18 mg). LC/MS: m/z 447. $^1$H NMR (DMSO-$d_6$, 400 MHz): δ 9.86 (br, 1H), 9.65 (s, 2H), 9.05 (br, 1H), 8.92 (m, 1H), 7.99 (d, 1H), 7.88 (s, 2H), 3.42 (s, 3H), and 1.81 (s, 3H).

Example 199

(1-Ethyl-5-trifluoromethanesulfonyl-1H-benzoimidazol-2-yl)-(6-trifluoromethoxy-benzothiazol-2-yl)-amine (1-Ethyl-5-trifluoromethanesulfonyl-1H-benzoimidazol-2-yl)-(6-trifluoromethoxy-benzothiazol-2-yl)-amine (399 mg) was prepared by following General Procedure D using N1-ethyl-4-trifluoromethanesulfonyl-benzene-1,2-diamine (187 mg), 6-trifluoro-methoxy-2-amino-benzothiazole (234 mg), 1,1'-thiocarbonyl-diimidazole (213 mg), and EDC (287 mg). LC/MS: m/z 512. $^1$H NMR (DMSO-$d_6$, 400 MHz): δ 8.12 (br, 1H), 7.98 (s, 1H), 7.88 (m, 1H), 7.85 (s, 1H), 7.46 (br, 1H), 7.40 (d, 2H), 4.12 (q, 2H), and 1.34 (t, 3H).

Example 200

1-[1-Methyl-2-(6-trifluoromethoxy-benzothiazol-2-ylamino)-1H-benzoimidazol-5-yl]-ethanone 1-(4-Methylamino-3-nitro-phenyl)-ethanone (153 mg) was prepared by following General Procedure A starting from methyl 1-(4-fluoro-3-nitro-phenyl)-ethanone (183 mg) and methylamine (2 M in THF, 1.0 ml) in DMF (5 mL). The crude product was used in the next step without further purification.

1-(3-Amino-4-methylamino-phenyl)-ethanone (66 mg) was prepared by following General Procedure B starting from 1-(4-methylamino-3-nitro-phenyl)-ethanone (97 mg) and Pd/C (10% by weight, 10 mg). The crude product was used in the next step without further purification.

1-[1-Methyl-2-(6-trifluoromethoxy-benzothiazol-2-ylamino)-1H-benzoimidazol-5-yl]-ethanone (69 mg) was prepared by following General Procedure D starting from 1-(3-amino-4-methylamino-phenyl)-ethanone (41 mg), 2-amino-6-(trifluoromethoxy)-benzothiazole (59 mg), 1,1'-thiocarbonyldiimidazole (44 mg), and EDC (48 mg). LC/MS: m/z 408.

Example 201

(5-Methanesulfonyl-1-methyl-1H-benzoimidazol-2-yl)-(6-trifluoromethoxy-benzothiazol-2-yl-amine (4-Methanesulfonyl-2-nitro-phenyl)-methyl-amine (182 mg) was prepared by following General Procedure A starting from 1-fluoro-4-methanesulfonyl-2-nitro-benzene (219 mg) and methylamine (2 M in THF, 1.0 ml) in DMF (5 mL). The crude product was used in the next step without further purification.

4-Methanesulfonyl-N$^1$-methyl-benzene-1,2-diamine (76 mg) was prepared by following General Procedure B starting from (4-methanesulfonyl-2-nitro-phenyl)-methyl-amine (115 mg) and Pd/C (10% by weight, 10 mg). The crude product was used in the next step without further purification.

(5-Methanesulfonyl-1-methyl-1H-benzoimidazol-2-yl)-(6-trifluoromethoxy-benzothiazol-2-yl)-amine (72 mg) was prepared by following General Procedure D starting from 4-methanesulfonyl-N$^1$-methyl-benzene-1,2-diamine (50 mg), 2-amino-6-(trifluoromethoxy)benzothiazole (59 mg), 1,1'-thiocarbonyl-diimidazole (44 mg), and EDC (48 mg). LC/MS: m/z 444.

Example 202

2-[1-Methyl-2-(6-trifluoromethoxy-benzothiazol-2-ylamino)-1H-benzoimidazol-6-yl]-acetamide 2-(3-Methylamino-4-nitro-phenyl)-acetamide (727.0 mg) was prepared by following General Procedure A beginning with 2-(3-chloro-4-nitro-phenyl)-acetamide (1.0 g) in methylamine (2.0 M in THF, 20 mL). The crude product was used in the next step without further purification.

2-(4-Amino-3-methylamino-phenyl)-acetamide (554 mg) was prepared by following General Procedure B beginning with 2-(3-methylamino-4-nitro-phenyl)-acetamide (727.0 mg) and Pd/C (20% by weight, 140.0 mg) in MeOH:EtOAc (1:1, 10.0 mL). The crude product was used in the next step without further purification.

2-[3-Methyl-2-(6-trifluoromethoxy-benzothiazol-2-ylamino)-3H-benzoimidazol-5-yl]-acetamide (240 mg) was prepared by following General Procedure D beginning with 2-(4-amino-3-methylamino-phenyl)-acetamide (554 mg), 2-amino-6-(trifluoromethoxy)-benzothiazole (600.0 mg), 1,1'-thiocarbonyldiimidazole (600.0 mg), and EDC (600.0 mg) in DMF (6.0 ml). LCMS: m/z 423.

Examples 203 and 204, as shown in Table 1, are made by procedures analogous to those described below for Example 205. Observed m/z values for these examples are as follows. Example 203: 415.8. Example 204: 415.8.

Example 205

1-Methyl-2-(6-trifluoromethyl-benzothiazol-2-ylamino)-1H-benzoimidazole-5-carboxylic acid ((R)-2-hydroxy-propyl)-amide 1-Methyl-2-(6-trifluoromethyl-benzothiazol-2-ylamino)-1H-benzoimidazole-5-carboxylic acid ((R)-2-hydroxy-propyl)-amide (30 mg) was prepared by following General Procedure F starting from 1-methyl-2-(6-trifluoromethyl-benzothiazol-2-ylamino)-1H-benzoimidazole-5-carboxylic acid (70 mg), (R)-1-amino-propan-2-ol (70 mg), HBTU (200 mg), and DIEA (100 uL) in DMF (1 mL). LC/MS: m/z 449.7. $^1$H NMR (DMSO-$d_6$, 400 MHz): δ 8.44-8.41 (t, 1H), 8.29 (s, 1H), 8.12 (s, 1H), 7.83-7.80 (d, 1H), 7.71 (s, 2H), 7.54-7.52 (d, 1H), 3.84-3.80 (m, 1H), 3.70 (s, 3H), 3.25-3.22 (m, 2H), 1.10-1.08 (d, 3H), —NH and OH proton signal was not observed.

Examples 206 to 213, as shown in Table 1, are made by procedures analogous to those described above for Example 205. Observed m/z values for these examples are as follows. Example 206: 449.7. Example 207: 443.8. Example 208: 477.7. Example 209: 403.7. Example 210: 437.7. Example 211: 446.4. Example 212: 460.0. Example 213: 412.0.

Example 214

2-(6-Chloro-benzothiazol-2-ylamino)-1-methyl-1H-benzoimidazole-5-carboxylic acid (3-hydroxy-propyl)-amide 2-(6-Chloro-benzothiazol-2-ylamino)-1-methyl-1H-benzoimidazole-5-carboxylic acid (3-hydroxy-propyl)-amide (136 mg) was prepared by following General Procedure F starting from 2-(6-chloro-benzothiazol-2-ylamino)-1-methyl-1H-benzoimidazole-5-carboxylic acid (179 mg), 3-amino-propan-1-ol (40 mg), HBTU (209 mg), and DIEA (200 uL) in DMF (1 mL). LC/MS: m/z 415.5.

Examples 215 to 219, as shown in Table 1, are made by procedures analogous to those described above for Example 205. Observed m/z values for these examples are as follows. Example 215: 429.9. Example 216: 465.7. Example 217: 495.0. Example 218: 444.9. Example 219: 479.6.

Example 220

2-(6-Chloro-1H-benzoimidazol-2-ylamino)-1-methyl-1H-benzoimidazole-5-carboxylic acid (4-hydroxy-butyl)-amide 2-(6-Chloro-benzothiazol-2-ylamino)-1-methyl-1H-benzoimidazole-5-carboxylic acid (4-hydroxy-butyl)-amide (37 mg) was prepared by following General Procedure F starting from 2-(6-chloro-benzothiazol-2-ylamino)-1-methyl-1H-benzoimidazole-5-carboxylic acid (70 mg), 4-amino-butan-1-ol (20 mg), HBTU (80 mg), and DIEA (70 uL) in DMF (1 mL). LC/MS: m/z 429.6.

Example 221, as shown in Table 1, is made by procedures analogous to those described above for Example 205. An observed m/z value for this example is 463.8.

Example 222

6-Fluoro-1-methyl-2-(6-trifluoromethoxy-benzothiazol-2-ylamino)-1H-benzoimidazole-5-carboxylic acid (4-hydroxy-butyl)-amide 6-Fluoro-1-methyl-2-(6-trifluoromethoxy-benzothiazol-2-ylamino)-1H-benzoimidazole-5-carboxylic acid (4-hydroxy-butyl)-amide (44 mg) was prepared by General Procedure F starting from 6-fluoro-1-methyl-2-(6-trifluoromethoxy-benzothiazol-2-ylamino)-1H-benzoimidazole-5-carboxylic acid (50 mg), 4-amino-1-butanol (12 mg), HBTU (53 mg), and DIEA (31 uL). LC/MS: m/z 497.1. $^1$H NMR (DMSO-d$_6$, 400 MHz): δ 12.34 (bs, 1H), 8.19 (s, 1H), 7.94 (s, 1H), 7.89-7.59 (m, 2H), 7.58-7.40 (m, 1H), 7.36 (d, 1H), 4.44 (s, 1H), 3.62 (s, 3H), 3.49-3.39 (m, 2H), 3.32-3.20 (m, 2H), 1.67-1.36 (m, 4H).

Example 223

1-Methyl-2-(6-trifluoromethoxy-benzothiazol-2-ylamino)-1H-benzoimidazole-5-carboxylic acid ((R)-4-hydroxy-3-methyl-butyl)-amide 1-Methyl-2-(6-trifluoromethoxy-benzothiazol-2-ylamino)-1H-benzoimidazole-5-carboxylic acid ((R)-4-hydroxy-3-methyl-butyl)-amide (45 mg) was prepared by following General Procedure F starting 1-methyl-2-(6-trifluoromethoxy-benzothiazol-2-ylamino)-1H-benzoimidazole-5-carboxylic acid (80 mg), (R)-4-amino-2-methyl-butan-1-ol (25 mg), HBTU (80 mg), and DIEA (70 uL) in DMF (1 mL). LC/MS: m/z 493.6.

Examples 224 and 225, as shown in Table 1, are made by procedures analogous to those described above for Example 205. Observed m/z values for these examples are as follows. Example 224: 443.9. Example 225: 455.8.

Example 226

1-Methyl-2-(6-trifluoromethoxy-benzothiazol-2-ylamino)-1H-benzoimidazole-5-carboxylic acid (5-hydroxy-pentyl)-amide 1-Methyl-2-(6-trifluoromethoxy-benzothiazol-2-ylamino)-1H-benzoimidazole-5-carboxylic acid (5-hydroxy-pentyl)-amide (59 mg) was prepared by following General Procedure F starting from 1-methyl-2-(6-trifluoromethoxy-benzothiazol-2-ylamino)-1H-benzoimidazole-5-carboxylic acid (75 mg), 5-amino-1-pentanol (21 mg), HBTU (84 mg), and DIEA (48 uL). LC/MS m/z 495.0. $^1$H NMR (DMSO-d$_6$, 400 MHz) δ 12.38 (bs, 1H), 8.53-8.33 (m, 1H), 8.09 (s, 1H), 7.91 (s, 1H), 7.83-7.66 (m, 2H), 7.49 (d, 1H), 7.36 (d, 1H), 4.38 (s, 1H), 3.64 (s, 3H), 3.41 (q, 2H), 3.27 (q, 2H), 1.63-1.41 (m, 4H), 1.41-1.28 (m, 2H).

Examples 227 to 231, as shown in Table 1, are made by procedures analogous to those described above for Example 205. Observed m/z values for these examples are as follows. Example 227: 443.8. Example 228: 477.9. Example 229: 523.1. Example 230: 513.5. Example 231: 543.6.

Example 232

1-Methyl-2-(6-trifluoromethoxy-benzothiazol-2-ylamino)-1H-benzoimidazole-5-carboxylic acid (trans-4-hydroxy-cyclohexylmethyl)-amide trans-4-Aminomethyl-cyclohexanol hydrochloride (342 mg) was prepared by following General Procedure L using trans-N-Boc-4-aminomethyl-cyclohexanol (500 mg) and hydrogen chloride (5.45 mL, 4.0 M solution in 1,4-dioxane).

1-Methyl-2-(6-trifluoromethoxy-benzothiazol-2-ylamino)-1H-benzoimidazole-5-carboxylic acid (trans-4-hydroxy-cyclohexylmethyl)-amide (60 mg) was prepared by following General Procedure F starting from 1-methyl-2-(6-trifluoromethoxy-benzothiazol-2-ylamino)-1H-benzoimidazole-5-carboxylic acid (75 mg), trans-4-aminomethyl-cyclohexanol hydrochloride (34 mg), HBTU (84 mg), and DIEA (48 uL). LC/MS: m/z 521.0. $^1$H NMR (DMSO-d$_6$, 400 MHz): δ 12.40 (bs, 1H), 8.47-8.35 (m, 1H), 8.08 (s, 1H), 7.92 (s, 1H), 7.80-7.65 (m, 2H), 7.49 (d, 1H), 7.36 (d, 1H), 4.49 (s, 1H), 3.63 (s, 3H), 3.11 (t, 2H), 1.92-1.68 (m, 3H), 1.66-1.18 (m, 4H), 1.17-0.88 (m, 3H).

Examples 233 and 234, as shown in Table 1, are made by procedures analogous to those described above for Example 232. Observed m/z values for these examples are as follows. Example 233: 469.9. Example 234: 503.8.

Example 235

2-(6-Chloro-benzothiazol-2-ylamino)-1-methyl-1H-benzoimidazole-5-carboxylic acid [2-(2-hydroxy-ethoxy)-ethyl]-amide 2-(6-Chloro-benzothiazol-2-ylamino)-1-methyl-1H-benzoimidazole-5-carboxylic acid [2-(2-hydroxy-ethoxy)-ethyl]-amide (72 mg) was prepared by following General Procedure F starting from 2-(6-chloro-benzothiazol-2- ylamino)-1-methyl-1H-benzoimidazole-5-carboxylic acid (92 mg), 2-(2-aminoethoxy)-ethanol (30 mg), HBTU (116 mg), and DIEA (67 uL). LC/MS: m/z 446.8. $^1$H NMR (DMSO-d$_6$, 400 MHz): δ 12.38 (bs, 1H), 8.47 (t, 1H), 8.08 (s, 1H), 7.93 (s, 1H), 7.84-7.58 (m, 2H), 7.48 (d, 1H), 7.40 (d, 1H), 4.63 (t, 1H), 3.64 (s, 3H), 3.56 (t, 2H), 3.51 (t, 2H), 3.49-3.41 (m, 4H).

Example 236

1-Methyl-2-(6-trifluoromethyl-benzothiazol-2-ylamino)-1H-benzoimidazole-5-carboxylic acid [2-(2-hydroxy-ethoxy)-ethyl]-amide 1-Methyl-2-(6-trifluoromethyl-benzothiazol-2-ylamino)-1H-benzoimidazole-5-carboxylic acid [2-(2-hydroxy-ethoxy)-ethyl]-amide (87 mg) was prepared by following General Procedure F starting from 1-methyl-2-(6-trifluoromethyl-benzothiazol-2-ylamino)-1H-benzoimidazole-5-carboxylic acid (100 mg), 2-(2-aminoethoxy)-ethanol (30 mg), HBTU (116 mg), and DIEA (67 uL). LC/MS: m/z 480.8. $^1$H NMR (DMSO-d$_6$, 400 MHz): δ 12.48 (bs, 1H), 8.48 (t, 1H), 8.27 (s, 1H), 8.11 (s, 1H), 7.78 (d, 1H), 7.69 (d, 1H), 7.51 (d, 1H), 7.36 (d, 1H), 3.68 (s, 3H), 3.57 (t, 2H), 3.52 (t, 2H), 3.49-3.41 (m, 4H), —OH proton signal was not observed.

Examples 237 and 238, as shown in Table 1, are made by procedures analogous to those described above for Example 205. Observed m/z values for these examples are as follows. Example 237: 514.7. Example 238: 496.7.

Example 239, as shown in Table 1, is made by procedures analogous to those described below for Example 240. An observed m/z value for this example is 538.8.

Example 240

2-(6-Chloro-benzothiazol-2-ylamino)-1-(2-methyl-amino-ethyl)-1H-benzoimidazole-5-carboxylic acid [2-(2-hydroxy-ethoxy)-ethyl]-amide hydrochloride (2-{2-(6-Chloro-benzothiazol-2-ylamino)-5-[2-(2-hydroxy-ethoxy)-ethylcarbamoyl]-benzoimidazol-1-yl}-ethyl)-methyl-carbamic acid tert-butyl ester (73 mg) was prepared by following General Procedure F starting from 1-[2-(tert-butoxycarbonyl-methyl-amino)-ethyl]-2-(6-chloro-benzothiazol-2-ylamino)-1H-benzoimidazole-5-carboxylic acid (145 mg), 2-(2-amino-ethoxy)-ethanol (35 mg), HBTU (125 mg), and DIEA (100 uL) in DMF (1 mL).

2-(6-Chloro-benzothiazol-2-ylamino)-1-(2-methylamino-ethyl)-1H-benzoimidazole-5-carboxylic acid [2-(2-hydroxy-ethoxy)-ethyl]-amide dihydrochloride (60 mg) was prepared by following General Procedure L starting from (2-{2-(6-chloro-benzothiazol-2-ylamino)-5-[2-(2-hydroxy-ethoxy)-ethylcarbamoyl]-benzoimidazol-1-yl}-ethyl)-methyl-carbamic acid tert-butyl ester (73 mg) in 4M HCl in dioxane (1 mL). LC/MS: m/z 488.5.

Examples 241 to 243, as shown in Table 1, are made by procedures analogous to those described above for Example 205. Observed m/z values for these examples are as follows. Example 241: 539.4. Example 242: 510.0. Example 243: 459.9.

Example 244, as shown in Table 1, is made by procedures analogous to those described below for Example 245. An observed m/z value for this example is 510.7.

Example 245

1-Methyl-2-(6-trifluoromethoxy-benzothiazol-2-ylamino)-1H-benzoimidazole-5-carboxylic acid [2-(2-hydroxy-2-methyl-propoxy)-ethyl]-amide 1-Methyl-2-(6-trifluoromethoxy-benzothiazol-2-ylamino)-1H-benzoimidazole-5-carboxylic acid [2-(2-hydroxy-2-methyl-propoxy)-ethyl]-amide (5 mg) was prepared by following General Procedure X starting from 1-methyl-2-(6-trifluoromethoxy-benzothiazol-2-ylamino)-1H-benzoimidazole-5-carboxylic acid (2-hydroxy-ethyl)-amide (100 mg), 1,2-epoxy-2-methyl-propane (19 mg), and KOH (19 mg) in DMF. LC/MS: m/z 524.7.

Example 246

1-Methyl-2-(6-trifluoromethoxy-benzothiazol-2-ylamino)-1H-benzoimidazole-5-carboxylic acid [2-(3-hydroxy-propoxy)-ethyl]-amide Toluene-4-sulfonic acid 3-benzyloxy-propyl ester (14.4 g) was prepared by following General Procedure V starting from 3-benzyloxy-1-propanol (8.4 g), p-tolulenesulfonyl chloride (12.52 g), and DMAP (84 mg).

Dibenzyl-[2-(3-benzyloxy-propoxy)-ethyl]-amine (860 mg) was prepared by following General Procedure W starting from toluene-4-sulfonic acid 3-benzyloxy-propyl ester (1.33 g), N,N-dibenzyl-2-aminoethanol (1.0 g), 50% aqueous sodium hydroxide solution (1.66 g in 1.66 mL of water), and tetrabutylammonium hydrogen sulfate (141 mg).

3-(2-Amino-ethoxy)-propan-1-ol (229 mg) was prepared by following General Procedure B starting from dibenzyl-[2-(3-benzyloxy-propoxy)-ethyl]-amine (860 mg) and Pd/C (86 mg).

1-Methyl-2-(6-trifluoromethoxy-benzothiazol-2-ylamino)-1H-benzoimidazole-5-carboxylic acid [2-(3-hydroxy-propoxy)-ethyl]-amide (85 mg) was prepared by following General Procedure F starting from 1-methyl-2-(6-trifluoromethoxy-benzothiazol-2-ylamino)-1H-benzoimidazole-5-carboxylic acid (82 mg), 3-(2-amino-ethoxy)-propan-1-ol (48 mg), HBTU (91 mg), and DIEA (52 uL). LC/MS: m/z 510.0.

Example 247, as shown in Table 1, is made by procedures analogous to those described below for Example 249. An observed m/z value for this example is 513.1.

Example 248, as shown in Table 1, is made by procedures analogous to those described above for Example 246. An observed m/z value for this example is 459.9.

Example 249

2-(6-Chloro-benzothiazol-2-ylamino)-1-methyl-1H-benzoimidazole-5-carboxylic acid [2-(3-fluoro-propoxy)-ethyl]-amide Dibenzyl-[2-(3-fluoro-propoxy)-ethyl]-amine (770 mg) was prepared by following General Procedure S starting from dibenzyl-(2-chloro-ethyl)-amine (1 g), 3-fluoro-propan-1-ol (295 mg), 50% (w/w) KOH solution (4.25 mL) and tetrabutylammonium bromide (130 mg) in dioxane (4.25 mL).

2-(3-Fluoro-propoxy)-ethylamine (94 mg) was prepared by following General Procedure T starting from dibenzyl-[2-(3-fluoro-propoxy)-ethyl]-amine (450 mg) and Pd—C (90 mg) in methanol (1.5 mL).

2-(6-Chloro-benzothiazol-2-ylamino)-1-methyl-1H-benzoimidazole-5-carboxylic acid [2-(3-fluoro-propoxy)-ethyl]-amide (12 mg) was prepared by following General Procedure F starting from 2-(6-chloro-benzothiazol-2-ylamino)-1-methyl-1H-benzoimidazole-5-carboxylic acid (55 mg), 2-(3-fluoro-propoxy)-ethylamine (50 mg), HBTU (60 mg), and DIEA (50 uL) in DMF (800 uL). LC/MS: m/z 463.0.

Example 250

1-Methyl-2-(6-trifluoromethoxy-benzothiazol-2-ylamino)-1H-benzoimidazole-5-carboxylic acid [3-(2-hydroxy-ethoxy)-propyl]-amide Toluene-4-sulfonic acid 2-benzyloxy-ethyl ester (11.3 g) was prepared by following General Procedure V starting from 2-benzyloxyethanol (9.57 g), p-tolulenesulfonyl chloride (16.73 g), and DMAP (96 mg).

Dibenzyl-[3-(2-benzyloxy-ethoxy)-propyl]-amine (378 mg) was prepared by following General Procedure W starting from toluene-4-sulfonic acid 2-benzyloxy-ethyl ester (1.0 g), 3-dibenzylamino-propan-1-ol (1.08 g), 50% aqueous sodium hydroxide solution (1.3 g in 1.3 mL of water), and tetrabutylammonium hydrogen sulfate (111 mg).

2-(3-Amino-propoxy)-ethanol (49 mg) was prepared by following General Procedure B starting from dibenzyl-[3-(2-benzyloxy-ethoxy)-propyl]-amine (378 mg) and Pd/C (38 mg).

1-Methyl-2-(6-trifluoromethoxy-benzothiazol-2-ylamino)-1H-benzoimidazole-5-carboxylic acid [3-(2-hydroxy-ethoxy)-propyl]-amide (41 mg) was prepared by following General Procedure F starting from 1-methyl-2-(6-trifluoromethoxy-benzothiazol-2-ylamino)-1H-benzoimidazole-5-carboxylic acid (82 mg), 2-(3-amino-propoxy)-ethanol (49 mg), HBTU (91 mg), and DIEA (52 uL). LC/MS: m/z 509.8.

Examples 251 to 256, as shown in Table 1, are made by procedures analogous to those described above for Example 205. Observed m/z values for these examples are as follows. Example 251: 528.9. Example 252: 529.0. Example 253: 535.0. Example 254: 535.1. Example 255: 485.0. Example 256: 539.5.

Example 257, is made by procedures analogous to those described above for Example 47. An observed m/z value for this example is 481.8.

Examples 258 and 259, as shown in Table 1, are made by procedures analogous to those described above for Example 249. Observed m/z values for these examples are as follows. Example 258: 516.8. Example 259: 465.8.

Example 260

1-Methyl-2-(6-trifluoromethoxy-benzothiazol-2-ylamino)-1H-benzoimidazole-5-carboxylic acid [2-(2-methoxy-ethoxy)-ethyl]-amide 1-Azido-2-(2-methoxy-ethoxy)-ethane (607 mg) was prepared by following General Procedure U starting from 1-bromo-2-(2-methoxy-ethoxy)-ethane (1.0 g) and sodium azide (1.07 g). The crude product was used in the next step without further purification.

2-(2-Methoxy-ethoxy)-ethylamine (425 mg) was prepared by following General Procedure B starting from 1-azido-2-(2-methoxy-ethoxy)-ethane (607 mg) and 10% Pd/C (60 mg). The crude product was used in the next step without further purification.

1-Methyl-2-(6-trifluoromethoxy-benzothiazol-2-ylamino)-1H-benzoimidazole-5-carboxylic acid [2-(2-methoxy-ethoxy)-ethyl]-amide (44 mg) was prepared by following General Procedure F starting from 1-methyl-2-(6-trifluoromethoxy-benzothiazol-2-ylamino)-1H-benzoimidazole-5-carboxylic acid (75 mg), 2-(2-methoxy-ethoxy)-ethylamine (24 mg), HBTU (84 mg), and DIEA (48 uL). LC/MS: m/z 511.0. $^1$H NMR (DMSO-$d_6$, 400 MHz): δ 12.40 (bs, 1H), 8.50 (t, 1H), 8.10 (s, 1H), 7.92 (s, 1H), 7.78 (d, 1H), 7.74 (d, 1H), 7.50 (d, 1H), 7.36 (d, 1H), 3.64 (s, 3H), 3.59-3.53 (m, 4H), 3.49-3.41 (m, 4H), 3.25 (s, 3H).

Examples 261 and 262, as shown in Table 1, are made by procedures analogous to those described above for Example 260. Observed m/z values for these examples are as follows. Example 261: 461.0. Example 262: 493.7.

Examples 263 and 264, as shown in Table 1, are made by procedures analogous to those described above for Example 205. Observed m/z values for these examples are as follows. Example 263: 520.8. Example 264: 520.8.

Example 265

1-Methyl-2-(6-trifluoromethoxy-benzothiazol-2-ylamino)-1H-benzoimidazole-5-carboxylic acid [2-(2-cyano-ethoxy)-ethyl]-amide 1-Methyl-2-(6-trifluoromethoxy-benzothiazol-2-ylamino)-1H-benzoimidazole-5-carboxylic acid [2-(2-cyano-ethoxy)-ethyl]-amide (54 mg) was prepared by following General Procedure F starting from 1-methyl-2-(6-trifluoromethoxy-benzothiazol-2-ylamino)-1H-benzoimidazole-5-carboxylic acid (82 mg), 3-(2-amino-ethoxy)-propionitrile hydrochloride (60 mg), HBTU (91 mg), and DIEA (52 uL). LC/MS: m/z 506.0.

Example 266

2-(6-Chloro-benzothiazol-2-ylamino)-1-methyl-1H-benzoimidazole-5-carboxylic acid [2-(2-cyano-ethoxy)-ethyl]-amide

[2-(2-Cyano-ethoxy)-ethyl]-carbamic acid tert-butyl ester (430 mg) was prepared starting from (2-hydroxy-ethyl)-carbamic acid tert-butyl ester (320 mg) in acrylonitrile (1.5 mL). The reaction was heated to 50° C. for 1 h. The reaction was added to ethyl acetate (20 mL) and water (20 mL). The phases were separated and the aqueous phase was extracted twice with ethyl acetate. The combined organics were dried over sodium sulfate and then filtered. The solvent was evaporated and crude compound was purified by flash chromatography using hexane:ethyl acetate gradient.

3-(2-Amino-ethoxy)-propionitrile hydrochloride (300 mg) was prepared by following General Procedure L starting from [2-(2-cyano-ethoxy)-ethyl]-carbamic acid tert-butyl ester (430 mg) in 2M HCl in ether (2 mL).

2-(6-Chloro-benzothiazol-2-ylamino)-1-methyl-1H-benzoimidazole-5-carboxylic acid [2-(2-cyano-ethoxy)-ethyl]-amide (60 mg) was prepared by following General Procedure F starting 2-(6-chloro-benzothiazol-2-ylamino)-1-methyl-1H-benzoimidazole-5-carboxylic acid (70 mg), 3-(2-amino-ethoxy)-propionitrile hydrochloride (100 mg), HBTU (85 mg), and DIEA (100 uL) in DMF (1 mL). LC/MS: m/z 456.0.

Example 267

1-Methyl-2-(6-trifluoromethoxy-benzothiazol-2-ylamino)-1H-benzoimidazole-5-carboxylic acid (2-carbamoylmethoxy-ethyl)-amide 1-Methyl-2-(6-trifluoromethoxy-benzothiazol-2-ylamino)-1H-benzoimidazole-5-carboxylic acid (2-carbamoylmethoxy-ethyl)-amide (20 mg) was prepared on solid phase starting from [2-(9H-fluoren-9-ylmethoxycarbonylamino)-ethoxy]-acetic acid (204 mg), HBTU (230 mg), DIEA (100 uL) and Rink amide resin (320 mg) in DMF (20 mL). The reaction was stirred at room temperature for 1 h and then washed with DMF (3×20 mL each). The reaction was then stirred at room temperature with 20% (v/v) piperidine in DMF (10 mL) for 1 h. The reaction was washed with DMF (3×20 mL each). In the next step the reaction was stirred at room temperature with 1-methyl-2-(6-trifluoromethoxy-benzothiazol-2-ylamino)-1H-benzoimidazole-5-carboxylic acid (244 mg), HBTU (230 mg) and DIEA (100 uL) in DMF (10 mL) for 2 h and washed with DMF (3×20 mL each). In the last step the reaction was stirred with TFA (10 mL) for 30 min and then filtered. The filtrate was evaporated and crude compound was purified by flash chromatography using DCM:10% methanol in DCM gradient. LC/MS: m/z 508.6.

Example 268

1-Methyl-2-(6-trifluoromethoxy-benzothiazol-2-ylamino)-1H-benzoimidazole-5-carboxylic acid [2-(2-amino-ethoxy)-ethyl]-amide

[2-(2-{[1-Methyl-2-(6-trifluoromethoxy-benzothiazol-2-ylamino)-1H-benzoimidazole-5-carbonyl]-amino}-ethoxy)-ethyl]-carbamic acid 9H-fluoren-9-ylmethyl ester (106 mg) was prepared by following General Procedure F starting from 1-methyl-2-(6-trifluoromethoxy-benzothiazol-2-ylamino)-1H-benzoimidazole-5-carboxylic acid (80 mg), [2-(2-amino-ethoxy)-ethyl]-carbamic acid 9H-fluoren-9-ylmethyl ester (80 mg), HBTU (95 mg), and DIEA (70 uL) in DMF (1 mL).

1-Methyl-2-(6-trifluoromethoxy-benzothiazol-2-ylamino)-1H-benzoimidazole-5-carboxylic acid [2-(2-amino-ethoxy)-ethyl]-amide (70 mg) was prepared by following General Procedure O starting from [2-(2-{[1-methyl-2-(6-trifluoromethoxy-benzothiazol-2-ylamino)-1H-benzoimidazole-5-carbonyl]-amino}-ethoxy)-ethyl]-carbamic acid 9H-fluoren-9-ylmethyl ester (106 mg), 20% (v/v) piperidine in DMF (1.5 mL). LC/MS: m/z 494.5. Examples 269 and 270, as shown in Table 1, are made by procedures analogous to those described above for Example 268. Observed m/z values for these examples are as follows. Example 269: 444.7. Example 270: 445.7.

Example 271

1-Methyl-2-(6-trifluoromethoxy-benzothiazol-2-ylamino)-1H-benzoimidazole-5-carboxylic acid [2-(2-methylamino-ethoxy)-ethyl]-amide hydrochloride

[2-(2-Dibenzylamino-ethoxy)-ethyl]-methyl-carbamic acid tert-butyl ester (200 mg) was prepared by following General Procedure S starting from dibenzyl-(2-chloro-ethyl)-amine (400 mg), (2-hydroxy-ethyl)-methyl-carbamic acid tert-butyl ester (525 mg), 50% (w/w) KOH solution (1.8 mL) and tetrabutylammonium bromide (57.7 mg) in dioxane (1.8 mL).

[2-(2-Amino-ethoxy)-ethyl]-methyl-carbamic acid tert-butyl ester (100 mg) was prepared following General Procedure T starting from [2-(2-dibenzylamino-ethoxy)-ethyl]-methyl-carbamic acid tert-butyl ester (200 mg) and Pd—C (40 mg) in methanol (1.5 mL).

Methyl-[2-(2-{[1-methyl-2-(6-trifluoromethoxy-benzothiazol-2-ylamino)-1H-benzoimidazole-5-carbonyl]-amino}-ethoxy)-ethyl]-carbamic acid tert-butyl ester (69 mg) was prepared by following General Procedure F starting from 1-methyl-2-(6-trifluoromethoxy-benzothiazol-2-ylamino)-1H-benzoimidazole-5-carboxylic acid (82 mg), [2-(2-amino-ethoxy)-ethyl]-methyl-carbamic acid tert-butyl ester (87 mg), HBTU (91 mg), and DIEA (52 uL). 1-Methyl-2-(6-trifluoromethoxy-benzothiazol-2-ylamino)-1H-benzoimidazole-5-carboxylic acid [2-(2-methylamino-ethoxy)-ethyl]-amide dihydrochloride (53 mg) was prepared by following General Procedure L using methyl-[2-(2-{[1-methyl-2-(6-trifluoromethoxy-benzothiazol-2-ylamino)-1H-benzoimidazole-5-carbonyl]-amino}-ethoxy)-ethyl]-carbamic acid tert-butyl ester (60 mg) and hydrogen chloride (250 uL, 4.0 M solution in 1,4-dioxane). LC/MS: m/z 509.0. Example 272, as shown in Table 1, is made by procedures analogous to those described above for Example 271. An observed m/z value for this example is 458.9.

Example 273

1-Methyl-2-(6-trifluoromethoxy-benzothiazol-2-ylamino)-1H-benzoimidazole-5-carboxylic acid [2-(2-dimethylamino-ethoxy)-ethyl]-amide

[2-(2-Dibenzylamino-ethoxy)-ethyl]-dimethyl-amine was prepared following General Procedure S starting from dibenzyl-(2-chloro-ethyl)-amine (640 mg), 2-dimethylamino-ethanol (325 mg), 50% (w/w) KOH solution (3 mL) and tetrabutylammonium bromide (95 mg) in dioxane (3 mL).

[2-(2-Amino-ethoxy)-ethyl]-dimethyl-amine (100 mg) was prepared following General Procedure T starting from [2-(2-dibenzylamino-ethoxy)-ethyl]-dimethyl-amine (430 mg) and Pd—C (86 mg) in methanol (1 mL).

1-Methyl-2-(6-trifluoromethoxy-benzothiazol-2-ylamino)-1H-benzoimidazole-5-carboxylic acid [2-(2-dimethylamino-ethoxy)-ethyl]-amide (25 mg) was prepared by following General Procedure F starting from 1-methyl-2-(6-trifluoromethoxy-benzothiazol-2-ylamino)-1H-benzoimidazole-5-carboxylic acid (93 mg), [2-(2-amino-ethoxy)-ethyl]-dimethyl-amine (60 mg), HBTU (103 mg), and DIEA (59 uL). LC/MS: m/z 523.0.

Example 274, as shown in Table 1, is made by procedures analogous to those described above for Example 273. An observed m/z value for this example is 473.0.

Example 275

1-Methyl-2-(6-trifluoromethoxy-benzothiazol-2-ylamino)-1H-benzoimidazole-5-carboxylic acid [2-(2-acetylamino-ethoxy)-ethyl]-amide 1-Methyl-2-(6-trifluoromethoxy-benzothiazol-2-ylamino)-1H-benzoimidazole-5-carboxylic acid [2-(2-acetylamino-ethoxy)-ethyl]-amide (25 mg) was prepared by following General Procedure R starting from 1-methyl-2-(6-trifluoromethoxy-benzothiazol-2-ylamino)-1H-benzo-

Example 276

1-Methyl-2-(6-trifluoromethoxy-benzothiazol-2-ylamino)-1H-benzoimidazole-5-carboxylic acid [2-(2-methanesulfonylamino-ethoxy)-ethyl]-amide 1-Methyl-2-(6-trifluoromethoxy-benzothiazol-2-ylamino)-1H-benzoimidazole-5-carboxylic acid [2-(2-methanesulfonylamino-ethoxy)-ethyl]-amide (22 mg) was prepared by following General Procedure Q starting from 1-methyl-2-(6-trifluoromethoxy-benzothiazol-2-ylamino)-1H-benzoimidazole-5-carboxylic acid [2-(2-amino-ethoxy)-ethyl]-amide (50 mg), methanesulfonyl chloride (1-2 drops) and triethylamine (30 uL) in DCM (1 mL). LC/MS: m/z 572.4.

Example 277, as shown in Table 1, is made by procedures analogous to those described below for Example 278. An observed m/z value for this example is 477.7.

Example 278

2-(6-Chloro-benzothiazol-2-ylamino)-1-methyl-1H-benzoimidazole-5-carboxylic acid [2-(2-hydroxy-ethanesulfonyl)-ethyl]-amide 2-(6-Chloro-benzothiazol-2-ylamino)-1-methyl-1H-benzoimidazole-5-carboxylic acid [2-(2-hydroxy-ethylsulfanyl)-ethyl]-amide (70 mg) was prepared by following General Procedure F starting from 2-(6-chloro-benzothiazol-2-ylamino)-1-methyl-1H-benzoimidazole-5-carboxylic acid (70 mg), 2-(2-amino-ethylsulfanyl)-ethanol (50 mg), HBTU (150 mg), and DIEA (100 uL) in DMF (1 mL).

2-(6-Chloro-benzothiazol-2-ylamino)-1-methyl-1H-benzoimidazole-5-carboxylic acid [2-(2-hydroxy-ethanesulfonyl)-ethyl]-amide (40 mg) was prepared by following General Procedure M starting from 2-(6-chloro-benzothiazol-2-ylamino)-1-methyl-1H-benzoimidazole-5-carboxylic acid [2-(2-hydroxy-ethylsulfanyl)-ethyl]-amide (60 mg) and 32 wt % peracetic acid solution (100 uL) in DCM (1 mL). LC/MS: m/z 493.8.

Example 279

2-(6-Chloro-benzothiazol-2-ylamino)-1-methyl-1H-benzoimidazole-5-carboxylic acid [2-(2-fluoro-ethylamino)-ethyl]-amide hydrochloride N,N-Dibenzyl-N'-(2-fluoro-ethyl)-ethane-1,2-diamine (160 mg) was prepared by following General Procedure S starting from dibenzyl-(2-chloro-ethyl)-amine (520 mg), 2-fluoro-ethylamine hydrochloride (250 mg), DIEA (900 uL) and tetrabutylammonium bromide (60 mg) in DMF (2 mL).

(2-Dibenzylamino-ethyl)-(2-fluoro-ethyl)-carbamic acid tert-butyl ester (216 mg) was prepared starting from N,N-dibenzyl-N'-(2-fluoro-ethyl)-ethane-1,2-diamine (160 mg), Boc₂O (146 mg) and triethylamine (170 uL) in DCM (1 mL). The reaction was stirred at room temperature for 1 h. The reaction was added to DCM and saturated sodium bicarbonate solution. The phases were separated, the combined organics were dried over sodium sulfate and then filtered. The filtrate was evaporated and compound was isolated without further purification.

(2-Amino-ethyl)-(2-fluoro-ethyl)-carbamic acid tert-butyl ester (95 mg) was prepared by following General Procedure T starting from (2-dibenzylamino-ethyl)-(2-fluoro-ethyl)-carbamic acid tert-butyl ester (216 mg) and Pd—C (40 mg) in methanol (1 mL).

(2-{[2-(6-Chloro-benzothiazol-2-ylamino)-1-methyl-1H-benzoimidazole-5-carbonyl]-amino}-ethyl)-(2-fluoro-ethyl)-carbamic acid tert-butyl ester (70 mg) was prepared by following General Procedure F starting from 2-(6-chloro-benzothiazol-2-ylamino)-1-methyl-1H-benzoimidazole-5-carboxylic acid (70 mg), (2-amino-ethyl)-(2-fluoro-ethyl)-carbamic acid tert-butyl ester (90 mg), HBTU (100 mg), and DIEA (70 uL) in DMF (1.5 mL).

2-(6-Chloro-benzothiazol-2-ylamino)-1-methyl-1H-benzoimidazole-5-carboxylic acid [2-(2-fluoro-ethylamino)-ethyl]-amide dihydrochloride (65 mg) was prepared by following General Procedure L starting from (2-{[2-(6-chloro-benzothiazol-2-ylamino)-1-methyl-1H-benzoimidazole-5-carbonyl]-amino}-ethyl)-(2-fluoro-ethyl)-carbamic acid tert-butyl ester (70 mg) in 4M HCl in dioxane (1 mL). LC/MS: m/z 446.6.

Examples 280 to 284, as shown in Table 1, are made by procedures analogous to those described above for Example 205. Observed m/z values for these examples are as follows. Example 280: 482.9. Example 281: 481.5. Example 282: 539.0. Example 283: 570.8. Example 284: 496.9.

Example 285, as shown in Table 1, is made by procedures analogous to those described below for Example 286. An observed m/z value for this example is 479.6.

Example 286

3-Methyl-2-(6-trifluoromethoxy-benzothiazol-2-ylamino)-3H-benzoimidazole-5-carboxylic acid [2-(2-hydroxy-ethoxy)-ethyl]-amide 3-Methylamino-4-nitro-benzoic acid ethyl ester (2.8 g) was prepared by following General Procedure A starting from 3-fluoro-4-nitro-benzoic acid ethyl ester (3 g) and 2 M methylamine in THF (15 mL) in DMF (15 mL).

4-Amino-3-methylamino-benzoic acid ethyl ester (2.1 g) was prepared by following General Procedure B starting from 3-methylamino-4-nitro-benzoic acid ethyl ester (2.8 g) and Pd—C (560 mg) in methanol (25 mL).

3-Methyl-2-(6-trifluoromethoxy-benzothiazol-2-ylamino)-3H-benzoimidazole-5-carboxylic acid ethyl ester (2.8 g) was prepared by following General Procedure D starting from 6-trifluoromethoxy-benzothiazol-2-ylamine (2.9 g), 4-amino-3-methylamino-benzoic acid ethyl ester (2.1 g), thioCDI (2.2 g) and EDC (2.4 g) in DMF (30 mL).

3-Methyl-2-(6-trifluoromethoxy-benzothiazol-2-ylamino)-3H-benzoimidazole-5-carboxylic acid (2.5 g) was prepared by following General Procedure E starting from 3-methyl-2-(6-trifluoromethoxy-benzothiazol-2-ylamino)-3H-benzoimidazole-5-carboxylic acid ethyl ester (2.8 g) and 2 N NaOH (6 mL) in methanol:THF (1:1, 12 mL).

3-Methyl-2-(6-trifluoromethoxy-benzothiazol-2-ylamino)-3H-benzoimidazole-5-carboxylic acid [2-(2-hydroxy-ethoxy)-ethyl]-amide (50 mg) was prepared by following General Procedure F starting from 3-methyl-2-(6-trifluoromethoxy-benzothiazol-2-ylamino)-3H-benzoimidazole-5-carboxylic acid (80 mg), 2-(2-amino-ethoxy)-ethanol (24 mg), HBTU (80 mg), and DIEA (70 uL) in DMF (1 mL). LC/MS: m/z 495.5.

Example 287, as shown in Table 1, is made by procedures analogous to those described below for Example 288. An observed m/z value for this example is 429.6.

Example 288

2-(6-Chloro-benzothiazol-2-ylamino)-3-methyl-3H-benzoimidazole-5-carboxylic acid [2-(2-hydroxy-ethoxy)-ethyl]-amide 2-(6-Chloro-benzothiazol-2-ylamino)-3-methyl-3H-benzoimidazole-5-carboxylic acid ethyl ester (1.2 g) was prepared by following General Procedure D starting from 6-chloro-benzothiazol-2-ylamine (1.2 g), 4-amino-3-methylamino-benzoic acid ethyl ester (1.2 g), thioCDI (1 g) and EDC (1.1 g) in DMF (20 mL).

2-(6-Chloro-benzothiazol-2-ylamino)-3-methyl-3H-benzoimidazole-5-carboxylic acid (1 g) was prepared by following General Procedure E starting from 2-(6-chloro-benzothiazol-2-ylamino)-3-methyl-3H-benzoimidazole-5-carboxylic acid ethyl ester (1.2 g) and 2 N NaOH (5 mL) in methanol:THF (1:1, 20 mL).

2-(6-Chloro-benzothiazol-2-ylamino)-3-methyl-3H-benzoimidazole-5-carboxylic acid [2-(2-hydroxy-ethoxy)-ethyl]-amide (40 mg) was prepared by following General Procedure F starting from 2-(6-chloro-benzothiazol-2-ylamino)-3-methyl-3H-benzoimidazole-5-carboxylic acid (70 mg), 2-(2-amino-ethoxy)-ethanol (23 mg), HBTU (80 mg), and DIEA (70 uL) in DMF (1 mL). LC/MS: m/z 445.6. Examples 289 to 291, as shown in Table 1, are made by procedures analogous to those described above for Example 55. Observed m/z values for these examples are as follows. Example 289: 476.6. Example 290: 426.6. Example 291: 426.5.

Example 292

2-(6-Chloro-benzothiazol-2-ylamino)-1-methyl-1H-benzoimidazole-5-carboxylic acid [(R)-1-(2-hydroxy-ethyl)-pyrrolidin-3-yl]-amide 2-(6-Chloro-benzothiazol-2-ylamino)-1-methyl-1H-benzoimidazole-5-carboxylic acid [(R)-1-(2-hydroxy-ethyl)-pyrrolidin-3-yl]-amide (25 mg) was prepared starting from 2-(6-chloro-benzothiazol-2-ylamino)-1-methyl-1H-benzoimidazole-5-carboxylic acid (R)-pyrrolidin-3-ylamide dihydrochloride (200 mg), 2-bromo-ethanol (50 uL) and $Cs_2CO_3$ (300 mg) in DMF (1 mL). The reaction was heated to 50° C. for 8 h. The reaction was filtered and purified with silica gel chromatography using DCM:10% methanol in DCM (100:0 to 0:100) as an eluent system to give pure product. LC/MS: m/z 470.6.

Example 293

2-(6-Chloro-benzothiazol-2-ylamino)-1-methyl-1H-benzoimidazole-5-carboxylic acid [(S)-1-(2-hydroxy-ethyl)-pyrrolidin-3-yl]-amide 2-(6-Chloro-benzothiazol-2-ylamino)-1-methyl-1H-benzoimidazole-5-carboxylic acid [(S)-1-(2-hydroxy-ethyl)-pyrrolidin-3-yl]-amide (20 mg) was prepared starting from 2-(6-chloro-benzothiazol-2-ylamino)-1-methyl-1H-benzoimidazole-5-carboxylic acid (S)-pyrrolidin-3-ylamide dihydrochloride (200 mg), 2-bromo-ethanol (50 uL) and $Cs_2CO_3$ (300 mg) in DMF (1 mL). The reaction was heated to 50° C. for 8 h. The reaction was filtered and purified with silica gel chromatography using DCM10% methanol in DCM (100:0 to 0:100) as an eluent system to give pure product. LC/MS: m/z 470.8.

Example 294

1-Methyl-2-(6-trifluoromethoxy-benzothiazol-2-ylamino)-1H-benzoimidazole-5-carboxylic acid [1-((R)-2-hydroxy-propyl)-pyrrolidin-3-yl]-amide 3-{[1-Methyl-2-(6-trifluoromethoxy-benzothiazol-2-ylamino)-1H-benzoimidazole-5 carbonyl]-amino}-pyrrolidine-1-carboxylic acid tert-butyl ester (400 mg) was prepared by following General Procedure F starting from 1-methyl-2-(6-trifluoromethoxy-benzothiazol-2-ylamino)-1H-benzoimidazole-5-carboxylic acid (408 mg), 3-amino-pyrrolidine-1-carboxylic acid tert-butyl ester (220 mg), HBTU (457 mg), and DIEA (350 uL) in DMF (3 mL).

1-Methyl-2-(6-trifluoromethoxy-benzothiazol-2-ylamino)-1H-benzoimidazole-5-carboxylic acid pyrrolidin-3-ylamide dihydrochloride (330 mg) was prepared by following General Procedure L starting from 3-{[1-methyl-2-(6-trifluoromethoxy-benzothiazol-2-ylamino)-1H-benzoimidazole-5 carbonyl]-amino}-pyrrolidine-1-carboxylic acid tert-butyl ester (400 mg) in 4M HCl in dioxane (2 mL).

1-Methyl-2-(6-trifluoromethoxy-benzothiazol-2-ylamino)-1H-benzoimidazole-5-carboxylic acid [1-((R)-2-hydroxy-propyl)-pyrrolidin-3-yl]-amide (15 mg) was prepared using 1-methyl-2-(6-trifluoromethoxy-benzothiazol-2-ylamino)-1H-benzoimidazole-5-carboxylic acid pyrrolidin-3-ylamide dihydrochloride (47 mg), (R)-2-methyl-oxirane (excess) and DIEA (35 uL) in DMF (1 mL). The reaction was stirred at 80° C. overnight. The pure product was isolated through silica gel chromatography using DCM: (10%) methanol in DCM (from 100:0 to 0:100) as eluent system. LC/MS: m/z 534.6.

Example 295

2-(6-Chloro-benzothiazol-2-ylamino)-1-methyl-1H-benzoimidazole-5-carboxylic acid [(R)-1-((R)-2-hydroxy-propionyl)-pyrrolidin-3-yl]-amide 2-(6-Chloro-benzothiazol-2-ylamino)-1-methyl-1H-benzoimidazole-5-carboxylic acid [(R)-1-((R)-2-hydroxy-propionyl)-pyrrolidin-3-yl]-amide (20 mg) was prepared by following General Procedure F starting from 2-(6-chloro-benzothiazol-2-ylamino)-1-methyl-1H-benzoimidazole-5-carboxylic acid (50 mg), (R)-1-((R)-3-amino-pyrrolidin-1-yl)-2-hydroxy-propan-1-one (100 mg), HBTU (150 mg), and DIEA (100 uL) in DMF (1 mL). LC/MS: m/z 498.6.

Example 296

2-(6-Chloro-benzothiazol-2-ylamino)-1-methyl-1H-benzoimidazole-5-carboxylic acid [(R)-1-((R)-2-hydroxy-propyl)-pyrrolidin-3-yl]-amide

[(R)-1-((R)-2-Hydroxy-propionyl)-pyrrolidin-3-yl]-carbamic acid tert-butyl ester (500 mg) was prepared by following General Procedure F starting from (R)-2-hydroxy-propionic acid (200 mg), (R)-pyrrolidin-3-yl-carbamic acid tert-butyl ester (372 mg), HBTU (800 mg), and DIEA (400 uL) in DMF (4 mL).

[(R)-1-((R)-2-Hydroxy-propyl)-pyrrolidin-3-yl]-carbamic acid tert-butyl ester (244 mg) was prepared from

[(R)-1-((R)-2-hydroxy-propionyl)-pyrrolidin-3-yl]-carbamic acid tert-butyl ester (500 mg) and 1 M borane in THF (6 mL). The reaction was stirred at room temperature for 30 min and then stirred at 50° C. for 8 h. The reaction was added to methanol (20 mL). The solvent was evaporated and crude compound was purified by flash chromatography using DCM:methanol gradient.

(R)-1-((R)-3-Amino-pyrrolidin-1-yl)-propan-2-ol dihydrochloride (140 mg) was prepared by following General Procedure L starting from [(R)-1-((R)-2-hydroxy-propyl)-pyrrolidin-3-yl]-carbamic acid tert-butyl ester (244 mg) and DCM (2 mL) in 4M HCl in dioxane (2 mL).

2-(6-Chloro-benzothiazol-2-ylamino)-1-methyl-1H-benzoimidazole-5-carboxylic acid [(R)-1-((R)-2-hydroxy-propyl)-pyrrolidin-3-yl]-amide (20 mg) was prepared by following General Procedure F starting from 2-(6-chloro-benzothiazol-2-ylamino)-1-methyl-1H-benzoimidazole-5-carboxylic acid (60 mg), (R)-1-((R)-3-amino-pyrrolidin-1-yl)-propan-2-ol (100 mg), HBTU (180 mg), and DIEA (100 uL) in DMF (1 mL). LC/MS: m/z 484.7. $^1$H NMR (DMSO-d$_6$, 400 MHz): δ 8.43 (m, 1H), 8.08 (s, 1H), 7.93-7.92 (d, 1H), 7.75 (br. m, 1H), 7.47-7.45 (br. d, 1H), 7.40-7.37 (m, 1H), 4.52-4.42 (m, 2H), 3.77-3.73 (m, 1H), 3.66 (s, 3H), 2.92-2.78 (m, 2H), 2.63-2.60 (m, 2H), 2.46-2.43 (m, 2H), 2.19-2.14 (m, 1H), 1.86-1.78 (m, 1H) 1.07-1.06 (d, 3H) —N$\underline{H}$ and OH proton signal was not observed.

Example 297, as shown in Table 1, is made by procedures analogous to those described above for Example 296. An observed m/z value for this example is 518.7.

Example 298

1-Methyl-2-(6-trifluoromethoxy-benzothiazol-2-ylamino)-1H-benzoimidazole-5-carboxylic acid [1-(2-hydroxy-2-methyl-propyl)-pyrrolidin-3-yl]-amide 1-Methyl-2-(6-trifluoromethoxy-benzothiazol-2-ylamino)-1H-benzoimidazole-5-carboxylic acid [1-(2-hydroxy-2-methyl-propyl)-pyrrolidin-3-yl]-amide (16 mg) was prepared using 1-methyl-2-(6-trifluoromethoxy-benzothiazol-2-ylamino)-1H-benzoimidazole-5-carboxylic acid pyrrolidin-3-ylamide dihydrochloride (47 mg), 2,2-dimethyl-oxirane (excess) and DIEA (70 uL) in DMF (1 mL). The reaction was stirred at 80° C. overnight. The pure product was isolated through silica gel chromatography using DCM: (10%) methanol in DCM (from 100:0 to 0:100) as eluent system. LC/MS: m/z 548.7.

Example 299, as shown in Table 1, is made by procedures analogous to those described above for Example 266. An observed m/z value for this example is 498.5.

Example 300

2-(6-Chloro-benzothiazol-2-ylamino)-1-methyl-1H-benzoimidazole-5-carboxylic acid [1-(2-methane-sulfonylamino-ethyl)-pyrrolidin-3-yl]-amide

[2-(3-{[2-(6-Chloro-benzothiazol-2-ylamino)-1-methyl-1H-benzoimidazole-5-carbonyl]-amino}-pyrrolidin-1-yl)-ethyl]-carbamic acid tert-butyl ester (56 mg) was prepared by following General Procedure P starting from 2-(6-chloro-benzothiazol-2-ylamino)-1-methyl-1H-benzoimidazole-5-carboxylic acid pyrrolidin-3-ylamide dihydrochloride (84 mg), (2-oxo-ethyl)-carbamic acid tert-butyl ester (40 mg), and Na(OAc)$_3$BH (65 mg) in DCM (2 mL).

2-(6-Chloro-benzothiazol-2-ylamino)-1-methyl-1H-benzoimidazole-5-carboxylic acid [1-(2-amino-ethyl)-pyrrolidin-3-yl]-amide trihydrochloride (46 mg) was prepared by following General Procedure L starting from [2-(3-{[2-(6-chloro-benzothiazol-2-ylamino)-1-methyl-1H-benzoimidazole-5-carbonyl]-amino}-pyrrolidin-1-yl)-ethyl]-carbamic acid tert-butyl ester (56 mg) in 4M HCl in dioxane (1 mL).

2-(6-Chloro-benzothiazol-2-ylamino)-1-methyl-1H-benzoimidazole-5-carboxylic acid [1-(2-methanesulfonylamino-ethyl)-pyrrolidin-3-yl]-amide (15 mg) was prepared by following General Procedure Q starting from 2-(6-chloro-benzothiazol-2-ylamino)-1-methyl-1H-benzoimidazole-5-carboxylic acid [1-(2-amino-ethyl)-pyrrolidin-3-yl]-amide dihydrochloride (46 mg), methanesulfonyl chloride (1-2 drops) and triethylamine (30 uL) in DCM (1 mL). LC/MS: m/z 547.6.

Example 301

2-(6-Chloro-benzothiazol-2-ylamino)-1-(2-methoxy-ethyl)-1H-benzoimidazole-5-carboxylic acid [1-(2-hydroxy-ethyl)-piperidin-4-yl]-amide 4-{[2-(6-Chloro-benzothiazol-2-ylamino)-1-(2-methoxy-ethyl)-1H-benzoimidazole-5-carbonyl]-amino}-piperidine-1-carboxylic acid tert-butyl ester (160 mg) was prepared by following General Procedure F starting from 2-(6-chloro-benzothiazol-2-ylamino)-1-(2-methoxy-ethyl)-1H-benzoimidazole-5-carboxylic acid (180 mg), 4-amino-piperidine-1-carboxylic acid tert-butyl ester (150 mg), HBTU (200 mg), and DIEA (1.2 mL) in DMF (2 mL).

2-(6-Chloro-benzothiazol-2-ylamino)-1-(2-methoxy-ethyl)-1H-benzoimidazole-5-carboxylic acid piperidin-4-ylamide dihydrochloride (150 mg) was prepared by following General Procedure L starting from 4-{[2-(6-chloro-benzothiazol-2-ylamino)-1-(2-methoxy-ethyl)-1H-benzoimidazole-5-carbonyl]-amino}-piperidine-1-carboxylic acid tert-butyl ester (160 mg) in 4M HCl in dioxane (2 mL).

2-(6-Chloro-benzothiazol-2-ylamino)-1-(2-methoxy-ethyl)-1H-benzoimidazole-5-carboxylic acid [1-(2-hydroxy-ethyl)-piperidin-4-yl]-amide (52 mg) was prepared by following General Procedure P starting from 2-(6-chloro-benzothiazol-2-ylamino)-1-(2-methoxy-ethyl)-1H-benzoimidazole-5-carboxylic acid piperidin-4-ylamide dihydrochloride (145 mg), [1,4]dioxane-2,5-diol (55 mg), and Na(OAc)$_3$BH (95 mg) in DCM (2 mL). LC/MS: m/z 528.6.

Example 302, as shown in Table 1, is made by procedures analogous to those described above for Example 55. An observed m/z value for this example is 454.5.

Example 303

2-(6-Chloro-benzothiazol-2-ylamino)-1-methyl-1H-benzoimidazole-5-carboxylic acid [1-(2-hydroxy-ethyl)-piperidin-4-ylmethyl]-amide 4-({[2-(6-Chloro-benzothiazol-2-ylamino)-1-methyl-1H-benzoimidazole-5-carbonyl]-amino}-methyl)-piperidine-1-carboxylic acid tert-butyl ester (155 mg) was prepared by following General Procedure F starting from 2-(6-chloro-benzothiazol-2-ylamino)-1-methyl-1H-benzoimidazole-5-carboxylic acid (150 mg), 4-aminomethyl-piperidine-1-carboxylic acid tert-butyl ester (100 mg), HBTU (200 mg), and DIEA (1.2 mL) in DMF (2 mL).

2-(6-Chloro-benzothiazol-2-ylamino)-1-methyl-1H-benzoimidazole-5-carboxylic acid (piperidin-4-ylmethyl)-amide dihydrochloride (150 mg) was prepared by following General Procedure L starting from 4-({[2-(6-chloro-benzothiazol-2-ylamino)-1-methyl-1H-benzoimidazole-5-carbonyl]-amino}-methyl)-piperidine-1-carboxylic acid tert-butyl ester (155 mg) in 4M HCl in dioxane (2 mL).

2-(6-Chloro-benzothiazol-2-ylamino)-1-methyl-1H-benzoimidazole-5-carboxylic acid [1-(2-hydroxy-ethyl)-piperidin-4-ylmethyl]-amide (35 mg) was prepared by following General Procedure P starting from 2-(6-chloro-benzothiazol-2-ylamino)-1-methyl-1H-benzoimidazole-5-carboxylic acid (piperidin-4-ylmethyl)-amide dihydrochloride (135 mg), [1,4]dioxane-2,5-dio (65 mg), and Na(OAc)$_3$BH (95 mg) in DCM (2 mL). LC/MS: m/z 498.5.

Example 304

2-(6-Chloro-benzothiazol-2-ylamino)-1-(2-methoxy-ethyl)-1H-benzoimidazole-5-carboxylic acid [1-(2-hydroxy-ethyl)-piperidin-4-ylmethyl]-amide 4-({[2-(6-Chloro-benzothiazol-2-ylamino)-1-(2-methoxy-ethyl)-1H-benzoimidazole-5-carbonyl]-amino}-methyl)-piperidine-1-carboxylic acid tert-butyl ester (160 mg) was prepared by following General Procedure F starting from 2-(6-Chloro-benzothiazol-2-ylamino)-1-(2-methoxy-ethyl)-1 H-benzoimidazole-5-carboxylic acid (180 mg), 4-aminomethyl-piperidine-1-carboxylic acid tert-butyl ester (150 mg), HBTU (200 mg), and DIEA (1.2 mL) in DMF (2 mL).

2-(6-Chloro-benzothiazol-2-ylamino)-1-(2-methoxy-ethyl)-1H-benzoimidazole-5-carboxylic acid (piperidin-4-ylmethyl)-amide dihydrochloride (145 mg) was prepared by following General Procedure L starting from 4-({[2-(6-chloro-benzothiazol-2-ylamino)-1-(2-methoxy-ethyl)-1H-benzoimidazole-5-carbonyl]-amino}-methyl)-piperidine-1-carboxylic acid tert-butyl ester (160 mg) in 4M HCl in dioxane (2 mL).

2-(6-Chloro-benzothiazol-2-ylamino)-1-(2-methoxy-ethyl)-1H-benzoimidazole-5-carboxylic acid [1-(2-hydroxy-ethyl)-piperidin-4-ylmethyl]-amide (45 mg) was prepared by following General Procedure P starting from 2-(6-chloro-benzothiazol-2-ylamino)-1-(2-methoxy-ethyl)-1H-benzoimidazole-5-carboxylic acid (piperidin-4-ylmethyl)-amide dihydrochloride (136 mg), [1,4]dioxane-2,5-diol (54 mg), and Na(OAc)$_3$BH (95 mg) in DCM (2 mL). LC/MS: m/z 542.7.

Example 305, as shown in Table 1, is made by procedures analogous to those described below for Example 306. An observed m/z value for this example is 520.6.

Example 306

[2-(6-Chloro-benzothiazol-2-ylamino)-1-methyl-1H-benzoimidazol-5-yl]-[4-(2-hydroxy-ethyl)-piperazin-1-yl]-methanone

[2-(6-Chloro-benzothiazol-2-ylamino)-1-methyl-1H-benzoimidazol-5-yl]-[4-(2-hydroxy-ethyl)-piperazin-1-yl]-methanone (315 mg) was prepared by following General Procedure F starting 2-(6-chloro-benzothiazol-2-ylamino)-1-methyl-1H-benzoimidazole-5-carboxylic acid (358 mg), 2-piperazin-1-yl-ethanol (143 mg), HBTU (419 mg), and DIEA (350 uL) in DMF (3 mL). LC/MS: m/z 470.6.

Example 307, as shown in Table 1, is made by procedures analogous to those described above for Example 205. An observed m/z value for this example is 533.5.

Example 308, as shown in Table 1, is made by procedures analogous to those described below for Example 313. An observed m/z value for this example is 511.5.

Examples 309 and 310, as shown in Table 1, are made by procedures analogous to those described above for Example 55. Observed m/z values for these examples are as follows. Example 309: 441.6. Example 310: 441.8.

Examples 311 and 312, as shown in Table 1, are made by procedures analogous to those described below for Example 313. Observed m/z values for these examples are as follows. Example 311: 526.9. Example 312: 526.7.

Example 313

2-(6-Chloro-benzothiazol-2-ylamino)-1-methyl-1H-benzoimidazole-5-carboxylic acid [1-(2-dimethyl-amino-acetyl)-piperidin-4-yl]-amide 4-{[2-(6-Chloro-benzothiazol-2-ylamino)-1-methyl-1H-benzoimidazole-5-carbonyl]-amino}-piperidine-1-carboxylic acid tert-butyl ester (800 mg) was prepared by following General Procedure F starting from 2-(6-chloro-benzothiazol-2-ylamino)-1-methyl-1H-benzoimidazole-5-carboxylic acid (716 mg), 4-amino-piperidine-1-carboxylic acid tert-butyl ester (500 mg), HBTU (952 mg), and DIEA (700 uL) in DMF (5 mL).

2-(6-Chloro-benzothiazol-2-ylamino)-1-methyl-1H-benzoimidazole-5-carboxylic acid piperidin-4-ylamide dihydrochloride (750 mg) was prepared by following General Procedure L starting from 4-{[2-(6-chloro-benzothiazol-2-ylamino)-1-methyl-1H-benzoimidazole-5-carbonyl]-amino}-piperidine-1-carboxylic acid tert-butyl ester (800 mg) in 4M HCl in dioxane (5 mL).

2-(6-Chloro-benzothiazol-2-ylamino)-1-methyl-1H-benzoimidazole-5-carboxylic acid [1-(2-dimethylamino-acetyl)-piperidin-4-yl]-amide (52 mg) was prepared by following General Procedure F starting from 2-(6-chloro-benzothiazol-2-ylamino)-1-methyl-1H-benzoimidazole-5-carboxylic acid piperidin-4-ylamide dihydrochloride (88 mg), dimethylamino-acetic acid (26 mg), HBTU (95 mg), and DIEA (70 uL) in DMF (1 mL). LC/MS: m/z 525.5. $^1$H NMR (DMSO-d$_6$, 400 MHz): δ 8.40-8.38 (d, 1H), 8.11 (s, 1H), 7.96 (m, 1H), 7.80-7.78 (d, 1H), 7.55-7.50 (m, 2H), 7.43-7.40 (d, 1H), 4.43-4.25 (m, 2H), 4.09-4.08 (br. m, 1H), 3.68 (s, 3H), 3.67-3.65 (m, 1H), 3.57-3.50 (m, 1H), 3.22-3.17 (m, 1H), 2.93-2.82 (m, 6H), 1.96-1.89 (m, 2H), 1.59-1.46 (m, 2H), 1.30-1.25 (m, 1H) —NH proton signal was not observed.

Examples 314 and 315, as shown in Table 1, are made by procedures analogous to those described above for Example 313. Observed m/z values for these examples are as follows. Example 314: 539.7. Example 315: 583.7.

Example 316

2-(6-Chloro-benzothiazol-2-ylamino)-1-methyl-1H-benzoimidazole-5-carboxylic acid ((R)-1-methyl-pyrrolidin-3-yl)-amide (R)-3-{[2-(6-Chloro-benzothiazol-2-ylamino)-1-methyl-1H-benzoimidazole-5-carbonyl]-amino}-pyrrolidine-1-carboxylic acid tert-butyl ester (55 mg) was prepared by following General Procedure F starting from 2-(6-chloro-benzothiazol-2-ylamino)-1-methyl-1H-benzoimidazole-5-carboxylic acid (70 mg), (R)-3-amino-pyrrolidine-1-carboxylic acid tert-butyl ester (45 mg), HBTU (95 mg), and DIEA (70 uL) in DMF (1 mL).

2-(6-Chloro-benzothiazol-2-ylamino)-1-methyl-1H-benzoimidazole-5-carboxylic acid (R)-pyrrolidin-3-ylamide dihydrochloride (45 mg) was prepared by following General Procedure L starting from (R)-3-{[2-(6-chloro-benzothiazol-2-ylamino)-1-methyl-1H-benzoimidazole-5-carbonyl]-amino}-pyrrolidine-1-carboxylic acid tert-butyl ester (55 mg) in 4M HCl in dioxane (1 mL).

2-(6-Chloro-benzothiazol-2-ylamino)-1-methyl-1H-benzoimidazole-5-carboxylic acid ((R)-1-methyl-pyrrolidin-3-yl)-amide (42 mg) was prepared by following General Procedure P starting from 2-(6-chloro-benzothiazol-2-ylamino)-1-methyl-1H-benzoimidazole-5-carboxylic acid (R)-pyrrolidin-3-ylamide dihydrochloride (51 mg), 37% formaldehyde (500 uL), and Na(OAc)$_3$BH (40 mg) in DCM (500 uL). LC/MS: m/z 440.5.

Example 317

2-(6-Chloro-benzothiazol-2-ylamino)-1-methyl-1H-benzoimidazole-5-carboxylic acid ((S)-1-methyl-pyrrolidin-3-yl)-amide (S)-3-{[2-(6-Chloro-benzothiazol-2-ylamino)-1-methyl-1H-benzoimidazole-5-carbonyl]-amino}-pyrrolidine-1-carboxylic acid tert-butyl ester (65 mg) was prepared by following General Procedure F starting from 2-(6-chloro-benzothiazol-2-ylamino)-1-methyl-1H-benzoimidazole-5-carboxylic acid (70 mg), (S)-3-amino-pyrrolidine-1-carboxylic acid tert-butyl ester (46 mg), HBTU (95 mg), and DIEA (70 uL) in DMF (1 mL).

2-(6-Chloro-benzothiazol-2-ylamino)-1-methyl-1H-benzoimidazole-5-carboxylic acid (S)-pyrrolidin-3-ylamide dihydrochloride (51 mg) was prepared by following General Procedure L starting from (S)-3-{[2-(6-chloro-benzothiazol-2-ylamino)-1-methyl-1H-benzoimidazole-5-carbonyl]-amino}-pyrrolidine-1-carboxylic acid tert-butyl ester (65 mg) in 4M HCl in dioxane (1 mL).

2-(6-Chloro-benzothiazol-2-ylamino)-1-methyl-1H-benzoimidazole-5-carboxylic acid ((S)-1-methyl-pyrrolidin-3-yl)-amide (35 mg) was prepared by following General Procedure P starting from 2-(6-chloro-benzothiazol-2-ylamino)-1-methyl-1H-benzoimidazole-5-carboxylic acid (S)-pyrrolidin-3-ylamide dihydrochloride (45 mg), 37% formaldehyde (500 uL), and Na(OAc)$_3$BH (32 mg) in DCM (500 uL). LC/MS: m/z 440.7.

Examples 318 to 321, as shown in Table 1, are made by procedures analogous to those described above for Example 205. Observed m/z values for these examples are as follows. Example 318: 469.8. Example 319: 455.8. Example 320: 519.6. Example 321: 442.8.

Example 322

1-Methyl-2-(6-trifluoromethoxy-benzothiazol-2-ylamino)-1H-benzoimidazole-5-carboxylic acid (2-methanesulfonylamino-ethyl)-amide 1-Methyl-2-(6-trifluoromethoxy-benzothiazol-2-ylamino)-1H-benzoimidazole-5-carboxylic acid (2-methanesulfonylamino-ethyl)-amide (57 mg) was prepared by following General Procedure Q starting from 1-methyl-2-(6-trifluoromethoxy-benzothiazol-2-ylamino)-1H-benzoimidazole-5-carboxylic acid (2-amino-ethyl)-amide dihydrochloride (75 mg), methanesulfonyl chloride (16 mg), and triethylamine (62 uL). LC/MS: m/z 529.6.

Example 323

1-Methyl-2-(6-trifluoromethoxy-benzothiazol-2-ylamino)-1H-benzoimidazole-5-carboxylic acid [2-(2-dimethylamino-acetylamino)-ethyl]-amide 1-Methyl-2-(6-trifluoromethoxy-benzothiazol-2-ylamino)-1H-benzoimidazole-5-carboxylic acid [2-(2-dimethylamino-acetylamino)-ethyl]-amide (62 mg) was prepared by following General Procedure F starting from 1-methyl-2-(6-trifluoromethoxy-benzothiazol-2-ylamino)-1H-benzoimidazole-5-carboxylic acid (2-amino-ethyl)-amide dihydrochloride (60 mg), N,N-dimethylglycine hydrochloride (18 mg), HBTU (57 mg), and DIEA (33 uL). LC/MS: m/z 536.8. $^1$H NMR (DMSO-d$_6$, 400 MHz): δ 12.37 (bs, 1H), 8.48 (s, 1H), 8.08 (s, 1H), 8.04 (s, 1H), 7.94 (s, 1H), 7.80-7.65 (m, 2H), 7.49 (d, 1H), 7.37 (d, 1H), 3.76-3.46 (m, 5H), 2.97 (s, 2H), 2.89 (s, 2H), 2.25 (s, 6H).

Example 324

2-(6-Chloro-benzothiazol-2-ylamino)-1-methyl-1H-benzoimidazole-5-carboxylic acid [2-(2-dimethyl-amino-acetylamino)-ethyl]-amide (2-{[2-(6-Chloro-benzothiazol-2-ylamino)-1-methyl-1H-benzoimidazole-5-carbonyl]-amino}-ethyl)-carbamic acid tert-butyl ester (290 mg) was prepared by following General Procedure F using 2-(6-chloro-benzothiazol-2-ylamino)-1-methyl-1H-benzoimidazole-5-carboxylic acid (300 mg), (2-amino-ethyl)-carbamic acid tert-butyl ester (147 mg), HBTU (380 mg), and DIEA (219 uL).

2-(6-Chloro-benzothiazol-2-ylamino)-1-methyl-1H-benzoimidazole-5-carboxylic acid (2-amino-ethyl)-amide dihydrochloride (225 mg) was prepared by following General Procedure L using (2-{[2-(6-chloro-benzothiazol-2-ylamino)-1-methyl-1H-benzoimidazole-5-carbonyl]-amino}-ethyl)-carbamic acid tert-butyl ester (250 mg) and hydrogen chloride (1.25 mL, 4.0 M solution in 1,4-dioxane).

2-(6-Chloro-benzothiazol-2-ylamino)-1-methyl-1H-benzoimidazole-5-carboxylic acid [2-(2-dimethylamino-acetylamino)-ethyl]-amide (64 mg) was prepared by following General Procedure F starting from 2-(6-chloro-benzothiazol-2-ylamino)-1-methyl-1H-benzoimidazole-5-carboxylic acid (2-amino-ethyl)-amide dihydrochloride (75 mg), N,N-dimethylglycine hydrochloride (24 mg), HBTU (79 mg), and DIEA (46 uL). LC/MS: m/z 486.9. $^1$H NMR (DMSO-d$_6$, 400 MHz): δ 12.38 (bs, 1H), 8.64-8.44 (m, 1H), 8.22 (bs, 1H), 8.08 (s, 1H), 7.93 (s, 1H), 7.83-7.59 (m, 2H), 7.55-7.45 (m, 1H), 7.41 (d, 1H), 3.79-3.56 (m, 5H), 3.44-3.34 (m, 2H), 3.20-3.09 (m, 2H), 2.71 (s, 6H).

Examples 325 and 326, as shown in Table 1, are made by procedures analogous to those described above for Example 313. Observed m/z values for these examples are as follows. Example 325: 508.0. Example 326: 524.0.

Examples 327 to 334, as shown in Table 1, are made by procedures analogous to those described above for Example 205. Observed m/z values for these examples are as follows. Example 327: 502.9. Example 328: 501.5. Example 329: 518.5. Example 330: 519.6. Example 331: 483.7. Example 332: 527.7. Example 333: 519.0. Example 334: 468.9.

Example 335

2-(6-Chloro-benzothiazol-2-ylamino)-1-methyl-1H-benzoimidazole-5-carboxylic acid [2-(4,4-difluoro-piperidin-1-yl)-ethyl]-amide 2-(6-Chloro-benzothiazol-2-ylamino)-1-methyl-1H-benzoimidazole-5-carboxylic acid (2,2-dimethoxy-ethyl)-amide (700 mg) was prepared by following General Procedure F starting from 2-(6-chloro-benzothiazol-2-ylamino)-1-methyl-1H-benzoimidazole-5-carboxylic acid (716 mg), 2,2-dimethoxy-ethylamine (265 mg), HBTU (952 mg), and DIEA (700 uL) in DMF (5 mL).

2-(6-Chloro-benzothiazol-2-ylamino)-1-methyl-1H-benzoimidazole-5-carboxylic acid (2-oxo-ethyl)-amide (574 mg) was prepared starting from 2-(6-chloro-benzothiazol-2-ylamino)-1-methyl-1H-benzoimidazole-5-carboxylic acid (2,2-dimethoxy-ethyl)-amide (700 mg) in 4M HCl-dioxane (3 mL). The reaction was heated to 50° C. for 5 h. The solvent was evaporated to give crude product.

2-(6-Chloro-benzothiazol-2-ylamino)-1-methyl-1H-benzoimidazole-5-carboxylic acid [2 (4,4-difluoro-piperidin-1-yl)-ethyl]-amide (45 mg) was prepared by following General Procedure P starting from 2-(6-chloro-benzothiazol-2-ylamino)-1-methyl-1H-benzoimidazole-5-carboxylic acid (2-oxo-ethyl)-amide (80 mg), 4,4-difluoro-piperidine (36 mg), and Na(OAc)$_3$BH (65 mg) in DCM (2 mL). LC/MS: m/z 504.5. $^1$H NMR (DMSO-d$_6$, 400 MHz): δ 8.97-8.88 (m, 1H), 8.14-8.12 (m, 1H), 7.97-7.96 (m, 1H), 7.88-7.80 (m, 1H), 7.56-7.52 (m, 2H), 7.43-7.40 (m, 1H), 4.08-4.05 (m, 1H), 3.74-3.69 (m, 7H), 3.57-3.47 (m, 1H), 3.46-3.17 (m, 3H), 2.46-2.43 (m, 3H), —N$\underline{H}$ proton signal was not observed.

Example 336, as shown in Table 1, is made by procedures analogous to those described above for Example 335. An observed m/z value for this example is 504.7.

Examples 337 and 338, as shown in Table 1, are made by procedures analogous to those described above for Example 205. Observed m/z values for these examples are as follows. Example 337: 534.0. Example 338: 483.8.

Example 339, as shown in Table 1, is made by procedures analogous to those described above for Example 55. An observed m/z value for this example is 469.9.

Examples 340 to 342, as shown in Table 1, are made by procedures analogous to those described above for Example 205. Observed m/z values for these examples are as follows. Example 340: 470.8. Example 341: 504.7. Example 342: 568.8.

Examples 343 to 347, as shown in Table 1, are made by procedures analogous to those described above for Example 104. Observed m/z values for these examples are as follows. Example 343: 401.8. Example 344: 464.9. Example 345: 414.8. Example 346: 478.9. Example 347: 428.8.

Examples 348 to 362, as shown in Table 1, are made by procedures analogous to those described above for Example 205. Observed m/z values for these examples are as follows. Example 348: 492.4. Example 349: 442.6. Example 350: 476.6. Example 351: 520.5. Example 352: 470.5. Example 353: 504.5. Example 354: 468.5. Example 355: 547.5. Example 356: 497.5. Example 357: 531.4. Example 358: 534.9. Example 359: 484.9. Example 360: 534.4. Example 361: 564.8. Example 362: 593.0.

Example 363, as shown in Table 1, is made by procedures analogous to those described below for Example 364. An observed m/z value for this example is 422.7.

Example 364

2-(6-Ethoxy-benzothiazol-2-ylamino)-1-methyl-1H-benzoimidazole-5-carboxylic acid dimethylcarbamoylmethyl-amide 4-Methylamino-3-nitro-benzoic acid (25 g) was prepared by following general procedure A starting from 4-fluoro-3-nitro-benzoic acid (25 g) and 2 M methylamine in THF (100 mL).

4-Methylamino-3-nitro-benzoyl chloride (4.3 g) was prepared starting from 4-methylamino-3-nitro-benzoic acid (4 g) in thionyl chloride (20 mL). The reaction was heated to 80° C. for 8 h. The solvent was evaporated to isolate pure compound without any further purification.

(4-Methylamino-3-nitro-benzoylamino)-acetic acid tert-butyl ester (1.2 g) was prepared starting from 4-methylamino-3-nitro-benzoyl chloride (1 g), amino-acetic acid tert-butyl ester (721 mg), triethylamine (1.4 mL) in DCM (10 mL). The reaction was stirred at 0° C. for 1 h. The reaction was added to DCM (50 mL) and saturated sodium bicarbonate solution (50 mL). The phases were separated, and the aqueous phase was extracted twice with DCM. The combined organics were dried over sodium sulfate and then filtered. The solvent was evaporated and crude compound was purified by flash chromatography using DCM:methanol gradient.

(4-Methylamino-3-nitro-benzoylamino)-acetic acid (800 mg) was prepared starting from (4-methylamino-3-nitro-benzoylamino)-acetic acid tert-butyl ester (1.2 g) in 4 M HCl-dioxane (2 mL) and DCM (2 mL). The reaction was stirred at room temperature for 8 h. The solvent was evaporated to isolate pure compound without any further purification.

N-Dimethylcarbamoylmethyl-4-methylamino-3-nitro-benzamide (800 mg) was prepared by following General Procedure F starting from (4-methylamino-3-nitro-benzoylamino)-acetic acid (800 mg), 2 M dimethylamine in THF (3 mL), HBTU (1.5 g), and DIEA (1.3 mL) in DMF (2 mL).

3-Amino-N-dimethylcarbamoylmethyl-4-methylamino-benzamide (700 mg) was prepared by following General Procedure B starting from N-dimethylcarbamoylmethyl-4-methylamino-3-nitro-benzamide (800 mg) and Pd—C (160 mg) in methanol (10 mL).

2-(6-Ethoxy-benzothiazol-2-ylamino)-1-methyl-1H-benzoimidazole-5-carboxylic acid dimethylcarbamoylmethyl-amide (15 mg) was prepared by following General Procedure D starting from 6-ethoxy-benzothiazol-2-ylamine (100 mg), 3-amino-N-dimethylcarbamoylmethyl-4-methylamino-benzamide (150 mg), thioCDI (150 mg) and EDC (150 mg) in DMF (3 mL). LC/MS: m/z 452.6.

Example 365

2-(6-Isopropyl-benzothiazol-2-ylamino)-1-methyl-1H-benzoimidazole-5-carboxylic acid dimethylcarbamoylmethyl-amide 2-(6-Isopropyl-benzothiazol-2-ylamino)-1-methyl-1H-benzoimidazole-5-carboxylic acid dimethylcarbamoylmethyl-amide (12 mg) was prepared by following General Procedure D starting from 6-isopropyl-benzothiazol-2-ylamine (150 mg), 3-amino-N-dimethylcarbamoylmethyl-4-methylamino-benzamide (200 mg), thioCDI (200 mg) and EDC (200 mg) in DMF (3 mL). LC/MS: m/z 450.6.

Example 366

2-(6-Chloro-benzothiazol-2-ylamino)-1-(2-methoxyethyl)-1H-benzoimidazole-5-carboxylic acid dimethylcarbamoylmethyl-amide 2-(6-Chloro-benzothiazol-2-ylamino)-1-(2-methoxyethyl)-1H-benzoimidazole-5-carboxylic acid dimethylcarbamoylmethyl-amide (24 mg) was prepared by following General Procedure F starting from 2-(6-chloro-benzothiazol-2-ylamino)-1-(2-methoxy-ethyl)-1H-benzoimidazole-5-carboxylic acid (80 mg), 2-amino-N,N-dimethyl-acetamide (40 mg), HBTU (95 mg), and DIEA (70 uL) in DMF (1 mL). LC/MS: m/z 486.5. $^1$H NMR (DMSO-d$_6$, 400

MHz): δ 8.57-8.56 (m, 1H), 8.11 (s, 1H), 8.01-8.00 (d, 1H), 7.84-7.82 (m, 1H), 7.63-7.61 (d, 1H), 7.57-7.54 (d, 1H), 7.46-7.44 (m, 1H), 4.43-4.40 (t, 2H), 4.14-4.13 (d, 2H), 3.75-3.72 (t, 2H), 3.24 (s, 3H), 3.04 (s, 3H), 2.87 (s, 3H), —NH proton signal was not observed.

Example 367

2-(6-Chloro-benzothiazol-2-ylamino)-1-(2-methyl-amino-ethyl)-1H-benzoimidazole-5-carboxylic acid dimethylcarbamoylmethyl-amide hydrochloride 4-[2-(tert-Butoxycarbonyl-methyl-amino)-ethylamino]-3-nitro-benzoic acid methyl ester (1.7 g) was prepared by following General Procedure A starting from 4-chloro-3-nitro-benzoic acid methyl ester (1 g), (2-amino-ethyl)-methyl-carbamic acid tert-butyl ester (1.2 g) and DIEA (1.7 mL) in THF (20 mL).

3-Amino-4-[2-(tert-butoxycarbonyl-methyl-amino)-ethylamino]-benzoic acid methyl ester (1.4 g) was prepared by following General Procedure B starting from 4-[2-(tert-butoxycarbonyl-methyl-amino)-ethylamino]-3-nitro-benzoic acid methyl ester (1.7 g) and Pd—C (350 mg) in methanol:EtOAc (1:1, 20 mL).

1-[2-(tert-Butoxycarbonyl-methyl-amino)-ethyl]-2-(6-chloro-benzothiazol-2-ylamino)-1H-benzoimidazole-5-carboxylic acid methyl ester (1.9 g) was prepared by following General Procedure D starting from 6-chloro-benzothiazol-2-ylamine (920 mg), 3-amino-4-[2-(tert-butoxycarbonyl-methyl-amino)-ethylamino]-benzoic acid methyl ester (1.4 g), thioCDI (900 mg) and EDC (960 mg) in DMF (15 mL).

1-[2-(tert-Butoxycarbonyl-methyl-amino)-ethyl]-2-(6-chloro-benzothiazol-2-ylamino)-1H-benzoimidazole-5-carboxylic acid (1.7 g) was prepared by following General Procedure E starting from 1-[2-(tert-butoxycarbonyl-methyl-amino)-ethyl]-2-(6-chloro-benzothiazol-2-ylamino)-1H-benzoimidazole-5-carboxylic acid methyl ester (1.9 g) and 2 N NaOH (5 mL) in methanol:THF (1:1, 10 mL).

{2-[2-(6-Chloro-benzothiazol-2-ylamino)-5-(dimethylcarbamoylmethyl-carbamoyl)-benzoimidazol-1-yl]-ethyl}-methyl-carbamic acid tert-butyl ester (70 mg) was prepared by following General Procedure F starting from 1-[2-(tert-butoxycarbonyl-methyl-amino)-ethyl]-2-(6-chloro-benzothiazol-2-ylamino)-1H-benzoimidazole-5-carboxylic acid (146 mg), 2-amino-N,N-dimethyl-acetamide (50 mg), HBTU (125 mg), and DIEA (100 uL) in DMF (1 mL).

2-(6-Chloro-benzothiazol-2-ylamino)-1-(2-methylamino-ethyl)-1H-benzoimidazole-5-carboxylic acid dimethylcarbamoylmethyl-amide dihydrochloride (60 mg) was prepared by following General Procedure L starting from {2-[2-(6-chloro-benzothiazol-2-ylamino)-5-(dimethylcarbamoylmethyl-carbamoyl)-benzoimidazol-1-yl]-ethyl}-methyl-carbamic acid tert-butyl ester (70 mg) in 4M HCl in dioxane (1 mL). LC/MS: m/z 485.5.

Example 368

1-Methyl-2-(6-trifluoromethoxy-benzothiazol-2-ylamino)-1H-benzoimidazole-5-carboxylic acid ((S)-1-dimethylcarbamoyl-2-hydroxy-ethyl)-amide (S)-3-Hydroxy-2-{[1-methyl-2-(6-trifluoromethoxy-benzothiazol-2-ylamino)-1H-benzoimidazole-5-carbonyl]-amino}-propionic acid ethyl ester (213 mg) was prepared by following General Procedure F starting from 1-methyl-2-(6-trifluoromethoxy-benzothiazol-2-ylamino)-1H-benzoimidazole-5-carboxylic acid (200 mg), L-serine ethyl ester hydrochloride (91 mg), HBTU (223 mg), and DIEA (128 uL).

(S)-3-Hydroxy-2-{[1-methyl-2-(6-trifluoromethoxy-benzothiazol-2-ylamino)-1H-benzoimidazole-5-carbonyl]-amino}-propionic acid (152 mg) was prepared by following General Procedure E starting from (S)-3-hydroxy-2-{[1-methyl-2-(6-trifluoromethoxy-benzothiazol-2-ylamino)-1H-benzoimidazole-5-carbonyl]-amino}-propionic acid ethyl ester (200 mg) and lithium hydroxide (64 mg).

1-Methyl-2-(6-trifluoromethoxy-benzothiazol-2-ylamino)-1H-benzoimidazole-5-carboxylic acid ((S)-1-dimethylcarbamoyl-2-hydroxy-ethyl)-amide (68 mg) was prepared by following General Procedure F starting from (S)-3-hydroxy-2-{[1-methyl-2-(6-trifluoromethoxy-benzothiazol-2-ylamino)-1H-benzoimidazole-5-carbonyl]-amino}-propionic acid (50 mg), dimethylamine (56 uL, 2 M in THF), HBTU (46 mg), and DIEA (27 uL). LC/MS: m/z 524.0.

Example 369

1-Methyl-2-(6-trifluoromethyl-benzothiazol-2-ylamino)-1H-benzoimidazole-5-carboxylic acid ((S)-5-amino-1-dimethylcarbamoyl-pentyl)-amide hydrochloride (S)-6-tert-Butoxycarbonylamino-2-(2-{[1-methyl-2-(6-trifluoromethyl-benzothiazol-2-ylamino)-1H-benzoimidazole-5-carbonyl]-amino}-acetylamino)-hexanoic acid methyl ester (300 mg) was prepared by following General Procedure F starting from 1-methyl-2-(6-trifluoromethyl-benzothiazol-2-ylamino)-1H-benzoimidazole-5-carboxylic acid (392 mg), (S)-2-amino-6-tert-butoxycarbonylamino-hexanoic acid methyl ester (280 mg), HBTU (400 mg), and DIEA (400 uL) in DMF (2 mL).

(S)-6-tert-Butoxycarbonylamino-2-(2-{[1-methyl-2-(6-trifluoromethyl-benzothiazol-2-ylamino)-1H-benzoimidazole-5-carbonyl]-amino}-acetylamino)-hexanoic acid (260 mg) was prepared by following General Procedure E starting from (S)-6-tert-butoxycarbonylamino-2-(2-{[1-methyl-2-(6-trifluoromethyl-benzothiazol-2-ylamino)-1H-benzoimidazole-5-carbonyl]-amino}-acetylamino)-hexanoic acid methyl ester (300 mg) and 2 N NaOH (2 mL) in MeOH:THF (1:1, 2 mL).

[(S)-5-Dimethylcarbamoyl-5-(2-{[1-methyl-2-(6-trifluoromethyl-benzothiazol-2-ylamino)-1H-benzoimidazole-5-carbonyl]-amino}-acetylamino)-pentyl]-carbamic acid tert-butyl ester (200 mg) was prepared by following General Procedure F starting from (S)-6-tert-butoxycarbonylamino-2-(2-{[1-methyl-2-(6-trifluoromethyl-benzothiazol-2-ylamino)-1H-benzoimidazole-5-carbonyl]-amino}-acetylamino)-hexanoic acid (260 mg), 2 M dimethylamine in THF (1 mL), HBTU (400 mg), and DIEA (400 uL) in DMF (2 mL).

1-Methyl-2-(6-trifluoromethyl-benzothiazol-2-ylamino)-1H-benzoimidazole-5-carboxylic acid [((S)-5-amino-1-dimethylcarbamoyl-pentylcarbamoyl)-methyl]-amide dihydrochloride (150 mg) was prepared by following General Procedure L starting from [(S)-5-dimethylcarbamoyl-5-(2-{[1-methyl-2-(6-trifluoromethyl-benzothiazol-2-ylamino)-1H-benzoimidazole-5-carbonyl]-amino}-acetylamino)-pentyl]-carbamic acid tert-butyl ester (200 mg) in 4M HCl in dioxane (1 mL) and DCM (2 mL). LC/MS: m/z 547.8.

Example 370

1-Methyl-2-(6-trifluoromethyl-benzothiazol-2-ylamino)-1H-benzoimidazole-5-carboxylic acid ((S)-5-dimethylamino-1-dimethylcarbamoyl-pentyl)-amide 1-Methyl-2-(6-trifluoromethyl-benzothiazol-2-ylamino)-1H-benzoimidazole-5-carboxylic acid [((S)-5-dimethylamino-1-dimethylcarbamoyl-pentylcarbamoyl)-methyl]-amide (20 mg) was prepared by following General Procedure P starting from 1-methyl-2-(6-trifluoromethyl-benzothiazol-2-ylamino)-1H-benzoimidazole-5-carboxylic acid [((S)-5-amino-1-dimethylcarbamoyl-pentylcarbamoyl)-methyl]-amide dihydrochloride (70 mg), 37% formaldehyde solution (500 uL), and Na(OAc)$_3$BH (100 mg) in DCM (1 mL) and DMF (500 uL). LC/MS: m/z 575.7.

Examples 371 to 377, as shown in Table 1, are made by procedures analogous to those described above for Example 135. Observed m/z values for these examples are as follows. Example 371: 456.6. Example 372: 490.6. Example 373: 498.7. Example 374: 532.7. Example 375: 545.5. Example 376: 471.9. Example 377: 526.8.

Example 378, as shown in Table 1, is made by procedures analogous to those described above for Example 83. An observed m/z value for this example is 484.8.

Example 379, as shown in Table 1, is made by procedures analogous to those described above for Example 135. An observed m/z value for this example is 512.7.

Examples 380 to 382, as shown in Table 1, are made by procedures analogous to those described below for Example 399. Observed m/z values for these examples are as follows. Example 380: 428.7. Example 381: 462.8. Example 382: 473.7.

Example 383, as shown in Table 1, is made by procedures analogous to those described above for Example 278. An observed m/z value for this example is 522.0.

Examples 384 to 386, as shown in Table 1, are made by procedures analogous to those described below for Example 399. Observed m/z values for these examples are as follows. Example 384: 485.7. Example 385: 499.8. Example 386: 512.8.

Example 387, as shown in Table 1, is made by procedures analogous to those described above for Example 152. An observed m/z value for this example is 498.4.

Example 388, as shown in Table 1, is made by procedures analogous to those described above for Example 316. An observed m/z value for this example is 512.7.

Examples 389 to 393, as shown in Table 1, are made by procedures analogous to those described below for Example 399. Observed m/z values for these examples are as follows. Example 389: 570.6. Example 390: 524.1. Example 391: 473.7. Example 392: 554.0. Example 393: 513.8.

Example 394, as shown in Table 1, is made by procedures analogous to those described above for Example 152. An observed m/z value for this example is 499.0.

Example 395, as shown in Table 1, is made by procedures analogous to those described below for Example 399. An observed m/z value for this example is 512.7.

Example 396, as shown in Table 1, is made by procedures analogous to those described above for Example 152. An observed m/z value for this example is 513.0.

Examples 397 and 398, as shown in Table 1, are made by procedures analogous to those described below for Example 399. Observed m/z values for these examples are as follows. Example 397: 468.5. Example 398: 535.7.

Example 399

2-(6-Chloro-benzothiazol-2-ylamino)-1-methyl-1H-benzoimidazole-5-carboxylic acid [2-(3-hydroxy-pyrrolidin-1-yl)-2-oxo-ethyl]-amide 2-(6-Chloro-benzothiazol-2-ylamino)-1-methyl-1H-benzoimidazole-5-carboxylic acid [2-(3-hydroxy-pyrrolidin-1-yl)-2-oxo-ethyl]-amide (102 mg) was prepared by following General Procedure F starting from {[2-(6-chloro-benzothiazol-2-ylamino)-1-methyl-1H-benzoimidazole-5-carbonyl]-amino}-acetic acid (100 mg), 3-pyrrolidinol (23 mg), HBTU (109 mg), and DIEA (63 uL). LC/MS: m/z 485.8. $^1$H NMR (DMSO-d$_6$, 400 MHz): δ 12.40 (bs, 1H), 8.54 (q, 1H), 8.11 (s, 1H), 7.93 (s, 1H), 7.82 (d, 1H), 7.67 (d, 1H), 7.51 (d, 1H), 7.39 (d, 1H), 5.04 (d, 1H), 4.32 (d, 1H), 4.15-3.97 (m, 2H), 3.63 (s, 3H), 3.62-3.51 (m, 2H), 3.50-3.33 (m, 2H), 2.05-1.70 (m, 2H).

Examples 400 to 410, as shown in Table 1, are made by procedures analogous to those described above for Example 399. Observed m/z values for these examples are as follows. Example 400: 484.7. Example 401: 484.7. Example 402: 518.7. Example 403: 518.7. Example 404: 529.8. Example 405: 529.8. Example 406: 549.7. Example 407: 551.8. Example 408: 498.7. Example 409: 498.7. Example 410: 532.7.

Examples 411 to 414, as shown in Table 1, are made by procedures analogous to those described above for Example 152. Observed m/z values for these examples are as follows. Example 411: 484.5. Example 412: 533.4. Example 413: 547.5. Example 414: 547.5.

Example 415

1-Methyl-2-(6-trifluoromethoxy-benzothiazol-2-ylamino)-1H-benzoimidazole-5-carboxylic acid [2-((R)-3-dimethylamino-pyrrolidin-1-yl)-2-oxo-ethyl]-amide 1-Methyl-2-(6-trifluoromethoxy-benzothiazol-2-ylamino)-1H-benzoimidazole-5-carboxylic acid [2-((R)-3-dimethylamino-pyrrolidin-1-yl)-2-oxo-ethyl]-amide (45 mg) was prepared by following General Procedure F starting from {[1-methyl-2-(6-trifluoromethoxy-benzothiazol-2-ylamino)-1H-benzoimidazole-5-carbonyl]-amino}-acetic acid (95 mg), dimethyl-(R)-pyrrolidin-3-yl-amine (20 mg), HBTU (85 mg), and DIEA (70 uL) in DMF (1 mL). LC/MS: m/z 561.4.

Example 416

1-Methyl-2-(6-trifluoromethoxy-benzothiazol-2-ylamino)-1H-benzoimidazole-5-carboxylic acid [2-((S)-3-dimethylamino-pyrrolidin-1-yl)-2-oxo-ethyl]-amide 1-Methyl-2-(6-trifluoromethoxy-benzothiazol-2-ylamino)-1H-benzoimidazole-5-carboxylic acid [2-((S)-3-dimethylamino-pyrrolidin-1-yl)-2-oxo-ethyl]-amide (35 mg) was prepared by following General Procedure F starting from {[1-methyl-2-(6-trifluoromethoxy-benzothiazol-2-ylamino)-1H-benzoimidazole-5-carbonyl]-amino}-acetic acid (95 mg), dimethyl-(S)-pyrrolidin-3-yl-amine (20 mg), HBTU (85 mg), and DIEA (70 uL) in DMF (1 mL). LC/MS:

m/z 561.6. ¹H NMR (DMSO-d$_6$, 400 MHz): δ 8.67-8.66 (m, 1H), 8.12 (s, 1H), 7.96 (s, 1H), 7.84-7.82 (d, 1H), 7.66-7.64 (d, 1H), 7.55-7.53 (d, 1H), 7.40-7.37 (d, 1H), 4.09-4.07 (m, 3H), 3.86-3.80 (m, 2H), 3.69 (s, 3H), 3.57 (s, 2H), 2.82-2.78 (m, 6H), 2.30-2.27 (m, 2H), —NH proton signal was not observed.

Examples 417 and 418, as shown in Table 1, are made by procedures analogous to those described above for Example 399. Observed m/z values for these examples are as follows. Example 417: 512.8. Example 418: 512.9.

Example 419

2-(6-Chloro-benzothiazol-2-ylamino)-1-methyl-1H-benzoimidazole-5-carboxylic acid [2-((S)-2-dimethylcarbamoyl-pyrrolidin-1-yl)-2-oxo-ethyl]-amide (S)-1-(2-{[2-(6-Chloro-benzothiazol-2-ylamino)-1-methyl-1H-benzoimidazole-5-carbonyl]-amino}-acetyl)-pyrrolidine-2-carboxylic acid methyl ester (114 mg) was prepared by following General Procedure F starting from 2-(6-chloro-benzothiazol-2-ylamino)-1-methyl-1H-benzoimidazole-5-carboxylic acid (100 mg), L-proline methyl ester hydrochloride (44 mg), HBTU (109 mg), and DIEA (63 uL).

(S)-1-(2-{[2-(6-Chloro-benzothiazol-2-ylamino)-1-methyl-1H-benzoimidazole-5-carbonyl]-amino}-acetyl)-pyrrolidine-2-carboxylic acid (54 mg) was prepared by following General Procedure E starting from (S)-1-(2-{[2-(6-chloro-benzothiazol-2-ylamino)-1-methyl-1H-benzoimidazole-5-carbonyl]-amino}-acetyl)-pyrrolidine-2-carboxylic acid methyl ester (90 mg) and lithium hydroxide (29 mg).

2-(6-Chloro-benzothiazol-2-ylamino)-1-methyl-1H-benzoimidazole-5-carboxylic acid [2-((S)-2-dimethylcarbamoyl-pyrrolidin-1-yl)-2-oxo-ethyl]-amide (23 mg) was prepared by following General Procedure F starting from (S)-1-(2-{[2-(6-chloro-benzothiazol-2-ylamino)-1-methyl-1H-benzoimidazole-5-carbonyl]-amino}-acetyl)-pyrrolidine-2-carboxylic acid (33 mg), dimethylamine (35 uL, 2 M in THF), HBTU (29 mg), and DIEA (17 uL). LC/MS: m/z 540.7.

Example 420, as shown in Table 1, is made by procedures analogous to those described above for Example 399. An observed m/z value for this example is 535.7.

Example 421

2-(6-Chloro-benzothiazol-2-ylamino)-1-methyl-1H-benzoimidazole-5-carboxylic acid (2-morpholin-4-yl-2-oxo-ethyl)-amide 2-(6-Chloro-benzothiazol-2-ylamino)-1-methyl-1H-benzoimidazole-5-carboxylic acid (2-morpholin-4-yl-2-oxo-ethyl)-amide (75 mg) was prepared by following General Procedure F starting from 2-(6-chloro-benzothiazol-2-ylamino)-1-methyl-1H-benzoimidazole-5-carboxylic acid (100 mg), 2-amino-1-morpholino-1-ethanone hydrochloride (56 mg), HBTU (127 mg), and DIEA (73 uL). LC/MS: m/z 485.7. ¹H NMR (DMSO-d$_6$, 400 MHz): δ 12.38 (bs, 1H), 8.53 (t, 1H), 8.11 (s, 1H), 7.93 (s, 1H), 7.81 (d, 1H), 7.67 (d, 1H), 7.51 (d, 1H), 7.40 (d, 1H), 4.16 (d, 2H), 3.64 (s, 3H), 3.63-3.60 (m, 2H), 3.58 (t, 2H), 3.55-3.50 (m, 2H), 3.50-3.45 (m, 2H).

Examples 422 to 424, as shown in Table 1, are made by procedures analogous to those described above for Example 399. Observed m/z values for these examples are as follows. Example 422: 518.7. Example 423: 501.6. Example 424: 533.8.

Example 425, as shown in Table 1, is made by procedures analogous to those described above for Example 152. An observed m/z value for this example is 484.8.

Examples 426 to 430, as shown in Table 1, are made by procedures analogous to those described above for Example 399. Observed m/z values for these examples are as follows. Example 426: 498.7. Example 427: 531.7. Example 428: 543.8. Example 429: 562.7. Example 430: 591.8.

Example 431

1-Methyl-2-(6-trifluoromethoxy-benzothiazol-2-ylamino)-1H-benzoimidazole-5-carboxylic acid [2-(3-hydroxy-piperidin-1-yl)-2-oxo-ethyl]-amide 1-Methyl-2-(6-trifluoromethoxy-benzothiazol-2-ylamino)-1H-benzoimidazole-5-carboxylic acid [2-(3-hydroxy-piperidin-1-yl)-2-oxo-ethyl]-amide (63 mg) was prepared by following General Procedure F starting from {[1-methyl-2-(6-trifluoromethoxy-benzothiazol-2-ylamino)-1H-benzoimidazole-5-carbonyl]-amino}-acetic acid (75 mg), 3-hydroxypiperidine (18 mg), HBTU (73 mg), and DIEA (42 uL), with a modification of General Procedure F where DIEA was slowly added to the reaction mixture as the last reagent. LC/MS: m/z 549.8. ¹H NMR (DMSO-d$_6$, 400 MHz): δ 8.53-8.42 (m, 1H), 8.11 (s, 1H), 7.94 (s, 1H), 7.79 (d, 1H), 7.66 (bs, 1H), 7.51 (d, 1H), 7.37 (d, 1H), 4.19-4.08 (m, 4H), 3.75-3.60 (m, 5H), 3.20 (dd, 1H), 3.05 (t, 1H), 2.01-1.95 (m, 2H), 1.57-1.27 (m, 2H), —NH proton signal was not observed.

Examples 432 to 434, as shown in Table 1, are made by procedures analogous to those described above for Example 399. Observed m/z values for these examples are as follows. Example 432: 532.7. Example 433: 498.7. Example 434: 532.7.

Example 435

1-Methyl-2-(6-trifluoromethoxy-benzothiazol-2-ylamino)-1H-benzoimidazole-5-carboxylic acid [2-(4-hydroxy-piperidin-1-yl)-2-oxo-ethyl]-amide 1-Methyl-2-(6-trifluoromethoxy-benzothiazol-2-ylamino)-1H-benzoimidazole-5-carboxylic acid [2-(4-hydroxy-piperidin-1-yl)-2-oxo-ethyl]-amide (65 mg) was prepared by following General Procedure F starting from {[1-methyl-2-(6-trifluoromethoxy-benzothiazol-2-ylamino)-1H-benzoimidazole-5-carbonyl]-amino}-acetic acid (75 mg), 4-hydroxypiperidine (18 mg), HBTU (73 mg), and DIEA (42 uL), with a modification of General Procedure F where DIEA was slowly added to the reaction mixture as the last reagent. LC/MS: m/z 549.7. ¹H NMR (DMSO-d$_6$, 400 MHz): δ 8.41 (t, 1H), 8.11 (s, 1H), 7.94 (s, 1H), 7.80 (d, 1H), 7.65 (bs, 1H), 7.51 (d, 1H), 7.37 (d, 1H), 4.15 (d, 2H), 3.98-3.89 (m, 2H), 3.78-3.69 (m, 2H), 3.68 (s, 3H), 3.20 (t, 1H), 3.04 (t, 1H), 1.84-1.67 (m, 2H), 1.45-1.20 (m, 2H), —NH proton signal was not observed.

Example 436

2-(6-Chloro-benzothiazol-2-ylamino)-1-methyl-1H-benzoimidazole-5-carboxylic acid [2-(4-hydroxy-piperidin-1-yl)-2-oxo-ethyl]-amide {[2-(6-Chloro-benzothiazol-2-ylamino)-1-methyl-1H-benzoimidazole-5-carbonyl]-amino}-acetic acid methyl ester (513 mg) was prepared by following General Procedure F starting from 2-(6-chloro-benzothiazol-2-ylamino)-1-methyl-1H-benzoimidazole-5-carboxylic acid (500 mg), glycine methyl ester hydrochloride (193 mg), HBTU (634 mg), and DIEA (364 uL).

{[2-(6-Chloro-benzothiazol-2-ylamino)-1-methyl-1H-benzoimidazole-5-carbonyl]-amino}-acetic acid (300 mg) was prepared by following General Procedure E starting from {[2-(6-chloro-benzothiazol-2-ylamino)-1-methyl-1H-benzoimidazole-5-carbonyl]-amino}-acetic acid methyl ester (493 mg) and lithium hydroxide (192 mg).

2-(6-Chloro-benzothiazol-2-ylamino)-1-methyl-1H-benzoimidazole-5-carboxylic acid [2-(4-hydroxy-piperidin-1-yl)-2-oxo-ethyl]-amide (77 mg) was prepared by following General Procedure F starting from {[2-(6-chloro-benzothiazol-2-ylamino)-1-methyl-1H-benzoimidazole-5-carbonyl]-amino}-acetic acid (100 mg), 4-hydroxypiperidine (27 mg), HBTU (109 mg), and DIEA (63 uL), with a modification of General Procedure F where DIEA was slowly added to the reaction mixture as the last reagent. LC/MS: m/z 499.8. $^1$H NMR (DMSO-$d_6$, 400 MHz): δ 8.48 (t, 1H), 8.11 (s, 1H), 7.92 (s, 1H), 7.81 (d, 1H), 7.67 (d, 1H), 7.51 (d, 1H), 7.39 (d, 1H), 4.80 (d, 1H), 4.15 (d, 2H), 3.98-3.88 (m, 1H), 3.76-3.68 (m, 2H), 3.63 (s, 3H), 3.20 (t, 1H), 3.05 (t, 1H), 1.85-1.65 (m, 2H), 1.46-1.20 (m, 2H), —N$\underline{H}$ proton signal was not observed.

Examples 437 to 439, as shown in Table 1, are made by procedures analogous to those described above for Example 399. Observed m/z values for these examples are as follows. Example 437: 532.6. Example 438: 542.9. Example 439: 563.8.

Example 440

1-Methyl-2-(6-trifluoromethoxy-benzothiazol-2-ylamino)-1H-benzoimidazole-5-carboxylic acid [2-(3-hydroxymethyl-piperidin-1-yl)-2-oxo-ethyl]-amide 1-Methyl-2-(6-trifluoromethoxy-benzothiazol-2-ylamino)-1H-benzoimidazole-5-carboxylic acid [2-(3-hydroxymethyl-piperidin-1-yl)-2-oxo-ethyl]-amide (72 mg) was prepared by following General Procedure F starting from {[1-methyl-2-(6-trifluoromethoxy-benzothiazol-2-ylamino)-1H-benzoimidazole-5-carbonyl]-amino}-acetic acid (75 mg), 3-piperidinemethanol (20 mg), HBTU (73 mg), and DIEA (42 uL), with a modification of General Procedure F where DIEA was slowly added to the reaction mixture as the last reagent. LC/MS: m/z 563.8. $^1$H NMR (DMSO-$d_6$, 400 MHz): δ 12.41 (bs, 1H), 8.53-8.40 (m, 1H), 8.10 (s, 1H), 7.93 (s, 1H), 7.87-7.60 (m, 2H), 7.50 (d, 1H), 7.36 (d, 1H), 4.73-4.50 (m, 1H), 4.43-4.01 (m, 3H), 3.82 (d, 1H), 3.67 (s, 3H), 3.31-3.16 (m, 2H), 3.06-2.87 (m, 1H), 2.86-2.34 (m, 1H), 1.82-1.41 (m, 3H), 1.40-1.10 (m, 2H).

Example 441

1-Methyl-2-(6-trifluoromethoxy-benzothiazol-2-ylamino)-1H-benzoimidazole-5-carboxylic acid [2-(4-hydroxymethyl-piperidin-1-yl)-2-oxo-ethyl]-amide 1-Methyl-2-(6-trifluoromethoxy-benzothiazol-2-ylamino)-1H-benzoimidazole-5-carboxylic acid [2-(4-hydroxymethyl-piperidin-1-yl)-2-oxo-ethyl]-amide (73 mg) was prepared by following General Procedure F starting from {[1-methyl-2-(6-trifluoromethoxy-benzothiazol-2-ylamino)-1H-benzoimidazole-5-carbonyl]-amino}-acetic acid (75 mg), 4-piperidinemethanol (20 mg), HBTU (73 mg), and DIEA (42 uL), with a modification of General Procedure F where DIEA was slowly added to the reaction mixture as the last reagent. LC/MS: m/z 563.8. $^1$H NMR (DMSO-$d_6$, 400 MHz): δ 8.48 (t, 1H), 8.11 (s, 1H), 7.94 (s, 1H), 7.79 (d, 1H), 7.67 (bs, 1H), 7.51 (d, 1H), 7.37 (d, 1H), 4.37 (d, 1H), 4.14 (d, 2H), 3.92 (d, 1H), 3.67 (s, 3H), 3.27 (d, 2H), 3.02 (t, 1H), 2.58 (t, 1H), 1.78-1.55 (m, 3H), 1.20-0.90 (m, 2H), —OH and —N$\underline{H}$ proton signal was not observed.

Examples 442 to 444, as shown in Table 1, are made by procedures analogous to those described above for Example 399. Observed m/z values for these examples are as follows. Example 442: 514.2. Example 443: 557.8. Example 444: 512.8.

Example 445

1-Methyl-2-(6-trifluoromethyl-benzothiazol-2-ylamino)-1H-benzoimidazole-5-carboxylic acid [2-((S)-3-methoxy-piperidin-1-yl)-2-oxo-ethyl]-amide 1-Methyl-2-(6-trifluoromethyl-benzothiazol-2-ylamino)-1H-benzoimidazole-5-carboxylic acid [2-((S)-3-methoxy-piperidin-1-yl)-2-oxo-ethyl]-amide (77 mg) was prepared by following General Procedure F starting from {[1-methyl-2-(6-trifluoromethyl-benzothiazol-2-ylamino)-1H-benzoimidazole-5-carbonyl]-amino}-acetic acid (100 mg), (S)-3-methoxy-piperidine hydrochloride (37 mg), HBTU (101 mg), and DIEA (58 uL), with a modification of General Procedure F where DIEA was slowly added to the reaction mixture as the last reagent. LC/MS: m/z 546.7. $^1$H NMR (DMSO-$d_6$, 400 MHz): δ 12.51 (bs, 1H), 8.57-8.47 (m, 1H), 8.26 (s, 1H), 8.14 (s, 1H), 7.89-7.66 (m, 3H), 7.54 (d, 1H), 4.33-4.15 (m, 1H), 4.15-4.00 (m, 1H), 3.81-3.56 (m, 4H), 3.55-3.44 (m, 1H), 3.43-3.18 (m, 6H), 2.01-1.21 (m, 4H).

Example 446

1-Methyl-2-(6-trifluoromethyl-benzothiazol-2-ylamino)-1H-benzoimidazole-5-carboxylic acid [2-((R)-3-methoxy-piperidin-1-yl)-2-oxo-ethyl]-amide {[1-Methyl-2-(6-trifluoromethyl-benzothiazol-2-ylamino)-1H-benzoimidazole-5-carbonyl]-amino}-acetic acid methyl ester (5.0 g) was prepared by following General Procedure F starting from 1-methyl-2-(6-trifluoromethyl-benzothiazol-2-ylamino)-1H-benzoimidazole-5-carboxylic acid (5.0 g), glycine methyl ester hydrochloride (1.76 g), HBTU (5.8 g), and DIEA (3.34 mL).

{[1-Methyl-2-(6-trifluoromethyl-benzothiazol-2-ylamino)-1H-benzoimidazole-5-carbonyl]-amino}-acetic acid (4.22 g) was prepared by following General Procedure E starting from {[1-methyl-2-(6-trifluoromethyl-benzothiazol-2-ylamino)-1H-benzoimidazole-5-carbonyl]-amino}-acetic acid methyl ester (5.0 g) and lithium hydroxide (1.81 g).

1-Methyl-2-(6-trifluoromethyl-benzothiazol-2-ylamino)-1H-benzoimidazole-5-carboxylic acid [2-((R)-3-methoxy-piperidin-1-yl)-2-oxo-ethyl]-amide (30 mg) was prepared by following General Procedure F starting from {[1-methyl-2-(6-trifluoromethyl-benzothiazol-2-ylamino)-1H-benzoimidazole-5-carbonyl]-amino}-acetic acid (80 mg), (R)-3-methoxy-piperidine (100 mg), HBTU (200 mg), and DIEA (100 uL) in DMF (1 mL). LC/MS: m/z 546.7. $^1$H NMR (DMSO-$d_6$, 400 MHz): δ 8.54-8.53 (m, 1H), 8.28 (s, 1H), 8.12 (s, 1H), 7.83-7.81 (d, 1H), 7.71 (m, 2H), 7.56-7.54 (d, 1H), 4.24-4.18 (m, 1H), 4.12-4.08 (m, 1H), 3.73-3.71 (m, 1H), 3.70 (s, 3H), 3.52-3.47 (m, 1H), 3.38-3.34 (m, 2H), 3.31-3.25 (m, 4H), 1.88-1.81 (m, 1H), 1.71-1.62 (m, 1H), 1.45-1.36 (m, 1H), —NH proton signal was not observed.

Example 447, as shown in Table 1, is made by procedures analogous to those described above for Example 399. An observed m/z value for this example is 576.5.

Example 448, as shown in Table 1, is made by procedures analogous to those described above for Example 47. An observed m/z value for this example is 566.2.

Examples 449 to 452, as shown in Table 1, are made by procedures analogous to those described above for Example 399. Observed m/z values for these examples are as follows. Example 449: 600.5. Example 450: 557.6. Example 451: 575.5. Example 452: 626.4.

Examples 453 and 454, as shown in Table 1, are made by procedures analogous to those described above for Example 152. Observed m/z values for these examples are as follows. Example 453: 561.5. Example 454: 513.0.

Examples 455 and 456, as shown in Table 1, are made by procedures analogous to those described above for Example 399. Observed m/z values for these examples are as follows. Example 455: 575.4. Example 456: 526.7.

Example 457, as shown in Table 1, is made by procedures analogous to those described above for Example 152. An observed m/z value for this example is 526.0.

Examples 458 and 459, as shown in Table 1, are made by procedures analogous to those described above for Example 399. Observed m/z values for these examples are as follows. Example 458: 589.5. Example 459: 541.0.

Example 460, as shown in Table 1, is made by procedures analogous to those described above for Example 152. An observed m/z value for this example is 526.1.

Example 461, as shown in Table 1, is made by procedures analogous to those described above for Example 399. An observed m/z value for this example is 540.7.

Example 462, as shown in Table 1, is made by procedures analogous to those described below for Example 463. An observed m/z value for this example is 456.7.

Example 463

1-Methyl-2-(6-trifluoromethyl-benzothiazol-2-ylamino)-1H-benzoimidazole-5-carboxylic acid ((S)-1-dimethylcarbamoyl-ethyl)-amide (S)-2-{[1-Methyl-2-(6-trifluoromethyl-benzothiazol-2-ylamino)-1H-benzoimidazole-5-carbonyl]-amino}-propionic acid methyl ester (863 mg) was prepared by following General Procedure F starting from 1-methyl-2-(6-trifluoromethyl-benzothiazol-2-ylamino)-1H-benzoimidazole-5-carboxylic acid (750 mg), L-alanine methyl ester hydrochloride (293 mg), HBTU (870 mg), and DIEA (500 uL).

(S)-2-{[1-Methyl-2-(6-trifluoromethyl-benzothiazol-2-ylamino)-1H-benzoimidazole-5-carbonyl]-amino}-propionic acid (743 mg) was prepared by following General Procedure E starting from (S)-2-{[1-methyl-2-(6-trifluoromethyl-benzothiazol-2-ylamino)-1H-benzoimidazole-5-carbonyl]-amino}-propionic acid methyl ester (850 mg) and lithium hydroxide (299 mg).

1-Methyl-2-(6-trifluoromethyl-benzothiazol-2-ylamino)-1H-benzoimidazole-5-carboxylic acid ((S)-1-dimethylcarbamoyl-ethyl)-amide (25 mg) was prepared by following General Procedure F starting from (S)-2-{[1-methyl-2-(6-trifluoromethyl-benzothiazol-2-ylamino)-1H-benzoimidazole-5-carbonyl]-amino}-propionic acid (100 mg), dimethylamine (119 uL, 2 M in THF), HBTU (98 mg), and DIEA (57 uL), with a modification of General Procedure F where DIEA was slowly added to the reaction mixture as the last reagent. LC/MS: m/z 490.6. $^1$H NMR (DMSO-$d_6$, 400 MHz): δ 8.56 (d, 1H), 8.28 (s, 1H), 8.13 (s, 1H), 7.84 (d, 1H), 7.71 (d, 2H), 7.53 (d, 1H), 5.00-4.87 (m, 1H), 3.70 (s, 3H), 3.07 (s, 3H), 2.86 (s, 3H), 1.32 (d, 3H), —NH proton signal was not observed.

Examples 464 to 468, as shown in Table 1, are made by procedures analogous to those described above for Example 463. Observed m/z values for these examples are as follows. Example 464: 511.8. Example 465: 498.7. Example 466: 532.7. Example 467: 456.6. Example 468: 490.7.

Example 469

2-(6-Chloro-benzothiazol-2-ylamino)-1-methyl-1H-benzoimidazole-5-carboxylic acid [(R)-1-methyl-2-(4-methyl-piperazin-1-yl)-2-oxo-ethyl]-amide (R)-2-{[2-(6-Chloro-benzothiazol-2-ylamino)-1-methyl-1H-benzoimidazole-5-carbonyl]-amino}-propionic acid methyl ester (508 mg) was prepared by following General Procedure F starting from 2-(6-chloro-benzothiazol-2-ylamino)-1-methyl-1H-benzoimidazole-5-carboxylic acid (500 mg), D-alanine methyl ester hydrochloride (214 mg), HBTU (634 mg), and DIEA (364 uL).

(R)-2-{[2-(6-Chloro-benzothiazol-2-ylamino)-1-methyl-1H-benzoimidazole-5-carbonyl]-amino}-propionic acid (341 mg) was prepared by following General Procedure E starting from (R)-2-{[2-(6-chloro-benzothiazol-2-ylamino)-1-methyl-1H-benzoimidazole-5-carbonyl]-amino}-propionic acid methyl ester (475 mg) and lithium hydroxide (180 mg).

2-(6-Chloro-benzothiazol-2-ylamino)-1-methyl-1H-benzoimidazole-5-carboxylic acid [(R)-1-methyl-2-(4-methyl-piperazin-1-yl)-2-oxo-ethyl]-amide (20 mg) was prepared by following General Procedure F starting from (R)-2-{[2-(6-chloro-benzothiazol-2-ylamino)-1-methyl-1H-benzoimidazole-5-carbonyl]-amino}-propionic acid (50 mg), 1-methyl-piperazine (50 mg), HBTU (150 mg), and DIEA (100 uL) in DMF (1 mL). LC/MS: m/z 511.7. $^1$H NMR (DMSO-$d_6$, 400 MHz): δ 8.82-8.67 (m, 1H), 8.12 (m, 1H), 7.97 (s, 1H), 7.85-7.83 (m, 1H), 7.56-7.52 (m, 2H), 7.44-7.41 (m, 1H), 5.02-4.96 (m, 1H), 4.50-4.43 (m, 1H), 4.35-4.19 (m, 1H), 3.69 (s, 3H), 3.62-3.51 (m, 2H), 3.45 (m, 1H), 3.28 (m, 1H), 3.10 (m, 1H), 2.78-2.77 (d, 3H), 1.44-1.35 (m, 3H) —NH proton signal was not observed.

Examples 470 to 472, as shown in Table 1, are made by procedures analogous to those described above for Example 463. Observed m/z values for these examples are as follows. Example 470: 545.7. Example 471: 498.7. Example 472: 532.7.

For each of the above 472 examples, the invention provides a separate embodiment that includes the free acid or base of the compound and pharmaceutically acceptable salts of the free acid or base. For each of these embodiments, the invention provides: (i) a further embodiment where the compound is in the form of a free acid or base, and (ii) a further embodiment where the compound is in the form of a pharmaceutically acceptable salt. Any of these embodiments may be used for making any of the pharmaceutical compositions described above, and may also be used in any of the methods of treatment or therapeutic uses described above.

Biological Assay

Cell Culture. Normal Human Fibroblast (NHLF), were obtained from Lonza. Cultures of cells were maintained in Fibroblast Growth Medium (FGM-2) medium supplemented with 2% fetal bovine serum (FBS), Fibroblast Growth Factor (hFGF-B) 0.5 mL, Insulin 0.5 mL, gentamicin/amphotericin-B 0.5 mL at 37° C. in a humidified atmosphere of 5% $CO_2$. Cells were grown to 80% confluence before treating.

HMOX1 Protein Assay. NHLF cells were grown to 80% confluency and harvested by washing once with HEPES and then trypsinized. Equal numbers ($2 \times 10^3$ cells per well) of NHLF cells were plated in 384 well optilux tissue culture (BD) plates. Cells were incubated overnight in FGM-2 medium prior to exposure to compound. Cells were treated with either vehicle (DMSO) or compound (dissolved in vehicle) for 16 h. Cells were washed 2× with 1×PBS and fixed with 4% Paraformaldyhyde for 15 min. The fixed cells were then permeablized with 0.1% Triton X-100 and blocked with 5% BSA in 1×PBS 0.05% Tween-20 for 15 min. HO-1 antibody (abcam) was used for immunostaining at 1:300 dilution in 1% BSA in 1×PBS for 1 hour. Cells were washed 2× with 1×PBS and secondary antibody goat anti-mouse Alexa 488 1:400 dilution (Invitrogen); Hoechst 1:2000 (Invitrogen) in 1% BSA in 1×PBS for 1 hour. Plate was washed 5× with 1×PBS and read at Hoechst Ex. 360 Em. 535; Alexa 488 Ex. 480 Em. 535 using GE InCell 1000. Results analyzed using GE InCell Analyzer software. Heme oxygenase data represents the fold change above DMSO treated cells.

Table 2, below, shows the fold change above DMSO for Examples 1 to 472. In general, the fold indiction data are reported for 5 µM concentration (i.e., µ-moles of compound to total volume, where the solvent is about 99.2% media and 0.8% DMSO). In some instances, the reported data are for 3 µM concentration, which are indicated by an asterisk (*).

TABLE 2

| Example No. | HMOX1 Fold Induction | Example No. | HMOX1 Fold Induction |
| --- | --- | --- | --- |
| 1 | 19.37 | 237 | 30.64 |
| 2 | 6.51 | 238 | 33.00 |
| 3 | 12.49 | 239 | 10.00* |
| 4 | 11.94 | 240 | 35.42 |
| 5 | 8.33 | 241 | 23.66 |
| 6 | 9.45 | 242 | 28.05* |
| 7 | 5.40 | 243 | 15.23* |
| 8 | 18.32 | 244 | 28.03 |
| 9 | 11.16 | 245 | 33.15 |
| 10 | 19.89 | 246 | 76.46 |
| 11 | 25.0 | 247 | 28.30 |
| 12 | 16.16 | 248 | 58.71 |
| 13 | 20.09 | 249 | 31.19 |
| 14 | 22.0 | 250 | 25.12* |
| 15 | 22.8 | 251 | 29.56 |
| 16 | 30.0 | 252 | 13.12 |
| 17 | 21.4 | 253 | 26.56 |
| 18 | 20.15 | 254 | 47.43 |
| 19 | 21.09 | 255 | 49.33 |
| 20 | 18.64 | 256 | 48.00 |
| 21 | 19.59 | 257 | 21.87 |
| 22 | 18.70 | 258 | 24.65 |
| 23 | 4.11 | 259 | 25.35* |
| 24 | 20.66 | 260 | 27.12 |
| 25 | 27.15 | 261 | 35.68 |
| 26 | 15.49 | 262 | 40.00* |
| 27 | 23.25 | 263 | 19.88 |
| 28 | 10.1 | 264 | 22.92 |
| 29 | 13.94 | 265 | 55.03 |
| 30 | 21.43 | 266 | 57.00 |
| 31 | 23.57 | 267 | 58.80 |
| 32 | 12.64 | 268 | 28.35 |
| 33 | 11.65 | 269 | 19.94* |
| 34 | 15.44 | 270 | 14.61 |
| 35 | 12.36 | 271 | 69.86 |
| 36 | 13.8 | 272 | 86.54 |
| 37 | 16.4 | 273 | 25.27 |
| 38 | 18.0 | 274 | 65.90 |
| 39 | 18.2 | 275 | 77.38 |
| 40 | 11.8 | 276 | 61.20 |
| 41 | 33.3 | 277 | 38.27* |
| 42 | 34.7 | 278 | 36.50* |
| 43 | 29.6 | 279 | 89.23 |
| 44 | 12.1 | 280 | 38.78 |
| 45 | 12.5 | 281 | 35.61 |
| 46 | 17.9 | 282 | 51.74 |
| 47 | 11.3 | 283 | 30.24 |
| 48 | 15.8 | 284 | 47.38 |
| 49 | 23.1 | 285 | 55.89 |
| 50 | 11.1 | 286 | 61.15 |
| 51 | 9.9 | 287 | 49.29 |
| 52 | 10.0 | 288 | 47.00 |
| 53 | 20.1 | 289 | 44.56 |
| 54 | 18.5 | 290 | 22.54 |
| 55 | 4.5 | 291 | 17.04 |
| 56 | 16.1 | 292 | 39.03 |
| 57 | 32.0 | 293 | 29.39 |
| 58 | 32.8 | 294 | 29.42 |
| 59 | 49.8 | 295 | 29.00* |
| 60 | 39.8 | 296 | 34.59* |
| 61 | 12.1 | 297 | 24.35* |
| 62 | 20.3 | 298 | 21.11 |
| 63 | 9.8 | 299 | 16.66 |
| 64 | 18.9 | 300 | 26.20 |
| 65 | 10.2 | 301 | 27.79 |
| 66 | 20.8 | 302 | 63.71 |
| 67 | 18.7 | 303 | 25.65 |
| 68 | 21.1 | 304 | 24.67 |
| 69 | 4.7 | 305 | 41.67 |
| 70 | 21.4 | 306 | 38.71 |
| 71 | 4.2 | 307 | 31.52 |
| 72 | 11.9 | 308 | 24.33 |
| 73 | 20.6 | 309 | 21.46 |
| 74 | 11.1 | 310 | 24.55 |
| 75 | 29.0 | 311 | 77.35 |
| 76 | 22.5 | 312 | 68.84 |
| 77 | 31.4 | 313 | 22.90 |
| 78 | 28.6 | 314 | 79.73 |
| 79 | 17.6 | 315 | 75.66 |
| 80 | 23.2 | 316 | 18.15 |
| 81 | 17.0 | 317 | 16.33 |
| 82 | 17.0 | 318 | 11.94 |
| 83 | 1.25 | 319 | 23.92 |
| 84 | 19.0 | 320 | 20.00 |
| 85 | 11.6 | 321 | 15.32* |
| 86 | 9.7 | 322 | 35.99 |
| 87 | 12.1 | 323 | 112.89 |
| 88 | 13.0 | 324 | 27.89 |
| 89 | 23.7 | 325 | 32.38 |
| 90 | 8.1 | 326 | 34.26 |
| 91 | 10.1 | 327 | 31.94 |
| 92 | 3.4 | 328 | 29.38 |
| 93 | 11.3 | 329 | 52.23 |
| 94 | 1.2 | 330 | 37.67 |
| 95 | 11.2 | 331 | 70.08 |
| 96 | 12.0 | 332 | 55.85 |
| 97 | 19.2 | 333 | 14.47 |
| 98 | 13.8 | 334 | 13.38* |
| 99 | 8.5 | 335 | 18.89 |
| 100 | 25.9 | 336 | 16.14 |
| 101 | 11.2 | 337 | 12.73* |
| 102 | 22.6 | 338 | 13.58* |
| 103 | 9.0 | 339 | 10.63* |
| 104 | 16.3 | 340 | 14.40* |
| 105 | 17.5 | 341 | 32.78* |
| 106 | 23.8 | 342 | 36.81* |
| 107 | 18.6 | 343 | 21.06 |
| 108 | 18.3 | 344 | 25.74* |

TABLE 2-continued

| Example No. | HMOX1 Fold Induction | Example No. | HMOX1 Fold Induction | Example No. | HMOX1 Fold Induction | Example No. | HMOX1 Fold Induction |
|---|---|---|---|---|---|---|---|
| 109 | 20.9 | 345 | 26.44* | 186 | 20.2 | 422 | 25.01* |
| 110 | 26.3 | 346 | 12.94* | 187 | 18.4 | 423 | 30.20 |
| 111 | 17.6 | 347 | 15.34* | 188 | 18.3 | 424 | 24.93 |
| 112 | 17.5 | 348 | 22.00* | 189 | 24.6 | 425 | 20.31 |
| 113 | 27.6 | 349 | 29.00* | 190 | 23.4 | 426 | 25.06 |
| 114 | 5.1 | 350 | 24.00* | 191 | 33.8 | 427 | 17.02* |
| 115 | 1.5 | 351 | 25.00* | 192 | 28.8 | 428 | 24.35 |
| 116 | 22.3 | 352 | 20.00* | 193 | 11.1 | 429 | 21.39 |
| 117 | 28.8 | 353 | 23.00* | 194 | 6.0 | 430 | 22.68 |
| 118 | 14.1 | 354 | 17.00* | 195 | 4.4 | 431 | 49.44 |
| 119 | 22.1 | 355 | 26.00* | 196 | 11.4 | 432 | 27.30* |
| 120 | 1.7 | 356 | 19.00* | 197 | 18.0 | 433 | 29.00* |
| 121 | 29.6 | 357 | 22.00* | 198 | 12 | 434 | 34.56* |
| 122 | 26.1 | 358 | 11.85* | 199 | 1.5 | 435 | 30.22 |
| 123 | 12.7 | 359 | 17.37* | 200 | 22.9 | 436 | 29.26 |
| 124 | 22.9 | 360 | 34.28 | 201 | 26.5 | 437 | 47.08* |
| 125 | 25.9 | 361 | 28.80 | 202 | 15.6 | 438 | 25.91 |
| 126 | 4.6 | 362 | 13.00 | 203 | 18.69* | 439 | 84.18 |
| 127 | 12.4 | 363 | 10.00 | 204 | 19.33* | 440 | 28.18 |
| 128 | 32.7 | 364 | 27.84* | 205 | 33.08* | 441 | 73.59 |
| 129 | 31.0 | 365 | 20.05* | 206 | 27.00* | 442 | 34.92 |
| 130 | 5.3 | 366 | 18.79 | 207 | 11.85* | 443 | 39.76 |
| 131 | 6.8 | 367 | 25.41 | 208 | 26.50* | 444 | 32.00* |
| 132 | 5.8 | 368 | 48.03 | 209 | 14.21* | 445 | 36.43* |
| 133 | 45.9 | 369 | 22.41* | 210 | 29.92* | 446 | 31.28* |
| 134 | 54.5 | 370 | 19.27* | 211 | 46.15 | 447 | 58.35 |
| 135 | 49.6 | 371 | 28.96* | 212 | 48.81 | 448 | 36.74 |
| 136 | 5.7 | 372 | 25.50* | 213 | 48.56 | 449 | 22.97 |
| 137 | 6.0 | 373 | 32.01* | 214 | 42.36 | 450 | 51.05* |
| 138 | 11.0 | 374 | 34.21* | 215 | 16.00* | 451 | 51.29 |
| 139 | 18.8 | 375 | 19.45* | 216 | 31.60* | 452 | 71.66 |
| 140 | 19.3 | 376 | 19.09 | 217 | 20.72 | 453 | 81.11 |
| 141 | 23.1 | 377 | 20.33 | 218 | 39.16 | 454 | 62.24 |
| 142 | 15.2 | 378 | 24.92 | 219 | 39.99 | 455 | 80.42 |
| 143 | 22.4 | 379 | 21.70 | 220 | 61.89 | 456 | 67.35 |
| 144 | 7.3 | 380 | 29.98* | 221 | 26.00* | 457 | 39.92 |
| 145 | 7.1 | 381 | 28.17* | 222 | 49.93 | 458 | 68.49 |
| 146 | 3.7 | 382 | 20.56 | 223 | 44.74 | 459 | 41.98 |
| 147 | 1.8 | 383 | 16.40 | 224 | 15.51* | 460 | 27.54 |
| 148 | 12.0 | 384 | 26.01 | 225 | 17.67* | 461 | 27.11 |
| 149 | 38.7 | 385 | 24.52 | 226 | 23.32 | 462 | 20.02* |
| 150 | 41.6 | 386 | 58.28 | 227 | 14.03* | 463 | 26.67* |
| 151 | 41.3 | 387 | 19.90 | 228 | 26.00* | 464 | 27.17* |
| 152 | 15.0 | 388 | 21.98 | 229 | 14.43 | 465 | 20.37* |
| 153 | 4.0 | 389 | 38.56 | 230 | 29.79 | 466 | 22.38* |
| 154 | 27.1 | 390 | 46.35 | 231 | 30.24 | 467 | 22.31* |
| 155 | 24.3 | 391 | 38.65 | 232 | 32.95 | 468 | 26.33* |
| 156 | 21.0 | 392 | 24.86 | 233 | 28.00* | 469 | 26.08* |
| 157 | 22.1 | 393 | 61.30 | 234 | 30.90* | 470 | 24.52* |
| 158 | 1.7 | 394 | 37.58 | 235 | 37.73 | 471 | 17.36* |
| 159 | 26.7 | 395 | 72.02 | 236 | 45.74 | 472 | 22.98* |
| 160 | 22.9 | 396 | 36.00 | | | | |
| 161 | 19.1 | 397 | 25.00* | | | | |
| 162 | — | 398 | 31.70 | | | | |
| 163 | 26.3 | 399 | 20.83 | | | | |
| 164 | 20.5 | 400 | 15.00* | | | | |
| 165 | 17.9 | 401 | 27.00* | | | | |
| 166 | 22.4 | 402 | 23.99* | | | | |
| 167 | 24.2 | 403 | 24.84* | | | | |
| 168 | 21.9 | 404 | 26.14 | | | | |
| 169 | 24.4 | 405 | 21.37 | | | | |
| 170 | 23.0 | 406 | 31.02 | | | | |
| 171 | 22.8 | 407 | 7.73 | | | | |
| 172 | 21.4 | 408 | 25.00* | | | | |
| 173 | 21.4 | 409 | 29.00* | | | | |
| 174 | 26.2 | 410 | 24.69* | | | | |
| 175 | 28.7 | 411 | 16.03 | | | | |
| 176 | 25.8 | 412 | 47.58 | | | | |
| 177 | 30.3 | 413 | 31.81 | | | | |
| 178 | 25.7 | 414 | 25.66 | | | | |
| 179 | 24.4 | 415 | 74.76 | | | | |
| 180 | 12.4 | 416 | 96.58 | | | | |
| 181 | 23.0 | 417 | 62.81 | | | | |
| 182 | 13.0 | 418 | 63.33 | | | | |
| 183 | — | 419 | 28.03 | | | | |
| 184 | 9.5 | 420 | 32.96 | | | | |
| 185 | 11.2 | 421 | 32.19 | | | | |

The invention claimed is:

1. A method of treating a disease comprising administering to a human subject a compound, wherein the disease is an inflammatory disease; and wherein the compound is a compound of Formula (I) or a pharmaceutically acceptable salt thereof

wherein
one of $X^1$, $X^2$, $X^3$, and $X^4$ is

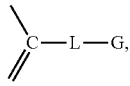

and the remaining members of $X^1$, $X^2$, $X^3$, and $X^4$ are independently N or

G is hydrogen, —$C_{1-8}$ alkyl, —$C_{3-10}$ cycloalkyl, —$C_{1-6}$ alkylene-$C_{3-10}$ cycloalkyl, heterocyclyl, —$C_{1-6}$ alkylene-$C_{3-10}$ heterocyclyl, phenyl, heteroaryl, or $NR^hR^k$, where the alkyl, alkylene, cycloalkyl, heterocyclyl, phenyl, and heteroaryl groups are optionally substituted one or more times with substituents independently selected from $R^c$;

L is —$CH_2$—$C(O)N(R^6)$—, —$C(O)N(R^6)$—, —$C(O)$—O—, —$SO_2$—, —$C(O)$—, heteroarylene optionally substituted one or more times with substituents independently selected from $R^x$, or heterocyclylene optionally substituted one or more times with substituents independently selected from $R^x$; or the group -L-G is -cyano;

$R^1$ is hydrogen, $R^a$, phenyl, or heteroaryl, where the phenyl and heteroaryl groups are optionally substituted one or more times with substituents independently selected from $R^x$;

$R^2$ is $R^b$;

$R^3$ is hydrogen, —$C_{1-6}$ alkyl, or —$C_{1-6}$ alkylene-$C_{3-10}$ cycloalkyl, where the alkyl, alkylene, and cycloalkyl groups are optionally substituted one or more times with substituents independently selected from $R^z$;

$R^4$ is —$C_{1-6}$ alkyl or —$C_{1-6}$ alkylene-$C_{3-10}$ cycloalkyl, where the alkyl, alkylene, and cycloalkyl groups are optionally substituted one or more times with substituents independently selected from $R^y$;

$R^6$ is hydrogen, —$C_{1-6}$ alkyl, —$C_{1-6}$ alkylene-$C_{3-10}$ cycloalkyl, where the alkyl, alkylene, and cycloalkyl groups are optionally substituted one or more times with substituents independently selected from $R^x$;

$R^a$ is
a) -halogen,
b) —$C_{1-6}$ alkyl,
c) —$C_{3-10}$ cycloalkyl,
d) -heterocyclyl,
e) -cyano,
f) —$CF_3$,
g) —$OCF_3$,
h) —O—$R^d$,
i) —$S(O)_w$—$R^d$,
j) —$S(O)_2O$—$R^d$,
k) —$NR^dR^e$,
l) —$C(O)$—$R^d$,
m) —$C(O)$—O—$R^d$,
n) —$OC(O)$—$R^d$,
o) —$C(O)NR^d R^e$,
p) —$C(O)$-heterocyclyl,
q) —$NR^d C(O)R^e$,
r) —$OC(O)NR^d R^e$,
s) —$NR^d C(O)OR^d$, or
t) —$NR^d C(O)NR^d R^e$,
where the alkyl, cycloalkyl, and heterocyclyl groups are optionally substituted one or more times with substituents independently selected from $R^y$;

$R^b$ is
a) -halogen,
b) —$C_{1-6}$ alkyl,
c) —$C_{3-10}$ cycloalkyl,
d) -heterocyclyl,
e) -phenyl,
f) -heteroaryl,
g) -cyano,
h) —$CF_3$,
i) —$OCF_3$,
j) —O—$R^f$,
k) —$S(O)_w$—$R^f$,
l) —$S(O)_2O$—$R^f$,
m) —$NR^fR^g$,
n) —$C(O)$—$R^f$,
o) —$C(O)$—O—$R^f$,
p) —$OC(O)$—$R^f$,
q) —$C(O)NR^fR^g$,
r) —$C(O)$-heterocyclyl,
s) —$NR^f C(O)R^g$,
t) —$OC(O)NR^f R^g$,
u) —$NR^f C(O)OR^f$, or
v) —$NR^f C(O)NR^f R^g$,
where the alkyl, cycloalkyl, heterocyclyl, phenyl, and heteroaryl groups are optionally substituted one or more times with substituents independently selected from $R^z$;

$R^c$ is
a) -halogen,
b) —$C_{1-6}$ alkyl,
c) —$C_{3-10}$ cycloalkyl,
d) -heterocyclyl,
e) -cyano,
f) —$CF_3$,
g) —$OCF_3$,
h) —O—$R^h$,
i) —$S(O)_w$—$R^h$,
j) —$S(O)_2O$—$R^h$,
k) —$NR^hR^k$,
l) —$C(O)$—$R^h$,
m) —$C(O)$—O—$R^h$,
n) —$OC(O)$—$R^h$,
o) —$C(O)NR^h R^k$,
p) —$C(O)$-heterocyclyl,
q) —$NR^h C(O)R^k$,
r) —$OC(O)NR^h R^k$,
s) —$NR^h C(O)OR^k$,
t) —$NR^h C(O)NR^h R^k$,
u) —$NR^h S(O)_wR^k$,
v) -phenyl,
w) -heteroaryl, or
x) —O—($C_{1-4}$ alkylene)-O—($C_{1-4}$ alkylene)-$N(R^h)C(O)$—$OR^k$,
where the alkylene, alkyl, cycloalkyl, heterocyclyl, phenyl, and heteroaryl groups are optionally substituted one or more times with substituents independently selected from $R^x$;

$R^d$ and $R^e$ are independently hydrogen, $C_{1-6}$ alkyl, or $C_{3-10}$ cycloalkyl, where the alkyl and cycloalkyl groups are optionally substituted one or more times with substituents independently selected from $R^y$; or, if $R^d$ and $R^e$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, and azepano, where each ring is optionally substituted one or more times with substituents independently selected from $R^y$;

$R^f$ and $R^g$ are independently hydrogen, $C_{1-6}$ alkyl, $C_{3-10}$ cycloalkyl, phenyl, or heteroaryl, where the alkyl, cycloalkyl, phenyl, and heteroaryl groups are optionally substituted one or more times with substituents independently selected from $R^z$; or, if $R^f$ and $R^g$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, and azepano, where each ring is optionally substituted one or more times with substituents independently selected from $R^z$;

$R^h$ and $R^k$ are independently hydrogen, $C_{1-6}$ alkyl, $C_{3-10}$ cycloalkyl, heterocyclyl, phenyl, or heteroaryl, where the alkyl, cycloalkyl, heterocyclyl, phenyl, and heteroaryl groups are optionally substituted one or more times with substituents independently selected from $R^x$; or, if $R^h$ and $R^k$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, and azepano, where each ring is optionally substituted one or more times with substituents independently selected from $R^x$;

$R^y$ is
  a) -halogen,
  b) —$NH_2$,
  c) -cyano,
  d) -carboxy,
  e) -hydroxy,
  f) -thiol,
  g) —$CF_3$,
  h) —$OCF_3$,
  i) —C(O)—$NH_2$,
  j) —$S(O)_2$—$NH_2$,
  k) oxo,
  l) —$C_{1-6}$ alkyl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
  m) -heterocyclyl optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
  n) —$C_{3-10}$ cycloalkyl optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
  o) —O—$C_{1-6}$ alkyl optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
  p) —O—$C_{3-10}$ cycloalkyl optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
  q) —NH—$C_{1-6}$ alkyl optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
  r) —N($C_{1-6}$ alkyl)$_2$ optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
  s) —C(O)—$C_{1-6}$ alkyl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
  t) —C(O)—O—$C_{1-6}$ alkyl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
  u) —S—$C_{1-6}$ alkyl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
  v) —$S(O)_2$—$C_{1-6}$ alkyl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
  w) —C(O)—NH—$C_{1-6}$ alkyl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
  x) —C(O)—N($C_{1-6}$ alkyl)$_2$, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
  y) —$S(O)_2$—NH—$C_{1-6}$ alkyl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
  z) —$S(O)_2$—N($C_{1-6}$ alkyl)$_2$, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
  aa) —NH—C(O)—$C_{1-6}$ alkyl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$, or
  bb) —NH—$S(O)_2$—$C_{1-6}$ alkyl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$;

$R^x$ is
  a) —$R^y$
  b) -phenyl, optionally substituted one or more times with substituents selected independently from the group consisting of halogen, —OH, —O—C$_{1-6}$ alkyl, —NH$_2$, —NH—C$_{1-6}$ alkyl, and —N(C$_{1-6}$ alkyl)$_2$,
c) -heteroaryl, optionally substituted one or more times with substituents selected independently from the group consisting of halogen, —OH, —O—C$_{1-6}$ alkyl, —NH$_2$, —NH—C$_{1-6}$ alkyl, and —N(C$_{1-6}$ alkyl)$_2$,
d) —O-phenyl,
e) —O-heteroaryl,
f) —C(O)-phenyl,
g) —C(O)-heteroaryl,
h) —C(O)—O-phenyl, or
i) —C(O)—O-heteroaryl;
R$^z$ is
a) —R$^y$
b) -phenyl,
c) -heteroaryl;
d) —O-phenyl,
e) —O-heteroaryl,
f) —C(O)-phenyl,
g) —C(O)-heteroaryl,
h) —C(O)—O-phenyl, or
i) —C(O)—O-heteroaryl;
v is an integer from 0 to 4, and
w is an integer from 0 to 2.

2. The method of claim 1, wherein the inflammatory disease is selected from the group consisting of: asthma, chronic obstructive pulmonary disease, idiopathic pulmonary fibrosis, inflammatory bowel syndrome, Crohn's disease, celiac disease, scleroderma, systemic lupus erythematosus, and rheumatoid arthritis.

3. The method of claim 1,
wherein R$^4$ is -methyl, -ethyl, -isopropyl, -isobutyl, —CH$_2$CH$_2$—OCH$_3$, —CH$_2$CH$_2$—F, —CH$_2$CH$_2$—NH$_2$, or —CH$_2$CH$_2$—NH—CH$_3$; and
wherein R$^3$ is hydrogen.

4. The method of claim 3, wherein X$^3$ is

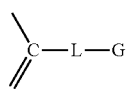

and X$^1$, X$^2$, and X$^4$ are each

5. The method of claim 4, wherein v is 1 and R$^2$ is attached at the 6-position of the benzothiazole ring.

6. The method of claim 4, wherein R$^2$ is fluoro, chloro, —CF$_3$, or —OCF$_3$.

7. The method of claim 4, wherein R$^1$ is hydrogen.

8. The method of claim 4, wherein R$^4$ is methyl.

9. The method of claim 4, wherein L is —C(O)NH—.

10. The method of claim 4, wherein G is C$_{1-8}$ alkyl optionally substituted one or more times with substituents independently selected from R$^c$.

11. The method of claim 10, wherein G is C$_{1-8}$ alkyl optionally substituted once by —C(O)NR$^h$R$^k$.

12. The method of claim 11, wherein G is —CH$_2$—C(O)NR$^h$R$^k$.

13. The method of claim 10, wherein G is C$_{1-8}$ alkyl optionally substituted once by —O—R$^h$.

14. The method of claim 13, wherein G is —(CH$_2$)$_2$—OR$^h$.

15. The method of claim 1, wherein the compound is selected from the group consisting of:
1-Methyl-2-(6-trifluoromethoxy-benzothiazol-2-ylamino)-1H-benzoimidazole-5-carboxylic acid (2-ethoxy-ethyl)-amide;
1-Methyl-2-(6-trifluoromethoxy-benzothiazol-2-ylamino)-1H-benzoimidazole-5-carboxylic acid (2-hydroxy-ethyl)-amide;
1-Methyl-2-(6-trifluoromethoxy-benzothiazol-2-ylamino)-1H-benzoimidazole-5-carboxylic acid (2-methoxy-2-methyl-propyl)-amide;
1-Methyl-2-(6-trifluoromethyl-benzothiazol-2-ylamino)-1H-benzoimidazole-5-carboxylic acid (2-methoxy-ethyl)-amide;
1-Methyl-2-(6-trifluoromethyl-benzothiazol-2-ylamino)-1H-benzoimidazole-5-carboxylic acid (2-hydroxy-ethyl)-amide;
2-(6-Chloro-benzothiazol-2-ylamino)-1-methyl-1H-benzoimidazole-5-carboxylic acid (2-methoxy-ethyl)-amide;
6-Fluoro-1-methyl-2-(6-trifluoromethoxy-benzothiazol-2-ylamino)-1H-benzoimidazole-5-carboxylic acid ethylamide;
1-Methyl-2-(6-trifluoromethoxy-benzothiazol-2-ylamino)-1H-benzoimidazole-5-carboxylic acid [2-(2-hydroxy-ethoxy)-ethyl]-amide;
1-Methyl-2-(6-trifluoromethoxy-benzothiazol-2-ylamino)-1H-benzoimidazole-5-carboxylic acid [2-(2-fluoro-ethoxy)-ethyl]-amide;
1-Methyl-2-(6-trifluoromethoxy-benzothiazol-2-ylamino)-1H-benzoimidazole-5-carboxylic acid ((S)-2-hydroxy-propyl)-amide;
1-Methyl-2-(6-trifluoromethoxy-benzothiazol-2-ylamino)-1H-benzoimidazole-5-carboxylic acid ((R)-2-hydroxy-propyl)-amide;
2-(6-Chloro-benzothiazol-2-ylamino)-1-methyl-1H-benzoimidazole-5-carboxylic acid (2-ethoxy-ethyl)-amide;
1-Ethyl-2-(6-trifluoromethoxy-benzothiazol-2-ylamino)-1H-benzoimidazole-5-carboxylic acid (2-ethoxy-ethyl)-amide;
1-(2-Methoxy-ethyl)-2-(6-trifluoromethoxy-benzothiazol-2-ylamino)-1H-benzoimidazole-5-carboxylic acid (2-ethoxy-ethyl)-amide;
2-(6-Chloro-benzothiazol-2-ylamino)-1-ethyl-1H-benzoimidazole-5-carboxylic acid (2-fluoro-ethyl)-amide;
2-(6-Chloro-benzothiazol-2-ylamino)-1-ethyl-1H-benzoimidazole-5-carboxylic acid (2-methoxy-ethyl)-amide;
1-Methyl-2-(6-trifluoromethyl-benzothiazol-2-ylamino)-1H-benzoimidazole-5-carboxylic acid ((R)-2-hydroxy-propyl)-amide
2-(6-Chloro-benzothiazol-2-ylamino)-1-methyl-1H-benzoimidazole-5-carboxylic acid [2-(2-hydroxy-ethoxy)-ethyl]-amide
1-Methyl-2-(6-trifluoromethoxy-benzothiazol-2-ylamino)-1H-benzoimidazole-5-carboxylic acid [2-(2-methoxy-ethoxy)-ethyl]-amide;
1-Methyl-2-(6-trifluoromethyl-benzothiazol-2-ylamino)-1H-benzoimidazole-5-carboxylic acid [2-(2-methoxy-ethoxy)-ethyl]-amide; and
1-Methyl-2-(6-trifluoromethoxy-benzothiazol-2-ylamino)-1H-benzoimidazole-5-carboxylic acid [2-(2-dimethylamino-ethoxy)-ethyl]-amide;
or a pharmaceutically acceptable salt thereof.

16. The method of claim 1, wherein the compound is selected from the group consisting of:

1-Methyl-2-(6-trifluoromethoxy-benzothiazol-2-ylamino)-1H-benzimidazole-5-carboxylic acid [2-(4-methyl-piperazin-1-yl)-2-oxo-ethyl]-amide;
1-Methyl-2-(6-trifluoromethyl-benzothiazol-2-ylamino)-1H-benzoimidazole-5-carboxylic acid (2-morpholin-4-yl-ethyl)-amide;
1-Methyl-2-(6-trifluoromethyl-benzothiazol-2-ylamino)-1H-benzoimidazole-5-carboxylic acid (3-morpholin-4-yl-3-oxo-propyl)-amide;
1-Methyl-2-(6-trifluoromethyl-benzothiazol-2-ylamino)-1H-benzoimidazole-5-carboxylic acid [2-((R)-3-hydroxy-pyrrolidin-1-yl)-2-oxo-ethyl]-amide;
2-(6-Chloro-benzothiazol-2-ylamino)-1-methyl-1H-benzoimidazole-5-carboxylic acid [2-((R)-3-methoxy-pyrrolidin-1-yl)-2-oxo-ethyl]-amide;
2-(6-Chloro-benzothiazol-2-ylamino)-1-methyl-1H-benzoimidazole-5-carboxylic acid [2-((S)-3-methoxy-pyrrolidin-1-yl)-2-oxo-ethyl]-amide;
1-Methyl-2-(6-trifluoromethyl-benzothiazol-2-ylamino)-1H-benzoimidazole-5-carboxylic acid [2-((S)-3-methoxy-pyrrolidin-1-yl)-2-oxo-ethyl]-amide;
1-Methyl-2-(6-trifluoromethoxy-benzothiazol-2-ylamino)-1H-benzoimidazole-5-carboxylic acid [2-((R)-3-dimethylamino-pyrrolidin-1-yl)-2-oxo-ethyl]-amide;
1-Methyl-2-(6-trifluoromethoxy-benzothiazol-2-ylamino)-1H-benzoimidazole-5-carboxylic acid [2-((S)-3-dimethylamino-pyrrolidin-1-yl)-2-oxo-ethyl]-amide;
1-Methyl-2-(6-trifluoromethyl-benzothiazol-2-ylamino)-1H-benzoimidazole-5-carboxylic acid (2-morpholin-4-yl-2-oxo-ethyl)-amide;
1-Methyl-2-(6-trifluoromethyl-benzothiazol-2-ylamino)-1H-benzoimidazole-5-carboxylic acid [2-(4-methyl-piperazin-1-yl)-2-oxo-ethyl]-amide;
1-Methyl-2-(6-trifluoromethyl-benzothiazol-2-ylamino)-1H-benzoimidazole-5-carboxylic acid [2-((R)-3-hydroxy-piperidin-1-yl)-2-oxo-ethyl]-amide;
1-Methyl-2-(6-trifluoromethyl-benzothiazol-2-ylamino)-1H-benzoimidazole-5-carboxylic acid [2-((S)-3-hydroxy-piperidin-1-yl)-2-oxo-ethyl]-amide;
1-Methyl-2-(6-trifluoromethoxy-benzothiazol-2-ylamino)-1H-benzoimidazole-5-carboxylic acid [2-(4-hydroxy-piperidin-1-yl)-2-oxo-ethyl]-amide;
2-(6-Chloro-benzothiazol-2-ylamino)-1-methyl-1H-benzoimidazole-5-carboxylic acid [2-(4-hydroxy-piperidin-1-yl)-2-oxo-ethyl]-amide;
1-Methyl-2-(6-trifluoromethyl-benzothiazol-2-ylamino)-1H-benzoimidazole-5-carboxylic acid ((S)-1-methyl-2-morpholin-4-yl-2-oxo-ethyl)-amide; and
1-Methyl-2-(6-trifluoromethyl-benzothiazol-2-ylamino)-1H-benzoimidazole-5-carboxylic acid [(R)-1-methyl-2-(4-methyl-piperazin-1-yl)-2-oxo-ethyl]-amide;
or a pharmaceutically acceptable salt thereof.

17. The method of claim 1, wherein the compound is selected from the group consisting of:

1-Methyl-2-(6-trifluoromethoxy-benzothiazol-2-ylamino)-1H-benzimidazole-5-carboxylic acid dimethylcarbamoylmethyl-amide;
2-(6-Chloro-benzothiazol-2-ylamino)-1-methyl-1H-benzimidazole-5-carboxylic acid dimethylcarbamoylmethyl-amide;
1-Methyl-2-(6-trifluoromethoxy-benzothiazol-2-ylamino)-1H-benzoimidazole-5-carboxylic acid (2-dimethylcarbamoyl-ethyl)-amide;
1-Methyl-2-(6-trifluoromethoxy-benzothiazol-2-ylamino)-1H-benzoimidazole-5-carboxylic acid ((S)-1-dimethylcarbamoyl-ethyl)-amide;
2-(6-Chloro-benzothiazol-2-ylamino)-1-methyl-1H-benzoimidazole-5-carboxylic acid (2-dimethylcarbamoyl-ethyl)-amide;
1-Methyl-2-(6-trifluoromethyl-benzothiazol-2-ylamino)-1H-benzoimidazole-5-carboxylic acid (2-dimethylcarbamoyl-ethyl)-amide;
1-Methyl-2-(6-trifluoromethyl-benzothiazol-2-ylamino)-1H-benzoimidazole-5-carboxylic acid methylcarbamoylmethyl-amide;
2-(6-Chloro-benzothiazol-2-ylamino)-1-methyl-1H-benzoimidazole-5-carboxylic acid ((S)-1-dimethylcarbamoyl-ethyl)-amide;
1-Methyl-2-(6-trifluoromethyl-benzothiazol-2-ylamino)-1H-benzoimidazole-5-carboxylic acid ((S)-1-dimethylcarbamoyl-ethyl)-amide; and
1-Methyl-2-(6-trifluoromethyl-benzothiazol-2-ylamino)-1H-benzoimidazole-5-carboxylic acid ((R)-1-dimethylcarbamoyl-ethyl)-amide;
or a pharmaceutically acceptable salt thereof.

18. The method of claim 1, wherein the compound is selected from the group consisting of:

1-Methyl-2-(6-trifluoromethoxy-benzothiazol-2-ylamino)-1H-benzimidazole-5-carboxylic acid (2-ethanesulfonyl-ethyl)-amide; and
1-Methyl-2-(6-trifluoromethoxy-benzothiazol-2-ylamino)-1H-benzimidazole-5-carboxylic acid (3-methanesulfonyl-propyl)-amide;
or a pharmaceutically acceptable salt thereof.

19. The method of claim 1, wherein the compound is
3-Methyl-2-(6-trifluoromethoxy-benzothiazol-2-ylamino)-3H-imidazo[4,5-b]pyridine-6-carboxylic acid dimethylcarbamoylmethyl-amide
or a pharmaceutically acceptable salt thereof.

20. The method of claim 1, wherein the compound is
1-Methyl-2-(6-trifluoromethoxy-benzothiazol-2-ylamino)-1H-benzoimidazole-5-carboxylic acid (2-methoxy-ethyl)-amide
or a pharmaceutically acceptable salt thereof.

21. The method of claim 1, wherein the compound is
3-Methyl-2-(6-trifluoromethoxy-benzothiazol-2-ylamino)-3H-imidazo[4,5-b]pyridine-6-carboxylic acid (2-methoxy-ethyl)-amide
or a pharmaceutically acceptable salt thereof.

22. The method of claim 1, wherein the compound is
1-Methyl-2-(6-trifluoromethyl-benzothiazol-2-ylamino)-1H-benzoimidazole-5-carboxylic acid [2-(2-hydroxy-ethoxy)-ethyl]-amide
or a pharmaceutically acceptable salt thereof.

23. The method of claim 1, wherein the compound is
6-Methoxy-1-methyl-2-(6-trifluoromethoxy-benzothiazol-2-ylamino)-1H-benzoimidazole-5-carboxylic acid (2-morpholin-4-yl-ethyl)-amide
or a pharmaceutically acceptable salt thereof.

24. The method of claim 1, wherein the compound is
3-Methyl-2-(6-trifluoromethoxy-benzothiazol-2-ylamino)-3H-imidazo[4,5-b]pyridine-6-carboxylic acid (2-morpholin-4-yl-ethyl)-amide
or a pharmaceutically acceptable salt thereof.

25. A method of treating a disease comprising administering to a human subject a compound,
wherein the disease is an inflammatory disease; and
wherein the compound is a compound of Formula (I) or a pharmaceutically acceptable salt thereof

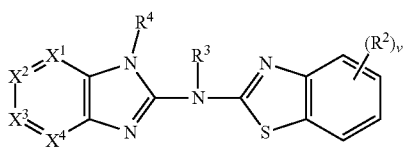

wherein
X³ is

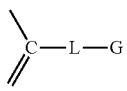

and X¹, X², and X⁴ are each

R¹ is hydrogen, —OCH₃, or —F,
v is an integer from 0 to 2,
R² is —Cl, —F, —CF₃, or —OCF₃,
R⁴ is -methyl, -ethyl, -isopropyl, or -isobutyl,
L is —C(O)N(R⁶)—,
R⁶ is hydrogen, and
G is —H, -methyl, -ethyl, -n-propyl, -isopropyl, -isobutyl, —CH₂Y³, —CH₂CH₂Y³, —CH₂CH₂CH₂Y³, —CH(CH₃)CH₂Y³, —CH₂CH(Y³)CH₃, —CH(Y³)CH₃, —CH₂C(Y³)(CH₃)₂, or —C(Y³)(CH₃)₂, where
Y³ is -cyclopropyl, —CF₃, —OCF₃, —OCH₃, —OCH₂CH₃, —F, —OH, —O(CH₂)₂—OH, —O(CH₂)₂—F, —SCH₃, —S(O)₂—CH₃, —SCH₂CH₃, —S(O)₂CH₂CH₃, —NH—CH₃, —NH—CH₂CH₃, —N(CH₃)₂, —NH—C(O)—CH₃, —NH—C(O)—CH₂CH₃, or C(O)—Y⁴, where
Y⁴ is —OH, —OCH₃, —OCH₂CH₃, —OC(CH₃)₃, —NH₂, —NH—CH₃, —NH—CH₂CH₃, —N(CH₃)₂, or —N(CH₂CH₃)₂.

26. The method of claim 25, wherein the inflammatory disease is selected from the group consisting of: asthma, chronic obstructive pulmonary disease, idiopathic pulmonary fibrosis, inflammatory bowel syndrome, Crohn's disease, celiac disease, scleroderma, systemic lupus erythematosus, and rheumatoid arthritis.

27. A method of treating a disease comprising administering to a human subject a compound, wherein the disease is an inflammatory disease, and wherein the compound is
1-Methyl-2-(6-trifluoromethyl-benzothiazol-2-ylamino)-1H-benzimidazole-5-carboxylic acid dimethylcarbamoylmethyl-amide or a pharmaceutically acceptable salt thereof.

28. The method of claim 27, wherein the renal disease is selected from the group consisting of: inflammatory disease is selected from the group consisting of: asthma, chronic obstructive pulmonary disease, idiopathic pulmonary fibrosis, inflammatory bowel syndrome, Crohn's disease, celiac disease, scleroderma, systemic lupus erythematosus, and rheumatoid arthritis.

29. The method of claim 27, wherein the compound is
1-Methyl-2-(6-trifluoromethyl-benzothiazol-2-ylamino)-1H-benzimidazole-5-carboxylic acid dimethylcarbamoylmethyl-amide.

* * * * *